US009206175B2

(12) United States Patent
Lyssikatos et al.

(10) Patent No.: US 9,206,175 B2
(45) **Date of Patent: *Dec. 8, 2015**

(54) SUBSTITUTED 6,6-FUSED NITROGENOUS HETEROCYCLIC COMPOUNDS AND USES THEREOF

(71) Applicant: Genentech, Inc., South San Francisco, CA (US)

(72) Inventors: Joseph P. Lyssikatos, Piedmont, CA (US); Lewis J. Gazzard, Belmont, CA (US); Emily Hanan, Redwood City, CA (US); Samuel S. Kintz, Stanford, CA (US); Hans Edward Purkey, Burlingame, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/068,774

(22) Filed: Oct. 31, 2013

(65) Prior Publication Data

US 2014/0088076 A1 Mar. 27, 2014

Related U.S. Application Data

(63) Continuation of application No. 13/325,751, filed on Dec. 14, 2011, now Pat. No. 8,623,889.

(60) Provisional application No. 61/424,567, filed on Dec. 17, 2010.

(51) Int. Cl.

| | |
|---|---|
| *A01N 43/42* | (2006.01) |
| *A61K 31/44* | (2006.01) |
| *A61K 31/47* | (2006.01) |
| *C07D 221/02* | (2006.01) |
| *C07D 471/02* | (2006.01) |
| *C07D 217/00* | (2006.01) |
| *C07D 471/04* | (2006.01) |
| *C07D 217/22* | (2006.01) |
| *C07D 401/04* | (2006.01) |
| *C07D 401/12* | (2006.01) |
| *C07D 405/12* | (2006.01) |
| *C07D 405/14* | (2006.01) |
| *C07D 413/12* | (2006.01) |
| *C07D 417/04* | (2006.01) |

(52) U.S. Cl.

CPC ............ *C07D 471/04* (2013.01); *C07D 217/22* (2013.01); *C07D 401/04* (2013.01); *C07D 401/12* (2013.01); *C07D 405/12* (2013.01); *C07D 405/14* (2013.01); *C07D 413/12* (2013.01); *C07D 417/04* (2013.01)

(58) Field of Classification Search

None

See application file for complete search history.

(56) References Cited

U.S. PATENT DOCUMENTS

| | | | |
|---|---|---|---|
| 3,535,321 | A | 10/1970 | Dunn et al. |
| 2002/0147203 | A1 | 10/2002 | Bilodeau et al. |
| 2004/0236084 | A1 | 11/2004 | Biwersi |
| 2005/0043309 | A1 | 2/2005 | Clark |
| 2005/0107361 | A1 | 5/2005 | Han |
| 2006/0276498 | A1 | 12/2006 | Green et al. |
| 2007/0032518 | A1 | 2/2007 | Norman et al. |
| 2007/0179151 | A1 | 8/2007 | Chen et al. |
| 2008/0300246 | A1 | 12/2008 | Xie |
| 2009/0088429 | A1 | 4/2009 | Plettenburg |
| 2009/0275537 | A1 | 11/2009 | Qian et al. |
| 2010/0056506 | A1 | 3/2010 | Huang |
| 2010/0099684 | A1 | 4/2010 | Cook, II et al. |
| 2010/0197688 | A1 | 8/2010 | Nantermet et al. |
| 2011/0009447 | A1 | 1/2011 | Huth et al. |

FOREIGN PATENT DOCUMENTS

| | | | |
|---|---|---|---|
| WO | 2006/124944 | A1 | 11/2006 |
| WO | 2007/071348 | A1 | 6/2007 |
| WO | 2009/023193 | | 2/2009 |
| WO | 2010/007374 | | 1/2010 |

OTHER PUBLICATIONS

English Translation of Search Report of EAPO.

Search Report of EAPO.

Andaloussi et al., "A convenient synthesis of linear pyridinoimidazo[1,2-α]pyridine and pyrroloimidazo[1,2-α]pyridine cores" Tetrahedron Letters 48:8392-8395 ( 2007).

(Partial International Search on patentability for international application No. PCT/EP2011/072666).

(Continued)

*Primary Examiner* — Jeffrey S Lundgren
*Assistant Examiner* — Michael Schmitt
(74) *Attorney, Agent, or Firm* — Tamara Kale

(57) ABSTRACT

The invention provides novel compounds having the general formula:

(I)

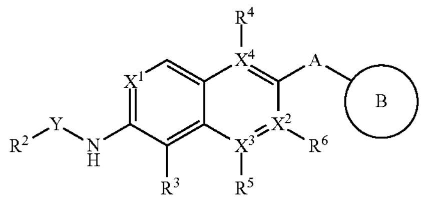

wherein $X^1$ is N or $N^+O^-$, and one of $X^2$, $X^3$ and $X^4$ is N or $N^+$—$O^-$ and the remainder of $X^2$, $X^3$ and $X^4$ is C. $R^2$, $R^3$, $R^4$, $R^5$, $R^6$. A, B and Y are as described herein. Additionally compositions compounds of Formula I and methods of use are further described herein.

22 Claims, 7 Drawing Sheets

(56) References Cited

OTHER PUBLICATIONS

Bartmann et al., "Synthesis of di- and tetraalkyl-3-piperazinoisoquinolines and related compounds as potential antidepressant agents" J Heterocyclic 24:677-682 ( 1987).

International Search Report and Written Opinion for International Patent Application No. PCT/EP2011/072666 dated Jul. 18, 2012.

Frohn et al., "An efficient syntheis of 1,6- and 1,7-dibromo-3-aminoisoquinolines: versatile templates for the preperation of functionalized isoquinolines" Tetrahedron Lett 48(3):487-489 (Dec. 14, 2006).

Gavrin et al., "Inhibition of Tp12 kinase and TNF-α production with 1,7-naphthyridine-3-carbonitriles: Synthesis and structure-acitivity relationships" Bioorg Med Chem Lett 15:5288-5292 ( 2005).

Taurins and Li, "Synthesis of 2,6-naphthyridine, 4-methyl-2,6-naphhyridine and their derivatives" Canadian J Chem 52:843-848 (Jan. 1, 1974).

Thompson et al., "Synthesis and structure-activity relationships of soluble 7-substrated 3-(3,5-dimethoxyphenyl)-1,6-naphthyridin-2-amines and related ureas as dual inhibitors of the fibroblast growth factor receptor-1 and vascular endothelial growth factor receptor-2 tyrosine kinases" J Med Chem 48:4628-2653 ( 2005).

Figure 1-A
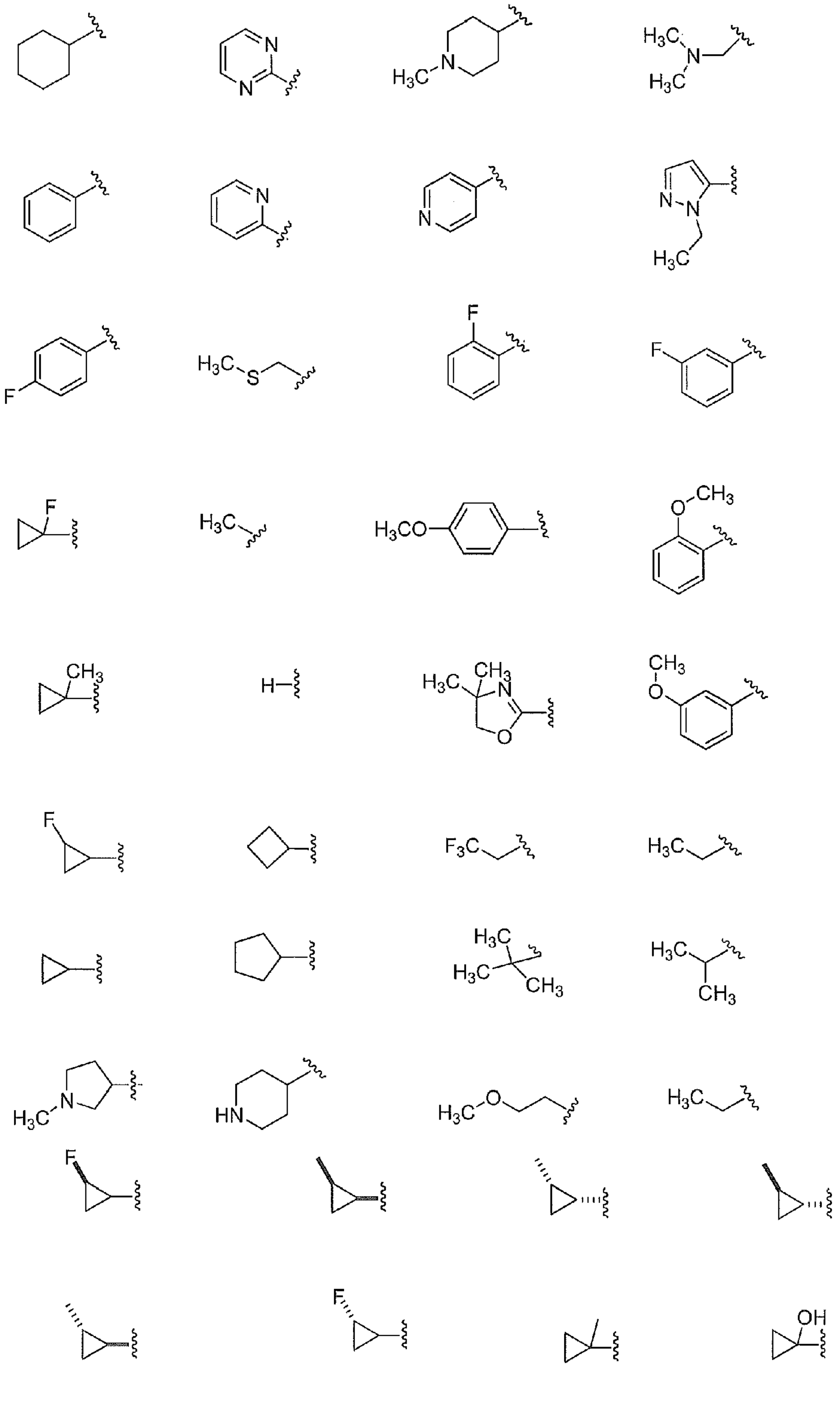

Figure 1-B
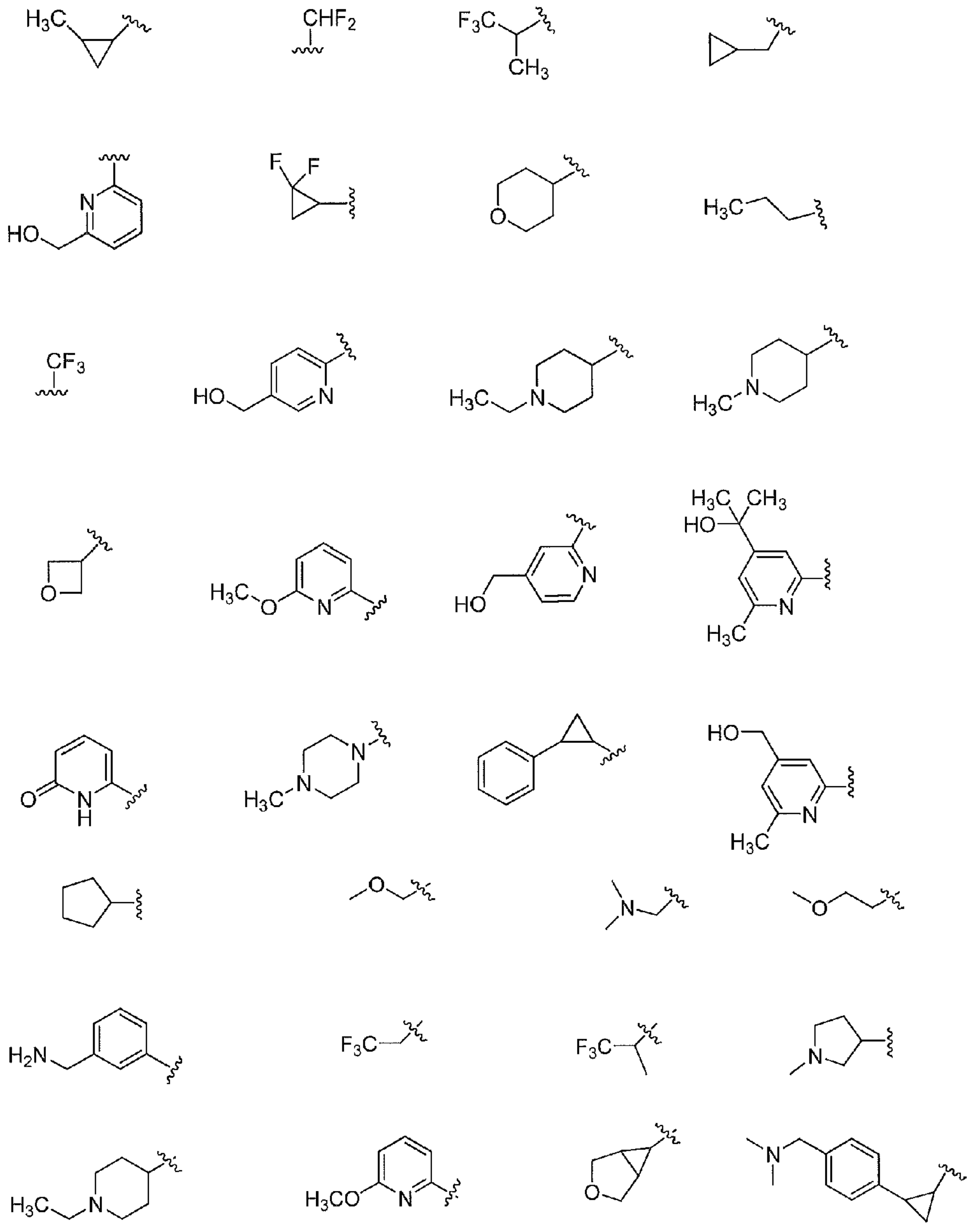

Figure 2-A
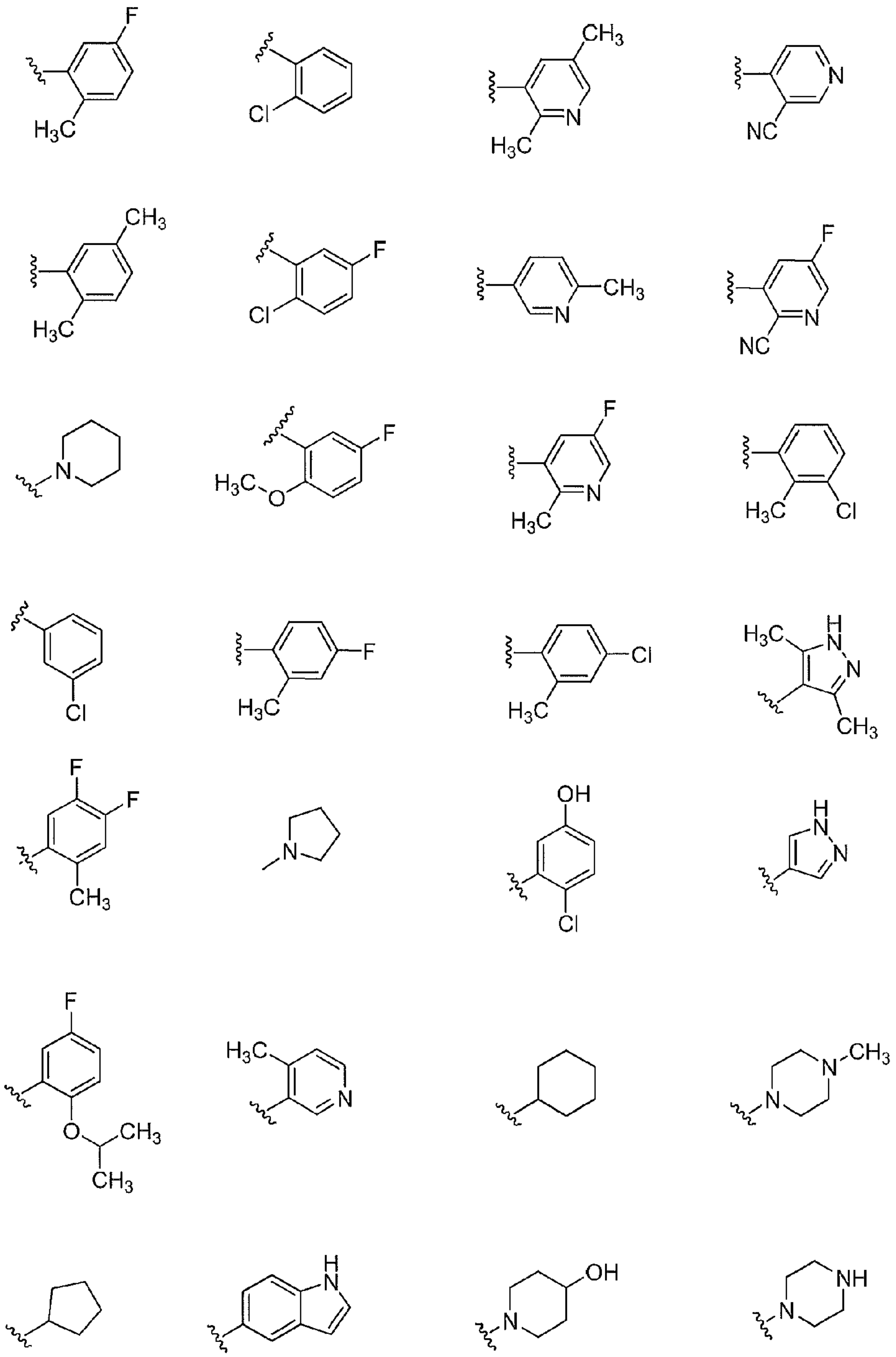

Figure 2-B
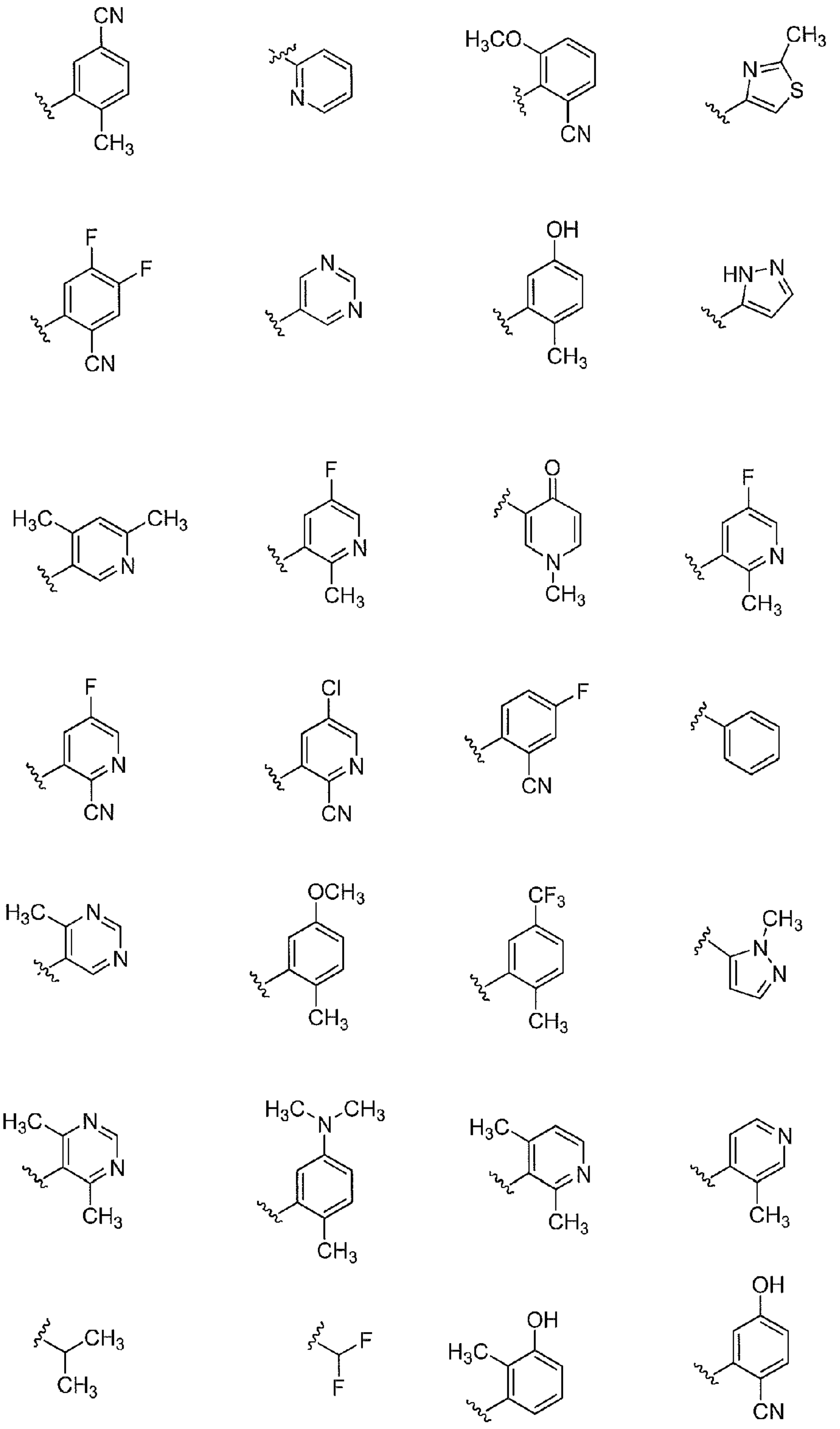

Figure 2-C
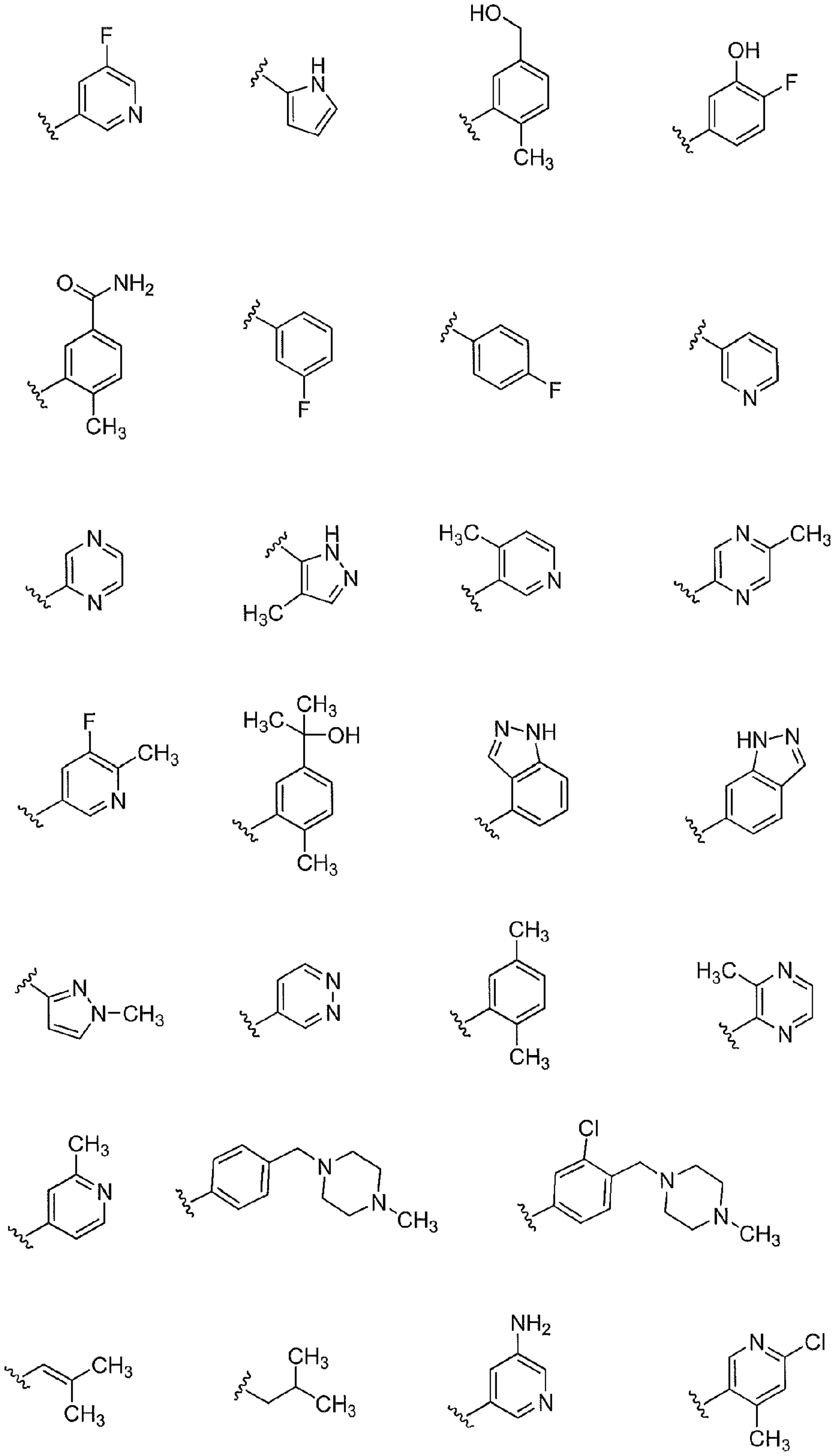

Figure 2-D
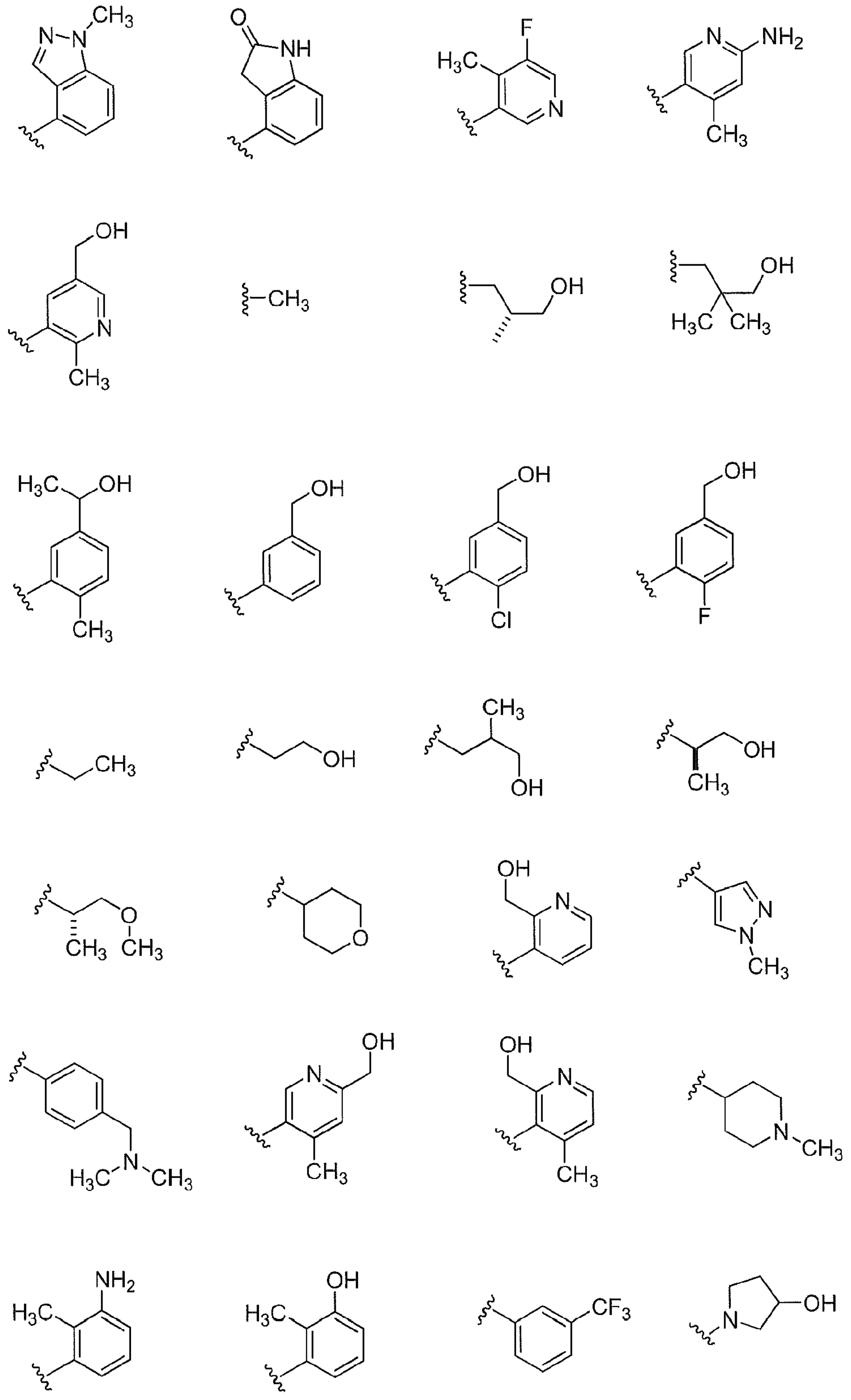

Figure 2-E
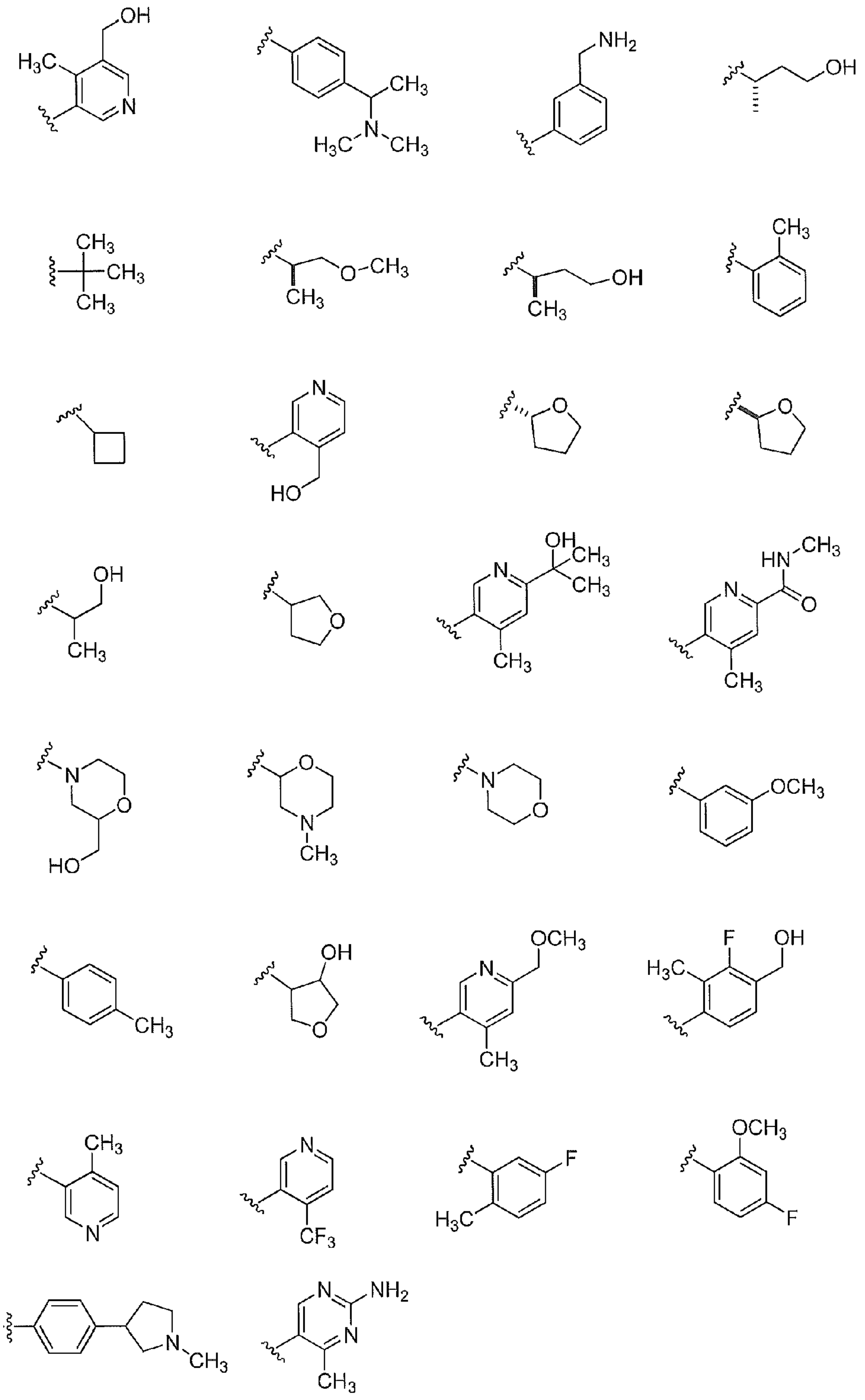

SUBSTITUTED 6,6-FUSED NITROGENOUS HETEROCYCLIC COMPOUNDS AND USES THEREOF

CROSS REFERENCE TO RELATED APPLICATION

This application claims the benefit of priority of provisional U.S. Application No. 61/424,567 filed Dec. 17, 2010 which is hereby incorporated by reference in its entirety.

FIELD OF THE INVENTION

The present invention relates to organic compounds useful for therapy and/or prophylaxis in a mammal, and in particular to inhibitors of Abl tyrosine kinases (e.g., c-Abl; ABL1, v-Abl) and related tyrosine kinases (e.g., Abl-related gene; ABL2) that are useful for treating diseases and disorders that result from over activation of Abl tyrosine kinase.

The Abl family of non-receptor kinases contain as key members: c-Abl and Arg. c-Abl is ubiquitously expressed in mammals and is found localized at many subcellular sites, including the nucleus, cytoplasm, mitochondria, the endoplasmic reticulum and the cell corex, where c-Abl interacts with a large variety of cellular proteins, including signaling adaptors, kinases, phosphatases, cell-cycle regulators, transcription factors and cytoskeleton proteins. The function of c-Abl in regulating cell growth is well established. Oncogenetically activated c-Abl kinase has been implicated to play a role in the progression of hematopoetic malignancies and solid tumor cancers. Additionally it has also been shown that c-Abl functions in the development and regeneration of the nervous system. In the brain, c-Abl is involved in neuronal plasticity, neurite outgrowth and neurogenesis. Overactivation or undesired activation of c-Abl can also play a role in neurological disorders, including but not limited to, Alzheimer's disease, Parkinson's disease, Pick's disease, Niemann-Pick's disease, among others. In view of the above, it is desirable to have small molecule inhibitors of Abl and/or Abl related kinases that can be used to treat diseases wherein aberrant Abl and/or Abl related kinase activity is observed, such as, for example, in cancer and in neurodegenerative diseases and/or disorders.

SUMMARY OF THE INVENTION

In one aspect, the present invention provides for compounds of Formula I (or stereoisomers, geometric isomers, tautomers, solvates, metabolites, isotopes, pharmaceutically acceptable salts, or prodrugs thereof) capable of inhibiting Abl and/or Abl related kinase. In another aspect, the present invention provides for pharmaceutical composition comprising a compound of Formula I and at least one pharmaceutically acceptable carrier, diluent or excipient. In another aspect, the present invention provides for the use of a compound of Formula I for the treatment of a neurodegenerative disease or disorder (e.g., of Alzheimer's Disease, Parkinson's Disease, Pick's Disease, Niemann-Pick's Disease, Tauopathies and Amyoloidosis).

In another aspect, the present invention provides for the use of a compound of Formula I (or stereoisomers, geometric isomers, tautomers, solvates, metabolites, isotopes, pharmaceutically acceptable salts, or prodrugs thereof) for the preparation of a medicament for the treatment of Alzheimer's Disease, Parkinson's Disease, Pick's Disease, Niemann-Pick's Disease, Tauopathies and Amyoloidosis. In another aspect, the present invention provides for a method for the treatment of a mammal having a disease or disorder selected from the group consisting of Alzheimer's Disease, Parkinson's Disease, Pick's Disease, Niemann-Pick's Disease, Tauopathies and Amyoloidosis, comprising administering to said mammal an effective amount of a compound of Formula I. In another aspect, the present invention provides for the use of a compound of Formula I (or stereoisomers, geometric isomers, tautomers, solvates, metabolites, isotopes, pharmaceutically acceptable salts, or prodrugs thereof) for the treatment of cancer (e.g., breast, ovarian, NSCLC, acute lymphocytic leukemia, acute myelogeneous leukemia, chronic myelogenous leukemia and chronic lymphocytic leukemia). In another aspect, the present invention provides for the use of a compound of Formula I (or stereoisomers, geometric isomers, tautomers, solvates, metabolites, isotopes, pharmaceutically acceptable salts, or prodrugs thereof) for the preparation of a medicament for the treatment of a cancer selected from the group consisting of breast, ovarian, NSCLC, acute lymphocytic leukemia, acute myelogeneous leukemia, chronic myelogenous leukemia and chronic lymphocytic leukemia. In another aspect, the present invention provides for a method for the treatment of a mammal having a cancer selected from the group consisting of breast, ovarian, NSCLC, acute lymphocytic leukemia, acute myelogeneous leukemia, chronic myelogenous leukemia and chronic lymphocytic leukemia, comprising administering to said mammal an effective amount of a compound of Formula I (or stereoisomers, geometric isomers, tautomers, solvates, metabolites, isotopes, pharmaceutically acceptable salts, or prodrugs thereof).

In compounds of Formula I:

(I)

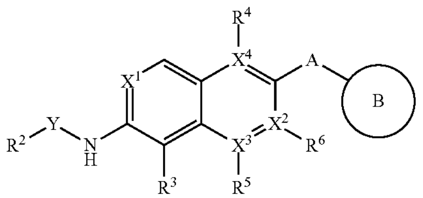

Y is absent or is selected from the group consisting of —C(═O)—, —N(H)C(═O)—, —N($R^a$)C(═O)—, —O—C(═O)—, —N(H)S(O)$_{1-2}$—, —N($R^a$)S(O)$_{1-2}$— and —S(O)$_2$—, wherein $R^a$ is selected from the group consisting of $C_{1-6}$ alkyl, $C_{1-6}$ haloalkyl, $C_{1-6}$ alkoxy, $C_{1-6}$ heteroalkyl, $C_{2-6}$ alkenyl and $C_{2-6}$ alkynyl; $R^2$ is —$(X^b)_{0-1}$—$R^b$, wherein $X^b$ is selected from the group consisting of $C_{1-6}$ alkylene, $C_{2-6}$ alkenylene, $C_{2-6}$ alkynylene, $C_{1-6}$ heteroalkylene, 3-6 membered cycloalkylene and 3-6 membered heterocycloalkylene, $R^b$ is selected from the group consisting of hydrogen, $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 3-6 membered heterocycloalkyl, 6-10 membered aryl and 5-10 membered heteroaryl, wherein the aliphatic and aromatic portions of $X^b$ and $R^b$ are each independently optionally substituted with 1 to 5 $R^{b1}$ substituents selected from the group consisting of $C_{1-6}$ alkyl, $C_{1-6}$ haloalkyl, $C_{1-6}$ heteroalkyl, F, Cl, Br, I, —OH, —$NH_2$, —SH, —CN, —$NO_2$, —$N_3$, —C(═O)OH, $C_{1-6}$ alkoxy, $C_{1-6}$ alkylamino, $C_{1-6}$ dialkylamino, —($C_{1-4}$ alkenylene)$_{0-1}$—C(═O)—($C_{1-4}$ alkyl), —($C_{1-4}$ alkenylene)$_{0-1}$-C(═O)O—($C_{1-4}$ alkyl), —($C_{1-4}$ alkenylene)$_{0-1}$-C(═O)N(H)—($C_{1-4}$ alkyl), —($C_{1-4}$ alkenylene)$_{0-1}$-C(═O)N($C_{1-4}$ alkyl)$_2$, —($C_{1-4}$ alkenylene)$_{0-1}$-S(O)$_2$—($C_{1-4}$ alkyl), —($C_{1-4}$ alkenylene)$_{0-1}$-C(═O)—($C_{1-4}$ heteroalkyl) and —($C_{1-4}$ alkenylene)$_{0-1}$-C (=O)—($C_{3-6}$ heterocycloalkyl), and wherein if $R^b$ is a 6 membered aryl or a 5-6 membered heteroaryl then any two substituents attached to adjacent atoms said aryl or heteroaryl are optionally combined to from a 3-6 membered carbocyclic or a 3-6 membered heterocyclic ring comprising 1-3 heteroatoms selected from N, O and S, and optionally substituted with 1 to 3 $R^{b1}$ substituents; $X^1$ is N or $N^+$—$O^-$; $X^2$, $X^3$ and $X^4$ are each C, or one of $X^2$, $X^3$ and $X^4$ is N or $N^+$—$O^-$ and the remainder of $X^2$, $X^3$ and $X^4$ are each C; $R^3$ is selected from the group consisting of hydrogen, $C_{1-6}$ alkyl, $C_{1-6}$ haloalkyl, $C_{1-6}$ alkoxy, $C_{1-6}$ alkylamino, $C_{1-6}$ dialkyamino, F, Cl, Br, I, —CN, —$CF_3$, —$OCF_3$, —$SF_5$ and —$N_3$; $R^4$ is selected from the group consisting of hydrogen, $C_{1-6}$ alkyl, $C_{1-6}$ haloalkyl, F, Cl, Br, I, —CN, —$NO_2$, —$N_3$, —SH, —OH, $C_{1-6}$ alkoxy, —$CF_3$, —$OCF_3$, —$SF_5$, $C_{1-6}$ alkylamino, and $C_{1-6}$ dialkylamino, or is absent if $X^4$ is N or $N^+$—O; $R^5$ is $(X^c)_{0-1}$—$R^c$, wherein $X^c$ is selected from the group consisting of $C_{1-6}$ alkylene, $C_{2-6}$ alkenylene, $C_{2-6}$ heteroalkylene, $C_{2-6}$alkynylene, —N(H)—, —N($R^{xc}$)—, —O—, —S(O)$_2$—, —C(=O)—, —C(=O)O—, —C(=O)N(H)—, —N(H)C(=O)— and —OC(=O)—, wherein $R^{xc}$ is selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, and wherein $R^c$ is selected from the group consisting of hydrogen, F, Cl, Br, I, —CN, —$NO_2$, —$NH_2$, —OH, —$CF_3$, —$OCF_3$, —$SF_5$, $C_{1-6}$ alkoxy, $C_{1-6}$ alkylamino, $C_{1-6}$ dialkylamino, $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 3-6 membered heterocycloalkyl, 6 membered aryl and 5-6 membered heteroaryl, wherein the aliphatic and aromatic portions of $X^c$ and $R^c$ are optionally substituted with 1 to 5 $R^{c1}$ substituents selected from the group consisting of $C_{1-6}$ alkyl, $C_{1-6}$ heteroalkyl, F, Cl, Br, I, —OH, —$NH_2$, —SH, —CN, —$NO_2$, —$N_3$, —C(=O)OH, alkyl)$_2$, —NH($C_{1-6}$ alkyl), —O($C_{1-6}$ alkyl), —($C_{1-4}$ alkenylene)$_{0-1}$-C(=O)—($C_{1-4}$ alkyl), —($C_{1-4}$ alkenylene)$_{0-1}$-C(=O)O—($C_{1-4}$ alkyl), —($C_{1-4}$ alkenylene)$_{0-1}$-C(=O)N(H)—($C_{1-4}$ alkyl), —($C_{1-4}$ alkenylene)$_{0-1}$-C(=O)N($C_{1-4}$ alkyl)$_2$, —($C_{1-4}$ alkenylene)$_{0-1}$-S(O)$_2$—($C_{1-4}$ alkyl), —($C_{1-4}$ alkenylene)$_{0-1}$-C(=O)—($C_{1-4}$ heteroalkyl) and —($C_{1-4}$ alkenylene)$_{0-1}$-C(=O)—($C_{3-6}$ heterocycloalkyl), or $R^5$ is absent if $X^3$ is N or $N^+$—$O^-$; $R^6$ is selected from the group consisting of hydrogen, $C_{1-6}$ alkyl, $C_{1-6}$ haloalkyl, $C_{1-6}$ heteroalkyl, $C_{1-6}$ alkoxy, $C_{1-6}$ alkylamino, $C_{1-6}$ dialkylamino, $C_{2-6}$ alkenyl, $C_{2-6}$ alkynyl, F, Cl, Br, I, —OH, —$NH_2$, —SH, —CN, —$NO_2$, —$CF_3$, —$OCF_3$, —$SF_5$, and —$N_3$, or $R^6$ is absent if $X^2$ is N or $N^+$—$O^-$; A is absent or is selected from the group consisting of —O—, —N(H)—, —N($R^d$)—, —S(O)$_2$—, —S(O)—, —S—, —($X^d$)$_{0-1}$—N(H)C(=O)—, —($X^d$)$_{0-1}$—N($R^d$)C(=O)—, —$X^d$—, —($X^d$)$_{0-1}$—C(=O)N(H)—, —($X^d$)$_{0-1}$—C(=O)N($R^d$)—, —($X^d$)$_{0-1}$—C(=O)—, —C(=O)—($X^d$)$_{0-1}$—, —($X^d$)$_{0-1}$—OC(=O)— and —($X^d$)$_{0-1}$C(=O)O—, wherein $X^d$ is selected from the group consisting of $C_{1-6}$ alkylene, $C_{2-6}$ alkenylene, $C_{2-6}$ alkynylene, $C_{1-6}$ alkoxy $C_{1-6}$ heteroalkylene, 6-10 membered arylene, 5-9 membered heteroarylene, 3-10 membered cycloalkylene, 3-10 membered heterocycloalkylene, and $R^d$ at each occurrence is independently selected from the group consisting of $C_{1-6}$ alkyl, $C_{2-6}$ alkenyl, $C_{1-6}$ heteroalkyl and $C_{1-6}$ haloalkyl, wherein the aliphatic or aromatic portions of $X^d$ and $R^d$ are each independently optionally substituted with 1 to 5 $R^{d1}$ substituents selected from the group consisting of $C_{1-6}$ alkyl, $C_{1-6}$ haloalkyl, $C_{2-6}$ alkenyl, $C_{2-6}$ alkynyl, $C_{1-6}$ alkylamino, $C_{1-6}$ dialkylamino, F, Cl, Br, I, —OH, —$NH_2$, —SH, —CN, —$NO_2$, —$CF_3$, —$OCF_3$, —$SF_5$ and —$N_3$; B is selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 4-9 membered heterocycloalkyl, 6-10 membered aryl and 5-6 membered heteroaryl, wherein the aliphatic or aromatic portions of B are independently optionally substituted with 1 to 5 $R^{B1}$ substituents selected from the group consisting of $C_{1-6}$ alkyl, $C_{1-6}$ haloalkyl, $C_{1-6}$ heteroalkyl, $C_{1-6}$ alkoxy, $C_{1-6}$ alkylamino, $C_{1-6}$ dialkylamino, $C_{3-6}$heterocycloalkyl, F, Cl, Br, I, —OH, —$NH_2$, —SH, —$CF_3$, —$OCF_3$, —$SF_5$, —($X^e$)$_{0-1}$—CN, —($X^e$)$_{0-1}$—$NO_2$, —($X^e$)$_{0-1}$—OH, —($X^e$)$_{0-1}$—H, —($X^e$)$_{0-1}$—N(H)$R^e$, —($X^e$)$_{0-1}$—N($R^e$), —($X^e$)$_{0-1}$—S$R^e$, —($X^e$)$_{0-1}$—C(O)$R^e$, —($X^e$)$_{0-1}$—S(O)$_2R^e$, —($X^e$)$_{0-1}$—S(O)$R^e$, —N(H)S(O)$_2R^e$, —N($R^e$)S(O)$_2R^e$, —($X^e$)$_{0-1}$—C(=O)O$R^e$, —($X^e$)$_{0-1}$—C(=O)OH, —($X^e$)$_{0-1}$—C(=O)N(H)$R^e$, —($X^e$)$_{0-1}$—C(=O)N($R^e$)$R^e$, —($X^e$)$_{0-1}$—N(H)C(=O)$R^e$, —($X^e$)$_{0-1}$—N($R^e$)C(=O)$R^e$, wherein if B is a 6 membered aryl or a 5-6 membered heteroaryl then any two substituents attached to adjacent atoms of said aryl or heteroaryl are optionally combined to from a 3-6 membered carbocyclic or a 3-6 membered heterocyclic ring optionally comprising 1-3 heteroatoms selected from N, O and S, and optionally substituted with 1 to 3 $R^{B1}$ substituents; wherein $X^e$ is selected from the group consisting of $C_{1-6}$ alkylene, $C_{2-6}$ alkenylene, $C_{2-6}$ alkynylene, $C_{1-6}$ heteroalkylene, $C_{3-6}$ cycloalkylene and $C_{3-6}$ heterocycloalkylene, and $R^e$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl, 3-7 membered heterocycloalkyl, phenyl and 5-6 membered heteroaryl, wherein the aliphatic or aromatic portions of $X^e$ and $R^e$ are each independently optionally substituted with 1 to 5 $R^{e1}$ substituents selected from the group consisting of $C_{1-6}$ alkyl, $C_{1-6}$ haloalkyl, $C_{2-6}$ alkenyl, $C_{2-6}$ alkynyl, $C_{1-6}$ alkylamino, $C_{1-6}$ dialkylamino, F, Cl, Br, I, —OH, —$NH_2$, —SH, —CN, —$NO_2$, —$CF_3$, —$OCF_3$, —$SF_5$ and —$N_3$, and wherein any two $R^e$ groups attached to the same nitrogen atom are optionally combined to form a 3-7 membered heterocyclic or 5-10 membered heteroaryl ring comprising 1-3 heteroatoms selected from N, O and S, with the provisos to Formula I as set forth hereinbelow.

DETAILED DESCRIPTION OF THE DRAWINGS

FIG. 1-A and FIG. 1-B illustrate certain $R^b$ substituents in the $R^2$ group of compounds of Formula I.

FIG. 2-A, FIG. 2-B, FIG. 2-C, FIG. 2-D and FIG. 2-E illustrate certain B groups of compounds of Formula I.

DETAILED DESCRIPTION OF THE INVENTION

Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl," "carbocyclic," or "carbocycle" refers to hydrocarbon rings having the indicated number of ring atoms (e.g., 3-6 membered cycloalkyl) and being fully saturated or having no more than one double bond between ring vertices. As used herein, "cycloalkyl," "carbocyclic," or "carbocycle" is also meant to refer to bicyclic, polycyclic and spirocyclic hydrocarbon rings such as, for example, bicyclo[2.2.1]heptane, pinane, bicyclo[2.2.2]octane, adamantane, norborene, spirocyclic $C_{5-12}$ alkane, etc. As used herein, the terms, "alkenyl," "alkynyl," "cycloalkyl,", "carbocycle," and "carbocyclic," are meant to include mono and polyhalogenated variants thereof.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include $-CH_2-CH_2-O-CH_3$, $-CH_2-CH_2-O-CF_3$, $-CH_2-CH_2-NH-CH_3$, $-CH_2-CH_2-N(CH_3)-CH_3$, $-CH_2-S-CH_2-CH_3$, $-S(O)-CH_3$, $-CH_2-CH_2-S(O)_2-CH_3$, $-CH{=}CH-O-CH_3$, $-Si(CH_3)_3$, $-CH_2-CH{=}N-OCH_3$, and $-CH{=}CH{=}N(CH_3)-CH_3$. Up to two heteroatoms can be consecutive, such as, for example, $-CH_2-NH-OCH_3$ and $-CH_2-O-Si(CH_3)_3$.

The term "heterocycloalkyl," "heterocyclic," or "heterocycle" refers to a cycloalkane group having the indicated number of ring atoms (e.g., 5-6 membered heterocycloalkyl) that contain from one to five heteroatoms selected from N, O, and S, wherein the nitrogen and sulfur atoms are optionally oxidized, nitrogen atom(s) are optionally quaternized, as ring atoms. Unless otherwise stated, a "heterocycloalkyl," "heterocyclic," or "heterocycle" ring can be a monocyclic, a bicyclic, spirocyclic or a polycylic ring system. Non limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-5-oxide, thiomorpholine-S,S-oxide, piperazine, pyran, pyridone, 3-pyrroline, thiopyran, pyrone, tetrahydrofuran, tetrhydrothiophene, quinuclidine, tropane and the like. A "heterocycloalkyl," "heterocyclic," or "heterocycle" group can be attached to the remainder of the molecule through one or more ring carbons or heteroatoms. A "heterocycloalkyl," "heterocyclic," or "heterocycle" can include mono- and poly-halogenated variants thereof.

The term "alkylene" by itself or as part of another substituent means a divalent radical derived from an alkane, as exemplified by $-CH_2CH_2CH_2CH_2-$. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively. "Alkylene", "alkenylene" and "alkynylene" are also meant to include mono and poly-halogenated variants.

The term "heteroalkylene" by itself or as part of another substituent means a divalent radical, saturated or unsaturated or polyunsaturated, derived from heteroalkyl, as exemplified by $-CH_2-CH_2-S-CH_2CH_2-$ and $-CH_2-S-CH_2-CH_2-NH-CH_2-$, $-O-CH_2-CH{=}CH-$, $-CH_2-CH{=}C(H)CH_2-O-CH_2-$ and $-S-CH_2-C{\equiv}C-$. For heteroalkylene groups, heteroatoms can also occupy either or both of the chain termini (e.g., alkyleneoxy, alkylenedioxy, alkyleneamino, alkylenediamino, and the like). The term "heteroalkylene" is also meant to include mono and poly-halogenated variants.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively, and further include mono- and poly-halogenated variants thereof. Additionally, for dialkylamino groups, the alkyl portions can be the same or different and can also be combined to form a 3-7 membered ring with the nitrogen atom to which each is attached. Accordingly, a group represented as $-NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like.

The term "aryl" means, unless otherwise stated, a polyunsaturated, typically aromatic, hydrocarbon group, which can be a single ring or multiple rings (up to three rings) which are fused together. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Optional substituents for each of the above noted aryl and heteroaryl ring systems can be selected from the group of acceptable substituents described further below.

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl and cycloalkyl) can be a variety of groups including, but not limited to, -halogen, $-OR'$, $-NR'R''$, $-SR'$, $-SiR'R''R'''$, $-OC(O)R'$, $-C(O)R'$, $-CO_2R'$, $-CONR'R''$, $-OC(O)NR'R''$, $-N R''C(O)R'$, $-NR'''C(O)NR'R''$, $-NR''C(O)_2R'$, $-NHC(NH_2){=}NH$, $-NR C(NH_2){=}NH$, $-NHC(NH_2){=}NR'$, $-NR'''C(NR'R''){=}N-CN$, $-NR'''C(NR'R''){=}NOR'$, $-NHC(NH_2){=}NR'$, $-S(O)R'$, $-S(O)_2R'$, $-S(O)_2NR'R''$, $-NR'S(O)_2R''$, $-NR''S(O)_2NR'R''$, $-CN$, $-NO_2$, $-(CH_2)_{1-4}-OR'$, $-(CH_2)_{1-4}-NR'R''$, $-(CH_2)_{1-4}-SR'$, $-(CH_2)_{1-4}-SiR'R''R'''$, $-(CH_2)_{1-4}-OC(O)R'$, $-(CH_2)_{1-4}-C(O)R$, $-(CH_2)_{1-4}-CO_2R'$, $-(CH_2)_{1-4}CONR'R''$, in a number ranging from zero to (2 m'+1), where m' is the total number of carbon atoms in such radical. R', R'' and R''' each independently refer groups including, for example, hydrogen, unsubstituted $C_{1-6}$ alkyl, unsubstituted heteroalkyl, unsubstituted aryl, aryl substituted with 1-3 halogens, unsubstituted $C_{1-6}$ alkyl, $C_{1-6}$ alkoxy or $C_{1-6}$ thioalkoxy groups, or unsubstituted aryl-$C_{1-4}$ alkyl groups, unsubstituted heteroaryl, substituted heteroaryl, among others. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other substitutents for alkyl radicals, including heteroalkyl, alkylene, include for example, =O, =NR', =N—OR', =N—CN, =NH, wherein R' include substituents as described above. When a substituent for the alkyl radicals (including those groups often referred to as alkylene, alkenyl, alkynyl, heteroalkyl and cycloalkyl) contains an alkylene linker (e.g., $—(CH_2)_{1-4}—$NR'R"), the alkylene linker includes halo variants as well. For example, the linker "$—(CH_2)_{1-4}—$" when used as part of a substituent is meant to include difluoromethylene, 1,2-difluoroethylene, etc.

Similarly, substituents for the aryl and heteroaryl groups are varied and are generally selected from the group including, but not limited to, -halogen, —OR', —OC(O)R', —NR'R", —SR', —R', —CN, $—NO_2$, $—CO_2R'$, —CONR'R", —C(O)R', —OC(O)NR'R", —NR"C(O)R', $—NR"C(O)_2R'$, —NR'C(O)NR"R"', $—NHC(NH_2)=NH$, $—NR'C(NH_2)=NH$, $—NHC(NH_2)=NR'$, —S(O)R', $—S(O)_2R'$, $—S(O)_2NR'R"$, $—NR'S(O)_2R"$, $—N_3$, perfluoro-$C_{1-4}$ alkoxy, and perfluoro-$C_{1-4}$ alkyl, $—(CH_2)_{1-4}—OR'$, $—(CH_2)_{1-4}—NR'R"$, $—(CH_2)_{1-4}—SR'$, $—(CH_2)_{1-4}—SiR'R"R"'$, $—(CH_2)_{1-4}—OC(O)R'$, $—(CH_2)_{1-4}—C(O)R'$, $—(CH_2)_{1-4}—CO_2R'$, $—(CH_2)_{1-4}CONR'R"$, in a number ranging from zero to the total number of open valences on the aromatic ring system; and where R', R" and R"' are independently selected from hydrogen, $C_{1-6}$ alkyl, $C_{3-6}$ cycloalkyl, $C_{2-6}$ alkenyl, $C_{2-6}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms. When a substituent for the aryl or heteroaryl group contains an alkylene linker (e.g., $—(CH_2)_{1-4}—$NR'R"), the alkylene linker includes halo variants as well. For example, the linker "$—(CH_2)_{1-4}—$" when used as part of a substituent is meant to include difluoromethylene, 1,2-difluoroethylene, etc.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "∿∿" that intersects a bond in a chemical structure indicate the point of attachment of the atom to which the wavy bond is connected in the chemical structure to the remainder of a molecule, or to the remainder of a fragment of a molecule.

As used herein, the representation of a group (e.g., $X^d$) in parenthesis followed by a subscript integer range (e.g., $(X^d)_{0-2}$) means that the group can have the number of occurrences as designated by the integer range. For example, $(X^d)_{0-2}$ means the group $X^d$ can be absent or can occur one or two times.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

As used herein, the phrase "aliphatic and aromatic portions" when used to described portions of a group (e.g., a $R^1$ group) on a compound formula that may be substituted with specified substituents is meant to include all portions of such group, including all non-aromatic and aromatic portions fo the group.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4th edition, Wiley-Interscience, New York, 2006.

As used herein, the term "mammal" includes, but is not limited to, humans, mice, rats, guinea pigs, monkeys, dogs, cats, horses, cows, pigs, and sheep As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-($(C_{1-6})$alkanoyloxy)ethyl, 1-methyl-1-($(C_{1-6})$alkanoyloxy) ethyl, $(C_{1-6})$alkoxycarbonyloxymethyl, N—$(C_{1-6})$alkoxycarbonylaminomethyl, succinoyl, $(C_{1-6})$alkanoyl, alpha-amino $(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, bur the for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include istopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically labeled compounds of the present invention (e.g., those labeled with $^{3}H$ or $^{14}C$) are useful in compound and/or substrate tissue distribution assays. Tritiated ($^{3}H$) and carbon-14 ($^{14}C$) isotopes are useful for their ease of preparation and detectability. Further substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies.

Compounds

In one aspect, the present invention provides for compounds of Formula I:

(I)

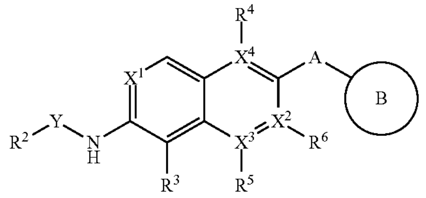

or stereoisomers, geometric isomers, tautomers, solvates, metabolites, isotopes, pharmaceutically acceptable salts, or prodrugs thereof; wherein Y is absent or is selected from the group consisting of —C(═O)—, —N(H)C(═O)—, —N($R^a$)C(═O)—, —O—C(═O)—, —N(H)S(O)$_{1-2}$—, —N($R^a$)S(O)$_{1-2}$— and —S(O)$_2$—, wherein $R^a$ is selected from the group consisting of $C_{1-6}$ alkyl, $C_{1-6}$ haloalkyl, $C_{1-6}$ alkoxy, $C_{1-6}$heteroalkyl, $C_{2-6}$ alkenyl and $C_{2-6}$ alkynyl. $R^2$ is —$(X^b)_{0-1}$—$R^b$, wherein $X^b$ is selected from the group consisting of $C_{1-6}$ alkylene, $C_{2-6}$ alkenylene, $C_{2-6}$ alkynylene, $C_{1-6}$ heteroalkylene, 3-6 membered cycloalkylene and 3-6 membered heterocycloalkylene, $R^b$ is selected from the group consisting of hydrogen, $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 3-6 membered heterocycloalkyl, 6-10 membered aryl, and 5-10 membered heteroaryl, wherein the aliphatic and aromatic portions of $X^b$ and $R^b$ are each independently optionally substituted with 1 to 5 $R^{b1}$ substituents selected from the group consisting of $C_{1-6}$ alkyl, $C_{1-6}$ haloalkyl, $C_{1-6}$ heteroalkyl, F, Cl, Br, I, —OH, —$NH_2$, —SH, —CN, —$NO_2$, —$N_3$, —C(═O)OH, $C_{1-6}$ alkoxy, $C_{1-6}$ alkylamino, $C_{1-6}$ dialkylamino, 3-6 membered heterocycloalkyl, —($C_{1-4}$ alkenylene)$_{0-1}$-C(═O)—($C_{1-4}$ alkyl), —($C_{1-4}$ alkenylene)$_{0-1}$-C(═O)O—($C_{1-4}$ alkyl), —($C_{1-4}$ alkenylene)$_{0-1}$-C(═O)N(H)—($C_{1-4}$ alkyl), —($C_{1-4}$ alkenylene)$_{0-1}$-C(═O)N($C_{1-4}$ alkyl)$_2$, —($C_{1-4}$ alkenylene)$_{0-1}$-S(O)$_2$—($C_{1-4}$ alkyl), —($C_{1-4}$ alkenylene)$_{0-1}$-C(═O)—($C_{1-4}$ heteroalkyl) and —($C_{1-4}$ alkenylene)$_{0-1}$-C(═O)—($C_{3-6}$ heterocycloalkyl), and wherein if $R^b$ is a 6 membered aryl or a 5-6 membered heteroaryl then any two substituents attached to adjacent atoms said aryl or heteroaryl are optionally combined to from a 3-6 membered carbocyclic or a 3-6 membered heterocyclic ring comprising 1-3 heteroatoms selected from N, O and S, and optionally substituted with 1 to 3 $R^{b1}$ substituents. $X^1$ is N or $N^+$—$O^-$; and $X^2$, $X^3$ and $X^4$ are each C, or one of $X^2$, $X^3$ and $X^4$ is N or $N^+$—$O^-$ and the remainder of $X^2$, $X^3$ and $X^4$ are each C. $R^3$ is selected from the group consisting of hydrogen, $C_{1-6}$ alkyl, $C_{1-6}$ haloalkyl, $C_{1-6}$ alkoxy, $C_{1-6}$ alkylamino, $C_{1-6}$ dialkyamino, F, Cl, Br, I, —CN, —$CF_3$, —$OCF_3$, —$SF_5$ and —$N_3$. $R^4$ is selected from the group consisting of hydrogen, $C_{1-6}$ alkyl, $C_{1-6}$ haloalkyl, F, Cl, Br, I, —CN, —$NO_2$, —$N_3$, —SH, —OH, $C_{1-6}$ alkoxy, —$CF_3$, —$OCF_3$, —$SF_5$, $C_{1-6}$ alkylamino and $C_{1-6}$ dialkylamino, or is absent if $X^4$ is N or $N^+$—$O^-$. $R^5$ is $(X^c)_{0-1}$—$R^c$, wherein $X^c$ is selected from the group consisting of $C_{1-6}$ alkylene, $C_{2-6}$ alkenylene, $C_{2-6}$ heteroalkylene, $C_{2-6}$alkynylene, —N(H)—, —N($R^{xc}$)—, —O—, —S(O)$_2$—, —C(═O)—, —C(═O)O—, —C(═O)N(H)—, —N(H)C(═O)— and —OC(═O)—, wherein $R^{xc}$ is selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, and wherein $R^c$ is selected from the group consisting of hydrogen, F, Cl, Br, I, —CN, —$NO_2$, —$NH_2$, —OH, —$CF_3$, —$OCF_3$, —$SF_5$, $C_{1-6}$ alkoxy, $C_{1-6}$ alkylamino, $C_{1-6}$ dialkylamino, $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 3-6 membered heterocycloalkyl, 6 membered aryl and 5-6 membered heteroaryl, wherein the aliphatic and aromatic portions of $X^c$ and $R^c$ are optionally substituted with 1 to 5 $R^{c1}$ substituents selected from the group consisting of $C_{1-6}$ alkyl, $C_{1-6}$ heteroalkyl, F, Cl, Br, I, —OH, —$NH_2$, —SH, —CN, —$NO_2$, —$N_3$, —C(═O)OH, —N($C_{1-6}$alkyl)$_2$, —NH($C_{1-6}$ alkyl), —O($C_{1-6}$ alkyl), —($C_{1-4}$ alkenylene)$_{0-1}$-C(═O)—($C_{1-4}$ alkyl), —($C_{1-4}$ alkenylene)$_{0-1}$-C(═O)O—($C_{1-4}$ alkyl), —($C_{1-4}$ alkenylene)$_{0-1}$-C(═O)N(H)—($C_{1-4}$ alkyl), —($C_{1-4}$ alkenylene)$_{0-1}$-C(═O)N($C_{1-4}$ alkyl)$_2$, —($C_{1-4}$ alkenylene)$_{0-1}$-S(O)$_2$—($C_{1-4}$ alkyl), —($C_{1-4}$ alkenylene)$_{0-1}$-C(═O)—($C_{1-4}$ heteroalkyl) and —($C_{1-4}$ alkenylene)$_{0-1}$-C(═O)—($C_{3-6}$heterocycloalkyl), or $R^5$ is absent if $X^3$ is N or $N^+$—$O^-$. $R^6$ is selected from the group consisting of hydrogen, $C_{1-6}$ alkyl, $C_{1-6}$ haloalkyl, $C_{1-6}$ heteroalkyl, $C_{1-6}$ alkoxy, $C_{1-6}$ alkylamino, $C_{1-6}$ dialkylamino, $C_{2-6}$ alkenyl, $C_{2-6}$ alkynyl, F, Cl, Br, I, —OH, —$NH_2$, —SH, —CN, —$NO_2$, —$CF_3$, —$OCF_3$, —$SF_5$, and —$N_3$, or $R^6$ is absent if $X^2$ is N or $N^+$—$O^-$. A is absent or is selected from the group consisting of —O—, —N(H)—, —N($R^d$)—, —S(O)$_2$—, —S(O)—, —S—, —$(X^d)_{0-1}$—N(H)C(═O)—, —$(X^d)_{0-1}$—N($R^d$)C(═O)—, —$X^d$—, —$(X^d)_{0-1}$—C(═O)N(H)—, —$(X^d)_{0-1}$—C(═O)N($R^d$)—, —$(X^d)_{0-1}$—C(═O)—, —C(═O)—$(X^d)_{0-1}$—, —$(X^d)_{0-1}$—OC(═O)— and —$(X^d)_{0-1}$C(═O)O—, wherein $X^d$ is selected from the group consisting of $C_{1-6}$ alkylene, $C_{2-6}$ alkenylene, $C_{2-6}$ alkynylene, $C_{1-6}$ heteroalkylene, 6-10 membered arylene, 5-10 membered heteroarylene, 3-10 membered cycloalkylene, 3-10 membered heterocycloalkylene, and $R^d$ at each occurrence is independently selected from the group consisting of $C_{1-6}$ alkyl, $C_{2-6}$ alkenyl, $C_{1-6}$ heteroalkyl and $C_{1-6}$ haloalkyl, wherein the aliphatic or aromatic portions of $X^d$ and $R^d$ are each independently optionally substituted with 1 to 5 $R^{d1}$ substituents selected from the group consisting of $C_{1-6}$ alkyl, $C_{1-6}$ haloalkyl, $C_{2-6}$ alkenyl, $C_{2-6}$ alkynyl, $C_{1-6}$ alkylamino, $C_{1-6}$ dialkylamino, F, Cl, Br, I, —OH, —$NH_2$, —SH, —CN, —$NO_2$, —$CF_3$, —$OCF_3$, —$SF_5$ and —$N_3$. B is selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 4-9 membered heterocycloalkyl, 6-10 membered aryl and 5-6 membered heteroaryl, wherein the aliphatic or aromatic portions of B are independently optionally substituted with 1 to 5 $R^{B1}$ substituents selected from the group consisting of $C_{1-6}$ alkyl, $C_{1-6}$ haloalkyl, $C_{1-6}$ heteroalkyl, $C_{1-6}$ alkoxy, $C_{1-6}$ alkylamino, $C_{1-6}$ dialkylamino, $C_{3-6}$ heterocycloalkyl, F, Cl, Br, I, —OH, —$NH_2$, —SH, —$CF_3$, —$OCF_3$, —$SF_5$, —$(X^e)_{0-1}$—$NO_2$, —$(X^e)_{0-1}$—$N_3$, —$(X^e)_{0-1}$—OH, —$(X^e)_{0-1}$—H, —$(X^e)_{0-1}$—N(H)$R^e$, —$(X^e)_{0-1}$—N($R^e$)$_2$, —$(X^e)_{0-1}$—S$R^e$, —$(X^e)_{0-1}$—C(O)$R^e$, —$(X^e)_{0-1}$—S(O)$_2R^e$, —$(X^e)_{0-1}$—S(O)$R^e$, —N(H)S(O)$_2R^e$, —N($R^e$)S(O)$_2R^e$, —$(X^e)_{0-1}$—C(═O)O$R^e$, —$(X^e)_{0-1}$—C(═O)OH, —$(X^e)_{0-1}$—C(═O)N(H)$R^e$, —$(X^e)_{0-1}$—C(═O)N($R^e$)$R^e$, —$(X^e)_{0-1}$—N(H)C(═O)$R^e$, —$(X^e)_{0-1}$—N($R^e$)C(═O)$R^e$, wherein if B is a 6 membered aryl or a 5-6 membered heteroaryl then any two substituents attached to adjacent atoms of said aryl or heteroaryl are optionally combined to from a 3-6 membered carbocyclic or a 3-6 membered heterocyclic ring optionally comprising 1-3 heteroatoms selected from N, O and S, and optionally substituted with 1 to 3 $R^{B1}$ substituents; wherein $X^e$ is selected from the group consisting of $C_{1-6}$ alkylene, $C_{2-6}$ alkenylene, $C_{2-6}$ alkynylene, $C_{1-6}$ heteroalkylene, $C_{3-6}$ cycloalkylene and $C_{3-6}$ heterocycloalkylene, and $R^e$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl, 3-7 membered heterocycloalkyl, phenyl and 5-6 membered heteroaryl, wherein the aliphatic or aromatic portions of $X^e$ and $R^e$ are each independently optionally substituted with 1 to 5 $R^{e1}$ substituents selected from the group consisting of $C_{1-6}$ alkyl, $C_{1-6}$ haloalkyl, $C_{2-6}$ alkenyl, $C_{2-6}$ alkynyl, $C_{1-6}$ alkylamino, $C_{1-6}$ dialkylamino, F, Cl, Br, I, —OH, —$NH_2$, —SH, —CN, —$NO_2$, —$CF_3$, —$OCF_3$, —$SF_5$ and —$N_3$, wherein any two $R^e$ groups attached to the same nitrogen atom are optionally combined to form a 3-7 membered heterocyclic or 5-10 membered heteroaryl ring comprising 1-3 heteroatoms selected from N, O and S. In compounds of Formula I there is the proviso that if $X^3$ is N, $R^3$ is H, $R^4$ is H or $NH_2$, $R^6$ is —OH and —Y—$R^2$ is other than H, then -A-B is not thiazol-4-yl substituted with 2-thiophenyl-S(O)$_2$CH$_2$—, phenyl-S(O)$_2$—CH$_2$—, 4-pyridyl, or pyridyl-S(O)$_2$CH$_2$—, if $X^3$ is N, $R^3$ is H or Cl, $R^4$ is H, $R^6$ is —OH, —$NH_2$, or —$NHCH_3$ and —Y—$R^2$ is hydrogen, 4-tetrahydropyranyl, 4-(($CH_3CH_2$)$_2$N($CH_2$)$_{3-4}$O)-phenyl, ($CH_3CH_2$)$_2$N($CH_2$)$_4$—, 3-(4-methylpiperazinyl)-propyl or trifluoroacetyl, then -A-B is not 2-chlorophenyl, 2-methylphenyl, 2,6-dichlorophenyl, 3,5-dimethoxyphenyl, 3,4-dimethoxypheny, phenyl, 2-chloro-6-(2-ethoxyethoxy)phenyl, if $X^3$ is N, $R^3$, $R^4$ and $R^6$ are each H, and —Y—$R^2$ is hydrogen, cyclohexyl, ($CH_3CH_2$)$_2$NCH$_2$CH$_2$—, CH$_3$N(H)CH$_2$CH$_2$—, ($CH_3$)$_2$NCH$_2$CH$_2$—, ($CH_3$)$_3$CC(═O)— or 2-(4-morpholinyl)ethyl, then -A-B is not 3,4-dimethoxyphenyl or optionally substituted pyridine-2-on-3-yl, if $X^4$ is N, $R^3$ is H, $R^5$ is isopropyl, $R^6$ is methoxy, -A-B is propyl or isopropyl, then —Y—$R^2$ is other than optionally substituted pyridyl, if $X^4$ is N, $R^3$, $R^5$, $R^6$ are each H, -A-B is methyl, then —Y—$R^2$ is other than hydrogen, if $R^3$, $R^4$, $R^5$ and $R^6$ are each H, and —Y—$R^2$ is hydrogen, cyclohexyl, $(CH_3CH_2)_2NCH_2CH_2$—, $CH_3N(H)CH_2CH_2$—, $(CH_3)_2NCH_2CH_2$—, $(CH_3)_3CC(=O)$— or 2-(4-morpholinyl)ethyl, then -A-B is not 3,4-dimethoxyphenyl or optionally substituted pyridine-2-on-3-yl, if $R^3$, $R^4$ and $R^5$ are each hydrogen, —Y—$R^2$ is other than hydrogen, then one of $R^6$ and -A-B is other than ethoxy.

In a first embodiment, in compounds of Formula I:

(I)

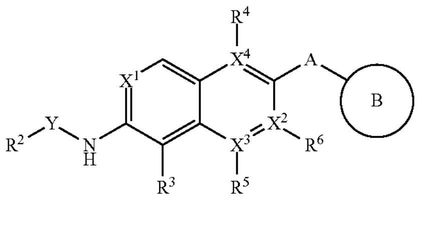

or stereoisomers, geometric isomers, tautomers, solvates, metabolites, isotopes, pharmaceutically acceptable salts, or prodrugs thereof; wherein Y is absent or is selected from the group consisting of —C(═O)—, —N(H)C(═O)—, —N($R^a$)C(═O)—, —O—C(═O)—, —N(H)S(O)$_{1-2}$—, —N($R^a$)S(O)$_{1-2}$— and —S(O)$_2$—, wherein $R^a$ is selected from the group consisting of $C_{1-6}$ alkyl, $C_{1-6}$ haloalkyl, $C_{1-6}$ alkoxy, $C_{1-6}$ heteroalkyl, $C_{2-6}$ alkenyl and $C_{2-6}$ alkynyl. $R^2$ is —$(X^b)_{0-1}$—$R^b$, wherein $X^b$ is selected from the group consisting of $C_{1-6}$ alkylene, $C_{2-6}$ alkenylene, $C_{2-6}$ alkynylene, $C_{1-6}$ heteroalkylene, 3-6 membered cycloalkylene and 3-6 membered heterocycloalkylene, $R^b$ is selected from the group consisting of hydrogen, $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 3-6 membered heterocycloalkyl, 6-10 membered aryl, and 5-10 membered heteroaryl, wherein the aliphatic and aromatic portions of $X^b$ and $R^b$ are each independently optionally substituted with 1 to 5 $R^{b1}$ substituents selected from the group consisting of $C_{1-6}$ alkyl, $C_{1-6}$ haloalkyl, $C_{1-6}$ heteroalkyl, F, Cl, Br, I, —OH, —$NH_2$, —SH, —CN, —$NO_2$, —$N_3$, —C(═O)OH, $C_{1-6}$ alkoxy, $C_{1-6}$ alkylamino, $C_{1-6}$ dialkylamino, —($C_{1-4}$ alkenylene)$_{0-1}$-C(═O)—($C_{1-4}$ alkyl), —($C_{1-4}$ alkenylene)$_{0-1}$-C(═O)O—($C_{1-4}$ alkyl), —($C_{1-4}$ alkenylene)$_{0-1}$-C(═O)N(H)—($C_{1-4}$ alkyl), —($C_{1-4}$ alkenylene)$_{0-1}$-C(═O)N($C_{1-4}$ alkyl)$_2$, —($C_{1-4}$ alkenylene)$_{0-1}$-S(O)$_2$—($C_{1-4}$ alkyl), —($C_{1-4}$ alkenylene)$_{0-1}$-C(═O)—($C_{1-4}$ heteroalkyl) and —($C_{1-4}$ alkenylene)$_{0-1}$-C(═O)—($C_{3-6}$ heterocycloalkyl), and wherein if $R^b$ is a 6 membered aryl or a 5-6 membered heteroaryl then any two substituents attached to adjacent atoms said aryl or heteroaryl are optionally combined to from a 3-6 membered carbocyclic or a 3-6 membered heterocyclic ring comprising 1-3 heteroatoms selected from N, O and S, and optionally substituted with 1 to 3 $R^{b1}$ substituents. X' is N or $N^+$—$O^-$; and $X^2$, $X^3$ and $X^4$ are each C, or one of $X^2$, $X^3$ and $X^4$ is N or $N^+$—$O^-$ and the remainder of $X^2$, $X^3$ and $X^4$ are each C. $R^3$ is selected from the group consisting of hydrogen, $C_{1-6}$ alkyl, $C_{1-6}$ haloalkyl, $C_{1-6}$ alkoxy, $C_{1-6}$ alkylamino, $C_{1-6}$ dialkyamino, F, Cl, Br, I, —CN, —$CF_3$, —$OCF_3$, —$SF_5$ and —$N_3$. $R^4$ is selected from the group consisting of hydrogen, $C_{1-6}$ alkyl, $C_{1-6}$ haloalkyl, F, Cl, Br, I, —CN, —$NO_2$, —$N_3$, —SH, —OH, $C_{1-6}$ alkoxy, —$CF_3$, —$OCF_3$, —$SF_5$, $C_{1-6}$ alkylamino and $C_{1-6}$ dialkylamino, or is absent if $X^4$ is N or $N^+$—$O^-$. $R^5$ is $(X')_{0-1}$—$R^c$, wherein $X^c$ is selected from the group consisting of $C_{1-6}$ alkylene, $C_{2-6}$ alkenylene, $C_{2-6}$ heteroalkylene, $C_{2-6}$alkynylene, —N(H)—, —N($R^{xc}$)—, —O—, —S(O)$_2$—, —C(═O)—, —C(═O)O—, —C(═O)N(H)—, —N(H)C(═O)— and —OC(═O)—, wherein $R^{xc}$ is selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, and wherein $R^c$ is selected from the group consisting of hydrogen, F, Cl, Br, I, —CN, —$NO_2$, —$NH_2$, —OH, —$CF_3$, —$OCF_3$, —$SF_5$, $C_{1-6}$ alkoxy, $C_{1-6}$ alkylamino, $C_{1-6}$ dialkylamino, $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 3-6 membered heterocycloalkyl, 6 membered aryl and 5-6 membered heteroaryl, wherein the aliphatic and aromatic portions of $X^c$ and $R^c$ are optionally substituted with 1 to 5 substituents selected from the group consisting of $C_{1-6}$ alkyl, $C_{1-6}$ heteroalkyl, F, Cl, Br, I, —OH, —$NH_2$, —SH, —CN, —$NO_2$, —$N_3$, —C(═O)OH, —N($C_{1-6}$ alkyl)$_2$, —NH($C_{1-6}$ alkyl), —O($C_{1-6}$ alkyl), —($C_{1-4}$ alkenylene)$_{0-1}$-C(═O)—($C_{1-4}$ alkyl), —($C_{1-4}$ alkenylene)$_{0-1}$-C(═O)O—($C_{1-4}$ alkyl), —($C_{1-4}$ alkenylene)$_{0-1}$-C(═O)N(H)—($C_{1-4}$ alkyl), —($C_{1-4}$ alkenylene)$_{0-1}$-C(═O)N($C_{1-4}$ alkyl)$_2$, —($C_{1-4}$ alkenylene)$_{0-1}$-S(O)$_2$—($C_{1-4}$ alkyl), —($C_{1-4}$ alkenylene)$_{0-1}$-C(═O)—($C_{1-4}$ heteroalkyl) and —($C_{1-4}$ alkenylene)$_{0-1}$-C(═O)—($C_{3-6}$ heterocycloalkyl), or $R^5$ is absent if $X^3$ is N or $N^+$—$O^-$. $R^6$ is selected from the group consisting of hydrogen, $C_{1-6}$ alkyl, $C_{1-6}$ haloalkyl, $C_{1-6}$ heteroalkyl, $C_{1-6}$ alkoxy, $C_{1-6}$ alkylamino, $C_{1-6}$ dialkylamino, $C_{2-6}$ alkenyl, $C_{2-6}$ alkynyl, F, Cl, Br, I, —OH, —$NH_2$, —SH, —CN, —$NO_2$, —$CF_3$, —$OCF_3$, —$SF_5$, and —$N_3$, or $R^6$ is absent if $X^2$ is N or $N^+$—$O^-$. A is absent or is selected from the group consisting of —O—, —N(H)—, —N($R^d$)—, —S(O)$_2$—, —S(O)—, —S—, —$(X^d)_{0-1}$—N(H)C(═O)—, —$(X^d)_{0-1}$—N($R^d$)C(═O)—, —$X^d$—, —$(X^d)_{0-1}$—C(═O)N(H)—, —$(X^d)_{0-1}$—C(═O)N($R^d$)—, —$(X^d)_{0-1}$—C(═O)—, —C(═O)—$(X^d)_{0-1}$—, —$(X^d)_{0-1}$—OC(═O)— and —$(X^d)_{0-1}$C(═O)O—, wherein $X^d$ is selected from the group consisting of $C_{1-6}$ alkylene, $C_{2-6}$ alkenylene, $C_{2-6}$ alkynylene, $C_{1-6}$ heteroalkylene, 6-10 membered arylene, 5-10 membered heteroarylene, 3-10 membered cycloalkylene, 3-10 membered heterocycloalkylene, and $R^d$ at each occurrence is independently selected from the group consisting of $C_{1-6}$ alkyl, $C_{2-6}$ alkenyl, $C_{1-6}$ heteroalkyl and $C_{1-6}$ haloalkyl, wherein the aliphatic or aromatic portions of $X^d$ and $R^d$ are each independently optionally substituted with 1 to 5 $R^{d1}$ substituents selected from the group consisting of $C_{1-6}$ alkyl, $C_{1-6}$ haloalkyl, $C_{2-6}$ alkenyl, $C_{2-6}$ alkynyl, $C_{1-6}$ alkylamino, $C_{1-6}$ dialkylamino, F, Cl, Br, I, —OH, —$NH_2$, —SH, —CN, —$NO_2$, —$CF_3$, —$OCF_3$, —$SF_5$ and —$N_3$. B is selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 4-9 membered heterocycloalkyl, 6-10 membered aryl and 5-6 membered heteroaryl, wherein the aliphatic or aromatic portions of B are independently optionally substituted with 1 to 5 $R^{B1}$ substituents selected from the group consisting of $C_{1-6}$ alkyl, $C_{1-6}$ haloalkyl, $C_{1-6}$ heteroalkyl, $C_{1-6}$ alkoxy, $C_{1-6}$ alkylamino, $C_{1-6}$ dialkylamino, $C_{3-6}$ heterocycloalkyl, F, Cl, Br, I, —OH, —$NH_2$, —SH, —$CF_3$, —$OCF_3$, —$SF_5$, —$(X^e)_{0-1}$—CN, —$(X^e)_{0-1}$—$NO_2$, —$(X^e)_{0-1}$—$N_3$, —$(X^e)_{0-1}$—OH, —$(X^e)_{0-1}$—H, —$(X^e)_{0-1}$—N(H)$R^e$, —$(X^e)_{0-1}$—N($R^e$)$_2$, —$(X^e)_{0-1}$—S$R^e$, —$(X^e)_{0-1}$—C(O)$R^e$, —$(X^e)_{0-1}$—S(O)$_2R^e$, —$(X^e)_{0-1}$—S(O)$R^e$, —N(H)S(O)$_2R^e$, —N($R^e$)S(O)$_2R^e$, —$(X^e)_{0-1}$—C(═O)O$R^e$, —$(X^e)_{0-1}$—C(═O)OH, —$(X^e)_{0-1}$—C(═O)N(H)$R^e$, —$(X^e)_{0-1}$—C(═O)N($R^e$)$R^e$, —$(X^e)_{0-1}$—N(H)C(═O)$R^e$, —$(X^e)_{0-1}$—N($R^e$)C(═O)$R^e$, wherein if B is a 6 membered aryl or a 5-6 membered heteroaryl then any two substituents attached to adjacent atoms of said aryl or heteroaryl are optionally combined to from a 3-6 membered carbocyclic or a 3-6 membered heterocyclic ring optionally comprising 1-3 heteroatoms selected from N, O and S, and optionally substituted with 1 to 3 $R^{B1}$ substituents; wherein $X^e$ is selected from the group consisting of $C_{1-6}$ alkylene, $C_{2-6}$ alkenylene, $C_{2-6}$ alkynylene, $C_{1-6}$ heteroalkylene, $C_{3-6}$ cycloalkylene and $C_{3-6}$ heterocycloalkylene, and $R^e$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl, 3-7 membered heterocycloalkyl, phenyl and 5-6 membered heteroaryl, wherein the aliphatic or aromatic portions of $X^e$ and $R^e$ are each independently optionally substituted with 1 to 5 $R^{e1}$ substituents selected from the group consisting of $C_{1-6}$ alkyl, $C_{1-6}$ haloalkyl, $C_{2-6}$ alkenyl, $C_{2-6}$ alkynyl, $C_{1-6}$ alkylamino, $C_{1-6}$ dialkylamino, F, Cl, Br, I, —OH, —SH, —CN, —$NO_2$, —$CF_3$, —$OCF_3$, —$SF_5$ and —$N_3$, wherein any two $R^e$ groups attached to the same nitrogen atom are optionally combined to form a 3-7 membered heterocyclic or 5-10 membered heteroaryl ring comprising 1-3 heteroatoms selected from N, O and S. In compounds of Formula I there is the proviso that if $X^3$ is N, $R^3$ is H, $R^4$ is H or $NH_2$, $R^6$ is —OH and —Y—$R^2$ is other than H, then -A-B is not thiazol-4-yl substituted with 2-thiophenyl-$S(O)_2CH_2$—, phenyl-$S(O)_2$—$CH_2$—, 4-pyridyl, or pyridyl-$S(O)_2CH_2$—, if $X^3$ is N, $R^3$ is H or $C^1$, $R^4$ is H, $R^6$ is —OH, —$NH_2$, or —$NHCH_3$ and —Y—$R^2$ is hydrogen, 4-tetrahydropyranyl, 4-(($CH_3CH_2)_2N(CH_2)_{3-4}O$)-phenyl, $(CH_3CH_2)_2N(CH_2)_4$—, 3-(4-methylpiperazinyl)-propyl or trifluoroacetyl, then -A-B is not 2-chlorophenyl, 2-methylphenyl, 2,6-dichlorophenyl, 3,5-dimethoxyphenyl, 3,4-dimethoxypheny, phenyl, 2-chloro-6-(2-ethoxyethoxy)phenyl, if $X^3$ is N, $R^3$, $R^4$ and $R^6$ are each H, and —Y—$R^2$ is hydrogen, cyclohexyl, $(CH_3CH_2)_2NCH_2CH_2$—, $CH_3N(H)CH_2CH_2$—, $(CH_3)_2NCH_2CH_2$ $(CH_3)_3CC(=O)$— or 2-(4-morpholinyl)ethyl, then -A-B is not 3,4-dimethoxyphenyl or optionally substituted pyridine-2-on-3-yl, if $X^4$ is N, $R^3$ is H, $R^5$ is isopropyl, $R^6$ is methoxy, -A-B is propyl or isopropyl, then —Y—$R^2$ is other than optionally substituted pyridyl, if $X^4$ is N, $R^3$, $R^5$, $R^6$ are each H, -A-B is methyl, then —Y—$R^2$ is other than hydrogen, if $R^3$, $R^4$, $R^5$ and $R^6$ are each H, and —Y—$R^2$ is hydrogen, cyclohexyl, $(CH_3CH_2)_2NCH_2CH_2$—, $CH_3N(H)CH_2CH_2$—, $(CH_3)_2NCH_2CH_2$—, $(CH_3)_3CC(=O)$— or 2-(4-morpholinyl)ethyl, then -A-B is not 3,4-dimethoxyphenyl or optionally substituted pyridine-2-on-3-yl, if $R^3$, $R^4$ and $R^5$ are each hydrogen, —Y—$R^2$ is other than hydrogen, then one of $R^6$ and -A-B is other than ethoxy.

In a second embodiment, and within certain aspects of the first embodiment, a compound of Formula I has the subformula Ia-Id selected from the group consisting of:

Ia

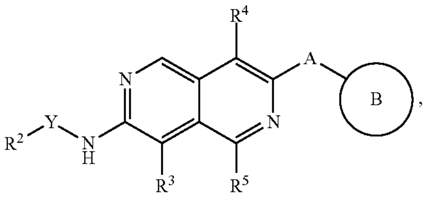

Ib

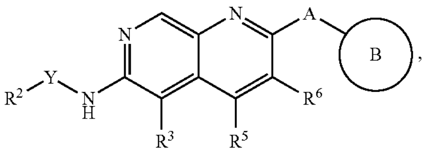

-continued

Ic

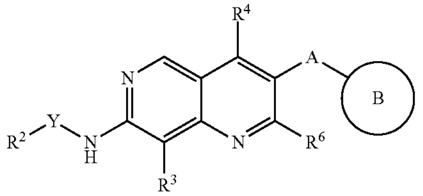

and

Id

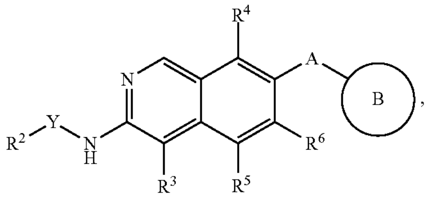

, or an N-oxide thereof.

In a a third embodiment and with certain aspects of the first and second embodiments, in Formula I or a subformula thereof, $R^3$, $R^4$ and $R^6$, if present, are each independently selected from the group consisting of hydrogen, $C_{1-6}$ alkyl, $C_{1-6}$ haloalkyl, —$CF_3$, —$OCF_3$, —$SF_5$, F, Cl, Br and I.

In a fourth embodiment in Formula I or a subformula thereof, and with in certain aspects of the first, second or third embodiments, in $R^2$, $X^b$ is absent or is selected from $C_{1-6}$ alkylene and 3-6 membered cycloalkylene; and $R^b$ is selected from the group consisting of hydrogen, $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 3-6 membered heterocycloalkyl, 6-10 membered aryl and 5-10 membered heteroaryl, wherein $X^b$ and $R^b$ are each independently optionally substituted.

In a fifth embodiment and within certain aspects of the first, second, third or fourth embodiment, in Formula I or a subformula thereof, in $R^2$, $X^b$ is absent.

In a sixth embodiment and within certain aspects of the first, second, third or fourth embodiment, in Formula I or a subformula thereof, in $R^2$, $R^b$ is selected from the group consisting of hydrogen, $C_{1-6}$ alkyl, $C_{1-6}$ haloalkyl, $C_{1-6}$ heteroalkyl, $C_{2-6}$ alkenyl and $C_{2-6}$ alkynyl.

In a seventh embodiment and within certain aspects of the first, second, third or fourth embodiment, in Formula I or a subformula thereof, in $R^2$, $R^b$ is optionally substituted with from 1 to 5 $R^{b1}$ groups selected from the group consisting of F, Cl, Br, I, OH, $NH_2$, SH, CN, $NO_2$, $C_{1-6}$ alkoxy, $C_{1-6}$ alkylamino and $C_{1-6}$ dialkylamino.

In an eighth embodiment, and within certain aspects of the first, second, third or forth embodiment, in Formula I or a subformula thereof, in $R^2$, $R^b$ is selected from the group consisting of cycloprop-1-yl, cyclobut-1-yl, cyclopent-1-yl, pyrimidin-2-yl, pyrimidin-4-yl, pyrimidin-5-yl, pyridin-2-yl, pyridin-4-yl, pyridin-3-yl, pyridin-2-on-6-yl, pyridine-2-on-5-yl, pyridine-2-on-4-yl, pyridine-2-on-3-yl, cyclohex-1-yl, phenyl, 4,5-dihydrooxazol-2-yl, oxazol-2-yl, piperidin-4-yl, piperidin-3-yl, piperidin-2-yl, piperidin-1-yl, piperazin-1-yl, piperazin-2-yl, piperazin-3-yl, morpholin-2-yl, morpholin-3-yl, morpholin-4-yl, tetrahydropyran-4-yl, tetrahydropyran-2-yl, tetrahydropyran-3-yl, oxetan-3-yl, oxetan-2-yl, pyrazol-5-yl, pyrazol-1-yl, pyrazol-3-yl, pyrazol-4-yl, methyl, ethyl, propyl, isopropyl, butyl, iso-butyl, tert-butyl, pyrrolidin-3-yl, pyrrolidin-2-yl, 2-tetrahydrofuranyl, 3-tetrahydrofuranyl and 3-oxabicyclo[3.1.0]hexan-6-yl, wherein said $R^b$ is further optionally substituted.

In a ninth embodiment, and within certain aspects of the first, second, third or fourth embodiment, in Formula I or a subformula thereof, Y is absent or is selected from the group consisting of —C(═O)—, —N(H)C(═O)—, —N($R^a$)C(═O)— and —$S(O)_2$—.

In a tenth embodiment, and within certain aspects of the ninth embodiment, in Formula I or a subformula thereof, $R^2$ is selected from the group consisting of cycloprop-1-yl, cyclobut-1-yl, cyclopent-1-yl, pyrimidin-2-yl, pyrimidin-4-yl, pyrimidin-5-yl, pyridin-2-yl, pyridin-4-yl, pyridin-3-yl, pyridin-2-on-6-yl, pyridine-2-on-5-yl, pyridine-2-on-4-yl, pyridine-2-on-3-yl, cyclohex-1-yl, phenyl, 4,5-dihydrooxazol-2-yl, oxazol-2-yl, piperidin-4-yl, piperidin-3-yl, piperidin-2-yl, piperidin-1-yl, piperazin-1-yl, piperazin-2-yl, piperazin-3-yl, morpholin-2-yl, morpholin-3-yl, morpholin-4-yl, tetrahydropyran-4-yl, tetrahydropyran-2-yl, tetrahydropyran-3-yl, oxetan-3-yl, oxetan-2-yl, pyrazol-5-yl, pyrazol-1-yl, pyrazol-3-yl, pyrazol-4-yl, methyl, ethyl, propyl, isopropyl, butyl, iso-butyl, tert-butyl, pyrrolidin-3-yl, pyrrolidin-2-yl, 2-tetrahydrofuranyl, 3-tetrahydrofuranyl and 3-oxabicyclo[3.1.0]hexan-6-yl, and wherein $R^2$ is optionally substituted.

In an eleventh embodiment, and within certain aspects of the tenth embodiment, in Formula I or a subformula thereof, Y is —C(═O)—.

In a twelfth embodiment, and within certain aspects of the first, second, third, fourth or eight embodiment, in Formula I or a subformula thereof, in $R^2$, $R^b$ is selected from the group as set forth on FIG. 1-A and FIG. 1-B.

In a thirteenth embodiment, and within certain aspects of the first, second, third, fourth, or eighth embodiment, in Formula I or a subformula thereof, A is absent.

In a fourteenth embodiment, and within certain aspects of the first, second, third, fourth or eighth embodiment, in Formula I or a subformula thereof, A is present is selected from the group consisting of O—, —N(H)—, —N($R^d$)—, —$S(O)_2$—, —S(O)— and —S—.

In a fifteenth embodiment, and within certain aspects of the first, second, third, fourth or eighth embodiment, in Formula I or a subformula thereof, A is present and is selected from the group consisting of —$(X^d)_{0-1}$—N(H)C(═O)—, —$(X^d)_{0-1}$—N($R^d$)C(═O)—, —$X^d$—, —$(X^d)_{0-1}$—C(═O)N(H)—, —$(X^d)_{0-1}$—C(═O)N($R^d$)—, —$(X^d)_{0-1}$—C(═O)—, —C(═O)—$(X^d)_{0-1}$—, —$(X^d)_{0-1}$—OC(═O)—, —$(X^d)_{0-1}$C(═O)O— and wherein the $X^d$ group in A is selected from the group consisting of $C_{1-6}$ alkylene, $C_{2-6}$ alkenylene $C_{1-6}$ heteroalkylene, 6-10 membered arylene and a 5-10 membered heteroarylene comprising 1 to 3 heteroatoms selected from N, O and S, wherein said $X^d$ is optionally substituted.

In a sixteenth embodiment and within certain aspects of the fifteenth embodiment, in Formula I or a subformula thereof, $X^d$ group in A is selected from the group consisting of phenylene, pyridylene, pyrimidinylene, pyridazinylene, pyrazinylene, and wherein said $X^d$ is optionally substituted.

In a seventeenth embodiment, and within certain aspects of the sixteenth embodiment, in Formula I or a subformula thereof, A is selected from the group consisting of:

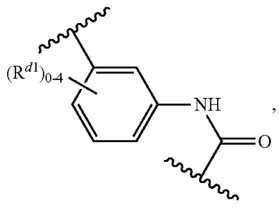
,
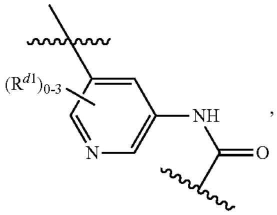
,

-continued

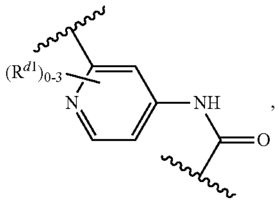
,
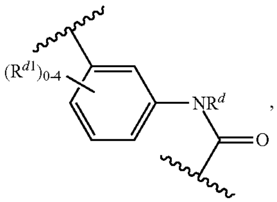
,
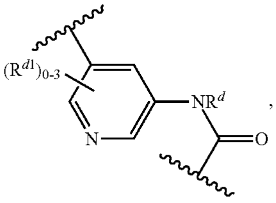
,
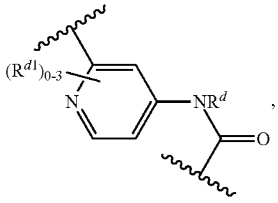
,
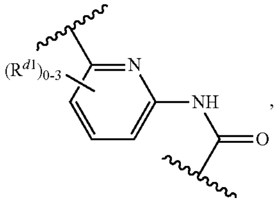
,
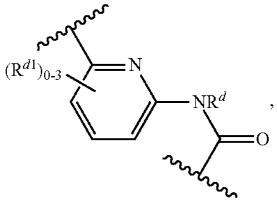
,
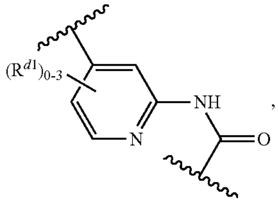
,
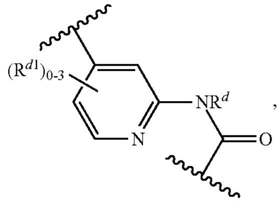
,
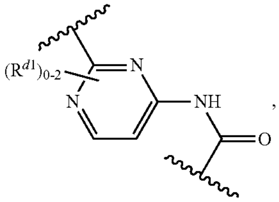
,
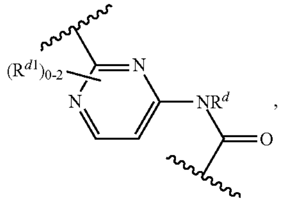
,
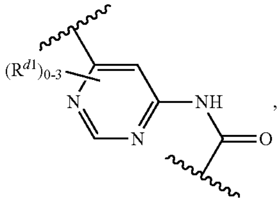
,
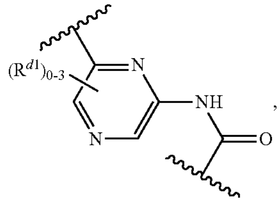
,
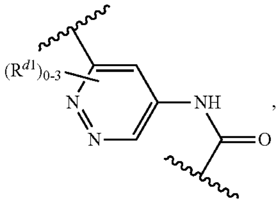
,
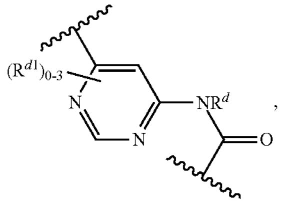
,
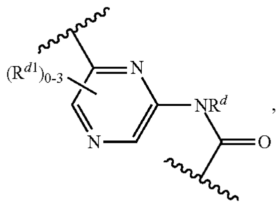
,
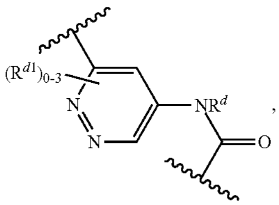
, -continued

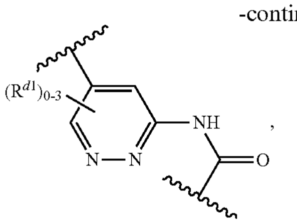
,
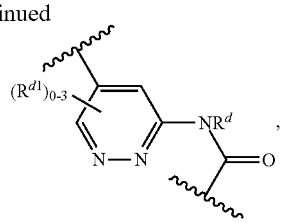
,
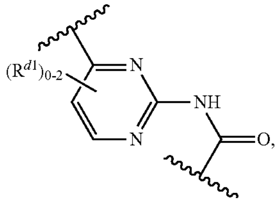
, and
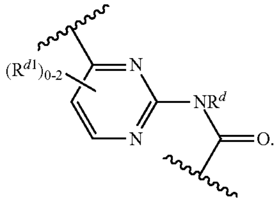
.

In an eighteen embodiment, and within certain aspects of the first, second, third, fourth or eighth embodiments, in Formula I or a subformula thereof, A is selected from the group consisting of:

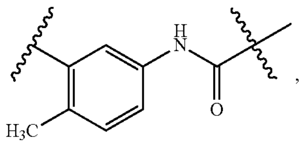
,
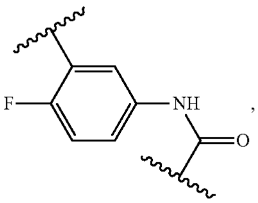
,
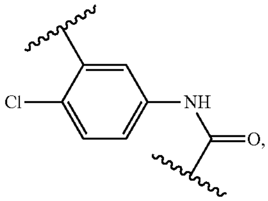
,
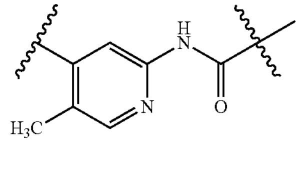
and
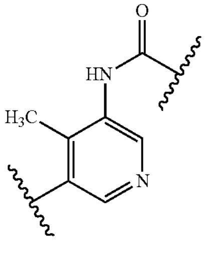
.

In a nineteenth embodiment, and within certain aspects of the first, second, thirteenth, fourteenth or fifteenth embodiment in Formula I or a subformula thereof, B is selected from the group consisting of phenyl, pyridin-2-yl, pyridin-3-yl, pyridin-4-yl, pyrrolidin-1-yl, pyrrolidin-2-yl, pyrrolidin-3-yl, pyrazol-1-yl, pyrazol-3-yl, pyrazol-4-yl, pyrazol-5-yl, thiazol-2-yl, thiazol-4-yl, thiazol-5-yl, pyridin-4-on-3-yl, pyridin-4-on-2-yl, pyridin-4-on-1-yl, pyridin-2-on-1-yl, pyridin-2-on-3-yl, pyridin-2-on-4-yl, pyrrol-1-yl, pyrrol-3-yl, pyrrol-4-yl, pyridazin-3-yl, pyridazin-4-yl, pyridazin-5-yl, pyrazin-2-yl, cyclohexyl, cyclobutyl, cyclopropyl, cyclopentyl, morpholin-4-yl, morpholin-2-yl, morpholin-3-yl, piperazin-1-yl, piperazin-2-yl, cyclopentyl, piperidin-1-yl, piperidin-4-yl, piperidin-2-yl, piperidin-3-yl, indol-5-yl, indol-4-yl, indol-3-yl, indol-2-yl, pyridimdin-5-yl, pyridimdin-4-yl, pyrimidin-2-yl, indazol-3-yl, indazol-4-yl, indazol-5-yl, indazol-6-yl, indazol-7-yl, indolin-2-on-4-yl, indolin-2-on-5-yl, indolin-2-on-6-yl, indolin-2-on-7-yl, tetrahydropyran-4-yl, tetrahydropyran-3-yl, tetrahydropyran-2-yl, tetrahydrofuran-2-yl, tetrahydrofuran-3-yl, tetrahydrofuran-4-yl, wherein B is optionally substituted and wherein any two substituent located on adjacent atoms of B are optionally combined to form an optionally substituted 5 to 7 membered heterocyclic ring comprising 1 to 3 heteroatoms selected from N, O and S.

In a twentieth embodiment, and within certain aspects of the first, second, fourteenth or fifteenth embodiments, in Formula I or a subformula thereof, B is selected from the group consisting of $C_{1-6}$ alkyl $C_{1-6}$ haloalkyl and $C_{1-6}$ heteroalkyl, wherein B is optionally substituted.

Within certain aspects of the twentieth embodiment, in Formula I or a subformula thereof, B is selected from the group consisting of methyl, ethyl, propyl, isopropyl, butyl, isobutyl, tert-butyl, wherein B is optionally substituted.

In a twenty-first embodiment, and with certain aspect of the first, second, third, fourth, eighth, or sixteenth embodiment, in Formula I or a subformula thereof, B is selected from the group consisting of phenyl, pyridin-2-yl, pyridin-3-yl and pyridin-4-yl, wherein the B is optionally substituted with 1 to 3 $R^{B1}$ substitutents selected from the group consisting of $C_{1-6}$ alkyl, $C_{1-6}$ haloalkyl, $C_{1-6}$ heteroalkyl, $C_{1-6}$ alkoxy, $C_{1-6}$ alkylamino, $C_{1-6}$ dialkylamino, F, Cl, Br, I, —OH, —$NH_2$, —SH, —$(X^e)_{0-1}$—CN, —$(X^e)_{0-1}$—$NO_2$, —$(X^e)_{0-1}$—$N_3$, —$(X^e)_{0-1}$—N(H)$R^e$, —$(X^e)_{0-1}$—N$(R^e)_2$, —$(X^e)_{0-1}$—S$R^e$, —$(X^e)_{0-1}$—C(O)$R^e$, —$(X^e)_{0-1}$—S(O)$_2R^e$, —$(X^e)_{0-1}$—S(O)$R^e$, —$(X^e)_{0-1}$—C(═O)O$R^e$, —$(X^e)_{0-1}$—C(═O)N(H)$R^e$, —$(X^e)_{0-1}$—C(═O)N$(R^e)R^e$, —$(X^e)_{0-1}$—N(H)C(═O)$R^e$ and —$(X^e)_{0-1}$—N$(R^e)$C(═O)$R^e$, and wherein any two substituent located on adjacent atoms of B are optionally combined to form an optionally substituted 5 to 7 membered heterocyclic ring comprising 1 to 3 heteroatoms selected from N, O and S.

In a twenty-second embodiment, and within certain aspects of the first, second, third fourth, eighth or eighteenth embodiment, in Formula I or a subformula thereof, B is selected from the group consisting of

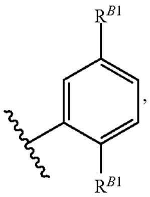
,
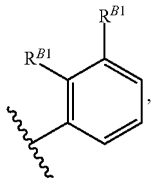
,
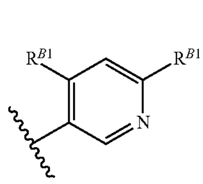
,
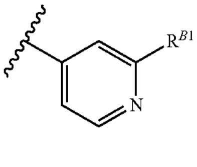
,
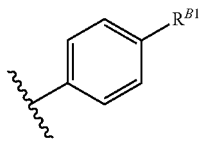
,

-continued

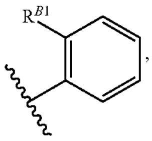,
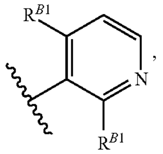,
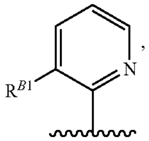,
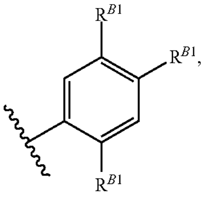
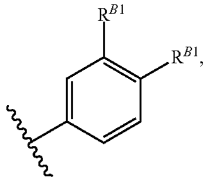
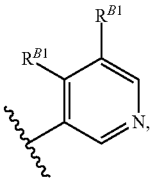
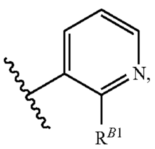
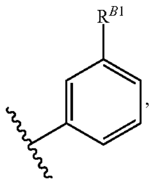,
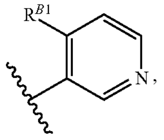

-continued

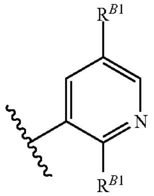
and
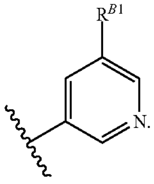

In a twenty-third embodiment, and within certain aspects of the first, second, third, fourth or eighth embodiments, in Formula I or a subformula thereof, B is selected from the group as set forth on FIG. 2-A, FIG. 2-B, FIG. 2-C, FIG. 2-D and FIG. 2-E.

In a twenty-fourth embodiment, and within certain aspects of the first, second, third, fourth or eighth embodiments, in Formula I or a subformula thereof, $R^5$ is $(X^c)$—$R^c$, wherein $X^c$ is absent or is selected from the group consisting of $C_{1-6}$ alkylene, —N(H)—, —N($R^{xc}$)—, —O—, —$S(O)_2$—, and $R^c$ is selected from the group consisting of hydrogen, F, Cl, Br, I, —CN, —$NO_2$, —$CF_3$, —$OCF_3$, —$SF_5$, $C_{1-6}$ alkyl, $C_{1-6}$ heteroalkyl, piperidin-1-yl, piperidin-2-yl, piperidin-3-yl, piperidin-4-yl, cyclopropyl, cyclopentyl, phenyl, pyrdin-2-yl, pyridin-3-yl, pyridine-4-yl, pyrazol-3-yl, pyrazol-4-yl, pyrazol-5-yl, thiazol-2-yl, thiazol-3-yl, thiazol-5-yl, piperazin-1yl, piperazin-2-yl, pyrrolidin-1-yl, pyrrolidin-2-yl, pyrroldin-3-yl, tetrahydrofuran-2-yl, tetrahydrofuran-3-yl, wherein $R^c$ is optionally substituted.

Particular compounds of Formula I include the following compounds in Table 1 and Table 1b:

TABLE 1

| No. | Structure | Name |
|---|---|---|
| 1 | 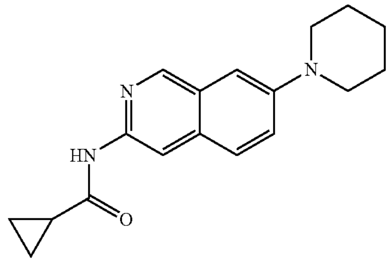 [SMILES: O=C(Nc1cc2ccc(N3CCCCC3)cc2cn1)C1CC1] | N-(7-(piperidin-1-yl)isoquinolin-3-yl)cyclopropanecarboxamide |
| 2 | 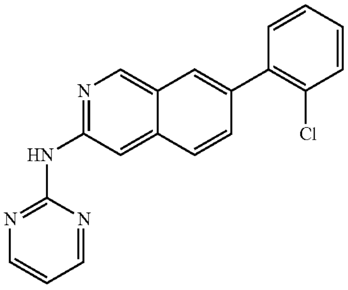 [SMILES: Clc1ccccc1-c1ccc2cc(Nc3ncccn3)ncc2c1] | 7-(2-chlorophenyl)-N-(pyrimidin-2-yl)isoquinolin-3-amine |

TABLE 1-continued

| No. | Structure | Name |
| --- | --- | --- |
| 3 | 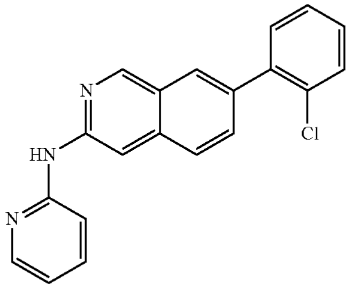 [SMILES: Clc1ccccc1-c1ccc2cc(Nc3ccccn3)ncc2c1] | 7-(2-chlorophenyl)-N-(pyridin-2-yl) isoquinolin-3-amine |
| 4 | 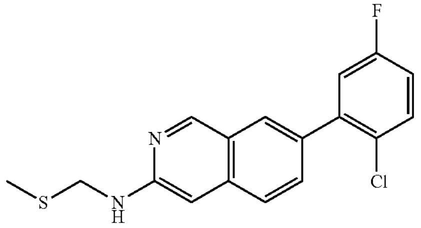 [SMILES: CSCNc1cc2ccc(-c3cc(F)ccc3Cl)cc2cn1] | 7-(2-chloro-5-fluorophenyl)-N-(methylthiomethyl)isoquinolin-3-amine |
| 5 | 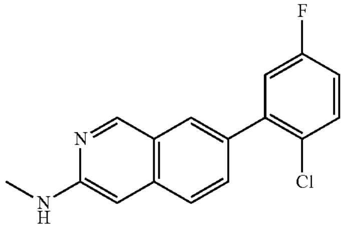 [SMILES: CNc1cc2ccc(-c3cc(F)ccc3Cl)cc2cn1] | 7-(2-chloro-5-fluorophenyl)-N-methylisoquinolin-3-amine |
| 6 | 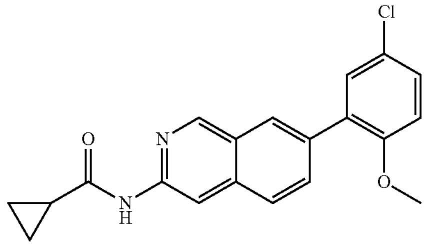 | N-(7-(5-chloro-2-methoxyphenyl) isoquinolin-3-yl)cyclopropanecarboxamide |
| 7 | 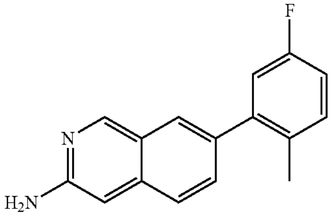 [SMILES: Cc1ccc(F)cc1-c1ccc2cc(N)ncc2c1] | 7-(5-fluoro-2-methylphenyl)isoquinolin-3-amine |
| 8 | 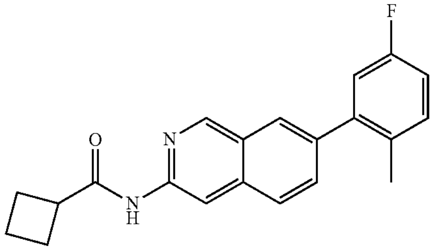 [SMILES: Cc1ccc(F)cc1-c1ccc2cc(NC(=O)C3CCC3)ncc2c1] | N-(7-(5-fluoro-2-methylphenyl) isoquinolin-3-yl)cyclobutanecarboxamide |

TABLE 1-continued
| No. | Structure | Name |
|---|---|---|
| 9 | 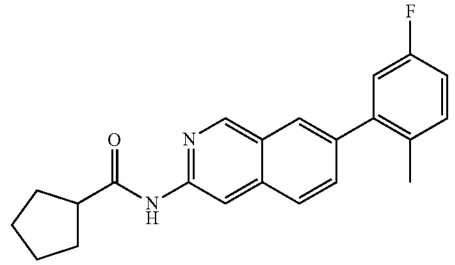 [SMILES: Cc1ccc(F)cc1-c1ccc2cc(NC(=O)C3CCCC3)ncc2c1] | N-(7-(5-fluoro-2-methylphenyl) isoquinolin-3-yl)cyclopentanecarboxamide |
| 10 | 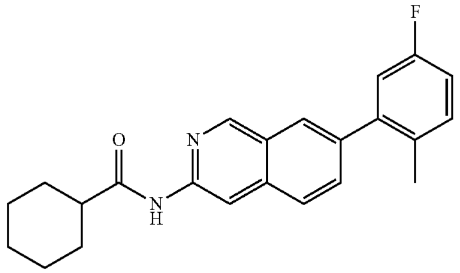 [SMILES: Cc1ccc(F)cc1-c1ccc2cc(NC(=O)C3CCCCC3)ncc2c1] | N-(7-(5-fluoro-2-methylphenyl) isoquinolin-3-yl)cyclohexanecarboxamide |
| 11 | 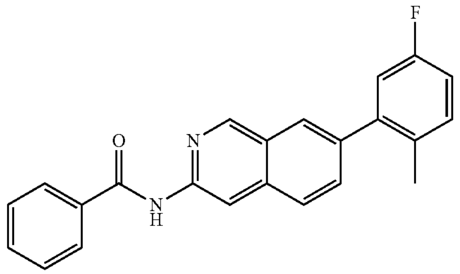 [SMILES: Cc1ccc(F)cc1-c1ccc2cc(NC(=O)c3ccccc3)ncc2c1] | N-(7-(5-fluoro-2-methylphenyl) isoquinolin-3-yl)benzamide |
| 12 | 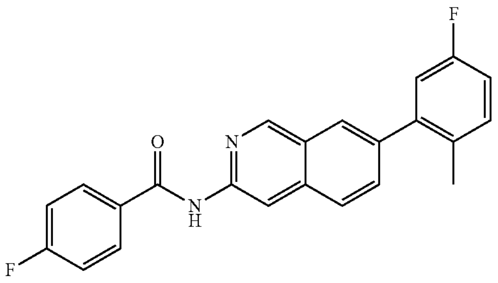 [SMILES: Cc1ccc(F)cc1-c1ccc2cc(NC(=O)c3ccc(F)cc3)ncc2c1] | 4-fluoro-N-(7-(5-fluoro-2-methylphenyl) isoquinolin-3-yl)benzamide |
| 13 | 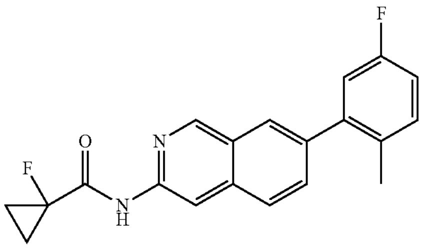 [SMILES: Cc1ccc(F)cc1-c1ccc2cc(NC(=O)C3(F)CC3)ncc2c1] | 1-fluoro-N-(7-(5-fluoro-2-methylphenyl) isoquinolin-3-yl)cyclopropanecarboxamide |

TABLE 1-continued

| No. | Structure | Name |
|---|---|---|
| 14 | 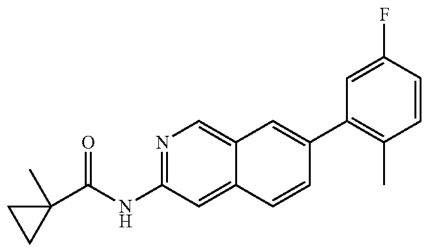 | N-(7-(5-fluoro-2-methylphenyl) isoquinolin-3-yl)-1-methylcyclopropanecarboxamide |
| 15 | 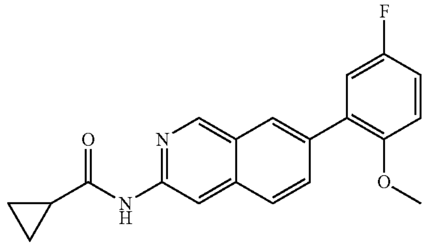 | 2-fluoro-N-(7-(5-fluoro-2-methylphenyl) isoquinolin-3-yl)cyclopropanecarboxamide |
| 16 | 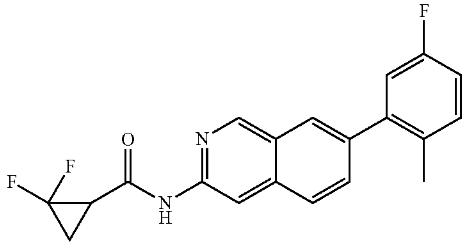 [SMILES: Cc1ccc(F)cc1-c1ccc2cc(NC(=O)C3CC3(F)F)ncc2c1] | 2,2-difluoro-N-(7-(5-fluoro-2-methylphenyl) isoquinolin-3-yl)cyclopropanecarboxamide |
| 17 | 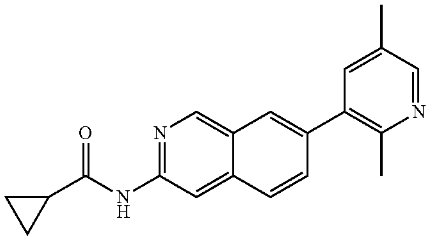 | N-(7-(2,5-dimethylpyridin-3-yl) isoquinolin-3-yl)cyclopropanecarboxamide |
| 18 | 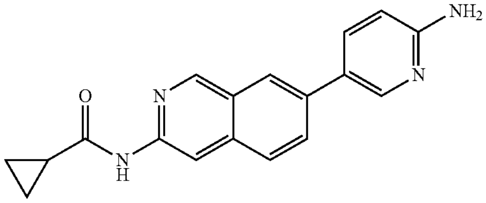 [SMILES: Nc1ccc(-c2ccc3cc(NC(=O)C4CC4)ncc3c2)cn1] | N-(7-(6-aminopyridin-3-yl) isoquinolin-3-yl)cyclopropanecarboxamide |
| 19 | 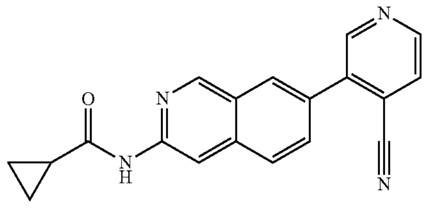 [SMILES: N#Cc1ccncc1-c1ccc2cc(NC(=O)C3CC3)ncc2c1] | N-(7-(4-cyanopyridin-3-yl) isoquinolin-3-yl)cyclopropanecarboxamide |

TABLE 1-continued

| No. | Structure | Name |
|---|---|---|
| 20 | 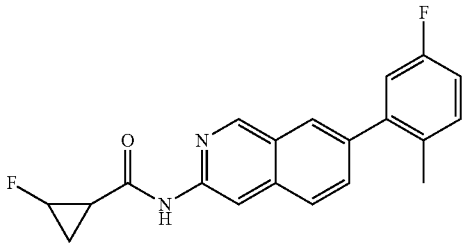 [SMILES: Cc1ccc(F)cc1-c1ccc2cc(NC(=O)C3CC3F)ncc2c1] | 2-fluoro-N-(7-(5-fluoro-2-methylphenyl) isoquinolin-3-yl)cyclopropanecarboxamide |
| 21 | 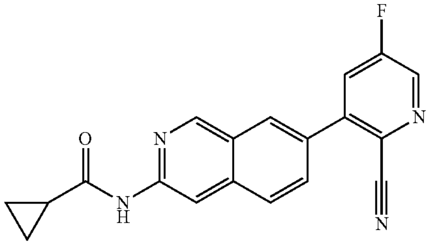 [SMILES: N#Cc1ncc(F)cc1-c1ccc2cc(NC(=O)C3CC3)ncc2c1] | N-(7-(2-cyano-5-fluoropyridin-3-yl) isoquinolin-3-yl)cyclopropanecarboxamide |
| 22 | 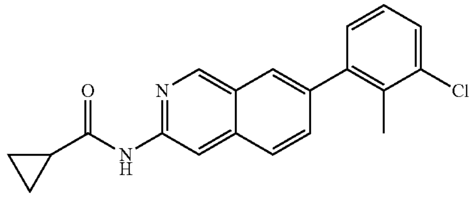 [SMILES: Cc1c(Cl)cccc1-c1ccc2cc(NC(=O)C3CC3)ncc2c1] | N-(7-(3-chloro-2-methylphenyl) isoquinolin-3-yl)cyclopropanecarboxamide |
| 23 | 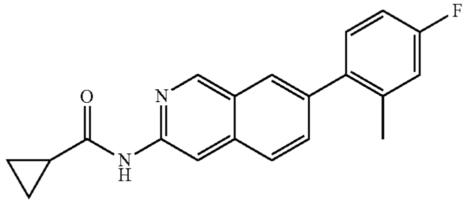 [SMILES: Cc1cc(F)ccc1-c1ccc2cc(NC(=O)C3CC3)ncc2c1] | N-(7-(4-fluoro-2-methylphenyl) isoquinolin-3-yl)cyclopropanecarboxamide |
| 24 | 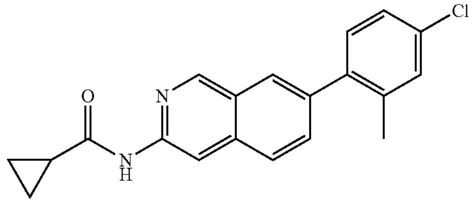 | N-(7-(4-chloro-2-methylphenyl) isoquinolin-3-yl)cyclopropanecarboxamide |
| 25 | 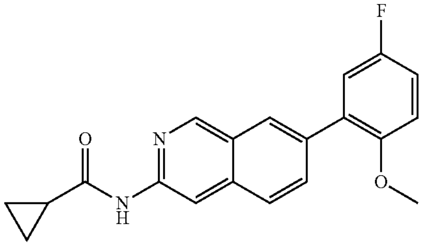 | N-(7-(5-fluoro-2-methoxyphenyl) isoquinolin-3-yl)cyclopropanecarboxamide |

TABLE 1-continued

| No. | Structure | Name |
|---|---|---|
| 26 | 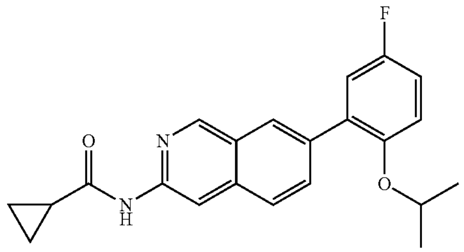 [SMILES: CC(C)Oc1ccc(F)cc1-c1ccc2cc(NC(=O)C3CC3)ncc2c1] | N-(7-(5-fluoro-2-isopropoxyphenyl) isoquinolin-3-ypcyclopropanecarboxamide |
| 27 | 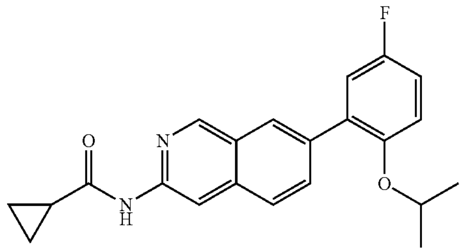 [SMILES: CC(C)Oc1ccc(F)cc1-c1ccc2cc(NC(=O)C3CC3)ncc2c1] | N-(7-(4-methylpyridin-3-yl) isoquinolin-3-yl)cyclopropanecarboxamide |
| 28 | 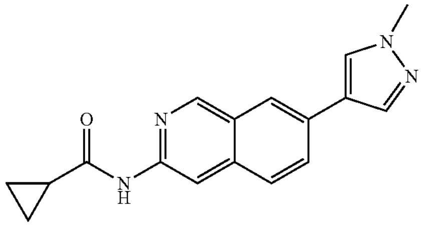 [SMILES: Cn1cc(-c2ccc3cc(NC(=O)C4CC4)ncc3c2)cn1] | N-(7-(1-methyl-1H-pyrazol-4-yl) isoquinolin-3-yl)cyclopropanecarboxamide |
| 29 | 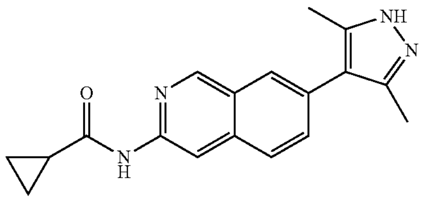 [SMILES: Cc1n[nH]c(C)c1-c1ccc2cc(NC(=O)C3CC3)ncc2c1] | N-(7-(3,5-dimethyl-1H-pyrazol-4-yl) isoquinolin-3-yl)cyclopropanecarboxamide |
| 30 | 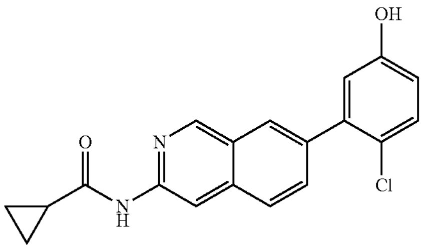 [SMILES: O=C(Nc1cc2ccc(-c3cc(O)ccc3Cl)cc2cn1)C1CC1] | N-(7-(2-chloro-5-hydroxyphenyl) isoquinolin-3-yl)cyclopropanecarboxamide |
| 31 | 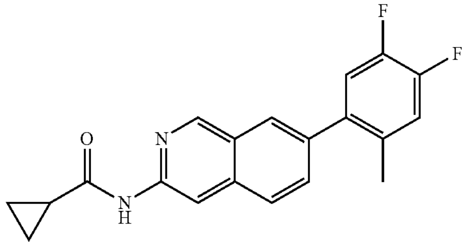 [SMILES: Cc1cc(F)c(F)cc1-c1ccc2cc(NC(=O)C3CC3)ncc2c1] | N-(7-(4,5-difluoro-2-methylphenyl) isoquinolin-3-yl)cyclopropanecarboxamide |

TABLE 1-continued

| No. | Structure | Name |
| --- | --- | --- |
| 32 | 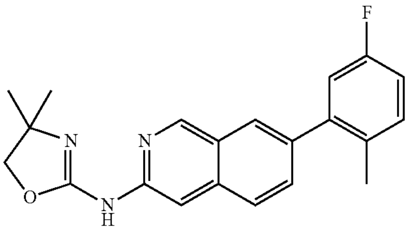 [SMILES: Cc1ccc(F)cc1-c1ccc2cc(NC3=NC(C)(C)CO3)ncc2c1] | N-(7-(5-fluoro-2-methylphenyl) isoquinolin-3-yl)-4,4-dimethyl-4,5-dihydrooxazol-2-amine |
| 33 | 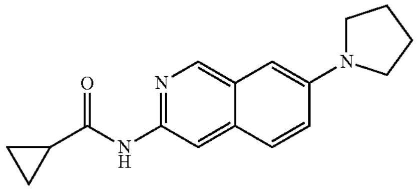 | N-(7-(pyrrolidin-1-yl)isoquinolin-3-yl)cyclopropanecarboxamide |
| 34 | 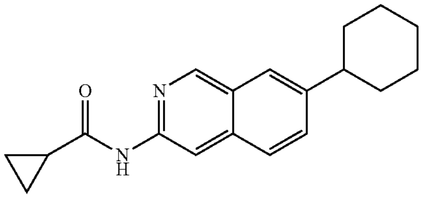 [SMILES: O=C(Nc1cc2ccc(C3CCCCC3)cc2cn1)C1CC1] | N-(7-cyclohexylisoquinolin-3-yl) cyclopropanecarboxamide |
| 35 | 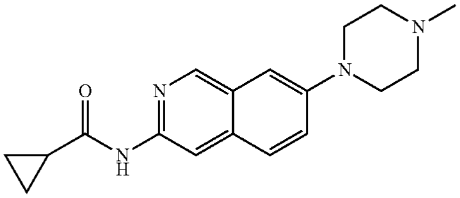 [SMILES: CN1CCN(c2ccc3cc(NC(=O)C4CC4)ncc3c2)CC1] | N-(7-(4-methylpiperazin-1-yl) isoquinolin-3-yl)cyclopropanecarboxamide |
| 36 | 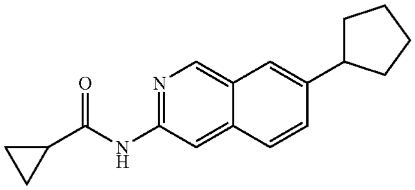 [SMILES: O=C(Nc1cc2ccc(C3CCCC3)cc2cn1)C1CC1] | N-(7-cyclopentylisoquinolin-3-yl) cyclopropanecarboxamide |
| 37 | 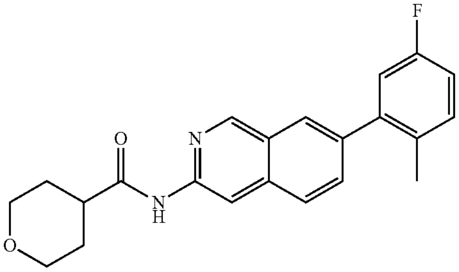 [SMILES: Cc1ccc(F)cc1-c1ccc2cc(NC(=O)C3CCOCC3)ncc2c1] | N-(7-(5-fluoro-2-methylphenyl) isoquinolin-3-yl)tetrahydro-2H-pyran-4-carboxamide |
| 38 | 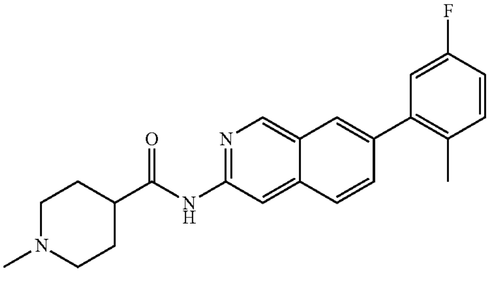 [SMILES: Cc1ccc(F)cc1-c1ccc2cc(NC(=O)C3CCN(C)CC3)ncc2c1] | N-(7-(5-fluoro-2-methylphenyl) isoquinolin-3-yl)-1-methylpiperidine-4-carboxamide |

TABLE 1-continued

| No. | Structure | Name |
|---|---|---|
| 39 | 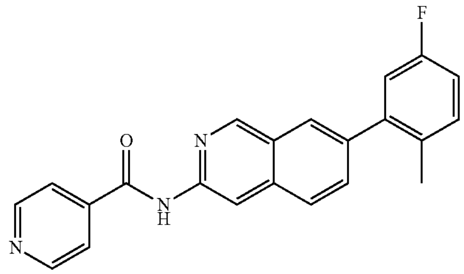 [SMILES: Cc1ccc(F)cc1-c1ccc2cc(NC(=O)c3ccncc3)ncc2c1] | N-(7-(5-fluoro-2-methylphenyl) isoquinolin-3-yl)isonicotinamide |
| 40 | 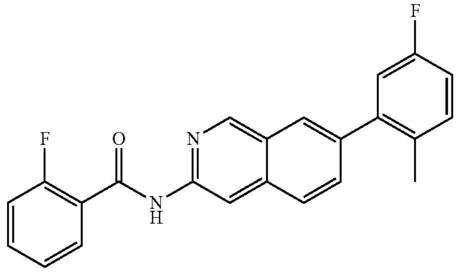 [SMILES: Cc1ccc(F)cc1-c1ccc2cc(NC(=O)c3ccccc3F)ncc2c1] | 2-fluoro-N-(7-(5-fluoro-2-methylphenyl) isoquinolin-3-yl)benzamide |
| 41 | 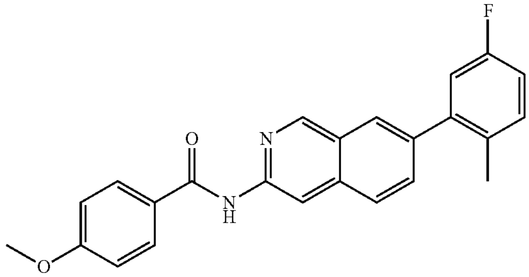 [SMILES: COc1ccc(C(=O)Nc2cc3ccc(-c4cc(F)ccc4C)cc3cn2)cc1] | N-(7-(5-fluoro-2-methylphenyl) isoquinolin-3-yl)-4-methoxybenzamide |
| 42 | 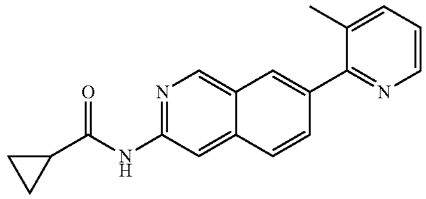 [SMILES: Cc1cccnc1-c1ccc2cc(NC(=O)C3CC3)ncc2c1] | N-(7-(3-methylpyridin-2-yl) isoquinolin-3-yl)cyclopropanecarboxamide |
| 43 | 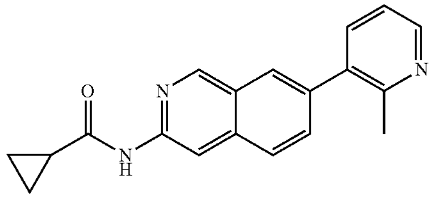 [SMILES: Cc1ncccc1-c1ccc2cc(NC(=O)C3CC3)ncc2c1] | N-(7-(2-methylpyridin-3-yl) isoquinolin-3-yl)cyclopropanecarboxamide |
| 44 | 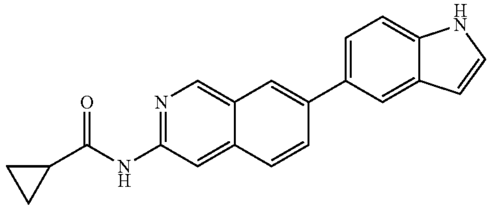 [SMILES: O=C(Nc1cc2ccc(-c3ccc4[nH]ccc4c3)cc2cn1)C1CC1] | N-(7-(1H-indol-5-yl)isoquinolin-3-yl)cyclopropanecarboxamide |

TABLE 1-continued

| No. | Structure | Name |
|---|---|---|
| 45 | 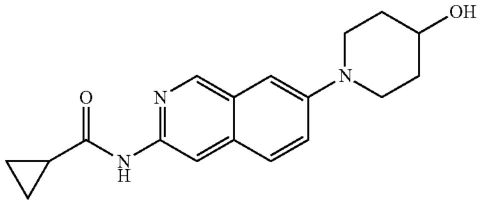 [SMILES: O=C(Nc1cc2ccc(N3CCC(O)CC3)cc2cn1)C1CC1] | N-(7-(4-hydroxypiperidin-1-yl) isoquinolin-3-yl)cyclopropanecarboxamide |
| 46 | 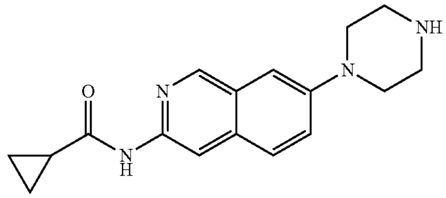 [SMILES: O=C(Nc1cc2ccc(N3CCNCC3)cc2cn1)C1CC1] | N-(7-(piperazin-1-yl)isoquinolin-3-yl)cyclopropanecarboxamide |
| 47 | 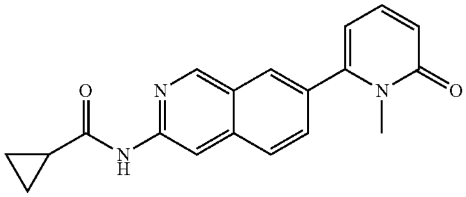 [SMILES: Cn1c(-c2ccc3cc(NC(=O)C4CC4)ncc3c2)cccc1=O] | N-(7-(1-methyl-6-oxo-1,6-dihydropyridin-2-yl) isoquinolin-3-yl) cyclopropanecarboxamide |
| 48 | 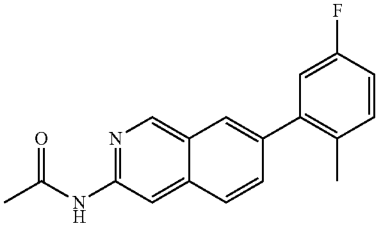 [SMILES: CC(=O)Nc1cc2ccc(-c3cc(F)ccc3C)cc2cn1] | N-(7-(5-fluoro-2-methylphenyl) isoquinolin-3-yl)acetamide |
| 49 | 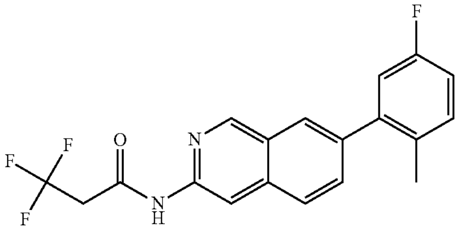 [SMILES: Cc1ccc(F)cc1-c1ccc2cc(NC(=O)CC(F)(F)F)ncc2c1] | 3,3,3-trifluoro-N-(7-(5-fluoro-2-methylphenyl)isoquinolin-3-yl)propanamide |
| 50 | 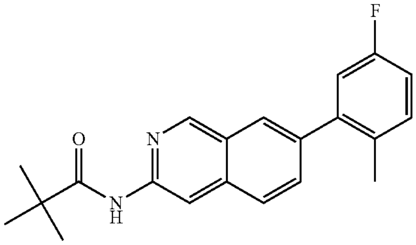 [SMILES: Cc1ccc(F)cc1-c1ccc2cc(NC(=O)C(C)(C)C)ncc2c1] | N-(7-(5-fluoro-2-methylphenyl) isoquinolin-3-yl)pivalamide |
| 51 | 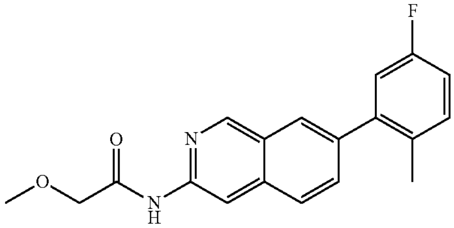 [SMILES: COCC(=O)Nc1cc2ccc(-c3cc(F)ccc3C)cc2cn1] | N-(7-(5-fluoro-2-methylphenyl) isoquinolin-3-yl)-2-methoxyacetamide |

TABLE 1-continued

| No. | Structure | Name |
| --- | --- | --- |
| 52 | 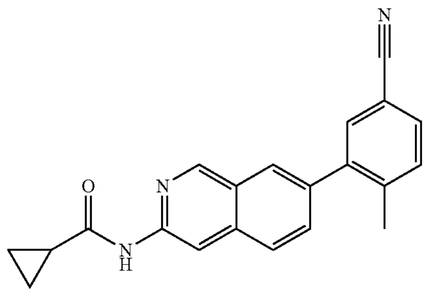 [SMILES: Cc1ccc(C#N)cc1-c1ccc2cc(NC(=O)C3CC3)ncc2c1] | N-(7-(5-cyano-2-methylphenyl) isoquinolin-3-yl)cyclopropanecarboxamide |
| 53 | 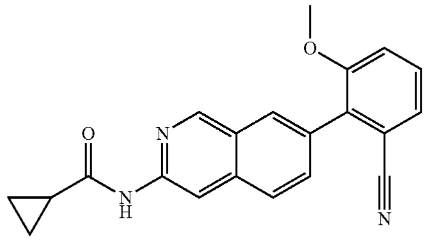 [SMILES: COc1cccc(C#N)c1-c1ccc2cc(NC(=O)C3CC3)ncc2c1] | N-(7-(2-cyano-6-methoxyphenyl) isoquinolin-3-yl)cyclopropanecarboxamide |
| 54 | 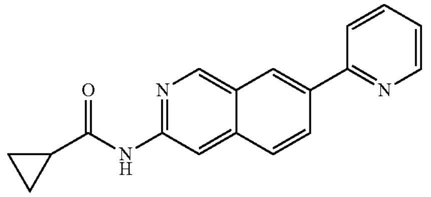 | N-(7-(pyridin-2-yl)isoquinolin-3-yl) cyclopropanecarboxamide |
| 55 | 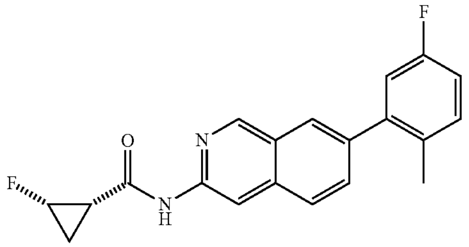 | (1S,2S)-2-fluoro-N-(7-(5-fluoro-2-methylphenyl)isoquinolin-3-yl) cyclopropanecarboxamide |
| 56 | 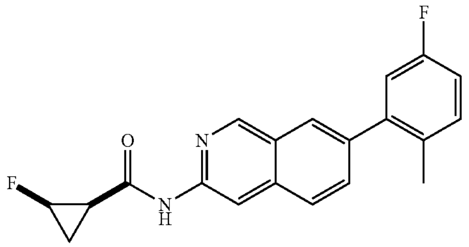 | (1R,2R)-2-fluoro-N-(7-(5-fluoro-2-methylphenyl)isoquinolin-3-yl) cyclopropanecarboxamidede |
| 57 | 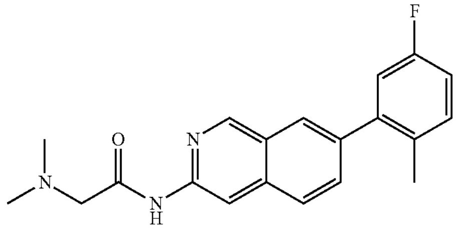 [SMILES: Cc1ccc(F)cc1-c1ccc2cc(NC(=O)CN(C)C)ncc2c1] | 2-(dimethylamino)-N-(7-(5-fluoro-2-methylphenyl)isoquinolin-3-yl)acetamide |

TABLE 1-continued
| No. | Structure | Name |
|---|---|---|
| 58 | 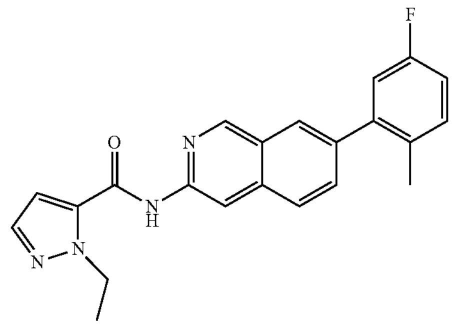 [SMILES: CCn1nccc1C(=O)Nc1cc2ccc(-c3cc(F)ccc3C)cc2cn1] | 1-ethyl-N-(7-(5-fluoro-2-methylphenyl) isoquinolin-3-yl)-1H-pyrazole-5-carboxamide |
| 59 | 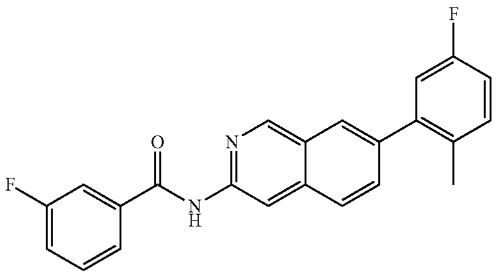 [SMILES: Cc1ccc(F)cc1-c1ccc2cc(NC(=O)c3cccc(F)c3)ncc2c1] | 3-fluoro-N-(7-(5-fluoro-2-methylphenyl) isoquinolin-3-yl)benzamide |
| 60 | 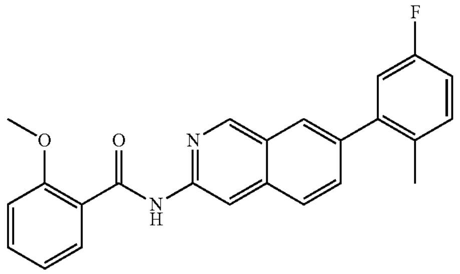 [SMILES: COc1ccccc1C(=O)Nc1cc2ccc(-c3cc(F)ccc3C)cc2cn1] | N-(7-(5-fluoro-2-methylphenyl) isoquinolin-3-yl)-2-methoxybenzamide |
| 61 | 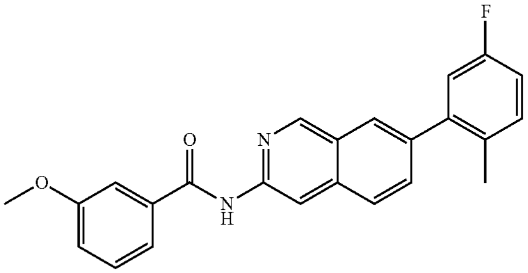 [SMILES: COc1cccc(C(=O)Nc2cc3ccc(-c4cc(F)ccc4C)cc3cn2)c1] | N-(7-(5-fluoro-2-methylphenyl) isoquinolin-3-yl)-3-methoxybenzamide |
| 62 | 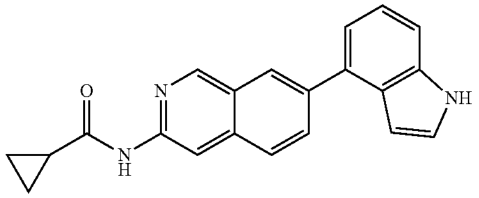 [SMILES: O=C(Nc1cc2ccc(-c3cccc4[nH]ccc34)cc2cn1)C1CC1] | N-(7-(1H-indol-4-yl)isoquinolin-3-yl)cyclopropanecarboxamide |

TABLE 1-continued

| No. | Structure | Name |
|---|---|---|
| 63 | 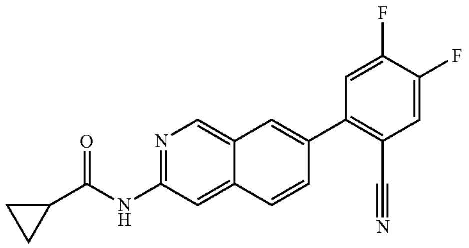 [SMILES: N#Cc1cc(F)c(F)cc1-c1ccc2cc(NC(=O)C3CC3)ncc2c1] | N-(7-(2-cyano-4,5-difluorophenyl) isoquinolin-3-yl)cyclopropanecarboxamide |
| 64 | 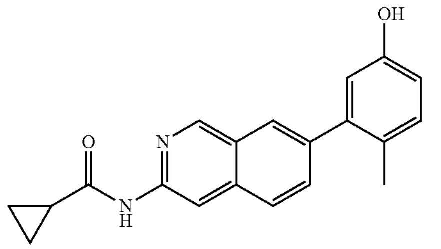 [SMILES: Cc1ccc(O)cc1-c1ccc2cc(NC(=O)C3CC3)ncc2c1] | N-(7-(5-hydroxy-2-methylphenyl) isoquinolin-3-yl)cyclopropanecarboxamide |
| 65 | 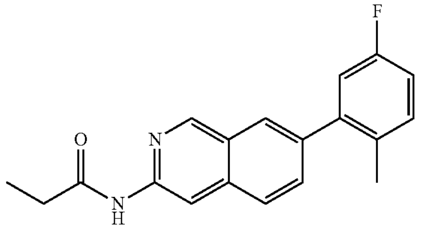 [SMILES: CCC(=O)Nc1cc2ccc(-c3cc(F)ccc3C)cc2cn1] | N-(7-(5-fluoro-2-methylphenyl) isoquinolin-3-yl)propionamide |
| 66 | 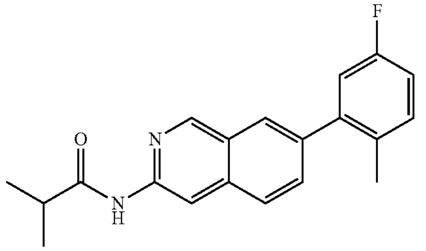 [SMILES: Cc1ccc(F)cc1-c1ccc2cc(NC(=O)C(C)C)ncc2c1] | N-(7-(5-fluoro-2-methylphenyl) isoquinolin-3-yl)isobutyramide |
| 67 | 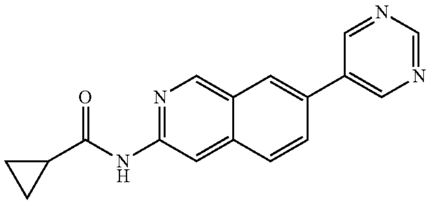 [SMILES: O=C(Nc1cc2ccc(-c3cncnc3)cc2cn1)C1CC1] | N-(7-(pyrimidin-5-yl)isoquinolin-3-yl)cyclopropanecarboxamide |
| 68 | 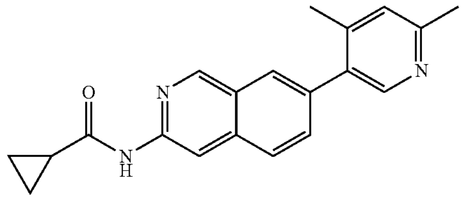 [SMILES: Cc1cc(C)c(-c2ccc3cc(NC(=O)C4CC4)ncc3c2)cn1] | N-(7-(4,6-dimethylpyridin-3-yl) isoquinolin-3-yl)cyclopropanecarboxamide |

TABLE 1-continued

| No. | Structure | Name |
|---|---|---|
| 69 | 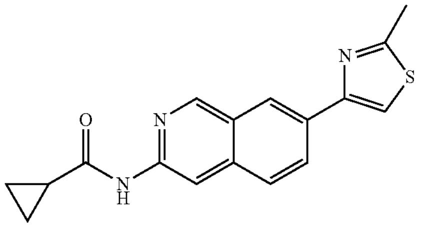 [SMILES: Cc1nc(-c2ccc3cc(NC(=O)C4CC4)ncc3c2)cs1] | N-(7-(2-methylthiazol-4-yl)isoquinolin-3-yl)cyclopropanecarboxamide |
| 70 | 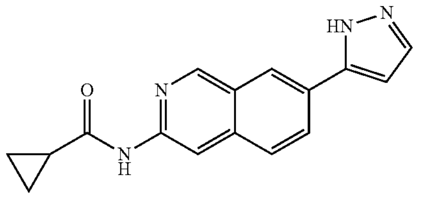 [SMILES: O=C(Nc1cc2ccc(-c3ccn[nH]3)cc2cn1)C1CC1] | N-(7-(1H-pyrazol-5-yl)isoquinolin-3-yl)cyclopropanecarboxamide |
| 71 | 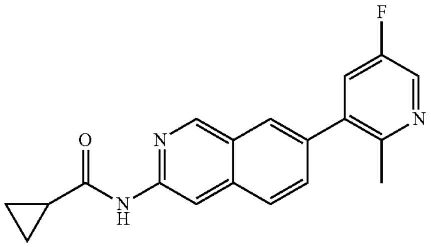 | N-(7-(5-fluoro-2-methylpyridin-3-yl)isoquinolin-3-yl)cyclopropanecarboxamide |
| 72 | 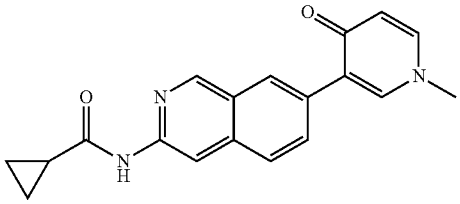 [SMILES: Cn1ccc(=O)c(-c2ccc3cc(NC(=O)C4CC4)ncc3c2)c1] | N-(7-(1-methyl-4-oxo-1,4-dihydropyridin-3-yl)isoquinolin-3-yl) cyclopropanecarboxamide |
| 73 | 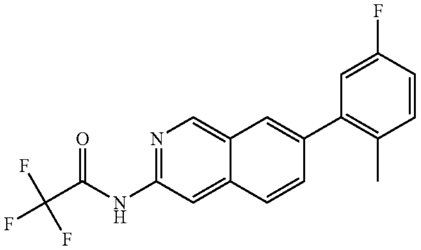 [SMILES: Cc1ccc(F)cc1-c1ccc2cc(NC(=O)C(F)(F)F)ncc2c1] | 2,2,2-trifluoro-N-(7-(5-fluoro-2-methylphenyl)isoquinolin-3-yl)acetamide |
| 74 | 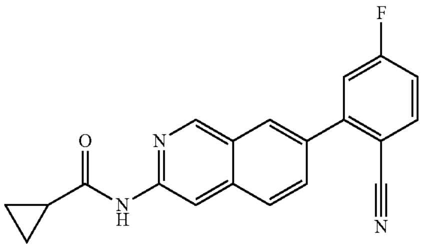 [SMILES: N#Cc1ccc(F)cc1-c1ccc2cc(NC(=O)C3CC3)ncc2c1] | N-(7-(2-cyano-5-fluorophenyl) isoquinolin-3-yl)cyclopropanecarboxamide |

TABLE 1-continued

| No. | Structure | Name |
|---|---|---|
| 75 | 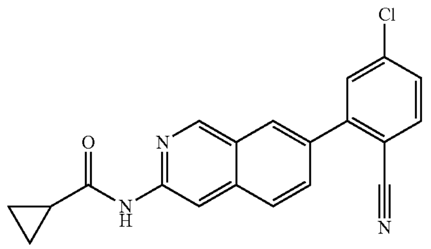 | N-(7-(5-chloro-2-cyanophenyl) isoquinolin-3-yl)cyclopropanecarboxamide |
| 76 | 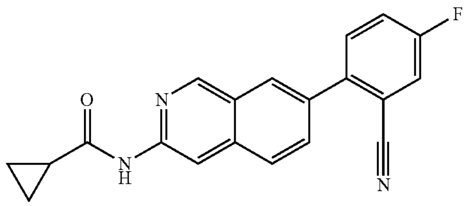 [SMILES: N#Cc1cc(F)ccc1-c1ccc2cc(NC(=O)C3CC3)ncc2c1] | N-(7-(2-cyano-4-fluorophenyl) isoquinolin-3-yl)cyclopropanecarboxamide |
| 77 | 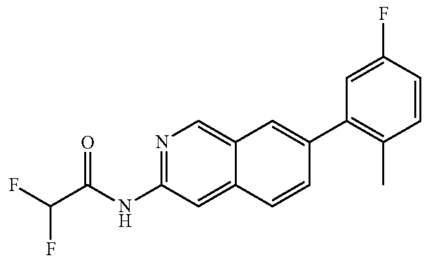 [SMILES: Cc1ccc(F)cc1-c1ccc2cc(NC(=O)C(F)F)ncc2c1] | 2,2-difluoro-N-(7-(5-fluoro-2-methylphenyl) isoquinolin-3-yl)acetamide |
| 78 | 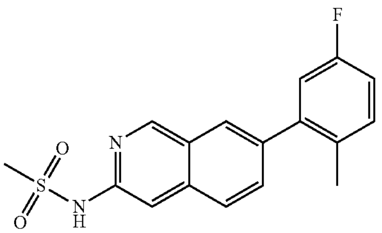 [SMILES: Cc1ccc(F)cc1-c1ccc2cc(NS(C)(=O)=O)ncc2c1] | N-(7-(5-fluoro-2-methylphenyl) isoquinolin-3-yl)methanesulfonamide |
| 79 | 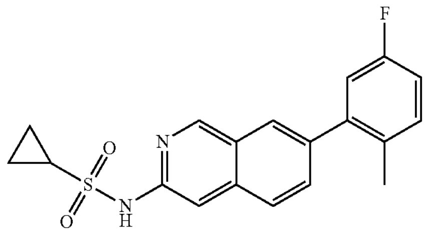 [SMILES: Cc1ccc(F)cc1-c1ccc2cc(NS(=O)(=O)C3CC3)ncc2c1] | N-(7-(5-fluoro-2-methylphenyl) isoquinolin-3-yl)cyclopropanesulfonamide |
| 80 | 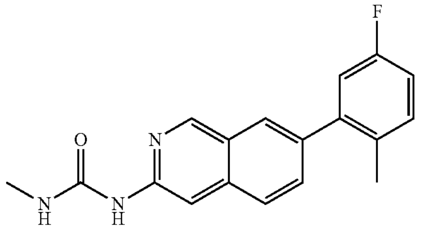 [SMILES: CNC(=O)Nc1cc2ccc(-c3cc(F)ccc3C)cc2cn1] | 1-(7-(5-fluoro-2-methylphenyl) isoquinolin-3-yl)-3-methylurea |
| 81 | 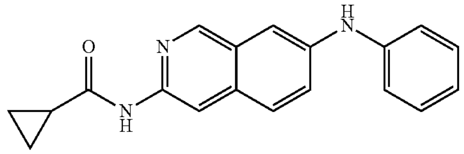 [SMILES: O=C(Nc1cc2ccc(Nc3ccccc3)cc2cn1)C1CC1] | N-(7-(phenylamino)isoquinolin-3-yl)cyclopropanecarboxamide |

TABLE 1-continued

| No. | Structure | Name |
| --- | --- | --- |
| 82 | 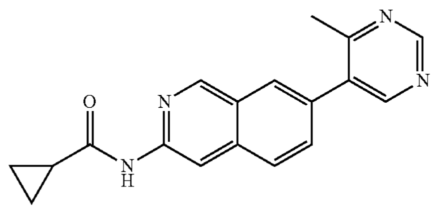 | N-(7-(4-methylpyrimidin-5-yl) isoquinolin-3-yl)cyclopropanecarboxamide |
| 83 | 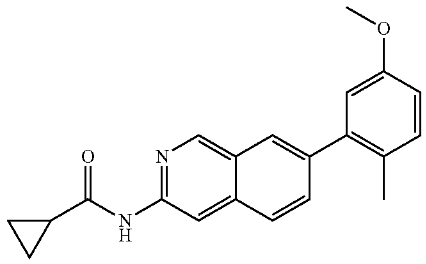 [SMILES: COc1ccc(C)c(-c2ccc3cc(NC(=O)C4CC4)ncc3c2)c1] | N-(7-(5-methoxy-2-methylphenyl) isoquinolin-3-yl)cyclopropanecarboxamide |
| 84 | 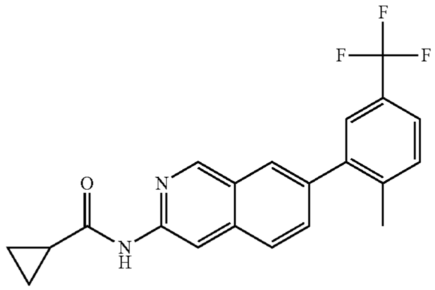 [SMILES: Cc1ccc(C(F)(F)F)cc1-c1ccc2cc(NC(=O)C3CC3)ncc2c1] | N-(7-(2-methyl-5-(trifluoromethyl) phenyl)isoquinolin-3-yl) cyclopropanecarboxamide |
| 85 | 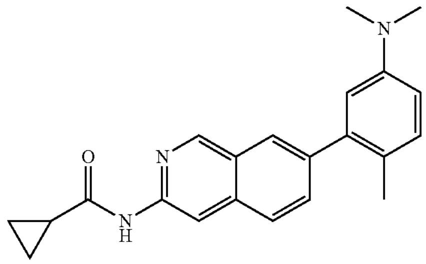 [SMILES: Cc1ccc(N(C)C)cc1-c1ccc2cc(NC(=O)C3CC3)ncc2c1] | N-(7-(5-(dimethylamino)-2-methyl phenyl)isoquinolin-3-yl) cyclopropanecarboxamide |
| 86 | 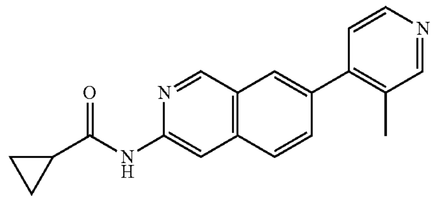 [SMILES: Cc1cnccc1-c1ccc2cc(NC(=O)C3CC3)ncc2c1] | N-(7-(3-methylpyridin-4-yl) isoquinolin-3-yl)cyclopropanecarboxamide |
| 87 | 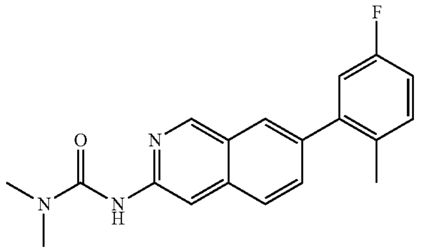 [SMILES: Cc1ccc(F)cc1-c1ccc2cc(NC(=O)N(C)C)ncc2c1] | 3-(7-(5-fluoro-2-methylphenyl) isoquinolin-3-yl)-1,1-dimethylurea |

TABLE 1-continued

| No. | Structure | Name |
|---|---|---|
| 88 | 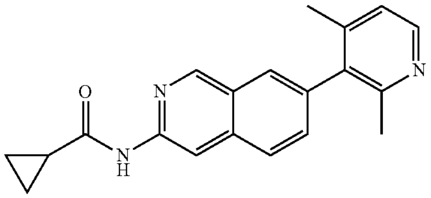 [SMILES: Cc1ccnc(C)c1-c1ccc2cc(NC(=O)C3CC3)ncc2c1] | N-(7-(2,4-dimethylpyridin-3-yl) isoquinolin-3-yl)cyclopropanecarboxamide |
| 89 | 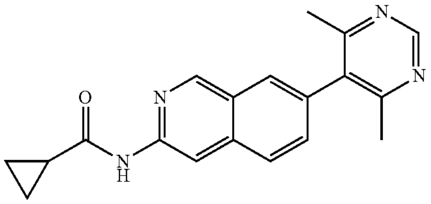 [SMILES: Cc1ncnc(C)c1-c1ccc2cc(NC(=O)C3CC3)ncc2c1] | N-(7-(4,6-dimethylpyrimidin-5-yl) isoquinolin-3-yl)cyclopropanecarboxamide |
| 90 | 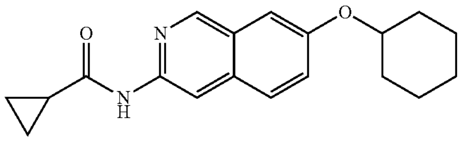 [SMILES: O=C(Nc1cc2ccc(OC3CCCCC3)cc2cn1)C1CC1] | N-(7-(cyclohexyloxy)isoquinolin-3-yl)cyclopropanecarboxamide |
| 91 | 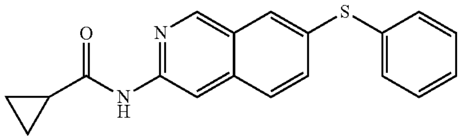 [SMILES: O=C(Nc1cc2ccc(Sc3ccccc3)cc2cn1)C1CC1] | N-(7-(phenylthio)isoquinolin-3-yl) cyclopropanecarboxamide |
| 92 | 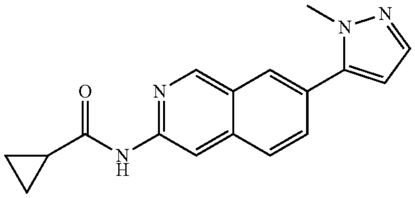 [SMILES: Cn1nccc1-c1ccc2cc(NC(=O)C3CC3)ncc2c1] | N-(7-(1-methyl-1H-pyrazol-5-yl) isoquinolin-3-yl)cyclopropanecarboxamide |
| 93 | 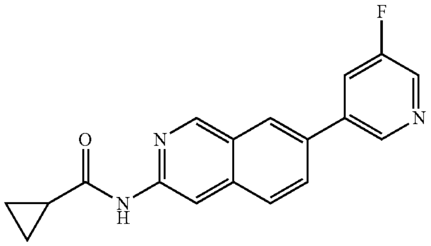 [SMILES: O=C(Nc1cc2ccc(-c3cncc(F)c3)cc2cn1)C1CC1] | N-(7-(5-fluoropyridin-3-yl) isoquinolin-3-yl)cyclopropanecarboxamide |
| 94 | 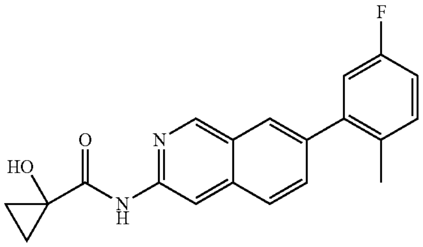 | N-(7-(5-fluoro-2-methylphenyl) isoquinolin-3-yl)-1-hydroxycyclopropanecarboxamide |

TABLE 1-continued

| No. | Structure | Name |
|---|---|---|
| 95 | 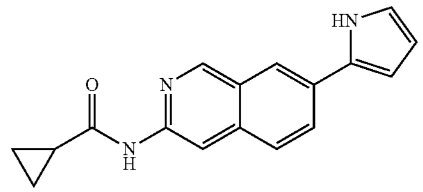 [SMILES: O=C(Nc1cc2ccc(-c3ccc[nH]3)cc2cn1)C1CC1] | N-(7-(1H-pyrrol-2-yl)isoquinolin-3-yl)cyclopropanecarboxamide |
| 96 | 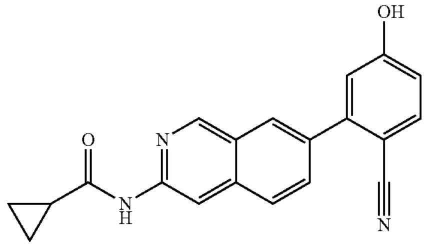 [SMILES: N#Cc1ccc(O)cc1-c1ccc2cc(NC(=O)C3CC3)ncc2c1] | N-(7-(2-cyano-5-hydroxyphenyl) isoquinolin-3-yl)cyclopropanecarboxamide |
| 97 | 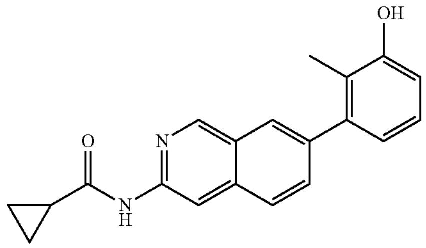 [SMILES: Cc1c(O)cccc1-c1ccc2cc(NC(=O)C3CC3)ncc2c1] | N-(7-(3-hydroxy-2-methylphenyl) isoquinolin-3-yl)cyclopropanecarboxamide |
| 98 | 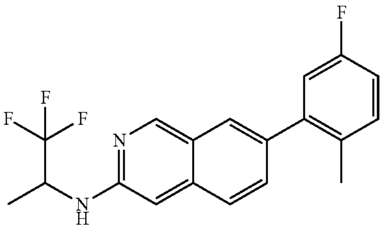 [SMILES: Cc1ccc(F)cc1-c1ccc2cc(NC(C)C(F)(F)F)ncc2c1] | 7-(5-fluoro-2-methylphenyl)-N-(1,1,1,-trifluoropropan-2-yl)isoquinolin-3-amine |
| 99 | 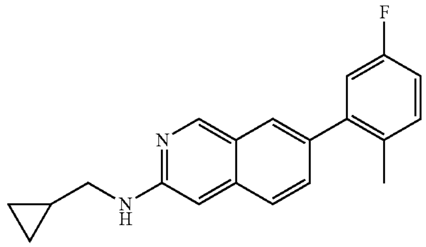 [SMILES: Cc1ccc(F)cc1-c1ccc2cc(NCC3CC3)ncc2c1] | N-(cyclopropylmethyl)-7-(5-fluoro-2-methylphenyl)isoquinolin-3-amine |
| 100 | 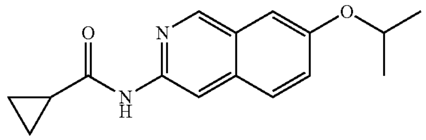 | N-(7-isopropoxyisoquinolin-3-yl) cyclopropanecarboxamide |
| 101 | 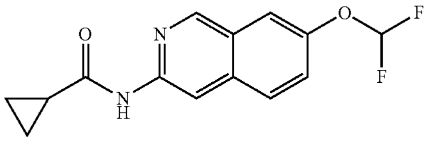 [SMILES: O=C(Nc1cc2ccc(OC(F)F)cc2cn1)C1CC1] | N-(7-(difluoromethoxy)isoquinolin-3-yl) cyclopropanecarboxamide |

TABLE 1-continued

| No. | Structure | Name |
| --- | --- | --- |
| 102 | 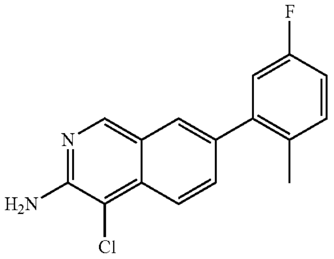 | 4-chloro-7-(5-fluoro-2-methylphenyl) isoquinolin-3-amine |
| 103 | 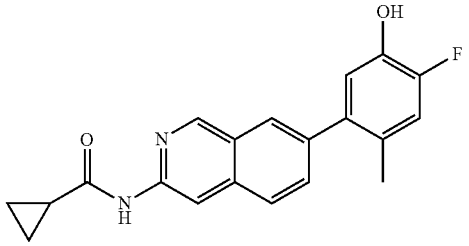 [SMILES: Cc1cc(F)c(O)cc1-c1ccc2cc(NC(=O)C3CC3)ncc2c1] | N-(7-(4-fluoro-5-hydroxy-2-methylphenyl) isoquinolin-3-yl)cyclopropanecarboxamide |
| 104 | 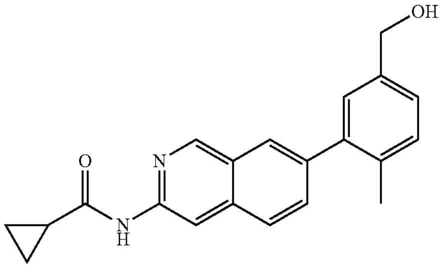 [SMILES: Cc1ccc(CO)cc1-c1ccc2cc(NC(=O)C3CC3)ncc2c1] | N-(7-(5-(hydroxymethyl)-2-methylphenyl) isoquinolin-3-yl)cyclopropanecarboxamide |
| 105 | 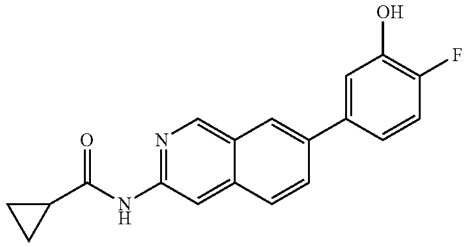 [SMILES: O=C(Nc1cc2ccc(-c3ccc(F)c(O)c3)cc2cn1)C1CC1] | N-(7-(4-fluoro-3-hydroxyphenyl) isoquinolin-3-yl)cyclopropanecarboxamide |
| 106 | 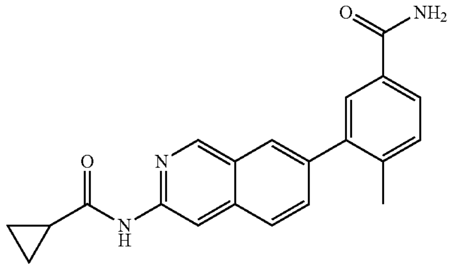 [SMILES: Cc1ccc(C(N)=O)cc1-c1ccc2cc(NC(=O)C3CC3)ncc2c1] | 3-(3-(cyclopropanecarboxamido) isoquinolin-7-yl)-4-methylbenzamide |
| 107 | 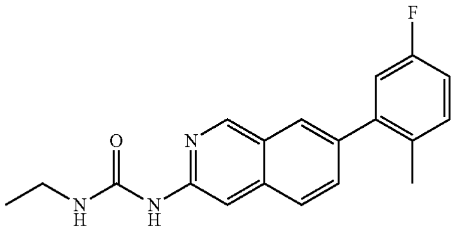 [SMILES: CCNC(=O)Nc1cc2ccc(-c3cc(F)ccc3C)cc2cn1] | 1-ethyl-3-(7-(5-fluoro-2-methylphenyl) isoquinolin-3-yl)urea |

TABLE 1-continued

| No. | Structure | Name |
| --- | --- | --- |
| 108 | 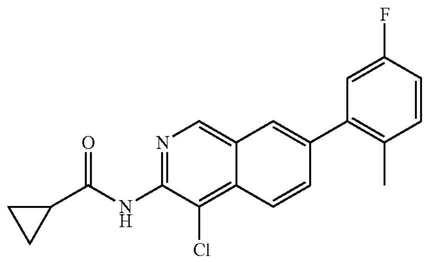 [SMILES: Cc1ccc(F)cc1-c1ccc2c(Cl)c(NC(=O)C3CC3)ncc2c1] | N-(4-chloro-7-(5-fluoro-2-methylphenyl) isoquinolin-3-yl)cyclopropanecarboxamide |
| 109 | 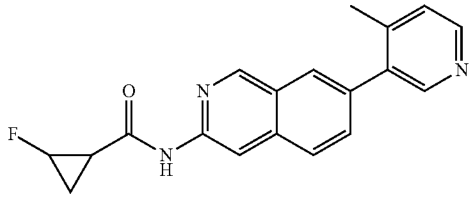 [SMILES: Cc1ccncc1-c1ccc2cc(NC(=O)C3CC3F)ncc2c1] | 2-fluoro-N-(7-(4-methylpyridin-3-yl)isoquinolin-3-yl)cyclopropanecarboxamide |
| 110 | 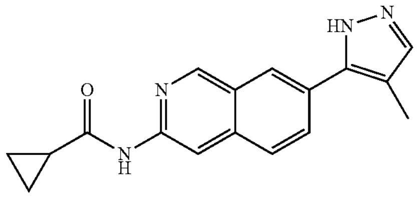 [SMILES: Cc1cn[nH]c1-c1ccc2cc(NC(=O)C3CC3)ncc2c1] | N-(7-(4-methyl-1H-pyrazol-5-yl) isoquinolin-3-yl)cyclopropanecarboxamide |
| 111 | 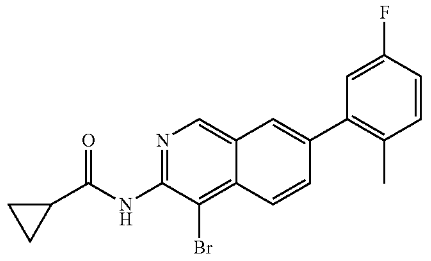 [SMILES: Cc1ccc(F)cc1-c1ccc2c(Br)c(NC(=O)C3CC3)ncc2c1] | N-(4-bromo-7-(5-fluoro-2-methylphenyl) isoquinolin-3-yl)cyclopropanecarboxamide |
| 112 | 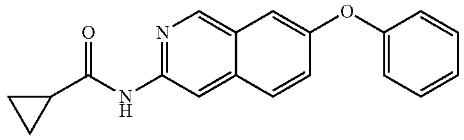 | N-(7-phenoxyisoquinolin-3-yl) cyclopropanecarboxamide |
| 113 | 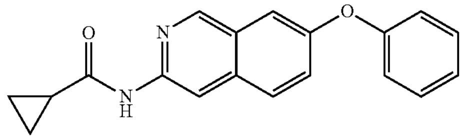 | N-(7-(2-chlorophenoxy)isoquinolin-3-yl)cyclopropanecarboxamide |
| 114 | 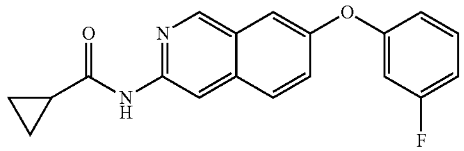 [SMILES: O=C(Nc1cc2ccc(Oc3cccc(F)c3)cc2cn1)C1CC1] | N-(7-(3-fluorophenoxy)isoquinolin-3-yl)cyclopropanecarboxamide |
| 115 | 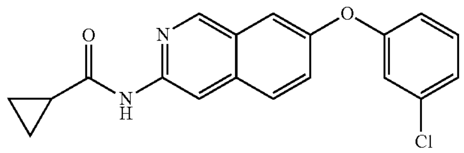 [SMILES: O=C(Nc1cc2ccc(Oc3cccc(Cl)c3)cc2cn1)C1CC1] | N-(7-(3-chlorophenoxy)isoquinolin-3-yl)cyclopropanecarboxamide |

TABLE 1-continued

| No. | Structure | Name |
|---|---|---|
| 116 | 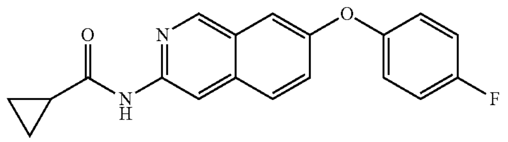 [SMILES: O=C(Nc1cc2ccc(Oc3ccc(F)cc3)cc2cn1)C1CC1] | N-(7-(4-fluorophenoxy)isoquinolin-3-yl)cyclopropanecarboxamide |
| 117 | 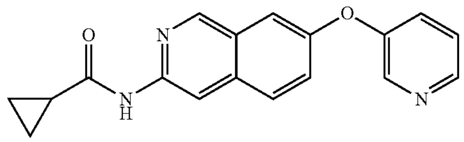 | N-(7-(pyridin-3-yloxy)isoquinolin-3-yl)cyclopropanecarboxamide |
| 118 | 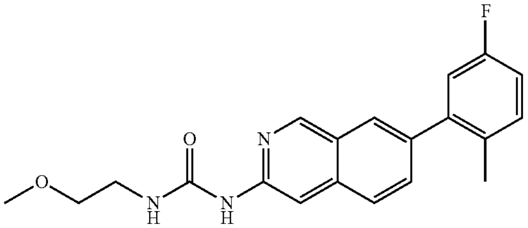 [SMILES: COCCNC(=O)Nc1cc2ccc(-c3cc(F)ccc3C)cc2cn1] | 1-(7-(5-fluoro-2-methylphenyl) isoquinolin-3-yl)-3-(2-methoxyethyl) urea |
| 119 | 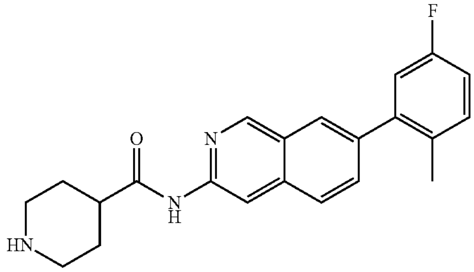 [SMILES: Cc1ccc(F)cc1-c1ccc2cc(NC(=O)C3CCNCC3)ncc2c1] | N-(7-(5-fluoro-2-methylphenyl) isoquinolin-3-yl)piperidine-4-carboxamide |
| 120 | 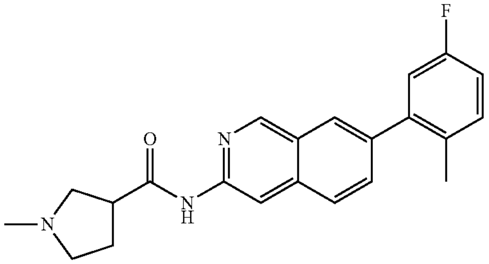 [SMILES: Cc1ccc(F)cc1-c1ccc2cc(NC(=O)C3CCN(C)C3)ncc2c1] | N-(7-(5-fluoro-2-methylphenyl) isoquinolin-3-yl)-1-methylpyrrolidine-3-carboxamide |
| 121 | 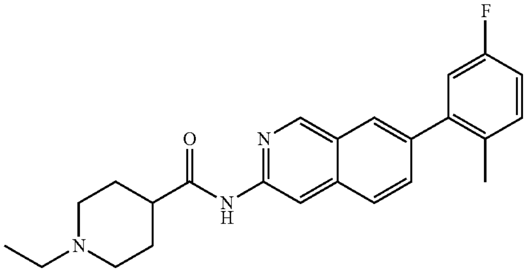 [SMILES: CCN1CCC(C(=O)Nc2cc3ccc(-c4cc(F)ccc4C)cc3cn2)CC1] | 1-ethyl-N-(7-(5-fluoro-2-methylphenyl) isoquinolin-3-yl)piperidine-4-carboxamide |
| 122 | 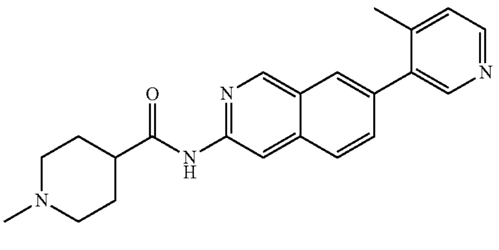 [SMILES: Cc1ccncc1-c1ccc2cc(NC(=O)C3CCN(C)CC3)ncc2c1] | 1-methyl-N-(7-(4-methylpyridin-3-yl)isoquinolin-3-yl)piperidine-4-carboxamide |

TABLE 1-continued

| No. | Structure | Name |
|---|---|---|
| 123 | 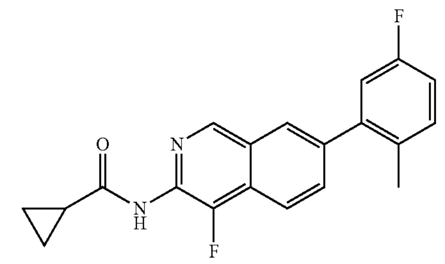 [SMILES: Cc1ccc(F)cc1-c1ccc2c(F)c(NC(=O)C3CC3)ncc2c1] | N-(4-fluoro-7-(5-fluoro-2-methylphenyl) isoquinolin-3-yl)cyclopropanecarboxamide |
| 124 | 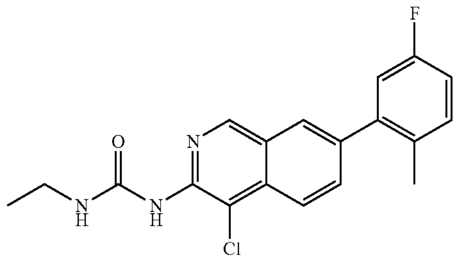 [SMILES: CCNC(=O)Nc1ncc2cc(-c3cc(F)ccc3C)ccc2c1Cl] | 1-(4-chloro-7-(5-fluoro-2-methylphenyl) isoquinolin-3-yl)-3-ethylurea |
| 125 | 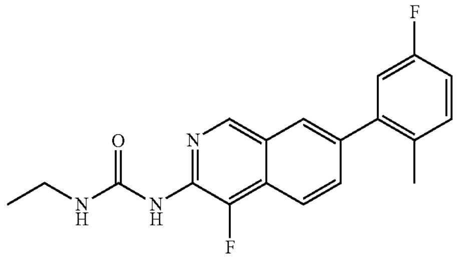 [SMILES: CCNC(=O)Nc1ncc2cc(-c3cc(F)ccc3C)ccc2c1F] | 1-ethyl-3-(4-fluoro-7-(5-fluoro-2-methylphenyl)isoquinolin-3-yl)urea |
| 126 | 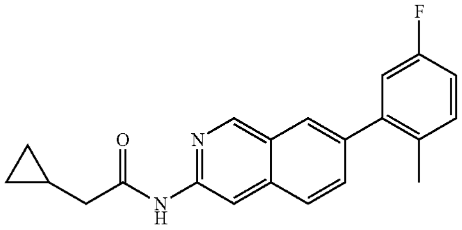 [SMILES: Cc1ccc(F)cc1-c1ccc2cc(NC(=O)CC3CC3)ncc2c1] | 2-cyclopropyl-N-(7-(5-fluoro-2-methylphenyl) isoquinolin-3-yl)acetamide |
| 127 | 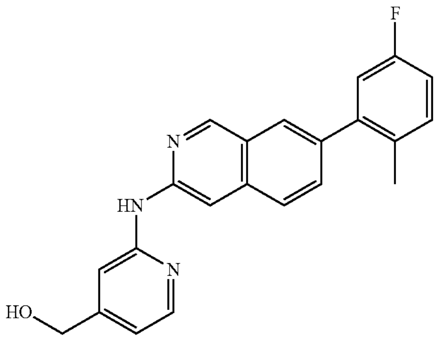 [SMILES: Cc1ccc(F)cc1-c1ccc2cc(Nc3cc(CO)ccn3)ncc2c1] | (2-(7-(5-fluoro-2-methylphenyl) isoquinolin-3-ylamino)pyridin-4-yl) methanol |
| 128 | 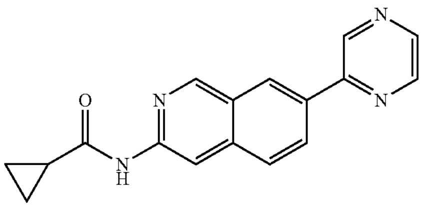 [SMILES: O=C(Nc1cc2ccc(-c3cnccn3)cc2cn1)C1CC1] | N-(7-(pyrazin-2-yl)isoquinolin-3-yl)cyclopropanecarboxamide |

TABLE 1-continued

| No. | Structure | Name |
|---|---|---|
| 129 | 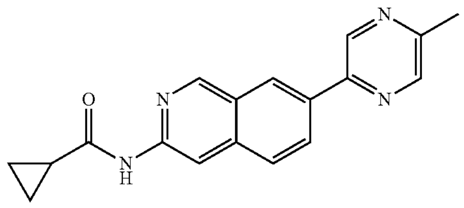 [SMILES: Cc1cnc(-c2ccc3cc(NC(=O)C4CC4)ncc3c2)cn1] | N-(7-(5-methylpyrazin-2-yl)isoquinolin-3-yl)cyclopropanecarboxamide |
| 130 | 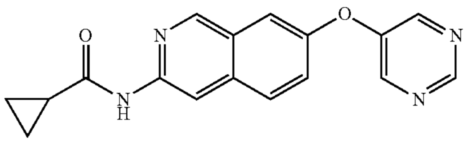 [SMILES: O=C(Nc1cc2ccc(Oc3cncnc3)cc2cn1)C1CC1] | N-(7-(pyrimidin-5-yloxy)isoquinolin-3-yl)cyclopropanecarboxamide |
| 131 | 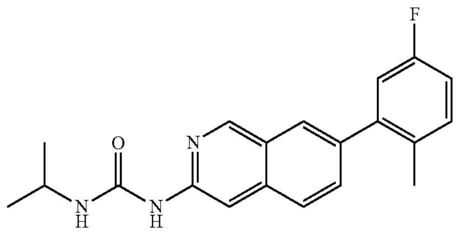 [SMILES: Cc1ccc(F)cc1-c1ccc2cc(NC(=O)NC(C)C)ncc2c1] | 1-(7-(5-fluoro-2-methylphenyl) isoquinolin-3-yl)-3-isopropylurea |
| 132 | 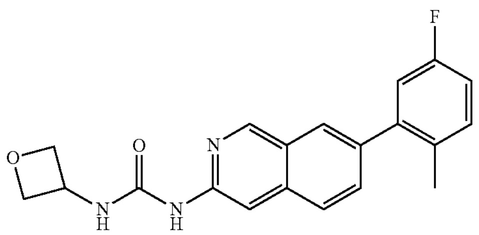 [SMILES: Cc1ccc(F)cc1-c1ccc2cc(NC(=O)NC3COC3)ncc2c1] | 1-(7-(5-fluoro-2-methylphenyl) isoquinolin-3-yl)-3-(oxetan-3-yl)urea |
| 133 | 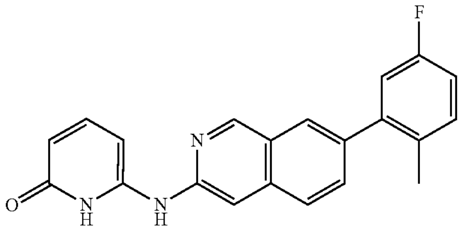 [SMILES: Cc1ccc(F)cc1-c1ccc2cc(Nc3cccc(=O)[nH]3)ncc2c1] | 6-(7-(5-fluoro-2-methylphenyl) isoquinolin-3-ylamino)pyridin-2(1H)-one |
| 134 | 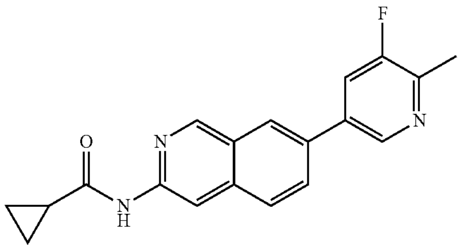 [SMILES: Cc1ncc(-c2ccc3cc(NC(=O)C4CC4)ncc3c2)cc1F] | N-(7-(5-fluoro-6-methylpyridin-3-yl)isoquinolin-3-yl)cyclopropanecarboxamide |

TABLE 1-continued

| No. | Structure | Name |
|---|---|---|
| 135 | 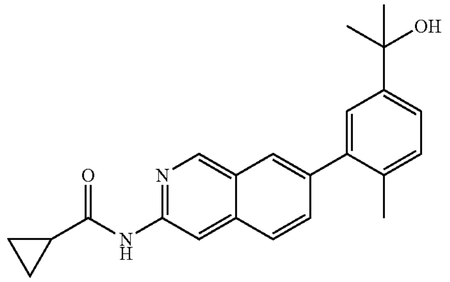 [SMILES: Cc1ccc(C(C)(C)O)cc1-c1ccc2cc(NC(=O)C3CC3)ncc2c1] | N-(7-(5-(2-hydroxypropan-2-yl)-2-methylphenyl)isoquinolin-3-yl) cyclopropanecarboxamide |
| 136 | 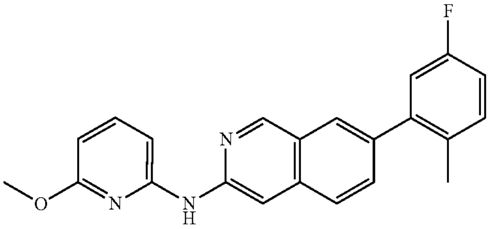 [SMILES: COc1cccc(Nc2cc3ccc(-c4cc(F)ccc4C)cc3cn2)n1] | 7-(5-fluoro-2-methylphenyl)-N-(6-methoxypyridin-2-yl)isoquinolin-3-amine |
| 137 | 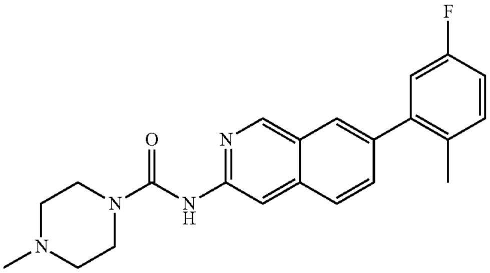 | N-(7-(5-fluoro-2-methylphenyl) isoquinolin-3-yl)-4-methylpiperazine-1-carboxamide |
| 138 | 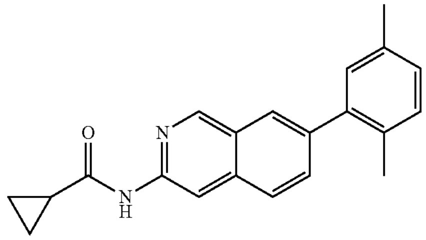 [SMILES: Cc1ccc(C)c(-c2ccc3cc(NC(=O)C4CC4)ncc3c2)c1] | N-(7-(2,5-dimethylphenyl)isoquinolin-3-yl)cyclopropanecarboxamide |
| 139 | 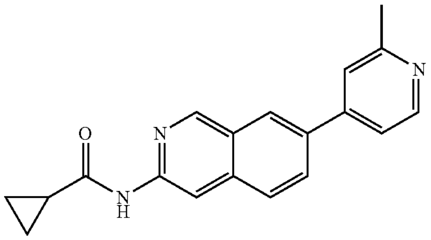 | N-(7-(2-methylpyridin-4-yl)isoquinolin-3-yl)cyclopropanecarboxamide |
| 140 | 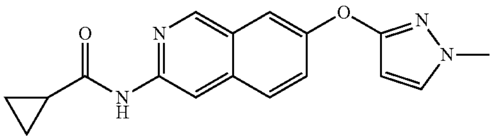 [SMILES: Cn1ccc(Oc2ccc3cc(NC(=O)C4CC4)ncc3c2)n1] | N-(7-( 1-methyl-1H-pyrazol-3-yloxy)isoquinolin-3-yl)cyclopropanecarboxamide |

TABLE 1-continued

| No. | Structure | Name |
|---|---|---|
| 141 | 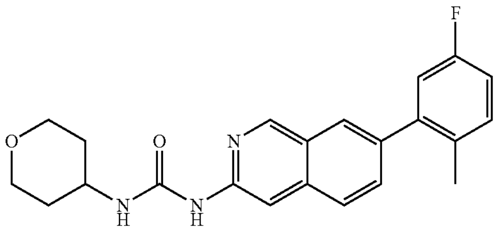 [SMILES: Cc1ccc(F)cc1-c1ccc2cc(NC(=O)NC3CCOCC3)ncc2c1] | 1-(7-(5-fluoro-2-methylphenyl)isoquinolin-3-yl)-3-(tetrahydro-2H-pyran-4-yl)urea |
| 142 | 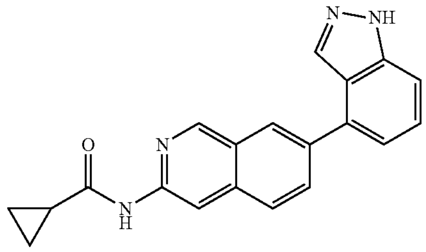 [SMILES: O=C(Nc1cc2ccc(-c3cccc4[nH]ncc34)cc2cn1)C1CC1] | N-(7-(1H-indazol-4-yl)isoquinolin-3-yl)cyclopropanecarboxamide |
| 143 | 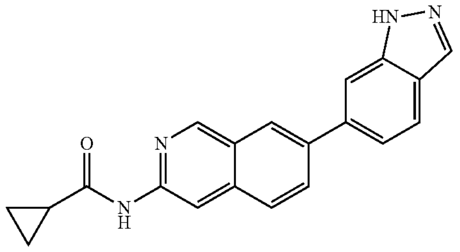 [SMILES: O=C(Nc1cc2ccc(-c3ccc4cn[nH]c4c3)cc2cn1)C1CC1] | N-(7-(1H-indazol-6-yl)isoquinolin-3-yl)cyclopropanecarboxamide |
| 144 | 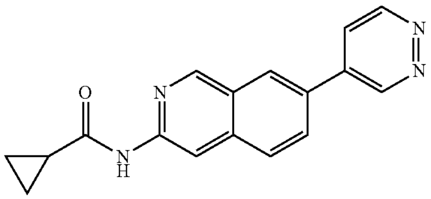 [SMILES: O=C(Nc1cc2ccc(-c3ccnnc3)cc2cn1)C1CC1] | N-(7-(pyridazin-4-yl)isoquinolin-3-yl)cyclopropanecarboxamide |
| 145 | 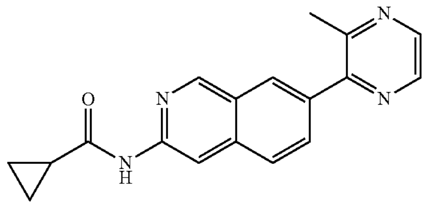 [SMILES: Cc1nccnc1-c1ccc2cc(NC(=O)C3CC3)ncc2c1] | N-(7-(3-methylpyrazin-2-yl)isoquinolin-3-yl)cyclopropanecarboxamide |
| 146 | 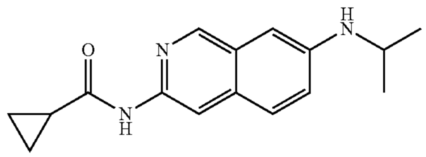 [SMILES: CC(C)Nc1ccc2cc(NC(=O)C3CC3)ncc2c1] | N-(7-(isopropylamino)isoquinolin-3-yl)cyclopropanecarboxamide |

TABLE 1-continued

| No. | Structure | Name |
|---|---|---|
| 147 | 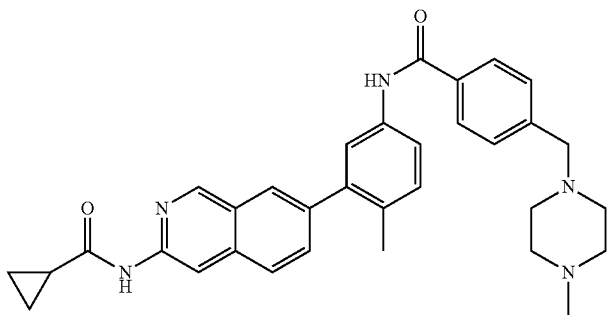 [SMILES: Cc1ccc(NC(=O)c2ccc(CN3CCN(C)CC3)cc2)cc1-c1ccc2cc(NC(=O)C3CC3)ncc2c1] | N-(3-(3-(cyclopropanecarboxamido) isoquinolin-7-yl)-4-methylphenyl)-4-((4-methylpiperazin-1-yl)methyl)benzamide |
| 148 | 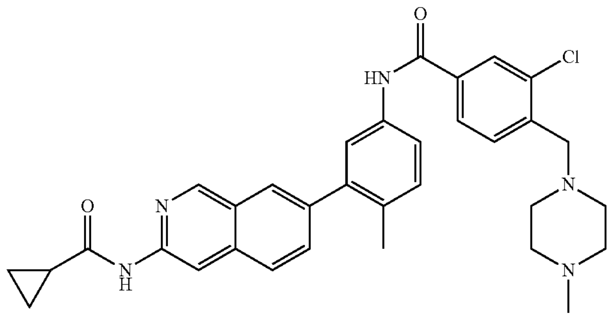 [SMILES: Cc1ccc(NC(=O)c2ccc(CN3CCN(C)CC3)c(Cl)c2)cc1-c1ccc2cc(NC(=O)C3CC3)ncc2c1] | 3-chloro-N-(3-(3-(cyclopropanecarboxamido) isoquinolin-7-yl)-4-methylphenyl)-4-((4-methylpiperazin-1-yl)methyl)benzamide |
| 149 | 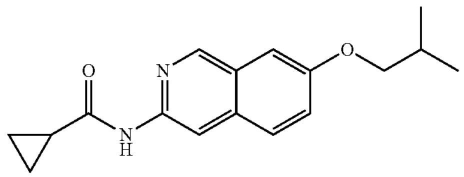 [SMILES: CC(C)COc1ccc2cc(NC(=O)C3CC3)ncc2c1] | N-(7-isobutoxyisoquinolin-3-yl) cyclopropanecarboxamide |
| 150 | 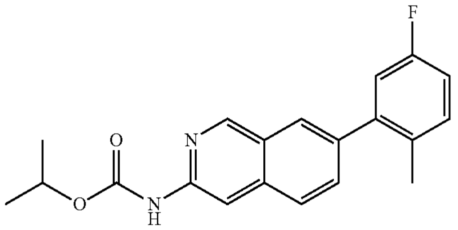 [SMILES: Cc1ccc(F)cc1-c1ccc2cc(NC(=O)OC(C)C)ncc2c1] | isopropyl 7-5-fluoro-2-methylphenyl) isoquinolin-3-ylcarbamate |
| 151 | 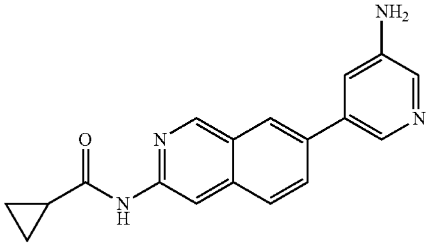 | N-(7-(5-aminopyridin-3-yl)isoquinolin-3-yl)cyclopropanecarboxamide |
| 152 | 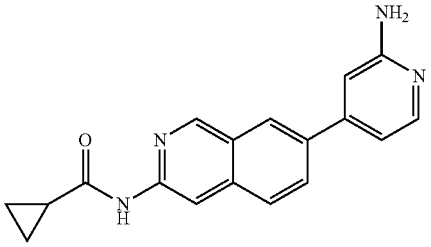 [SMILES: Nc1cc(-c2ccc3cc(NC(=O)C4CC4)ncc3c2)ccn1] | N-(7-(2-aminopyridin-4-yl)isoquinolin-3-yl)cyclopropanecarboxamide |

TABLE 1-continued

| No. | Structure | Name |
|---|---|---|
| 153 | 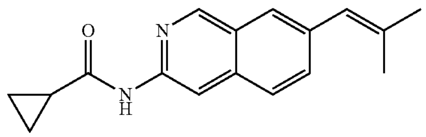 [SMILES: CC(C)=Cc1ccc2cc(NC(=O)C3CC3)ncc2c1] | N-(7-(2-methylprop-1-enyl)isoquinolin-3-yl)cyclopropanecarboxamide |
| 154 | 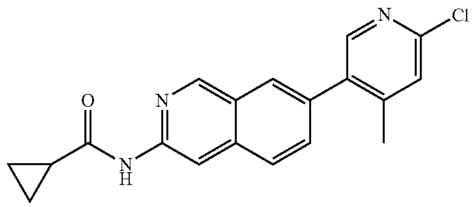 [SMILES: Cc1cc(Cl)ncc1-c1ccc2cc(NC(=O)C3CC3)ncc2c1] | N-(7-(6-chloro-4-methylpyridin-3-yl)isoquinolin-3-yl)cyclopropanecarboxamide |
| 155 | 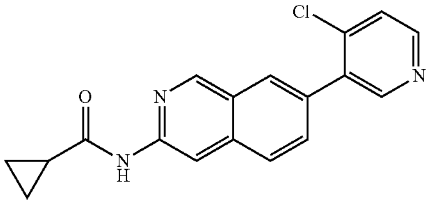 [SMILES: O=C(Nc1cc2ccc(-c3cnccc3Cl)cc2cn1)C1CC1] | N-(7-(4-chloropyridin-3-yl)isoquinolin-3-yl)cyclopropanecarboxamide |
| 156 | 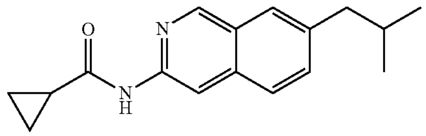 [SMILES: CC(C)Cc1ccc2cc(NC(=O)C3CC3)ncc2c1] | N-(7-isobutylisoquinolin-3-yl) cyclopropanecarboxamide |
| 157 | 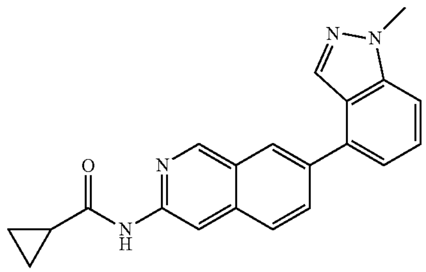 [SMILES: Cn1ncc2c(-c3ccc4cc(NC(=O)C5CC5)ncc4c3)cccc21] | N-(7-(1-methyl-1H-indazol-4-yl) isoquinolin-3-yl)cyclopropanecarboxamide |
| 158 | 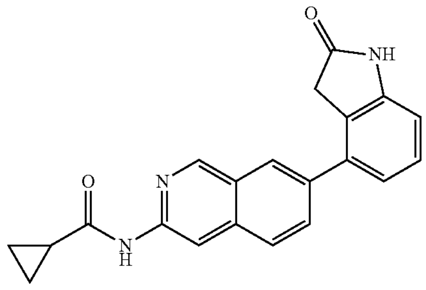 [SMILES: O=C1Cc2c(cccc2-c2ccc3cc(NC(=O)C4CC4)ncc3c2)N1] | N-(7-(2-oxoindolin-4-yl)isoquinolin-3-yl)cyclopropanecarboxamide |
| 159 | 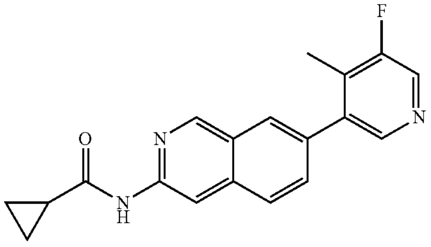 [SMILES: Cc1c(F)cncc1-c1ccc2cc(NC(=O)C3CC3)ncc2c1] | N-(7-(5-fluoro-4-methylpyridin-3-yl)isoquinolin-3-yl)cyclopropanecarboxamide |

TABLE 1-continued

| No. | Structure | Name |
| --- | --- | --- |
| 160 | 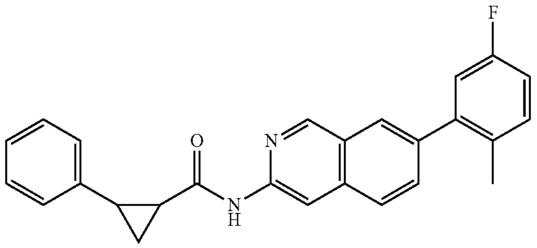 [SMILES: Cc1ccc(F)cc1-c1ccc2cc(NC(=O)C3CC3c3ccccc3)ncc2c1] | N-(7-(5-fluoro-2-methylphenyl)isoquinolin-3-yl)-2-phenylcyclopropanecarboxamide |
| 161 | 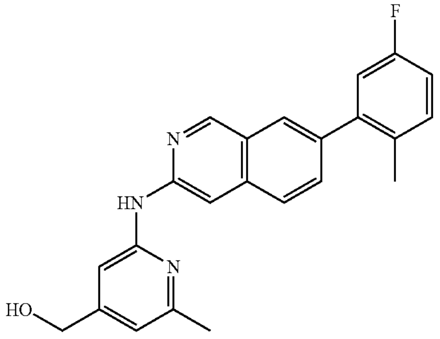 [SMILES: Cc1cc(CO)cc(Nc2cc3ccc(-c4cc(F)ccc4C)cc3cn2)n1] | (2-(7-(5-fluoro-2-methylphenyl)isoquinolin-3-ylamino)-6-methylpyridin-4-yl)methanol |
| 162 | 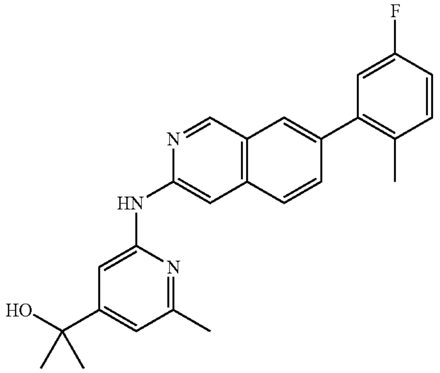 [SMILES: Cc1cc(C(C)(C)O)cc(Nc2cc3ccc(-c4cc(F)ccc4C)cc3cn2)n1] | 2-(2-(7-(5-fluoro-2-methylphenyl) isoquinolin-3-ylamino)-6-methylpyridin-4-yl)propan-2-ol |
| 163 | 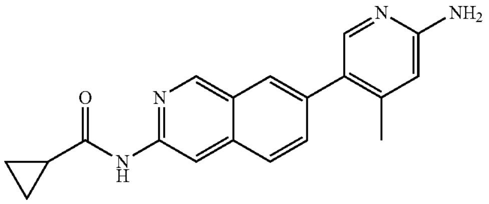 [SMILES: Cc1cc(N)ncc1-c1ccc2cc(NC(=O)C3CC3)ncc2c1] | N-(7-(6-amino-4-methylpyridin-3-yl)isoquinolin-3-yl)cyclopropanecarboxamide |
| 164 | 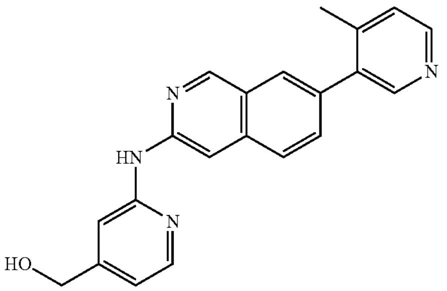 [SMILES: Cc1ccncc1-c1ccc2cc(Nc3cc(CO)ccn3)ncc2c1] | (2-(7-(4-methylpyridin-3-yl)isoquinolin-3-ylamino)pyridin-4-yl)methanol |

TABLE 1-continued

| No. | Structure | Name |
| --- | --- | --- |
| 165 | 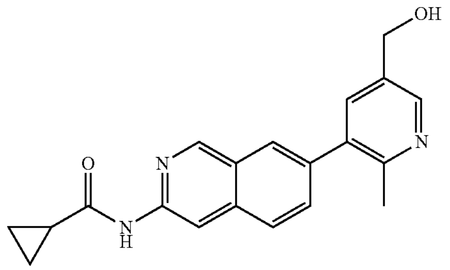 [SMILES: Cc1ncc(CO)cc1-c1ccc2cc(NC(=O)C3CC3)ncc2c1] | N-(7-(5-(hydroxymethyl)-2-methyl pyridin-3-yl)isoquinolin-3-yl)cyclopropanecarboxamide |
| 166 | 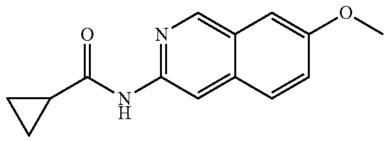 [SMILES: COc1ccc2cc(NC(=O)C3CC3)ncc2c1] | N-(7-methoxyisoquinolin-3-yl)cyclopropanecarboxamide |
| 167 | 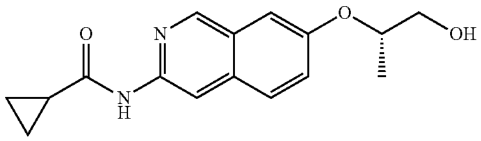 [SMILES: C[C@@H](CO)Oc1ccc2cc(NC(=O)C3CC3)ncc2c1] | (S)-N-(7-(1-hydroxypropan-2-yloxy) isoquinolin-3-yl)cyclopropanecarboxamide |
| 168 | 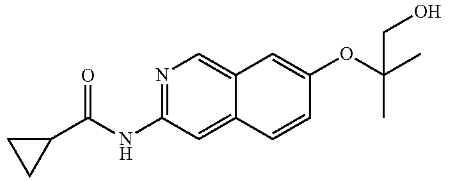 [SMILES: CC(C)(CO)Oc1ccc2cc(NC(=O)C3CC3)ncc2c1] | N-(7-(1-hydroxy-2-methylpropan-2-yloxy)isoquinolin-3-yl) cyclopropanecarboxamide |
| 169 | 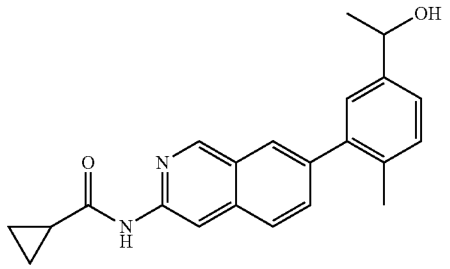 [SMILES: Cc1ccc(C(C)O)cc1-c1ccc2cc(NC(=O)C3CC3)ncc2c1] | N-(7-(5-(1-hydroxyethyl)-2-methyl phenyl)isoquinolin-3-yl) cyclopropanecarboxamide |
| 170 | 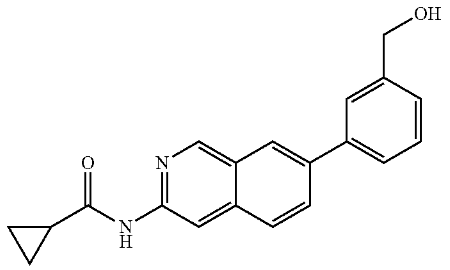 [SMILES: O=C(Nc1cc2ccc(-c3cccc(CO)c3)cc2cn1)C1CC1] | N-(7-(3-(hydroxymethyl)phenyl) isoquinolin-3-yl)cyclopropanecarboxamide |
| 171 | 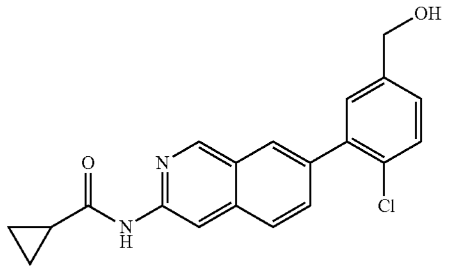 [SMILES: O=C(Nc1cc2ccc(-c3cc(CO)ccc3Cl)cc2cn1)C1CC1] | N-(7-(2-chloro-5-(hydroxymethyl) phenyl)isoquinolin-3-yl) cyclopropanecarboxamide |

TABLE 1-continued

| No. | Structure | Name |
| --- | --- | --- |
| 172 | 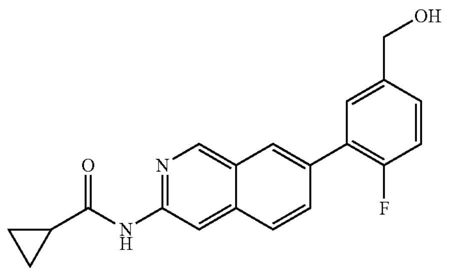 [SMILES: O=C(Nc1cc2ccc(-c3cc(CO)ccc3F)cc2cn1)C1CC1] | N-(7-(2-fluoro-5-(hydroxymethyl) phenyl)isoquinolin-3-yl) cyclopropanecarboxamide |
| 173 | 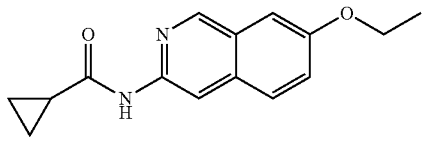 [SMILES: CCOc1ccc2cc(NC(=O)C3CC3)ncc2c1] | N-(7-ethoxyisoquinolin-3-yl)cyclopropanecarboxamide |
| 174 | 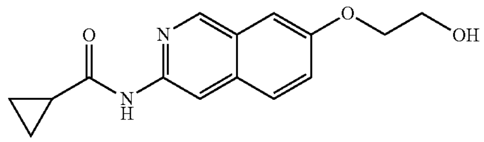 [SMILES: O=C(Nc1cc2ccc(OCCO)cc2cn1)C1CC1] | N-(7-(2-hydroxyethoxy)isoquinolin-3-yl)cyclopropanecarboxamide |
| 175 | 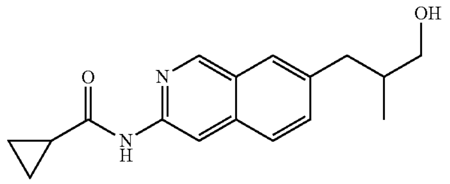 [SMILES: CC(CO)Cc1ccc2cc(NC(=O)C3CC3)ncc2c1] | N-(7-(3-hydroxy-2-methylpropyl)isoquinolin-3-yl)cyclopropanecarboxamide |
| 176 | 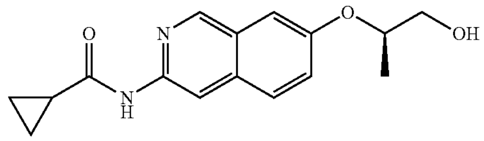 [SMILES: C[C@H](CO)Oc1ccc2cc(NC(=O)C3CC3)ncc2c1] | (R)-N-(7-(1-hydroxypropan-2-yloxy) isoquinolin-3-yl)cyclopropanecarboxamide |
| 177 | 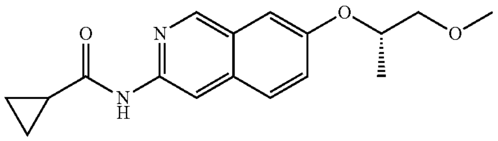 [SMILES: COC[C@H](C)Oc1ccc2cc(NC(=O)C3CC3)ncc2c1] | (S)-N-(7-(1-methoxypropan-2-yloxy) isoquinolin-3-yl)cyclopropanecarboxamide |
| 178 | 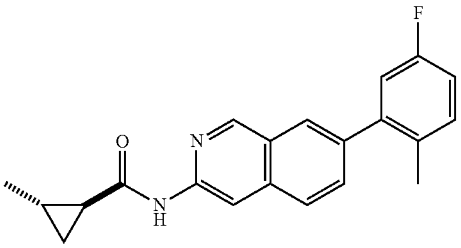 | (1S,2S)-N-(7-(5-fluoro-2-methylphenyl) isoquinolin-3-yl)-2-methylcyclopropanecarboxamide |
| 179 | 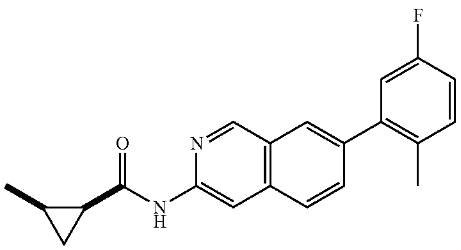 | (1S,2R)-N-(7-(5-fluoro-2-methylphenyl) isoquinolin-3-yl)-2-methylcyclopropanecarboxamide |

TABLE 1-continued

| No. | Structure | Name |
|---|---|---|
| 180 | 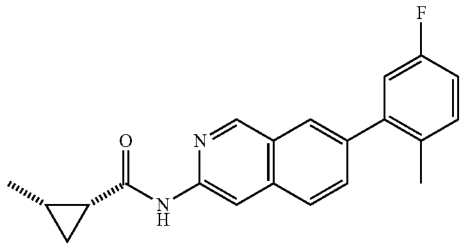 | (1R,2S)-N-(7-(5-fluoro-2-methylphenyl) isoquinolin-3-yl)-2-methylcyclopropanecarboxamide |
| 181 | 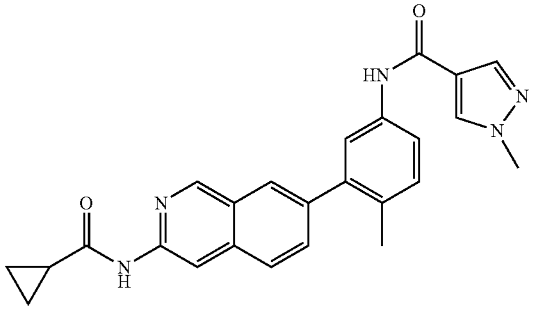 [SMILES: Cc1ccc(NC(=O)c2cnn(C)c2)cc1-c1ccc2cc(NC(=O)C3CC3)ncc2c1] | N-(3-(3-(cyclopropanecarboxamido) isoquinolin-7-yl)-4-methylphenyl)-1-methyl-1H-pyrazole-4-carboxamide |
| 182 | 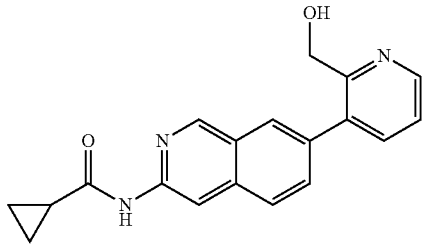 [SMILES: O=C(Nc1cc2ccc(-c3cccnc3CO)cc2cn1)C1CC1] | N-(7-(2-(hydroxymethyl)pyridin-3-yl)isoquinolin-3-yl) cyclopropanecarboxamide |
| 183 | 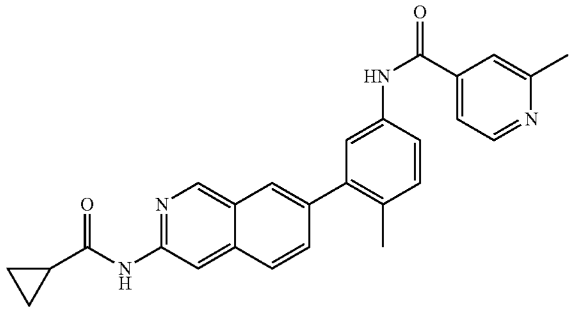 [SMILES: Cc1cc(C(=O)Nc2ccc(C)c(-c3ccc4cc(NC(=O)C5CC5)ncc4c3)c2)ccn1] | N-(3-(3-(cyclopropanecarboxamido) isoquinolin-7-yl)-4-methylphenyl)-2-methylisonicotinamide |
| 184 | 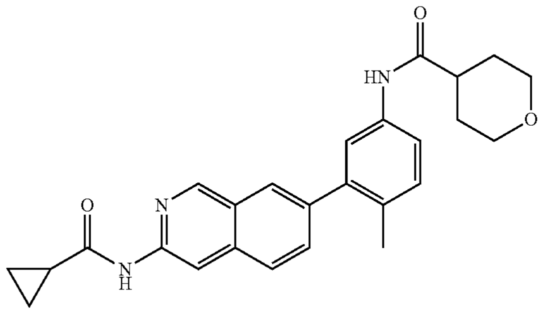 [SMILES: Cc1ccc(NC(=O)C2CCOCC2)cc1-c1ccc2cc(NC(=O)C3CC3)ncc2c1] | N-(3-(3-(cyclopropanecarboxamido) isoquinolin-7-yl)-4-methylphenyl) tetrahydro-2H-pyran-4-carboxamide |

TABLE 1-continued

| No. | Structure | Name |
|---|---|---|
| 185 | 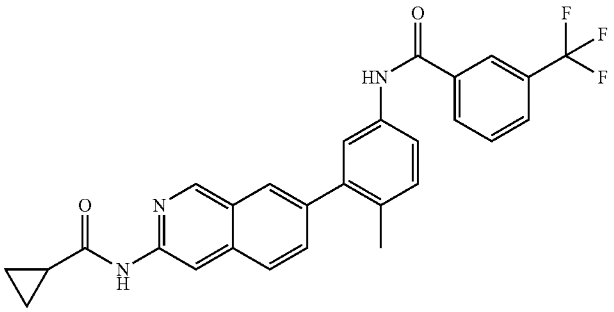 [SMILES: Cc1ccc(NC(=O)c2cccc(C(F)(F)F)c2)cc1-c1ccc2cc(NC(=O)C3CC3)ncc2c1] | N-(3-(3-(cyclopropanecarboxamido) isoquinolin-7-yl)-4-methylphenyl)-3-(trifluoromethyl)benzamide |
| 186 | 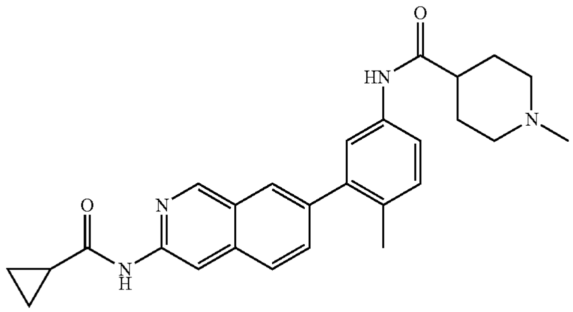 [SMILES: Cc1ccc(NC(=O)C2CCN(C)CC2)cc1-c1ccc2cc(NC(=O)C3CC3)ncc2c1] | N-(3-(3-(cyclopropanecarboxamido) isoquinolin-7-yl)-4-methylphenyl)-1-methylpiperidine-4-carboxamide |
| 187 | 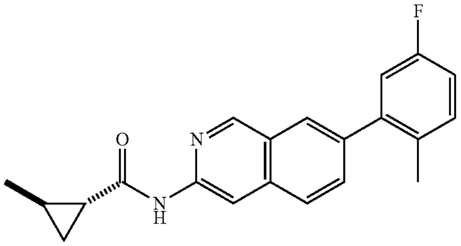 | (1R,2R)-N-(7-(5-fluoro-2-methylphenyl) isoquinolin-3-yl)-2-methylcyclopropanecarboxamide |
| 188 | 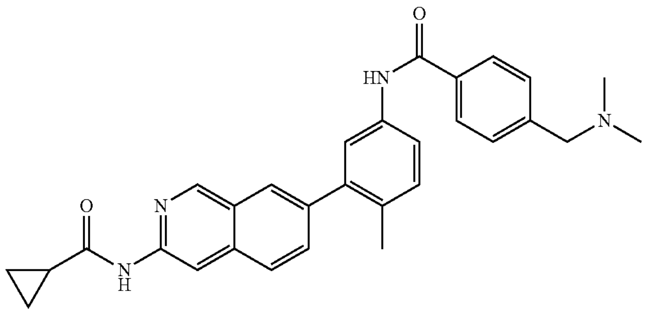 [SMILES: Cc1ccc(NC(=O)c2ccc(CN(C)C)cc2)cc1-c1ccc2cc(NC(=O)C3CC3)ncc2c1] | N-(3-(3-(cyclopropanecarboxamido) isoquinolin-7-yl)-4-methylphenyl)-4-((dimethylamino)methyl)benzamide |
| 189 | 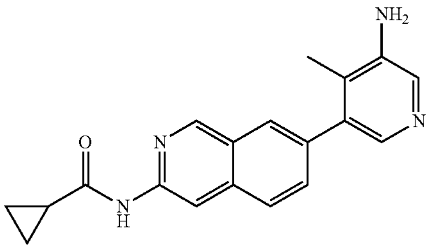 | N-(7-(5-amino-4-methylpyridin-3-yl)isoquinolin-3-yl)cyclopropanecarboxamide |

TABLE 1-continued

| No. | Structure | Name |
|---|---|---|
| 190 | 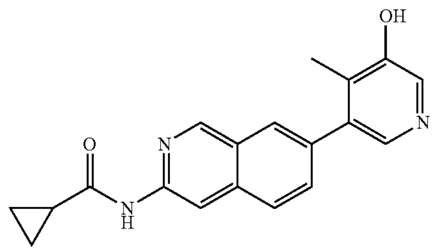 [SMILES: Cc1c(O)cncc1-c1ccc2cc(NC(=O)C3CC3)ncc2c1] | N-(7-(5-hydroxy-4-methylpyridin-3-yl)isoquinolin-3-yl)cyclopropanecarboxamide |
| 191 | 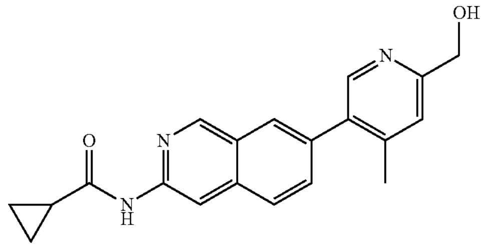 [SMILES: Cc1cc(CO)ncc1-c1ccc2cc(NC(=O)C3CC3)ncc2c1] | N-(7-(6-(hydroxymethyl)-4-methylpyridin-3-yl)isoquinolin-3-yl)cyclopropanecarboxamide |
| 192 | 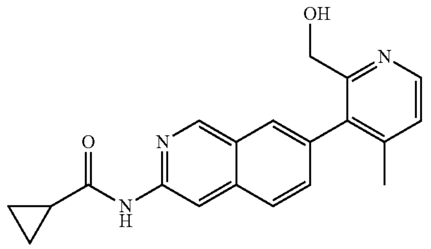 [SMILES: Cc1ccnc(CO)c1-c1ccc2cc(NC(=O)C3CC3)ncc2c1] | N-(7-(2-(hydroxymethyl)-4-methylpyridin-3-yl)isoquinolin-3-yl)cyclopropanecarboxamide |
| 193 | 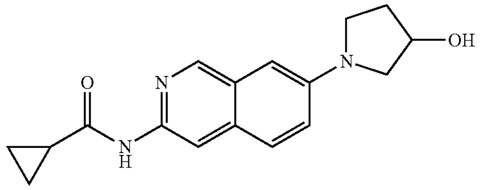 [SMILES: O=C(Nc1cc2ccc(N3CCC(O)C3)cc2cn1)C1CC1] | N-(7-(3-hydroxypyrrolidin-1-yl)isoquinolin-3-yl)cyclopropanecarboxamide |
| 194 | 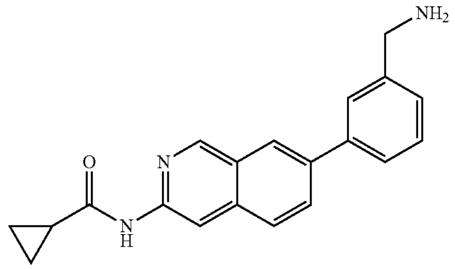 [SMILES: NCc1cccc(-c2ccc3cc(NC(=O)C4CC4)ncc3c2)c1] | N-(7-(3-(aminomethyl)phenyl)isoquinolin-3-yl)cyclopropanecarboxamide |
| 195 | 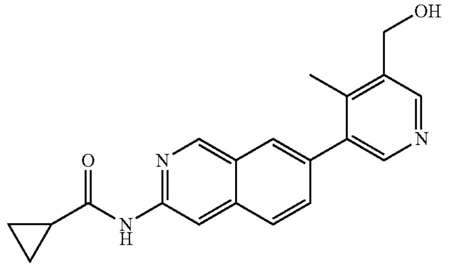 [SMILES: Cc1c(CO)cncc1-c1ccc2cc(NC(=O)C3CC3)ncc2c1] | N-(7-(5-(hydroxymethyl)-4-methylpyridin-3-yl)isoquinolin-3-yl)cyclopropanecarboxamide |

TABLE 1-continued

| No. | Structure | Name |
| --- | --- | --- |
| 196 | 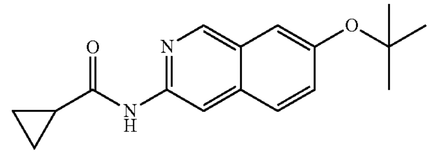 [SMILES: CC(C)(C)Oc1ccc2cc(NC(=O)C3CC3)ncc2c1] | N-(7-tert-butoxyisoquinolin-3-yl) cyclopropanecarboxamide |
| 197 | 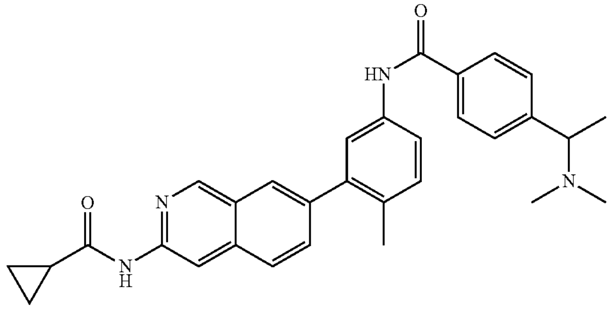 [SMILES: Cc1ccc(NC(=O)c2ccc(C(C)N(C)C)cc2)cc1-c1ccc2cc(NC(=O)C3CC3)ncc2c1] | N-(3-(3-(cyclopropanecarboxamido) isoquinolin-7-yl)-4-methylphenyl)-4-(1-(dimethylamino)ethyl)benzamide |
| 198 | 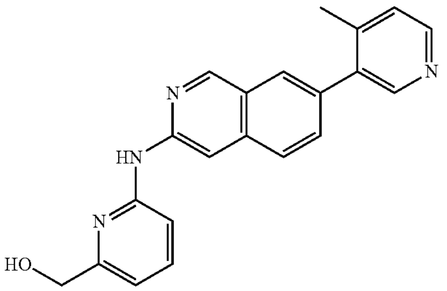 [SMILES: Cc1ccncc1-c1ccc2cc(Nc3cccc(CO)n3)ncc2c1] | (6-(7-(4-methylpyridin-3-yl)isoquinolin-3-ylamino)pyridin-2-yl)methanol |
| 199 | 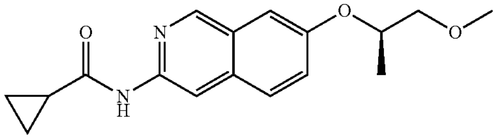 [SMILES: COC[C@@H](C)Oc1ccc2cc(NC(=O)C3CC3)ncc2c1] | (R)-N-(7-(1-methoxypropan-2-yloxy) isoquinolin-3-yl)cyclopropanecarboxamide |
| 200 | 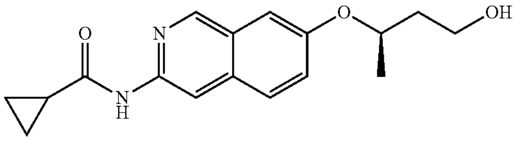 [SMILES: C[C@H](CCO)Oc1ccc2cc(NC(=O)C3CC3)ncc2c1] | (R)-N-(7-(4-hydroxybutan-2-yloxy) isoquinolin-3-yl)cyclopropanecarboxamide |
| 201 | 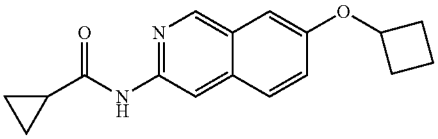 [SMILES: O=C(Nc1cc2ccc(OC3CCC3)cc2cn1)C1CC1] | N-(7-cyclobutoxyisoquinolin-3-yl) cyclopropanecarboxamide |
| 202 | 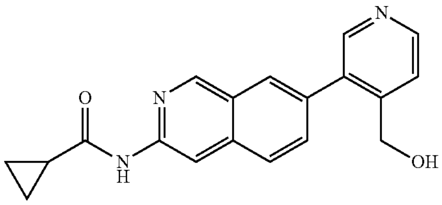 [SMILES: O=C(Nc1cc2ccc(-c3cnccc3CO)cc2cn1)C1CC1] | N-(7-(4-(hydroxymethyl)pyridin-3-yl)isoquinolin-3-yl)cyclopropanecarboxamide |

TABLE 1-continued

| No. | Structure | Name |
|---|---|---|
| 203 | 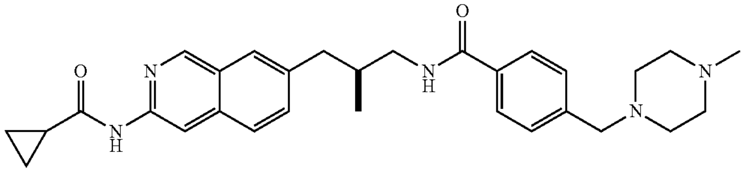 [SMILES: C[C@H](CNC(=O)c1ccc(CN2CCN(C)CC2)cc1)Cc1ccc2cc(NC(=O)C3CC3)ncc2c1] | (S)-N-(3-(3-(cyclopropanecarboxamido) isoquinolin-7-yl)-2-methylpropyl)-4-((4-methylpiperazin-1-yl) methyl)benzamide |
| 204 | 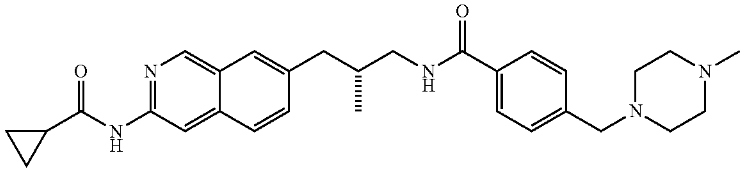 [SMILES: C[C@@H](CNC(=O)c1ccc(CN2CCN(C)CC2)cc1)Cc1ccc2cc(NC(=O)C3CC3)ncc2c1] | (R)-N-(3-(3-(cyclopropanecarboxamido) isoquinolin-7-yl)-2-methylpropyl)-4-((4-methylpiperazin-1-yl) methyl)benzamide |
| 205 | 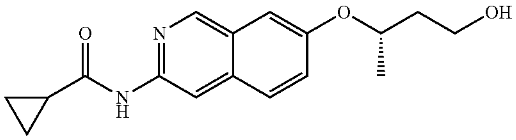 [SMILES: C[C@@H](CCO)Oc1ccc2cc(NC(=O)C3CC3)ncc2c1] | (S)-N-(7-(4-hydroxybutan-2-yloxy) isoquinolin-3-yl)cyclopropanecarboxamide |
| 206 | 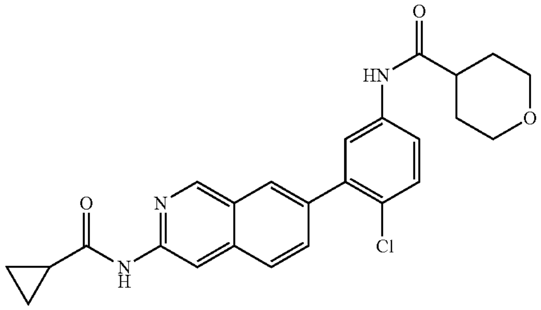 [SMILES: O=C(Nc1ccc(Cl)c(-c2ccc3cc(NC(=O)C4CC4)ncc3c2)c1)C1CCOCC1] | N-(4-chloro-3-(3-(cyclopropanecarboxamido) isoquinolin-7-yl)phenyl)tetrahydro-2H-pyran-4-carboxamide |
| 207 | 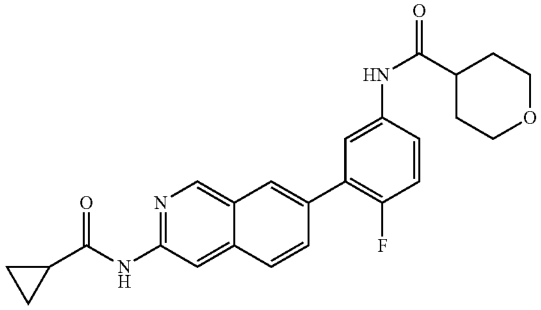 | N-(3-(3-(cyclopropanecarboxamido) isoquinolin-7-yl)-4-fluorophenyl) tetrahydro-2H-pyran-4-carboxamide |
| 208 | 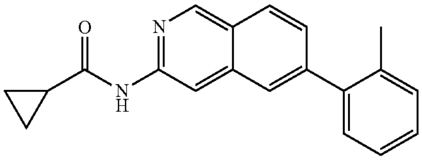 [SMILES: Cc1ccccc1-c1ccc2cnc(NC(=O)C3CC3)cc2c1] | N-(6-o-tolylisoquinolin-3-yl)cyclopropanecarboxamide |

TABLE 1-continued

| No. | Structure | Name |
|---|---|---|
| 209 | 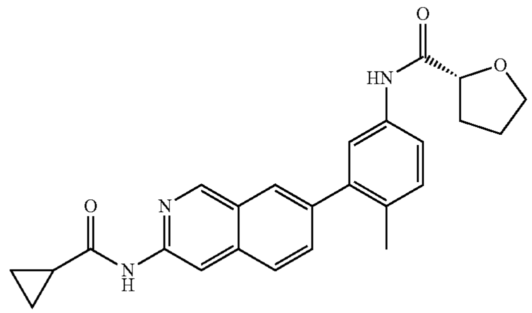 [SMILES: Cc1ccc(NC(=O)[C@H]2CCCO2)cc1-c1ccc2cc(NC(=O)C3CC3)ncc2c1] | (R)-N-(3-(3-(cyclopropanecarboxamido) isoquinolin-7-yl)-4-methylphenyl) tetrahydrofuran-2-carboxamide |
| 210 | 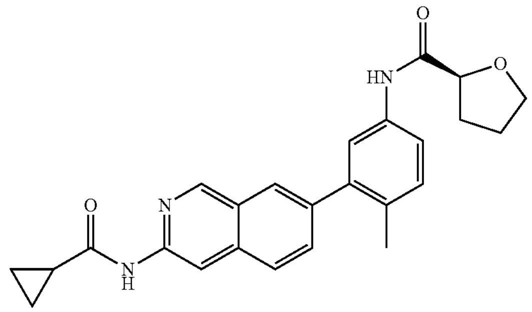 [SMILES: Cc1ccc(NC(=O)[C@@H]2CCCO2)cc1-c1ccc2cc(NC(=O)C3CC3)ncc2c1] | (S)-N-(3-(3-(cyclopropanecarboxamido) isoquinolin-7-yl)-4-methylphenyl) tetrahydrofuran-2-carboxamide |
| 211 | 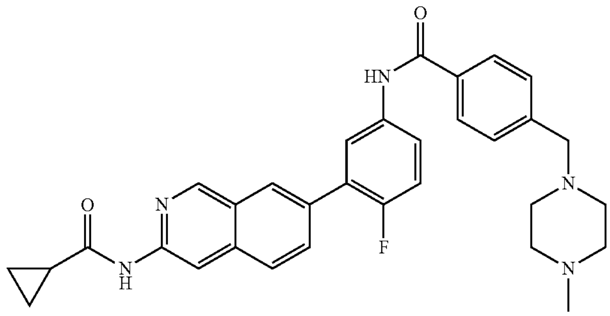 [SMILES: CN1CCN(Cc2ccc(C(=O)Nc3ccc(F)c(-c4ccc5cc(NC(=O)C6CC6)ncc5c4)c3)cc2)CC1] | N-(3-(3-(cyclopropanecarboxamido) isoquinolin-7-yl)-4-fluorophenyl)-4-((4-methylpiperazin-1-yl)methyl)benzamide |
| 212 | 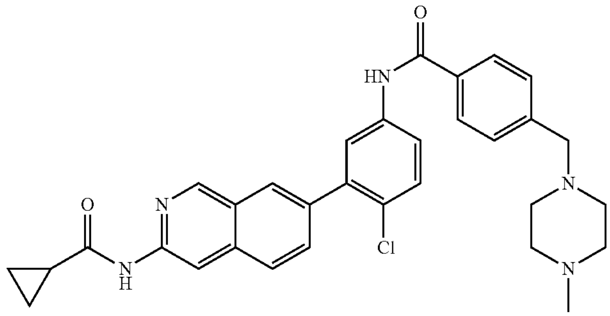 [SMILES: CN1CCN(Cc2ccc(C(=O)Nc3ccc(Cl)c(-c4ccc5cc(NC(=O)C6CC6)ncc5c4)c3)cc2)CC1] | N-(4-chloro-3-(3-(cyclopropanecarboxamido) isoquinolin-7-yl)phenyl)-4-((4-methylpiperazin-1-yl)methyl)benzamide |
| 213 | 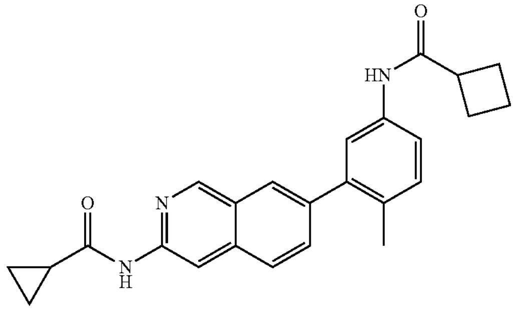 [SMILES: Cc1ccc(NC(=O)C2CCC2)cc1-c1ccc2cc(NC(=O)C3CC3)ncc2c1] | N-(3-(3-(cyclopropanecarboxamido) isoquinolin-7-yl)-4-methylphenyl) cyclobutanecarboxamide |

TABLE 1-continued

| No. | Structure | Name |
| --- | --- | --- |
| 214 | 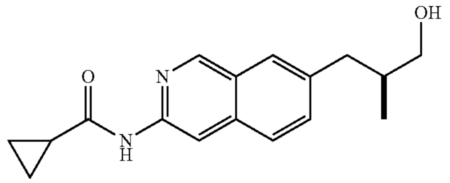 [SMILES: C[C@H](CO)Cc1ccc2cc(NC(=O)C3CC3)ncc2c1] | (S)-N-(7-(3-hydroxy-2-methylpropyl) isoquinolin-3-yl)cyclopropanecarboxamide |
| 215 | 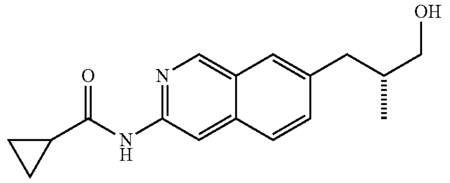 [SMILES: C[C@@H](CO)Cc1ccc2cc(NC(=O)C3CC3)ncc2c1] | (R)-N-(7-(3-hydroxy-2-methylpropyl) isoquinolin-3-yl)cyclopropanecarboxamide |
| 216 | 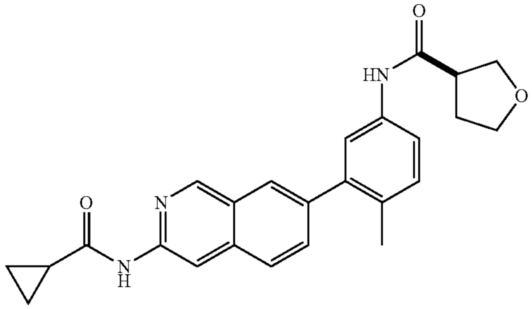 | (R)-N-(3-(3-(cyclopropanecarboxamido) isoquinolin-7-yl)-4-methylphenyl) tetrahydrofuran-3-carboxamide |
| 217 | 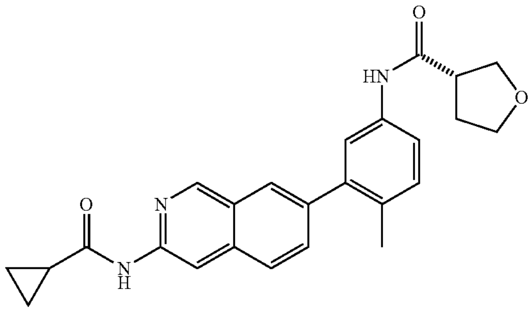 | (S)-N-(3-(3-(cyclopropanecarboxamido) isoquinolin-7-yl)-4-methylphenyl) tetrahydrofuran-3-carboxamide |
| 218 | 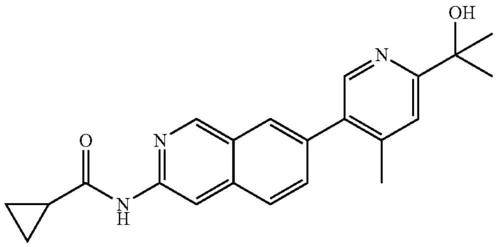 [SMILES: Cc1cc(C(C)(C)O)ncc1-c1ccc2cc(NC(=O)C3CC3)ncc2c1] | N-(7-(6-(2-hydroxypropan-2-yl)-4-methylpyridin-3-yl)isoquinolin-3-yl) cyclopropanecarboxamide |
| 219 | 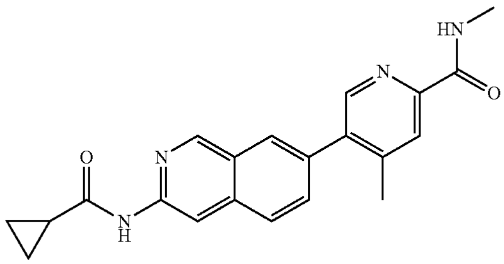 [SMILES: CNC(=O)c1cc(C)c(-c2ccc3cc(NC(=O)C4CC4)ncc3c2)cn1] | 5-(3-(cyclopropanecarboxamido) isoquinolin-7-yl)-N,4-dimethylpicolinamide |

TABLE 1-continued

| No. | Structure | Name |
| --- | --- | --- |
| 220 | 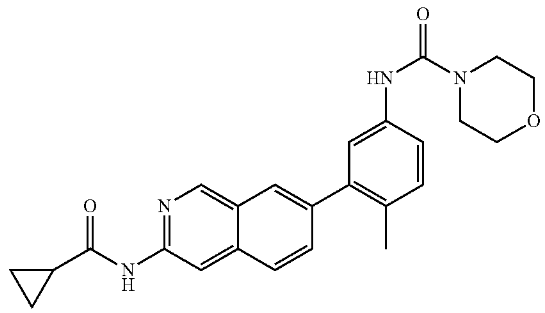 [SMILES: Cc1ccc(NC(=O)N2CCOCC2)cc1-c1ccc2cc(NC(=O)C3CC3)ncc2c1] | N-(3-(3-(cyclopropanecarboxamido) isoquinolin-7-yl)-4-methylphenyl) morpholine-4-carboxamide |
| 221 | 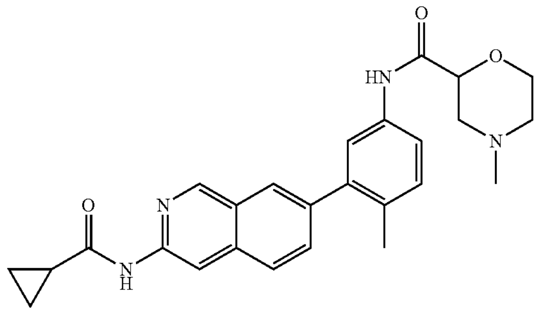 [SMILES: Cc1ccc(NC(=O)C2CN(C)CCO2)cc1-c1ccc2cc(NC(=O)C3CC3)ncc2c1] | N-(3-(3-(cyclopropanecarboxamido) isoquinolin-7-yl)-4-methylphenyl)-4-methylmorpholine-2-carboxamide |
| 222 | 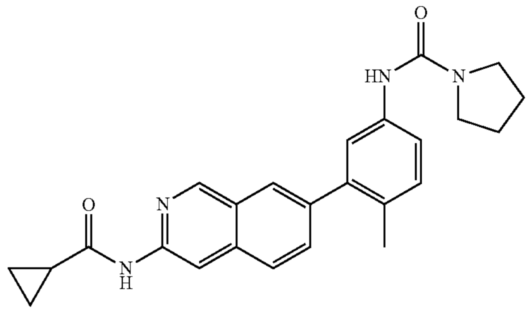 [SMILES: Cc1ccc(NC(=O)N2CCCC2)cc1-c1ccc2cc(NC(=O)C3CC3)ncc2c1] | N-(3-(3-(cyclopropanecarboxamido) isoquinolin-7-yl)-4-methylphenyl) pyrrolidine-1-carboxamide |
| 223 | 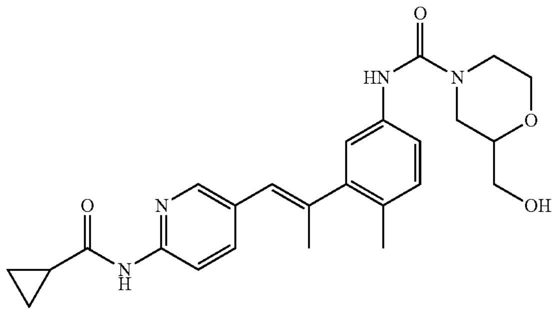 [SMILES: C/C(=C\c1ccc(NC(=O)C2CC2)nc1)c1cc(NC(=O)N2CCOC(CO)C2)ccc1C] | N-(3-(3-(cyclopropanecarboxamido) isoquinolin-7-yl)-4-methylphenyl)-2-(hydroxymethyl)morpholine-4-carboxamide |
| 224 | 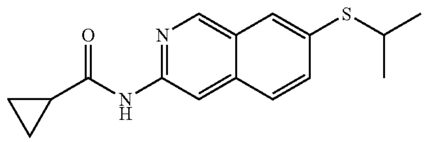 | N-(7-(isopropylthio)isoquinolin-3-yl)cyclopropanecarboxamide |
| 225 | 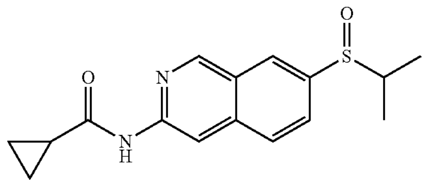 [SMILES: CC(C)S(=O)c1ccc2cc(NC(=O)C3CC3)ncc2c1] | N-(7-(isopropylsulfinyl)isoquinolin-3-yl)cyclopropanecarboxamide |

TABLE 1-continued

| No. | Structure | Name |
|---|---|---|
| 226 | 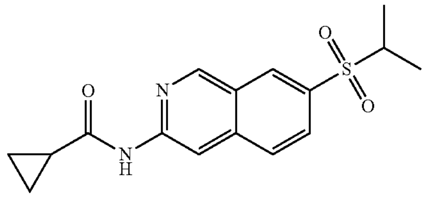 [SMILES: CC(C)S(=O)(=O)c1ccc2cc(NC(=O)C3CC3)ncc2c1] | N-(7-(isopropylsulfonyl)isoquinolin-3-yl)cyclopropanecarboxamide |
| 227 | 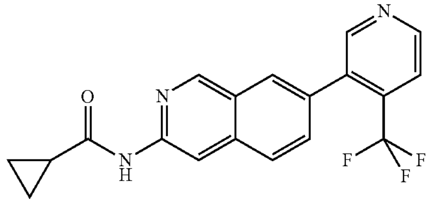 [SMILES: O=C(Nc1cc2ccc(-c3cnccc3C(F)(F)F)cc2cn1)C1CC1] | N-(7-(4-(trifluoromethyl)pyridin-3-yl)isoquinolin-3-yl)cyclopropanecarboxamide |
| 228 | 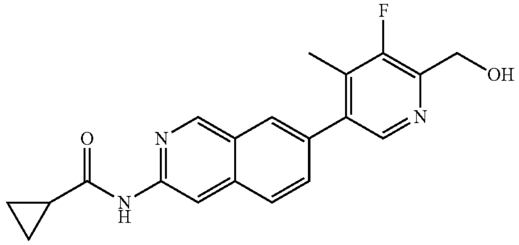 [SMILES: Cc1c(-c2ccc3cc(NC(=O)C4CC4)ncc3c2)cnc(CO)c1F] | N-(7-(5-fluoro-6-(hydroxymethyl)-4-methylpyridin-3-yl)isoquinolin-3-yl)cyclopropanecarboxamide |
| 229 | 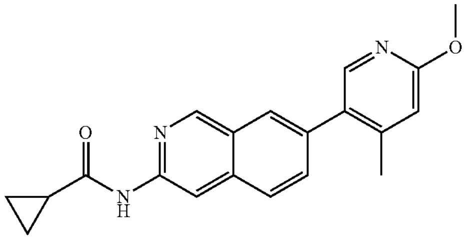 [SMILES: COc1cc(C)c(-c2ccc3cc(NC(=O)C4CC4)ncc3c2)cn1] | N-(7-(6-methoxy-4-methylpyridin-3-yl)isoquinolin-3-yl) cyclopropanecarboxamide |
| 230 | 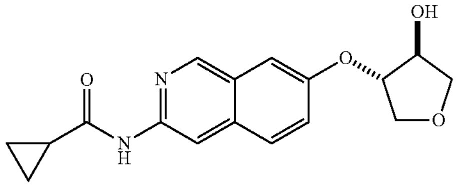 | N-(7-((3S,4S)-4-hydroxytetrahydrofuran-3-yloxy)isoquinolin-3-yl) cyclopropanecarboxamide |
| 231 | 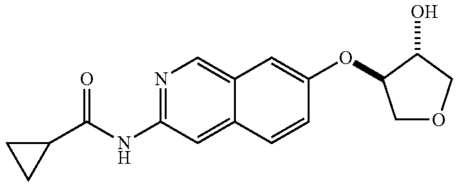 | N-(7-((3R,4R)-4-hydroxytetrahydrofuran-3-yloxy)isoquinolin-3-yl) cyclopropanecarboxamide |

TABLE 1-continued

| No. | Structure | Name |
|---|---|---|
| 232 | 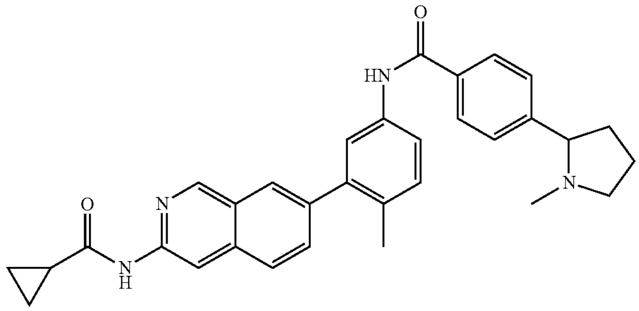 [SMILES: Cc1ccc(NC(=O)c2ccc(C3CCCN3C)cc2)cc1-c1ccc2cc(NC(=O)C3CC3)ncc2c1] | N-(3-(3-(cyclopropanecarboxamido) isoquinolin-7-yl)-4-methylphenyl)-4-(1-methylpyrrolidin-2-yl)benzamide |
| 233 | 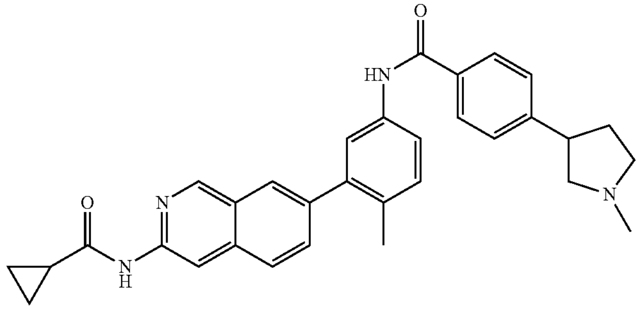 [SMILES: Cc1ccc(NC(=O)c2ccc(C3CCN(C)C3)cc2)cc1-c1ccc2cc(NC(=O)C3CC3)ncc2c1] | N-(3-(3-(cyclopropanecarboxamido) isoquinolin-7-yl)-4-methylphenyl)-4-(1-methylpyrrolidin-3-yl)benzamide |
| 234 | 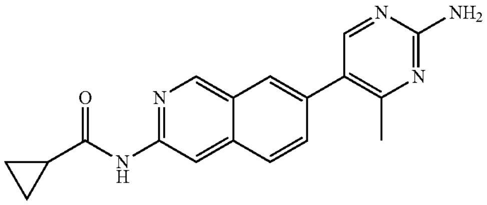 [SMILES: Cc1nc(N)ncc1-c1ccc2cc(NC(=O)C3CC3)ncc2c1] | N-(7-(2-amino-4-methylpyrimidin-5-yl)isoquinolin-3-yl) cyclopropanecarboxamide |
| 235 | 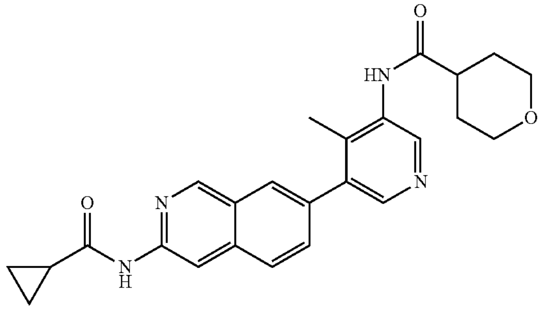 [SMILES: Cc1c(NC(=O)C2CCOCC2)cncc1-c1ccc2cc(NC(=O)C3CC3)ncc2c1] | N-(5-(3-(cyclopropanecarboxamido) isoquinolin-7-yl)-4-methylpyridin-3-yl)tetrahydro-2H-pyran-4-carboxamide |
| 236 | 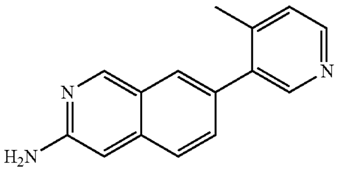 [SMILES: Cc1ccncc1-c1ccc2cc(N)ncc2c1] | 7-(4-methylpyridin-3-yl)isoquinolin-3-amine |
| 237 | 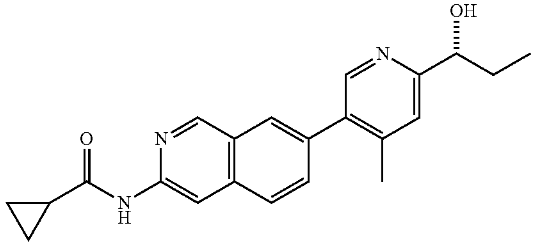 [SMILES: CC[C@@H](O)c1cc(C)c(-c2ccc3cc(NC(=O)C4CC4)ncc3c2)cn1] | (R)-N-(7-(6-(1-hydroxypropyl)-4-methylpyridin-3-yl)isoquinolin-3-yl)cyclopropanecarboxamide |

TABLE 1-continued

| No. | Structure | Name |
| --- | --- | --- |
| 238 | 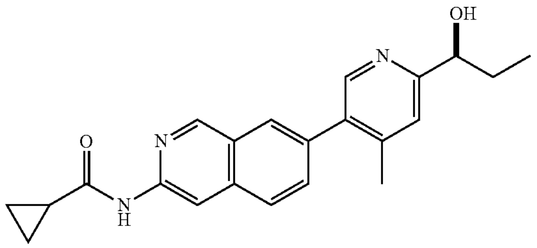 | (S)-N-(7-(6-(1-hydroxypropyl)-4-methylpyridin-3-yl)isoquinolin-3-yl)cyclopropanecarboxamide |
| 239 | 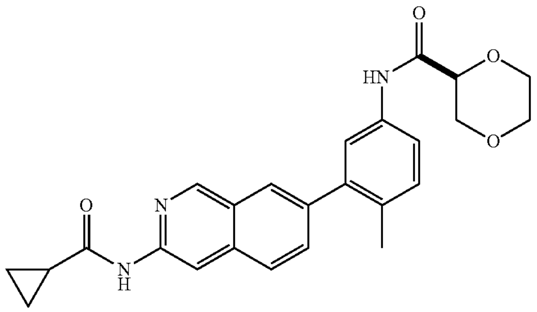 | (S)-N-(3-(3-(cyclopropanecarboxamido) isoquinolin-7-yl)-4-methylphenyl)-1,4-dioxane-2-carboxamide |
| 240 | 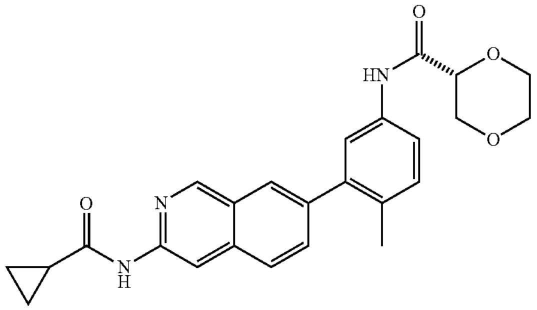 | (R)-N-(3-(3-(cyclopropanecarboxamido) isoquinolin-7-yl)-4-methylphenyl)-1,4-dioxane-2-carboxamide |
| 241 | 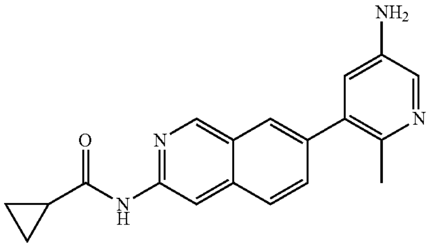 | N-(7-(5-amino-2-methylpyridin-3-yl)isoquinolin-3-yl)cyclopropanecarboxamide |
| 242 | 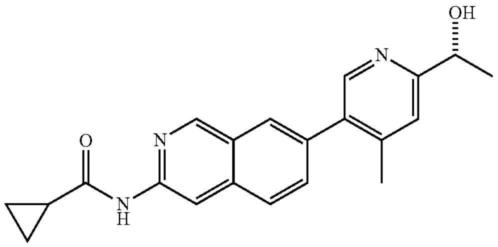 [SMILES: Cc1cc([C@@H](C)O)ncc1-c1ccc2cc(NC(=O)C3CC3)ncc2c1] | (R)-N-(7-(6-(1-hydroxyethyl)-4-methylpyridin-3-yl)isoquinolin-3-yl) cyclopropanecarboxamide |

TABLE 1-continued

| No. | Structure | Name |
|---|---|---|
| 243 | 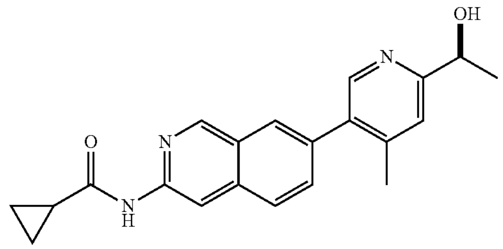 [SMILES: Cc1cc([C@H](C)O)ncc1-c1ccc2cc(NC(=O)C3CC3)ncc2c1] | (S)-N-(7-(6-(1-hydroxyethyl)-4-methylpyridin-3-yl)isoquinolin-3-yl)cyclopropanecarboxamide |
| 244 | 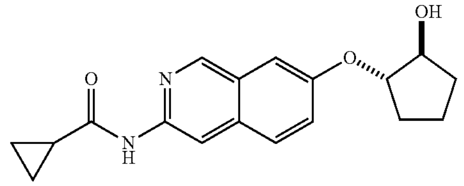 | N-(7-((1S,2S)-2-hydroxycyclopentyloxy)isoquinolin-3-yl)cyclopropanecarboxamide |
| 245 | 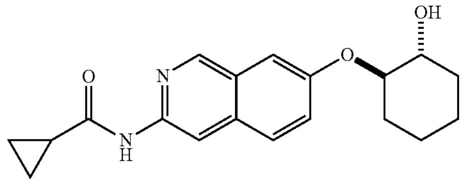 | N-(7-((1R,2R)-2-hydroxycyclohexyloxy)isoquinolin-3-yl)cyclopropanecarboxamide |
| 246 | 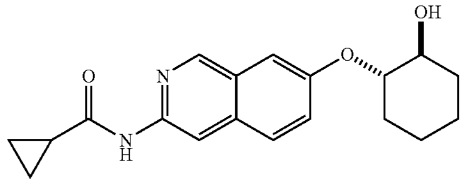 | N-(7-((1S,2S)-2-hydroxycyclohexyloxy)isoquinolin-3-yl)cyclopropanecarboxamide |
| 247 | 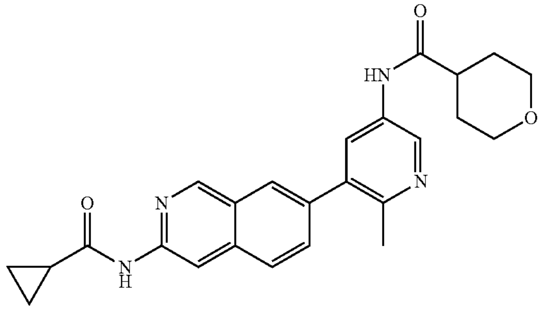 [SMILES: Cc1ncc(NC(=O)C2CCOCC2)cc1-c1ccc2cc(NC(=O)C3CC3)ncc2c1] | N-(5-(3-(cyclopropanecarboxamido)isoquinolin-7-yl)-6-methylpyridin-3-yl)tetrahydro-2H-pyran-4-carboxamide |
| 248 | 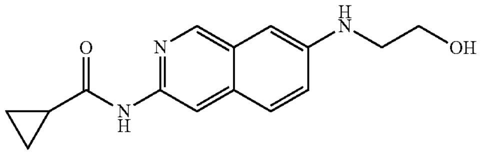 [SMILES: O=C(Nc1cc2ccc(NCCO)cc2cn1)C1CC1] | N-(7-(2-hydroxyethylamino)isoquinolin-3-yl)cyclopropanecarboxamide |
| 249 | 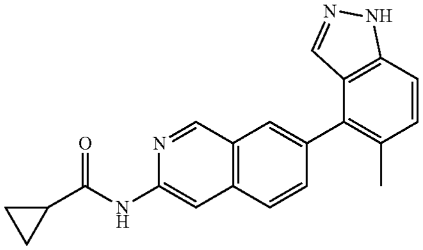 [SMILES: Cc1ccc2[nH]ncc2c1-c1ccc2cc(NC(=O)C3CC3)ncc2c1] | N-(7-(5-methyl-1H-indazol-4-yl)isoquinolin-3-yl)cyclopropanecarboxamide |

TABLE 1-continued

| No. | Structure | Name |
|---|---|---|
| 250 | 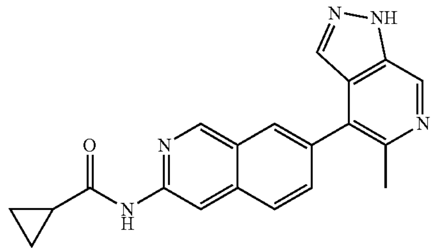 [SMILES: Cc1ncc2[nH]ncc2c1-c1ccc2cc(NC(=O)C3CC3)ncc2c1] | N-(7-(5-methyl-1H-pyrazolo[3,4-c] pyridin-4-yl)isoquinolin-3-yl)cyclopropanecarboxamide |
| 251 | 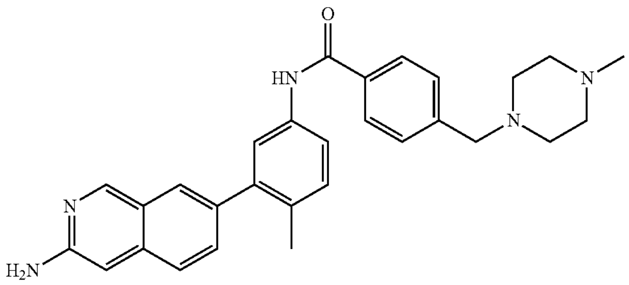 [SMILES: Cc1ccc(NC(=O)c2ccc(CN3CCN(C)CC3)cc2)cc1-c1ccc2cc(N)ncc2c1] | N-(3-(3-aminoisoquinolin-7-yl)-4-methylphenyl)-4-((4-methylpiperazin-1-yl)methyl)benzamide |
| 252 | 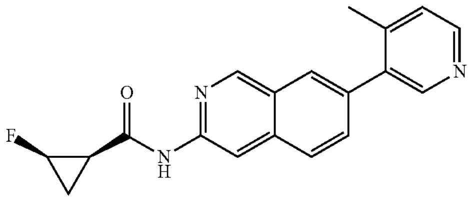 [SMILES: Cc1ccncc1-c1ccc2cc(NC(=O)[C@H]3C[C@H]3F)ncc2c1] | (1R,2R)-2-fluoro-N-(7-(4-methylpyridin-3-yl)isoquinolin-3-yl)cyclopropanecarboxamide |
| 253 | 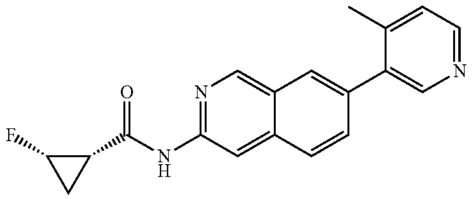 [SMILES: Cc1ccncc1-c1ccc2cc(NC(=O)[C@@H]3C[C@@H]3F)ncc2c1] | (1S,2S)-2-fluoro-N-(7-(4-methylpyridin-3-yl)isoquinolin-3-yl)cyclopropanecarboxamide |
| 254 | 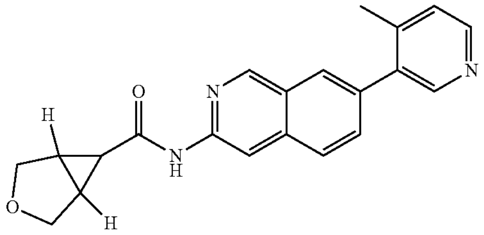 [SMILES: Cc1ccncc1-c1ccc2cc(NC(=O)C3C4COCC43)ncc2c1] | N-(7-(4-methylpyridin-3-yl)isoquinolin-3-yl)-3-oxabicyclo[3.1.0]hexane-6-carboxamide |
| 255 | 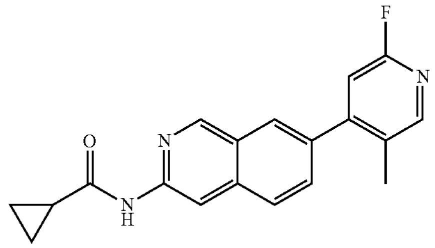 | N-(7-(2-fluoro-5-methylpyridin-4-yl)isoquinolin-3-yl)cyclopropanecarboxamide |

TABLE 1-continued

| No. | Structure | Name |
|---|---|---|
| 256 | 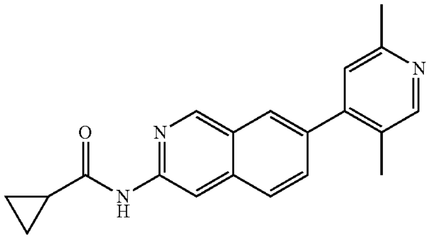 | N-(7-(2,5-dimethylpyridin-4-yl)isoquinolin-3-yl)cyclopropanecarboxamide |
| 257 | 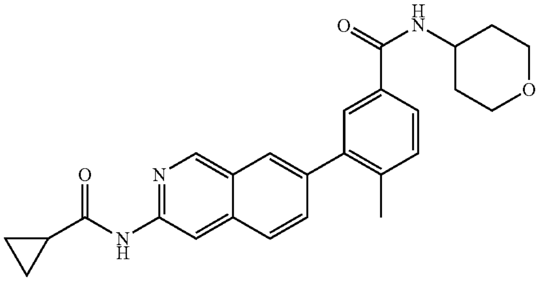 [SMILES: Cc1ccc(C(=O)NC2CCOCC2)cc1-c1ccc2cc(NC(=O)C3CC3)ncc2c1] | 3-(3-(cyclopropanecarboxamido) isoquinolin-7-yl)-4-methyl-N-(tetrahydro-2H-pyran-4-yl)benzamide |
| 258 | 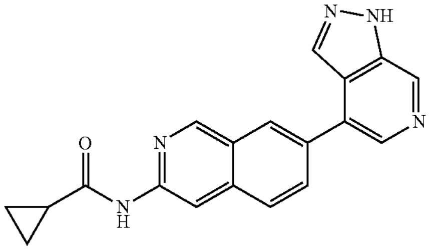 [SMILES: O=C(Nc1cc2ccc(-c3cncc4[nH]ncc34)cc2cn1)C1CC1] | N-(7-(1H-pyrazolo[3,4-c]pyridin-4-yl)isoquinolin-3-yl)cyclopropanecarboxamide |
| 259 | 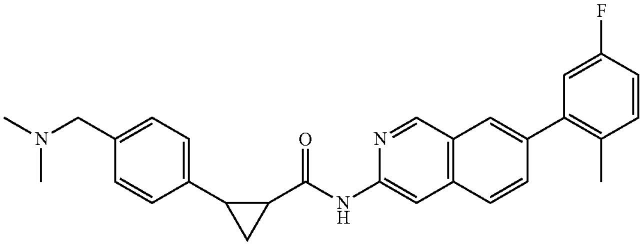 [SMILES: Cc1ccc(F)cc1-c1ccc2cc(NC(=O)C3CC3c3ccc(CN(C)C)cc3)ncc2c1] | 2-(4-((dimethylamino)methyl)phenyl)-N-(7-(5-fluoro-2-methylphenyl) isoquinolin-3-yl)cyclopropanecarboxamide |
| 260 | 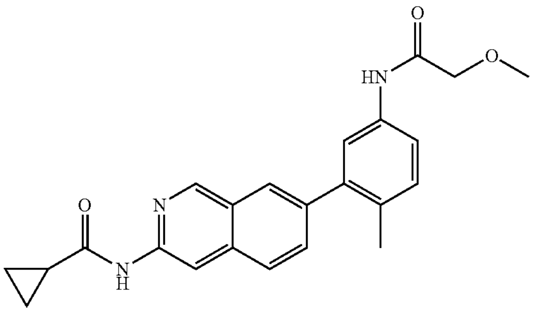 [SMILES: COCC(=O)Nc1ccc(C)c(-c2ccc3cc(NC(=O)C4CC4)ncc3c2)c1] | N-(7-(5-(2-methoxyacetamido)-2-methylphenyl)isoquinolin-3-yl)cyclopropanecarboxamide |

TABLE 1-continued

| No. | Structure | Name |
|---|---|---|
| 261 | 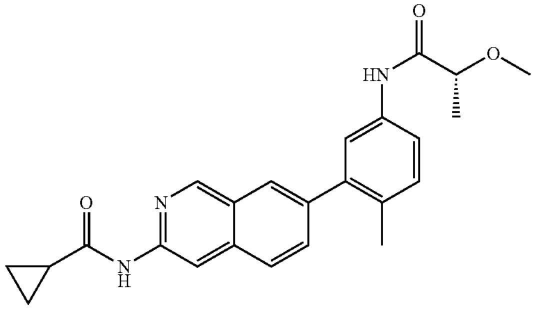 [SMILES: CO[C@H](C)C(=O)Nc1ccc(C)c(-c2ccc3cc(NC(=O)C4CC4)ncc3c2)c1] | (R)-N-(7-(5-(2-methoxypropanamido)-2-methylphenyl)isoquinolin-3-yl)cyclopropanecarboxamide |
| 262 | 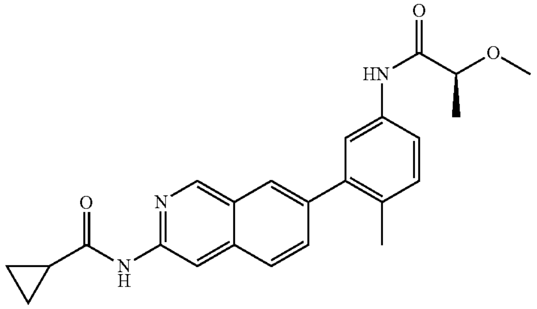 [SMILES: CO[C@@H](C)C(=O)Nc1ccc(C)c(-c2ccc3cc(NC(=O)C4CC4)ncc3c2)c1] | (S)-N-(7-(5-(2-methoxypropanamido)-2-methylphenyl)isoquinolin-3-yl)cyclopropanecarboxamide |
| 263 | 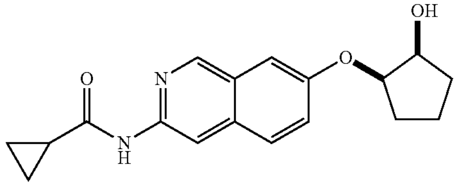 | N-(7-((1R,2S)-2-hydroxycyclopentyloxy) isoquinolin-3-yl)cyclopropanecarboxamide |
| 264 | 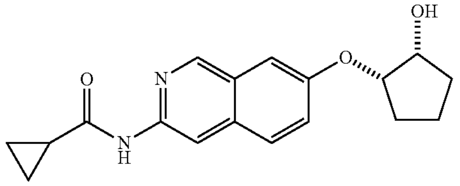 | N-(7-((1S,2R)-2-hydroxycyclopentyloxy) isoquinolin-3-yl)cyclopropanecarboxamide |
| 265 | 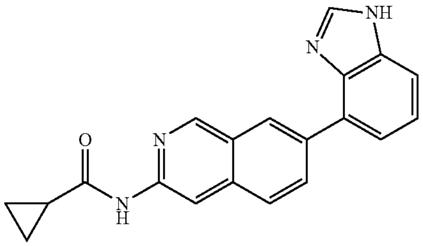 [SMILES: O=C(Nc1cc2ccc(-c3cccc4[nH]cnc34)cc2cn1)C1CC1] | N-(7-(1H-benzo[d]imidazol-4-yl) isoquinolin-3-yl)cyclopropanecarboxamide |
| 266 | 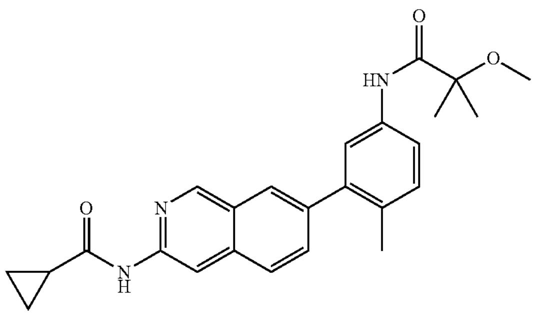 [SMILES: COC(C)(C)C(=O)Nc1ccc(C)c(-c2ccc3cc(NC(=O)C4CC4)ncc3c2)c1] | N-(7-(5-(2-methoxy-2-methylpropanamido)-2-methylphenyl)isoquinolin-3-yl)cyclopropanecarboxamide |

TABLE 1-continued

| No. | Structure | Name |
|---|---|---|
| 267 | 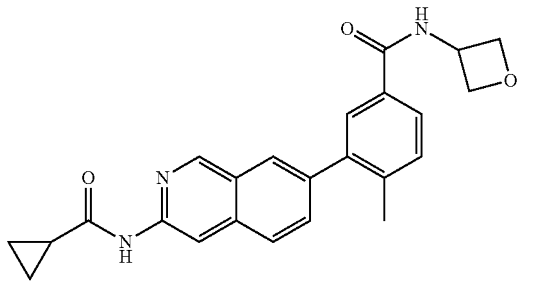 [SMILES: Cc1ccc(C(=O)NC2COC2)cc1-c1ccc2cc(NC(=O)C3CC3)ncc2c1] | 3-(3-(cyclopropanecarboxamido) isoquinolin-7-yl)-4-methyl-N-(oxetan-3-yl)benzamide |
| 268 | 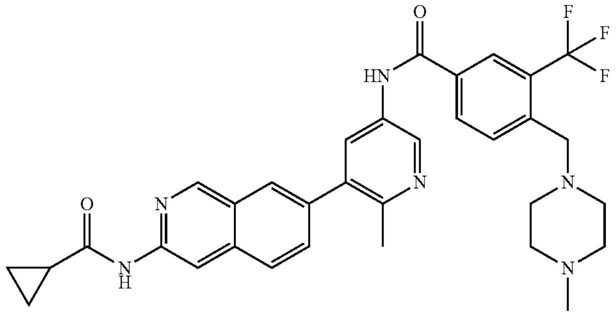 [SMILES: Cc1ncc(NC(=O)c2ccc(CN3CCN(C)CC3)c(C(F)(F)F)c2)cc1-c1ccc2cc(NC(=O)C3CC3)ncc2c1] | N-(5-(3-(cyclopropanecarboxamido) isoquinolin-7-yl)-6-methylpyridin-3-yl)-4-((4-methylpiperazin-1-yl) methyl)-3-(trifluoromethyl)benzamide |
| 269 | 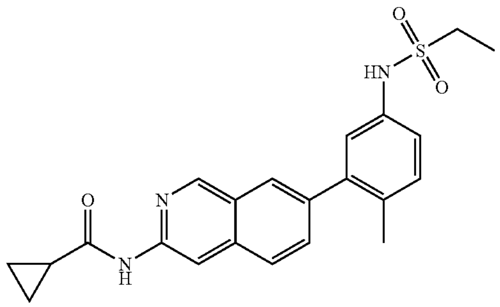 [SMILES: CCS(=O)(=O)Nc1ccc(C)c(-c2ccc3cc(NC(=O)C4CC4)ncc3c2)c1] | N-(7-(5-(ethylsulfonamido)-2-methylphenyl) isoquinolin-3-yl)cyclopropanecarboxamide |
| 270 | 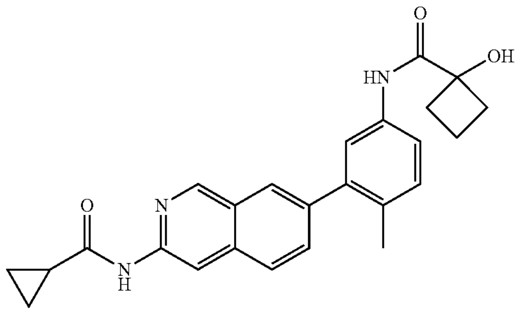 [SMILES: Cc1ccc(NC(=O)C2(O)CCC2)cc1-c1ccc2cc(NC(=O)C3CC3)ncc2c1] | N-(3-(3-(cyclopropanecarboxamido) isoquinolin-7-yl)-4-methylphenyl)-1-hydroxycyclobutanecarboxamide |
| 271 | 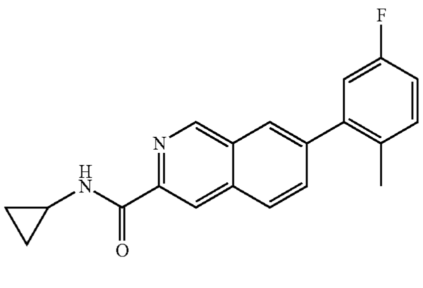 [SMILES: Cc1ccc(F)cc1-c1ccc2cc(C(=O)NC3CC3)ncc2c1] | N-cyclopropyl-7-(5-fluoro-2-methylphenyl) isoquinoline-3-carboxamide |

TABLE 1-continued

| No. | Structure | Name |
|---|---|---|
| 272 | 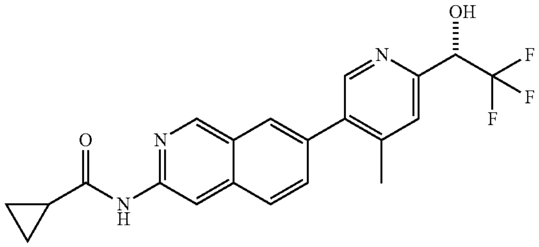 [SMILES: Cc1cc([C@H](O)C(F)(F)F)ncc1-c1ccc2cc(NC(=O)C3CC3)ncc2c1] | (S)-N-(7-(4-methyl-6-(2,2,2-trifluoro-1-hydroxyethyl)pyridin-3-yl) isoquinolin-3-yl) cyclopropanecarboxamidearboxamide |
| 273 | 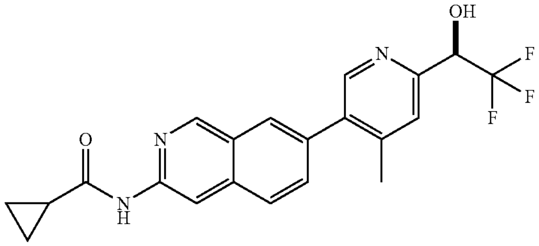 [SMILES: Cc1cc([C@@H](O)C(F)(F)F)ncc1-c1ccc2cc(NC(=O)C3CC3)ncc2c1] | (R)-N-(7-(4-methyl-6-(2,2,2-trifluoro-1-hydroxyethyl)pyridin-3-yl) isoquinolin-3-yl) cyclopropanecarboxamideecarboxamide |
| 274 | 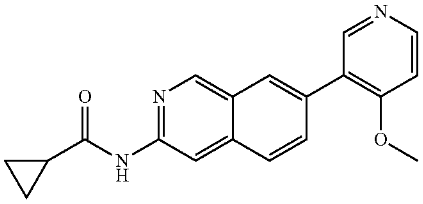 [SMILES: COc1ccncc1-c1ccc2cc(NC(=O)C3CC3)ncc2c1] | N-(7-(4-methoxypyridin-3-yl) isoquinolin-3-yl)cyclopropanecarboxamide |
| 275 | 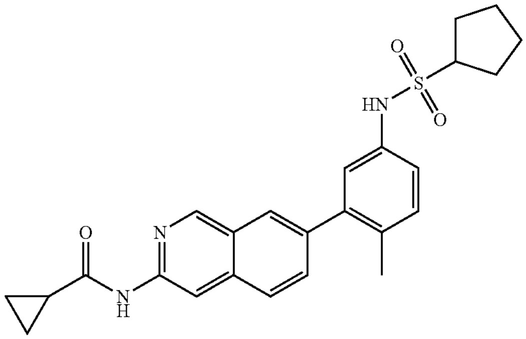 [SMILES: Cc1ccc(NS(=O)(=O)C2CCCC2)cc1-c1ccc2cc(NC(=O)C3CC3)ncc2c1] | N-(7-(5-(cyclopentanesulfonamido)-2-methylphenyl)isoquinolin-3-yl) cyclopropanecarboxamide |
| 276 | 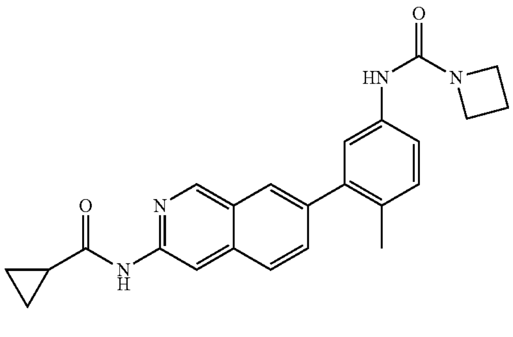 [SMILES: Cc1ccc(NC(=O)N2CCC2)cc1-c1ccc2cc(NC(=O)C3CC3)ncc2c1] | N-(3-(3-(cyclopropanecarboxamido) isoquinolin-7-yl)-4-methylphenyl)azetidine-1-carboxamide |

TABLE 1-continued

| No. | Structure | Name |
| --- | --- | --- |
| 277 | 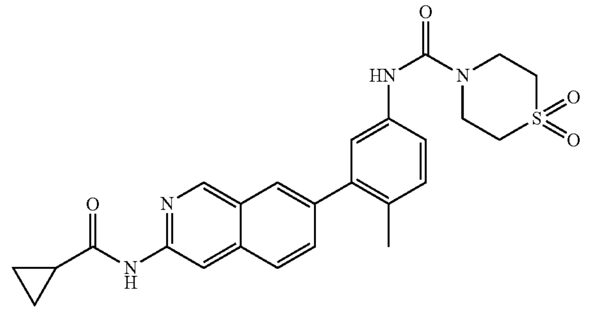 [SMILES: Cc1ccc(NC(=O)N2CCS(=O)(=O)CC2)cc1-c1ccc2cc(NC(=O)C3CC3)ncc2c1] | N-(3-(3-(cyclopropanecarboxamido) isoquinolin-7-yl)-4-methylphenyl)-1,1-dioxo-1-thiomorpholine-4-carboxamide |
| 278 | 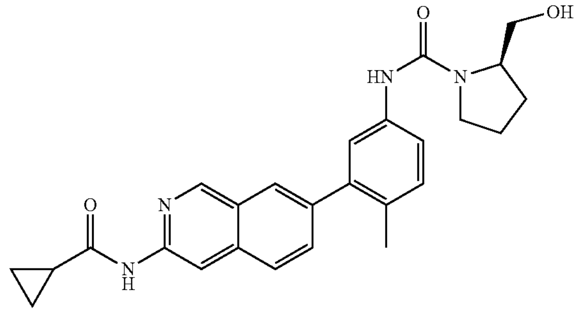 [SMILES: Cc1ccc(NC(=O)N2CCC[C@@H]2CO)cc1-c1ccc2cc(NC(=O)C3CC3)ncc2c1] | (R)-N-(3-(3-(cyclopropanecarboxamido) isoquinolin-7-yl)-4-methylphenyl)-2-(hydroxymethyl)pyrrolidine-1-carboxamide |
| 279 | 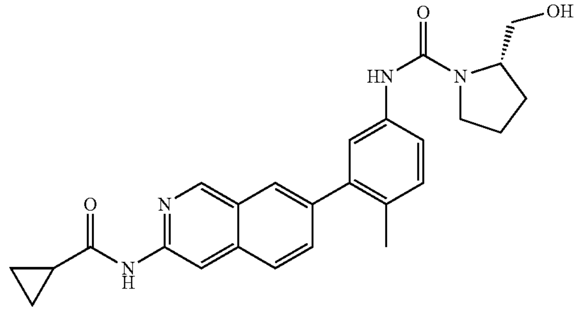 [SMILES: Cc1ccc(NC(=O)N2CCC[C@H]2CO)cc1-c1ccc2cc(NC(=O)C3CC3)ncc2c1] | (S)-N-(3-(3-(cyclopropanecarboxamido) isoquinolin-7-yl)-4-methylphenyl)-2-(hydroxymethyl)pyrrolidine-1-carboxamide |
| 280 | 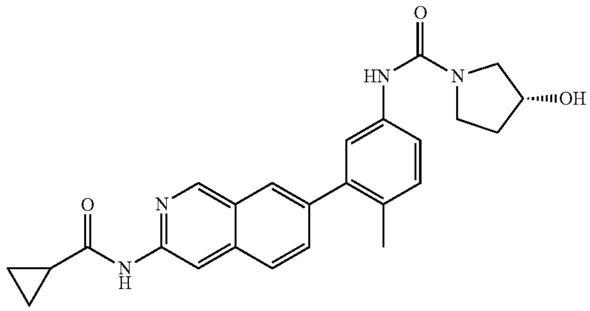 [SMILES: Cc1ccc(NC(=O)N2CC[C@@H](O)C2)cc1-c1ccc2cc(NC(=O)C3CC3)ncc2c1] | (R)-N-(3-(3-(cyclopropanecarboxamido) isoquinolin-7-yl)-4-methylphenyl)-3-hydroxypyrrolidine-1-carboxamide |
| 281 | 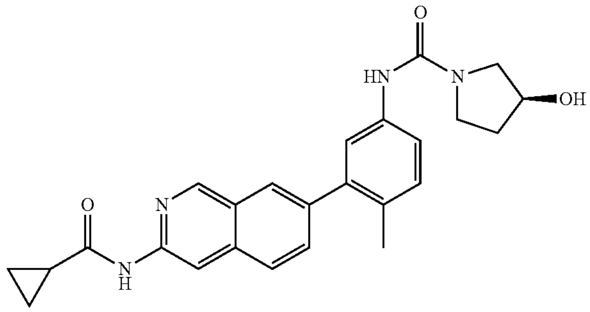 [SMILES: Cc1ccc(NC(=O)N2CC[C@H](O)C2)cc1-c1ccc2cc(NC(=O)C3CC3)ncc2c1] | (S)-N-(3-(3-(cyclopropanecarboxamido) isoquinolin-7-yl)-4-methylphenyl)-3-hydroxypyrrolidine-1-carboxamide |

TABLE 1-continued

| No. | Structure | Name |
|---|---|---|
| 282 | 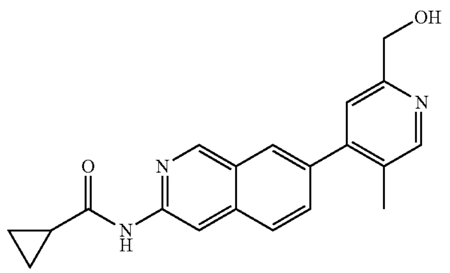 [SMILES: Cc1cnc(CO)cc1-c1ccc2cc(NC(=O)C3CC3)ncc2c1] | N-(7-(2-(hydroxymethyl)-5-methyl pyridin-4-yl)isoquinolin-3-yl) cyclopropanecarboxamide |
| 283 | 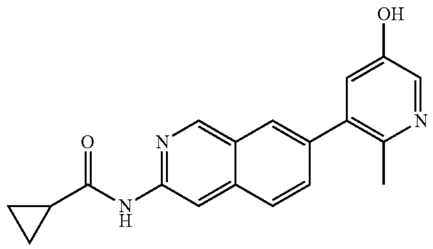 [SMILES: Cc1ncc(O)cc1-c1ccc2cc(NC(=O)C3CC3)ncc2c1] | N-(7-(5-hydroxy-2-methylpyridin-3-yl)isoquinolin-3-yl)cyclopropanecarboxamide |
| 284 | 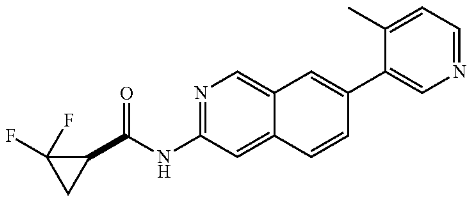 | (R)-2,2-difluoro-N-(7-(4-methylpyridin-3-yl)isoquinolin-3-yl)cyclopropanecarboxamide |
| 285 | 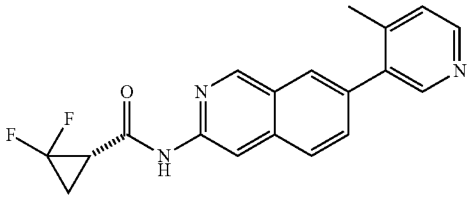 | (S)-2,2-difluoro-N-(7-(4-methylpyridin-3-yl)isoquinolin-3-yl)cyclopropanecarboxamide |
| 286 | 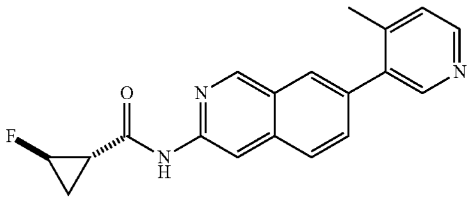 | (1S,2R)-2-fluoro-N-(7-(4-methylpyridin-3-yl)isoquinolin-3-yl)cyclopropanecarboxamide |
| 287 | 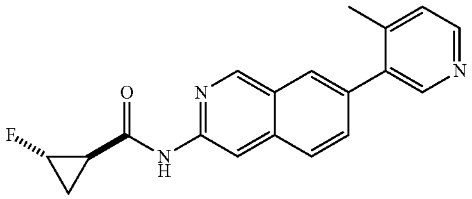 | (1R,2S)-2-fluoro-N-(7-(4-methylpyridin-3-yl)isoquinolin-3-yl)cyclopropanecarboxamide |

TABLE 1-continued

| No. | Structure | Name |
|---|---|---|
| 288 | 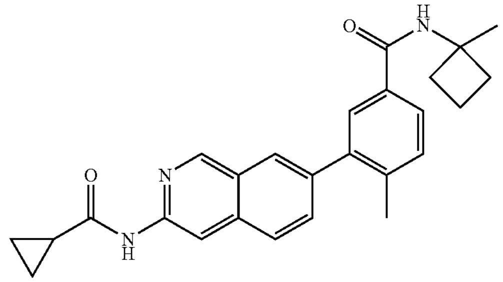 [SMILES: Cc1ccc(C(=O)NC2(C)CCC2)cc1-c1ccc2cc(NC(=O)C3CC3)ncc2c1] | 3-(3-(cyclopropanecarboxamido) isoquinolin-7-yl)-4-methyl-N-(1-methylcyclobutyl)benzamide |
| 289 | 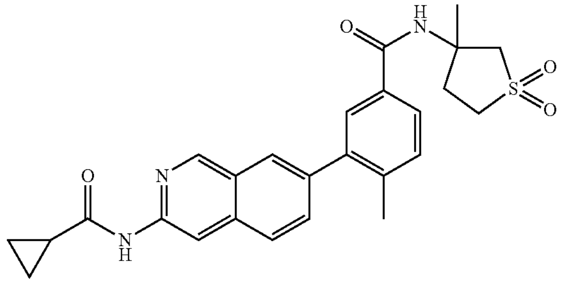 [SMILES: Cc1ccc(C(=O)NC2(C)CCS(=O)(=O)C2)cc1-c1ccc2cc(NC(=O)C3CC3)ncc2c1] | 3-(3-(cyclopropanecarboxamido) isoquinolin-7-yl)-4-methyl-N-(1,1-dioxo-3-methyltetrahydrothiophen-3-yl)benzamide |
| 290 | 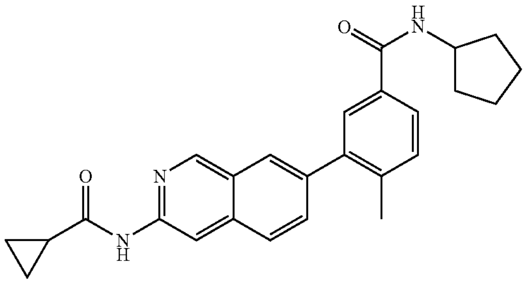 [SMILES: Cc1ccc(C(=O)NC2CCCC2)cc1-c1ccc2cc(NC(=O)C3CC3)ncc2c1] | N-cyclopentyl-3-(3-(cyclopropanecarboxamido) isoquinolin-7-yl)-4-methylbenzamide |
| 291 | 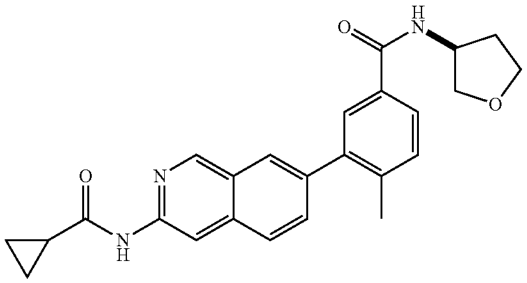 | (S)-3-(3-(cyclopropanecarboxamido) isoquinolin-7-yl)-4-methyl-N-(tetrahydrofuran-3-yl)benzamidede |
| 292 | 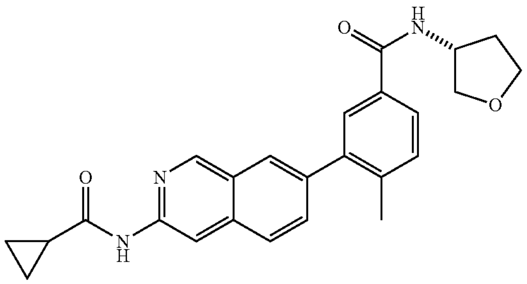 | (R)-3-(3-(cyclopropanecarboxamido) isoquinolin-7-yl)-4-methyl-N-(tetrahydrofuran-3-yl)benzamide |

TABLE 1-continued

| No. | Structure | Name |
| --- | --- | --- |
| 293 | 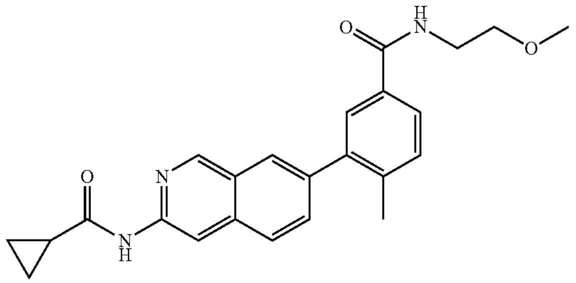 [SMILES: COCCNC(=O)c1ccc(C)c(-c2ccc3cc(NC(=O)C4CC4)ncc3c2)c1] | 3-(3-(cyclopropanecarboxamido) isoquinolin-7-yl)-N-(2-methoxyethyl)-4-methylbenzamide |
| 294 | 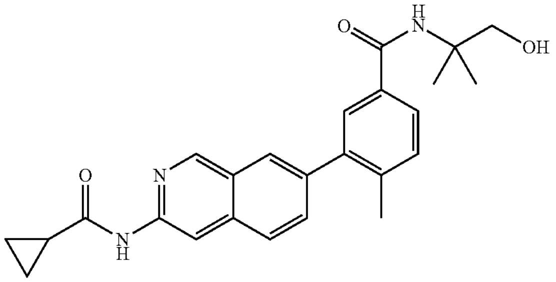 [SMILES: Cc1ccc(C(=O)NC(C)(C)CO)cc1-c1ccc2cc(NC(=O)C3CC3)ncc2c1] | 3-(3-(cyclopropanecarboxamido) isoquinolin-7-yl)-N-(1-hydroxy-2-methylpropan-2-yl)-4-methylbenzamide |
| 295 | 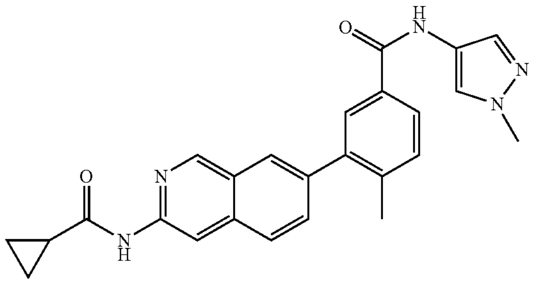 [SMILES: Cc1ccc(C(=O)Nc2cnn(C)c2)cc1-c1ccc2cc(NC(=O)C3CC3)ncc2c1] | 3-(3-(cyclopropanecarboxamido) isoquinolin-7-yl)-4-methyl-N-(1-methyl-1H-pyrazol-4-yl)benzamide |
| 296 | 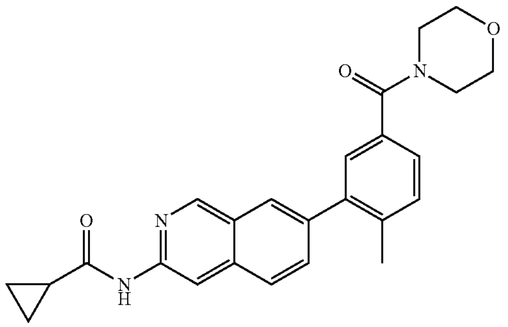 [SMILES: Cc1ccc(C(=O)N2CCOCC2)cc1-c1ccc2cc(NC(=O)C3CC3)ncc2c1] | N-(7-(2-methyl-5-(morpholine-4-carbonyl)phenyl)isoquinolin-3-yl)cyclopropanecarboxamide |
| 297 | 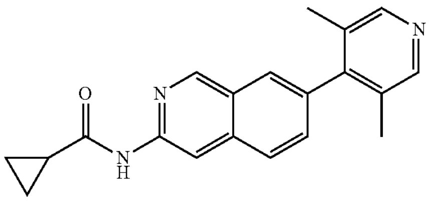 | N-(7-(3,5-dimethylpyridin-4-yl) isoquinolin-3-yl)cyclopropanecarboxamide |

TABLE 1-continued

| No. | Structure | Name |
|---|---|---|
| 298 | 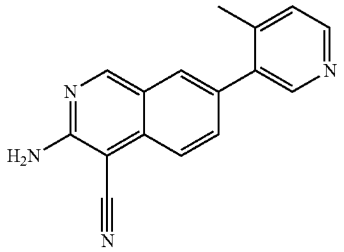 [SMILES: Cc1ccncc1-c1ccc2c(C#N)c(N)ncc2c1] | 3-amino-7-(4-methylpyridin-3-yl) isoquinoline-4-carbonitrile |
| 299 | 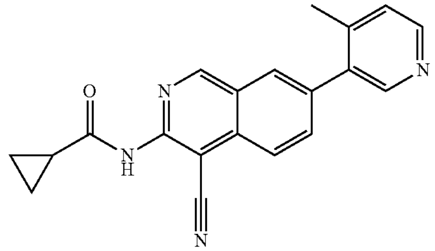 [SMILES: Cc1ccncc1-c1ccc2c(C#N)c(NC(=O)C3CC3)ncc2c1] | N-(4-cyano-7-(4-methylpyridin-3-yl)isoquinolin-3-yl)cyclopropanecarboxamide |
| 300 | 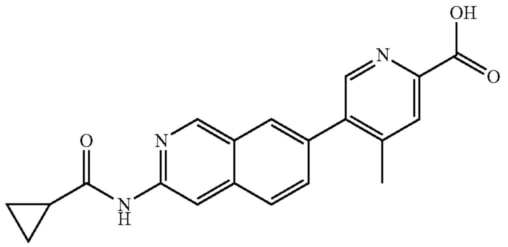 [SMILES: Cc1cc(C(=O)O)ncc1-c1ccc2cc(NC(=O)C3CC3)ncc2c1] | 5-(3-(cyclopropanecarboxamido) isoquinolin-7-yl)-4-methylpicolinic acid |
| 301 | 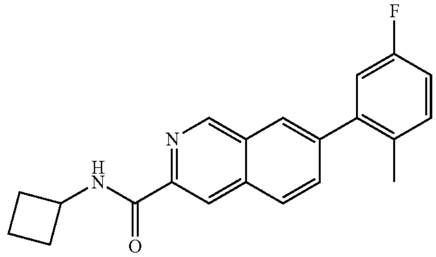 [SMILES: Cc1ccc(F)cc1-c1ccc2cc(C(=O)NC3CCC3)ncc2c1] | N-cyclobutyl-7-(5-fluoro-2-methylphenyl) isoquinoline-3-carboxamide |
| 302 | 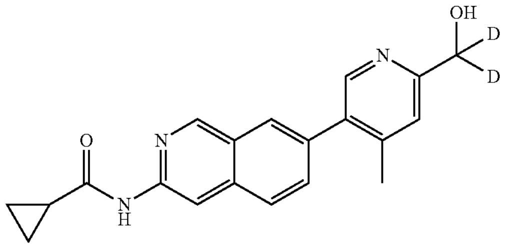 [SMILES: [2H]C([2H])(O)c1cc(C)c(-c2ccc3cc(NC(=O)C4CC4)ncc3c2)cn1] | N-(7-(6-(hydroxy(2H2)methyl)-4-methylpyridin-3-yl)isoquinolin-3-yl)cyclopropanecarboxamide |
| 303 | 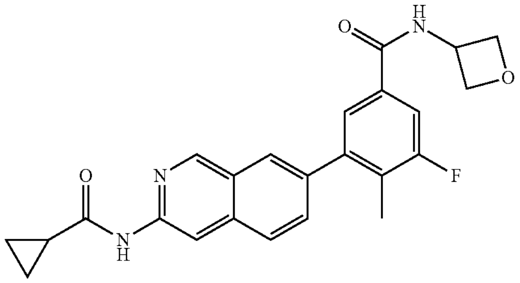 [SMILES: Cc1c(F)cc(C(=O)NC2COC2)cc1-c1ccc2cc(NC(=O)C3CC3)ncc2c1] | 3-(3-(cyclopropanecarboxamido) isoquinolin-7-yl)-5-fluoro-4-methyl-N-(oxetan-3-yl)benzamide |

TABLE 1-continued

| No. | Structure | Name |
|---|---|---|
| 304 | 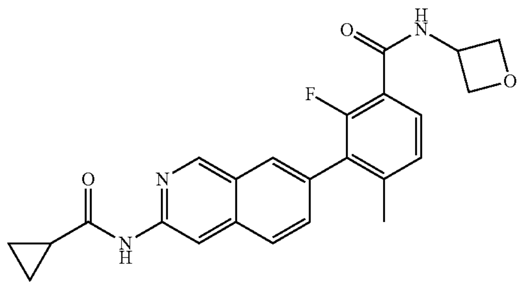 [SMILES: Cc1ccc(C(=O)NC2COC2)c(F)c1-c1ccc2cc(NC(=O)C3CC3)ncc2c1] | 3-(3-(cyclopropanecarboxamido) isoquinolin-7-yl)-2-fluoro-4-methyl-N-(oxetan-3-yl)benzamide |
| 305 | 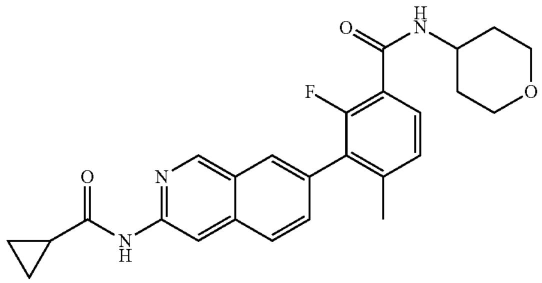 [SMILES: Cc1ccc(C(=O)NC2CCOCC2)c(F)c1-c1ccc2cc(NC(=O)C3CC3)ncc2c1] | 3-(3-(cyclopropanecarboxamido) isoquinolin-7-yl)-2-fluoro-4-methyl-N-(tetrahydro-2H-pyran-4-yl)benzamide |
| 306 | 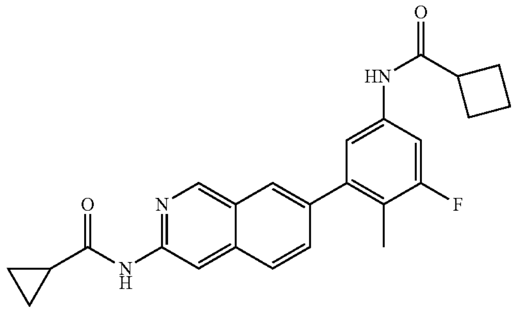 [SMILES: Cc1c(F)cc(NC(=O)C2CCC2)cc1-c1ccc2cc(NC(=O)C3CC3)ncc2c1] | N-(3-(3-(cyclopropanecarboxamido) isoquinolin-7-yl)-5-fluoro-4-methylphenyl) cyclobutanecarboxamide |
| 307 | 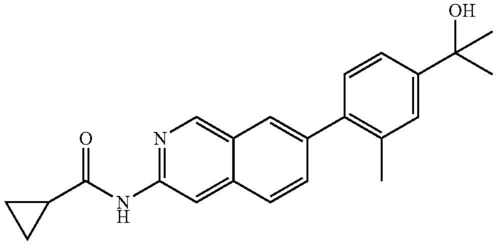 | N-(7-(4-(2-hydroxypropan-2-yl)-2-methylphenyl)isoquinolin-3-yl)cyclopropanecarboxamide |
| 308 | 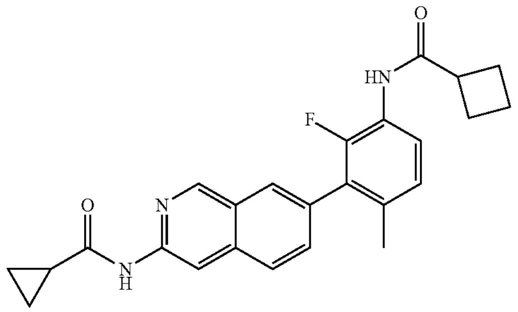 [SMILES: Cc1ccc(NC(=O)C2CCC2)c(F)c1-c1ccc2cc(NC(=O)C3CC3)ncc2c1] | N-(3-(3-(cyclopropanecarboxamido) isoquinolin-7-yl)-2-fluoro-4-methylphenyl) cyclobutanecarboxamide |

TABLE 1-continued

| No. | Structure | Name |
|---|---|---|
| 309 | 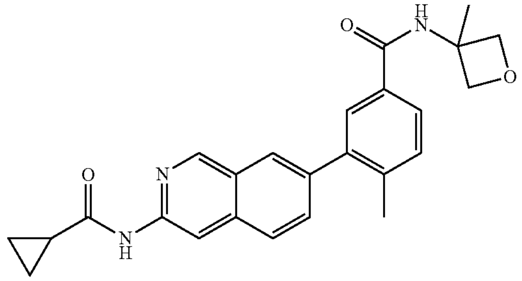 [SMILES: Cc1ccc(C(=O)NC2(C)COC2)cc1-c1ccc2cc(NC(=O)C3CC3)ncc2c1] | 3-(3-(cyclopropanecarboxamido) isoquinolin-7-yl)-4-methyl-N-(3-methyloxetan-3-yl)benzamide |
| 310 | 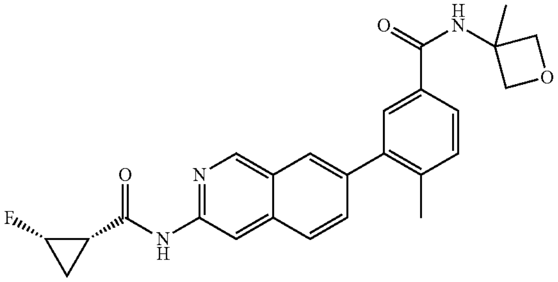 [SMILES: Cc1ccc(C(=O)NC2(C)COC2)cc1-c1ccc2cc(NC(=O)[C@@H]3C[C@@H]3F)ncc2c1] | 3-(3-((1S,2S)-2-fluorocyclopropanecarboxamido) isoquinolin-7-yl)-4-methyl-N-(3-methyloxetan-3-yl)benzamide |
| 311 | 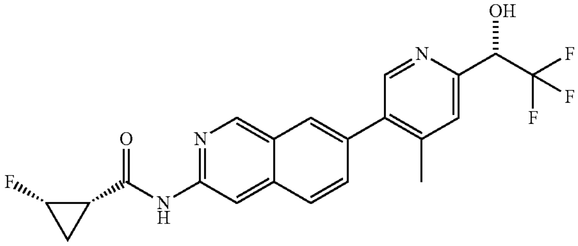 | 2-fluoro-N-(7-(4-methyl-6-(2,2,2-trifluoro-1-hydroxyethyl)pyridin-3-yl)isoquinolin-3-yl) cyclopropanecarboxamide |
| 312 | 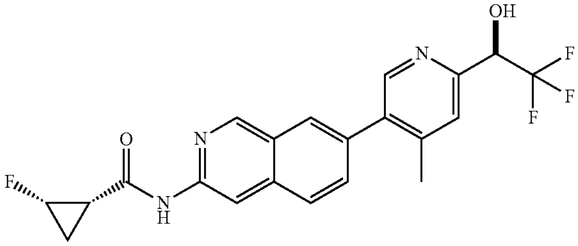 [SMILES: Cc1cc([C@@H](O)C(F)(F)F)ncc1-c1ccc2cc(NC(=O)[C@@H]3C[C@@H]3F)ncc2c1] | (1S,2S)-2-fluoro-N-(7-(4-methyl-6-((R)-2,2,2-trifluoro-1-hydroxyethyl) pyridin-3-yl)isoquinolin-3-yl) cyclopropanecarboxamide |
| 313 | 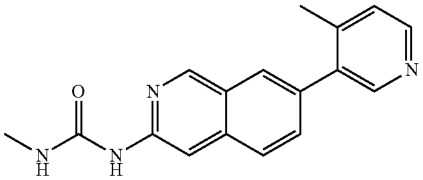 [SMILES: CNC(=O)Nc1cc2ccc(-c3cnccc3C)cc2cn1] | 1-methyl-3-(7-(4-methylpyridin-3-yl)isoquinolin-3-yl)urea |
| 314 | 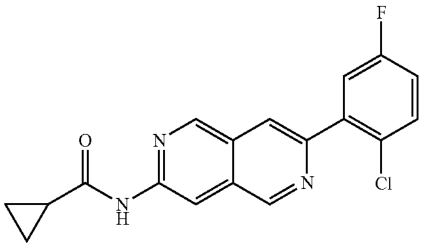 [SMILES: O=C(Nc1cc2cnc(-c3cc(F)ccc3Cl)cc2cn1)C1CC1] | N-(7-(2-chloro-5-fluorophenyl)-2,6-naphthyridin-3-yl)cyclopropanecarboxamide |

TABLE 1-continued

| No. | Structure | Name |
|---|---|---|
| 315 | 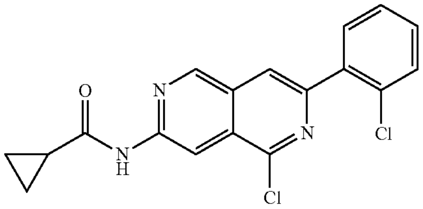 [SMILES: O=C(Nc1cc2c(Cl)nc(-c3ccccc3Cl)cc2cn1)C1CC1] | N-(5-chloro-7-(2-chlorophenyl)-2,6-naphthyridin-3-yl)cyclopropanecarboxamide |
| 316 | 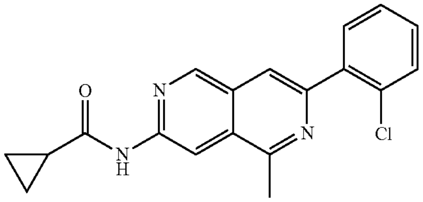 [SMILES: Cc1nc(-c2ccccc2Cl)cc2cnc(NC(=O)C3CC3)cc12] | N-(7-(2-chlorophenyl)-5-methyl-2,6-naphthyridin-3-yl) cyclopropanecarboxamide |
| 317 | 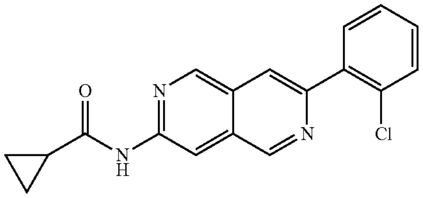 | N-(7-(2-chlorophenyl)-2,6-naphthyridin-3-yl) cyclopropanecarboxamide |
| 318 | 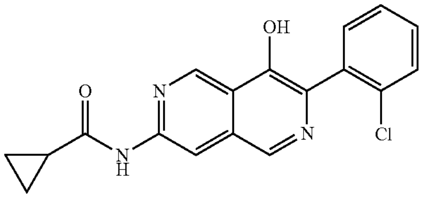 [SMILES: O=C(Nc1cc2cnc(-c3ccccc3Cl)c(O)c2cn1)C1CC1] | N-(7-(2-chlorophenyl)-8-hydroxy-2,6-naphthyridin-3-yl)cyclopropanecarboxamide |
| 319 | 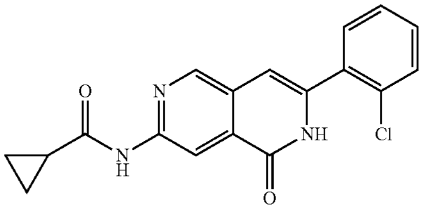 [SMILES: O=C(Nc1cc2c(=O)[nH]c(-c3ccccc3Cl)cc2cn1)C1CC1] | N-(7-(2-chlorophenyl)-5-oxo-5,6-dihydro-2,6-naphthyridin-3-yl)cyclopropanecarboxamide |
| 320 | 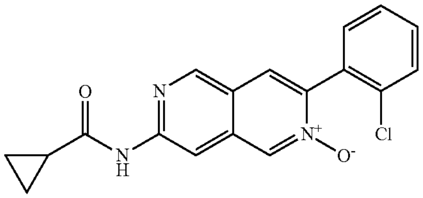 [SMILES: O=C(Nc1cc2c[n+]([O-])c(-c3ccccc3Cl)cc2cn1)C1CC1] | 3-(2-chlorophenyl)-7-(cyclopropanecarboxamido)-2,6-naphthyridine 2-oxide |
| 321 | 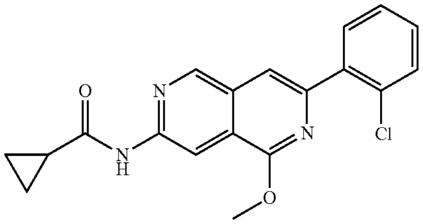 | N-(7-(2-chlorophenyl)-5-methoxy-2,6-naphthyridine-3-yl)cyclopropanecarboxamide |

TABLE 1-continued

| No. | Structure | Name |
|---|---|---|
| 322 | 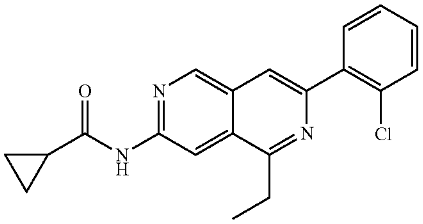 [SMILES: CCc1nc(-c2ccccc2Cl)cc2cnc(NC(=O)C3CC3)cc12] | N-(7-(2-chlorophenyl)-5-ethyl-2,6-naphthyridin-3-yl)cyclopropanecarboxamide |
| 323 | 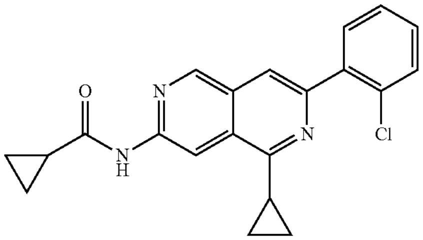 [SMILES: O=C(Nc1cc2c(C3CC3)nc(-c3ccccc3Cl)cc2cn1)C1CC1] | N-(7-(2-chlorophenyl)-5-cyclopropyl-2,6-naphthyridin-3-yl)cyclopropanecarboxamide |
| 324 | 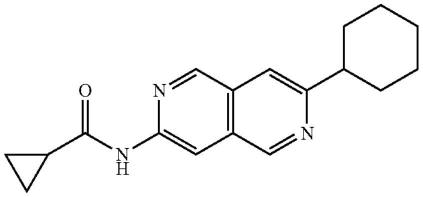 [SMILES: O=C(Nc1cc2cnc(C3CCCCC3)cc2cn1)C1CC1] | N-(7-cyclohexyl-2,6-naphthyridin-3-yl)cyclopropanecarboxamide |
| 325 | 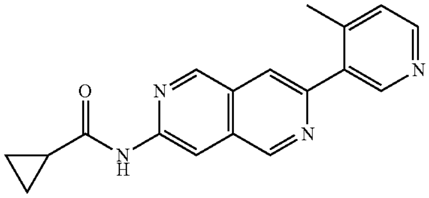 [SMILES: Cc1ccncc1-c1cc2cnc(NC(=O)C3CC3)cc2cn1] | N-(7-(4-methylpyridin-3-yl)-2,6-naphthyridin-3-yl) cyclopropanecarboxamide |
| 326 | 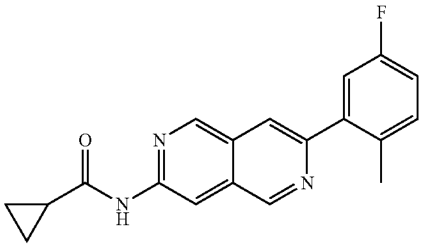 [SMILES: Cc1ccc(F)cc1-c1cc2cnc(NC(=O)C3CC3)cc2cn1] | N-(7-(5-fluoro-2-methylphenyl)-2,6-naphthyridin-3-yl) cyclopropanecarboxamide |
| 327 | 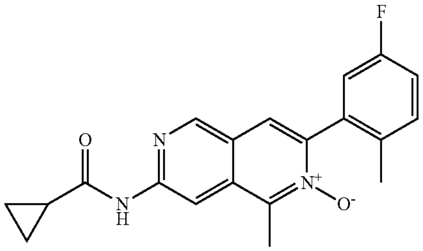 [SMILES: Cc1ccc(F)cc1-c1cc2cnc(NC(=O)C3CC3)cc2c(C)[n+]1[O-]] | 7-(cyclopropanecarboxamido)-3-(5-fluoro-2-methylphenyl)-1-methyl-2,6-naphthyridine 2-oxide |

TABLE 1-continued

| No. | Structure | Name |
| --- | --- | --- |
| 328 | 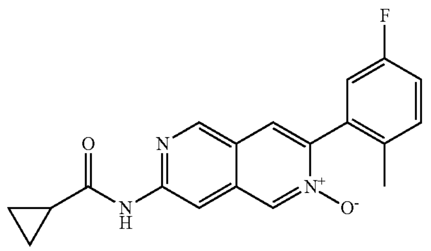 [SMILES: Cc1ccc(F)cc1-c1cc2cnc(NC(=O)C3CC3)cc2c[n+]1[O-]] | 7-(cyclopropanecarboxamido)-3-(5-fluoro-2-methylphenyl)-2,6-naphthyridine 2-oxide |
| 329 | 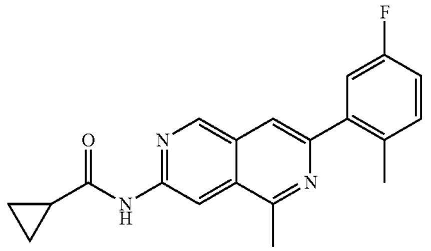 [SMILES: Cc1ccc(F)cc1-c1cc2cnc(NC(=O)C3CC3)cc2c(C)n1] | N-(7-(5-fluoro-2-methylphenyl)-5-methyl-2,6-naphthyridin-3-yl)cyclopropanecarboxamide |
| 330 | 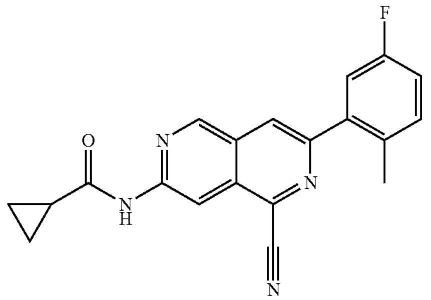 [SMILES: Cc1ccc(F)cc1-c1cc2cnc(NC(=O)C3CC3)cc2c(C#N)n1] | N-(5-cyano-7-(5-fluoro-2-methylphenyl)-2,6-naphthyridin-3-yl)cyclopropanecarboxamide |
| 331 | 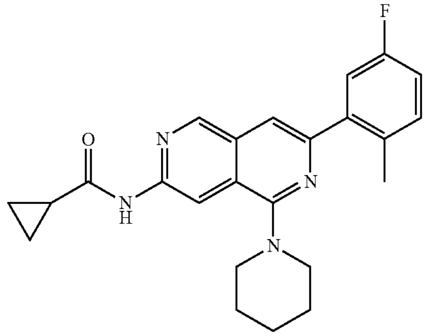 [SMILES: Cc1ccc(F)cc1-c1cc2cnc(NC(=O)C3CC3)cc2c(N2CCCCC2)n1] | N-(7-(5-fluoro-2-methylphenyl)-5-(piperidin-1-yl)-2,6-naphthyridin-3-yl)cyclopropanecarboxamide |
| 332 | 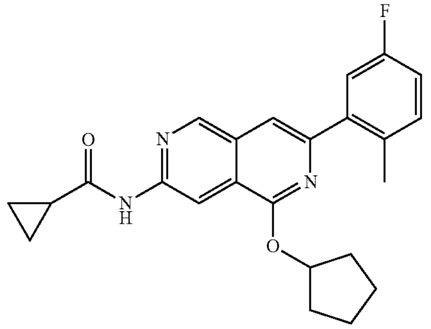 [SMILES: Cc1ccc(F)cc1-c1cc2cnc(NC(=O)C3CC3)cc2c(OC2CCCC2)n1] | N-(5-(cyclopentyloxy)-7-(5-fluoro-2-methylphenyl)-2,6-naphthyridin-3-yl)cyclopropanecarboxamide |

TABLE 1-continued
| No. | Structure | Name |
|---|---|---|
| 333 | 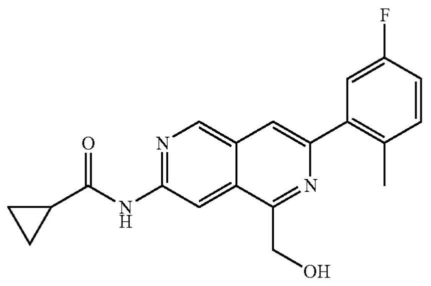 [SMILES: Cc1ccc(F)cc1-c1cc2cnc(NC(=O)C3CC3)cc2c(CO)n1] | N-(7-(5-fluoro-2-methylphenyl)-5-(hydroxymethyl)-2,6-naphthyridin-3-yl)cyclopropanecarboxamide |
| 334 | 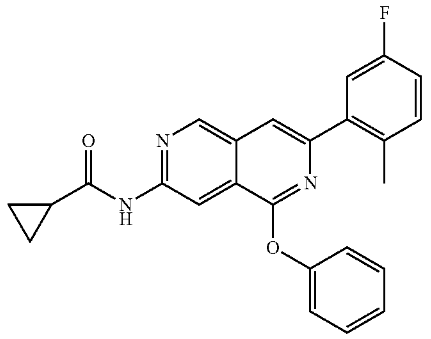 [SMILES: Cc1ccc(F)cc1-c1cc2cnc(NC(=O)C3CC3)cc2c(Oc2ccccc2)n1] | N-(7-(5-fluoro-2-methylphenyl)-5-phenoxy-2,6-naphthyridin-3-yl)cyclopropanecarboxamide |
| 335 | 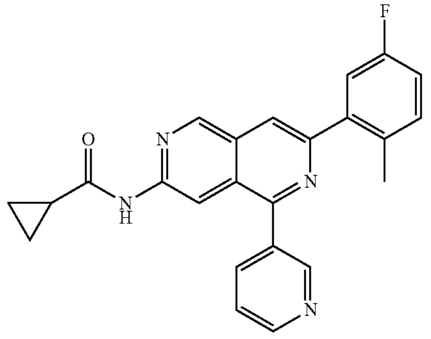 [SMILES: Cc1ccc(F)cc1-c1cc2cnc(NC(=O)C3CC3)cc2c(-c2cccnc2)n1] | N-(7-(5-fluoro-2-methylphenyl)-5-(pyridin-3-yl)-2,6-naphthyridin-3-yl)cyclopropanecarboxamide |
| 336 | 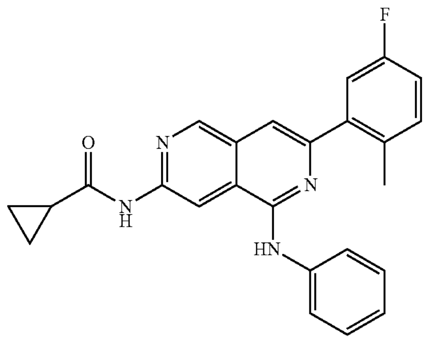 [SMILES: Cc1ccc(F)cc1-c1cc2cnc(NC(=O)C3CC3)cc2c(Nc2ccccc2)n1] | N-(7-(5-fluoro-2-methylphenyl)-5-(phenylamino)-2,6-naphthyridin-3-yl)cyclopropanecarboxamide |

TABLE 1-continued

| No. | Structure | Name |
|---|---|---|
| 337 | 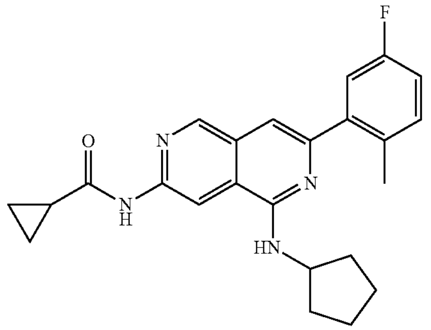 [SMILES: Cc1ccc(F)cc1-c1cc2cnc(NC(=O)C3CC3)cc2c(NC2CCCC2)n1] | N-(5-(cyclopentylamino)-7-(5-fluoro-2-methylphenyl)-2,6-naphthyridin-3-yl)cyclopropanecarboxamide |
| 338 | 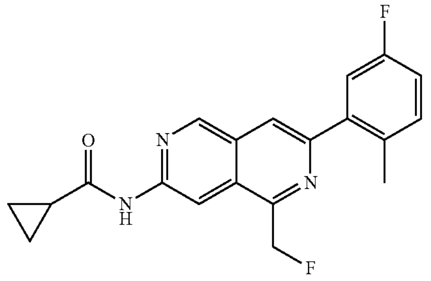 [SMILES: Cc1ccc(F)cc1-c1cc2cnc(NC(=O)C3CC3)cc2c(CF)n1] | N-(7-(5-fluoro-2-methylphenyl)-5-(fluoromethyl)-2,6-naphthyridin-3-yl)cyclopropanecarboxamide |
| 339 | 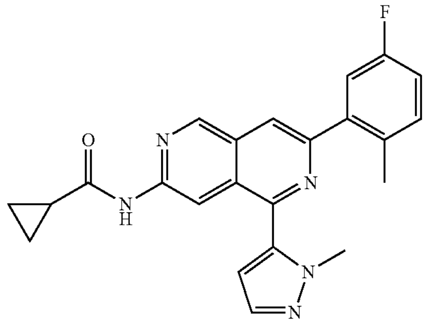 [SMILES: Cc1ccc(F)cc1-c1cc2cnc(NC(=O)C3CC3)cc2c(-c2ccnn2C)n1] | N-(7-(5-fluoro-2-methylphenyl)-5-(1-methyl-1H-pyrazol-5-yl)-2,6-naphthyridin-3-yl)cyclopropanecarboxamide |
| 340 | 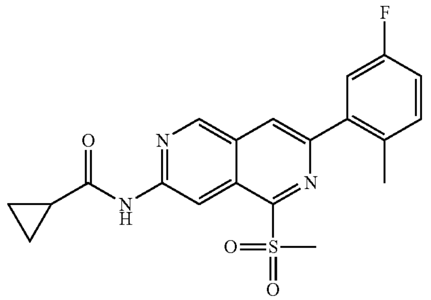 [SMILES: Cc1ccc(F)cc1-c1cc2cnc(NC(=O)C3CC3)cc2c(S(C)(=O)=O)n1] | N-(7-(5-fluoro-2-methylphenyl)-5-(methylsulfonyl)-2,6-naphthyridin-3-yl)cyclopropanecarboxamide |
| 341 | 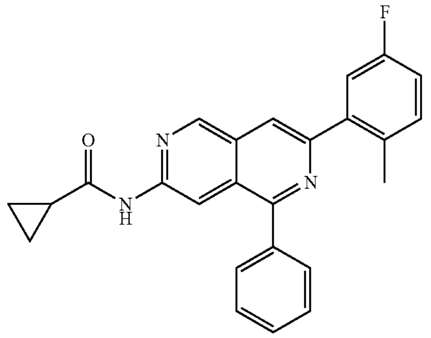 [SMILES: Cc1ccc(F)cc1-c1cc2cnc(NC(=O)C3CC3)cc2c(-c2ccccc2)n1] | N-(7-(5-fluoro-2-methylphenyl)-5-phenyl-2,6-naphthyridin-3-yl)cyclopropanecarboxamide |

TABLE 1-continued

| No. | Structure | Name |
| --- | --- | --- |
| 342 | 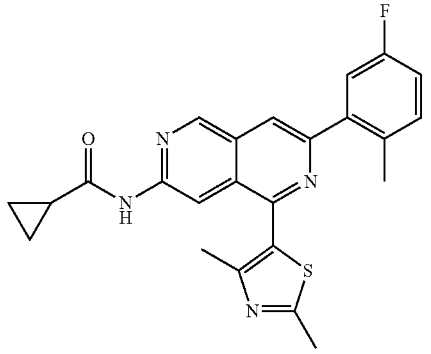 [SMILES: Cc1nc(C)c(-c2nc(-c3cc(F)ccc3C)cc3cnc(NC(=O)C4CC4)cc23)s1] | N-(5-(2,4-dimethylthiazol-5-yl)-7-(5-fluoro-2-methylphenyl)-2,6-naphthyridin-3-yl)cyclopropanecarboxamide |
| 343 | 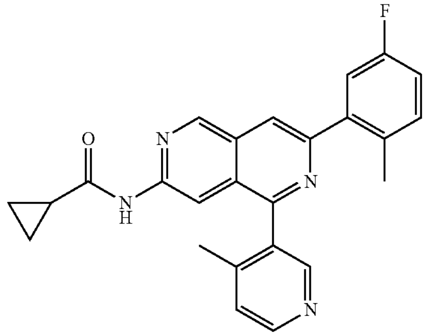 [SMILES: Cc1ccc(F)cc1-c1cc2cnc(NC(=O)C3CC3)cc2c(-c2cnccc2C)n1] | N-(7-(5-fluoro-2-methylphenyl)-5-(4-methylpyridin-3-yl)-2,6-naphthyridin-3-yl)cyclopropanecarboxamide |
| 344 | 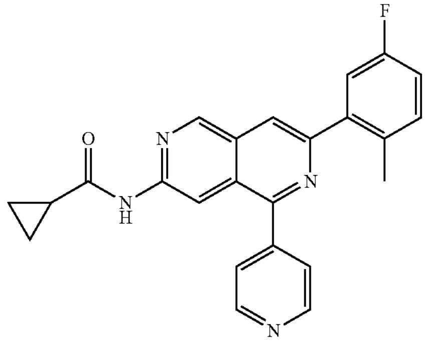 [SMILES: Cc1ccc(F)cc1-c1cc2cnc(NC(=O)C3CC3)cc2c(-c2ccncc2)n1] | N-(7-(5-fluoro-2-methylphenyl)-5-(pyridin-4-yl)-2,6-naphthyridin-3-yl)cyclopropanecarboxamide |
| 345 | 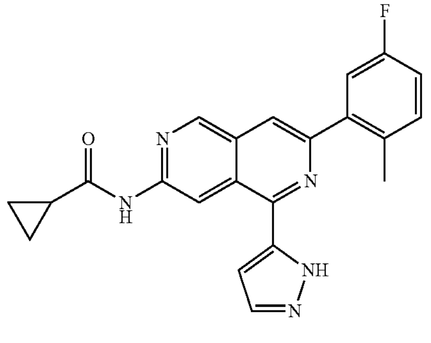 [SMILES: Cc1ccc(F)cc1-c1cc2cnc(NC(=O)C3CC3)cc2c(-c2ccn[nH]2)n1] | N-(7-(5-fluoro-2-methylphenyl)-5-(1H-pyrazol-5-yl)-2,6-naphthyridin-3-yl)cyclopropecarboxamide |

TABLE 1-continued

| No. | Structure | Name |
|---|---|---|
| 346 | 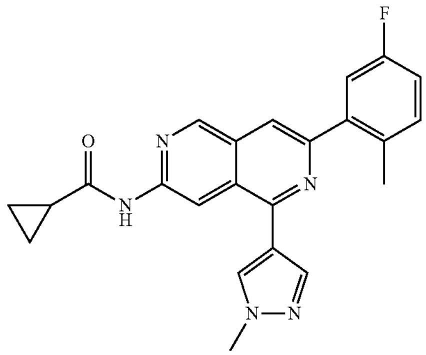 [SMILES: Cc1ccc(F)cc1-c1cc2cnc(NC(=O)C3CC3)cc2c(-c2cnn(C)c2)n1] | N-(7-(5-fluoro-2-methylphenyl)-5-(1-methyl-1H-pyrazol-4-yl)-2,6-naphthyridin-3-yl) cyclopropanecarboxamide |
| 347 | 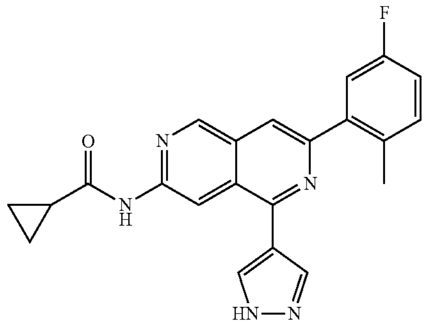 [SMILES: Cc1ccc(F)cc1-c1cc2cnc(NC(=O)C3CC3)cc2c(-c2cn[nH]c2)n1] | N-(7-(5-fluoro-2-methylphenyl)-5-(1H-pyrazol-4-yl)-2,6-naphthyridin-3-yl)cyclopropanecarboxamide |
| 348 | 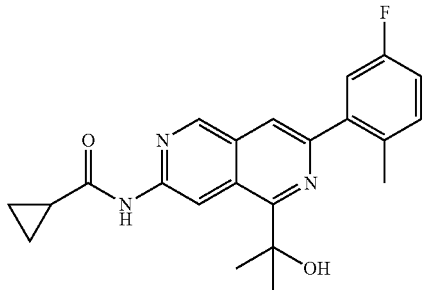 [SMILES: Cc1ccc(F)cc1-c1cc2cnc(NC(=O)C3CC3)cc2c(C(C)(C)O)n1] | N-(7-(5-fluoro-2-methylphenyl)-5-(2-hydroxypropan-2-yl)-2,6-naphthyridin-3-yl)cyclopropanecarboxamide |
| 349 | 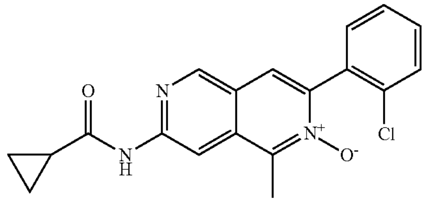 [SMILES: Cc1c2cc(NC(=O)C3CC3)ncc2cc(-c2ccccc2Cl)[n+]1[O-]] | 3-(2-chlorophenyl)-7-(cyclopropanecarboxamido)-1-methyl-2,6-naphthyridine 2-oxide |
| 350 | 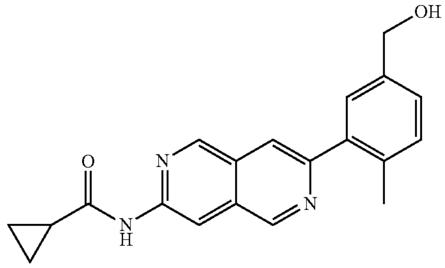 [SMILES: Cc1ccc(CO)cc1-c1cc2cnc(NC(=O)C3CC3)cc2cn1] | N-(7-(5-(hydroxymethyl)-2-methyl phenyl)-2,6-naphthyridin-3-yl)cyclopropanecarboxamide |

TABLE 1-continued

| No. | Structure | Name |
|---|---|---|
| 351 | 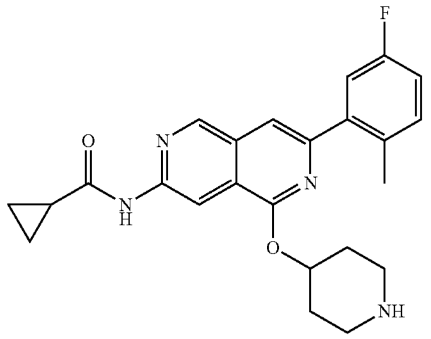 [SMILES: Cc1ccc(F)cc1-c1cc2cnc(NC(=O)C3CC3)cc2c(OC2CCNCC2)n1] | N-(7-(5-fluoro-2-methylphenyl)-5-(piperidin-4-yloxy)-2,6-naphthyridin-3-yl)cyclopropanecarboxamide |
| 352 | 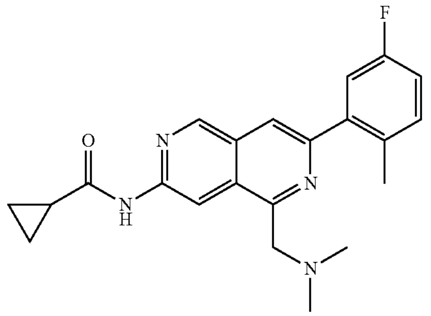 [SMILES: Cc1ccc(F)cc1-c1cc2cnc(NC(=O)C3CC3)cc2c(CN(C)C)n1] | N-(5-((dimethylamino)methyl)-7-(5-fluoro-2-methylphenyl)-2,6-naphthyridin-3-yl) cyclopropanecarboxamide |
| 353 | 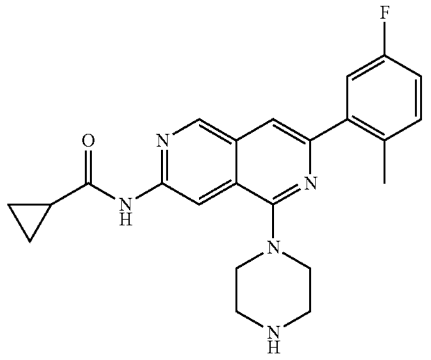 [SMILES: Cc1ccc(F)cc1-c1cc2cnc(NC(=O)C3CC3)cc2c(N2CCNCC2)n1] | N-(7-(5-fluoro-2-methylphenyl)-5-(piperazin-1-yl)-2,6-naphthyridin-3-yl)cyclopropanecarboxamide |
| 354 | 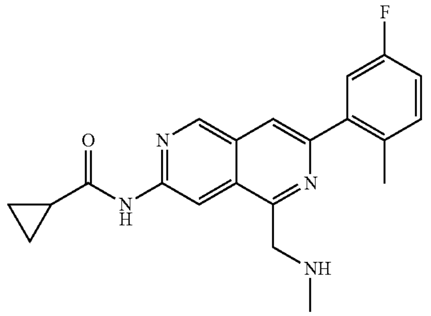 [SMILES: CNCc1nc(-c2cc(F)ccc2C)cc2cnc(NC(=O)C3CC3)cc12] | N-(7-(5-fluoro-2-methylphenyl)-5-((methylamino)methyl)-2,6-naphthyridin-3-yl)cyclopropanecarboxamide |

TABLE 1-continued

| No. | Structure | Name |
|---|---|---|
| 355 | 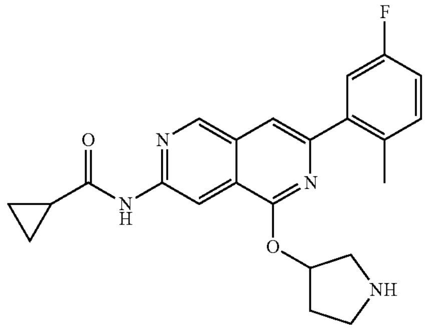 [SMILES: Cc1ccc(F)cc1-c1cc2cnc(NC(=O)C3CC3)cc2c(OC2CCNC2)n1] | N-(7-(5-fluoro-2-methylphenyl)-5-(pyrrolidin-3-yloxy)-2,6-naphthyridin-3-yl)cyclopropanecarboxamide |
| 356 | 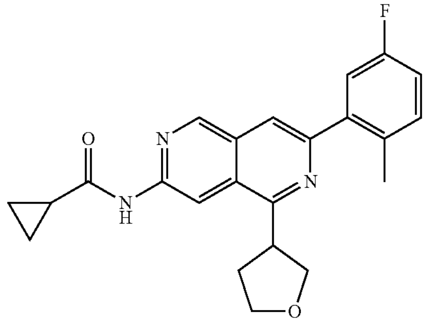 [SMILES: Cc1ccc(F)cc1-c1cc2cnc(NC(=O)C3CC3)cc2c(C2CCOC2)n1] | N-(7-(5-fluoro-2-methylphenyl)-5-(tetrahydrofuran-3-yl)-2,6-naphthyridin-3-yl)cyclopropanecarboxamide |
| 357 | 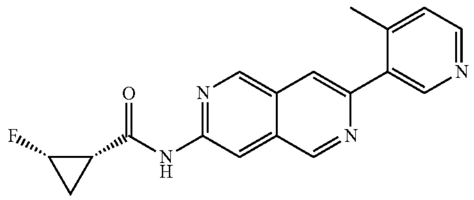 [SMILES: Cc1ccncc1-c1cc2cnc(NC(=O)[C@@H]3C[C@@H]3F)cc2cn1] | (1S,2S)-2-fluoro-N-(7-(4-methylpyridin-3-yl)-2,6-naphthyridin-3-yl)cyclopropanecarboxamide |
| 358 | 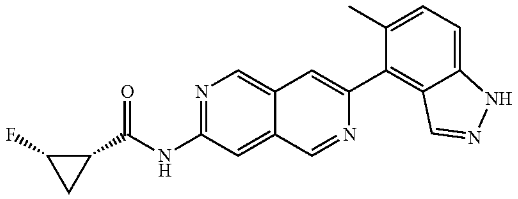 [SMILES: Cc1ccc2[nH]ncc2c1-c1cc2cnc(NC(=O)[C@@H]3C[C@@H]3F)cc2cn1] | (1S,2S)-2-fluoro-N-(7-(5-methyl-1 H-indazol-4-yl)-2,6-naphthyridin-3-yl)cyclopropanecarboxamide |
| 359 | 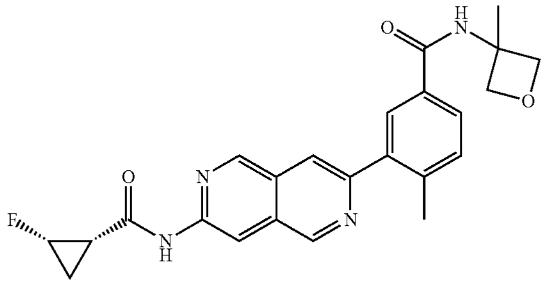 [SMILES: Cc1ccc(C(=O)NC2(C)COC2)cc1-c1cc2cnc(NC(=O)[C@@H]3C[C@@H]3F)cc2cn1] | 3-(7-((1S,2S)-2-fluorocyclopropane-carboxamido)-2,6-naphthyridin-3-yl)-4-methyl-N-(3-methyloxetan-3-yl)benzamide |

TABLE 1-continued

| No. | Structure | Name |
| --- | --- | --- |
| 360 | 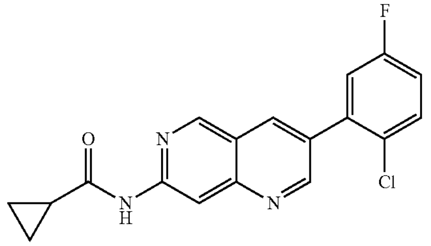 [SMILES: O=C(Nc1cc2ncc(-c3cc(F)ccc3Cl)cc2cn1)C1CC1] | N-(3-(2-chloro-5-fluorophenyl)-1,6-naphthyridin-7-yl) cyclopropanecarboxamide |
| 361 | 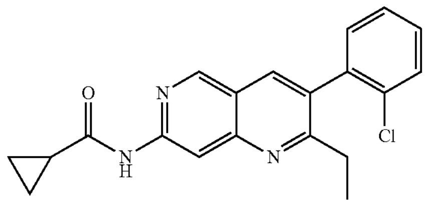 [SMILES: CCc1nc2cc(NC(=O)C3CC3)ncc2cc1-c1ccccc1Cl] | N-(3-(2-chlorophenyl)-2-ethyl-1,6-naphthyridin-7-yl) cyclopropanecarboxamide |
| 362 | 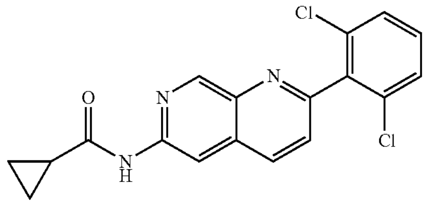 [SMILES: O=C(Nc1cc2ccc(-c3c(Cl)cccc3Cl)nc2cn1)C1CC1] | N-(2-(2,6-dichlorophenyl)-1,7-naphthyridin-6-yl) cyclopropanecarboxamide |
| 363 | 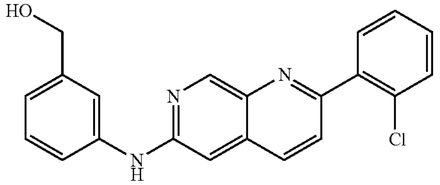 [SMILES: OCc1cccc(Nc2cc3ccc(-c4ccccc4Cl)nc3cn2)c1] | (3-(2-(2-chlorophenyl)-1,7-naphthyridin-6-ylamino)phenyl)methanol |
| 364 | 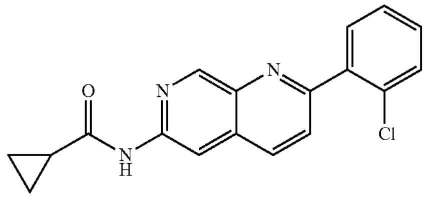 [SMILES: O=C(Nc1cc2ccc(-c3ccccc3Cl)nc2cn1)C1CC1] | N-(2-(2-chlorophenyl)-1,7-naphthyridin-6-yl)cyclopropanecarboxamide |
| 365 | 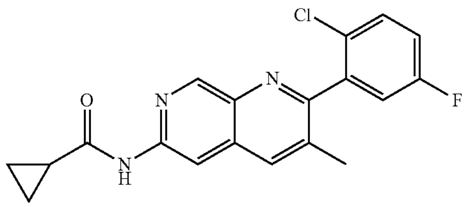 [SMILES: Cc1cc2cc(NC(=O)C3CC3)ncc2nc1-c1cc(F)ccc1Cl] | N-(2-(2-chloro-5-fluorophenyl)-3-methyl-1,7-naphthyridin-6-yl)cyclopropanecarboxamide |
| 366 | 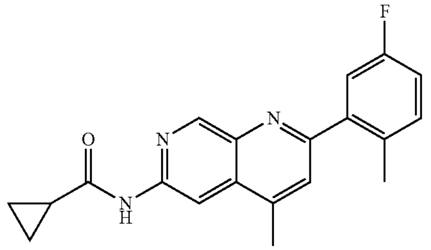 [SMILES: Cc1ccc(F)cc1-c1cc(C)c2cc(NC(=O)C3CC3)ncc2n1] | N-(2-(5-fluoro-2-methylphenyl)-4-methyl-1,7-naphthyridin-6-yl)cyclopropanecarboxamide |

TABLE 1-continued

| No. | Structure | Name |
|---|---|---|
| 367 | 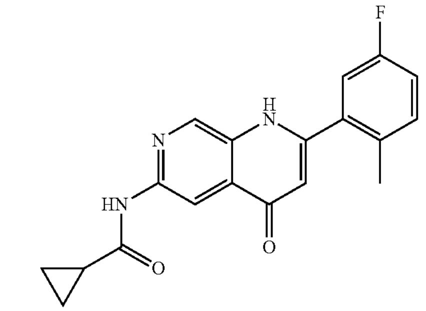 [SMILES: Cc1ccc(F)cc1-c1cc(=O)c2cc(NC(=O)C3CC3)ncc2[nH]1] | N-(2-(5-fluoro-2-methylphenyl)-4-oxo-1,4-dihydro-1,7-naphthyridin-6-yl)cyclopropanecarboxamide |
| 368 | 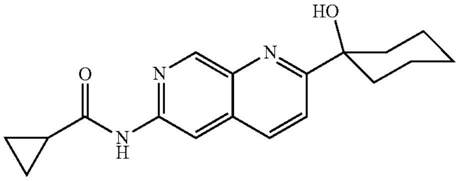 [SMILES: O=C(Nc1cc2ccc(C3(O)CCCCC3)nc2cn1)C1CC1] | N-(2-(1-hydroxycyclohexyl)-1,7-naphthyridin-6-yl)cyclopropanecarboxamide |
| 369 | 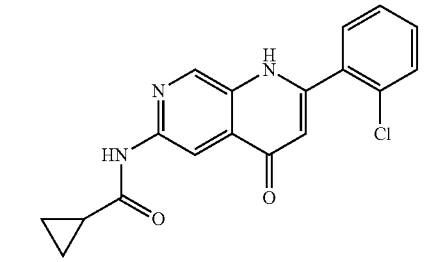 [SMILES: O=C(Nc1cc2c(=O)cc(-c3ccccc3Cl)[nH]c2cn1)C1CC1] | N-(2-(2-chlorophenyl)-4-oxo-1,4-dihydro-1,7-naphthyridin-6-yl)cyclopropanecarboxamide |
| 370 | 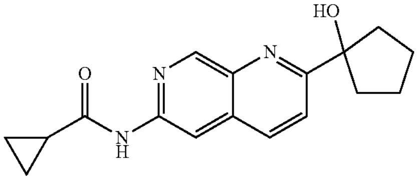 [SMILES: O=C(Nc1cc2ccc(C3(O)CCCC3)nc2cn1)C1CC1] | N-(2-(1-hydroxycyclopentyl)-1,7-naphthyridin-6-yl)cyclopropanecarboxamide |
| 371 | 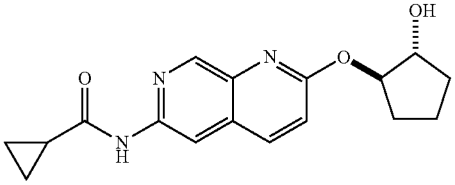 | N-(7-((1R,2R)-2-hydroxycyclopentyloxy) isoquinolin-3-yl) cyclopropanecarboxamide |

TABLE 1b

| No. | Structure | Name |
|---|---|---|
| 372 | 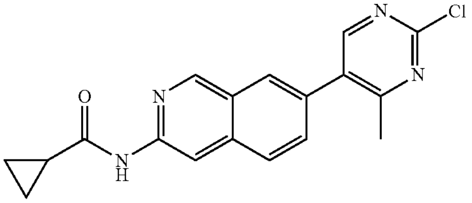 [SMILES: Cc1nc(Cl)ncc1-c1ccc2cc(NC(=O)C3CC3)ncc2c1] | Cyclopropanecarboxylic acid [7-(2-chloro-4-methyl-pyrimidin-5-yl)-isoquinolin-3-yl]-amide |

TABLE 1b-continued

| No. | Structure | Name |
|---|---|---|
| 373 | 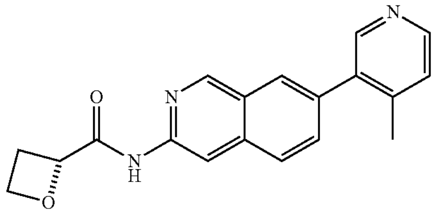 | (R)-N-(7-(4-methylpyridin-3-yl) isoquinolin-3-yl)oxetane-2-carboxamide |
| 374 | 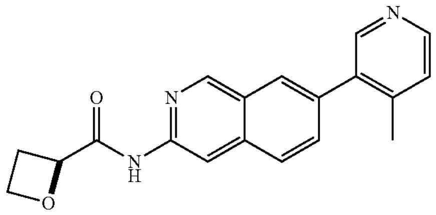 | (S)-N-(7-(4-methylpyridin-3-yl) isoquinolin-3-yl)oxetane-2-carboxamide |
| 375 | 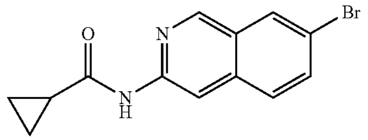 [SMILES: O=C(Nc1cc2ccc(Br)cc2cn1)C1CC1] | Cyclopropanecarboxylic acid (7-bromo-isoquinolin-3-yl)-amide |
| 376 | 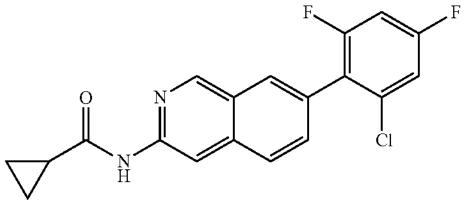 [SMILES: O=C(Nc1cc2ccc(-c3c(F)cc(F)cc3Cl)cc2cn1)C1CC1] | Cyclopropanecarboxylic acid [7-(2-chloro-4,6-difluoro-phenyl)-isoquinolin-3-yl]-amide |
| 377 | 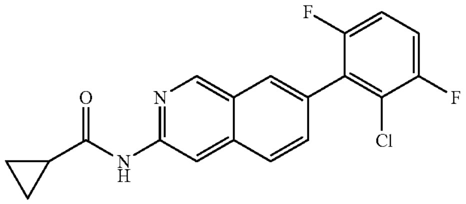 [SMILES: O=C(Nc1cc2ccc(-c3c(F)ccc(F)c3Cl)cc2cn1)C1CC1] | Cyclopropanecarboxylic acid [7-(2-chloro-3,6-difluoro-phenyl)-isoquinolin-3-yl]-amide |
| 378 | 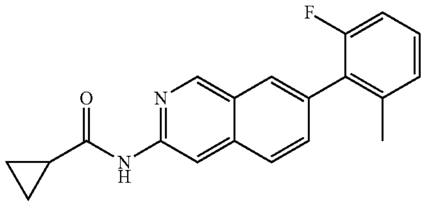 [SMILES: Cc1cccc(F)c1-c1ccc2cc(NC(=O)C3CC3)ncc2c1] | Cyclopropanecarboxylic acid [7-(2-fluoro-6-methyl-phenyl)-isoquinolin-3-yl]-amide |
| 379 | 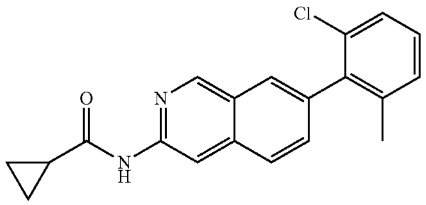 [SMILES: Cc1cccc(Cl)c1-c1ccc2cc(NC(=O)C3CC3)ncc2c1] | Cyclopropanecarboxylic acid [7-(2-chloro-6-methyl-phenyl)-isoquinolin-3-yl]-amide |

TABLE 1b-continued

| No. | Structure | Name |
|---|---|---|
| 380 | 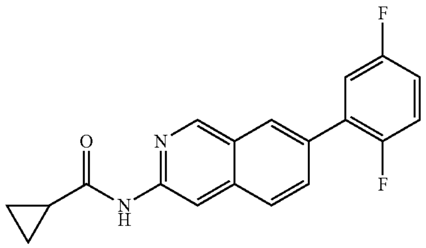 [SMILES: Cc1ccc(F)cc1-c1ccc2cc(NC(=O)C3CC3)ncc2c1] | Cyclopropanecarboxylic acid [7-(2,5-difluoro-phenyl)-isoquinolin-3-yl]-amide |
| 381 | 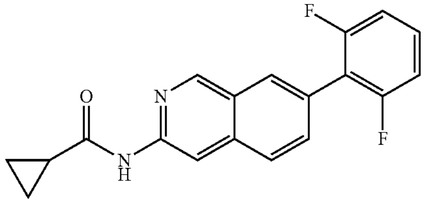 | Cyclopropanecarboxylic acid [7-(2,6-difluoro-phenyl)-isoquinolin-3-yl]-amide |
| 382 | 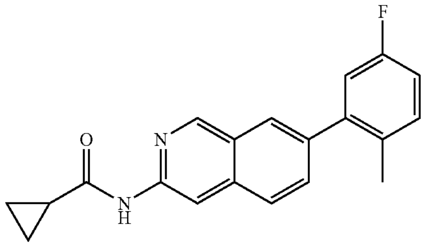 | Cyclopropanecarboxylic acid [7-(5-fluoro-2-methyl-phenyl)-isoquinolin-3-yl]-amide |
| 383 | 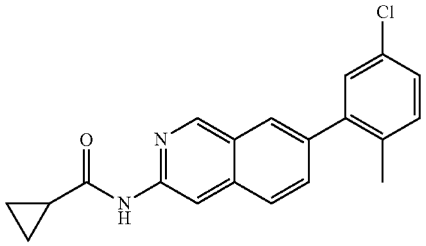 [SMILES: Cc1ccc(Cl)cc1-c1ccc2cc(NC(=O)C3CC3)ncc2c1] | Cyclopropanecarboxylic acid [7-(5-chloro-2-methyl-phenyl)-isoquinolin-3-yl]-amide |
| 384 | 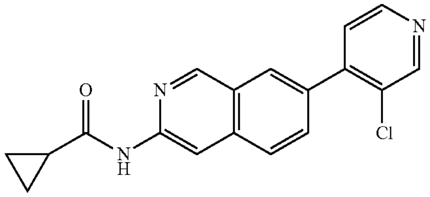 [SMILES: O=C(Nc1cc2ccc(-c3ccncc3Cl)cc2cn1)C1CC1] | Cyclopropanecarboxylic acid [7-(3-chloro-pyridin-4-yl)-isoquinolin-3-yl]-amide |
| 385 | 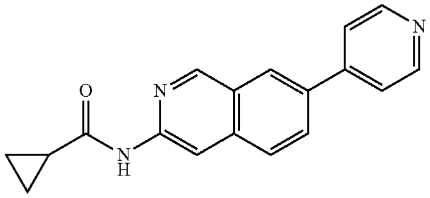 [SMILES: O=C(Nc1cc2ccc(-c3ccncc3)cc2cn1)C1CC1] | Cyclopropanecarboxylic acid (7-pyridin-4-yl-isoquinolin-3-yl)-amide |
| 386 | 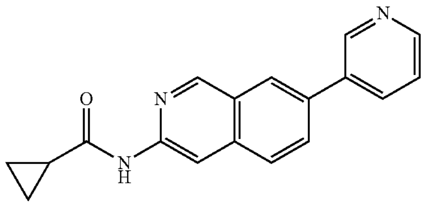 [SMILES: O=C(Nc1cc2ccc(-c3cccnc3)cc2cn1)C1CC1] | Cyclopropanecarboxylic acid (7-pyridin-3-yl-isoquinolin-3-yl)-amide |

TABLE 1b-continued

| No. | Structure | Name |
|---|---|---|
| 387 | 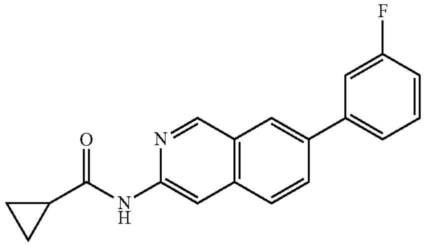 | Cyclopropanecarboxylic acid [7-(3-fluoro-phenyl)-isoquinolin-3-yl]-amide |
| 388 | 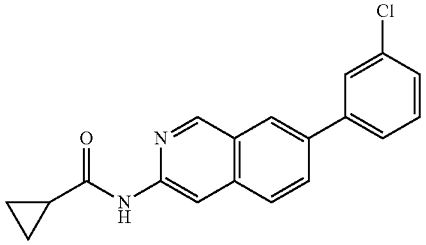 [SMILES: O=C(Nc1cc2ccc(-c3cccc(F)c3)cc2cn1)C1CC1] | Cyclopropanecarboxylic acid [7-(3-chloro-phenyl)-isoquinolin-3-yl]-amide |
| 389 | 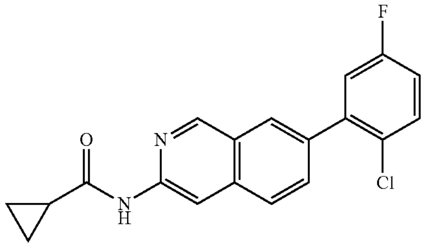 [SMILES: O=C(Nc1cc2ccc(-c3cc(F)ccc3Cl)cc2cn1)C1CC1] | Cyclopropanecarboxylic acid [7-(2-chloro-5-fluoro-phenyl)-isoquinolin-3-yl]-amide |
| 390 | 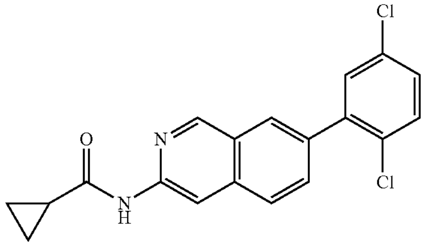 [SMILES: O=C(Nc1cc2ccc(-c3cc(Cl)ccc3Cl)cc2cn1)C1CC1] | Cyclopropanecarboxylic acid [7-(2,5-dichloro-phenyl)-isoquinolin-3-yl]-amide |
| 391 | 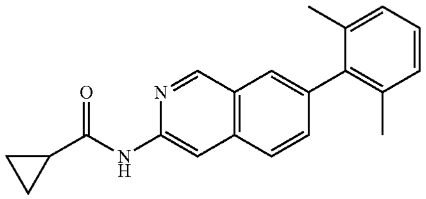 [SMILES: Cc1cccc(C)c1-c1ccc2cc(NC(=O)C3CC3)ncc2c1] | Cyclopropanecarboxylic acid [7-(2,6-dimethyl-phenyl)-isoquinolin-3-yl]-amide |
| 392 | 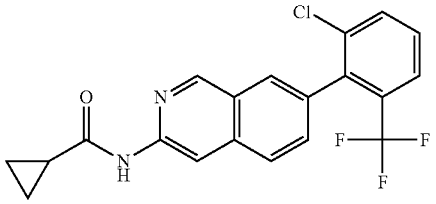 [SMILES: O=C(Nc1cc2ccc(-c3c(Cl)cccc3C(F)(F)F)cc2cn1)C1CC1] | Cyclopropanecarboxylic acid [7-(2-chloro-6-trifluoromethyl-phenyl)-isoquinolin-3-yl]-amide |

TABLE 1b-continued

| No. | Structure | Name |
|---|---|---|
| 393 | 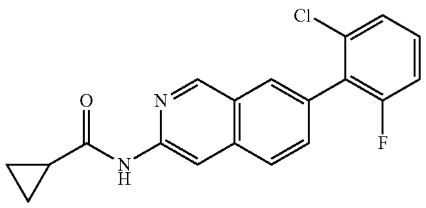 [SMILES: O=C(Nc1cc2ccc(-c3c(F)cccc3Cl)cc2cn1)C1CC1] | Cyclopropanecarboxylic acid [7-(2-chloro-6-fluoro-phenyl)-isoquinolin-3-yl]-amide |
| 394 | 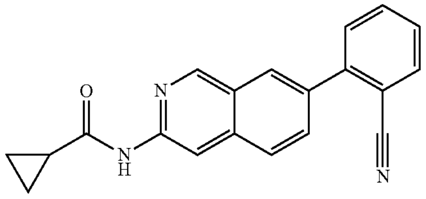 [SMILES: N#Cc1ccccc1-c1ccc2cc(NC(=O)C3CC3)ncc2c1] | Cyclopropanecarboxylic acid [7-(2-cyano-phenyl)-isoquinolin-3-yl]-amide |
| 395 | 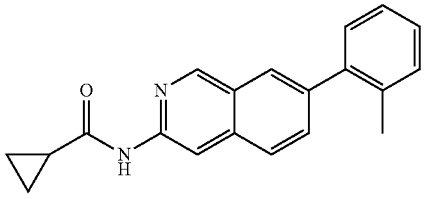 [SMILES: Cc1ccccc1-c1ccc2cc(NC(=O)C3CC3)ncc2c1] | Cyclopropanecarboxylic acid (7-o-tolyl-isoquinolin-3-yl)-amide |
| 396 | 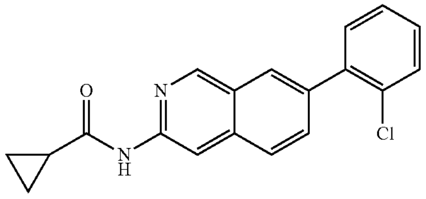 [SMILES: O=C(Nc1cc2ccc(-c3ccccc3Cl)cc2cn1)C1CC1] | Cyclopropanecarboxylic acid [7-(2-chloro-phenyl)-isoquinolin-3-yl]-amide |
| 397 | 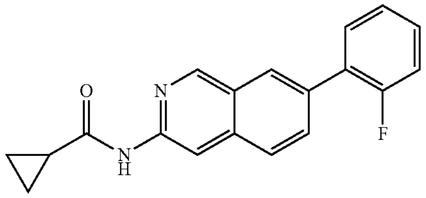 | Cyclopropanecarboxylic acid [7-(2-fluoro-phenyl)-isoquinolin-3-yl]-amide |
| 398 | 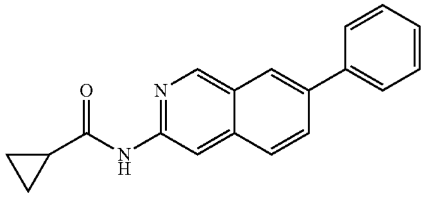 [SMILES: O=C(Nc1cc2ccc(-c3ccccc3)cc2cn1)C1CC1] | Cyclopropanecarboxylic acid (7-phenyl-isoquinolin-3-yl)-amide |
| 399 | 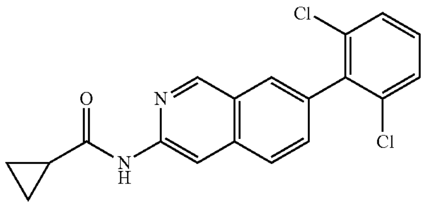 [SMILES: O=C(Nc1cc2ccc(-c3c(Cl)cccc3Cl)cc2cn1)C1CC1] | Cyclopropanecarboxylic acid [7-(2,6-dichloro-phenyl)-isoquinolin-3-yl]-amide |

TABLE 1b-continued

| No. | Structure | Name |
|---|---|---|
| 400 | 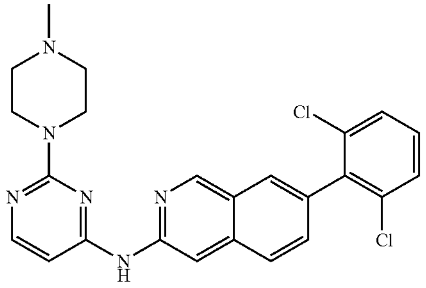 [SMILES: CN1CCN(c2nccc(Nc3cc4ccc(-c5c(Cl)cccc5Cl)cc4cn3)n2)CC1] | [7-(2,6-Dichloro-phenyl)-isoquinolin-3-yl]-[2-(4-methyl-piperazin-1-yl)-pyrimidin-4-yl]-amine |
| 401 | 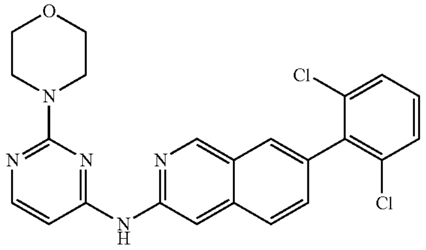 [SMILES: Clc1cccc(Cl)c1-c1ccc2cc(Nc3ccnc(N4CCOCC4)n3)ncc2c1] | [7-(2,6-Dichloro-phenyl)-isoquinolin-3-yl]-(2-morpholin-4-yl-pyrimidin-4-yl)-amine |
| 402 | 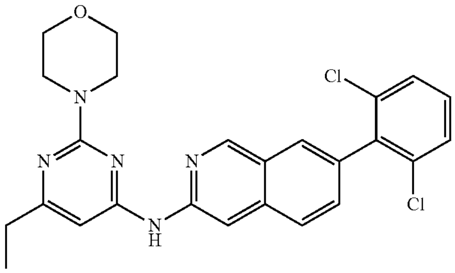 [SMILES: CCc1cc(Nc2cc3ccc(-c4c(Cl)cccc4Cl)cc3cn2)nc(N2CCOCC2)n1] | [7-(2,6-Dichloro-phenyl)-isoquinolin-3-yl]-(6-ethyl-2-morpholin-4-yl-pyrimidin-4-yl)-amine |
| 403 | 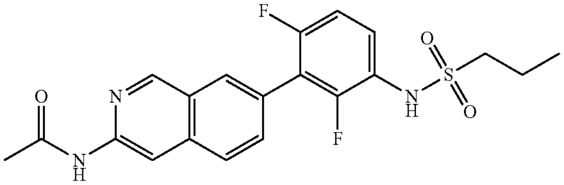 [SMILES: CCCS(=O)(=O)Nc1ccc(F)c(-c2ccc3cc(NC(C)=O)ncc3c2)c1F] | N-{7-[2,6-Difluoro-3-(propane-1-sulfonylamino)-pheny]-isoquinolin-3-yl}-acetamide |
| 404 | 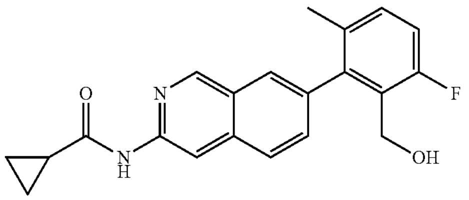 [SMILES: Cc1ccc(F)c(CO)c1-c1ccc2cc(NC(=O)C3CC3)ncc2c1] | Cyclopropanecarboxylic acid [7-(3-fluoro-2-hydroxymethyl-6-methyl-phenyl)-isoquinolin-3-yl]-amide |
| 405 | 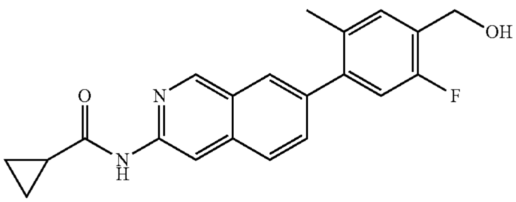 [SMILES: Cc1cc(CO)c(F)cc1-c1ccc2cc(NC(=O)C3CC3)ncc2c1] | Cyclopropanecarboxylic acid [7-(5-fluoro-4-hydroxymethyl-2-methyl-phenyl)-isoquinolin-3-yl]-amide |

TABLE 1b-continued

| No. | Structure | Name |
|---|---|---|
| 406 | 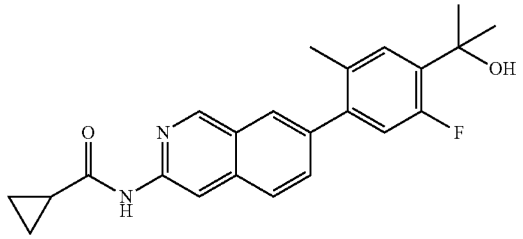 [SMILES: Cc1cc(C(C)(C)O)c(F)cc1-c1ccc2cc(NC(=O)C3CC3)ncc2c1] | Cyclopropanecarboxylic acid-{7-[5-fluoro-4-(1-hydroxy-1-methyl-ethyl)-2-methyl-phenyl]-isoquinolin-3-yl}-amide |
| 407 | 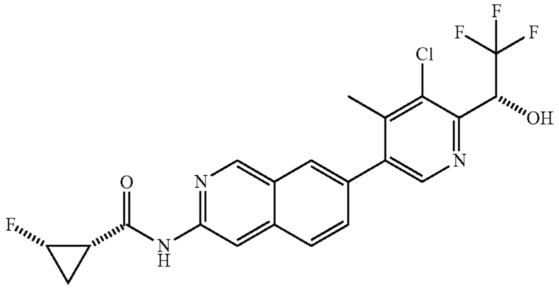 | (1S,2S)-N-(7-(5-chloro-4-methyl-6-((R)-2,2,2-trifluoro-1-hydroxyethyl)pyridin-3-yl)isoquinolin-3-yl)-2-fluorocyclopropanecarboxamide |
| 408 | 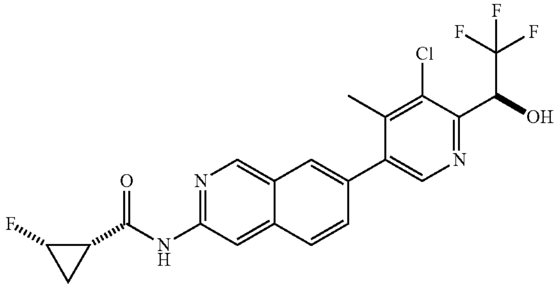 | (1S,2S)-N-(7-(5-chloro-4-methyl-6-((S)-2,2,2-trifluoro-1-hydroxyethyl)pyridin-3-yl)isoquinolin-3-yl)-2-fluorocyclopropanecarboxamide |
| 409 | 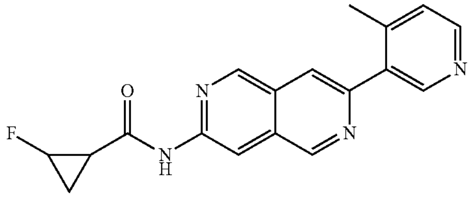 [SMILES: Cc1ccncc1-c1cc2cnc(NC(=O)C3CC3F)cc2cn1] | 2-Fluoro-cyclopropanecarboxylic acid [7-(4-methyl-pyridin-3-yl)-[2,6]naphthyridin-3-yl]-amide |
| 410 | 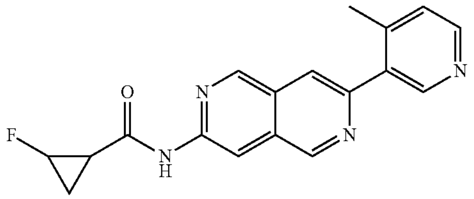 [SMILES: Cc1ccncc1-c1cc2cnc(NC(=O)C3CC3F)cc2cn1] | 2-Fluoro-cyclopropanecarboxylic acid [7-(4-methyl-pyridin-3-yl)-[2,6]naphthyridin-3-yl]-amide |
| 411 | 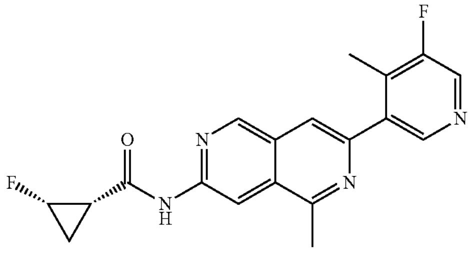 [SMILES: Cc1c(F)cncc1-c1cc2cnc(NC(=O)[C@@H]3C[C@@H]3F)cc2c(C)n1] | (1S,2S)-2-Fluoro-cyclopropanecarboxylic acid [7-(5-fluoro-4-methyl-pyridin-3-yl)-5-methyl-[2,6]naphthyridin-3-yl]-amide |

TABLE 1b-continued

| No. | Structure | Name |
|---|---|---|
| 412 | 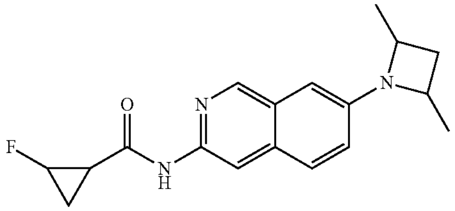 [SMILES: CC1CC(C)N1c1ccc2cc(NC(=O)C3CC3F)ncc2c1] | 2-Fluoro-cyclopropanecarboxylic acid [7-(2,4-dimethyl-azetidin-1-yl)-isoquinolin-3-yl]-amide |
| 413 | 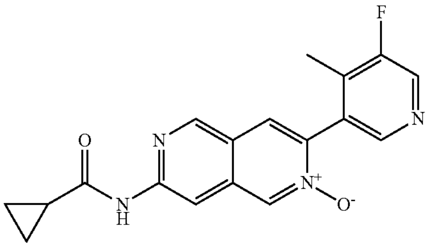 [SMILES: Cc1c(F)cncc1-c1cc2cnc(NC(=O)C3CC3)cc2c[n+]1[O-]] | Cyclopropanecarboxylic acid [7-(5-fluoro-4-methyl-pyridin-3-yl)-6-oxy-[2,6]naphthyridin-3-yl]amide |
| 414 | 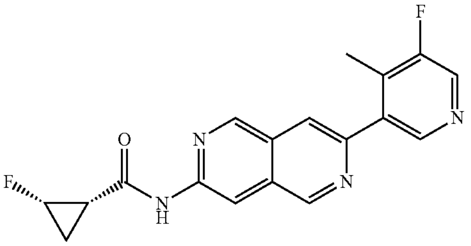 [SMILES: Cc1c(F)cncc1-c1cc2cnc(NC(=O)[C@@H]3C[C@@H]3F)cc2cn1] | (1S,2S)-2-Fluoro-cyclopropanecarboxylic acid [7-(5-fluoro-4-methyl-pyridin-3-yl)-[2,6]naphthyridin-3-yl]-amide |
| 415 | 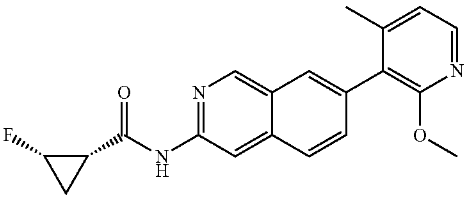 [SMILES: COc1nccc(C)c1-c1ccc2cc(NC(=O)[C@@H]3C[C@@H]3F)ncc2c1] | (1S,2S)-2-Fluoro-cyclopropanecarboxylic acid [7-(2-methoxy-4-methyl-pyridin-3-yl)-isoquinolin-3-yl]-amide |
| 416 | 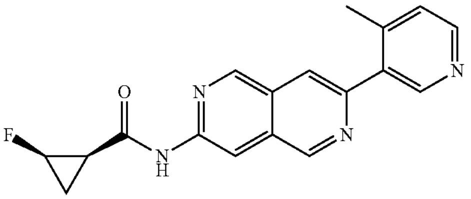 [SMILES: Cc1ccncc1-c1cc2cnc(NC(=O)[C@H]3C[C@H]3F)cc2cn1] | (1R,2R)-2-Fluoro-cyclopropanecarboxylic acid [7-(4-methyl-pyridin-3-yl)-[2,6] naphthyridin-3-yl]-amide |
| 417 | 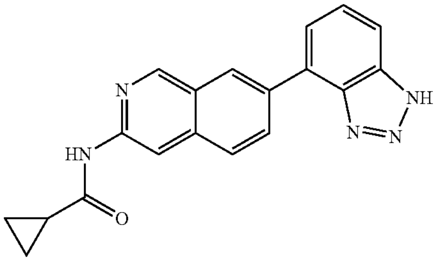 [SMILES: O=C(Nc1cc2ccc(-c3cccc4[nH]nnc34)cc2cn1)C1CC1] | Cyclopropanecarboxylic acid [7-(1H-benzotriazol-4-yl)-isoquinolin-3-yl]-amide |

TABLE 1b-continued

| No. | Structure | Name |
|---|---|---|
| 418 | 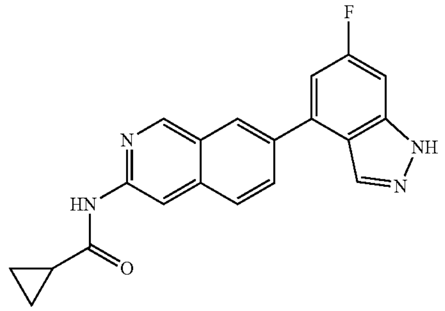 [SMILES: O=C(Nc1cc2ccc(-c3cc(F)cc4[nH]ncc34)cc2cn1)C1CC1] | Cyclopropanecarboxylic acid [7-(6-fluoro-1H-indazol-4-yl)-isoquinolin-3-yl]-amide |
| 419 | 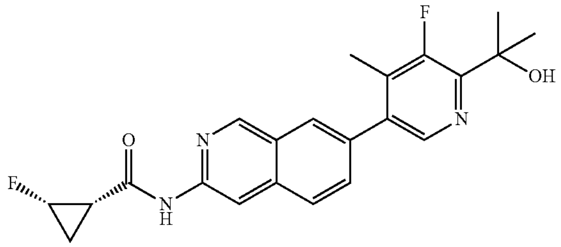 [SMILES: Cc1c(-c2ccc3cc(NC(=O)[C@@H]4C[C@@H]4F)ncc3c2)cnc(C(C)(C)O)c1F] | (1S,2S)-2-Fluoro-cyclopropanecarboxylic acid {7-[5-fluoro-6-(1-hydroxy-1-methyl-ethyl)-4-methyl-pyridin-3-yl]-isoquinolin-3-yl}-amide |
| 420 | 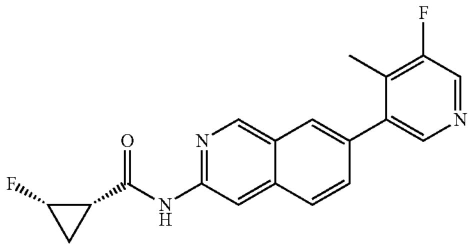 [SMILES: Cc1c(F)cncc1-c1ccc2cc(NC(=O)[C@@H]3C[C@@H]3F)ncc2c1] | (1S,2S)-2-Fluoro-cyclopropanecarboxylic acid [7-(5-fluoro-4-methyl-pyridin-3-yl)-isoquinolin-3-yl]-amide |
| 421 | 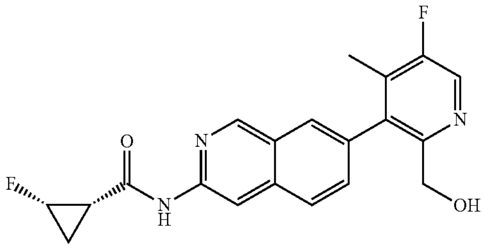 [SMILES: Cc1c(F)cnc(CO)c1-c1ccc2cc(NC(=O)[C@@H]3C[C@@H]3F)ncc2c1] | (1S,2S)-2-Fluoro-cyclopropanecarboxylic acid [7-(5-fluoro-2-hydroxymethyl-4-methyl-pyridin-3-yl)-isoquinolin-3-yl]-amide |
| 422 | 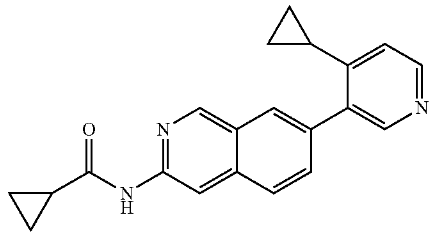 [SMILES: O=C(Nc1cc2ccc(-c3cnccc3C3CC3)cc2cn1)C1CC1] | Cyclopropanecarboxylic acid [7-(4-cyclopropyl-pyridin-3-yl)-isoquinolin-3-yl]-amide |
| 423 | 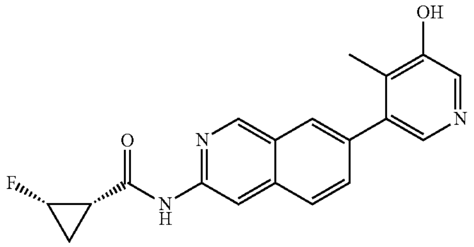 [SMILES: Cc1c(O)cncc1-c1ccc2cc(NC(=O)[C@@H]3C[C@@H]3F)ncc2c1] | (1S,2S)-2-Fluoro-cyclopropanecarboxylic acid [7-(5-hydroxy-4-methyl-pyridin-3-yl)-isoquinolin-3-yl]-amide |

TABLE 1b-continued

| No. | Structure | Name |
|---|---|---|
| 424 | 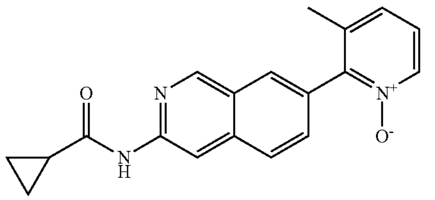 [SMILES: Cc1ccc[n+]([O-])c1-c1ccc2cc(NC(=O)C3CC3)ncc2c1] | Cyclopropanecarboxylic acid [7-(3-methyl-1-oxy-pyridin-2-yl)-isoquinolin-3-yl]-amide |
| 425 | 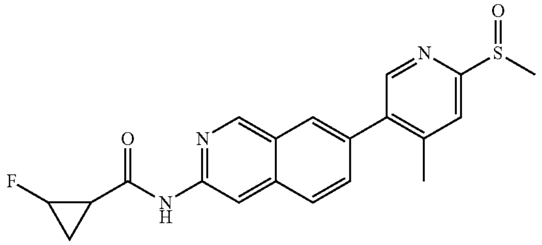 [SMILES: Cc1cc(S(C)=O)ncc1-c1ccc2cc(NC(=O)C3CC3F)ncc2c1] | 2-Fluoro-cyclopropanecarboxylic acid [7-(6-methanesulfinyl-4-methyl-pyridin-3-yl)-isoquinolin-3-yl]-amide |
| 426 | 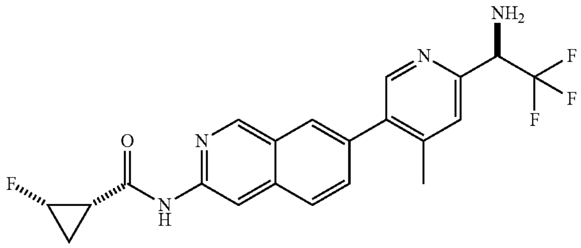 | (1S,2S)-N-(7-(6-((R)-1-amino-2,2,2-trifluoroethyl)-4-methylpyridin-3-yl)isoquinolin-3-yl)-2-fluorocyclopropanecarboxamide |
| 427 | 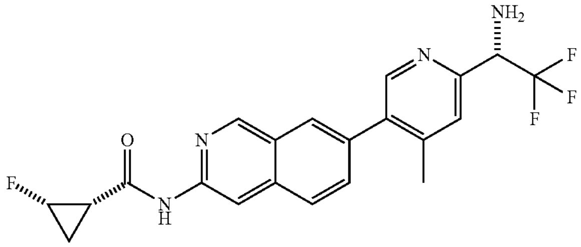 | (1S,2S)-N-(7-(6-((S)-1-amino-2,2,2-trifluoroethyl)-4-methylpyridin-3-yl)isoquinolin-3-yl)-2-fluorocyclopropanecarboxamideyl}-amide |
| 428 | 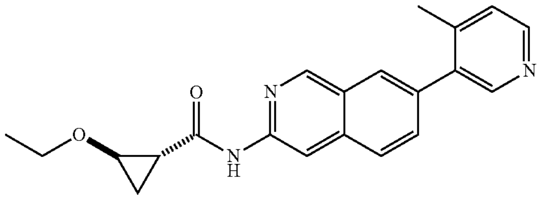 | (1R,2R)-2-ethoxy-N-(7-(4-methylpyridin-3-yl)isoquinolin-3-yl) cyclopropanecarboxamide |
| 429 | 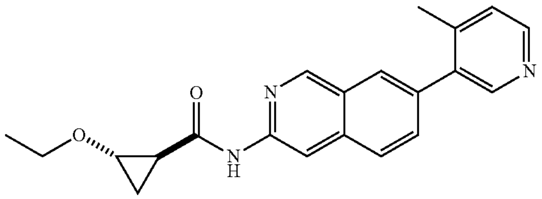 | (1S,2S)-2-ethoxy-N-(7-(4-methylpyridin-3-yl)isoquinolin-3-yl) cyclopropanecarboxamide |
| 430 | 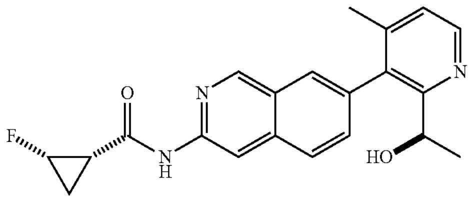 | (1S,2S)-2-fluoro-N-(7-(2-((R)-1-hydroxyethyl)-4-methylpyridin-3-yl) isoquinolin-3-yl) cyclopropanecarboxamide |

TABLE 1b-continued

| No. | Structure | Name |
|---|---|---|
| 431 | 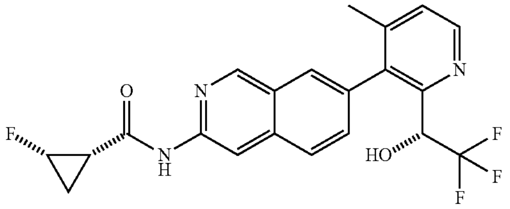 | (1S,2S)-2-fluoro-N-(7-(4-methyl-2-((R)-2,2,2-trifluoro-1-hydroxyethyl)pyridin-3-yl)isoquinolin-3-yl)cyclopropanecarboxamide |
| 432 | 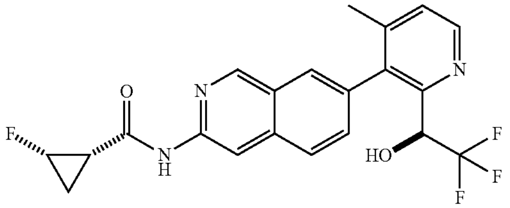 | (1S,2S)-2-fluoro-N-(7-(4-methyl-2-((S)-2,2,2-trifluoro-1-hydroxyethyl)pyridin-3-yl)isoquinolin-3-yl)cyclopropanecarboxamide |
| 433 | 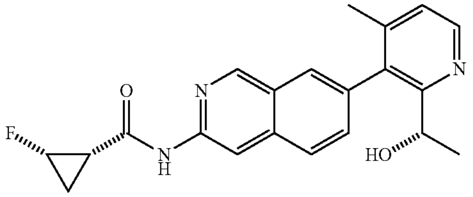 | (1S,2S)-2-fluoro-N-(7-(2-((S)-1-hydroxyethyl)-4-methylpyridin-3-yl)isoquinolin-3-yl)cyclopropanecarboxamide |
| 434 | 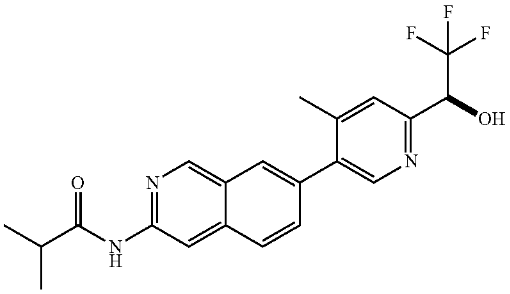 [SMILES: Cc1cc([C@H](O)C(F)(F)F)ncc1-c1ccc2cc(NC(=O)C(C)C)ncc2c1] | (S)-N-(7-(4-methyl-6-(2,2,2-trifluoro-1-hydroxyethyl)pyridin-3-yl)isoquinolin-3-yl)isobutyramide |
| 435 | 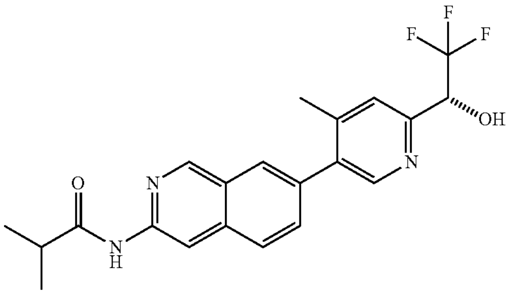 [SMILES: Cc1cc([C@@H](O)C(F)(F)F)ncc1-c1ccc2cc(NC(=O)C(C)C)ncc2c1] | (R)-N-(7-(4-methyl-6-(2,2,2-trifluoro-1-hydroxyethyl)pyridin-3-yl)isoquinolin-3-yl)isobutyramide |
| 436 | 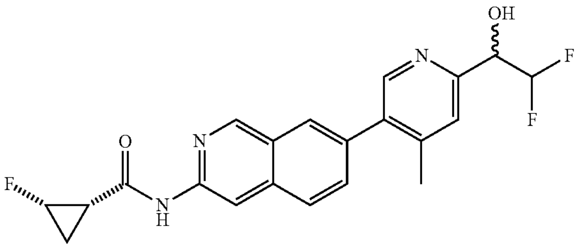 | (1S,2S)-N-(7-(6-(2,2-difluoro-1-hydroxyethyl)-4-methylpyridin-3-yl)isoquinolin-3-yl)-2-fluorocyclopropanecarboxamide |

TABLE 1b-continued

| No. | Structure | Name |
|---|---|---|
| 437 | 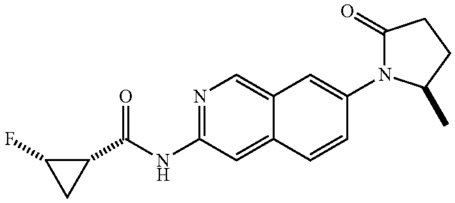 | (1S,2S)-2-fluoro-N-(7-((R)-2-methyl-5-oxopyrrolidin-1-yl)isoquinolin-3-yl)cyclopropanecarboxamide |
| 438 | 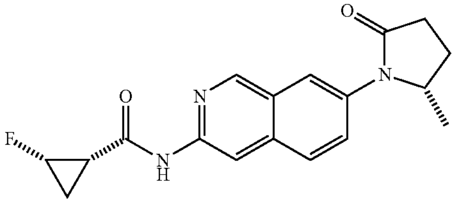 | (1S,2S)-2-fluoro-N-(7-((S)-2-methyl-5-oxopyrrolidin-1-yl)isoquinolin-3-yl)cyclopropanecarboxamide |
| 439 | 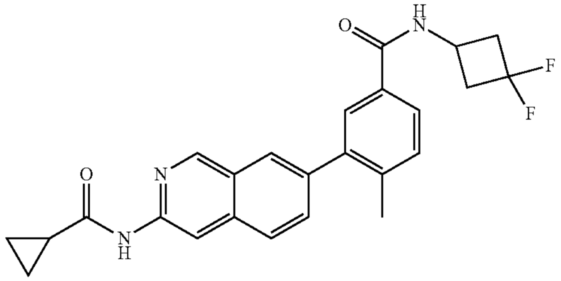 [SMILES: Cc1ccc(C(=O)NC2CC(F)(F)C2)cc1-c1ccc2cc(NC(=O)C3CC3)ncc2c1] | 3-[3-(Cyclopropanecarbonyl-amino)-isoquinolin-7-yl]-N-(3,3-difluoro-cyclobutyl)-4-methyl-benzamide |
| 440 | 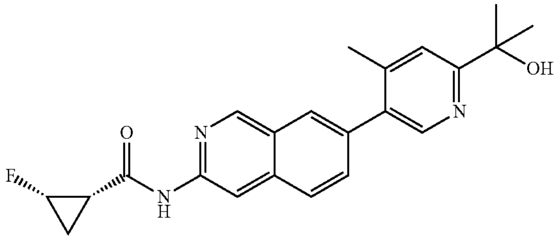 | (1S,2S)-2-Fluoro-cyclopropanecarboxylic acid {7-[6-(1-hydroxy-1-methyl-ethyl)-4-methyl-pyridin-3-yl]-isoquinolin-3-yl}-amide |
| 441 | 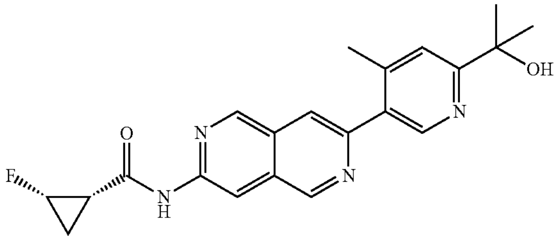 | (1S,2S)-2-Fluoro-cyclopropanecarboxylic acid {7-[6-(1-hydroxy-1-methyl-ethyl)-4-methyl-pyridin-3-yl]-[2,6] naphthyridin-3-yl}-amide |
| 442 | 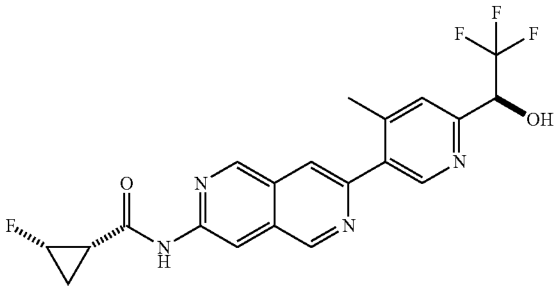 | (1S,2S)-2-fluoro-N-(7-(4-methyl-6-((S)-2,2,2-trifluoro-1-hydroxyethyl) pyridin-3-yl)-2,6-naphthyridin-3-yl)cyclopropanecarboxamide |

TABLE 1b-continued

| No. | Structure | Name |
|---|---|---|
| 443 | 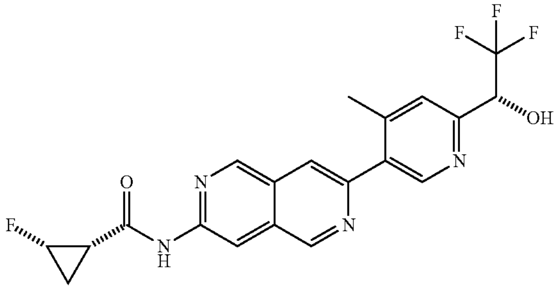 | (1S,2S)-2-fluoro-N-(7-(4-methyl-6-((R)-2,2,2-trifluoro-1-hydroxyethyl)pyridin-3-yl)-2,6-naphthyridin-3-yl)cyclopropanecarboxamide |
| 444 | 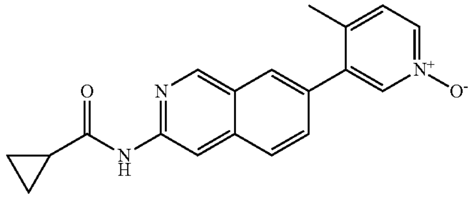 [SMILES: Cc1cc[n+]([O-])cc1-c1ccc2cc(NC(=O)C3CC3)ncc2c1] | Cyclopropanecarboxylic acid [7-(4-methyl-1-oxy-pyridin-3-yl)-isoquinolin-3-yl]-amide |
| 445 | 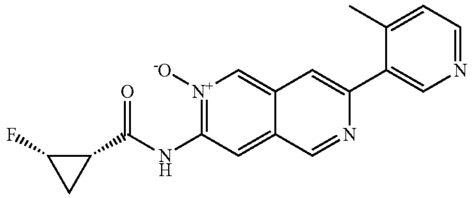 | (1S,2S)-2-Fluoro-cyclopropanecarboxylic acid [7-(4-methyl-pyridin-3-yl)-2-oxy-[2,6]naphthyridin-3-yl]-amide |
| 446 | 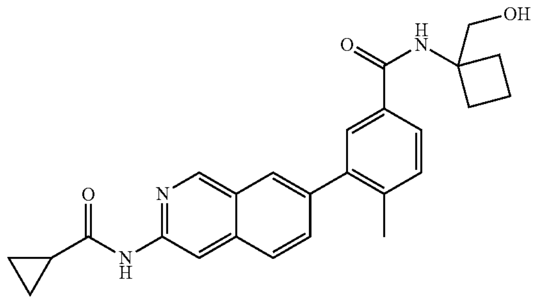 [SMILES: Cc1ccc(C(=O)NC2(CO)CCC2)cc1-c1ccc2cc(NC(=O)C3CC3)ncc2c1] | 3-[3-(Cyclopropanecarbonyl-amino)-isoquinolin-7-yl]-N-(1-hydroxymethyl-cyclobutyl)-4-methyl-benzamide |
| 447 | 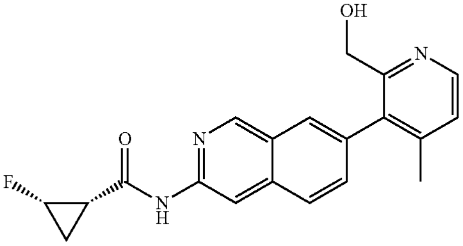 [SMILES: Cc1ccnc(CO)c1-c1ccc2cc(NC(=O)[C@@H]3C[C@@H]3F)ncc2c1] | (1S,2S)-2-Fluoro-cyclopropanecarboxylic acid [7-(2-hydroxymethyl-4-methyl-pyridin-3-yl)-isoquinolin-3-yl]-amide |
| 448 | 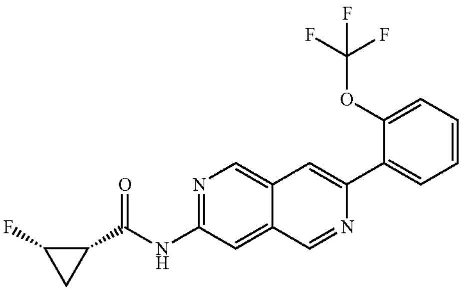 [SMILES: O=C(Nc1cc2cnc(-c3ccccc3OC(F)(F)F)cc2cn1)[C@@H]1C[C@@H]1F] | (1S,2S)-2-Fluoro-cyclopropanecarboxylic acid [7-(2-trifluoromethoxy-phenyl)-[2,6]naphthyridin-3-yl]-amide |

TABLE 1b-continued

| No. | Structure | Name |
| --- | --- | --- |
| 449 | 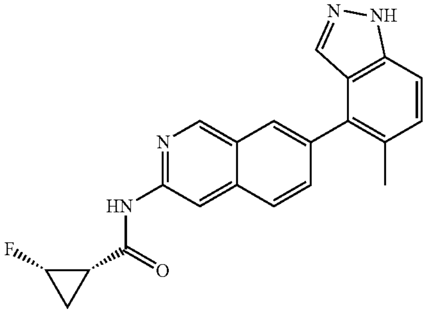 [SMILES: Cc1ccc2[nH]ncc2c1-c1ccc2cc(NC(=O)[C@@H]3C[C@@H]3F)ncc2c1] | (1S,2S)-2-Fluoro-cyclopropanecarboxylic acid [7-(5-methyl-1H-indazol-4-yl)-isoquinolin-3-yl]-amide |
| 450 | 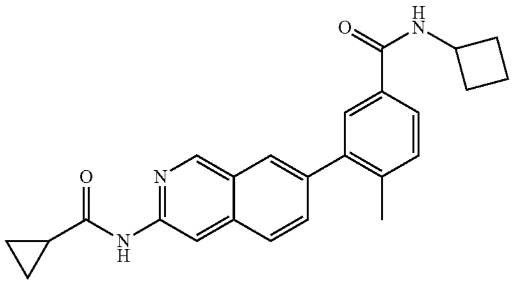 [SMILES: Cc1ccc(C(=O)NC2CCC2)cc1-c1ccc2cc(NC(=O)C3CC3)ncc2c1] | N-Cyclobutyl-3-[3-(cyclopropanecarbonyl-amino)-isoquinolin-7-yl]-4-methyl-benzamide |
| 451 | 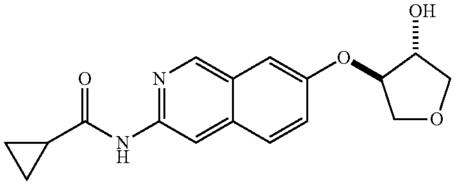 | N-(7-((3R,4R)-4-hydroxytetrahydrofuran-3-yloxy)isoquinolin-3-yl) cyclopropanecarboxamide |
| 452 | 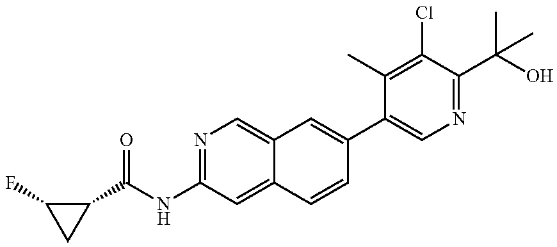 | (1S,2S)-N-(7-(5-chloro-6-(2-hydroxypropan-2-yl)-4-methylpyridin-3-yl)isoquinolin-3-yl)-2-fluorocyclopropanecarboxamide |
| 453 | 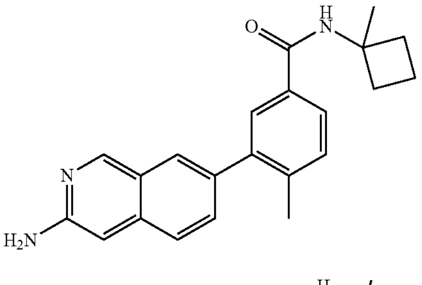 | 3-(3-aminoisoquinolin-7-yl)-4-methyl-N-(1-methylcyclobutyl)benzamide |
| 454 | 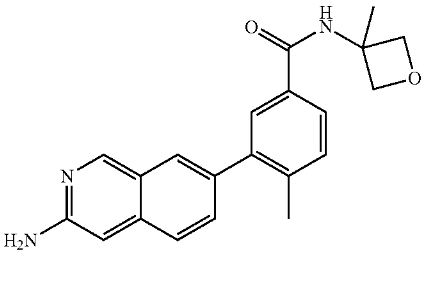 | 3-(3-aminoisoquinolin-7-yl)-4-methyl-N-(3-methyloxetan-3-yl)benzamide |

TABLE 1b-continued

| No. | Structure | Name |
|---|---|---|
| 455 | 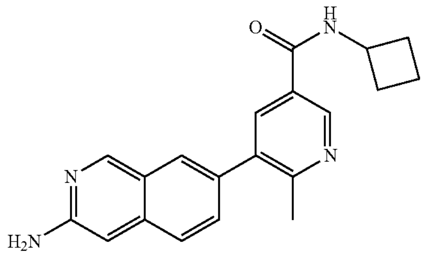 [SMILES: Cc1ncc(C(=O)NC2CCC2)cc1-c1ccc2cc(N)ncc2c1] | 5-(3-aminoisoquinolin-7-yl)-N-cyclobutyl-6-methylnicotinamide |
| 456 | 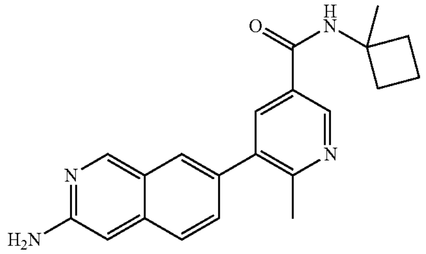 [SMILES: Cc1ncc(C(=O)NC2(C)CCC2)cc1-c1ccc2cc(N)ncc2c1] | 5-(3-aminoisoquinolin-7-yl)-6-methyl-N-(1-methylcyclobutyl)nicotinamide |
| 457 | 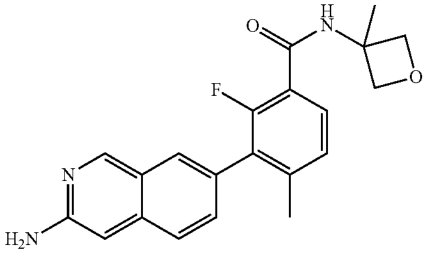 [SMILES: Cc1ccc(C(=O)NC2(C)COC2)c(F)c1-c1ccc2cc(N)ncc2c1] | 3-(3-aminoisoquinolin-7-yl)-2-fluoro-4-methyl-N-(3-methyloxetan-3-yl)benzamide |
| 458 | 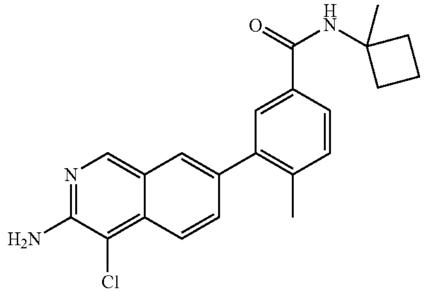 [SMILES: Cc1ccc(C(=O)NC2(C)CCC2)cc1-c1ccc2c(Cl)c(N)ncc2c1] | 3-(3-amino-4-chloroisoquinolin-7-yl)-4-methyl-N-(1-methylcyclobutyl) benzamide |

Synthesis of Compounds

For illustrative purposes, Schemes 1-5 show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethylenoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Compounds of the invention can be synthesized as shown in Scheme 1. In Scheme 1, 5-bromo-2-iodobenzonitrile 2 is generated through diazotization and iodination of 2-amino-5-bromobenzonitrile. Borane reduction, followed by condensation with malononitrile generates dihydroisoquinoline intermediate 4. Atmospheric oxidization in the presence of ammonia provides isoquinoline 5. Nitrile hydrolysis and decarboxylation provides 7-bromo-isoquinolin-3-amine 6. Compound 6 is reacted with acid chlorides or carboxylic acids to provide amide compounds 7, which may then be subjected to Suzuki coupling conditions to provide compounds of 8c. Alternately, compound 6 is used in Suzuki coupling reactions to yield amino-isoquinoline compounds 8, which is then be derivatized as shown in amide coupling reactions to yield 8c, reaction with isocyanates to provide ureas of 8b, and in Buchwald-Hartwig type arylations to provide isoquinolines of 8d.

Scheme 1

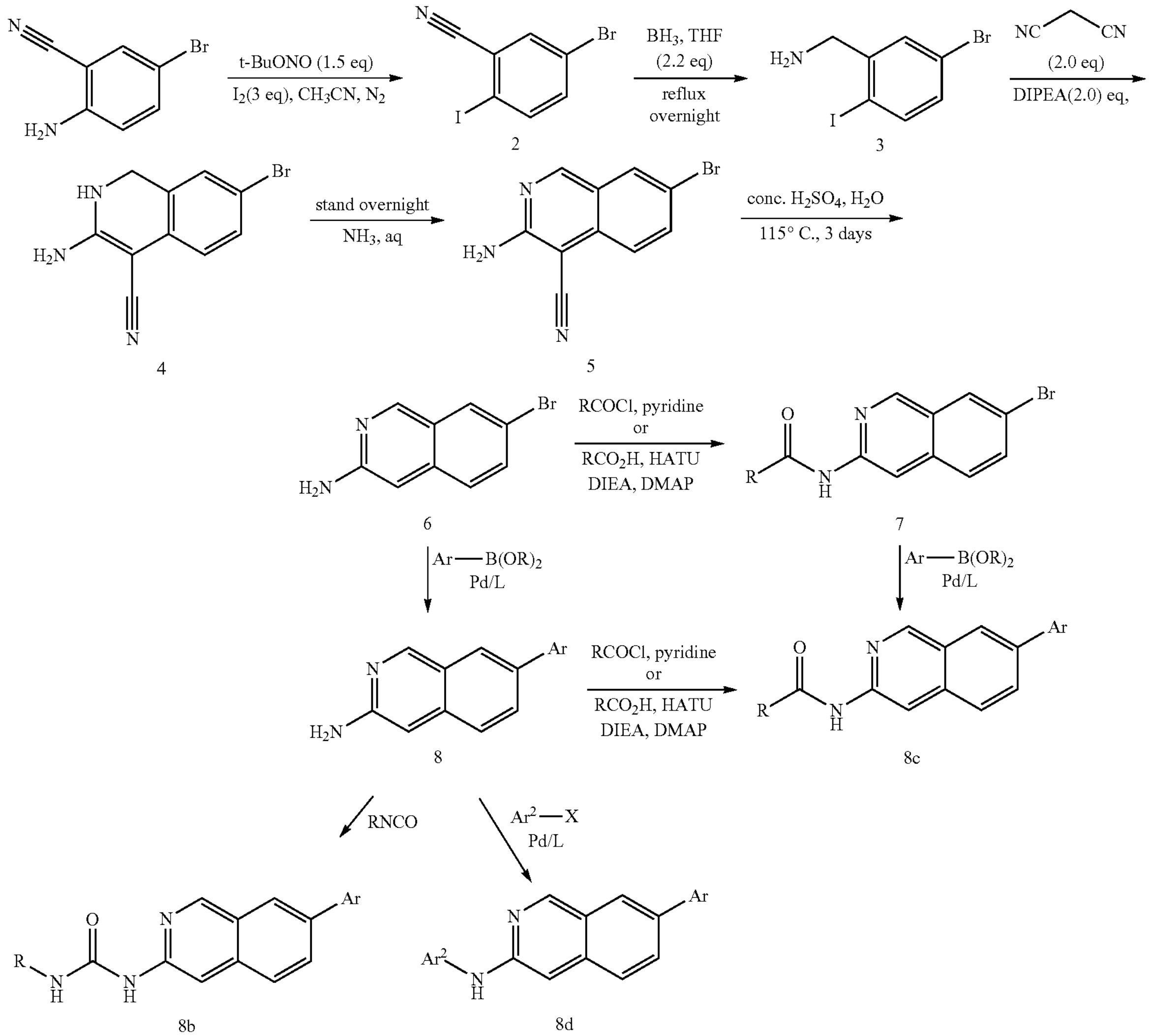

Compounds of the invention can be synthesized as shown in Scheme 2. Compound 7, described in Scheme 1, is converted to the boronic acid pinacol ester 9. Compound 9 is reacted under standard Suzuki coupling conditions with aryl halides to generate isoquinoline compound 8b.

Scheme 2

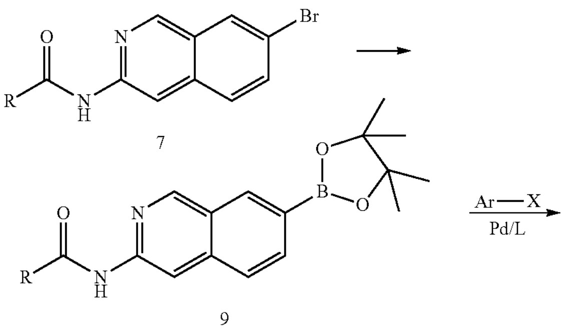

-continued

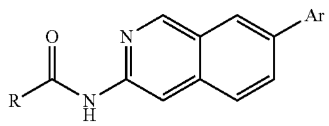

8b

Compounds of the invention can be synthesized as shown in Scheme 3 below. Displacement of the chloride group in chloropyridine 10 followed by reduction of the nitro group in nitropyridine 11 provides aminopyridine 12. Protection of the aminopyridine 12 with di-t-butyl dicarbonate followed by directed deprotonation with t-butyl lithium and formylation with DMF provides aldehyde 14. Condensation of 14 with a beta-keto ester provides compound 15 which upon deprotection under acidic conditions produces 1,7-naphthyridine 16.

Scheme 3

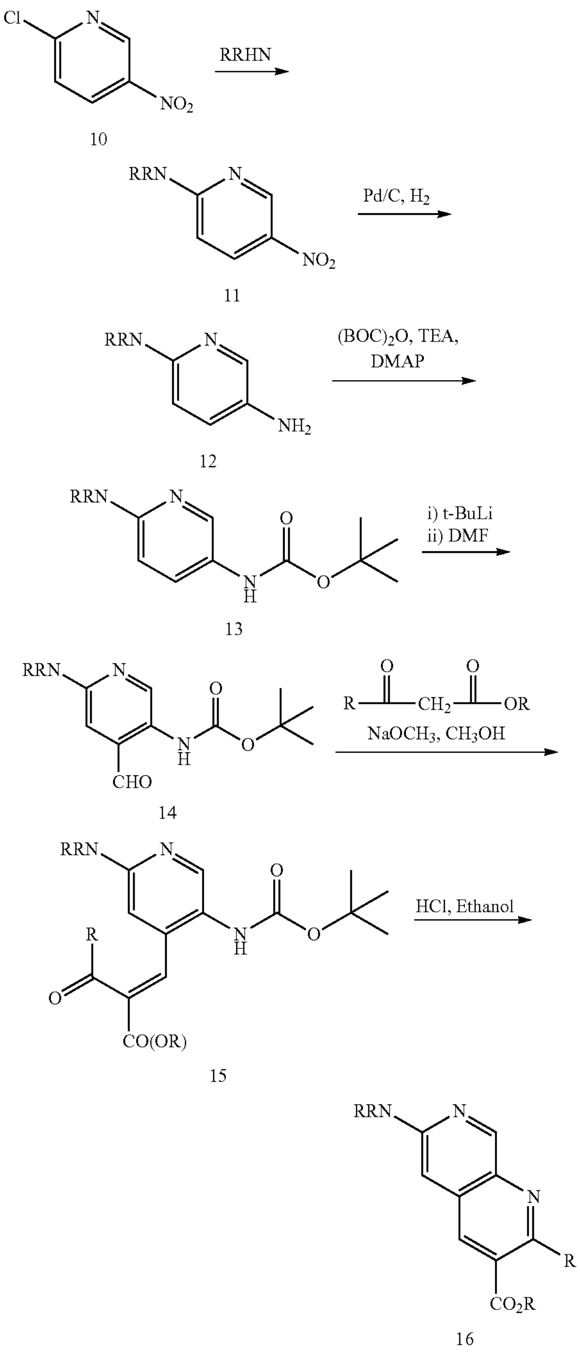

Scheme 4

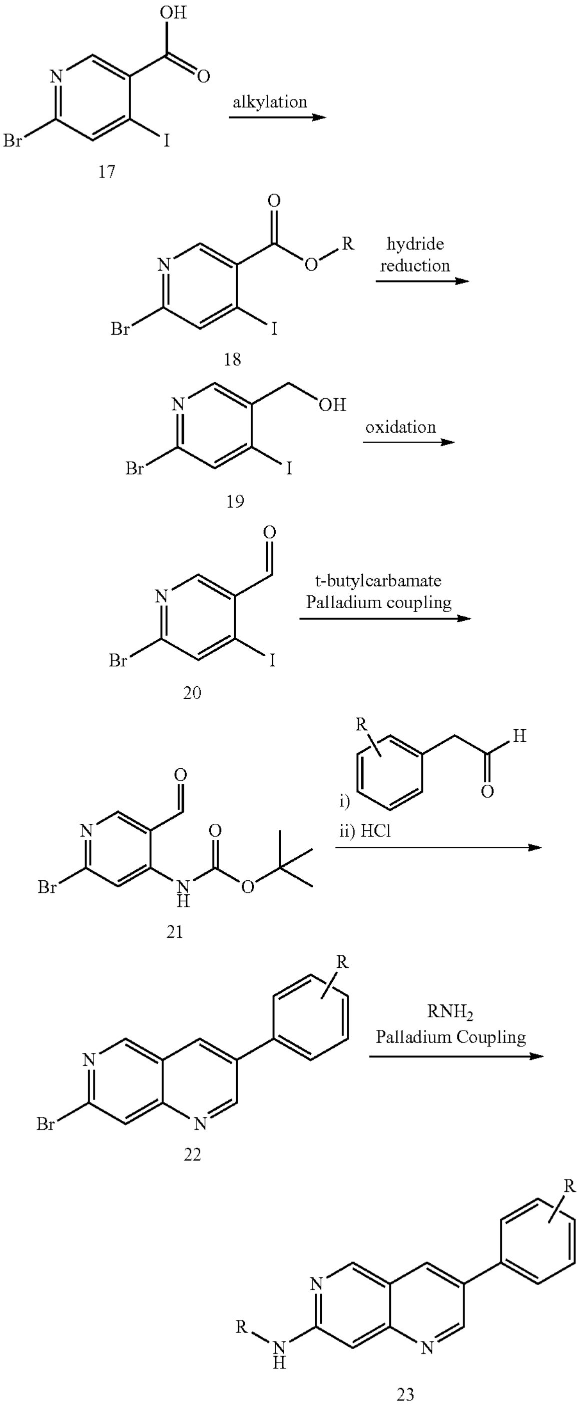

Compounds of the invention can be prepared as shown in Scheme 4 below. Alkylation of carboxylic acid 17 provides ester 18. Subsequent reduction of the ester group of ester 18 and reoxidation of the resultant alcohol 19 provides aldehyde 20. Palladium mediated coupling of compound 20 with t-butyl carbamate provides carbamate 21, which is further condensed with an optionally substituted phenyl acetaldehyde to produce heterocycle 22. A second palladium mediated coupling of compound 22 with an optionally substituted amine (e.g., a carboxamide, aryl amine, etc) provides 1,5 naphthyridine 23.

Compounds of the invention can be synthesized as shown in Scheme 5 below. Bromoaldehyde 24 is coupled with an ethynylbenzene in the presence of an appropriate palladium catalyst. The resultant aldehyde 25 is treated with hydroxylamine to form hydroxylimine 26. Cyclization of 26 is catalyzed by sliver nitrate to produce N-oxide 27. A second palladium mediated coupling of compound 27 to a suitable amine (e.g. a carboxamide, aryl amine, etc) then produces 1,6 naphthyridine 29.

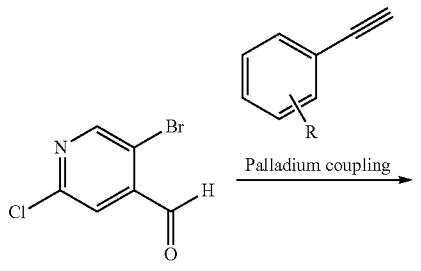

24

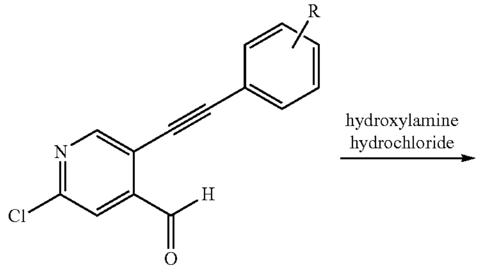

25

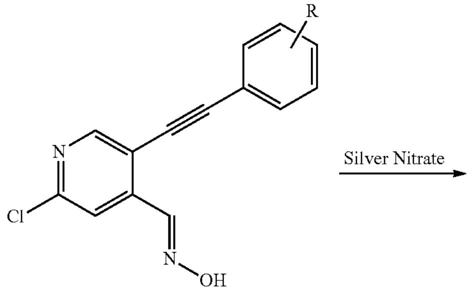

26

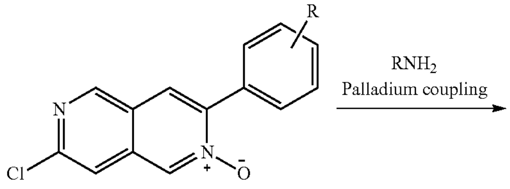

27

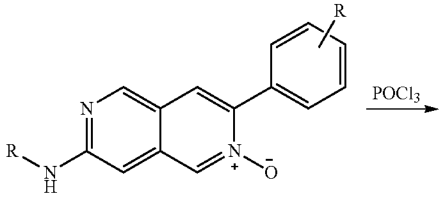

28

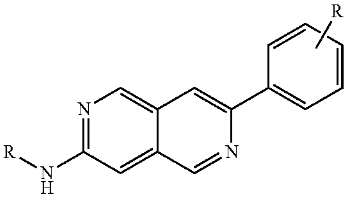

29

Pharmaceutical Compositions and Administration

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of Formula I and at least one pharmaceutically acceptable carrier, diluent or excipient. The compositions of the invention can be used for inhibiting Abl and/or Abl related kinases (e.g., c-Abl) activity in mammals (e.g, human patients)

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of Formula I (or stereoisomers, geometric isomers, tautomers, solvates, metabolites, isotopes, pharmaceutically acceptable salts, or prodrugs thereof), or a subformula thereof and a pharmaceutically acceptable carrier, diluent or excipient. In another embodiment, the invention provides for preparing compositions (or medicaments) comprising compounds of the invention. In another embodiment, the invention provides for administering compounds of Formula I and compositions comprising compounds of Formula I to a mammal (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit Abl and/or Abl related kinases (e.g., c-Abl) activity as required to prevent or treat the undesired disease or disorder, such as for example, neurodegeneration, amyloidosis, formation of neurofibrillary tangles, or undesired cell growth (e.g., cancer cell growth). For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compositions comprising compounds of Formula I are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of Formula I) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, Pa.

Sustained-release preparations of a compound of the invention (e.g., compound of Formula I) can be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) $21^{st}$ Edition, Lippincott Williams & Wilkins, Philadelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of Formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of Formula I is formulated in an acetate buffer, at pH 5. In another embodiment, the compounds of Formula I are sterile. The compound may be stored, for example, as a solid or amorphous composition, as a lyophilized formulation or as an aqueous solution.

Formulations of a compound of the invention (e.g., compound of Formula I) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention (e.g., compound of Formula I) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of Formula I) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

Formulations suitable for vaginal administration can be presented as pessaries, tampons, creams, gels, pastes, foams or spray formulations containing in addition to the active ingredient such carriers as are known in the art to be appropriate.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

Indications and Methods of Treatment

The compounds of the invention inhibit the activity of Abl and/or Abl related kinases, including c-Abl kinase. Accordingly, the compounds of the invention (e.g., compounds of Formula I, or stereoisomers, geometric isomers, tautomers, solvates, metabolites, isotopes, pharmaceutically acceptable salts, or prodrugs thereof) can be used for the treatment of diseases and disorders in a mammal, for example a human patient, wherein for which the inhibition of Abl and/or Abl related kinases, for example c-Abl kinase, in the patient would be therapeutically effective. For example, the compounds of the invention are useful for the treatment of diseases or disorders in a mammal (e.g., human patient) associated with overactive or undesired Abl and/or Abl related kinase activity (e.g., c-Abl kinase activity). In one embodiment, the compounds of the invention (e.g., compounds of Formula I, or stereoisomers, geometric isomers, tautomers, solvates, metabolites, isotopes, pharmaceutically acceptable salts, or prodrugs thereof) are used to inhibit the activity of c-Abl kinase, for example in an in vitro assay setting, by contacting said compound of Formula I with c-Abl kinase. For example, compounds of Formula I can be used as a control compound in an in vitro assay setting. In another embodiments the compounds of the invention (e.g., compounds of Formula I, or stereoisomers, geometric isomers, tautomers, solvates, metabolites, isotopes, pharmaceutically acceptable salts, or prodrugs thereof) are used to inhibit the activity of c-Abl kinase in cells that exhibit undesired expression (e.g., overexpression) or undesired activity of c-Abl kinase, e.g. in an cell proliferation assay, by introducing into a cell a compound of Formula I. In another embodiment, the present invention provides the treatment of diseases or disorders in a mammal (e.g., human patient) associated with overactive or undesired Abl and/or Abl related kinase activity (e.g., c-Abl kinase activity) said method comprise administering to a mammal (e.g., human patient) in need thereof a therapeutically effective amount of a compound of the invention (e.g., compounds of Formula I, or stereoisomers, geometric isomers, tautomers, solvates, metabolites, isotopes, pharmaceutically acceptable salts, or prodrugs thereof). In another embodiment, the present invention provides for the treatment of disease or disorders affecting the nervous system comprising administering to a mammal (e.g., a human patient) in need thereof a therapeutically effective amount of a compound of the invention (e.g., compounds of Formula I, or stereoisomers, geometric isomers, tautomers, solvates, metabolites, isotopes, pharmaceutically acceptable salts, or prodrugs thereof). In another embodiment, the present invention provides for the treatment of cancer or undesired cell proliferation comprising administering to a mammal (e.g., a human patient) in need thereof a therapeutically effective amount of a compound of the invention (e.g., compounds of Formula I, or stereoisomers, geometric isomers, tautomers, solvates, metabolites, isotopes, pharmaceutically acceptable salts, or prodrugs thereof).

Diseases and disorders treatable according to the methods of this invention include, cancer and diseases or disorders affecting the nervous system, for example neurological diseases related to neurodegeneration. In one embodiment, a patient is treated with a compound of a compound of the invention (e.g., compound of Formula I) and a pharmaceutically acceptable carrier, adjuvant, or vehicle, wherein a compound of the invention (e.g., compounds of Formula I, or stereoisomers, geometric isomers, tautomers, solvates, metabolites, isotopes, pharmaceutically acceptable salts, or prodrugs thereof) is present in an amount to inhibit Abl and/or Abl related kinase (e.g., c-Abl kinase) activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia. In a certain embodiment, compounds of Formula I (or stereoisomer, geometric isomer, tautomer, solvate, metabolite, pharmaceutically acceptable salt, or prodrug thereof), are useful for the treatment of a cancer selected from the group consisting of breast, ovarian, NSCLC, small cell lung cancers, leukemias (acute, myelogenous, chronic), lymphomas and other solid tumors in a mammal, for example, a human, suffering from such cancer. In a certain embodiment, compounds of Formula I (or stereoisomer, geometric isomer, tautomer, solvate, metabolite, pharmaceutically acceptable salt, or prodrug thereof), are useful for the treatment of a cancer selected from the group consisting of breast, ovarian, NSCLC, acute lymphocytic leukemia, acute myelogeneous leukemia, chronic myelogenous leukemia, chronic lymphocytic leukemia.

Disease and disorders affecting the nervous system which can be treated according to the methods of this invention include, but are not limited to, Alzheimer's disease, Parkinson's disease, amyotrophic lateral sclerosis, Huntington's disease, and Cerebral Ischemia, and neurodegenerative disease caused by traumatic injury, progressive supranuclear palsy, corticobasal degeneration, glutamate neurotoxicity, hypoxia, mild cognitive impairment (MCI), vascular dementia, mixed dementia, dementia with Lewy bodies, dementia pugilistica, Parkinson's disease, Lytico-Bodig disease, ganglioglioma, gangliocytoma, meningioangiomatosis, subacute sclerosing panencephalitis, frontotemporal dementia, parkinsonism linked to chromosome 17, lead encephalopathy, pantothenate kinase-associated neurodegeneration (PKAN), tuberous sclerosis, lipofuscinosis, Creutzfeldt-Jakob Disease (CJD), prion disorders, normal pressure hydrocephalus, Huntington's disease, Wernicke-Korsakoff Syndrome, trisomy 21 (Down Syndrome), cerebral amyloid angiopathy, degenerative dementia, hereditary cerebral hemorrhage with amyloidosis of the Dutch-Type (HCHWA-D), amyotrophic lateral sclerosis, head trauma, stroke, pancreatitis, inclusion body myositis, other peripheral amyloidoses, tauopathies, diabetes and atherosclerosis.

In a certain embodiment, compounds of Formula I (or stereoisomer, geometric isomer, tautomer, solvate, metabolite, pharmaceutically acceptable salt, or prodrug thereof), are useful for the treatment of a disease or disorder described hereinabove affecting the nervous system in a mammal, for example, a human, suffering from such disease or disorder. In one embodiment, compounds of Formula I (or stereoisomer, geometric isomer, tautomer, solvate, metabolite, pharmaceutically acceptable salt, or prodrug thereof), are useful for the treatment of a disease or disorder selected from the group consisting of Alzheimer's Disease, Parkinson's Disease, Pick's Disease, Niemann-Pick's Disease, Tauopathies and Amyoloidosis.

Also provided is the use of a compound of this invention, or stereoisomer, geometric isomer, tautomer, solvate, metabolite, or pharmaceutically acceptable salt, or prodrug thereof, in the preparation of a medicament for the treatment of the diseases and conditions described hereinabove (and any specific embodiments set forth thereof) in a mammal, for example a human, suffering from such disease or disorder.

Combination Therapy

In one embodiment, a compound of the invention (e.g., compound of Formula I), or stereoisomer, geometric isomer, tautomer, solvate, metabolite, pharmaceutically acceptable salt, or prodrug thereof, is used as an anticancer agent or as an adjunct agent for the treatment of cancer in a mammal in a combination therapy. One of ordinary skill in the art is readily able to determine whether or not a candidate compound treats a cancerous condition for any particular cell type, either alone or in combination. Within certain aspects of this embodiment, compounds of the invention are used in adjunct (or in conjunction) with other therapies, including conventional surgery, radiotherapy and chemotherapy, for the treatment of cancer. Such chemotherapy can include, but are not limited to one or more of the chemotherapeutic agents described herein. Examples of chemotherapeutic agents that can be combined with compounds of the invention include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), Bosutinib (Wyeth), Dasatinib (SPRYCEL®, BMS), SGX-393 (Oregon Health Sciences), Nilotinib (TAGSIGNA®, Novartis), Eribulin Mesylate (HALAVEN®, Eisai), Cabazitaxel (JEVTANA®, Sanofi Aventis), Sipuleucel-T (PROVENGE®, Dendreon), Denosumab (XGEVA®, Amgen), Ondanstron (ZUPLENZ®, Strativa Pharmaceuticals), PTK787/ZK 222584 (Novartis), Oxaliplatin (ELOXATIN®, Sanofi), Bendamustine (TREANDA®, Cephalon), Plerixafor Injection (MOZOBIL®, Genzyme), Topotecan Hydrochloride (HYCAMTIN®, GSK), Ixabepilone (IXEMPRA, GSK), Pazopanib (VOTRIENT®, GSK), Ofatumumab (ARZERRA®, GSK), Pralatrexate Injection (FOLOTYN®, Allos Therapeutics), Romidepsin (ISTODAX, Gloucester Pharmaceuticals); 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma11 and calicheamicin omega11 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors, for example a PI3K inhibitor, a MEK inhibitor, etc; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Active compounds can also be used as cell culture additives to inhibit Abl and/or Abl related kinases (e.g., c-Abl), for example, in order to sensitize cells to known chemotherapeutic agents or ionising radiation treatments in vitro.

In another embodiment, a compound of the invention (e.g., a compound of Formula I), or stereoisomer, geometric isomer, tautomer, solvate, metabolite, pharmaceutically acceptable salt, or prodrug thereof, is used in combination with other therapeutic agents for the treatment of diseases and disorders affecting the nervous system in a mammal, such therapeutic agents including, for example beta-secretase inhibitors, including CTS21166 (CoMentis); gamma-secretase inhibitors, including, (Eli Lilly), E2012 (Eisai) and AC-91 (AC Immune); tau phosphorylation inhibitors (e.g, Imatinib (Gleevec), Bosutinib (Wyeth), Dasatinib (BMS), SGX-393 (SGX Pharmaceuticals); blockers of Aβ oligomer formation; metal protein attenuation compounds, including PBT2 (Prana Biotechnology); p25/CDK5 inhibitors, including, MDL28170, Roscovitine and Aloisine; HMG-CoA reductase inhibitors; oxidative stress inhibitors, including, Gingko biloba, Tocopherol, Selegiline and Alpha-Lipoid Acid; NK1/NK3 receptor antagonists; anti-inflammatory compounds such as NSAID's, including, Ibuprofen and (R)-Flurbiprofen; peroxisome proliferator-activated receptor gamma (PPAR-gamma) agonists, including Berberine; anti-amyloid antibodies, including Bapineuzumab; CB-1 receptor antagonists or CB-1 receptor inverse agonists; antibiotics such as Doxycycline and Rifampin; N-methyl-D-aspartate (NMDA) receptor antagonists, such as Memantine; cholinesterase inhibitors such as Galantamine, Rivastigmine, Donepezil, and Tacrine; growth hormone secretagogues such as Ibutamoren, Ibutamoren mesylate and Capromorelin; Histamine H3 antagonists; AMPA agonists; PDE IV inhibitors; GABAA inverse agonists; neuronal nicotinic agonists; P-450 inhibitors, such as ritonavir; dopamine precursors such as Levodopa, Carbidopa; agents that prevent the metabolisom of dopamine, including Selegiline, Rasagiline, Entacapone, Tolcapone; dopamine receptor agonists, including Apomorphine, Bromocriptine, Pramipexole, Ropinirole, Rotigotine; anti-cholinergic agents; and anti-muscarinic agents. The foregoing list of combinations is illustrative only and not intended to be limiting in any way.

In another embodiment, a compound of the invention (e.g., a compound of Formula I) or stereoisomer, geometric isomer, tautomer, solvate, metabolite, pharmaceutically acceptable salt, or prodrug thereof, is used in combination with another therapeutic agent (described herein for the treatment of diseases and disorders affecting the nervous system) for the treatment of Alzheimer's disease. In certain aspects of this embodiment, a compound of the invention (e.g., a compound of Formula I) or stereoisomer, geometric isomer, tautomer, solvate, metabolite, pharmaceutically acceptable salt, or prodrug thereof, is used in combination with another therapeutic agent (described herein for the treatment of diseases and disorders affecting the nervous system) for the treatment of Parkinson's disease. In certain aspects of this embodiment, a compound of the invention (e.g., a compound of Formula I) or stereoisomer, geometric isomer, tautomer, solvate, metabolite, pharmaceutically acceptable salt, or prodrug thereof, is used in combination with another therapeutic agent (described herein for the treatment of diseases and disorders affecting the nervous system) for the treatment of Pick's disease. In certain aspects of this embodiment, a compound of the invention (e.g., a compound of Formula I) or stereoisomer, geometric isomer, tautomer, solvate, metabolite, pharmaceutically acceptable salt, or prodrug thereof, is used in combination with another therapeutic agent (described herein for the treatment of diseases and disorders affecting the nervous system) for the treatment of Niemann-Pick's disease. In certain aspects of this embodiment, a compound of the invention (e.g., a compound of Formula I) or stereoisomer, geometric isomer, tautomer, solvate, metabolite, pharmaceutically acceptable salt, or prodrug thereof, is used in combination with another therapeutic agent (described herein for the treatment of diseases and disorders affecting the nervous system) for the treatment of tauopathies. In certain aspects of this embodiment, a compound of the invention (e.g., a compound of Formula I) or stereoisomer, geometric isomer, tautomer, solvate, metabolite, pharmaceutically acceptable salt, or prodrug thereof, is used in combination with another therapeutic agent (described herein for the treatment of diseases and disorders affecting the nervous system) for the treatment of amyloidosis.

The combination therapy can be administered as a simultaneous or sequential regimen. When administered sequentially, the combination can be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and can be lowered due to the combined action (synergy) of the newly identified agent and other chemotherapeutic agents or treatments.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

EXAMPLES

The invention will be more fully understood by reference to the following examples. They should not, however, be construed as limiting the scope of the invention. These examples are not intended to limit the scope of the present invention, but rather to provide guidance to a skilled artisan to prepare and use the compounds, compositions, and methods of the present invention. While particular embodiments of the present invention are described, the skilled artisan will appreciate that various changes and modifications can be made without departing from the spirit and scope of the invention.

The chemical reactions in the Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interferring groups, by utilizing other suitable reagents known in the art other than those described, and/or by making routine modifications of reaction conditions. Alternatively, other reactions disclosed herein or known in the art will be recognized as having applicability for preparing other compounds of the invention. Accordingly, the following examples are provided to illustrate but not limit the invention.

In the Examples described below, unless otherwise indicated all temperatures are set forth in degrees Celsius. Commercially available reagents were purchased from suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters); or alternatively column chromatography was carried out using on an ISCO chromatography system (Manufacturer: Teledyne ISCO) having a silica gel column. $^1H$ NMR spectra were recorded on a Varian instrument operating at 400 MHz. $^1H$ NMR spectra were obtained in deuterated $CDCl_3$, $d_6$-DMSO, $CH_3OD$ or $d_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

When possible, product formed in the reaction mixtures were monitored by LC/MS. High Pressure Liquid Chromatography—Mass Spectrometry (LCMS) experiments to determine retention times ($R_T$) and associated mass ions were performed using one of the following methods.

Method A: Experiments were performed on Agilent or Shimadzu system using ESI as ionization source with an Xtimate C18 (3 μm), 30×2.1 mm column, at a 1.2 mL/minute flow rate. The solvent system was a gradient starting with 90% water with 0.0375% TFA (solvent A) and 10% acetonitrile with 0.01875% TFA (solvent B), ramping up to 20% solvent A and 80% solvent B over 2 minutes.

Method B: Experiments were performed on Agilent or Shimadzu system using ESI as ionization source with an Xtimate C18 (3 μm), 30×2.1 mm column, at a 1.2 mL/minute flow rate. The solvent system was a gradient starting with 100% water with 0.0375% TFA (solvent A) and 0% acetonitrile with 0.01875% TFA (solvent B), ramping up to 40% solvent A and 60% solvent B over 2 minutes.

Method C: Experiments were performed on Agilent or Shimadzu system using ESI as ionization source with an Xtimate C18 (3 μm), 30×2.1 mm column, at a 1.2 mL/minute flow rate. The solvent system was a gradient starting with 100% water with 0.0375% TFA (solvent A) and 0% acetonitrile with 0.01875% TFA (solvent B), ramping up to 70% solvent A and 30% solvent B over 2 minutes.

Method D: Experiments performed on an Agilent 1100 HPLC with Agilent MSD mass spectrometer using ESI as ionization source using an Agilent ZORBAX SB-C18 100×3.0 mm column and a 0.7 ml/minute flow rate. The solvent system was a gradient starting with 98% water with 0.05% TFA (solvent A) and 2% acetonitrile with 0.05% TFA (solvent B), ramping up to 2% solvent A and 98% solvent B over 25.5 minutes. The final solvent system was held constant for a further 2.5 minutes.

Method E: Experiments performed on an Agilent 1100 HPLC with Agilent MSD mass spectrometer using ESI as ionization source using an Agilent ZORBAX SB-C18 30×2.1 mm column and a 0.4 ml/minute flow rate. The solvent system was a gradient starting with 97% water with 0.05% TFA (solvent A) and 3% acetonitrile with 0.05% TFA (solvent B), ramping up to 5% solvent A and 95% solvent B over 7 minutes. The final solvent system was held constant for a further 1.5 minute.

Method F: Experiments performed on a Waters Acquity UHPLC with Waters—LCT Premier XE mass spectrometer using ESI as ionization source using an Acquity UPLC BEH C18, 1.7 um, 2.1*50 mm column and a 0.6 ml/minute flow rate. The solvent system was a gradient starting with 98% water with 0.05% TFA (solvent A) and 2% acetonitrile with 0.05% TFA (solvent B), ramping up to 2% solvent A and 98% solvent B over 2.5 minutes. The final solvent system was held constant for a further 0.5 minute.

Method G: Experiments performed on a Waters Acquity UHPLC with Waters—LCT Premier XE mass spectrometer using ESI as ionization source using an Acquity UPLC BEH C18, 1.7 um, 2.1*50 mm column and a 0.6 ml/minute flow rate. The solvent system was a gradient starting with 98% water with 0.05% TFA (solvent A) and 2% acetonitrile with 0.05% TFA (solvent B), ramping up to 2% solvent A and 98% solvent B over 17 minutes. The final solvent system was held constant for a further 1.5 minutes.

Method H: Experiments performed on a Waters Acquity UHPLC with Waters—LCT Premier XE mass spectrometer using ESI as ionization source using an Acquity UPLC BEH C18, 1.7 um, 2.1*50 mm column and a 0.6 ml/minute flow rate. The solvent system was a gradient starting with 98% water with 0.05% TFA (solvent A) and 2% acetonitrile with 0.05% TFA (solvent B), ramping up to 2% solvent A and 98% solvent B over 7.5 minutes. The final solvent system was held constant for a further 1.0 minutes.

Method I: Experiments were performed on Agilent or Shimadzu system using ESI as ionization source with an Xtimate C18 (3 μm), 30×2.1 mm column, at a 1.2 mL/minute flow rate. The solvent system was a gradient starting with 70% water with 0.0375% TFA (solvent A) and 30% acetonitrile with 0.01875% TFA (solvent B), ramping up to 10% solvent A and 90% solvent B over 2 minutes.

Method J: Experiments were performed on Agilent or Shimadzu system using ESI as ionization source with an Xtimate C18 (3 μm), 30×2.1 mm column, at a 1.2 mL/minute flow rate. The solvent system was a gradient starting with 90% water with 0.0375% TFA (solvent A) and 10% acetonitrile with 0.01875% TFA (solvent B), ramping up to 20% solvent A and 80% solvent B over 7 minutes.

All abbreviations used to described reagents, reaction conditions, or equipment used are consistent with the definitions set forth in the "List of standard abbreviations and acronyms" published yearly by the Journal of Organic Chemistry (an American Chemical Society journal). The chemical names of discrete compounds of the invention were obtained using the structure naming feature ChemBioDraw Version 11.0 or from Accelrys' Pipeline Pilot IUPAC compound naming program.

BIOLOGICAL EXAMPLES

The compounds of the present invention were tested for their capacity to inhibit c-Abl kinase activity.

a. In Vitro Enzyme Assay

Using the following procedure, varying concentration of compounds of the invention were assessed for their ability to inhibit c-Abl enzyme's phosphorylation of 5-FAM-EAIYAHPFAKKK-$CONH_2$ (Caliper LifeSciences, cat#760346) peptide substrate in the presence of ATP at ~$K_m^{app}$. The phosphorylated product is detected using the Caliper mobility shift detection method where product and substrate are electrophoretically separated.

Materials:

| | |
|---|---|
| 1. Compound plates | Polypropylene 384 (Greiner, cat #781280) |
| 2. Reaction plates | Matrical 50 μl |
| 3. Substrate | FL-Peptide 2 5-FAM-EAIYAHPFAKKK-$CONH_2$ (Caliper LifeSciences, cat #760346) |
| 4. HEPES | 1M pH 7.5 |
| 5. $MgCl_2$ | 1M |
| 6. DTT | 1M |
| 7. Tween-20 | 10% (v/v) in mQ $H_2O$ |
| 8. Coating Reagent 3 | 3% (v/v) (Caliper LS, cat#) |
| 9. ATP | ATP, 10 mM (Cell Signaling, cat #9804) |
| 10. Kinase | His-Abl1, full length (Invitrogen, cat #P3049) |
| 11. EDTA | 0.25M |
| 12. Control Agent | Compound CAS No. CAS 220127-57-1 ($IC_{50}$ 0.05 nM) |

Working Reagents:

1. 1× Reaction Buffer:
   50 mM HEPES, pH 7.2
   10 mM $MgCl_2$
   0.01% Tween-20
   1 mM DTT
2. 2× ATP solution
   1 mM ATP in 1× reaction buffer
3. Separation Buffer:
   100 mM HEPES, pH 7.2
   0.015% Brij-35
   10 mM EDTA
   0.1% Coating-3 reagent (Caliper LifeSciences)
   5% DMSO
4. 2× ATP: For 2 plates prepare 30 mL 16 μM ATP (final=8 μM). Use Multidrop to dispense 50 μl/well into ATP/compound plate.
5. 2× enzyme+2× substrate: For 2 plates prepare 9 mL @ 0.3 nM enzyme (final=0.15 nM) and 2 μM substrate (final=1 μM) in 1× reaction buffer.

Compound Dilution:

1. Carry out 3-fold serial dilutions of compound in DMSO. Include volumes used in compound dilution protocol.
2. Transfer 1 μl of each well of compound plate to ATP/compound plate.

Kinase Reaction:

1. While compound dilution underway, prepare 2× enzyme+2× substrate stock.
2. Add 10 μl/well 2× enzyme+2× substrate to reaction plate.

3. Transfer 10 μl from ATP/compound plate to reaction plate.
4. Incubate at room temperature 30 minutes.
5. Add 10 μl/well 0.25 mM EDTA to stop the reaction.

Detection: Measure the amounts of substrate and product in each well.

The Examples were tested in the above c-Abl kinase inhibition assay and found to have Ki of about 0.0000001 μM to about 5 μM. Particular compounds of Formula I were found to have Ki of about 0.0000001 μM to about 1 μM. Particular compounds of Formula I were found to have Ki of about 0.0000001 μM to about 0.5 Particular compounds of Formula I were found to have Ki of about 0.0000001 μM to about 0.01 μM.

Following the order in which compounds of the invention are presented the Table 1 and Table 1b hereinabove, the c-Abl activity level of said compounds of the invention have the corresponding activity level as set forth in Table 2 and Table 2b, respectively, below.

TABLE 2

| Number | c-Abl Ki (uM) |
|---|---|
| 1 | 0.006 |
| 2 | 0.139 |
| 3 | 0.007 |
| 4 | 0.072 |
| 5 | 0.416 |
| 6 | 0.002 |
| 7 | 0.440 |
| 8 | 0.001 |
| 9 | 0.012 |
| 10 | 0.039 |
| 11 | 0.041 |
| 12 | 0.026 |
| 13 | 0.015 |
| 14 | 0.050 |
| 15 | 0.0001 |
| 16 | 0.0004 |
| 17 | 0.003 |
| 18 | 0.001 |
| 19 | 0.001 |
| 20 | 0.0003 |
| 21 | 0.0009 |
| 22 | 0.001 |
| 23 | 0.0003 |
| 24 | 0.001 |
| 25 | 0.0006 |
| 26 | 0.0004 |
| 27 | 0.00003 |
| 28 | 0.003 |
| 29 | 0.003 |
| 30 | 0.00004 |
| 31 | 0.0005 |
| 32 | 0.213 |
| 33 | 0.017 |
| 34 | 0.002 |
| 35 | 0.403 |
| 36 | 0.002 |
| 37 | 0.003 |
| 38 | 0.001 |
| 39 | 0.007 |
| 40 | 0.086 |
| 41 | 0.052 |
| 42 | 0.0001 |
| 43 | 0.001 |
| 44 | 0.001 |
| 45 | 0.003 |
| 46 | 0.238 |
| 47 | 0.016 |
| 48 | 0.0003 |
| 49 | 0.003 |
| 50 | 0.002 |
| 51 | 0.0003 |
| 52 | 0.0002 |
| 53 | 0.003 |

TABLE 2-continued

| Number | c-Abl Ki (uM) |
|---|---|
| 54 | 0.002 |
| 55 | 0.0001 or 0.00009 |
| 56 | 0.0001 or 0.00009 |
| 57 | 0.001 |
| 58 | 0.0342 |
| 59 | 0.058 |
| 60 | 0.132 |
| 61 | 0.36 |
| 62 | 0.0003 |
| 63 | 0.00007 |
| 64 | 0.00002 |
| 65 | 0.0005 |
| 66 | 0.009 |
| 67 | 0.004 |
| 68 | 0.0007 |
| 69 | 0.013 |
| 70 | 0.0005 |
| 71 | 0.0007 |
| 72 | 0.042 |
| 73 | 0.033 |
| 74 | 0.0002 |
| 75 | 0.0009 |
| 76 | 0.00006 |
| 77 | 0.001 |
| 78 | 0.027 |
| 79 | 0.042 |
| 80 | 0.0001 |
| 81 | 0.001 |
| 82 | 0.0005 |
| 83 | 0.0006 |
| 84 | 0.020 |
| 85 | 0.001 |
| 86 | 0.002 |
| 87 | 0.003 |
| 88 | 0.0003 |
| 89 | 0.002 |
| 90 | 0.027 |
| 91 | 0.013 |
| 92 | 0.002 |
| 93 | 0.0005 |
| 94 | 0.042 |
| 95 | 0.0007 |
| 96 | 0.0002 |
| 97 | 0.00003 |
| 98 | 0.042 |
| 99 | 0.042 |
| 100 | 0.0008 |
| 101 | 0.004 |
| 102 | 0.015 |
| 103 | 0.00003 |
| 104 | 0.00003 |
| 105 | 0.00009 |
| 106 | 0.0009 |
| 107 | 0.0002 |
| 108 | 0.002 |
| 109 | 0.00002 |
| 110 | 0.0001 |
| 111 | 0.0009 |
| 112 | 0.003 |
| 113 | 0.005 |
| 114 | 0.005 |
| 115 | 0.008 |
| 116 | 0.020 |
| 117 | 0.006 |
| 118 | 0.0002 |
| 119 | 0.002 |
| 120 | 0.003 |
| 121 | 0.002 |
| 122 | 0.002 |
| 123 | 0.0007 |
| 124 | 0.037 |
| 125 | 0.004 |
| 126 | 0.0009 |
| 127 | 0.0006 |
| 128 | 0.018 |

TABLE 2-continued

| Number | c-Abl Ki (uM) |
|---|---|
| 129 | 0.042 |
| 130 | 0.042 |
| 131 | 0.001 |
| 132 | 0.0002 |
| 133 | 0.021 |
| 134 | 0.004 |
| 135 | 0.022 |
| 136 | 0.004 |
| 137 | 0.004 |
| 138 | 0.002 |
| 139 | 0.042 |
| 140 | 0.007 |
| 141 | 0.0006 |
| 142 | 0.00004 |
| 143 | 0.011 |
| 144 | 0.034 |
| 145 | 0.001 |
| 146 | 0.0007 |
| 147 | 0.0003 |
| 148 | 0.0007 |
| 149 | 0.012 |
| 150 | 0.005 |
| 151 | 0.004 |
| 152 | 0.007 |
| 153 | 0.003 |
| 154 | 0.0001 |
| 155 | 0.00007 |
| 156 | 0.001 |
| 157 | 0.009 |
| 158 | 0.0006 |
| 159 | 0.00002 |
| 160 | 0.007 |
| 161 | 0.005 |
| 162 | 0.005 |
| 163 | 0.0009 |
| 164 | 0.0001 |
| 165 | 0.003 |
| 166 | 0.030 |
| 167 | 0.002 |
| 168 | 0.011 |
| 169 | 0.001 |
| 170 | 0.002 |
| 171 | 0.0002 |
| 172 | 0.0008 |
| 173 | 0.007 |
| 174 | 0.006 |
| 175 | 0.0008 |
| 176 | 0.011 |
| 177 | 0.008 |
| 178 | 0.0002 or 0.0005 |
| 179 | 0.004 or 0.0008 |
| 180 | 0.004 or 0.0008 |
| 181 | 0.001 |
| 182 | 0.0001 |
| 183 | 0.0008 |
| 184 | 0.0002 |
| 185 | 0.002 |
| 186 | 0.007 |
| 187 | 0.0002 or 0.0005 |
| 188 | 0.0001 |
| 189 | 0.00009 |
| 190 | 0.00004 |
| 191 | 0.00002 |
| 192 | 0.00007 |
| 193 | 0.001 |
| 194 | 0.041 |
| 195 | 0.0002 |
| 196 | 0.013 |
| 197 | 0.0003 |
| 198 | 0.0002 |
| 199 | 0.027 |
| 200 | 0.023 |
| 201 | 0.007 |

TABLE 2-continued

| Number | c-Abl Ki (uM) |
|---|---|
| 202 | 0.0004 |
| 203 | 0.042 and 0.005 |
| 204 | 0.042 and 0.005 |
| 205 | 0.002 |
| 206 | 0.002 |
| 207 | 0.027 |
| 208 | 0.004 |
| 209 | 0.0006 |
| 210 | 0.0004 |
| 211 | 0.0005 |
| 212 | 0.0004 |
| 213 | 0.0003 |
| 214 | 0.0005 or 0.001 |
| 215 | 0.0005 or 0.001 |
| 216 | 0.0008 or 0.0006 |
| 217 | 0.0008 or 0.0006 |
| 218 | 0.0001 |
| 219 | 0.010 |
| 220 | 0.0004 |
| 221 | 0.0002 |
| 222 | 0.00009 |
| 223 | 0.0005 |
| 224 | 0.001 |
| 225 | 0.001 |
| 226 | 0.001 |
| 227 | 0.0003 |
| 228 | 0.00002 |
| 229 | 0.002 |
| 230 | 0.005 or 0.022 |
| 231 | 0.005 or 0.022 |
| 232 | 0.0003 |
| 233 | 0.0007 |
| 234 | 0.002 |
| 235 | 0.042 |
| 236 | 0.036 |
| 237 | 0.001 or 0.0001 |
| 238 | 0.001 or 0.0001 |
| 239 | 0.0002 or 0.0009 |
| 240 | 0.0002 or 0.0009 |
| 241 | 0.004 |
| 242 | 0.00005 or 0.00009 |
| 243 | 0.00005 or 0.00009 |
| 244 | 0.002 |
| 245 | 0.009 or 0.042 |
| 246 | 0.009 or 0.042 |
| 247 | 0.009 |
| 248 | 0.017 |
| 249 | 0.00003 |
| 250 | 0.00004 |
| 251 | 0.0004 |
| 252 | 0.00006 |
| 253 | 0.00005 |
| 254 | 0.0004 |
| 255 | 0.002 |
| 256 | 0.020 |
| 257 | 0.0008 |
| 258 | 0.001 |
| 259 | 0.0002 |
| 260 | 0.002 |
| 261 | 0.004 |
| 262 | 0.002 |

TABLE 2-continued

| Number | c-Abl Ki (uM) |
|---|---|
| 263 | 0.040 pr 0.004 |
| 264 | 0.040 or 0.004 |
| 265 | 0.001 |
| 266 | 0.003 |
| 267 | 0.001 |
| 268 | 0.0002 |
| 269 | 0.003 |
| 270 | 0.0003 |
| 271 | 0.042 |
| 272 | 0.00003 or 0.0002 |
| 273 | 0.00003 or 0.0002 |
| 274 | 0.002 |
| 275 | 0.010 |
| 276 | 0.0003 |
| 277 | 0.002 |
| 278 | 0.0002 |
| 279 | 0.0002 |
| 280 | 0.0004 |
| 281 | 0.0006 |
| 282 | 0.004 |
| 283 | 0.0001 |
| 284 | 0.0001 or 0.0004 |
| 285 | 0.0001 or 0.0004 |
| 286 | 0.00007 or 0.00003 |
| 287 | 0.00007 or 0.00003 |
| 288 | 0.0003 |
| 289 | 0.001 |
| 290 | 0.0005 |
| 291 | 0.0009 or 0.003 |
| 292 | 0.0009 or 0.003 |
| 293 | 0.001 |
| 294 | 0.011 |
| 295 | 0.0006 |
| 296 | 0.040 |
| 297 | 0.001 |
| 298 | 0.005 |
| 299 | 0.0007 |
| 300 | 0.003 |
| 301 | 0.042 |
| 302 | 0.00002 |
| 303 | 0.001 |
| 304 | 0.001 |
| 305 | 0.001 |
| 306 | 0.002 |
| 307 | 0.007 |
| 308 | 0.0002 |
| 309 | 0.002 |
| 310 | 0.010 |
| 311 | 0.00002 |
| 312 | 0.0001 |
| 313 | 0.0001 |
| 314 | 0.0004 |
| 315 | 0.0008 |
| 316 | 0.0001 |
| 317 | 0.0003 |
| 318 | 0.020 |
| 319 | 0.005 |
| 320 | 0.0008 |
| 321 | 0.002 |
| 322 | 0.0003 |
| 323 | 0.002 |
| 324 | 0.002 |
| 325 | 0.0003 |
| 326 | 0.0001 |
| 327 | 0.0003 |
| 328 | 0.0004 |
| 329 | 0.00008 |

TABLE 2-continued

| Number | c-Abl Ki (uM) |
|---|---|
| 330 | 0.001 |
| 331 | 0.003 |
| 332 | 0.004 |
| 333 | 0.0002 |
| 334 | 0.012 |
| 335 | 0.0002 |
| 336 | 0.011 |
| 337 | 0.005 |
| 338 | 0.0002 |
| 339 | 0.0003 |
| 340 | 0.0003 |
| 341 | 0.0004 |
| 342 | 0.0003 |
| 343 | 0.001 |
| 344 | 0.0002 or 0.013 |
| 345 | 0.0002 |
| 346 | 0.0001 |
| 347 | 0.0001 |
| 348 | 0.0002 |
| 349 | 0.001 |
| 350 | 0.0001 |
| 351 | 0.0007 |
| 352 | 0.010 |
| 353 | 0.001 |
| 354 | 0.005 |
| 355 | 0.002 |
| 356 | 0.0004 |
| 357 | 0.0004 |
| 358 | 0.00002 |
| 359 | 0.042 |
| 360 | 0.0003 |
| 361 | 0.011 |
| 362 | 0.015 |
| 363 | 0.214 |
| 364 | 0.003 |
| 365 | 0.017 |
| 366 | 0.019 |
| 367 | 0.008 |
| 368 | 0.013 |
| 369 | 0.006 |
| 370 | 0.007 |
| 371 | 0.0002 or 0.013 |

TABLE 2B

| Number | c-Abl Ki (uM) |
|---|---|
| 372 | 0.000789 |
| 373 | 0.00307 or 0.00119 |
| 374 | 0.00307 or 0.00119 |
| 375 | 0.0249 |
| 376 | 0.000236 |
| 377 | 0.000164 |
| 378 | 0.0000709 |
| 379 | 0.000158 |
| 380 | 0.000349 |
| 381 | 0.000175 |
| 382 | 0.000116 |
| 383 | 0.000671 |
| 384 | 0.00139 |
| 385 | 0.00565 |
| 386 | 0.000712 |
| 387 | |
| 388 | |
| 389 | |
| 390 | |
| 391 | 0.000204 |
| 392 | 0.0196 |
| 393 | |

TABLE 2B-continued

| Number | c-Abl Ki (uM) |
|---|---|
| 394 | 0.000173 |
| 395 | |
| 396 | 0.000312 |
| 397 | 0.000545 |
| 398 | |
| 399 | |
| 400 | 0.00242 |
| 401 | 0.00103 |
| 402 | 0.00502 |
| 403 | 0.0217 |
| 404 | |
| 405 | |
| 406 | |
| 407 | 0.00202 or 0.0000841 |
| 408 | 0.00202 or 0.0000841 |
| 409 | 0.000637 or 0.000434 |
| 410 | 0.000637 or 0.000434 |
| 411 | |
| 412 | 0.0416 |
| 413 | 0.00104 |
| 414 | 0.000168 |
| 415 | |
| 416 | |
| 417 | 0.0000723 |
| 418 | 0.000158 |
| 419 | 0.000268 |
| 420 | 0.0000186+ |
| 421 | |
| 422 | |
| 423 | |
| 424 | 0.0000896 |
| 425 | 0.0253 |
| 426 | 0.01 or 0.00175 |
| 427 | 0.01 or 0.00175 |
| 428 | 0.000451 or 0.00045 |
| 429 | 0.000451 or 0.00045 |
| 430 | 0.000802 or 0.000246 |
| 431 | 0.000398 or 0.000265 |
| 432 | 0.000398 or 0.000265 |
| 433 | 0.000802 or 0.000246 |
| 434 | 0.0416 or 0.00346 |
| 435 | 0.0416 or 0.00346 |
| 436 | 0.0335 |
| 437 | 0.0034 or 0.0000799 |
| 438 | 0.0034 or 0.0000799 |
| 439 | 0.000706 |
| 440 | 0.00208 |
| 441 | 0.000218 |
| 442 | 0.00255 |
| 443 | 0.00171 |
| 444 | 0.000167 |
| 445 | 0.0416++ |
| 446 | 0.000586 |
| 447 | 0.000193 |
| 448 | 0.022 |
| 449 | 0.005 |
| 450 | 0.000417 |
| 451 | |
| 452 | |
| 453 | 0.0077 |
| 454 | 0.0416 |
| 455 | 0.024 |
| 456 | 0.0416 |
| 457 | 0.0416 |
| 458 | 0.0335 |

b. K-562 Cell Proliferation Assay

K-562 cells are a Philadelphia Chromosome Positive (Ph+) cell line that proliferate through the expression of the Bcr-Abl fusion protein and the cell line is useful for assessing Abl small molecule inhibitors, such as compounds of Formula I, by monitoring cellular proliferation in the presence such compounds.

This assay determines the number of viable cells in a culture by quantification of ATP. Promega's CellTiter-Glo® Luminescent Cell Viability Assay (CTG) is the reagent used for this determination. The assay is homogenous. Addition of the CTG reagent results in cell lysis and generation of a luminescent signal through the luciferase reaction. The luminescent signal is proportional to the amount of ATP present. For compounds that interfere with cell division and/or have effects on cell size, the readout is not necessarily proportional to cell number/viability.

Compounds of the invention were tested to determine the effective concentrations of compounds (EC50) required to inhibit K-562 cell growth by relating cell number to cellular ATP detection.

Final Assay Conditions:

Cell Line: K-562 cells seeded at 5000 cells/well at 20 ul/well

Compounds: 10 uM starting concentration; 1:3 serial dilution, 10 pts (0.5% final DMSO conc.)

CTG reagent: 1:1 CTG reagent added to assay plate

Materials:

Cell Line: K-562 (ATCC CCL-243)

Media: Iscove's Modified Dulbecco's Medium (ATCC 30-2005), 20% FBS, 1% Pen/Strep Stock Compound Plate: 384-well polypropylene v bottom (Greiner cat #781280)

Intermediate Compound Plate: 384-well polypropylene v bottom (Greiner cat #781280)

Cell Plates: 384-well polypropylene BW flat/clear bottom (Corning cat #3712)

Read Reagent Cell Titer-Glo (Promega cat #G7572)

Standards: Nocodazole (expected EC50~0.04 uM) and Compound CAS NO 220127-57-1 (expected EC50~0.125 uM)

Controls: Cytostatic: Luminescence counts should be equivalent to counts obtained from a Day 0 read; and Cytotoxic: Luminescence counts should be equivalent to background.

Procedures:

Cell Plating:

Seed cells at 5000 cells/well in 20 ul cell plating media into a 384 well cell plate.

Compound Dilution:

Add 40 ul DMSO to columns 1-2, 4-12, 14-24 to a stock compound plate.

Add 60 ul 1 mM test compound to columns 3 and 13 in duplicate down rows i.e. A/B, C/D, Serial dilute compound across plate from 3 to 12 and 13 to 22 for 3 fold dilutions across 10 compound concentrations i.e. 12 ul into 24 ul.

Add 30 ul control compounds to column 24.

Wells A-H include a cytostatic agent e.g. aphidocoline, nocodozole, taxol

Wells I-P include a cytotoxic agent e.g. staurosporine, digitonin

Add 99 ul of assay media to an intermediate compound plate.

Transfer 1 ul of stock compound plate to intermediate compound plate for 100× dilution.

Cellular Assay:

Transfer 20 ul of intermediate compound plate for 2× dilution.

Incubate in humidified $CO_2$ incubator four (4) days.

CellTiter-Glo Assay:

add 40 ul of reconstituted Cell Titer-Glo reagent

Incubate at RT for 20-30 minutes.

read luminescence on plate reader

Timing of Additions Summary:

Day 0a: Seed 20 uL of 5000 cells per well

Day 0b: Serial dilute compounds in DMSO

Day 0c: Create Intermediate Compound plate

Day 0d: Transfer 20 uL of cmpd/assay media to cells

Day 2-4: Incubate in humidified CO2 incubator

Day 4a: Add 40 uL of Cell Titer-Glo solution

Day 4b: Incubate CTG reaction

Day 4c: Read luminescence c. HL-60 Cell Proliferation Assay

HL-60 cells are a Philadelphia Chromosome Negative (Ph-) cell line that serve as a control for the K-562 proliferation assay. Compounds that exert their activity by inhibition of Abl kinase should not inhibit proliferation of HL-60 cells unless such activity is due to off-target activity.

This assay determines the number of viable cells in a culture by quantification of ATP. Promega's CellTiter-Glo® Luminescent Cell Viability Assay (CTG) is the reagent used for this determination. The assay is homogenous. Addition of the CTG reagent results in cell lysis and generation of a luminescent signal through the luciferase reaction. The luminescent signal is proportional to the amount of ATP present. For compounds that interfere with cell division and/or have effects on cell size, the readout is not necessarily proportional to cell number/viability. Compounds of the invention were tested to determine the effective concentrations of compounds (EC50) required to inhibit HL-60 cell growth by relating cell number to cellular ATP detection.

Final Assay Conditions:

Cell Line: HL-60 cells seeded at 20000 cells/well at 20 ul/well

Compounds: 10 uM starting concentration; 1:3 serial dilution, 10 pts (0.5% final DMSO conc.)

CTG reagent: 1:1 CTG reagent added to assay plate

Materials:

Cell Line: HL-60 (ATCC CCL-240)

Media: Iscove's Modified Dulbecco's Medium (ATCC 30-2005), 20% FBS, 1% Pen/Strep Stock Compound Plate: 384-well polypropylene v bottom (Greiner cat #781280)

Intermediate Compound Plate: 384-well polypropylene v bottom (Greiner cat #781280)

Cell Plates: 384-well polypropylene BW flat/clear bottom (Corning cat #3712)

Read Reagent Cell Titer-Glo (Promega cat #G7572)

Standards: Nocodazole (expected EC50~0.04 uM), and Compound CAS NO 220127-57-1 (expected EC50—Inactive)

Controls: Cytostatic: Luminescence counts should be equivalent to counts obtained from a Day 0 read; and Cytotoxic: Luminescence counts should be equivalent to background.

Procedures:

Cell Plating:

Seed cells at 20000 cells/well in 20 ul cell plating media into a 384 well cell plate.

Compound Dilution:

Add 40 ul DMSO to columns 1-2, 4-12, 14-24 to a stock compound plate.

Add 60 ul 1 mM test compound to columns 3 and 13 in duplicate down rows i.e. A/B, C/D, Serial dilute compound across plate from 3 to 12 and 13 to 22 for 3 fold dilutions across 10 compound concentrations i.e. 12 ul into 24 ul.

Add 30 ul control compounds to column 24.

Wells A-H include a cytostatic agent e.g. aphidocoline, nocodozole, taxol

Wells I-P include a cytotoxic agent e.g. staurosporine, digitonin

Add 99 ul of assay media to an intermediate compound plate.

Transfer 1 ul of stock compound plate to intermediate compound plate for 100× dilution.

Cellular Assay:

Transfer 20 ul of intermediate compound plate for 2× dilution.

Incubate in humidified $CO_2$ incubator four (4) days.

CellTiter-Glo Assay:

add 40 ul of reconstituted Cell Titer-Glo reagent (see product insert)

Incubate at RT for 20-30 minutes.

read luminescence on plate reader

Timing of Additions Summary:

Day 0a: Seed 20 uL of 20000 cells per well

Day 0b: Serial dilute compounds in DMSO

Day 0c: Create Intermediate Compound plate

Day 0d: Transfer 20 uL of cmpd/assay media to cells

Day 2-4: Incubate in humidified CO2 incubator

Day 4a: Add 40 uL of Cell Titer-Glo solution

Day 4b: Incubate CTG reaction

Day 4c: Read luminescence

PREPARATIVE EXAMPLES

Example 1

3-bromo-1-methylpyridin-4(1H)-one

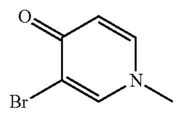

To a solution of 3-bromo-4-pyridinol (308.2 mg, 1.771 mmol) in N,N-dimethylformamide (10 mL, 100 mmol) was added potassium carbonate (371.0 mg, 2.684 mmol) and methyl iodide (133 uL, 2.14 mmol). The reaction was stirred at room temperature for 18 hours. The reaction mixture was filtered and evaporated in vacuo. The crude product was purified via flash chromatography on silica gel (12 g silica, solvent gradient: 0-20% methanol in dichloromethane) to yield 269.9 mg (81%) of 3-bromo-1-methylpyridin-4(1H)-one.

LCMS (ESI): M+H=188.2; $^{1}$H NMR (400 MHz, DMSO-$d_6$) δ 8.24 (d, J=2.1 Hz, 1H), 7.68 (dd, J=7.4, 2.1 Hz, 1H), 6.21 (d, J=7.4 Hz, 1H), 3.65 (s, 3H).

Example 2

5-bromo-4-methylpyrimidine

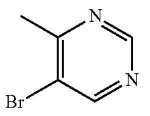

To a solution of 2-amino-5-bromo-4-methylpyrimidine (0.5102 g, 2.713 mmol) in tetrahydrofuran (10 mL, 200 mmol) was dropwise added tert-butyl nitrite (1.50 mL, 11.4 mmol). The reaction was then stirred at 60° C., for 19 hours. The reaction mixture was evaporated in vacuo, and the crude product was purified via flash chromatography on silica gel (24 g silica, solvent gradient: 0-100% ethyl acetate in dichloromethane) to yield 110.5 mg (24%) of 5-bromo-4-methylpyrimidine. LCMS (ESI): M+H=173.2; $^{1}$H NMR (400 MHz, DMSO-$d_6$) δ 9.01 (s, 1H), 8.90 (s, 1H), 2.57 (s, 3H).

Example 3

5-bromo-4-methylpyridin-3-yl acetate

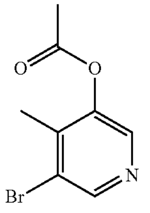

To a flask containing boron trifluoride etherate (0.35 mL, 2.8 mmol) at −15° C. was added a solution of 5-bromo-4-methylpyridin-3-amine (249.0 mg, 1.331 mmol) in 1,2-dimethoxyethane (2.0 mL, 19 mmol). Tert-butyl nitrite (0.20 mL, 1.7 mmol) was then added dropwise and the reaction mixture stirred at −15° C. for one hour. 3 mL pentane was then added and the solid material collected by vacuum filtration. The solid material was dissolved in acetic anhydride (2.0 mL, 21 mmol) and stirred at 100° C. for one hour. The solvent was evaporated in vacuo, and the residue then suspended in 2M aqueous $Na_2CO_3$ and extracted twice with dichloromethane. The combined organic extracts were dried over $MgSO_4$, filtered, and evaporated in vacuo. The crude product was purified via flash chromatography on silica gel (24 g silica, solvent gradient: 0-40% ethyl acetate in heptanes) to yield 117.7 mg (38%) of 5-bromo-4-methylpyridin-3-yl acetate. LCMS (ESI): M+H=230.2; $^{1}$H NMR (400 MHz, DMSO-$d_6$) δ 8.61 (s, 1H), 8.35 (s, 1H), 2.37 (s, 3H), 2.23 (s, 3H).

Example 4 methyl 5-bromo-4-methylnicotinate

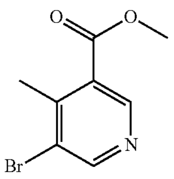

To a solution of 5-bromo-4-methylnicotinic acid (223.4 mg, 1.034 mmol) in methylene chloride (3.0 mL, 47 mmol) and methanol (3.0 mL, 74 mmol) was added 2.0 M of trimethylsilyldiazomethane in ether (0.70 mL). The reaction mixture was stirred at room temperature for one hour, and then 2.0 M of tTrimethylsilyldiazomethane in ether (0.50 mL) was added. After an additional two hours, the crude reaction mixture was evaporated in vacuo to yield 237.2 mg (100%) of methyl 5-bromo-4-methylnicotinate which was carried forward without further purification. LCMS (ESI): M+H=230.2; $^{1}$H NMR (400 MHz, DMSO-$d_6$) δ 8.86 (s, 1H), 8.82 (s, 1H), 3.89 (s, 3H), 2.58 (s, 3H).

Example 5

N-(5-bromo-4-methylpyridin-3-yl)tetrahydro-2H-pyran-4-carboxamide

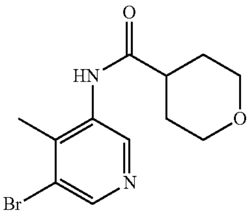 [SMILES: Cc1c(Br)cncc1NC(=O)C1CCOCC1]

To a solution of 5-bromo-4-methylpyridin-3-amine (128.9 mg, 0.6892 mmol) in tetrahydrofuran (4.0 mL, 49 mmol) at 0° C. was added 1.4 M of methylmagnesium bromide in toluene (0.55 mL). After stirring at 0° C. for 10 minutes, methyl tetrahydro-2H-pyran-4-carboxylate (92.00 g, 638.1 mmol) was added. The reaction mixture was stirred overnight while warming to room temperature. The reaction mixture was poured into dichloromethane, washed with saturated aqueous $NaHCO_3$, dried over $MgSO_4$, and evaporated in vacuo. The crude product was purified via flash chromatography on silica gel (12 g silica, solvent gradient: 0-10% methanol in dichloromethane) to yield 53.5 mg (26%) of N-(5-bromo-4-methylpyridin-3-yl)tetrahydro-2H-pyran-4-carboxamide. LCMS (ESI): M+H=299.2.

Example 6

3-fluoro-2-methyl-5-(tributylstannyl)pyridine

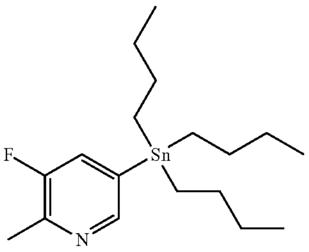 [SMILES: CCC[CH2][Sn]([CH2]CCC)([CH2]CCC)[c]1cnc(C)c(F)c1]

To a mixture of 2,2,6,6-tetramethyl-piperidine (0.30 mL, 1.8 mmol) and 10 mL tetrahydrofuran at −78° C. was dropwise added 2.5 M of n-butyllithium in hexane (0.80 mL). The reaction vessel was then placed into a 0° C. ice bath and stirred for 60 minutes. The reaction vessel was then cooled to −78° C., and 3-fluoro-5-tributylstannylpyridine (504.7 mg, 1.307 mmol) was added as a solution in tetrahydrofuran (2 mL). The reaction mixture was stirred at −78° C. for 90 minutes, and then methyl iodide (0.15 mL, 2.4 mmol) was added. After an additional 30 minutes, the reaction was quenched with saturated aqueous $NH_4Cl$, and extracted with ethyl acetate. The organic extract was dried over $MgSO_4$, filtered, and evaporated in vacuo. The crude product was purified via flash chromatography on silica gel (2 g silica, solvent gradient: 0-30% ethyl acetate in heptanes) to yield 381.8 mg (50% pure, 37% yield) of 3-fluoro-2-methyl-5-(tributylstannyl)pyridine. LCMS (ESI): M+H=402.2.

Example 7

5-bromo-6-methylpyridin-3-amine

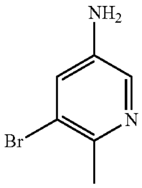

Step 1: 3-Bromo-2-methyl-5-nitropyridine

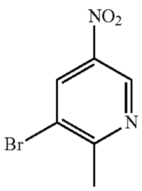

To a cold solution of diethyl malonate (2.2 mL, 14.5 mmol) in THF (30 mL) was added NaH (0.58 g, 60% in mineral oil) over 5 minutes. 3-Bromo-2-chloro-5-nitropyridine (3.13 g, 13.15 mmol) was added in 4 portions over 15 minutes. The reaction mixture was warmed to room temperature and THF was removed under reduced pressure. The mixture was heated at 115° C. for 75 minutes. After the reaction mixture was cooled to room temperature, $H_2SO_4$ (6.0 M, 17 mL) was added and the mixture was heated at 110° C. overnight. It was cooled to 0° C. and a KOH solution (25%) in water was added until pH=7.0. The reaction mixture was kept at 0° C. for 30 min. The crude product was collected by filtration and washed with cold water. dichloromethane (100 mL) was added to the solids and stirred at r.t. for 30 min. The solid was filtered off and the filtrate was concentrated to 30 mL. Petroleum ether (60 mL) was added and the solid was filtered off and the filtrate was concentrated to give the product as a red solid (2.3 g, 73%).

Step 2: 5-bromo-6-methylpyridin-3-amine

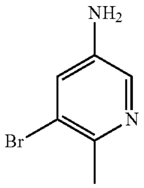

To a solution of 3-bromo-2-methyl-5-nitropyridine (2.3 g, 10.5 mmol) in EtOH (20 mL) was added water (40 mL), $NH_4Cl$ (2.25 g, 42 mmol) and iron powder (2.94 g, 52.5 mmol). The mixture was stirred at 75° C. for 2 hours. After the reaction mixture was cooled to room temperature, it was filtered through a celite pad. Organic solvent was removed under reduced pressure, and it was extracted with $CH_2Cl_2$ (3×30 mL). The combined organic layer was dried over $Na_2SO_4$, and solvent was removed to give an off-white solid (1.52 g, 77%).

LCMS (ESI): $R_T$ (min)=0.840, M+$H^+$=186.7, method=B. $^1H$ NMR (400 MHz, DMSO-$d_6$) δ 7.92 (d, J=2.4 Hz, 1 H), 7.18 (d, J=2.4 Hz, 1 H), 2.53 (3, 3H).

Example 8

2,2-difluoro-N-(7-(5-fluoro-2-methylphenyl)isoquinolin-3-yl)cyclopropanecarboxamide

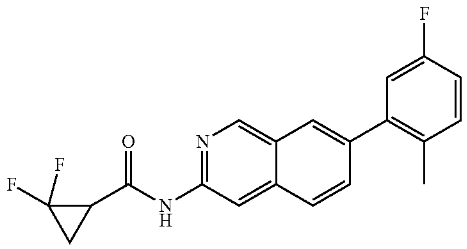 [SMILES: Cc1ccc(F)cc1-c1ccc2cc(NC(=O)C3CC3(F)F)ncc2c1]

Step 1: 5-bromo-2-iodobenzonitrile

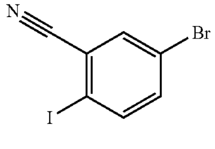

2-amino-5-bromobenzonitrile (100 g, 0.5 mol) was added during 1 hour to tert-butyl nitrite (117 mL, 0.75 mol) and iodine (250 g, 1.1 mol) in dry acetonitrile (600 mL) under nitrogen while maintaining the temperature between 30° C. and 35° C. Stirring was continued for 60 minutes at 23° C. Subsequent addition of saturated aqueous $Na_2SO_3$ (2 L) gave precipitate which was collected by filtration, and washed with hexanes to obtain 100 g (65%) of 5-bromo-2-iodobenzonitrile. $^1$H NMR (400 MHz, DMSO-$d_6$) δ 8.14 (d, J=2.4 Hz, 1H), 7.95 (d, J=8.4 Hz, 1H), 7.64 (dd, J=2.4, 8.4 Hz, 1H).

Step 2: (5-bromo-2-iodophenyl)methanamine

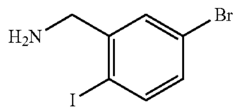

To a solution of 5-bromo-2-iodobenzonitrile (9.21 g, 0.03 mol) in tetrahydrofuran (140 mL) at 0° C. was added $BH_3$-THF (66 mL, 66 mmol, 1 M solution in tetrahydrofuran) dropwise over 1 hour. The reaction solution was stirred at room temperature for 10 minutes, and then heated to reflux for overnight. 10% aqueous HCl was added (to adjust to pH 2-3) and stirred for 20 minutes, then the mixture was basified with 10 M aqueous KOH up to pH>10. The mixture was extracted with ethyl acetate three times. Organics were combined, dried with sodium sulfate, filtered and concentrated in vacuo to yield 6.2 g of crude (5-bromo-2-iodophenyl)methanamine as a yellow oil. LCMS (ESI): M+H=311.7; $^1$H NMR (400 MHz, DMSO-$d_6$): δ 7.71 (d, J=8.4 Hz, 1H), 7.67 (d, J=2.4 Hz, 1H), 7.18 (dd, J=2.4, 8.4 Hz, 1H).

Step 3: 3-amino-7-bromoisoquinoline-4-carbonitrile

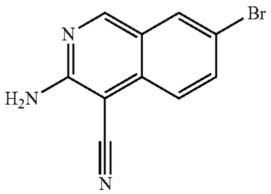 [SMILES: N#Cc1c(N)ncc2cc(Br)ccc12]

To a stirred solution of (5-bromo-2-iodophenyl)methanamine (40 g, 0.129 mol) in N,N-dimethylformamide (500 mL) was sequentially added N,N-diisopropylethylamine (33.3 g, 0.257 mol), malononitrile (16.9 g, 0.257 mol) and CuBr (36.9 g, 0.257 mol). The mixture was stirred at room temperature overnight. After that, to the reaction mixture was added ether and 10% $NH_3$ (1 L, 1:1) and stirred at room temperature overnight open to the air. The mixture was separated and the residue was extracted with ethyl acetate three times, and the combined organic extracts were washed with brine, filtered, and evaporated to yield 20 g (62%) of 3-amino-7-bromoisoquinoline-4-carbonitrile. LCMS (ESI): M+H=247.7; $^1$H NMR (400 MHz, DMSO-$d_6$) δ 9.03 (s, 1H), 8.23 (d, J=2.0 Hz, 1H), 7.81 (dd, J=2.0, 9.2 Hz, 1H), 7.56 (d, J=9.2 Hz, 1H), 7.42 (s, 2H).

Step 4: 7-bromo-isoquinolin-3-amine

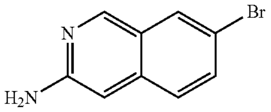

To a stirred solution of 3-amino-7-bromoisoquinoline-4-carbonitrile (25 g, 101 mmol) in water (100 mL) was added $H_2SO_4$ (100 mL) dropwise while cooling in an ice-water bath. Then the mixture was stirred and heated to 115° C. for 3 days. After that, the reaction was cooled down to 0° C. 10 M aqueous NaOH was added to adjust to pH>12. The resulting solid precipitate was collected by filtration, washed with water, and dried under vacuum to yield 4.2 g (19%) of 7-bromo-isoquinolin-3-amine. LCMS (ESI): M+H=222.8; $^1$H NMR (400 MHz, DMSO-$d_6$) δ 8.76 (s, 1H), 8.00 (t, J=0.8 Hz, 1H), 7.49-7.48 (m, 2H), 6.58 (s, 1H), 6.06 (s, 1H).

Step 5: 7-(5-fluoro-2-methylphenyl)isoquinolin-3-amine

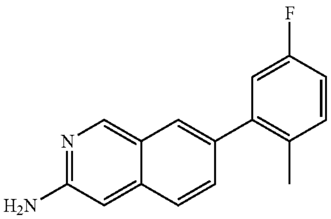 [SMILES: Cc1ccc(F)cc1-c1ccc2cc(N)ncc2c1]

7-Bromoisoquinolin-3-amine (15.0 g, 67.4 mmol), 5-fluoro-2-methylphenylboronic acid (12.4 g, 81.0 mmol), Pd(dppf)$Cl_2$ (2.76 g, 3.38 mmol) and $Cs_2CO_3$ (26.4 g, 81.0 mmol) in MeCN/$H_2O$ (10:1, 150 mL) was stirred at 120° C. for 6 h under $N_2$. After the reaction mixture was filtered, the filtrate was concentrated and purified by chromatography on silica gel to give the desired product (13.5 g, 79.4%). LCMS (ESI): $R_T$ (Min)=0.869, M+H$^+$=252.8, method=A. $^1$H NMR (400 MHz, DMSO-$d_6$) δ 8.84 (s, 1H), 7.75 (s, 1H), 7.55 (d, J=8.8 Hz, 1H), 7.44 (d, J=8.4 Hz, 1H), 7.34-7.30 (m, 1H), 7.11-7.07 (m, 2H), 6.64 (s, 1H), 6.00 (s, 2H), 2.22 (s, 3H).

Step 6: 2,2-difluoro-N-(7-(5-fluoro-2-methylphenyl)isoquinolin-3-yl)cyclopropanecarboxamide

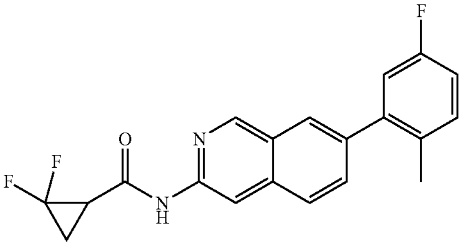 [SMILES: Cc1ccc(F)cc1-c1ccc2cc(NC(=O)C3CC3(F)F)ncc2c1]

To a mixture of 7-(5-fluoro-2-methylphenyl)isoquinolin-3-amine (103.2 mg, 0.4090 mmol), 2,2-difluorocyclopropanecarboxylic acid (79.6 mg, 0.652 mmol) and (7-azabenzotriazol-1-yloxy)tripyrrolidinophosphonium hexafluorophosphate (326.5 mg, 0.6298 mmol) in N,N-dimethylformamide (2 mL, 20 mmol) was added N,N-diisopropylethylamine (0.25 mL, 1.4 mmol) and 4-dimethylaminopyridine (6.7 mg, 0.055 mmol). The reaction mixture was stirred at 50° C. for 2.5 hours. The reaction mixture was then poured into ethyl acetate, which was washed with two portions water, dried with brine and $MgSO_4$, and filtered through a plug of silica gel, which was rinsed with ethyl acetate, and evaporated in vacuo. The resulting residue was purified via reverse phase HPLC and lyophilized to yield 106.4 mg (73%) of 2,2-difluoro-N-(7-(5-fluoro-2-methylphenyl)isoquinolin-3-yl)cyclopropanecarboxamide. LCMS (ESI): $R_T$ (Min)=5.701, M+H=357.1, Method=E; $^1$H NMR (400 MHz, DMSO-$d_6$) δ 11.14 (s, 1H), 9.21 (s, 1H), 8.50 (s, 1H), 8.07 (s, 1H), 7.98 (d, J=8.4 Hz, 1H), 7.74 (d, J=8.4 Hz, 1H), 7.39 (s, 1H), 7.18 (d, J=8.7 Hz, 2H), 3.07 (d, J=10.0 Hz, 1H), 2.25 (s, 3H), 2.07 (s, 2H).

Example 9

N-(7-(5-fluoro-2-methylphenyl)isoquinolin-3-yl)-2-phenylcyclopropanecarboxamide (Mixture of Trans Stereoisomers)

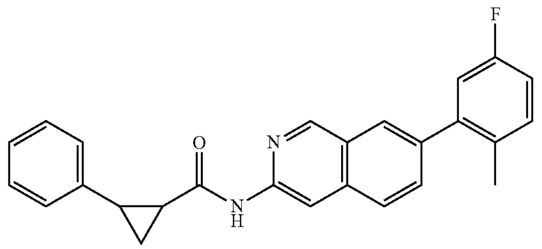 [SMILES: Cc1ccc(F)cc1-c1ccc2cc(NC(=O)C3CC3c3ccccc3)ncc2c1]

To a mixture of 7-(5-fluoro-2-methylphenyl)isoquinolin-3-amine (50.5 mg, 0.200 mmol) in methylene chloride (2.0 mL, 31 mmol) was added pyridine (0.04 mL, 0.5 mmol) and trans-2-phenyl-1-cyclopropanecarbonyl chloride (35.0 uL, 0.225 mmol). The reaction mixture was stirred at room temperature for one hour and then evaporated in vacuo. The resulting residue was purified via reverse phase HPLC and lyophilized to yield 29.1 mg (37%) of N-(7-(5-fluoro-2-methylphenyl)isoquinolin-3-yl)-2-phenylcyclopropanecarboxamide (mixture of trans stereoisomers). LCMS (ESI): $R_T$ (Min)=6.288, M+H=397.1, Method=E; $^1$H NMR (400 MHz, DMSO-$d_6$) δ 10.94 (s, 1H), 9.17 (s, 1H), 8.54 (s, 1H), 8.04 (s, 1H), 7.95 (d, J=8.6 Hz, 1H), 7.72 (d, J=8.5 Hz, 1H), 7.38 (t, J=7.0 Hz, 1H), 7.31 (t, J=7.6 Hz, 2H), 7.25-7.12 (m, 5H), 2.47-2.40 (m, 2H), 2.25 (s, 3H), 1.60-1.48 (m, 1H), 1.39 (dd, J=11.0, 7.4 Hz, 1H).

Example 10

N-(7-(2-methylthiazol-4-yl)isoquinolin-3-yl)cyclopropanecarboxamide

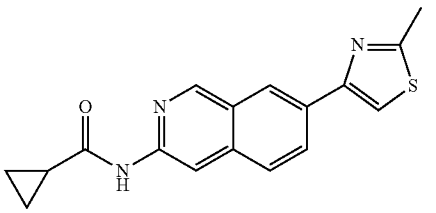 [SMILES: Cc1nc(-c2ccc3cc(NC(=O)C4CC4)ncc3c2)cs1]

Step 1: N-(7-bromoisoquinolin-3-yl)cyclopropanecarboxamide

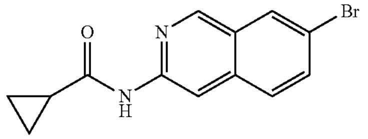 [SMILES: O=C(Nc1cc2ccc(Br)cc2cn1)C1CC1]

To a cold solution (below 0° C.) of 7-bromoisoquinolin-3-amine (20 g, 0.09 mol) in pyridine (150 mL) was added cyclopropanecarbonyl chloride (11.2 g, 0.108 mol) dropwise. The mixture was stirred at room temperature overnight. After water (500 mL) was added, the reaction mixture was stirred for 30 min. Solid was collected by filtration and washed with water to give the desired product (21 g, 80.4%). LCMS (ESI): $R_T$ (Min)=1.009, M+H$^+$=290.7, method=A. $^1$H NMR (400 MHz, DMSO-$d_6$) δ 10.96 (s, 1H), 9.10 (s, 1H), 8.44 (s, 1H), 8.30 (s, 1H), 7.22 (d, J=8.8 Hz, 1H), 7.67 (d, J=8.8 Hz, 1H), 2.02-2.10 (m, 1H), 0.84-0.79 (m, 4H).

Step 2: N-(7-(2-methylthiazol-4-yl)isoquinolin-3-yl)cyclopropanecarboxamide

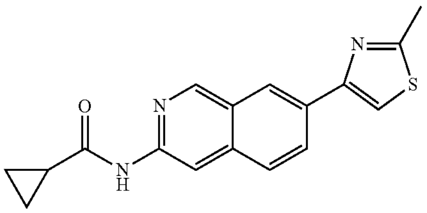 [SMILES: Cc1nc(-c2ccc3cc(NC(=O)C4CC4)ncc3c2)cs1]

To a mixture of N-(7-bromoisoquinolin-3-yl)cyclopropanecarboxamide (101 mg, 0.347 mmol), 2-methyl-4-(4,4,5,5-tetramethyl-1,3,2-dioxaborolan-2-yl)thiazole (0.10 g, 0.44 mmol), potassium carbonate (147.9 mg, 1.070 mmol), and bis(di-tert-butyl(4-dimethylaminophenyl)phosphine)dichloropalladium(II) (24.3 mg, 0.0343 mmol) was added acetonitrile (3 mL, 60 mmol) and water (0.3 mL, 20 mmol). The reaction mixture was then stirred in a sealed vial at 90° C. for 8 hours, and then cooled to room temperature. The reaction mixture was poured into dichloromethane, washed once with saturated aqueous $NaHCO_3$, dried over $MgSO_4$, filtered, and evaporated in vacuo. The resulting residue was purified via reverse phase HPLC and lyophilized to yield 22.7 mg (21%) of N-(7-(2-methylthiazol-4-yl)isoquinolin-3-yl)cyclopropanecarboxamide. LCMS (ESI): $R_T$ (Min)=4.328, M+H=310.0, method=E; $^1$H NMR (400 MHz, DMSO-$d_6$) δ 10.89 (s, 1H), 9.20 (s, 1H), 8.60 (s, 1H), 8.45 (s, 1H), 8.24 (dd, J=8.7, 1.5 Hz, 1H), 8.08 (s, 1H), 7.90 (d, J=8.7 Hz, 1H), 2.76 (s, 3H), 2.08 (ddd, J=12.2, 7.8, 4.7 Hz, 1H), 0.85 (dd, J=9.3, 6.3 Hz, 4H).

Example 11

N-(isoquinolin-3-yl)cyclopropanecarboxamide

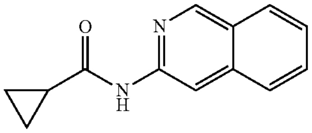 [SMILES: O=C(Nc1cc2ccccc2cn1)C1CC1]

The title compound was synthesized following the same method as described for the synthesis of N-(7-bromoisoquinolin-3-yl)cyclopropanecarboxamide, using commercially available isoquinolin-3-amine instead of 7-bromo-isoquinolin-3-amine. LCMS (ESI): $R_T$ (Min)=3.537, M+H=213.1, method=E; $^1$H NMR (400 MHz, DMSO-$d_6$) δ 10.89 (s, 1H), 9.14 (s, 1H), 8.45 (s, 1H), 8.04 (d, J=8.2 Hz, 1H), 7.85 (d, J=8.3 Hz, 1H), 7.69 (t, J=7.5 Hz, 1H), 7.51 (t, J=7.5 Hz, 1H), 2.06 (d, J=4.4 Hz, 1H), 0.89-0.77 (m, 4H).

Example 12

N-(7-(5-amino-4-methylpyridin-3-yl)isoquinolin-3-yl)cyclopropanecarboxamide

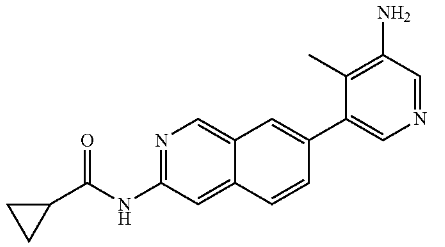

Step 1: N-(7-(4,4,5,5-tetramethyl-1,3,2-dioxaborolan-2-yl)isoquinolin-3-yl)cyclopropanecarboxamide

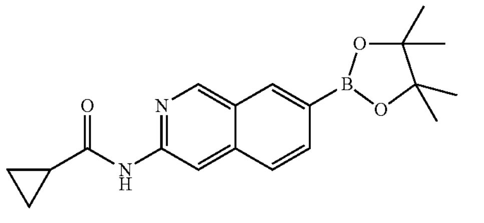 [SMILES: CC1(C)OB(c2ccc3cc(NC(=O)C4CC4)ncc3c2)OC1(C)C]

To a solution of N-(7-bromoisoquinolin-3-yl)cyclopropanecarboxamide (1.506 g, 5.173 mmol) in 1,4-dioxane (40 mL, 600 mmol) is added bispinacol ester boronate (1.619 g, 6.376 mmol), 1,1'-bis(diphenylphosphino)ferrocenepalladium (II) chloride (212.2 mg, 0.2598 mmol), and potassium acetate (1.031 g, 10.50 mmol). The reaction is stirred at 100° C. for 3.5 hours. After cooling to room temperature, the reaction mixture is dilute with dichloromethane, filtered through celite, and concentrated to dry. The resulting residue was purified via flash chromatography on silica gel (80 g silica, solvent gradient: 10-40% ethyl acetate in heptanes) to yield 2.1341 g (80% pure, 98% yield) of N-(7-(4,4,5,5-tetramethyl-1,3,2-dioxaborolan-2-yl)isoquinolin-3-yl)cyclopropanecarboxamide. LCMS (ESI): M+H=339.3; $^1$H NMR (400 MHz, DMSO-$d_6$) δ 10.93 (s, 1H), 9.22 (s, 1H), 8.43 (overlapping s and s, 2H), 7.85 (d, J=8.3 Hz, 1H), 7.80 (d, J=8.3 Hz, 1H), 2.08 (m, 1H), 1.34 (s, 12H), 0.91-0.77 (m, 4H).

Step 2: N-(7-(5-amino-4-methylpyridin-3-yl)isoquinolin-3-yl)cyclopropanecarboxamide

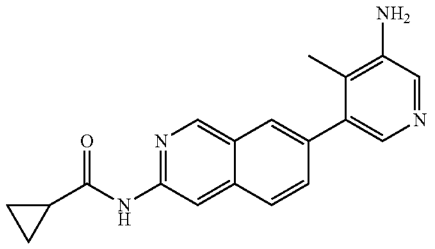 [SMILES: Cc1c(N)cncc1-c1ccc2cc(NC(=O)C3CC3)ncc2c1]

To a mixture of N-(7-(4,4,5,5-tetramethyl-1,3,2-dioxaborolan-2-yl)isoquinolin-3-yl)cyclopropanecarboxamide (119.4 mg, 0.3530 mmol), 5-bromo-4-methylpyridin-3-amine (83.7 mg, 0.448 mmol), cesium carbonate (286.6 mg, 0.8796 mmol), and bis(di-tert-butyl(4-dimethylaminophenyl)phosphine)dichloropalladium(II) (19.2 mg, 0.0271 mmol) was added 1,4-dioxane (4 mL, 50 mmol) and water (0.4 mL, 20 mmol). The reaction was then stirred in a sealed vial at 100° C. for two hours. The reaction mixture was poured into saturated aqueous sodium bicarbonate, and extracted four times with dichloromethane. The combined organic extracts were dried over $MgSO_4$, filtered, and evaporated in vacuo. The crude residue was purified via flash chromatography on silica gel (12 g silica, solvent gradient: 0-15% MeOH in dichloromethane) followed by reverse phase HPLC purification and lyophilization to yield 41.3 mg (37%) of N-(7-(5-amino-4-methylpyridin-3-yl)isoquinolin-3-yl)cyclopropanecarboxamide. LCMS (ESI): $R_T$ (min)=2.42, M+H=319.2, method=H; $^1$H NMR (400 MHz, DMSO-$d_6$) δ 10.90 (s, 1H), 9.18 (s, 1H), 8.49 (s, 1H), 7.98 (s, 2H), 7.91 (d, J=8.5 Hz, 1H), 7.72 (s, 1H), 7.68-7.57 (m, 1H), 5.22 (s, 2H), 2.14-2.03 (m, 1H), 2.01 (s, 3H), 0.85 (dd, J=11.6, 6.1 Hz, 4H).

Example 13

7-(5-fluoro-2-methylphenyl)-N-(6-methoxypyridin-2-yl)isoquinolin-3-amine

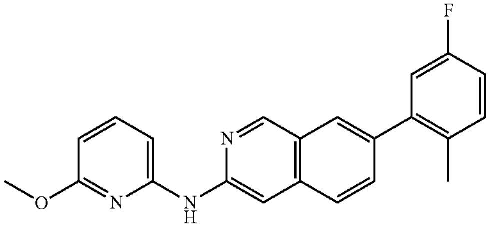 [SMILES: COc1cccc(Nc2cc3ccc(-c4cc(F)ccc4C)cc3cn2)n1]

To 7-(5-fluoro-2-methylphenyl)isoquinolin-3-amine (151.4 mg, 0.6001 mmol) and 2-bromo-6-methoxypyridine (110.0 uL, 0.8951 mmol) was added 1,4-dioxane (4.0 mL, 51 mmol). Nitrogen gas was bubbled through this mixture while stirring for 10 minutes, and then palladium (II) acetate (14.5 mg, 0.0646 mmol), 4,5-bis(diphenylphosphino)-9,9-dimethylxanthene (57.1 mg, 0.0987 mmol), and cesium carbonate (397.6 mg, 1.220 mmol) were added. The reaction mixture was stirred in a sealed vial at 100° C. for 90 minutes. The reaction mixture was diluted with dichloromethane, filtered through celite, and evaporated in vacuo. The crude residue was purified via flash chromatography on silica gel (12 g silica, solvent gradient: 0-80% ethyl acetate in dichloromethane) to yield 227.4 mg of the title compound as 80% pure material. 52.4 mg of this material was purified via reverse phase HPLC and lyophilized to yield 17.9 mg of 7-(5-fluoro-2-methylphenyl)-N-(6-methoxypyridin-2-yl) isoquinolin-3-amine. LCMS (ESI): $R_T$ (min)=5.057, M+H=360.1, method=E; $^1$H NMR (400 MHz, DMSO-$d_6$) δ 9.80 (s, 1H), 9.11 (s, 1H), 8.58 (s, 1H), 7.97 (s, 1H), 7.84 (d, J=8.5 Hz, 1H), 7.64 (d, J=8.4 Hz, 1H), 7.56 (t, J=7.8 Hz, 1H), 7.38 (q, J=6.3 Hz, 1H), 7.15 (t, J=8.5 Hz, 2H), 6.82 (d, J=7.8 Hz, 1H), 6.28 (d, J=7.8 Hz, 1H), 4.01 (s, 3H), 2.26 (s, 3H).

Example 14

6-(7-(5-fluoro-2-methylphenyl)isoquinolin-3-ylamino)pyridin-2(1H)-one

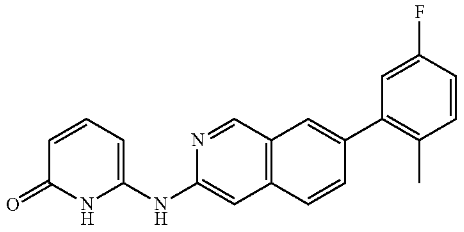 [SMILES: Cc1ccc(F)cc1-c1ccc2cc(Nc3cccc(=O)[nH]3)ncc2c1]

To a solution of 7-(5-fluoro-2-methylphenyl)-N-(6-methoxypyridin-2-yl)isoquinolin-3-amine (80% pure, 175 mg, 0.390 mmol) in acetic acid (3 mL, 50 mmol) was added hydrogen bromide (2 mL, 20 mmol) (48% in acetic acid). The reaction mixture was stirred at 100° C. under nitrogen for 16 hours. The reaction mixture was cooled to room temperature and then evaporated in vacuo. The resulting residue was dissolved in dichloromethane, washed with saturated aqueous $NaHCO_3$, dried over $MgSO_4$, filtered, and evaporated in vacuo. The crude material was purified via flash chromatography on silica gel (12 g silica, solvent gradient: 0-5% methanol in dichloromethane) followed by reverse phase HPLC purification and lyophilization to yield 4.3 mg (3.2%) of 6-(7-(5-fluoro-2-methylphenyl)isoquinolin-3-ylamino)pyridin-2(1H)-one. LCMS (ESI): $R_T$ (Min)=5.219, M+H=346.0, method=E; $^1$H NMR (400 MHz, DMSO-$d_6$) δ 9.85 (broad s, 1H), 9.15 (s, 1H), 8.00 (s, 1H), 7.88 (d, J=8.0 Hz, 1H), 7.69 (d, J=8.5 Hz, 1H), 7.54-7.29 (m, 2H), 7.16 (t, J=9.6 Hz, 2H), 5.93 (m, 2H), 2.27 (s, 3H).

Example 15

(R)-N-(3-(3-(cyclopropanecarboxamido)isoquinolin-7-yl)-4-methylphenyl)tetrahydrofuran-2-carboxamide

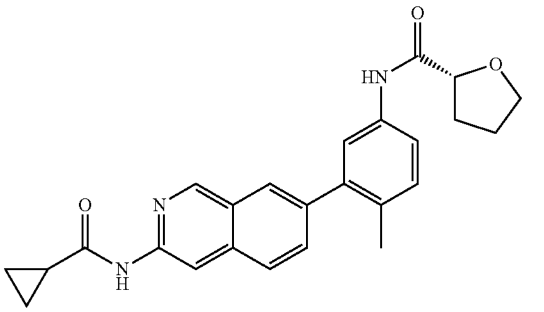 [SMILES: Cc1ccc(NC(=O)[C@H]2CCCO2)cc1-c1ccc2cc(NC(=O)C3CC3)ncc2c1]

Step 1: N-(7-(5-amino-2-methylphenyl)isoquinolin-3-yl)cyclopropanecarboxamide

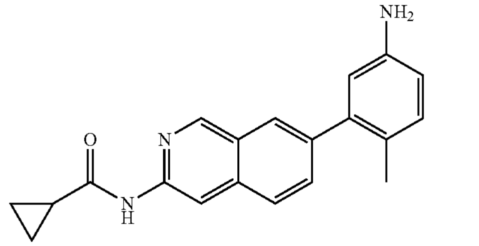

To a mixture of N-(7-bromoisoquinolin-3-yl)cyclopropanecarboxamide (1.053 g, 3.617 mmol), 5-amino-2-methylphenylboronic acid pinacol ester (1.2607 g, 5.4081 mmol), bis (di-tert-butyl(4-dimethylaminophenyl)phosphine) dichloropalladium(II) (0.1311 g, 0.1852 mmol), and potassium carbonate (1.385 g, 10.02 mmol) was added 1,4-dioxane (20 mL, 200 mmol) and water (2 mL, 100 mmol). The reaction mixture was then heated at 90° C. for 2 hours and then cooled to room temperature. The reaction mixture was poured into saturated aqueous $NaHCO_3$ and extracted twice with dichloromethane. The combined organics were dried over $MgSO_4$, filtered, and evaporated in vacuo. The crude product was purified via flash chromatography on silica gel (40 g silica, solvent gradient: 0-80% ethyl acetate in dichloromethane) to yield 1.3653 g (119%) of N-(7-(5-amino-2-methylphenyl)isoquinolin-3-yl)cyclopropanecarboxamide. LCMS (ESI): M+H=318.2; $^1$H NMR (400 MHz, DMSO-$d_6$) δ 10.87 (s, 1H), 9.16 (s, 1H), 8.47 (s, 1H), 7.92 (s, 1H), 7.87 (d, J=8.5 Hz, 1H), 7.63 (dd, J=8.5, 1.5 Hz, 1H), 6.97 (d, J=8.8 Hz, 1H), 6.60-6.49 (m, 2H), 4.93 (s, 2H), 2.14-2.02 (m, 4H), 0.85 (dd, J=12.4, 6.1 Hz, 4H).

Step 2: (R)-N-(3-(3-(cyclopropanecarboxamido) isoquinolin-7-yl)-4-methylphenyl)tetrahydrofuran-2-carboxamide

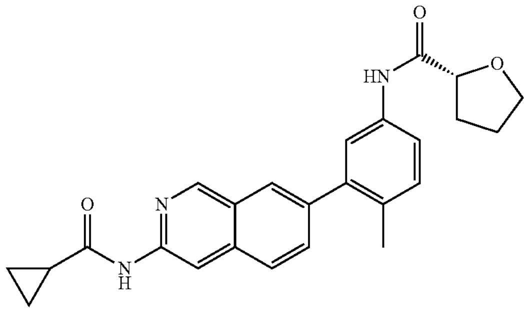 [SMILES: Cc1ccc(NC(=O)[C@H]2CCCO2)cc1-c1ccc2cc(NC(=O)C3CC3)ncc2c1]

To a mixture of N-(7-(5-amino-2-methylphenyl)isoquinolin-3-yl)cyclopropanecarboxamide (62.4 mg, 0.167 mmol), (R)-(+)-tetrahydro-2-furoic acid (21.0 uL, 0.217 mmol), (7-azabenzotriazol-1-yloxy)tripyrrolidinophosphonium hexafluorophosphate (118.4 mg, 0.2284 mmol), and 4-dimethylaminopyridine (4.083 mg, 0.03342 mmol) was added N,N-dimethylformamide (2.0 mL, 26 mmol) and N,N-diisopropylethylamine (88 uL, 0.50 mmol). The reaction mixture was stirred at room temperature for 2 hours. The reaction mixture was then diluted with ethyl acetate and washed twice with water and once with brine. The organic layer was dried over $MgSO_4$, and filtered through a plug of silica gel, rinsing with ethyl acetate. The filtrate was concentrated and then purified via reverse phase HPLC and lyophilized to yield 45.0 mg (65%) of (R)-N-(3-(3-(cyclopropanecarboxamido)isoquinolin-7-yl)-4-methylphenyl)tetrahydrofuran-2-carboxamide. LCMS (ESI): $R_T$ (min)=4.594, M+H=416.2, method=E; $^1$H NMR (400 MHz, DMSO-$d_6$) δ 10.89 (s, 1H), 9.64 (s, 1H), 9.18 (s, 1H), 8.49 (s, 1H), 7.99 (s, 1H), 7.91 (d, J=8.6 Hz, 1H), 7.68 (dd, J=11.6, 1.9 Hz, 2H), 7.64 (dd, J=8.3, 2.1 Hz, 1H), 7.27 (d, J=8.3 Hz, 1H), 4.38 (dd, J=8.1, 5.6 Hz, 1H), 3.98 (dd, J=14.5, 6.8 Hz, 1H), 3.82 (dd, J=14.5, 6.9 Hz, 1H), 2.23 (s, 3H), 2.22-2.14 (m, 1H), 2.13-2.03 (m, 1H), 1.98 (td, J=12.6, 6.6 Hz, 1H), 1.86 (p, J=6.9 Hz, 2H), 0.95-0.77 (m, 4H).

Example 16

N-(3-(3-(cyclopropanecarboxamido)isoquinolin-7-yl)-4-methylphenyl)-1-methyl-1H-pyrazole-4-carboxamide

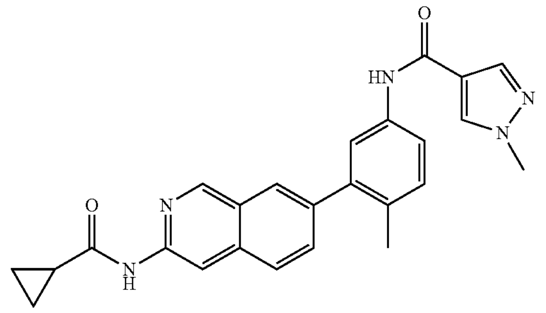 [SMILES: Cc1ccc(NC(=O)c2cnn(C)c2)cc1-c1ccc2cc(NC(=O)C3CC3)ncc2c1]

To a solution of N-(7-(5-amino-2-methylphenyl)isoquinolin-3-yl)cyclopropanecarboxamide (53.8 mg, 0.144 mmol) in methylene chloride (2.0 mL, 31 mmol) was added pyridine (0.10 mL, 1.2 mmol) and 1-methyl-1H-pyrazole-4-carbonyl chloride (27.7 mg, 0.192 mmol). The reaction mixture was stirred at room temperature for 15 hours. The reaction mixture was then poured into 50 mL dichloromethane, washed with aqueous $NaHCO_3$, dried over $MgSO_4$, filtered, and evaporated in vacuo. The crude product was purified via reverse phase HPLC and lyophilized to yield 37.1 mg (61%) of N-(3-(3-(cyclopropanecarboxamido)isoquinolin-7-yl)-4-methylphenyl)-1-methyl-1H-pyrazole-4-carboxamide. LCMS (ESI): $R_T$ (Min)=4.307, M+H=426.1, method=E; $^1$H NMR (400 MHz, DMSO-$d_6$) δ 10.89 (s, 1H), 9.80 (s, 1H), 9.19 (s, 1H), 8.50 (s, 1H), 8.28 (s, 1H), 8.01 (d, J=4.9 Hz, 2H), 7.93 (d, J=8.6 Hz, 1H), 7.70 (dd, J=10.3, 4.6 Hz, 3H), 7.30 (d, J=8.0 Hz, 1H), 3.89 (s, 3H), 2.25 (s, 3H), 2.19-1.98 (m, 1H), 0.85 (m, 4H).

Example 17

N-(3-(3-(cyclopropanecarboxamido)isoquinolin-7-yl)-4-methylphenyl)morpholine-4-carboxamide

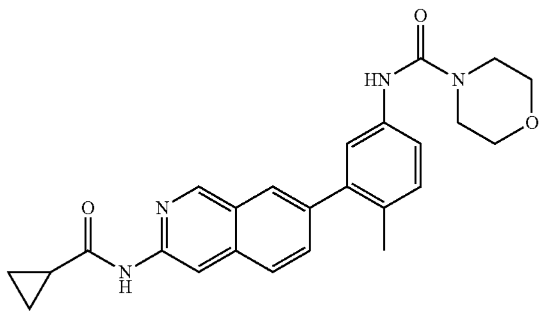 [SMILES: Cc1ccc(NC(=O)N2CCOCC2)cc1-c1ccc2cc(NC(=O)C3CC3)ncc2c1]

Step 1: 4-nitrophenyl 3-(3-(cyclopropanecarboxamido)isoquinolin-7-yl)-4-methylphenylcarbamate

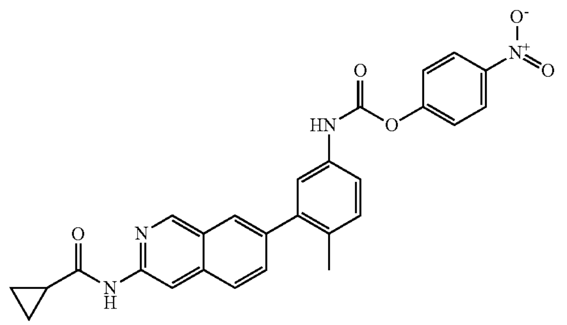 [SMILES: Cc1ccc(NC(=O)Oc2ccc([N+](=O)[O-])cc2)cc1-c1ccc2cc(NC(=O)C3CC3)ncc2c1]

To a suspension of N-(7-(5-amino-2-methylphenyl)isoquinolin-3-yl)cyclopropanecarboxamide (196.8 mg, 0.6201 mmol) in 1,2-dichloroethane (6.0 mL, 76 mmol) was added pyridine (0.15 mL, 1.8 mmol) and p-nitrophenyl chloroformate (0.1406 g, 0.6975 mmol). The reaction mixture was stirred at room temperature for 2 hours and then pyridine (0.15 mL, 1.8 mmol) and p-nitrophenyl chloroformate (131.9 mg, 0.6544 mmol) were added. After an additional hour at room temperature, the reaction mixture was evaporated in vacuo and purified via flash chromatography on silica gel (25 g silica, solvent gradient: 0-100% ethyl acetate in heptanes) to yield 114.8 mg (38%) of 4-nitrophenyl 3-(3-(cyclopropanecarboxamido)isoquinolin-7-yl)-4-methylphenylcarbamate. LCMS (ESI): M+H=483.2; $^1$H NMR (400 MHz, DMSO-$d_6$) δ 10.87 (s, 1H), 9.16 (s, 1H), 8.47 (s, 1H), 8.10 (d, J=9.0 Hz, 2H), 7.92 (s, 1H), 7.87 (d, J=8.5 Hz, 1H), 7.63 (d, J=8.5 Hz, 1H), 6.97 (d, J=8.7 Hz, 1H), 6.90 (d, J=8.9 Hz, 2H), 6.54 (d, J=5.8 Hz, 2H), 2.14-2.02 (m, 4H), 0.85 (m, 4H).

Step 2: N-(3-(3-(cyclopropanecarboxamido)isoquinolin-7-yl)-4-methylphenyl)morpholine-4-carboxamide

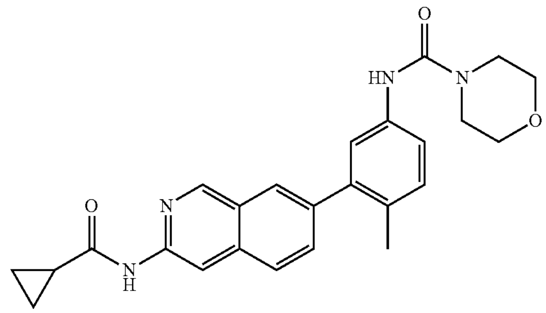

To a solution of 4-nitrophenyl 3-(3-(cyclopropanecarboxamido)isoquinolin-7-yl)-4-methylphenylcarbamate (55.5 mg, 0.115 mmol) in tetrahydrofuran (1.5 mL, 18 mmol) was added morpholine (0.0500 mL, 0.573 mmol) and triethylamine (0.0500 mL, 0.359 mmol). The reaction mixture was stirred at room temperature for 16 hours. The reaction mixture was poured into ethyl acetate, washed with saturated aqueous sodium bicarbonate and brine, dried over $MgSO_4$, filtered, and evaporated in vacuo. The crude product was purified via reverse phase HPLC and lyophilized to yield 33.4 mg (67%) of N-(3-(3-(cyclopropanecarboxamido)isoquinolin-7-yl)-4-methylphenyl)morpholine-4-carboxamide. LCMS (ESI): $R_T$ (Min)=4.234, M+H=431.2, method=E; $^1$H NMR (400 MHz, DMSO-$d_6$) δ 10.88 (s, 1H), 9.17 (s, 1H), 8.52 (s, 1H), 8.48 (s, 1H), 7.97 (s, 1H), 7.90 (d, J=8.6 Hz, 1H), 7.67 (d, J=8.6 Hz, 1H), 7.46 (s, 1H), 7.43 (d, J=8.3 Hz, 1H), 7.20 (d, J=8.3 Hz, 1H), 3.66-3.53 (m, 4H), 3.47-3.37 (m, 4H), 2.21 (s, 3H), 2.15-2.00 (m, 1H), 0.98-0.67 (m, 4H).

Example 18

N-(3-(3-(cyclopropanecarboxamido)isoquinolin-7-yl)-4-methylphenyl)-2-(hydroxymethyl)morpholine-4-carboxamide

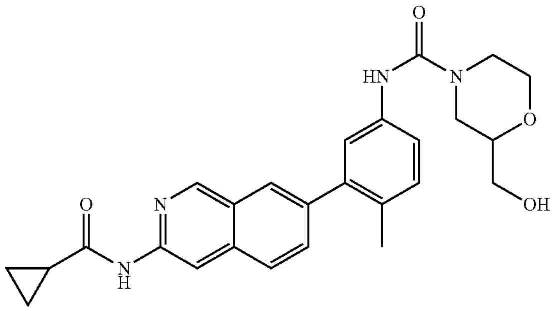 [SMILES: Cc1ccc(NC(=O)N2CCOC(CO)C2)cc1-c1ccc2cc(NC(=O)C3CC3)ncc2c1]

To a solution of triphosgene (22.7 mg, 0.0765 mmol) and N,N-diisopropylethylamine (0.20 mL, 1.1 mmol) in methylene chloride (4.0 mL, 62 mmol) was added a solution of N-(7-(5-amino-2-methylphenyl)isoquinolin-3-yl)cyclopropanecarboxamide (59.9 mg, 0.189 mmol) and N,N-diisopropylethylamine (0.10 mL, 0.57 mmol) in methylene chloride (2.0 mL, 31 mmol). The resulting mixture was stirred at room temperature for 5 minutes, and then morpholin-2-ylmethanol (37.5 mg, 0.320 mmol) was added. The reaction mixture was stirred at room temperature for an additional 30 minutes, and then filtered through silica which was rinsed with ethyl acetate, and evaporated in vacuo. The crude product was purified via reverse phase HPLC and lyophilized to yield 34.6 mg (40%) of N-(3-(3-(cyclopropanecarboxamido)isoquinolin-7-yl)-4-methylphenyl)-2-(hydroxymethyl)morpholine-4-carboxamide. LCMS (ESI): $R_T$(Min)=3.964, M+H=461.2, method=E; $^1$H NMR (400 MHz, DMSO-$d_6$) δ 10.87 (s, 1H), 9.18 (s, 1H), 8.56 (s, 1H), 8.47 (s, 1H), 7.98 (s, 1H), 7.91 (d, J=8.5 Hz, 1H), 7.68 (d, J=8.5 Hz, 1H), 7.50-7.37 (m, 2H), 7.21 (d, J=8.2 Hz, 1H), 4.82 (t, J=5.5 Hz, 1H), 4.04 (d, J=12.9 Hz, 2H), 3.97-3.81 (m, 3H), 2.90 (t, J=6.0 Hz, 2H), 2.64 (dd, J=12.9, 10.0 Hz, 2H), 2.21 (s, 3H), 2.11-2.03 (m, 1H), 0.86 (m, 4H).

Example 19

N-(7-(5-(ethylsulfonamido)-2-methylphenyl)isoquinolin-3-yl)cyclopropanecarboxamide

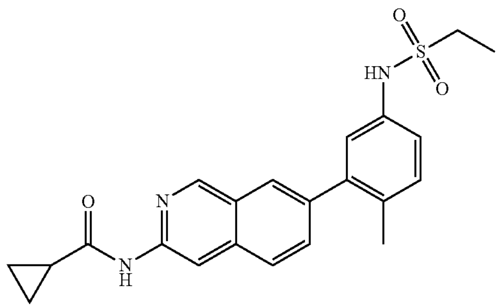 [SMILES: CCS(=O)(=O)Nc1ccc(C)c(-c2ccc3cc(NC(=O)C4CC4)ncc3c2)c1]

To a solution of N-(7-(5-amino-2-methylphenyl)isoquinolin-3-yl)cyclopropanecarboxamide (56.2 mg, 0.177 mmol) in methylene chloride (2.0 mL, 31 mmol) was added pyridine (0.20 mL, 2.5 mmol) and ethanesulfonyl chloride (23.0 uL, 0.243 mmol). The reaction mixture was stirred at room temperature for 2 hours. The reaction mixture was then poured into dichloromethane, washed with water, dried over $MgSO_4$, filtered, and evaporated in vacuo. The crude product was purified via reverse phase HPLC and lyophilized to yield 39.5 mg (54%) of N-(7-(5-(ethylsulfonamido)-2-methylphenyl)isoquinolin-3-yl)cyclopropanecarboxamide. LCMS (ESI): $R_T$ (min)=4.534, M+H=410.1, method=E; $^1$H NMR (400 MHz, DMSO-$d_6$) δ 10.90 (s, 1H), 9.73 (s, 1H), 9.18 (s, 1H), 8.49 (s, 1H), 7.98 (s, 1H), 7.92 (d, J=8.6 Hz, 1H), 7.66 (dd, J=8.5, 1.6 Hz, 1H), 7.29 (d, J=8.2 Hz, 1H), 7.18 (dd, J=8.1, 2.3 Hz, 1H), 7.15 (d, J=2.2 Hz, 1H), 3.10 (q, J=7.3 Hz, 2H), 2.21 (s, 3H), 2.12-2.04 (m, 1H), 1.21 (t, J=7.3 Hz, 3H), 0.84 (m, 4H).

Example 20

3-(3-(cyclopropanecarboxamido)isoquinolin-7-yl)-4-methyl-N-(1-methylcyclobutyl)benzamide

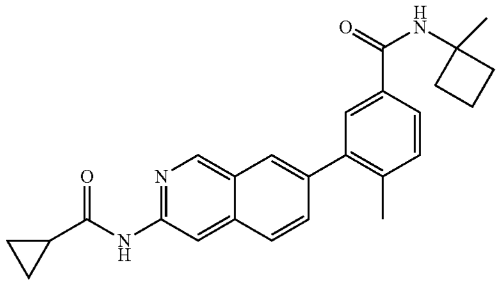 [SMILES: Cc1ccc(C(=O)NC2(C)CCC2)cc1-c1ccc2cc(NC(=O)C3CC3)ncc2c1]

Step 1: 3-(3-(cyclopropanecarboxamido)isoquinolin-7-yl)-4-methylbenzoic acid

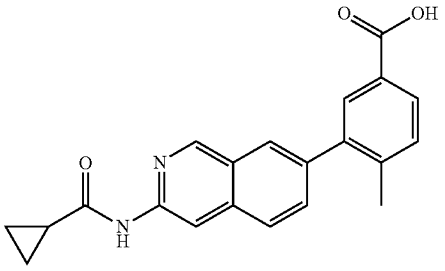 [SMILES: Cc1ccc(C(=O)O)cc1-c1ccc2cc(NC(=O)C3CC3)ncc2c1]

A mixture of N-(7-bromoisoquinolin-3-yl)cyclopropanecarboxamide (0.3305 g, 1.135 mmol), 4-methyl-3-(4,4,5,5-tetramethyl-1,3,2-dioxaborolan-2-yl)benzoic acid (0.3782 g, 1.443 mmol), potassium carbonate (0.3196 g, 2.312 mmol), and bis(di-tert-butyl(4-dimethylaminophenyephosphine) dichloropalladium(II) (81.9 mg, 0.116 mmol) in 1,4-dioxane (5.0 mL, 64 mmol) and water (0.5 mL, 30 mmol) was heated at 90° C. for 2 hours. The reaction mixture was cooled to room temperature, acidified with 10% aqueous citric acid, and extracted twice with ethyl acetate. The combined organic extracts were reduced in volume under evaporation and the product collected via filtration as a white precipitate and dried under vacuum to yield 365.5 mg (91%) of 3-(3-(cyclopropanecarboxamido)isoquinolin-7-yl)-4-methylbenzoic acid.

LCMS (ESI): M+H=347.2; $^1$H NMR (400 MHz, DMSO-$d_6$) δ 10.90 (s, 1H), 9.19 (s, 1H), 8.50 (s, 1H), 8.04 (s, 1H), 7.93 (d, J=8.6 Hz, 1H), 7.89-7.83 (m, 2H), 7.72 (d, J=8.5 Hz, 1H), 7.45 (d, J=7.7 Hz, 1H), 2.34 (s, 3H), 2.14-2.02 (m, 1H), 0.85 (m, 4H).

Step 2: 3-(3-(cyclopropanecarboxamido)isoquinolin-7-yl)-4-methyl-N-(1-methylcyclobutyl)benzamide

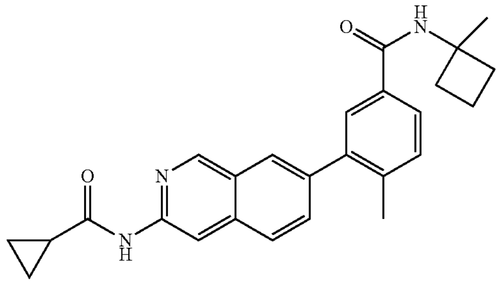 [SMILES: Cc1ccc(C(=O)NC2(C)CCC2)cc1-c1ccc2cc(NC(=O)C3CC3)ncc2c1]

A mixture of 3-(3-(cyclopropanecarboxamido)isoquinolin-7-yl)-4-methylbenzoic acid (41.0 mg, 0.118 mmol), 1-methylcyclobutylamine (22.5 mg, 0.264 mmol), (7-azabenzotriazol-1-yloxy)tripyrrolidinophosphonium hexafluorophosphate (81.1 mg, 0.156 mmol), N,N-diisopropylethylamine (64 uL, 0.37 mmol), 4-dimethylaminopyridine (2.89 mg, 0.0237 mmol), and N,N-dimethylformamide (2.0 mL, 26 mmol) was stirred at 50° C. for 15 hours. The reaction mixture was poured into ethyl acetate and washed with water and brine, filtered through a plug of silica gel, and evaporated in vacuo. The crude product was purified via reverse phase HPLC and lyophilized to yield 23.3 mg (78%) of 3-(3-(cyclopropanecarboxamido)isoquinolin-7-yl)-4-methyl-N-(1-methylcyclobutyl)benzamide. LCMS (ESI): $R_T$ (Min)=5.083, M+H=414.2, method=E; $^1$H NMR (400 MHz, DMSO) δ 10.90 (s, 1H), 9.19 (s, 1H), 8.51 (s, 1H), 8.35 (s, 1H), 8.04 (s, 1H), 7.94 (d, J=8.5 Hz, 1H), 7.82 (s, 1H), 7.80 (d, J=7.9 Hz, 1H), 7.73 (dd, J=8.5, 1.5 Hz, 1H), 7.41 (d, J=7.9 Hz, 1H), 2.40-2.29 (m, 5H), 2.13-2.04 (m, 1H), 2.03-1.92 (m, 2H), 1.86-1.75 (m, 2H), 1.47 (s, 3H), 0.91-0.80 (m, 4H).

Example 21

N-(7-(piperidin-1-yl)isoquinolin-3-yl)cyclopropanecarboxamide

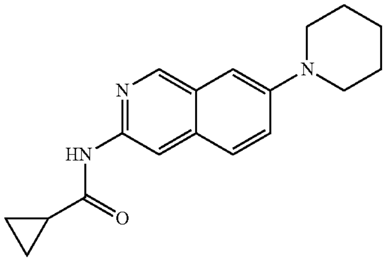 [SMILES: O=C(Nc1cc2ccc(N3CCCCC3)cc2cn1)C1CC1]

A solution was made of N-(7-bromoisoquinolin-3-yl)cyclopropanecarboxamide (66.6 mg, 0.229 mmol) and piperidine (46 uL, 0.46 mmol) in 1,4-dioxane (1.5 mL, 19 mmol). Nitrogen gas was bubbled through the mixture for 10 minutes, and then palladium (II) acetate (6.0 mg, 0.027 mmol), rac-2,2'-bis(diphenylphosphino)-1,1'-binaphthyl (15.2 mg, 0.0244 mmol), and cesium carbonate (231 mg, 0.709 mmol) were added. The reaction mixture was stirred in a sealed vial at 100° C. for 18 hours. The reaction mixture was then cooled to room temperature, diluted in ethyl acetate, filtered through celite, washed with saturated aqueous $NaHCO_3$, dried over $MgSO_4$, and evaporated in vacuo. The crude product was purified via reverse phase HPLC and lyophilized to yield 3.8 mg (6%) of N-(7-(piperidin-1-yl)isoquinolin-3-yl)cyclopropanecarboxamide. LCMS (ESI): $R_T$ (min)=3.481, M+H=416.2, method=E; $^1$H NMR (400 MHz, DMSO-$d_6$) δ 10.64 (s, 1H), 8.89 (s, 1H), 8.27 (s, 1H), 7.67 (d, J=9.1 Hz, 1H), 7.55 (dd, J=9.1, 2.4 Hz, 1H), 7.25 (d, J=2.1 Hz, 1H), 3.27-3.20 (m, 4H), 2.03 (m, 1H), 1.66 (d, J=4.6 Hz, 4H), 1.58 (d, J=4.7 Hz, 2H), 0.81 (m, 4H).

Example 22

N-(7-(4-methylpiperazin-1-yl)isoquinolin-3-yl)cyclopropanecarboxamide

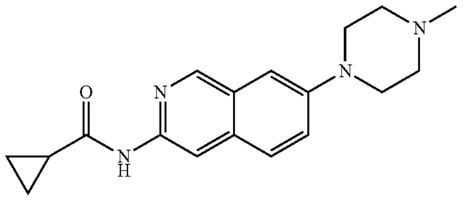 [SMILES: CN1CCN(c2ccc3cc(NC(=O)C4CC4)ncc3c2)CC1]

To a mixture of N-(7-bromoisoquinolin-3-yl)cyclopropanecarboxamide (131.4 mg, 0.4513 mmol), 1-methyl-piperazine (0.11 mL, 0.99 mmol), palladium (II) acetate (10.4 mg, 0.0463 mmol), XPhos (35.4 mg, 0.0742 mmol), and cesium carbonate (462 mg, 1.42 mmol) was added N,N-dimethylacetamide (4 mL). The reaction mixture was then stirred in a sealed vial at 120° C. for 18 hours. The reaction mixture was then cooled to room temperature and partitioned between ethyl acetate and half-saturated aqueous $NaHCO_3$. The organic layer was dried over $MgSO_4$, filtered, and evaporated in vacuo. The crude product was purified via flash chromatography on silica gel (12 g silica, solvent gradient: 10-30% methanol in dichloromethane) to yield 57.2 mg (41%) of N-(7-(4-methylpiperazin-1-yl)isoquinolin-3-yl)cyclopropanecarboxamide. LCMS (ESI): $R_T$ (min)=2.744, M+H=311.1, method=E; $^1$H NMR (400 MHz, $CDCl_3$) δ 8.81 (s, 1H), 8.42 (s, 1H), 8.14 (s, 1H), 7.67 (d, J=9.1 Hz, 1H), 7.44 (dd, J=9.1, 2.5 Hz, 1H), 7.12 (d, J=2.4 Hz, 1H), 3.36-3.25 (m, 4H), 2.69-2.58 (m, 4H), 2.39 (s, 3H), 1.58 (m, 1H), 1.18-1.08 (m, 2H), 0.94-0.85 (m, 2H).

Example 23

N-(7-cyclohexylisoquinolin-3-yl)cyclopropanecarboxamide

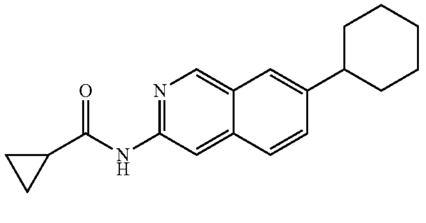 [SMILES: O=C(Nc1cc2ccc(C3CCCCC3)cc2cn1)C1CC1]

To a solution of N-(7-bromoisoquinolin-3-yl)cyclopropanecarboxamide (131.8 mg, 0.4527 mmol) in tetrahydrofuran (6.0 mL, 74 mmol) in an oven-dried flask at 0° C. was added $DPPPNiCl_2$ (18.2 mg, 0.0336 mmol) followed by 2.0 M of cyclohexylmagnesium chloride in ether (0.60 mL). The reaction was stirred at 0° C. for 1.5 hours and then heated at 40° C. overnight. $DPPPNiCl_2$ (21 mg) and 2.0 M of cyclohexylmagnesium chloride in ether (0.60 mL) were added. The reaction was heated at 50° C. for an additional 3.5 hours. The mixture was then partitioned between ethyl acetate and water, and the organic layer was washed with water and brine, dried over $MgSO_4$, filtered, and evaporated in vacuo. The crude product was purified via reverse phase HPLC and lyophilized to yield 24.8 mg (19%) of N-(7-cyclohexylisoquinolin-3-yl)cyclopropanecarboxamide. LCMS (ESI): $R_T$ (min)=5.228, M+H=295.1, method=E; $^1$H NMR (400 MHz, DMSO-$d_6$) δ 10.84 (s, 1H), 9.06 (s, 1H), 8.40 (s, 1H), 7.82 (s, 1H), 7.77 (d, J=8.6 Hz, 1H), 7.61 (dd, J=8.6, 1.7 Hz, 1H), 2.67 (t, J=11.7 Hz, 1H), 2.10-1.99 (m, 1H), 1.93-1.79 (m, 4H), 1.74 (d, J=12.3 Hz, 1H), 1.58-1.20 (m, 5H), 0.82 (dq, J=4.9, 2.9 Hz, 4H).

Example 24

N-(7-(5-fluoro-2-methylpyridin-3-yl)isoquinolin-3-yl)cyclopropanecarboxamide

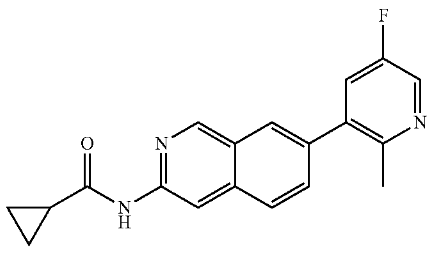 [SMILES: Cc1ncc(F)cc1-c1ccc2cc(NC(=O)C3CC3)ncc2c1]

Step 1: N-(7-(2-chloro-5-fluoropyridin-3-yl)isoquinolin-3-yl)cyclopropanecarboxamide

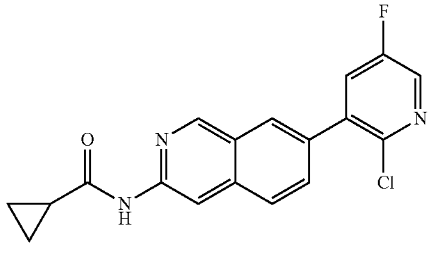 [SMILES: O=C(Nc1cc2ccc(-c3cc(F)cnc3Cl)cc2cn1)C1CC1]

The title compound was prepared following the procedure described for Example 12. LCMS (ESI): M+H=342.2.

Step 2: N-(7-(5-fluoro-2-methylpyridin-3-yl)isoquinolin-3-yl)cyclopropanecarboxamide

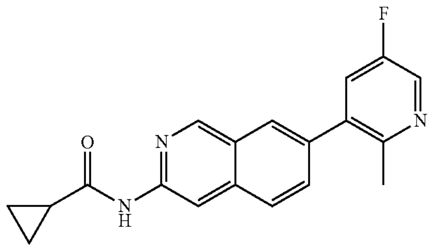 [SMILES: Cc1ncc(F)cc1-c1ccc2cc(NC(=O)C3CC3)ncc2c1]

A mixture of N-(7-(2-chloro-5-fluoropyridin-3-yl)isoquinolin-3-yl)cyclopropanecarboxamide (105.4 mg, 0.3084 mmol), trimethylboroxine (129.0 uL, 0.9228 mmol), bis(di-tert-butyl(4-dimethylaminophenyl)phosphine)dichloropalladium(II) (22.3 mg, 0.0315 mmol), and potassium carbonate (112.5 mg, 0.8140 mmol) in 1,4-dioxane (2.0 mL, 26 mmol) was heated at 90° C. for 26 hours. The reaction mixture was then diluted with dichloromethane, washed with water, dried over $MgSO_4$, filtered, and evaporated in vacuo. The crude product was purified via reverse phase HPLC and lyophilized to yield 50.6 mg (51%) of N-(7-(5-fluoro-2-methylpyridin-3-yl)isoquinolin-3-yl)cyclopropanecarboxamide. LCMS (ESI): $R_T$ (Min)=3.972, M+H=322.0, method=E; $^1$H NMR (400 MHz, DMSO-$d_6$) δ 10.96 (s, 1H), 9.19 (s, 1H), 8.52 (s, 2H), 8.12 (s, 1H), 7.97 (d, J=8.6 Hz, 1H), 7.86-7.67 (m, 2H), 2.47 (s, 3H), 2.08 (dd, J=12.4, 7.3 Hz, 1H), 0.86 (dd, J=9.3, 6.4 Hz, 4H).

Example 25

N-(7-(1H-pyrrol-2-yl)isoquinolin-3-yl)cyclopropanecarboxamide

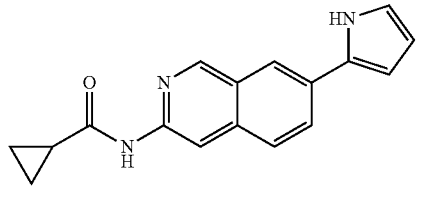 [SMILES: O=C(Nc1cc2ccc(-c3ccc[nH]3)cc2cn1)C1CC1]

To a mixture of N-(7-bromoisoquinolin-3-yl)cyclopropanecarboxamide (116.6 mg, 0.4005 mmol) and potassium (1-(tert-butoxycarbonyl)-1H-pyrrol-2-yl)trifluoroborate (215 mg, 0.787 mmol) was added acetonitrile (3 mL, 60 mmol) and water (0.3 mL, 20 mmol). Potassium carbonate (173.6 mg, 1.256 mmol) and bis(di-tert-butyl(4-dimethylaminophenyl)phosphine)dichloropalladium(II) (13.4 mg, 0.0189 mmol) were added and the reaction was stirred in a sealed vial at 90° C. for two hours. The reaction mixture was then poured into ethyl acetate, which was washed with two portions water, dried with brine and $MgSO_4$, filtered, and evaporated in vacuo. The resulting residue was dissolved in 1,2-dichloroethane (3 mL, 40 mmol), and trifluoroacetic acid (0.30 mL, 3.9 mmol) was added. The mixture was stirred at room temperature for 15 hours, and then trifluoroacetic acid (1.0 mL) was added and the mixture was stirred at 40° C. for 4 hours. The reaction mixture was evaporated in vacuo, dissolved in dichloromethane and washed once with saturated aqueous $NaHCO_3$. The organic portion was dried over $MgSO_4$, filtered, and evaporated in vacuo. The crude product was purified via reverse phase HPLC and lyophilized to yield 17.4 mg (16%) of N-(7-(1H-pyrrol-2-yl)isoquinolin-3-yl)cyclopropanecarboxamide. LCMS (ESI): $R_T$ (Min)=4.073, M+H=278.0, method=E; $^1$H NMR (400 MHz, DMSO-$d_6$) δ 11.49 (s, 1H), 10.81 (s, 1H), 9.02 (s, 1H), 8.39 (s, 1H), 8.17 (s, 1H), 7.99 (d, J=8.7 Hz, 1H), 7.82 (d, J=8.7 Hz, 1H), 6.93 (s, 1H), 6.67 (s, 1H), 6.17 (s, 1H), 2.15-1.99 (m, 1H), 0.84 (m, 4H).

Example 26

7-(5-fluoro-2-methylphenyl)-N-(1,1,1-trifluoropropan-2-yl)isoquinolin-3-amine

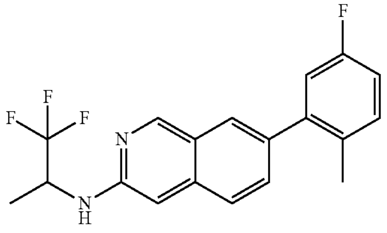 [SMILES: Cc1ccc(F)cc1-c1ccc2cc(NC(C)C(F)(F)F)ncc2c1]

Step 1: 3-chloro-7-(5-fluoro-2-methylphenyl)isoquinoline

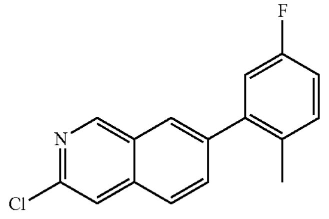 [SMILES: Cc1ccc(F)cc1-c1ccc2cc(Cl)ncc2c1]

To a solution of 7-(5-fluoro-2-methylphenyl)isoquinolin-3-amine (0.5177 g, 2.052 mmol) in chloroform (10 mL, 100 mmol) was added cuprous monochloride (0.3159 g, 3.191 mmol) and tert-butyl nitrite (0.50 mL, 3.8 mmol). The reaction mixture was stirred at room temperature in a flask shielded from the light with foil for 20 hours. To the reaction mixture was added 2M aqueous $Na_2CO_3$ and ethyl acetate, and the resulting mixture was filtered through celite. The organic layer was then dried over $MgSO_4$, filtered, and evaporated in vacuo. The resulting residue was purified via flash chromatography on silica gel (40 g silica, solvent gradient: 0-50% ethyl acetate in heptanes) to yield 202.6 mg (36%) of 3-chloro-7-(5-fluoro-2-methylphenyl)isoquinoline. LCMS (ESI): M+H=272.2; $^1$H NMR (400 MHz, DMSO-$d_6$) δ 9.26 (s, 1H), 8.19 (s, 1H), 8.11 (s, 1H), 8.05 (d, J=8.5 Hz, 1H), 7.87 (d, J=8.5 Hz, 1H), 7.45-7.36 (m, 1H), 7.19 (t, J=7.9 Hz, 2H), 2.24 (s, 3H).

Step 2: 7-(5-fluoro-2-methylphenyl)-N-(1,1,1-trifluoropropan-2-yl)isoquinolin-3-amine

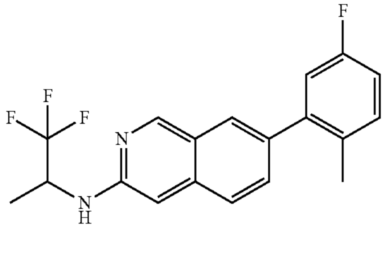 [SMILES: Cc1ccc(F)cc1-c1ccc2cc(NC(C)C(F)(F)F)ncc2c1]

A mixture of 3-chloro-7-(5-fluoro-2-methylphenyl)isoquinoline (41 mg, 0.15 mmol), 1-methyl-2,2,2-trifluoroethylamine, hydrochloride (36.5 mg, 0.244 mmol), 2-(dicyclohexylphosphino)-3,6-dimethoxy-2'-4'-6'-tri-1-propyl-1,1'-biphenyl (8.4 mg, 0.016 mmol), chloro[2-(dicyclohexylphosphino)-3-,6-dimethoxy-2-4'-6'-tri-i-pr-1,1'-biphenyl)][2-(2-aminoethyl)Ph]Pd(II) (13.7 mg, 0.0172 mmol), and cesium carbonate (148 mg, 0.454 mmol) in 1,4-dioxane (1.5 mL, 19 mmol) was purged with nitrogen and then heated at 90° C., for 2 hours. Sodium-tert-butoxide (49.2 mg, 0.512 mmol) was then added and the reaction mixture heated at 90° C. overnight. The mixture was then partitioned between ethyl acetate and water, and the organic layer was washed with water and brine, dried over $MgSO_4$, filtered, and evaporated in vacuo. The crude product was purified via reverse phase HPLC and lyophilized to yield 19.7 mg (37%) of 7-(5-fluoro-2-methylphenyl)-N-(1,1,1-trifluoropropan-2-yl)isoquinolin-3-amine. LCMS (ESI): $R_T$ (Min)=5.716, M+H=349.1, method=E; $^1$H NMR (400 MHz, DMSO-$d_6$) δ 8.96 (s, 1H), 7.84 (s, 1H), 7.66 (d, J=8.6 Hz, 1H), 7.53 (d, J=8.6 Hz, 1H), 7.36 (dd, J=9.3, 5.9 Hz, 1H), 7.13 (dd, J=7.8, 5.1 Hz, 2H), 7.01 (d, J=9.1 Hz, 1H), 6.88 (s, 1H), 5.11-4.91 (m, 1H), 2.25 (s, 3H), 1.37 (d, J=6.9 Hz, 3H).

Example 27

N-(cyclopropylmethyl)-7-(5-fluoro-2-methylphenyl)isoquinolin-3-amine

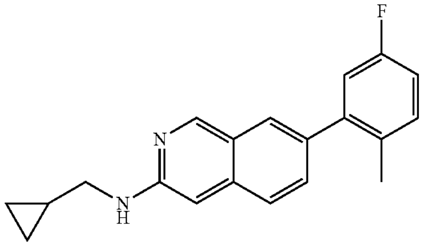 [SMILES: Cc1ccc(F)cc1-c1ccc2cc(NCC3CC3)ncc2c1]

To a solution of 7-(5-fluoro-2-methylphenyl)isoquinolin-3-amine (61.7 mg, 0.244 mmol) in N,N-dimethylformamide (2.0 mL, 26 mmol) at room temperature was added sodium hydride (20.1 mg, 0.502 mmol, 60% dispersion in mineral oil). The reaction mixture was stirred at room temperature for 30 minutes, and then cyclopropylmethyl bromide (24.0 uL, 0.247 mmol) was added and the reaction mixture was heated at 50° C. for 3 hours. The reaction mixture was cooled to room temperature and sodium hydride (66 mg, 60% dispersion in mineral oil) was added, followed by cyclopropylmethyl bromide (30.0 uL). The reaction mixture was then stirred at room temperature overnight. The mixture was then partitioned between ethyl acetate and water, and the organic layer was washed with water and brine, dried over $MgSO_4$, filtered, and evaporated in vacuo. The crude product was purified via flash chromatography on silica gel (12 g silica, solvent gradient: 0-50% ethyl acetate in dichloromethane) to yield 11.8 mg (16%) of N-(cyclopropylmethyl)-7-(5-fluoro-2-methylphenyl)isoquinolin-3-amine. LCMS (ESI): $R_T$ (min)=4.807, M+H=307.1, method=E; $^1$H NMR (400 MHz, DMSO-$d_6$) δ 8.89 (s, 1H), 7.77 (s, 1H), 7.61 (d, J=8.7 Hz, 1H), 7.47 (d, J=8.7 Hz, 1H), 7.40-7.30 (m, 1H), 7.17-7.06 (m, 2H), 6.64 (s, 1H), 6.54 (t, J=5.3 Hz, 1H), 3.16 (t, J=6.2 Hz, 2H), 2.25 (s, 3H), 1.12 (dd, J=12.4, 6.7 Hz, 1H), 0.46 (d, J=6.8 Hz, 2H), 0.26 (d, J=4.3 Hz, 2H).

Example 28

N-(7-(4-methyl-1H-pyrazol-5-yl)isoquinolin-3-yl) cyclopropanecarboxamide hydrochloride

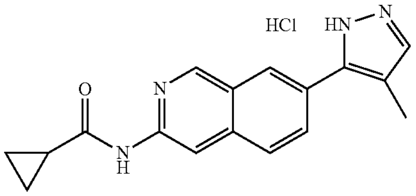 [SMILES: Cc1cn[nH]c1-c1ccc2cc(NC(=O)C3CC3)ncc2c1 ; Cl]

Step 1: 4-methyl-1-(tetrahydro-2H-pyran-2-yl)-1H-pyrazole

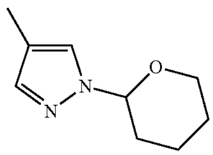

Trifluoroacetic acid (40.0 uL, 0.519 mmol) was added to a solution of 4-methylpyrazole (0.901 g, 11.0 mmol) in dihydropyran (2.0 mL, 22 mmol). The reaction mixture was stirred at 90° C. for 20 hours. The mixture was cooled to room temperature, and then quenched with Sodium hydride (92 mg, 2.3 mmol). After stirring at room temperature for 10 minutes more, the solvent was removed under vacuum. The residue was suspended in dichloromethane, and passed through a short plug of silica, rinsed with dichloromethane. The filtrate was evaporated in vacuo to yield 1.5213 g (83%) of 4-methyl-1-(tetrahydro-2H-pyran-2-yl)-1H-pyrazole. LCMS (ESI): M+H=167.4; $^{1}$H NMR (400 MHz, DMSO-$d_6$) δ 7.60 (s, 1H), 7.27 (s, 1H), 5.29 (d, J=9.9 Hz, 1H), 3.89 (d, J=11.2 Hz, 1H), 3.64-3.51 (m, 1H), 2.00 (overlapping s and m, 4H), 1.88 (dd, J=27.1, 13.0 Hz, 1H), 1.64 (m, 1H), 1.51 (m, 2H).

Step 2: 4-methyl-1-(tetrahydro-2H-pyran-2-yl)-5-(tributylstannyl)-1H-pyrazole

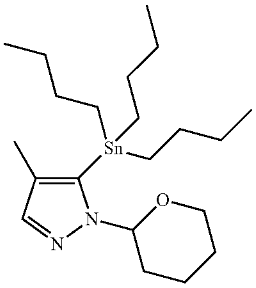 [SMILES: CCC[CH2][Sn]([CH2]CCC)([CH2]CCC)[c]1c(C)cnn1C1CCCCO1]

To a solution of 4-methyl-1-(tetrahydro-2H-pyran-2-yl)-1H-pyrazole (0.258 g, 1.55 mmol) in tetrahydrofuran (6 mL, 70 mmol) at −78° C. was added 2.5 M of n-butyllithium in hexane (0.80 mL). The reaction was stirred at −78° C. for 50 minutes, and then tributyltin chloride (0.60 mL, 2.2 mmol) was added. The reaction was kept at −78° C. for 2 hours and then quenched with saturated aqueous $NH_4Cl$ and warmed to room temperature. The reaction mixture was diluted with more water and extracted with ethyl acetate. The organic portion was dried with $MgSO_4$, filtered, and evaporated in vacuo. The crude product was purified via flash chromatography on silica gel (40 g silica, solvent gradient: 0-50% ethyl acetate in heptanes) to yield 520.6 mg (74%) of 4-methyl-1-(tetrahydro-2H-pyran-2-yl)-5-(tributylstannyl)-1H-pyrazole. LCMS (ESI): M+H=457.2; $^{1}$H NMR (400 MHz, DMSO-$d_6$) δ 7.31 (s, 1H), 5.11 (d, J=8.3 Hz, 1H), 3.81 (d, J=11.4 Hz, 1H), 3.59-3.48 (m, 1H), 2.23 (dd, J=20.7, 9.4 Hz, 1H), 2.04 (s, 3H), 1.97 (d, J=12.8 Hz, 1H), 1.90 (d, J=13.3 Hz, 1H), 1.48 (m, 9H), 1.30 (dd, J=14.5, 7.3 Hz, 6H), 1.20-0.97 (m, 6H), 0.86 (t, J=7.3 Hz, 9H).

Step 3: N-(7-(4-methyl-1-(tetrahydro-2H-pyran-2-yl)-1H-pyrazol-5-yl)isoquinolin-3-yl)cyclopropanecarboxamide

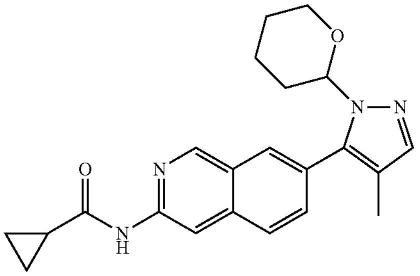 [SMILES: Cc1cnn(C2CCCCO2)c1-c1ccc2cc(NC(=O)C3CC3)ncc2c1]

To a mixture of N-(7-bromoisoquinolin-3-yl)cyclopropanecarboxamide (50.4 mg, 0.173 mmol) and 4-methyl-1-(tetrahydro-2H-pyran-2-yl)-5-(tributylstannyl)-1H-pyrazole (76.9 mg, 0.169 mmol) was added N,N-dimethylformamide (1.5 mL, 19 mmol). Nitrogen gas was bubbled through the reaction mixture for 5 minutes, and then bis(tri-t-butylphosphine)palladium (11.5 mg, 0.0225 mmol), copper(I) iodide (6.1 mg, 0.032 mmol), and cesium fluoride (53.4 mg, 0.352 mmol) was added. The reaction mixture was stirred in a sealed vial at 50° C. for 2 hours, and then at 80° C. for 16 hours. The mixture was then partitioned between ethyl acetate and water, and the organic layer was washed with water and brine, dried over $MgSO_4$, filtered, and evaporated in vacuo. The crude product was purified via flash chromatography on silica gel (12 g silica, solvent gradient: 20-100% ethyl acetate in heptanes) to yield 43.0 mg (67%) of N-(7-(4-methyl-1-(tetrahydro-2H-pyran-2-yl)-1H-pyrazol-5-yl)isoquinolin-3-yl)cyclopropanecarboxamide. LCMS (ESI): M+H=377.2.

Step 4: N-(7-(4-methyl-1H-pyrazol-5-yl)isoquinolin-3-yl)cyclopropanecarboxamide hydrochloride

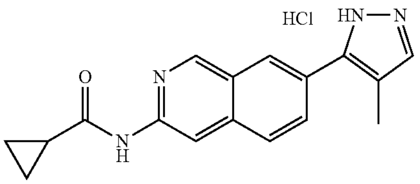 [SMILES: Cc1cn[nH]c1-c1ccc2cc(NC(=O)C3CC3)ncc2c1 ; Cl]

To a solution of N-(7-(4-methyl-1-(tetrahydro-2H-pyran-2-yl)-1H-pyrazol-5-yl)isoquinolin-3-yl)cyclopropanecarboxamide (43 mg, 0.11 mmol) in methanol (3 mL, 70 mmol) was added 4.0 M of hydrogen chloride in 1,4-dioxane (0.30 mL). The reaction mixture was stirred at 40° C. for 1 hour and then evaporated in vacuo. The residue was triturated with 0.5 mL N,N-dimethylformamide, and the resulting light yellow precipitate was collected, rinsed with ethyl acetate, and dried under vacuum to yield 17.3 mg (46%) of N-(7-(4-methyl-1H-pyrazol-5-yl)isoquinolin-3-yl)cyclopropanecarboxamide hydrochloride. LCMS (ESI): $R_T$ (Min)=3.816, M+H=293.0, method=E; $^1$H NMR (400 MHz, DMSO-$d_6$) δ 10.96 (s, 1H), 9.22 (s, 1H), 8.44 (s, 1H), 8.27 (s, 1H), 8.06 (d, J=8.8 Hz, 1H), 7.92 (d, J=8.7 Hz, 1H), 7.63 (s, 1H), 2.31 (s, 3H), 2.14-2.01 (m, 1H), 0.93-0.76 (m, 4H).

Example 29

1-ethyl-N-(7-(5-fluoro-2-methylphenyl)isoquinolin-3-yl)piperidine-4-carboxamide

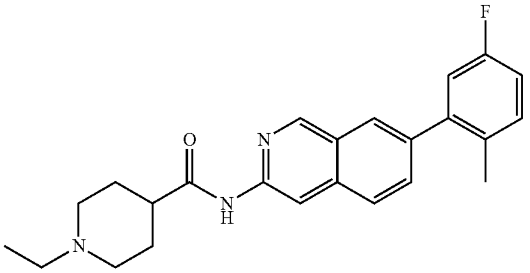 [SMILES: CCN1CCC(C(=O)Nc2cc3ccc(-c4cc(F)ccc4C)cc3cn2)CC1]

To a solution of N-(7-(5-fluoro-2-methylphenyl)isoquinolin-3-yl)piperidine-4-carboxamide (110.6 mg, 0.1936 mmol) in N,N-dimethylformamide (2.0 mL, 26 mmol) was added N,N-diisopropylethylamine (0.1 mL, 0.574 mmol) and iodoethane (19.0 uL, 0.238 mmol). The reaction was stirred at room temperature for 19 hours, and then N,N-diisopropylethylamine (0.1 mL) and iodoethane (30 uL, 0.375 mmol) were added. After an additional 4 hours, the mixture was evaporated in vacuo. The crude product was purified via reverse phase HPLC and lyophilized to yield 31.4 mg (41%) of 1-ethyl-N-(7-(5-fluoro-2-methylphenyl)isoquinolin-3-yl)piperidine-4-carboxamide. LCMS (ESI): $R_T$ (Min)=4.370, M+H=392.1, method=E; $^1$H NMR (400 MHz, DMSO-$d_6$) δ 10.76 (s, 1H), 9.19 (s, 1H), 8.53 (s, 1H), 8.06 (s, 1H), 7.96 (d, J=8.6 Hz, 1H), 7.73 (d, J=8.5 Hz, 1H), 7.39 (s, 1H), 7.18 (d, J=8.9 Hz, 2H), 3.53 (unresolved, 2H), 3.08 (unresolved, 2H), 2.83 (unresolved, 3H), 2.25 (s, 3H), 2.07 (unresolved, 2H), 1.90 (unresolved, 2H), 1.22 (unresolved, 3H).

Example 30

N-(7-(pyrazin-2-yl)isoquinolin-3-yl)cyclopropanecarboxamide

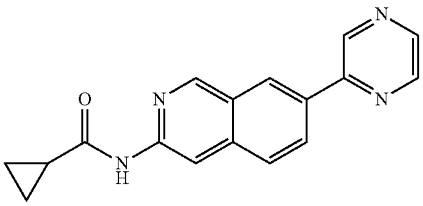 [SMILES: O=C(Nc1cc2ccc(-c3cnccn3)cc2cn1)C1CC1]

To a mixture of N-(7-bromoisoquinolin-3-yl)cyclopropanecarboxamide 1 (42.8 mg, 0.147 mmol) and 1,4-Dioxane (1.5 mL, 19 mmol) was added 2-(tributylstannyl)pyrazine (51.0 uL, 0.162 mmol) and tetrakis(triphenylphosphine)palladium (0) (14.0 mg, 0.0121 mmol). The reaction mixture was subjected to microwave irradiation at 130° C. for 30 minutes. The reaction mixture is poured into ethyl acetate and washed with dilute $NH_4OH$. The organic layer was dried over $MgSO_4$, filtered, and evaporated in vacuo. The crude product was purified via reverse phase HPLC and lyophilized to yield 23.4 mg (55%) of N-(7-(pyrazin-2-yl)isoquinolin-3-yl)cyclopropanecarboxamide. LCMS (ESI): $R_T$ (min)=4.106, M+H=291.0, method=E; $^1$H NMR (400 MHz, DMSO-$d_6$) δ 10.96 (s, 1H), 9.42 (s, 1H), 9.27 (s, 1H), 8.87 (s, 1H), 8.78 (s, 1H), 8.66 (s, 1H), 8.51 (s, 1H), 8.45 (d, J=8.6 Hz, 1H), 8.01 (d, J=8.7 Hz, 1H), 2.10 (s, 1H), 0.94-0.74 (m, 4H).

Example 31

N-(7-(5-fluoro-2-methylphenyl)isoquinolin-3-yl)-4-methylpiperazine-1-carboxamide

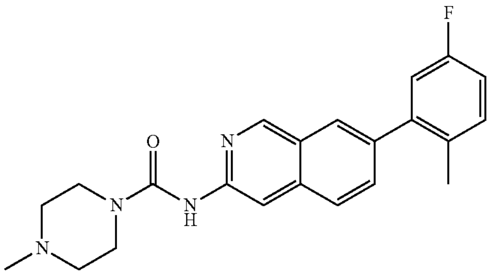

Step 1: 4-nitrophenyl 7-(5-fluoro-2-methylphenyl)isoquinolin-3-ylcarbamate

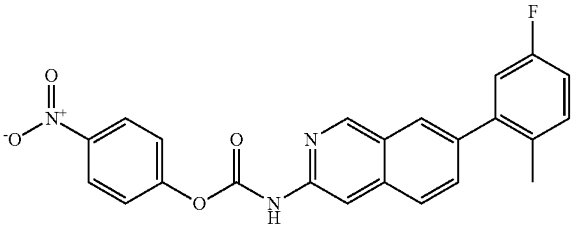

To a suspension of 7-(5-fluoro-2-methylphenyl)isoquinolin-3-amine (0.5145 g, 2.039 mmol) in 1,2-dichloroethane (10 mL, 100 mmol) was added triethylamine (0.35 mL, 2.5 mmol) and p-nitrophenyl chloroformate (0.452 g, 2.24 mmol). The reaction mixture was stirred at room temperature for 16 hours and then pyridine (0.50 mL, 6.2 mmol) and p-nitrophenyl chloroformate (0.452 g, 2.24 mmol) were added. After an additional 2 hours, the reaction mixture was diluted with dichloromethane, washed with saturated aqueous $NaHCO_3$, dried over $MgSO_4$, and evaporated in vacuo. 1.069 g of 4-nitrophenyl 7-(5-fluoro-2-methylphenyl)isoquinolin-3-ylcarbamate was obtained, and carried forward without purification. LCMS (ESI): M+H=poor ionization.

Step 2: N-(7-(5-fluoro-2-methylphenyl)isoquinolin-3-yl)-4-methylpiperazine-1-carboxamide

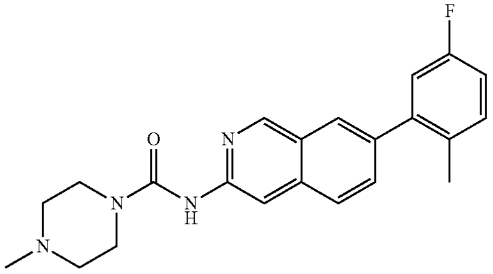

4-nitrophenyl 7-(5-fluoro-2-methylphenyl)isoquinolin-3-ylcarbamate (0.156 g, 0.374 mmol) was dissolved in N,N-dimethylformamide (2.0 mL, 26 mmol) and 1-methyl-piperazine (0.20 mL, 1.8 mmol) was added. The reaction mixture was heated at 90° C. for 1 hour. The reaction mixture was then diluted with dichloromethane, washed with saturated aqueous $NaHCO_3$, dried over $MgSO_4$, and evaporated in vacuo. The crude product was purified via flash chromatography on silica gel (12 g silica, solvent gradient: 0-20% methanol in dichloromethane with 2% triethylamine) followed by reverse phase HPLC and lyophilization to yield 5.4 mg (4%) of N-(7-(5-fluoro-2-methylphenyl)isoquinolin-3-yl)-4-methylpiperazine-1-carboxamide. LCMS (ESI): $R_T$ (min)=4.017, M+H=379.1, method=E; $^1$H NMR (400 MHz, DMSO-$d_6$) δ 9.22 (s, 1H), 9.12 (s, 1H), 8.23 (s, 1H), 7.99 (s, 1H), 7.88 (d, J=8.3 Hz, 1H), 7.67 (d, J=8.7 Hz, 1H), 7.38 (s, 1H), 7.16 (t, J=8.3 Hz, 2H), 3.52 (s, 4H), 2.33 (s, 4H), 2.25 (s, 3H), 2.21 (s, 3H).

Example 32

N-(7-(2-methylprop-1-enyl)isoquinolin-3-yl)cyclopropanecarboxamide

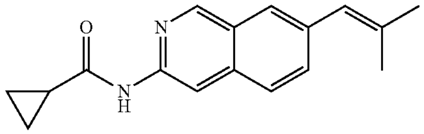 [SMILES: CC(C)=Cc1ccc2cc(NC(=O)C3CC3)ncc2c1]

To a mixture of N-(7-bromoisoquinolin-3-yl)cyclopropanecarboxamide (121.6 mg, 0.4177 mmol, 2-methyl-1-propenylboronic acid pinacol ester (129 uL, 0.629 mmol), bis(di-tert-butyl(4-dimethylaminophenyl)phosphine) dichloropalladium(II) (15.9 mg, 0.0224 mmol), and potassium carbonate (150.5 mg, 1.089 mmol) was added 1,4-dioxane (2 mL, 20 mmol) and water (0.2 mL, 10 mmol). The reaction mixture was stirred at 90° C. for 3 hours. The reaction mixture was then poured into ethyl acetate, which was washed with two portions water, dried with brine and $MgSO_4$, filtered, and evaporated in vacuo to yield 144.5 mg of crude product. 44 mg of this crude material was purified via reverse phase HPLC and lyophilized to yield 28.2 mg N-(7-(2-methylprop-1-enyl)isoquinolin-3-yl)cyclopropanecarboxamide. LCMS (ESI): $R_T$ (min)=4.919, M+H=267.1, method=E; $^1$H NMR (400 MHz, DMSO-$d_6$) δ 10.89 (s, 1H), 9.10 (s, 1H), 8.41 (s, 1H), 7.86 (s, 1H), 7.80 (d, J=8.6 Hz, 1H), 7.57 (dd, J=8.6, 1.4 Hz, 1H), 6.41 (s, 1H), 2.12-1.99 (m, 1H), 1.93 (d, J=7.7 Hz, 6H), 0.83 (m, 4H).

Example 33

N-(7-isobutylisoquinolin-3-yl)cyclopropanecarboxamide

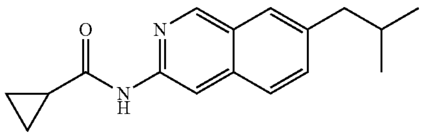 [SMILES: CC(C)Cc1ccc2cc(NC(=O)C3CC3)ncc2c1]

To a solution of N-(7-(2-methylprop-1-enyl)isoquinolin-3-yl)cyclopropanecarboxamide (100.0 mg, 0.2891 mmol) in ethyl acetate (10.0 mL, 102 mmol) was added palladium (30.6 mg, 0.0288 mmol) (10 wt % on carbon). The reaction vessel was purged first with nitrogen and then with hydrogen, and stirred at room temperature under a hydrogen balloon for 2 hours. Ethanol (5.0 mL, 86 mmol) and palladium (41.9 mg, 0.0394 mmol) were added, and the reaction maintained at room temperature for 19 hours. The reaction mixture was then filtered through celite and evaporated in vacuo. The crude product was purified via reverse phase HPLC and lyophilized to yield 54.4 mg (70%) of N-(7-isobutylisoquinolin-3-yl)cyclopropanecarboxamide. LCMS (ESI): $R_T$ (min)=5.079, M+H=269.1, method=E; $^1$H NMR (400 MHz, DMSO-$d_6$) δ 10.85 (s, 1H), 9.06 (s, 1H), 8.41 (s, 1H), 7.86-7.70 (m, 2H), 7.54 (dd, J=8.6, 1.3 Hz, 1H), 2.62 (d, J=7.1 Hz, 2H), 2.13-2.01 (m, 1H), 1.94 (dp, J=13.4, 6.7 Hz, 1H), 0.90 (d, J=6.6 Hz, 6H), 0.86-0.75 (m, 4H).

Example 34

N-(7-(5-fluoro-4-methylpyridin-3-yl)isoquinolin-3-yl)cyclopropanecarboxamide

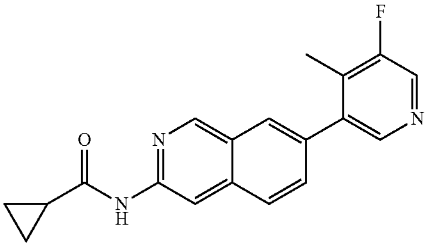 [SMILES: Cc1c(F)cncc1-c1ccc2cc(NC(=O)C3CC3)ncc2c1]

Step 1: 2-chloro-3-fluoro-4-iodopyridine

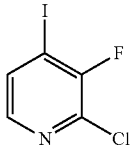

In an oven-dried flask, to a solution of 2.0 M of lithium diisopropylamide in tetrahydrofuran (6.0 mL) in tetrahydrofuran (30 mL, 400 mmol) at −78° C. was added 2-chloro-3-fluoropyridine (1.000 mL, 10.06 mmol). The resulting mixture was stirred at −78° C. for 2 hours. Iodine (3.899 g, 15.36 mmol) was then added as a solution in 5 mL tetrahydrofuran and the reaction was maintained −78° C. for an additional 2.5 hours. The reaction was then quenched with saturated aqueous $NH_4Cl$ and warmed to room temp. The reaction mixture was poured into ethyl acetate and washed sequentially with 10% aqueous $Na_2S_2O_3$ and brine, dried over $MgSO_4$, filtered, and evaporated in vacuo to yield 2.7279 g (100%) of 2-chloro- 3-fluoro-4-iodopyridine. LCMS (ESI): M+H=258.0; $^1$H NMR (500 MHz, $CDCl_3$) δ 7.87 (d, J=4.9 Hz, 1H), 7.71-7.59 (m, 1H).

Step 2: 2-chloro-3-fluoro-5-iodo-4-methylpyridine

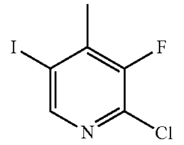

To a solution of 2.0 M of lithium diisopropylamide in tetrahydrofuran (5.5 mL) in tetrahydrofuran (20 mL, 200 mmol) at −78° C. was slowly added 2-chloro-3-fluoro-4-iodopyridine (2.589 g, 10.06 mmol) as a solution in tetrahydrofuran (8 mL). The reaction mixture was then stirred at −78° C. for 4 hours. Methyl iodide (0.70 mL, 11 mmol) was then added. After an additional 1 hour, the reaction was then quenched with saturated aqueous $NH_4Cl$ and warmed to room temp. The reaction mixture was poured into ethyl acetate and washed sequentially with water and brine, dried over $MgSO_4$, filtered, and evaporated in vacuo. The crude product was purified via flash chromatography on silica gel (80 g silica, solvent gradient: 0-30% ethyl acetate in heptanes) to yield 2.212 g (57%) of 2-chloro-3-fluoro-5-iodo-4-methylpyridine. LCMS (ESI): M+H=272.0; $^1$H NMR (500 MHz, $CDCl_3$) δ 8.46 (s, 1H), 2.44 (d, J=1.2 Hz, 3H).

Step 3: N-(7-(6-chloro-5-fluoro-4-methylpyridin-3-yl)isoquinolin-3-yl)cyclopropanecarboxamide

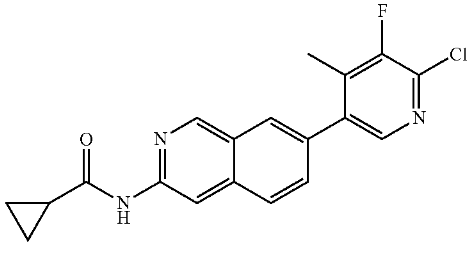 [SMILES: Cc1c(-c2ccc3cc(NC(=O)C4CC4)ncc3c2)cnc(Cl)c1F]

The title compound was prepared following the procedures described for Example 12. LCMS (ESI): M+H=356.2.

Step 4: N-(7-(5-fluoro-4-methylpyridin-3-yl)isoquinolin-3-yl)cyclopropanecarboxamide

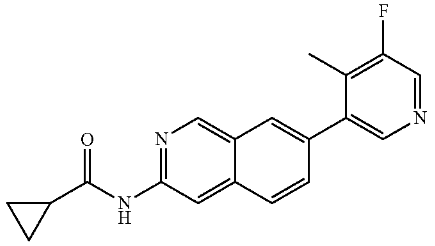 [SMILES: Cc1c(F)cncc1-c1ccc2cc(NC(=O)C3CC3)ncc2c1]

To a solution of N-(7-(6-chloro-5-fluoro-4-methylpyridin-3-yl)isoquinolin-3-yl)cyclopropanecarboxamide (180.0 mg, 0.5059 mmol) in ethanol (10 mL, 200 mmol) was added sodium bicarbonate (95.2 mg, 1.13 mmol) and palladium (60.1 mg, 0.0565 mmol) (10 wt % on carbon). The reaction vessel was purged first with nitrogen and then hydrogen, and then stirred under a hydrogen balloon at 40° C. for 12 hours. The reaction mixture was then filtered through celite and evaporated in vacuo. The crude product was purified via reverse phase HPLC and lyophilized to yield 77.3 mg (48%) of N-(7-(5-fluoro-4-methylpyridin-3-yl)isoquinolin-3-yl)cyclopropanecarboxamide. LCMS (ESI): $R_T$ (Min)=4.130, M+H=322.1, method=E; $^1$H NMR (400 MHz, DMSO-$d_6$) δ 10.95 (s, 1H), 9.20 (s, 1H), 8.55 (s, 1H), 8.52 (s, 1H), 8.42 (s, 1H), 8.12 (s, 1H), 7.98 (d, J=8.5 Hz, 1H), 7.76 (dd, J=8.5, 1.4 Hz, 1H), 2.26 (d, J=1.8 Hz, 3H), 2.15-2.03 (m, 1H), 0.94-0.75 (m, 4H).

Example 35

(2-(7-(5-fluoro-2-methylphenyl)isoquinolin-3-ylamino)-6-methylpyridin-4-yl)methanol

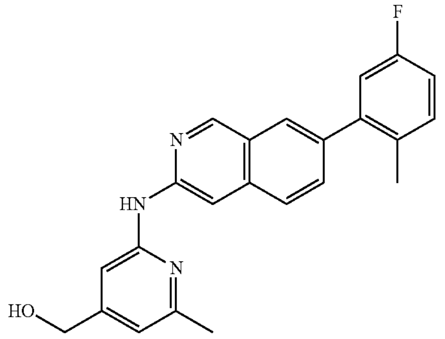 [SMILES: Cc1cc(CO)cc(Nc2cc3ccc(-c4cc(F)ccc4C)cc3cn2)n1]

To a solution of methyl 2-(7-(5-fluoro-2-methylphenyl) isoquinolin-3-ylamino)-6-methylisonicotinate (prepared as described for Example 13, using methyl 2-bromo-6-methylisonicotinate) (55.0 mg, 0.137 mmol) in tetrahydrofuran (5.0 mL, 62 mmol) at 0° C. was slowly added 1.0 M of lithium tetrahydroaluminate in tetrahydrofuran (0.20 mL). The reaction was stirred at 0° C. for 30 minutes, and then quenched by the sequential addition of 8 μL water, then 8 μL 15% aq NaOH, then 23 μL water. The resulting mixture was diluted with dichloromethane and stirred at room temperature for 10 minutes, then dried with $MgSO_4$ and filtered through celite. The solution was evaporated in vacuo and the crude product was purified via reverse phase HPLC and lyophilized to yield 20.8 mg (41%) of (2-(7-(5-fluoro-2-methylphenyl)isoquinolin-3-ylamino)-6-methylpyridin-4-yl)methanol. LCMS (ESI): $R_T$ (Min)=4.542, M+H=374.1, method=E; $^1$H NMR (400 MHz, DMSO-$d_6$) δ 9.68 (s, 1H), 9.10 (s, 1H), 8.54 (s, 1H), 7.95 (s, 1H), 7.82 (d, J=8.6 Hz, 1H), 7.63 (dd, J=8.5, 1.6 Hz, 1H), 7.42-7.29 (m, 1H), 7.22-7.06 (m, 3H), 6.68 (s, 1H), 5.29 (t, J=5.4 Hz, 1H), 4.46 (d, J=4.7 Hz, 2H), 2.47 (s, 3H), 2.27 (s, 3H).

Example 36

2-(2-(7-(5-fluoro-2-methylphenyl)isoquinolin-3-ylamino)-6-methylpyridin-4-yl)propan-2-ol

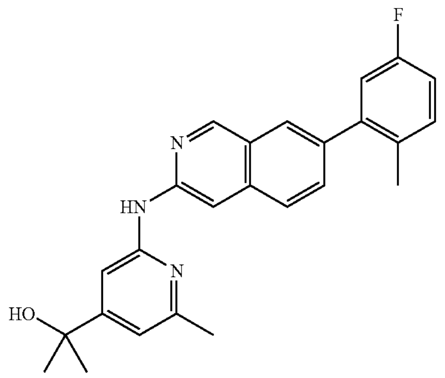 [SMILES: Cc1cc(C(C)(C)O)cc(Nc2cc3ccc(-c4cc(F)ccc4C)cc3cn2)n1]

To a solution of methyl 2-(7-(5-fluoro-2-methylphenyl) isoquinolin-3-ylamino)-6-methylisonicotinate (prepared as described for Example 13, using methyl 2-bromo-6-methyl-isonicotinate) (67.2 mg, 0.167 mmol) in tetrahydrofuran (5.0 mL, 62 mmol) at 0° C. was slowly added 3.0 M of methylmagnesium chloride in tetrahydrofuran (0.20 mL). The reaction mixture was kept at 0° C. for 20 minutes and then warmed to room temperature. After an additional 30 minutes, 3.0 M of methylmagnesium chloride in tetrahydrofuran (0.20 mL) was added and the reaction mixture stirred at room temperature for 2 hours. The reaction was quenched with aqueous saturated sodium bicarbonate and extracted with dichloromethane. The organic extract was dried over $MgSO_4$, filtered, and evaporated in vacuo. The crude product was purified via reverse phase HPLC and lyophilized to yield 36.8 mg (55%) of 2-(2-(7-(5-fluoro-2-methylphenyl)isoquinolin-3-ylamino)-6-methylpyridin-4-yl)propan-2-ol. LCMS (ESI): $R_T$ (min)=4.722, M+H=402.1, method=E; $^1H$ NMR (400 MHz, DMSO-$d_6$) δ 9.61 (s, 1H), 9.09 (s, 1H), 8.58 (s, 1H), 7.94 (s, 1H), 7.82 (d, J=8.6 Hz, 1H), 7.62 (dd, J=8.5, 1.7 Hz, 1H), 7.43-7.31 (m, 1H), 7.26 (s, 1H), 7.15 (t, J=9.3 Hz, 2H), 6.82 (s, 1H), 5.08 (s, 1H), 2.48 (s, 3H), 2.27 (s, 3H), 1.41 (s, 6H).

Example 37

(2-(7-(4-methylpyridin-3-yl)isoquinolin-3-ylamino) pyridin-4-yl)methanol

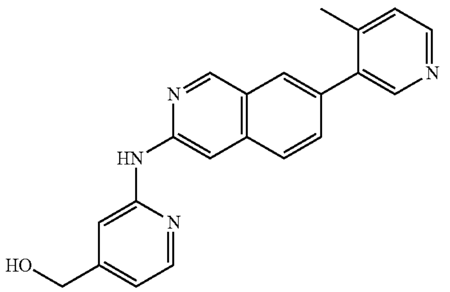 [SMILES: Cc1ccncc1-c1ccc2cc(Nc3cc(CO)ccn3)ncc2c1]

Step 1: 7-(4-methylpyridin-3-yl)isoquinolin-3-amine

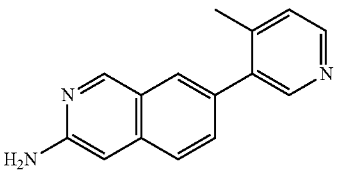 [SMILES: Cc1ccncc1-c1ccc2cc(N)ncc2c1]

To a mixture of 7-bromoisoquinolin-3-amine (253.2 mg, 1.135 mmol), 4-methylpyridine-3-boronic acid (188.8 mg, 1.379 mmol), bis(di-tert-butyl(4-dimethylaminophenyl) phosphine)dichloropalladium(II) (81.0 mg, 0.114 mmol), and cesium carbonate (0.7432 g, 2.281 mmol) was added 1,2-dimethoxyethane (5 mL, 50 mmol) and water (0.5 mL, 30 mmol). The reaction mixture was subjected to microwave irradiation at 130° C. for 30 minutes. 4-Methylpyridine-3-boronic acid (197.2 mg, 1.440 mmol) was added and the reaction mixture was subjected to microwave irradiation at 130° C. for 45 min. The reaction mixture was diluted with dichloromethane, washed with saturated aqueous $NaHCO_3$, dried over $MgSO_4$, and evaporated in vacuo. The crude material was purified via flash chromatography on silica gel (25 g silica, solvent gradient: 0-10% methanol in dichloromethane) to yield 111.1 mg (42%) of 7-(4-methylpyridin-3-yl)isoquinolin-3-amine. LCMS (ESI): M+H=236.2; $^1H$ NMR (400 MHz, DMSO-$d_6$) δ 8.87 (s, 1H), 8.43 (d, J=6.4 Hz, 2H), 7.81 (s, 1H), 7.60 (d, J=8.5 Hz, 1H), 7.49 (dd, J=8.6, 1.7 Hz, 1H), 7.35 (d, J=5.0 Hz, 1H), 6.67 (s, 1H), 5.99 (s, 2H), 2.31 (s, 3H).

Step 2: (2-(7-(4-methylpyridin-3-yl)isoquinolin-3-ylamino)pyridin-4-yl)methanol

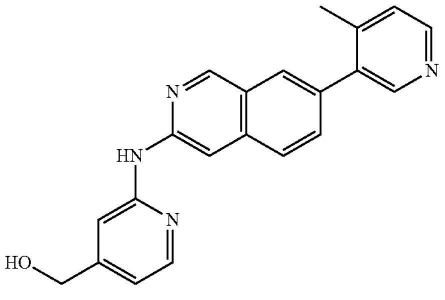

The title compound was prepared following the procedures described for Example 13, using 7-(4-methylpyridin-3-yl) isoquinolin-3-amine and 2-bromopyridine-4-methanol, to yield 26.2 mg (44%) of (2-(7-(4-methylpyridin-3-yl)isoquinolin-3-ylamino)pyridin-4-yl)methanol. LCMS (ESI): $R_T$ (min)=2.759, M+H=343.1, method=E; $^1H$ NMR (400 MHz, DMSO-$d_6$) δ 9.79 (s, 1H), 9.12 (s, 1H), 8.57 (s, 1H), 8.49 (s, 1H), 8.47 (d, J=5.0 Hz, 1H), 8.23 (d, J=5.2 Hz, 1H), 8.00 (s, 1H), 7.88 (d, J=8.5 Hz, 1H), 7.67 (d, J=8.6 Hz, 1H), 7.38 (d, J=4.9 Hz, 1H), 7.29 (s, 1H), 6.81 (d, J=5.1 Hz, 1H), 5.35 (t, J=5.7 Hz, 1H), 4.50 (d, J=5.6 Hz, 2H), 2.34 (s, 3H).

Example 38

N-(7-(5-(hydroxymethyl)-2-methylpyridin-3-yl)isoquinolin-3-yl)cyclopropanecarboxamide

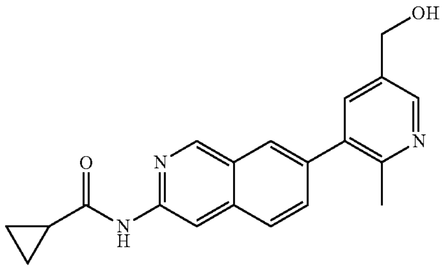 [SMILES: Cc1ncc(CO)cc1-c1ccc2cc(NC(=O)C3CC3)ncc2c1]

Step 1: Methyl 5-(3-(cyclopropanecarboxamido) isoquinolin-7-yl)-6-methylnicotinate

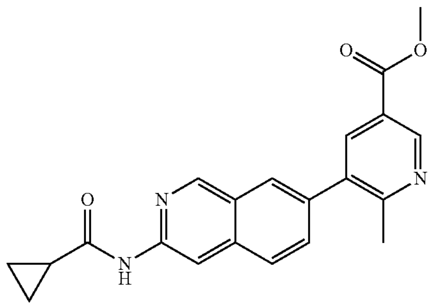 [SMILES: COC(=O)c1cnc(C)c(-c2ccc3cc(NC(=O)C4CC4)ncc3c2)c1]

The title compound was prepared following the procedures described for Example 24, using methyl 6-chloro-5-iodonicotinate. LCMS (ESI): $R_T$ (Min)=M+H=362.2.

Step 2: N-(7-(5-(hydroxymethyl)-2-methylpyridin-3-yl)isoquinolin-3-yl)cyclopropanecarboxamide

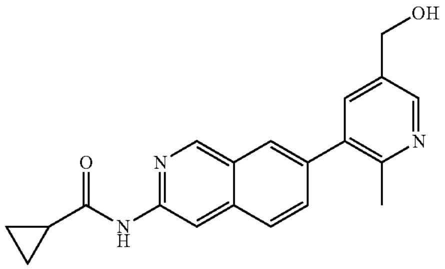 [SMILES: Cc1ncc(CO)cc1-c1ccc2cc(NC(=O)C3CC3)ncc2c1]

To a solution of Methyl 5-(3-(cyclopropanecarboxamido) isoquinolin-7-yl)-6-methylnicotinate (11.9 mg, 0.0329 mmol) in tetrahydrofuran (3 mL, 40 mmol) was added 1.0 M of lithium tetrahydroaluminate in tetrahydrofuran (0.10 mL). The reaction mixture was stirred at room temperature for 30 minutes. The reaction was then quenched with water and extracted twice with dichloromethane. The combined organic extracts were dried over $MgSO_4$, filtered, and evaporated in vacuo. The crude material was purified via flash chromatography on silica gel (25 g silica, solvent gradient: 0-10% methanol in dichloromethane) to yield 4.5 mg (41%) of N-(7-(5-(hydroxymethyl)-2-methylpyridin-3-yl)isoquinolin-3-yl) cyclopropanecarboxamide. LCMS (ESI): $R_T$ (Min)=2.995, M+H=334.1, method=E; $^1$H NMR (400 MHz, DMSO-$d_6$) δ 10.91 (s, 1H), 9.19 (s, 1H), 8.50 (s, 1H), 8.46 (s, 1H), 8.06 (s, 1H), 7.95 (d, J=8.7 Hz, 1H), 7.74 (d, J=8.6 Hz, 1H), 7.64 (s, 1H), 5.30 (t, J=5.4 Hz, 1H), 4.58 (d, J=5.2 Hz, 2H), 2.47 (s, 3H), 2.08 (s, 1H), 0.91-0.78 (m, 4H).

Example 39

(R)-N-(7-(1-hydroxypropan-2-yloxy)isoquinolin-3-yl)cyclopropanecarboxamide

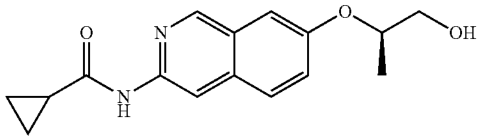 [SMILES: C[C@H](CO)Oc1ccc2cc(NC(=O)C3CC3)ncc2c1]

Step 1: N-(7-hydroxyisoquinolin-3-yl)cyclopropanecarboxamide

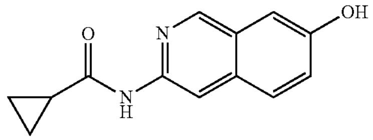 [SMILES: O=C(Nc1cc2ccc(O)cc2cn1)C1CC1]

A round-bottom flask was charged with N-(7-bromoisoquinolin-3-yl)cyclopropanecarboxamide (3.0058 g, 10.324 mmol), tris(dibenzylideneacetone)dipalladium(0) chloroform adduct (0.1843 g, 0.1780 mmol), and 2-di-t-butylphosphino-3,4,5,6-tetramethyl-2',4',6'-tri-1-propylbiphenyl (0.2514 g, 0.5229 mmol). The flask was evacuated and backfilled with nitrogen five times and then 1,4-dioxane (10 mL, 200 mmol) and potassium hydroxide (2.413 g, 43.01 mmol) dissolved in water (10 mL, 800 mmol) were added. The reaction mixture was heated at 90° C. under a nitrogen balloon for 2 hours. The reaction mixture was then cooled to room temperature and poured into 150 mL water. The resulting precipitate was filtered, rinsed with water, and dried under vacuum to yield 1.7974 g (76%) of N-(7-hydroxyisoquinolin-3-yl)cyclopropanecarboxamide. LCMS (ESI): M+H=229.2; $^1$H NMR (400 MHz, DMSO-$d_6$) δ 10.67 (s, 1H), 9.90 (s, 1H), 8.91 (s, 1H), 8.32 (s, 1H), 7.71 (d, J=8.9 Hz, 1H), 7.27 (dd, J=8.9, 2.3 Hz, 1H), 7.22 (s, 1H), 2.13-1.95 (m, 1H), 0.91-0.70 (m, 4H).

Step 2: (R)-methyl 2-(3-(cyclopropanecarboxamido) isoquinolin-7-yloxy)propanoate

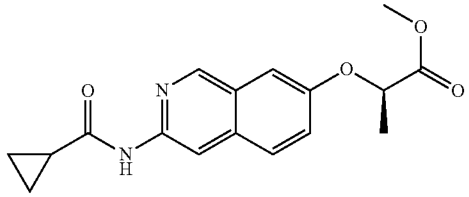 [SMILES: COC(=O)[C@@H](C)Oc1ccc2cc(NC(=O)C3CC3)ncc2c1]

To a solution of N-(7-hydroxyisoquinolin-3-yl)cyclopropanecarboxamide (68.7 mg, 0.301 mmol) in tetrahydrofuran (3.0 mL, 37 mmol) was added ethyl L-(-)-lactate (44 uL, 0.39 mmol) and triphenylphosphine (108.4 mg, 0.4133 mmol), followed by dropwise addition of diethyl azodicarboxylate (62 uL, 0.39 mmol). The resulting mixture was stirred at room temperature for 1 hour, and then ethyl L-(-)-lactate (13 uL, 0.11 mmol) and diethyl azodicarboxylate (19 uL, 0.12 mmol) were added. After an additional 2.5 hours, the reaction mixture was poured into ethyl acetate, washed with water and brine, dried over $MgSO_4$, filtered, and evaporated in vacuo. The crude material was purified via flash chromatography on silica gel (12 g silica, solvent gradient: 0-80% ethyl acetate in heptanes) to provide a quantitative yield of (R)-methyl 2-(3-(cyclopropanecarboxamido)isoquinolin-7-yloxy)propanoate. LCMS (ESI): M+H=329.2.

Step 3: (R)-N-(7-(1-hydroxypropan-2-yloxy)isoquinolin-3-yl)cyclopropanecarboxamide

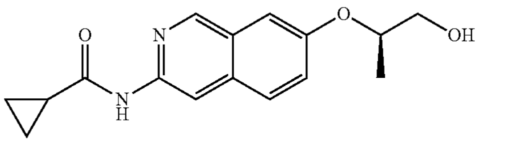 [SMILES: C[C@H](CO)Oc1ccc2cc(NC(=O)C3CC3)ncc2c1]

To a solution of (R)-methyl 2-(3-(cyclopropanecarboxamido)isoquinolin-7-yloxy)propanoate (0.301 mmol, 0.301 mmol) in tetrahydrofuran (5.0 mL, 62 mmol) at −78° C. was added 1.0 M of lithium tetrahydroaluminate in tetrahydrofuran (0.40 mL). The reaction mixture was cooled at −78° C. for one hour, and then stirred at room temperature for an additional hour. The reaction mixture was quenched by sequential addition of 20 μL water, then 20 μL 15% aq NaOH, then 60 μL water. The resulting mixture was stirred at room temperature for 15 minutes, then diluted with dichloromethane, dried over $MgSO_4$, filtered through celite, and evaporated in vacuo. The crude product was purified via reverse phase HPLC and lyophilized to yield 37.2 mg (43%) of (R)-N-(7-(1-hydroxypropan-2-yloxy)isoquinolin-3-yl)cyclopropanecarboxamide. LCMS (ESI): $R_T$ (Min)=3.213, M+H=287.1, method=E; $^1$H NMR (400 MHz, DMSO-$d_6$) δ 10.72 (s, 1H), 8.98 (s, 1H), 8.36 (s, 1H), 7.77 (d, J=9.0 Hz, 1H), 7.47 (d, J=2.0 Hz, 1H), 7.34 (dd, J=9.0, 2.4 Hz, 1H), 4.89 (s, 1H), 4.58 (dd, J=11.2, 5.7 Hz, 1H), 3.56 (t, J=15.1 Hz, 2H), 2.04 (td, J=7.7, 3.9 Hz, 1H), 1.28 (d, J=6.1 Hz, 3H), 0.89-0.71 (m, 4H).

Example 40

N-(7-(1-hydroxy-2-methylpropan-2-yloxy)isoquinolin-3-yl)cyclopropanecarboxamide

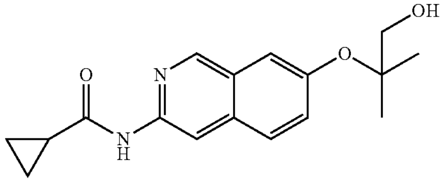 [SMILES: CC(C)(CO)Oc1ccc2cc(NC(=O)C3CC3)ncc2c1]

Step 1: Ethyl 2-(3-(cyclopropanecarboxamido)isoquinolin-7-yloxy)-2-methylpropanoate

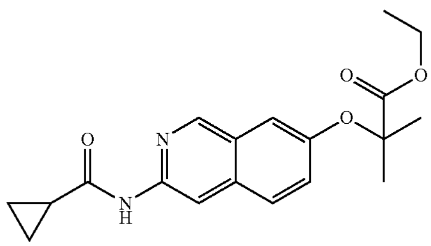 [SMILES: CCOC(=O)C(C)(C)Oc1ccc2cc(NC(=O)C3CC3)ncc2c1]

A mixture of N-(7-hydroxyisoquinolin-3-yl)cyclopropanecarboxamide (53 mg, 0.23 mmol), ethyl 2-bromoisobutyrate (69 uL, 0.47 mmol), cesium carbonate (166.8 mg, 0.5119 mmol), and 1,4-dioxane (2.0 mL, 26 mmol) was heated in a sealed vial at 100° C. for 22 hours. The reaction mixture was poured into ethyl acetate, washed with water and brine, dried over $MgSO_4$, filtered, and evaporated in vacuo to yield 63.4 mg (80%) of ethyl 2-(3-(cyclopropanecarboxamido)isoquinolin-7-yloxy)-2-methylpropanoate which was carried forward without purification. LCMS (ESI): M+H=343.2.

Step 2: N-(7-(1-hydroxy-2-methylpropan-2-yloxy)isoquinolin-3-yl)cyclopropanecarboxamide

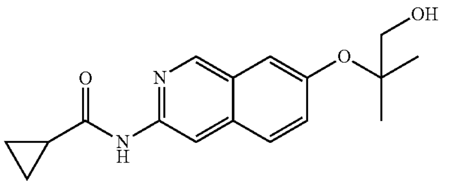 [SMILES: CC(C)(CO)Oc1ccc2cc(NC(=O)C3CC3)ncc2c1]

To a solution of ethyl 2-(3-(cyclopropanecarboxamido)isoquinolin-7-yloxy)-2-methylpropanoate (63.4 mg, 0.185 mmol) in tetrahydrofuran (3 mL, 40 mmol) was added 1.0 M of lithium tetrahydroaluminate in tetrahydrofuran (0.20 mL). The reaction mixture was stirred at room temperature for 1 hour. The reaction was quenched by sequential addition of 9 μL water, then 9 μL 15% aq NaOH, then 26 μL water. The resulting mixture was stirred at room temperature for 15 minutes, then diluted with dichloromethane, dried with $MgSO_4$, filtered through celite, and evaporated in vacuo. The crude product was purified via reverse phase HPLC and lyophilized to yield 4.8 mg (9%) of N-(7-(1-hydroxy-2-methylpropan-2-yloxy)isoquinolin-3-yl)cyclopropanecarboxamide. LCMS (ESI): $R_T$ (min)=3.414, M+H=301.1, method=E; $^1$H NMR (400 MHz, DMSO-$d_6$) δ 10.77 (s, 1H), 9.03 (s, 1H), 8.38 (s, 1H), 7.76 (d, J=8.9 Hz, 1H), 7.61 (d, J=2.0 Hz, 1H), 7.39 (dd, J=8.9, 2.3 Hz, 1H), 4.93 (t, J=5.6 Hz, 1H), 3.45 (d, J=5.7 Hz, 2H), 3.27 (s, overlapping water non-integratable), 2.12-1.97 (m, 1H), 0.83 (dt, J=10.1, 5.4 Hz, 4H).

Example 41

N-(7-tert-butoxyisoquinolin-3-yl)cyclopropanecarboxamide

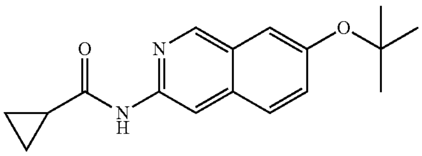 [SMILES: CC(C)(C)Oc1ccc2cc(NC(=O)C3CC3)ncc2c1]

A mixture of N-(7-bromoisoquinolin-3-yl)cyclopropanecarboxamide (70.6 mg, 0.242 mmol), sodium tert-butoxide (36.0 mg, 0.374 mmol), tris(dibenzylideneacetone)dipalladium(0) chloroform adduct (13.0 mg, 0.0126 mmol), and Q-Phos (19.3 mg, 0.0272 mmol) in toluene (1.0 mL, 9.4 mmol) was subjected to microwave irradiation at 120° C. for 30 minutes. The reaction mixture was neutralized with 10% aqueous citric acid and extracted with dichloromethane. The organic extract was dried over $MgSO_4$, filtered, and evaporated in vacuo. The crude product was purified via reverse phase HPLC and lyophilized to yield 3.6 mg (5.2%) of N-(7- tert-butoxyisoquinolin-3-yl)cyclopropanecarboxamide. LCMS (ESI): $R_T$ (min)=4.371, M+H=285.1, method=E; $^1$H NMR (400 MHz, DMSO-$d_6$) δ 10.78 (s, 1H), 9.06 (s, 1H), 8.40 (s, 1H), 7.78 (d, J=8.9 Hz, 1H), 7.60 (d, J=2.2 Hz, 1H), 7.35 (dd, J=8.9, 2.4 Hz, 1H), 2.12-1.97 (m, 1H), 1.39 (s, 9H), 0.91-0.75 (m, 4H).

Example 42

N-(3-(3-(cyclopropanecarboxamido)isoquinolin-7-yl)-4-methylphenyl)-4-(1-(dimethylamino)ethyl) benzamide

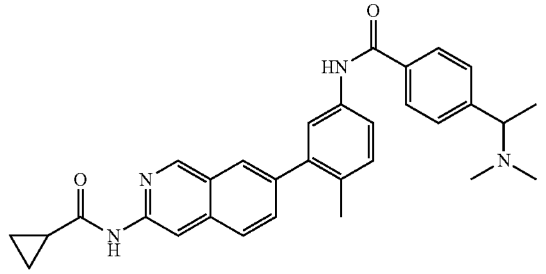 [SMILES: Cc1ccc(NC(=O)c2ccc(C(C)N(C)C)cc2)cc1-c1ccc2cc(NC(=O)C3CC3)ncc2c1]

Step 1: 4-(1-bromoethyl)benzoyl chloride

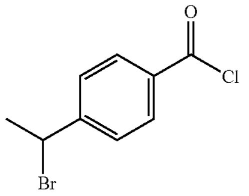

To a solution of 4-(1-bromoethyl)benzoic acid (50.7 mg, 0.221 mmol) in methylene chloride (4.0 mL, 62 mmol) was added 2.0 M of oxalyl chloride in methylene chloride (0.25 mL) followed by 3 drops of N,N-dimethylformamide. The reaction mixture was stirred at room temperature for one hour, and then evaporated in vacuo to remove dichloromethane and excess oxalyl chloride. The crude product was carried forward without purification.

Step 2: 4-(1-bromoethyl)-N-(3-(3-(cyclopropanecarboxamido)isoquinolin-7-yl)-4-methylphenyl)benzamide

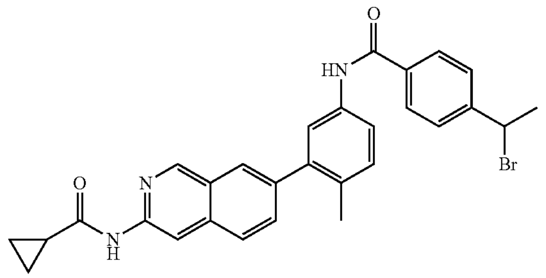 [SMILES: Cc1ccc(NC(=O)c2ccc(C(C)Br)cc2)cc1-c1ccc2cc(NC(=O)C3CC3)ncc2c1]

To a solution of N-(7-(5-amino-2-methylphenyl)isoquinolin-3-yl)cyclopropanecarboxamide (51.8 mg, 0.163 mmol) and pyridine (0.05 mL, 0.6 mmol) in 2 mL dichloromethane was added a solution of the residue from Step 1 in 2 mL dichloromethane. The resulting mixture was stirred at room temperature for 1.5 hours, and then carried forward without purification.

Step 3: N-(3-(3-(cyclopropanecarboxamido)isoquinolin-7-yl)-4-methylphenyl)-4-(1-(dimethylamino)ethyl)benzamide

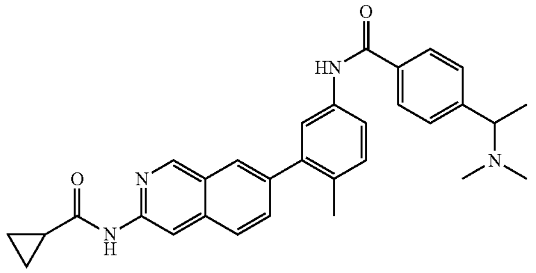 [SMILES: Cc1ccc(NC(=O)c2ccc(C(C)N(C)C)cc2)cc1-c1ccc2cc(NC(=O)C3CC3)ncc2c1]

To the crude reaction mixture from Step 2 was added 2.0 M of dimethylamine in tetrahydrofuran (0.15 mL). The resulting mixture was then stirred at 40° C. After 1.5 hours, 2.0 M of dimethylamine in tetrahydrofuran (0.20 mL), triethylamine (0.05 mL, 0.4 mmol), and 1 mL N,N-dimethylformamide were added and the reaction mixture was heated at 50° C. After an additional hour, the reaction was poured into dichloromethane and washed once with saturated aqueous $NaHCO_3$, dried over $MgSO_4$, filtered, and evaporated in vacuo. The crude product was purified via reverse phase HPLC and lyophilized to yield 17.6 mg (22%) of N-(3-(3-(cyclopropanecarboxamido)isoquinolin-7-yl)-4-methylphenyl)-4-(1-(dimethylamino)ethyl) benzamide. LCMS (ESI): $R_T$ (Min)=4.090, M+H=493.2, method=E; $^1$H NMR (400 MHz, DMSO-$d_6$) δ 10.90 (s, 1H), 10.20 (s, 1H), 9.19 (s, 1H), 8.50 (s, 1H), 8.02 (s, 1H), 7.92 (overlapping, 3H), 7.79 (d, J=1.9 Hz, 1H), 7.77-7.67 (m, 2H), 7.44 (d, J=8.2 Hz, 2H), 7.32 (d, J=8.4 Hz, 1H), 3.35 (q, J=6.8 Hz, 1H), 2.26 (s, 3H), 2.11 (s, 7H), 1.29 (d, J=6.7 Hz, 3H), 0.85 (m, 4H).

Example 43

(R)-N-(7-(4-hydroxybutan-2-yloxy)isoquinolin-3-yl) cyclopropanecarboxamide

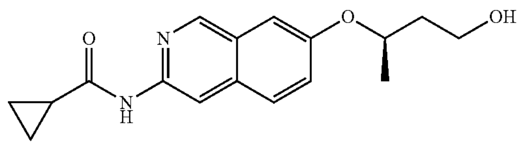 [SMILES: C[C@H](CCO)Oc1ccc2cc(NC(=O)C3CC3)ncc2c1]

Step 1: (S)-3-(methylsulfonyloxy)butyl benzoate

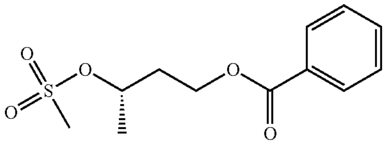 [SMILES: C[C@@H](CCOC(=O)c1ccccc1)OS(C)(=O)=O]

To a mixture of (S)-butane-1,3-diol (0.2450 g, 2.718 mmol), pyridine (1.50 mL, 18.5 mmol), and methylene chloride (10.0 mL, 156 mmol) at −15° C. was dropwise added benzoyl chloride (0.32 mL, 2.8 mmol). After 3.5 hours, methanesulfonyl chloride (0.300 mL, 3.88 mmol) was added to the reaction mixture, and the temperature was maintained at 0° C. After 1.5 hours, the reaction was warmed to room temperature. After 2 additional hours, triethylamine (1.0 mL, 7.2 mmol) was added. After one additional hour, the reaction mixture was poured into 50 mL dichloromethane and washed once with 50 mL water. The aqueous layer was extracted with an additional 50 mL of dichloromethane. The combined organic portions were dried over $MgSO_4$, filtered, and evaporated in vacuo. The crude material was purified via flash chromatography on silica gel (40 g silica, solvent gradient: 0-100% ethyl acetate in heptanes) to yield 0.3603 g (49%) of (S)-3-(methylsulfonyloxy)butyl benzoate. LCMS (ESI): M+H=273.2; $^1$H NMR (400 MHz, DMSO-$d_6$) δ 7.99 (d, J=7.6 Hz, 2H), 7.66 (t, J=7.4 Hz, 1H), 7.53 (t, J=7.7 Hz, 2H), 4.94 (h, J=6.3 Hz, 1H), 4.45-4.26 (m, 2H), 3.17 (s, 3H), 2.09 (q, J=6.2 Hz, 2H), 1.42 (d, J=6.3 Hz, 3H).

Step 2: (R)-N-(7-(4-hydroxybutan-2-yloxy)isoquinolin-3-yl)cyclopropanecarboxamide

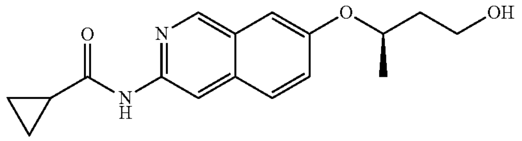 [SMILES: C[C@H](CCO)Oc1ccc2cc(NC(=O)C3CC3)ncc2c1]

To a solution of (S)-3-(methylsulfonyloxy)butyl benzoate (82.6 mg, 0.303 mmol) in N,N-dimethylformamide (2.0 mL, 26 mmol) was added N-(7-hydroxyisoquinolin-3-yl)cyclopropanecarboxamide (49.7 mg, 0.218 mmol) and cesium carbonate (147.4 mg, 0.4524 mmol). The reaction mixture was stirred at 50° C. for 4 hours. To the reaction mixture was then added 2.0 M of potassium hydroxide in methanol (1.0 mL), and the temperature was maintained at 50° C. for one hour. The reaction was neutralized with 10% aqueous citric acid and extracted with dichloromethane (3×50 mL). The combined organic extracts were dried over $MgSO_4$, filtered, and evaporated in vacuo. The crude product was purified via reverse phase HPLC and lyophilized to yield 29.5 mg (45%) of (R)-N-(7-(4-hydroxybutan-2-yloxy)isoquinolin-3-yl)cyclopropanecarboxamide. LCMS (ESI): $R_T$ (min)=3.446, M+H=301.1, method=E; $^1$H NMR (400 MHz, DMSO-$d_6$) δ 10.72 (s, 1H), 8.98 (s, 1H), 8.36 (s, 1H), 7.77 (d, J=9.0 Hz, 1H), 7.45 (d, J=2.3 Hz, 1H), 7.32 (dd, J=8.9, 2.5 Hz, 1H), 4.73 (h, J=6.1 Hz, 1H), 4.52 (t, J=5.0 Hz, 1H), 3.56 (dd, J=11.5, 6.1 Hz, 2H), 2.10-1.98 (m, 1H), 1.92 (td, J=12.9, 6.2 Hz, 1H), 1.74 (td, J=12.6, 6.5 Hz, 1H), 1.33 (d, J=6.1 Hz, 3H), 0.90-0.73 (m, 4H).

Example 44

N-(7-((3S,4S)-4-hydroxytetrahydrofuran-3-yloxy)isoquinolin-3-yl)cyclopropanecarboxamide and N-(7-((3R,4R)-4-hydroxytetrahydrofuran-3-yloxy)isoquinolin-3-yl)cyclopropanecarboxamide

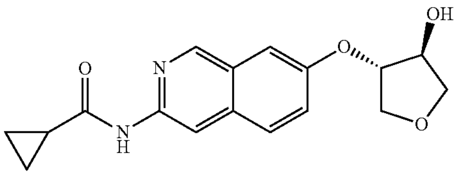

and

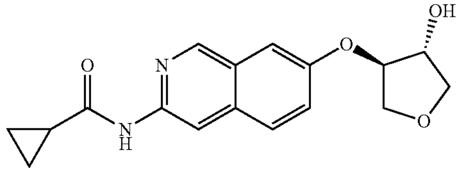

A mixture of N-(7-hydroxyisoquinolin-3-yl)cyclopropanecarboxamide (59.4 mg, 0.260 mmol), 3,4-epoxytetrahydrofuran (128.4 mg, 1.491 mmol), and cesium carbonate (182.4 mg, 0.5598 mmol) in N,N-dimethylacetamide (3.0 mL, 32 mmol) was stirred in a sealed tube at 120° C. for 22 hours. The reaction mixture was poured into dichloromethane, washed with water, dried over $MgSO_4$, filtered, and evaporated in vacuo to yield a mixture of trans-stereoisomers. The crude products were purified and the enantiomers are separated via chiral supercritical fluid chromotagraphy to yield 14.4 mg (18%) of one enantiomer and 14.5 mg (18%) of the other enantiomer.

Enantiomer #1:

LCMS (ESI): $R_T$ (Min)=3.216, M+H=315.1, method=E; $^1$H NMR (400 MHz, DMSO-$d_6$) δ 10.75 (s, 1H), 8.99 (s, 1H), 8.39 (s, 1H), 7.80 (d, J=9.0 Hz, 1H), 7.50 (s, 1H), 7.36 (dd, J=9.0, 2.3 Hz, 1H), 5.53 (d, J=3.6 Hz, 1H), 4.80 (d, J=3.9 Hz, 1H), 4.30 (s, 1H), 4.13 (dd, J=10.2, 4.2 Hz, 1H), 3.95 (dd, J=9.5, 4.5 Hz, 1H), 3.84 (d, J=10.2 Hz, 1H), 3.62 (d, J=9.5 Hz, 1H), 2.13-1.94 (m, 1H), 0.92-0.72 (m, 4H).

Enantiomer #2:

LCMS (ESI): $R_T$ (min)=3.215, M+H=315.1, method=E; $^1$H NMR (400 MHz, DMSO-$d_6$) δ $^1$H NMR (400 MHz, DMSO) δ 10.75 (s, 1H), 8.99 (s, 1H), 8.39 (s, 1H), 7.81 (d, J=9.0 Hz, 1H), 7.50 (d, J=1.9 Hz, 1H), 7.36 (dd, J=9.0, 2.4 Hz, 1H), 5.53 (d, J=3.7 Hz, 1H), 4.80 (d, J=3.9 Hz, 1H), 4.30 (s, 1H), 4.13 (dd, J=10.2, 4.2 Hz, 1H), 3.95 (dd, J=9.5, 4.5 Hz, 1H), 3.84 (d, J=10.2 Hz, 1H), 3.62 (d, J=9.5 Hz, 1H), 2.09-1.98 (m, 1H), 0.89-0.75 (m, 4H).

Example 45

N-(7-((1S,2R)-2-hydroxycyclopentyloxy)isoquinolin-3-yl)cyclopropanecarboxamide and N-(7-((1R,2S)-2-hydroxycyclopentyloxy)isoquinolin-3-yl)cyclopropanecarboxamide

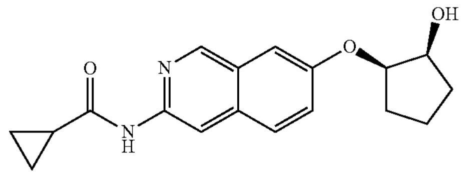

and

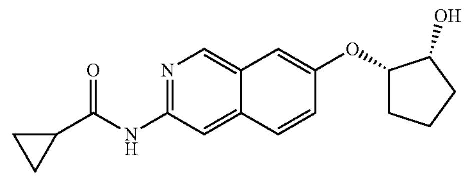

Step 1: (1R,2R)-2-(3-(cyclopropanecarboxamido)isoquinolin-7-yloxy)cyclopentyl methanesulfonate and (1S,2S)-2-(3-(cyclopropanecarboxamido)isoquinolin-7-yloxy)cyclopentyl methanesulfonate

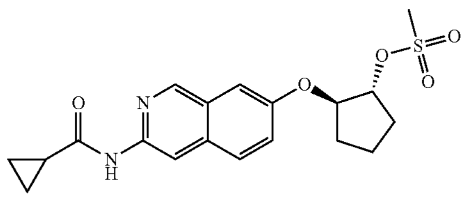

and

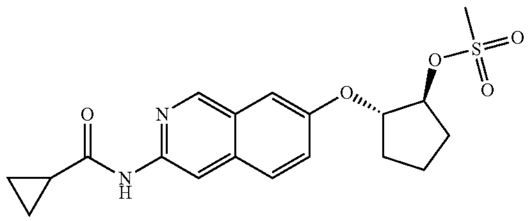

To a mixture of N-(7-(2-hydroxycyclopentyloxy)isoquinolin-3-yl)cyclopropanecarboxamide (95 mg, 0.30 mmol) (mixture of trans stereoisomers) and triethylamine (0.10 mL, 0.72 mmol) in methylene chloride (5.0 mL, 78 mmol) at 0° C. was dropwise added methanesulfonyl chloride (35 uL, 0.46 mmol). The reaction mixture was stirred at room temperature for 1.5 hours. The reaction mixture was then diluted with dichloromethane and washed with water, dried over $MgSO_4$, filtered, and evaporated in vacuo. The crude residue was carried forward without purification.

Step 2: N-(7-((1S,2R)-2-hydroxycyclopentyloxy)isoquinolin-3-yl)cyclopropanecarboxamide and N-(7-((1R,2S)-2-hydroxycyclopentyloxy)isoquinolin-3-yl)cyclopropanecarboxamide

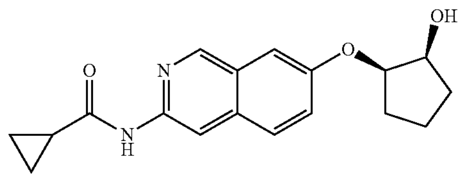

and

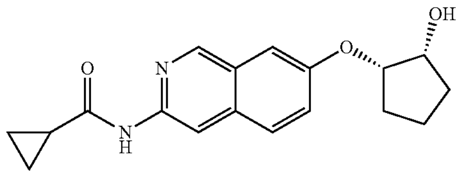

To a solution of 1,8-Diazabicyclo[5.4.0]undec-7-ene (80.0 uL, 0.535 mmol) in toluene (1.5 mL, 14 mmol) was added acetic acid (61.0 uL, 1.07 mmol). This mixture was stirred at room temperature for 30 minutes. The crude product from Step 1 was then added as a solution in toluene (1.5 mL, 14 mmol). The mixture was heated at 80° C. for 15 hours, and then acetic acid (31 uL, 0.54 mmol) and 1,8-diazabicyclo[5.4.0]undec-7-ene (40.0 μL, 0.267 mmol) were added, and the temperature was increased to 110° C. After an additional 24 hours, the reaction mixture was cooled to room temperature and 1 M of sodium hydroxide in water (3.00 mL) and tetrahydrofuran (3.0 mL, 37 mmol) were added. After an additional 24 hours, the reaction mixture was neutralized with 10% aqueous citric acid and extracted 2× with dichloromethane. The combined organic extracts were dried over $MgSO_4$, filtered, and evaporated in vacuo. The crude product was purified by flash chromatography on silica gel (12 g silica, 30-100% ethyl acetate in dichloromethane) to yield 38.5 mg as mixture of cis enantiomers. The enantiomers were separated via chiral supercritical fluid chromotagraphy to yield 8.0 mg (10%) of one enantiomer and 9.7 mg (12%) of the other enantiomer.

Enantiomer #1:

LCMS (ESI): $R_T$ (Min)=3.476, M+H=313.1, method=E; $^1$H NMR (400 MHz, DMSO) δ 10.71 (s, 1H), 8.98 (s, 1H), 8.36 (s, 1H), 7.76 (d, J=9.0 Hz, 1H), 7.46 (d, J=2.1 Hz, 1H), 7.37 (dd, J=9.0, 2.4 Hz, 1H), 4.63 (dd, J=10.1, 5.2 Hz, 2H), 4.20 (dd, J=9.9, 5.0 Hz, 1H), 2.14-1.97 (m, 2H), 1.91-1.74 (m, 3H), 1.74-1.62 (m, 1H), 1.62-1.48 (m, 1H), 0.82 (m, 4H).

Enantiomer #2:

LCMS (ESI): $R_T$ (Min)=3.481, M+H=313.1, method=E; $^1$H NMR (400 MHz, DMSO) δ 10.71 (s, 1H), 8.98 (s, 1H), 8.36 (s, 1H), 7.76 (d, J=9.0 Hz, 1H), 7.46 (d, J=2.3 Hz, 1H), 7.37 (dd, J=9.0, 2.5 Hz, 1H), 4.63 (dd, J=10.4, 5.2 Hz, 2H), 4.25-4.15 (m, 1H), 2.11-1.97 (m, 2H), 1.90-1.74 (m, 3H), 1.70 (m, 1H), 1.61-1.46 (m, 1H), 0.82 (m, 4H).

Example 46

N-(3-(3-(cyclopropanecarboxamido)isoquinolin-7-yl)-4-methylphenyl)-4-(1-methylpyrrolidin-2-yl) benzamide

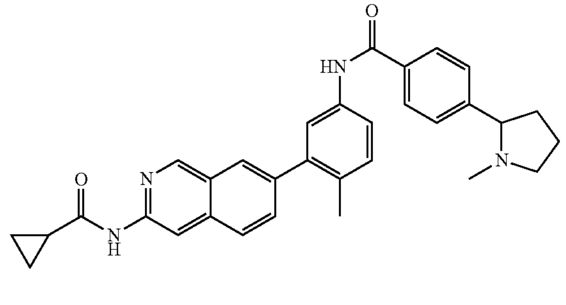 [SMILES: Cc1ccc(NC(=O)c2ccc(C3CCCN3C)cc2)cc1-c1ccc2cc(NC(=O)C3CC3)ncc2c1]

Step 1: 2-(4-bromophenyl)-1-methylpyrrolidine

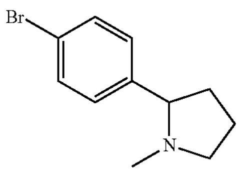

To a mixture of 2-(4-bromophenyl)pyrrolidine (231.9 mg, 1.026 mmol) and potassium carbonate (216.6 mg, 1.567 mmol) was added N,N-dimethylformamide (4.0 mL, 52 mmol) and methyl iodide (77 uL, 1.2 mmol). The reaction mixture was stirred at room temperature for 2 days and then methyl iodide (39.0 uL, 0.626 mmol) was added. After stirring at room temperature for an additional two hours, the reaction mixture was poured into ethyl acetate and washed three times with 2M aqueous $Na_2CO_3$. The ethyl acetate layer was then dried over $MgSO_4$, filtered, and evaporated in vacuo to yield 108.9 mg (44%) of 2-(4-bromophenyl)-1-methylpyrrolidine. LCMS (ESI): M+H=240.2.

Step 2: N-(3-(3-(cyclopropanecarboxamido)isoquinolin-7-yl)-4-methylphenyl)-4-(1-methylpyrrolidin-2-yl)benzamide

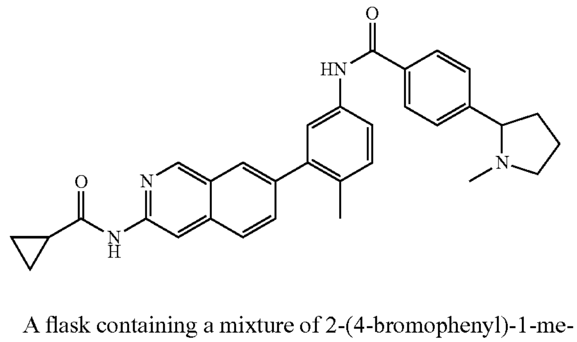

A flask containing a mixture of 2-(4-bromophenyl)-1-methylpyrrolidine (58.8 mg, 0.245 mmol), palladium acetate (8.9 mg, 0.040 mmol), 1,3-bis(dicyclohexylphosphino)propane bis(tetrafluoroborate) (35.5 mg, 0.0582 mmol), potassium carbonate (79.0 mg, 0.572 mmol), and N-(7-(5-amino-2-methylphenyl)isoquinolin-3-yl)cyclopropanecarboxamide (89.0 mg, 0.280 mmol) in N,N-dimethylformamide (2.0 mL, 26 mmol) was evacuated purged with nitrogen five times, and then evacuated and purged three times with CO gas. The reaction was stirred under a CO gas balloon, at 100° C., for 15 hours. The reaction mixture was poured into ethyl acetate, washed with saturated aqueous sodium bicarbonate and brine, dried over $MgSO_4$, filtered, and evaporated in vacuo. The crude product was purified via flash chromatography on silica gel (12 g silica, solvent gradient: 0-10% methanol in dichloromethane) followed by purification via reverse phase HPLC and lyophilized to yield 10.3 mg (8%) of N-(3-(3-(cyclopropanecarboxamido)isoquinolin-7-yl)-4-methylphenyl)-4-(1-methylpyrrolidin-2-ye benzamide. LCMS (ESI): $R_T$ (min)=4.125, M+H=505.3, method=E; $^1$H NMR (400 MHz, DMSO-$d_6$) δ 10.90 (s, 1H), 10.20 (s, 1H), 9.20 (s, 1H), 8.50 (s, 1H), 8.02 (s, 1H), 7.92 (t, J=8.2 Hz, 3H), 7.79 (s, 1H), 7.77-7.67 (m, 2H), 7.46 (d, J=8.0 Hz, 2H), 7.32 (d, J=8.3 Hz, 1H), 2.26 (s, 3H), 2.21-2.13 (m, 1H), 2.10 (m, 4H), 1.79 (m, 4H), 1.71-1.50 (m, 2H), 0.85 (m, 4H).

Example 47

N-(3-(3-(cyclopropanecarboxamido)isoquinolin-7-yl)-4-methylphenyl)-4-(1-methylpyrrolidin-3-yl) benzamide

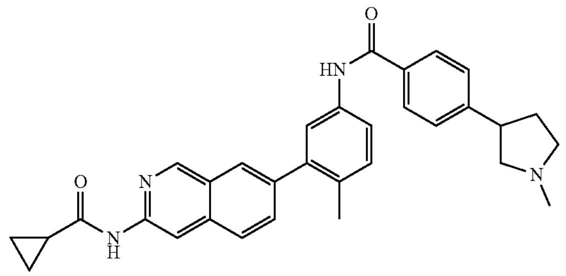 [SMILES: Cc1ccc(NC(=O)c2ccc(C3CCN(C)C3)cc2)cc1-c1ccc2cc(NC(=O)C3CC3)ncc2c1]

To a solution of tert-butyl 3-(4-(3-(3-(cyclopropanecarboxamido)isoquinolin-7-yl)-4-methylphenylcarbamoyl) phenyl)pyrrolidine -1-carboxylate (prepared following the procedures described for Example 15) (0.135 mmol) in methylene chloride (3.0 mL, 47 mmol) was added 4.0 M of hydrogen chloride in 1,4-dioxane (0.50 mL). The reaction mixture was stirred at room temperature for three hours, and then evaporated in vacuo. To this crude product was added potassium carbonate (53.6 mg, 0.388 mmol), N,N-dimethylformamide (3.0 mL, 39 mmol), and methyl iodide (9.0 uL, 0.14 mmol). The reaction mixture was stirred at room temperature for 18 hours, and then potassium carbonate (33.1 mg, 0.239 mmol) and methyl iodide (7.0 uL, 0.11 mmol) were added. The reaction mixture was stirred at room temperature for 24 hours, and then poured into ethyl acetate, washed with 2M aqueous $Na_2CO_3$, dried over $MgSO_4$, filtered, and evaporated in vacuo. The crude product was purified via flash chromatography on silica gel (12 g silica, solvent gradient: 5-20% 1M $NH_3$/MeOH in dichloromethane) to yield 6.0 mg (9%) of N-(3-(3-(cyclopropanecarboxamido)isoquinolin-7-yl)-4-methylphenyl)-4-(1-methylpyrrolidin-3-yl)benzamide. LCMS (ESI): $R_T$ (Min)=4.104, M+H=505.2, method=E; $^1$H NMR (400 MHz, DMSO) δ 10.90 (s, 1H), 10.18 (s, 1H), 9.19 (s, 1H), 8.50 (s, 1H), 8.02 (s, 1H), 7.92 (t, J=9.3 Hz, 3H), 7.81-7.67 (m, 3H), 7.44 (d, J=8.1 Hz, 2H), 7.32 (d, J=8.4 Hz, 1H), 3.52-3.40 (m, 2H), 3.01 (unresolved, 1H), 2.82 (unresolved, 2H), 2.44 (s, 3H), 2.26 (s, 3H), 2.08 (m, 1H), 1.84 (m, 2H), 0.85 (m, 4H).

Example 48

N-(7-cyclohexyl-2,6-naphthyridin-3-yl)cyclopropanecarboxamide

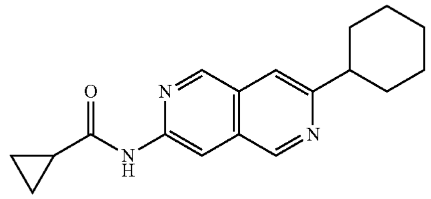 [SMILES: O=C(Nc1cc2cnc(C3CCCCC3)cc2cn1)C1CC1]

Step 1: N-((5-bromo-2-chloropyridin-4-yl)methylene)-2-methylpropan-2-amine

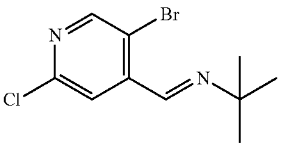

To a mixture of 5-bromo-2-chloroisonicotinaldehyde (1.047 g, 4.749 mmol) and Water (2.0 mL, 110 mmol) was added tert-butylamine (2.0 mL, 19 mmol). The reaction mixture was stirred at room temperature for 20 hours, and then excess tert-butylamine was removed by rotary evaporation. The resulting residue was partitioned between ethyl acetate and water, and the organic layer dried with brine and $MgSO_4$, filtered, and evaporated in vacuo to yield 1.401 g (87%) of N-((5-bromo-2-chloropyridin-4-yl)methylene)-2-methylpropan-2-amine. $^1$H NMR (400 MHz, DMSO) δ 8.72 (s, 1H), 8.43 (s, 1H), 7.78 (s, 1H), 1.28 (s, 9H).

Step 2: 3-chloro-7-cyclohexyl-2,6-naphthyridine

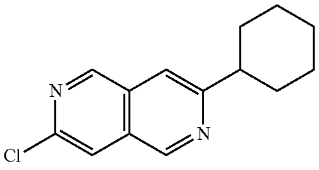 [SMILES: Clc1cc2cnc(C3CCCCC3)cc2cn1]

A round-bottom flask containing N-((5-bromo-2-chloropyridin-4-yl)methylene)-2-methylpropan-2-amine (164.5 mg, 0.5969 mmol), $DPPPNiCl_2$ (16.0 mg, 0.0295 mmol) and zinc (84.0 mg, 1.28 mmol) was evacuated and purged with nitrogen 5 times. Acetonitrile (6 mL, 100 mmol) and cyclohexylacetylene (86.0 uL, 0.658 mmol) were added to the flask and the reaction mixture was stirred at 80° C. under a nitrogen balloon for 30 minutes. The reaction mixture was cooled to room temperature, diluted with dichloromethane, and filtered through celite, rinsing with dichloromethane. The filtrate was evaporated in vacuo and the crude product purified via flash chromatography on silica gel (12 g silica, solvent gradient: 0-40% ethyl acetate in dichloromethane) to yield 80.4 mg (55%) of 3-chloro-7-cyclohexyl-2,6-naphthyridine. LCMS (ESI): M+H=247.2; $^1$H NMR (500 MHz, DMSO) δ 9.39 (s, 1H), 9.28 (s, 1H), 8.20 (s, 1H), 7.88 (s, 1H), 2.91-2.81 (m, 1H), 1.97 (d, J=11.3 Hz, 2H), 1.84 (d, J=13.0 Hz, 2H), 1.75 (d, J=12.9 Hz, 1H), 1.58 (ddd, J=24.8, 12.5, 2.9 Hz, 2H), 1.49-1.37 (m, 2H), 1.27 (ddd, J=16.3, 12.6, 9.2 Hz, 1H).

Step 3: N-(7-cyclohexyl-2,6-naphthyridin-3-yl)cyclopropanecarboxamide

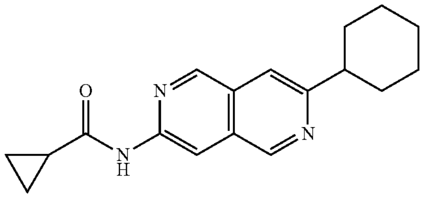 [SMILES: O=C(Nc1cc2cnc(C3CCCCC3)cc2cn1)C1CC1]

A mixture of 3-chloro-7-cyclohexyl-2,6-naphthyridine (80.0 mg, 0.324 mmol), cyclopropanecarboxamide (47.7 mg, 0.560 mmol), 2-(dicyclohexylphosphino)-3,6-dimethoxy-2'-4'-6'-tri-1-propyl-1,1'-biphenyl (6.0 mg, 0.011 mmol), chloro [2-(dicyclohexylphosphino)-3-,6-dimethoxy-2-4'-6'-tri-i-pr-1,1'-biphenyl)][2-(2-aminoethyl)Ph]Pd(II) (9.2 mg, 0.012 mmol), and cesium carbonate (240.1 mg, 0.7369 mmol) in 1,4-dioxane (2 mL, 20 mmol) was heated at 90° C. for 2 hours. The reaction mixture was cooled to room temperature, diluted in ethyl acetate, washed with water and brine, dried over $MgSO_4$, filtered, and evaporated in vacuo. The crude product was purified via reverse phase HPLC and lyophilized to yield 63.2 mg (66%) of N-(7-cyclohexyl-2,6-naphthyridin-3-yl)cyclopropanecarboxamide. LCMS (ESI): $R_T$ (Min)=4.090, M+H=296.1, method=E; $^1$H NMR (400 MHz, DMSO) δ 11.02 (s, 1H), 9.28 (s, 1H), 9.19 (s, 1H), 8.55 (s, 1H), 7.72 (s, 1H), 2.89-2.73 (m, 1H), 2.14-2.03 (m, 1H), 1.96 (d, J=11.6 Hz, 2H), 1.84 (d, J=12.8 Hz, 2H), 1.74 (d, J=12.6 Hz, 1H), 1.63-1.51 (m, 2H), 1.43 (dd, J=25.4, 12.6 Hz, 2H), 1.34-1.18 (m, 1H), 0.85 (dd, J=8.3, 6.5 Hz, 4H).

Example 49

N-(2-(5-fluoro-2-methylphenyl)-4-methyl-1,7-naphthyridin-6-yl)cyclopropanecarboxamide

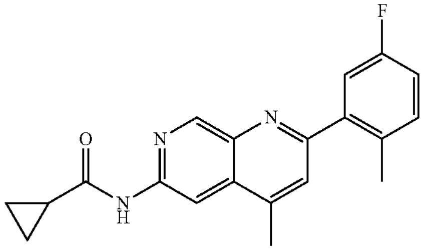 [SMILES: Cc1ccc(F)cc1-c1cc(C)c2cc(NC(=O)C3CC3)ncc2n1]

Step 1: tert-butyl 6-chloro-4-(1-hydroxyethyl)pyridin-3-ylcarbamate

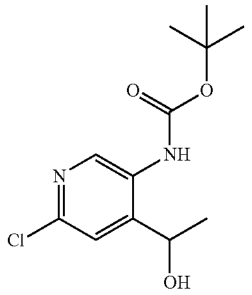 [SMILES: CC(O)c1cc(Cl)ncc1NC(=O)OC(C)(C)C]

To an ice-cooled solution of tert-butyl 6-chloro-4-formylpyridin-3-ylcarbamate (1.0091 g, 3.9313 mmol) in tetrahydrofuran (20 mL, 200 mmol) in an oven-dried flask was added 3.0 M of methylmagnesium iodide in ether (3.4 mL). The reaction mixture was stirred at 0° C. for one hour and then quenched with 10 mL saturated aqueous $NH_4Cl$. The resulting mixture was partitioned between ethyl acetate and saturated aqueous $NaHCO_3$, and the organic layer was dried with brine and $MgSO_4$ and evaporated in vacuo. The crude product was purified via flash chromatography on silica gel (40 g silica, solvent gradient: 0-40% ethyl acetate in heptane) to yield 0.870 g (81%) of tert-butyl 6-chloro-4-(1-hydroxyethyl)pyridin-3-ylcarbamate. LCMS (ESI): M+H=273.2; $^1H$ NMR (400 MHz, DMSO) δ 8.89 (s, 1H), 8.43 (s, 1H), 7.45 (s, 1H), 5.76 (s, 1H), 4.95 (d, J=6.4 Hz, 1H), 1.46 (s, 9H), 1.28 (d, J=6.5 Hz, 3H).

Step 2: 1-(5-amino-2-chloropyridin-4-yl)ethanol

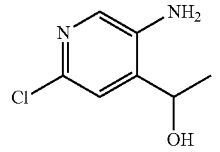

To a solution of tert-butyl 6-chloro-4-(1-hydroxyethyl)pyridin-3-ylcarbamate (823 mg, 3.02 mmol) in methylene chloride (40 mL, 500 mmol) was added trifluoroacetic acid (2 mL, 20 mmol). The reaction mixture was stirred at room temperature for 5 hours and then evaporated in vacuo. The resulting residue was dissolved in dichloromethane and washed with saturated aqueous $NaHCO_3$. The organic layer was dried over $MgSO_4$ and evaporated in vacuo to yield 455.2 mg (87%) of 1-(5-amino-2-chloropyridin-4-yl)ethanol which was carried forward without purification.

Step 3: 6-chloro-2-(5-fluoro-2-methylphenyl)-4-methyl-1,7-naphthyridine

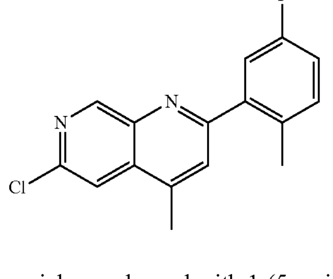

A screw-top vial was charged with 1-(5-amino-2-chloropyridin-4-yl)ethanol (46.3 mg, 0.268 mmol), 5'-fluoro-2'-methylacetophenone (82.0 mg, 0.540 mmol), tris(triphenylphosphine)ruthenium(II) dichloride (13.0 mg, 0.013 mmol), potassium hydroxide (15 mg, 0.27 mmol), and 1,4-dioxane (1.5 mL, 19 mmol). The reaction vial was flushed with nitrogen gas, sealed with a teflon lined cap, and heated at 80° C. for 2 hours. The reaction mixture was then diluted in ethyl acetate, filtered through celite, washed with water and brine, dried over $MgSO_4$, and evaporated in vacuo. The crude product was purified via flash chromatography on silica gel (12 g silica, solvent gradient: 0-100% ethyl acetate in heptane) to yield 27.9 mg (36%) of 6-chloro-2-(5-fluoro-2-methylphenyl)-4-methyl-1,7-naphthyridine. LCMS (ESI): M+H=287.2; $^1H$ NMR (400 MHz, DMSO) δ 9.27 (s, 1H), 8.20 (s, 1H), 7.91 (s, 1H), 7.41 (m, 2H), 7.26 (m, 1H), 2.75 (s, 3H), 2.37 (s, 3H).

Step 4: N-(2-(5-fluoro-2-methylphenyl)-4-methyl-1,7-naphthyridin-6-yl)cyclopropanecarboxamide

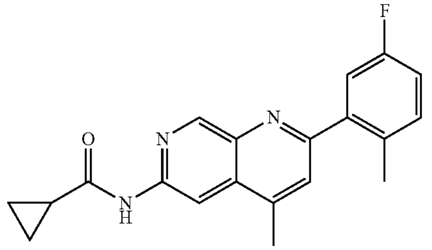 [SMILES: Cc1ccc(F)cc1-c1cc(C)c2cc(NC(=O)C3CC3)ncc2n1]

To a mixture of 6-chloro-2-(5-fluoro-2-methylphenyl)-4-methyl-1,7-naphthyridine (140.1 mg, 0.4886 mmol) and cyclopropanecarboxamide (85.9 mg, 1.01 mmol) in 1,4-dioxane (4.0 mL, 51 mmol) was added palladium (II) acetate (11.9 mg, 0.053 mmol), 4,5-bis(diphenylphosphino)-9,9-dimethylxanthene (38.8 mg, 0.067 mmol), and cesium carbonate (417.3 mg, 1.281 mmol). The reaction vial was purged with nitrogen gas and then heated at 90° C. under a nitrogen balloon for 5 hours. Cyclopropanecarboxamide (38.0 mg, 0.447 mmol), palladium (II) acetate (32.0 mg, 0.143 mmol), and 4,5-bis(diphenylphosphino)-9,9-dimethylxanthene (78.9 mg, 0.136 mmol) were added and the reaction heated at 100° C. for 15 hours. The reaction mixture was then diluted in ethyl acetate, washed with water and brine, dried over $MgSO_4$, and evaporated in vacuo. The crude product was purified via reverse phase HPLC and lyophilized to yield 0.1227 g (78%) of N-(2-(5-fluoro-2-methylphenyl)-4-methyl-1,7-naphthyridin-6-yl)cyclopropanecarboxamide. LCMS (ESI): $R_T$ (Min)=5.239, M+H=336.1, method=E; $^1H$ NMR (400 MHz, DMSO) δ 11.12 (s, 1H), 9.21 (s, 1H), 8.65 (s, 1H), 7.79 (s, 1H), 7.38 (m, 3.6H), 7.23 (td, J=8.5, 2.8 Hz, 1H), 2.66 (s, 3H), 2.37 (s, 3H), 2.11 (s, 1H), 0.93-0.81 (m, 4H).

Example 50

N-(7-(5-hydroxy-2-methylpyridin-3-yl)isoquinolin-3-yl)cyclopropanecarboxamide

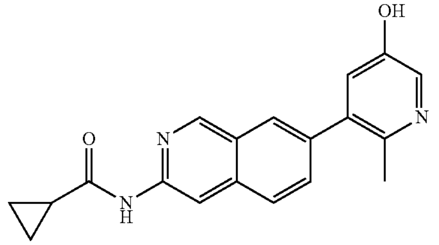 [SMILES: Cc1ncc(O)cc1-c1ccc2cc(NC(=O)C3CC3)ncc2c1]

To a flask containing boron trifluoride etherate (0.100 mL, 0.789 mmol) at −15° C. (brine/ice bath) was added a solution of N-(7-(5-amino-2-methylpyridin-3-yl)isoquinolin-3-yl)cyclopropanecarboxamide (119.1 mg, 0.3741 mmol) in 1,2-dimethoxyethane (1.0 mL, 9.6 mmol). tert-Butyl nitrite (67.0 uL, 0.563 mmol) was then added dropwise and the reaction mixture was stirred at −15° C. for one hour. 3 mL pentane was added and the mixture stirred for 5 minutes. The pentane layer was decanted, and the remaining oil was then dissolved in acetic anhydride (0.60 mL, 6.4 mmol) and stirred at 100° C. for 1.5 hours. The solvent was evaporated in vacuo, and the residue was suspended in 2M aqueous $Na_2CO_3$ and extracted twice with dichloromethane. The combined organic extracts were dried over $MgSO_4$, filtered, and evaporated in vacuo. The crude material was purified via flash chromatography on silica gel (12 g silica, solvent gradient: 0-100% ethyl acetate in dichloromethane) to yield 5-(3-(cyclopropanecarboxamido)isoquinolin-7-yl)-6-methylpyridin-3-yl acetate. This material was dissolved in tetrahydrofuran (3 mL, 40 mmol) and 1.0 M of lithium hydroxide in Water (1.0 mL) was added. The reaction mixture was stirred at room temperature for 3 hours. The reaction mixture was then neutralized with 10% aqueous citric acid and extracted 3× with dichloromethane. The combined organic extracts were dried over $MgSO_4$, filtered, and evaporated in vacuo. The crude material was purified via flash chromatography on silica gel (12 g silica, solvent gradient: 30-100% ethyl acetate in dichloromethane) followed by reverse phase HPLC to yield 3.3 mg (3%) of N-(7-(5-hydroxy-2-methylpyridin-3-yl)isoquinolin-3-yl)cyclopropanecarboxamide. LCMS (ESI): $R_T$ (min)=3.237, M+H=320.1, method=E; $^1$H NMR (400 MHz, DMSO) δ 10.91 (s, 1H), 9.17 (s, 1H), 8.49 (s, 1H), 8.02 (d, J=8.2 Hz, 2H), 7.91 (d, J=8.6 Hz, 1H), 7.69 (d, J=9.7 Hz, 1H), 7.04 (s, 1H), 2.33 (s, 3H), 2.14-2.03 (m, 1H), 0.91-0.78 (m, 4H).

Example 51

N-(7-(5-fluoro-2-methylphenyl)isoquinolin-3-yl)acetamide

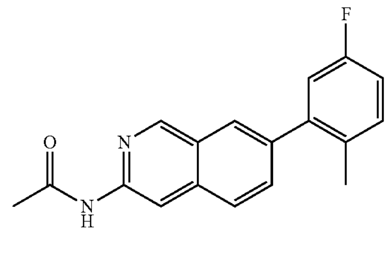 [SMILES: CC(=O)Nc1cc2ccc(-c3cc(F)ccc3C)cc2cn1]

To a solution of 7-(5-fluoro-2-methylphenyl)isoquinolin-3-amine (150 mg, 0.595 mmol) in pyridine (2 mL) was added acetyl chloride (56 mg, 0.714 mmol) dropwise at a temperature below 0° C. After the resulting mixture was stirred at room temperature for 2 h, water (2 mL) was added and it was concentrated under reduced pressure. The solid was washed with methanol and water to give the desired product (26.7 mg, 15.2%). LCMS (ESI): $R_T$ (Min)=1.150, M+H$^+$=294.8, method=A; $^1$H NMR (400 MHz, DMSO-$d_6$) δ 10.62, (s, 1H), 9.14 (s, 1H), 8.47 (s, 1H), 8.00 (s, 1H), 7.93 (d, J=8.0 Hz, 1H), 7.68 (d, J=6.8 Hz, 1H), 7.35 (s, 1H), 7.15 (d, J=8.8 Hz, 2H), 2.22 (s, 3H), 2.12 (s, 3H).

Example 52

N-(7-(5-fluoro-2-methylphenyl)isoquinolin-3-yl)tetrahydro-2H-pyran-4-carboxamide

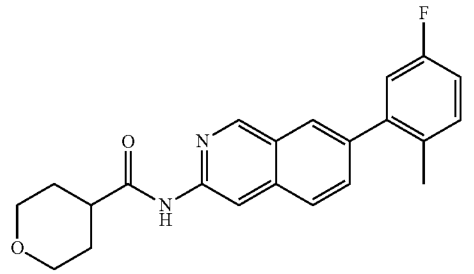 [SMILES: Cc1ccc(F)cc1-c1ccc2cc(NC(=O)C3CCOCC3)ncc2c1]

7-(5-Fluoro-2-methylphenyl)isoquinolin-3-amine (150 mg, 0.595 mmol), tetrahydro-2H-pyran-4-carboxylic acid (1.43 mmol, 185 mg), N,N-diisopropylethylamine (384 mg, 2.98 mmol) and O-(7-azabenzotriazol-1-yl)-N,N,N',N'-tetramethyluronium hexafluorophosphate (543 mg, 1.43 mmol) were dissolved in dichloromethane (10 mL). The reaction mixture was stirred at room temperature for 48 hours. Water (1 mL) was added, and the mixture was concentrated, washed with methanol to give the product (45.2 mg, 21.0%). LCMS (ESI): $R_T$ (Min)=1.203, M+H$^+$=365.0, method=A; $^1$H NMR (400 MHz, DMSO-$d_6$) δ 10.60 (s, 1H), 9.15 (s, 1H), 8.52 (s, 1H), 8.02 (s, 1H), 7.93 (d, J=8.8 Hz, 1H), 7.69 (d, J=8.8 Hz, 1H), 7.36 (s, 1H), 7.14 (d, J=12.0 Hz, 2H), 3.92-3.88 (m, 2H), 3.36-3.32 (m, 2H), 2.81-2.80 (m, 1H), 2.23 (s, 3H), 1.71-1.66 (m, 4H).

Example 53

2,2,2-Trifluoro-N-(7-(5-fluoro-2-methylphenyl)isoquinolin-3-yl)acetamide

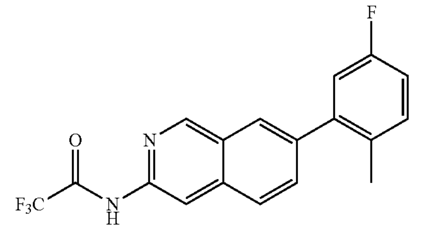 [SMILES: Cc1ccc(F)cc1-c1ccc2cc(NC(=O)C(F)(F)F)ncc2c1]

To a solution of 7-(5-fluoro-2-methylphenyl)isoquinolin-3-amine (150 mg, 0.595 mmol) in dichloromethane (20 mL) at 0° C. was added N,N-diisopropylethylamine (383 mg, 2.9 mmol). 2,2,2-trifluoroacetic anhydride (376 mg, 1.79 mmol) was added dropwise. The reaction mixture was stirred at 0° C. for 1 hour. After a small amount water was added to the reaction mixture, it was extracted with ethyl acetate. The pooled organic phase was concentrated, purified by prep-HPLC to give the desired product (85.9 mg, 41.4%). LCMS (ESI): $R_T$ (min)=1.344, M+H$^+$=348.9, method=A; $^1$H NMR (400 MHz, DMSO-$d_6$) δ 12.13 (s, 1H), 9.29 (s, 1H), 8.54 (s, 1H), 8.13 (s, 1H), 8.84 (d, J=8.8 Hz, 1H), 8.80 (d, J=8.4 Hz, 1H), 7.38-7.36 (m, 1H), 7.18 (d, J=9.2 Hz, 2H), 2.24 (s, 1H).

Example 54

2,2-Difluoro-N-(7-(5-fluoro-2-methylphenyl)isoquinolin-3-yl)acetamide

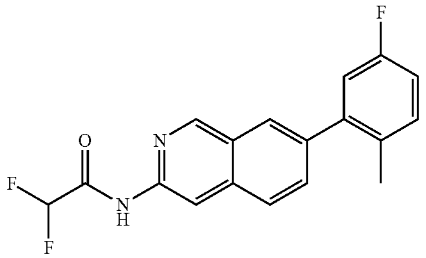 [SMILES: Cc1ccc(F)cc1-c1ccc2cc(NC(=O)C(F)F)ncc2c1]

7-(5-Fluoro-2-methylphenyl)isoquinolin-3-amine (150 mg, 0.595 mmol), 2,2-difluoroacetic acid (171 mg, 1.78 mmol), 4-(Dimethylamino)pyridine (18 mg, 0.15 mmol) and O-(7-azabenzotriazol-1-yl)-N,N,N',N'-tetramethyluronium hexafluorophosphate (676 mg, 1.78 mmol) were dissolved in pyridine (20 mL). After the reaction mixture was stirred at room temperature overnight, water (1 mL) was added and it was extracted with ethyl acetate. It was concentrated and purified by prep-HPLC to give the desired product (59.6 mg). LCMS (ESI): $R_T$ (Min)=1.161, M+H$^+$=330.9, method=A; $^1$H NMR (400 MHz, DMSO-$d_6$) δ 11.48 (s, 1H), 9.22 (s, 1H), 8.50 (s, 1H), 8.08 (s, 1H), 8.03 (d, J=8.4 Hz, 1H), 7.75 (d, J=8.4 Hz, 1H), 7.38-7.34 (m, 1H), 7.16 (d, J=8.8 Hz, 2H), 6.44 (t, J=54.0 Hz, 1H), 2.22 (s, 3H).

Example 55

N-(7-(5-fluoro-2-methylphenyl)isoquinolin-3-yl)methanesulfonamide

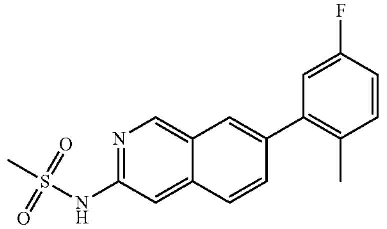 [SMILES: Cc1ccc(F)cc1-c1ccc2cc(NS(C)(=O)=O)ncc2c1]

To a solution of 7-(5-fluoro-2-methylphenyl)isoquinolin-3-amine (150 mg, 0.595 mmol) in pyridine (5 mL) was added methanesulfonyl chloride (137 mg, 1.20 mmol) dropwise at 0° C. The resulting mixture was stirred at room temperature overnight. A small amount of water was added to the reaction mixture, and it was extracted with ethyl acetate. The organic phase was pooled and concentrated. It was purified by prep-HPLC to give the desired product (80.5 mg, 41.0%). LCMS (ESI): $R_T$ (Min)=1.181, M+H$^+$=330.9, method=A; $^1$H NMR (400 MHz, DMSO-$d_6$) δ 10.57 (s, 1H), 9.17 (s, 1H), 8.04 (s, 1H), 7.93 (d, J=8.8 Hz, 1H), 7.70 (d, J=8.4 Hz, 1H), 7.44 (s, 1H), 7.38-7.34 (m, 1H), 7.15 (d, J=9.2 Hz, 2H), 3.30 (s, 3H), 2.22 (s, 3H).

Example 56

1-(7-(5-fluoro-2-methylphenyl)isoquinolin-3-yl)-3-isopropylurea

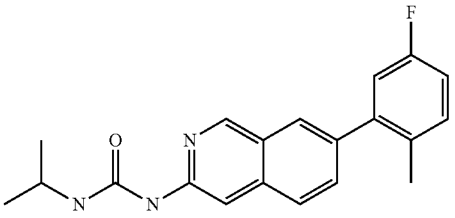 [SMILES: Cc1ccc(F)cc1-c1ccc2cc(NC(=O)NC(C)C)ncc2c1]

To a solution of 7-(5-fluoro-2-methylphenyl)isoquinolin-3-amine (0.10 g, 0.40 mmol) in tetrahydrofuran (2 mL) was added pyridine (0.1 mL). The mixture was cooled to 0° C. and triphosgene (59.4 mg, 0.20 mmol) in tetrahydrofuran (2 mL) was added dropwise. After the reaction mixture was stirred for 1 h, propan-2-amine (0.10 g, 1.7 mmol) was added and the mixture was stirred for 2 h. The reaction was quenched with methanol (2.0 mL), and the mixture was purified by preparative TLC (Hexanes/ethyl acetate=1:1) to give the desired product (20.6 mg, 15%). LCMS (ESI): $R_T$ (min)=1.163, M+H$^+$=338.1, method=A; $^1$H NMR (DMSO-$d_6$, 400 MHz): δ 9.05 (s, 1H), 8.94 (s, 1H), 8.09 (s, 1H), 7.95 (t, J=0.8 Hz, 1H), 7.83 (d, J=8.8 Hz, 1H), 7.64 (dd, J=1.6, 8.8 Hz, 1H), 7.37-7.33 (m, 1H), 7.15-7.11 (m, 1H), 6.89 (d, J=6.8 Hz, 1H), 3.83-3.78 (m, 1H), 2.22 (s, 3H), 1.13 (d, J=6.6 Hz, 6H).

Example 57

2-Bromo-4-methoxy-1-methylbenzene

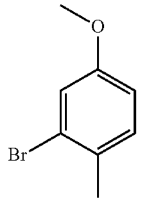

Melted 5-methoxy-2-methylaniline (1.0 g, 7.3 mmol) was added to a tetrafluoroboric acid solution (15 mL). A solution of sodium nitrite (0.55 g, 7.8 mmol) in water (2.0 mL) was added dropwise. The temperature of the diazotization reaction was maintained below 15° C. during the addition. After the diazotization mixture was stirred at that temperature for 15 minutes, it was filtered through a sintered glass funnel. The solid was collected and washed with water and cold ethanol. The solid was dissolved in DMSO (5 mL) and added to a vigorously stirred mixture of copper(II) bromide (3.2 g, 14.3 mmol) and DMSO (20 mL) over a period of about 15 min while the maintaining the temperature in the range of 25-30° C. The reaction mixture was pour to water (100 mL). The aqueous solution was extracted ethyl acetate three times, washed with water and saturated aqueous sodium chloride, dried over sodium sulfate to give the crude product without further purification.

Example 58

2-Bromo-1-methyl-4-(trifluoromethyl)benzene

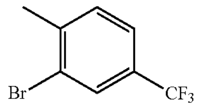

2-Methyl-5-(trifluoromethyl)aniline (3.3 g, 18.9 mmol) was melted and added to of a cold tetrafluoroboric acid solution (48%, 100 mL). Sodium nitrite (1.6 g, 23.2 mmol) in water (10 mL) was added to the mixture dropwise at a temperature below 15° C. The reaction mixture was stirred at that temperature for 15 minutes and the solid was collected by filtration. The solid was washed with cold tetrafluoroboric acid solution, cold ethanol and cold ethylacetate. The solid (3.5 g, 15.6 mmol) was dissolved in DMSO (20 mL) and added to a suspension of copper(II) bromide (5.8 g) and DMSO (50 mL) with vigorously stirring at a temperature below 25-30° C. The reaction mixture was poured to an ice-water mixture (1.0 L) and extracted by ethyl acetate, concentrated, and purified by column chromatography on silica gel (Hexanes:ethyl acetate=10:1) to give the product (1.0 g, 22.2%). $^1H$ NMR (DMSO-$d_6$, 400 MHz): δ 7.87-7.88 (m, 1H), 7.56-7.57 (m, 1H), 7.54-7.55 (m, 1H), 2.37 (s, 3H).

Example 59

3-bromo-4-methylaniline

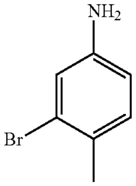

2-Bromo-4-nitrotoluene (10.0 g, 46.3 mmol) was added to a mixture of water (60 mL), ethanol (130 mL) and acetic acid (40 mL) under nitrogen. The mixture was heated to 70° C. and iron powder (10.3 g, 185 mmol) was added portionwise. After the mixture was heated at refluxed for 2 hours, it was cooled and aqueous ammonia (34%, 180 mL) was added slowly. The mixture is filtered through celite and the aqueous phase was extracted with ethyl acetate. It was dried over $MgSO_4$, filtered, and solvent was removed to give the product as a brown oil (6.0 g, 71%). LCMS (ESI): M+H=185.8.

Example 60

3-bromo-N,N,4-trimethylaniline

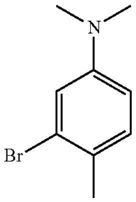

A mixture of 3-bromo-4-methylaniline (5.89 g, 32 mmol) and trimethyl phosphate (2.8 g, 20 mmol) was heated at reflux for 16 hours. After it was cooled to 50° C., a solution of sodium hydroxide (25 g) in water (40 mL) was added and the mixture was heated at reflux for 1 hour. After it was cooled to room temperature, the oil layer was separated and the aqueous layer was extracted with ether. The combined extracts and the oil were dried over anhydrous sodium sulfate. The ether was removed under vacuum, and the residue was treated with an equal volume of acetic anhydride and allowed to stand overnight to give the product (2.0 g, 30%). MS (ESI): M+1=213.8.

Example 61

N-(7-(5-methoxy-2-methylphenyl)isoquinolin-3-yl) cyclopropanecarboxamide

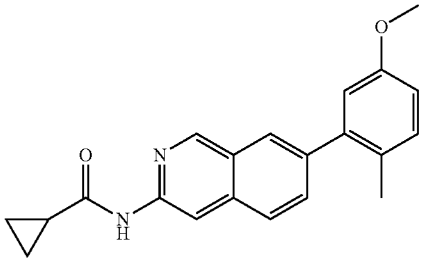 [SMILES: COc1ccc(C)c(-c2ccc3cc(NC(=O)C4CC4)ncc3c2)c1]

To a solution of N-(7-(4,4,5,5-tetramethyl-1,3,2-dioxaborolan-2-yl)isoquinolin-3-yl)cyclopropanecarboxamide (200 mg, 0.59 mmol) in dioxane/water (5.0 ml) were added 2-bromo-4-methoxy-1-methylbenzene (100 mg, 0.50 mmol), cesium carbonate (391 mg, 1.2 mmol) and [1,1'-Bis(diphenylphosphino)ferrocene]dichloropalladium(II) (22 mg, 0.03 mmol). It was purged with nitrogen and heated at 130° C. for 30 min under microwave irradiation. The reaction mixture was concentrated, washed with water and extracted with ethyl acetate. It was dried over sodium sulfate, concentrated and purified by pre-HPLC to give the product (36 mg, 18.4%). LCMS (ESI): $R_T$(Min)=1.214, M+H$^+$=332.9, method=A; $^1H$ NMR (400 MHz, DMSO-$d_6$) δ 9.17 (s, 1H), 8.49 (s, 1H), 8.00 (s, 1H), 7.90 (d, J=8.8 Hz, 1H), 7.70-7.68 (m, 1H), 7.24 (d, J=8.4 Hz, 1H), 6.91-6.86 (m, 2H), 3.76 (s, 3H), 2.19 (s, 3H), 2.09-2.05 (m, 1H), 0.87-0.81 (m, 4H).

Example 62

N-(7-(5-chloro-2-cyanophenyl)isoquinolin-3-yl)cyclopropanecarboxamide

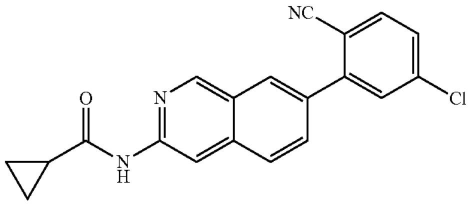 [SMILES: N#Cc1ccc(Cl)cc1-c1ccc2cc(NC(=O)C3CC3)ncc2c1]

A solution of N-(7-bromoisoquinolin-3-yl)cyclopropanecarboxamide (200 mg, 0.68 mmol), 4-chloro-2-(5,5-dimethyl-1,3,2-dioxaborinan-2-yl)benzonitrile (205 mg, 0.816 mmol), cesium carbonate (0.22 g, 0.68 mmol) and bis(di-tert-butyl(4-dimethylaminophenyl)phosphine) palladium dichloride (24.0 mg, 0.05 eq) in a mixture of acetonitrile and water (10 mL, 10:1) was purged with nitrogen and stirred at 90° C. for 45 minutes under microwave irradiation. Ethyl acetate (20 mL) was added to the reaction mixture and it was filtered. The solid was extracted with ethyl acetate (20 mL×4). The combined organic layer was dried over sodium sulfate, filtered and concentrated in vacuo. The residue was purified by HPLC separation to give the product (13.7 mg, 5.8%). LCMS (ESI): $R_T$ (min)=1.099, M+H$^+$=347.9, method=A. $^1$H NMR (400 MHz, DMSO-$d_6$) δ 11.04 (s, 1H), 9.24 (s, 1H), 8.54 (s, 1H), 8.33 (t, J=0.8 Hz, 1H), 8.08-7.72 (m, 5H), 2.09-2.05 (m, 1H), 0.88-0.83 (m, 4H).

Example 63

N-(7-(4-chloro-2-methylphenyl)isoquinolin-3-yl) cyclopropanecarboxamide

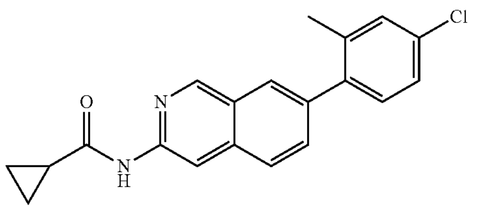 [SMILES: Cc1cc(Cl)ccc1-c1ccc2cc(NC(=O)C3CC3)ncc2c1]

A mixture of N-(7-bromoisoquinolin-3-yl)cyclopropanecarboxamide (200 mg, 0.68 mmol), 4-chloro-2-methylphenylboronic acid (138.72 mg, 0.816 mmol), cesium carbonate (268 mg, 0.816 mmol) and [1,1'-bis(diphenylphosphino)ferrocene]dichloropalladium(II) (25 mg, 0.05 eq) in acetonitrile/water (10 mL, 10:1) was stirred at 130° C. under microwave irradiation for 30 min under nitrogen. The reaction mixture was diluted with ethyl acetate (20 mL) and filtered. The solid was washed with ethyl acetate (20 mL×4). The organic layer was combined, dried over sodium sulfate, filtered and concentrated. The crude product was purified by prep-HPLC to give the desired product (94.6 mg, 41.3%). LCMS (ESI): $R_T$ (Min)=1.328, M+H$^+$=336.8, method=A. $^1$H NMR (400 MHz, DMSO-$d_6$) δ0.95 (s, 1H), 9.16 (s, 1H), 8.49 (s, 1H), 7.99 (s, 1H), 7.92 (d, J=8.4 Hz, 1H), 7.68 (dd, J=1.6, 8.4 Hz, 1H), 7.48-7.34 (m, 3H), 2.28 (s, 3H), 2.07-2.05 (m, 1H), 0.86-0.82 (m, 4H).

Example 64

N-(7-(5-chloro-2-methoxyphenyl)isoquinolin-3-yl) cyclopropanecarboxamide

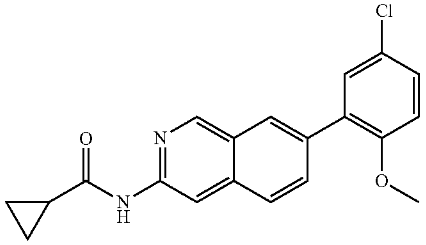 [SMILES: COc1ccc(Cl)cc1-c1ccc2cc(NC(=O)C3CC3)ncc2c1]

N-(7-bromoisoquinolin-3-yl)cyclopropanecarboxamide (150 mg, 0.595 mmol), 5-chloro-2-methoxyphenylboronic acid (132 mg, 0.714 mmol), [1,1'-bis(diphenylphosphino) ferrocene]dichloropalladium(II) (24 mg, 0.03 mmol) and cesium carbonate (232 mg, 0.714 mmol) were mixed in acetonitrile and water (10:1, 20 mL). The reaction mixture was stirred at 120° C. under nitrogen for 6 hours. The reaction mixture was concentrated, diluted with water and extracted with ethyl acetate, concentrated and purified by prep-HPLC to give the desired product (21.3 mg, 10.2%). LCMS (ESI): $R_T$ (min)=1.216, M+H$^+$=352.9, Method=I; $^1$H NMR (400 MHz, DMSO-$d_6$) δ 10.93 (s, 1H), 9.14 (s, 1H), 8.46 (s, 1H), 8.12 (s, 1H), 7.84-7.42 (m, 4H), 7.18 (d, J=8.4 Hz, 1H), 3.78 (s, 3H), 2.09-2.05 (m, 1H), 0.88-0.83 (m, 4H).

Example 65

N-(7-phenoxyisoquinolin-3-yl)cyclopropanecarboxamide

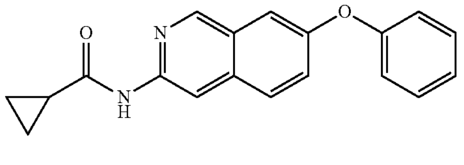

N-(7-bromoisoquinolin-3-yl)cyclopropanecarboxamide (89 mg, 0.30 mmol), phenol (86.5 mg, 0.92 mmol, 3 eq), 3,4,7,8-tetramethyl-1,10-phenanthrolin (35.4 mg, 0.15 mmol, 0.5 eq), copper(I) iodide (57.3 mg, 0.3 mmol, 1 eq) and cesium carbonate (293.2 mg, 0.9 mmol, 3 eq) in 1-methyl-2-pyrrolidinone (2.5 ml) were stirred under microwave irradiation at 180° C. for 99 min under nitrogen. The mixture was diluted with dichloromethane and filtered through a pad of Celite. The filer cake was washed with dichloromethane and the combined filtrate was concentrated and purified by prep-HPLC to give product (30 mg, 26%). LCMS (ESI): $R_T$(Min)=1.107, M+H$^+$=305.0, method=A. $^1$H NMR (400 MHz, $CDCl_3$) δ 8.76 (s, 1H), 8.46 (s, 1H), 8.24 (s, 1H), 7.72 (d, J=9.2 Hz, 1H), 7.38-7.00 (m, 5H), 1.55-1.52 (m, 1H), 1.10-1.06 (m, 2H), 0.87-0.82 (m, 2H).

Example 66

N-(7-(3-chlorophenoxy)isoquinolin-3-yl)cyclopropanecarboxamide

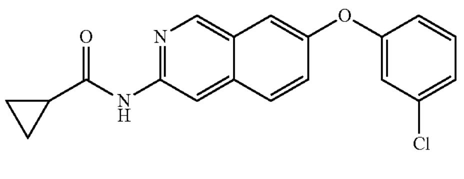 [SMILES: O=C(Nc1cc2ccc(Oc3cccc(Cl)c3)cc2cn1)C1CC1]

A mixture of N-(7-Bromoisoquinolin-3-yl)cyclopropanecarboxamide (89 mg, 0.30 mmol), 3-chlorophenol (115.2 mg, 0.90 mmol), 2,2,6,6-tetramethylheptane-3,5-dione (27.6 mg, 0.15 mmol), copper(I) chloride (30 mg, 0.30 mmol) and cesium carbonate (292.5 mg, 0.90 mmol) in 1-methyl-2-pyrrolidinone (2.5 mL) was stirred under microwave irradiation at 180° C. for 99 minutes under nitrogen. The mixture was diluted with dichloromethane and filtered through a pad of Celite. The filer cake was washed with dichloromethane and the combined filtrates were concentrated and purified by prep-HPLC to give the product (28.5 mg, 13%). LCMS (ESI): $R_T$ (min)=1.237, M+H$^+$=338.8, method=A; $^1$H NMR (400 MHz, DMSO-$d_6$) δ 10.93 (s, 1H), 9.06 (s, 1H), 8.41 (s, 1H), 8.02 (t, J=0.8 Hz, 1H), 7.84 (d, J=8.8 Hz, 1H), 7.53 (dd, J=1.6, 8.4 Hz, 1H), 7.38-7.31 (m, 5H), 2.09-1.99 (m, 1H), 0.83-0.79 (m, 4H).

Example 67

N-(7-Isopropoxyisoquinolin-3-yl)cyclopropanecarboxamide

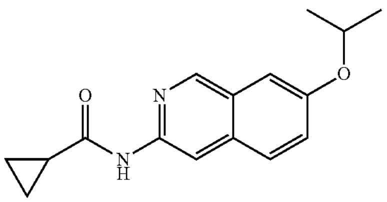 [SMILES: CC(C)Oc1ccc2cc(NC(=O)C3CC3)ncc2c1]

A mixture of N-(7-iodoisoquinolin-3-yl)cyclopropanecarboxamide (338 mg, 1.0 mmol), 1,10-phenanthroline (180 mg, 1.0 mmol), copper(I) iodide (190 mg, 1.0 mmol) and cesium carbonate (422.5 mg, 1.3 mmol) in isopropanol (25 mL) were stirred at 210° C. for 5 hours under nitrogen in a sealed stainless container. After being cooled to room temperature, the mixture was diluted with dichloromethane and filtered through a pad of Celite and filter cake was washed with dichloromethane. The combined filtrates were concentrated and purified by prep-HPLC to give product (18.9 mg, 26%). LCMS (ESI): $R_T$ (min)=0.967, M+H$^+$=271.1, method=A. $^1$H NMR (400 MHz, $CDCl_3$) δ 8.80 (s, 1H), 8.45 (s, 1H), 8.28 (s, 1H), 7.68 (d, J=9.2 Hz, 1H), 8.02 (t, J=0.8 Hz, 1H), 7.84 (d, J=8.8 Hz, 1H), 7.53 (dd, J=1.6, 8.4 Hz, 1H), 7.38-7.31 (m, 5H), 2.09-1.99 (m, 1H).

Example 68

N-(7-(cyclohexyloxy)isoquinolin-3-yl)cyclopropanecarboxamide

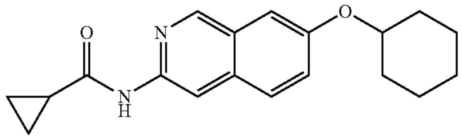 [SMILES: O=C(Nc1cc2ccc(OC3CCCCC3)cc2cn1)C1CC1]

Cyclohexanol (10 mL) was added to a mixture of N-(7-bromoisoquinolin-3-yl)cyclopropanecarboxamide (150 mg, 0.44 mmol), copper(I) iodide (83.9 mg, 0.44 mmol), 1,10-phenanthroline (79.2 mg, 0.44 mmol) and cesium carbonate (188 mg, 0.58 mmol). The resulting mixture was stirred at 140-160° C. for 2 hours under nitrogen. The reaction mixture was concentrated and purified by prep-HPLC to give the product (31.5 mg, 22.9%). LCMS (ESI): $R_T$ (min)=1.141, M+H$^+$=310.9, method=A. $^1$H NMR (400 MHz, DMSO-$d_6$) δ 10.73 (s, 1H), 8.97 (s, 1H), 8.34 (s, 1H), 7.74 (d, J=9.2 Hz, 1H), 7.45 (s, 1H), 7.31 (d, J=8.8 Hz, 1H), 4.40-4.50 (m, 1H), 2.01-1.98 (m, 3H), 1.80-1.70 (m, 2H), 1.60-1.21 (m, 6H), 0.82-0.78 (m, 4H).

Example 69

N-(7-(Difluoromethoxy)isoquinolin-3-yl)cyclopropanecarboxamide

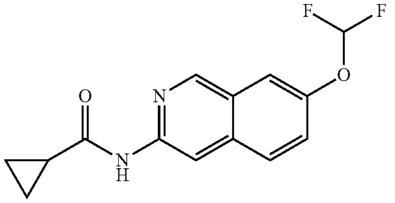 [SMILES: O=C(Nc1cc2ccc(OC(F)F)cc2cn1)C1CC1]

A solution of N-(7-hydroxyisoquinolin-3-yl)cyclopropanecarboxamide (91.2 mg, 0.40 mmol), diethyl bromodifluoromethylphosphonate (212 mg, 0.80 mmol) in acetonitrile/water (1:1, 5 mL) was mixed and stirred at −78° C. After the reaction mixture was warmed to room temperature and stirred for 20 minutes, the reaction mixture was diluted with ethyl acetate, and the organic phase was separated. The water phase was extracted with ethyl acetate, and the combined organic layer was dried, concentrated and purified by prep-HPLC to give product (42.8 mg, 26%). LCMS (ESI): $R_T$ (min)=0.994, M+H$^+$=279.0, method=A. $^1$H NMR (400 MHz, DMSO-$d_6$) δ 8.92 (s, 1H), 8.54 (s, 1H), 8.37 (s, 1H), 7.79 (d, J=8.8 Hz, 1H), 7.54 (s, 1H), 7.43 (dd, J=2.4, 8.8 Hz, 1H), 6.61 (t, J=73.2 Hz, 1H), 1.71-1.57 (m, 1H), 1.15-1.11 (m, 2H), 0.95-0.89 (m, 2H).

Example 70

N-(7-(phenylamino)isoquinolin-3-yl)cyclopropanecarboxamide

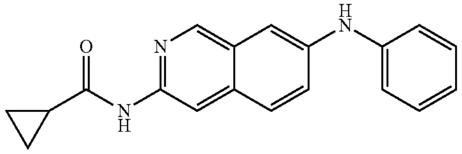 [SMILES: O=C(Nc1cc2ccc(Nc3ccccc3)cc2cn1)C1CC1]

N-(7-bromoisoquinolin-3-yl)cyclopropanecarboxamide (200 mg, 0.69 mmol), aniline (76 mg, 0.83 mmol), palladium (II) acetate (30 mg, 0.15 mmol), X-Phos (66 mg, 0.15 mmol) and cesium carbonate (450 mg, 1.4 mmol) were mixed in 1,2-dimethoxyethane (50 mL). After the reaction mixture was stirred at 100° C. under nitrogen for 3 hours, it was concentrated, washed with water and extracted with ethyl acetate, and purified by prep-HPLC to give the desired product (93.2 mg, 44.5%). LCMS (ESI): $R_T$ (min)=1.018, M+H$^+$=303.8, Method=A; $^1$H NMR (400 MHz, DMSO-$d_6$) δ 10.70 (s, 1H), 8.89 (s, 1H), 8.51 (s, 1H), 8.29 (s, 1H), 7.72 (d, J=8.8 Hz, 1H), 7.56 (s, 1H), 7.42 (d, J=8.8 Hz, 1H), 7.30-7.20 (m, 2H), 7.20-7.18 (m, 2H), 6.90-6.89 (m, 1H), 2.05-2.01 (m, 1H), 0.82-0.76 (m, 4H).

Example 71

N-(7-(phenylthio)isoquinolin-3-yl)cyclopropanecarboxamide

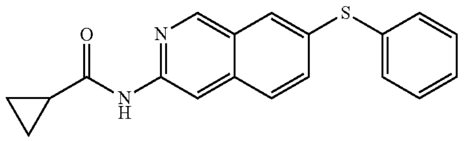

A mixture of N-(7-bromoisoquinolin-3-yl)cyclopropanecarboxamide (145 mg, 0.5 mmol), benzenethiol (55 mg, 0.50 mmol), 1,1'-bis(diphenylphosphino)ferrocene (41.8 mg, 0.10 mmol), palladium(II) acetate (22.4 mg, 0.10 mmol) and sodium tert-butoxide (96 mg, 1.0 mmol) in dioxane (15 mL) were stirred at 100° C. overnight under nitrogen. The mixture was diluted with methanol and filtered through a pad of Celite. The pad was washed with methanol. The combined filtrates were concentrated to dryness and purify by Prep-HPLC to give the product (42.5 mg, 26%). LCMS (ESI): $R_T$ (Min)=1.202, M+H$^+$=320.9, method=A. $^1$H NMR (400 MHz, DMSO-d$_6$) δ 10.93 (s, 1H), 9.06 (s, 1H), 8.41 (s, 1H), 8.02 (t, J=0.8 Hz, 1H), 7.84 (d, J=8.8 Hz, 1H), 7.53 (dd, J=1.6, 8.4 Hz, 1H), 7.38-7.31 (m, 5H), 2.09-1.99 (m, 1H), 0.83-0.79 (m, 4H).

Example 72

N-(3-(3-(cyclopropanecarboxamido)isoquinolin-7-yl)-4-methylphenyl)-4-(4-methylpiperazin-1-yl)methyl)benzamide

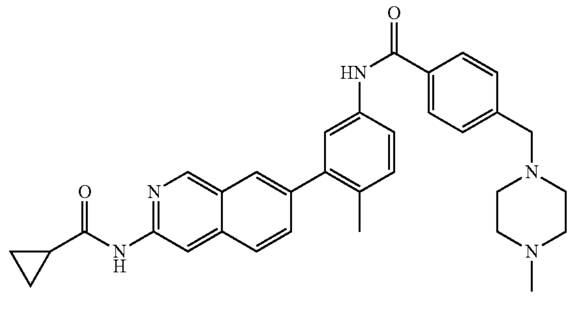 [SMILES: Cc1ccc(NC(=O)c2ccc(CN3CCN(C)CC3)cc2)cc1-c1ccc2cc(NC(=O)C3CC3)ncc2c1]

To a solution of 4-((4-methylpiperazin-1-yl)methyl)benzoic acid (147 mg, 0.48 mmol) in anhydrous N,N-dimethylformamide (10 mL) was added O-(7-azabenzotriazol-1-yl)-N,N,N',N'-tetramethyluronium hexafluorophosphate (729 mg, 1.92 mmol) at 0° C. A solution of N-(7-(5-amino-2-methylphenyl)isoquinolin-3-yl)cyclopropanecarboxamide (150 mg, 0.47 mmol) in anhydrous N,N-dimethylformamide (5 mL) was treated with pyridine (227 mg, 2.83 mmol) and immediately added to the reaction mixture. It was stirred at 0° C. for 10 minutes and then at room temperature for 4-5 hours. The reaction was diluted with ethyl acetate (15 mL) and water (10 mL) and the aqueous layer was extracted with ethyl acetate (3×15 mL). The combined organic layer was dried, concentrated and purified by prep-HPLC to give the product (73.6 mg, 34%). LCMS (ESI): $R_T$ (min)=0.890, M+H$^+$=534.1, method=A. $^1$H NMR (400 MHz, DMSO-d$_6$) δ 10.92 (s, 1H), 10.23 (s, 1H), 9.18 (s, 1H), 8.48 (s, 1H), 8.00-7.91 (m, 4H), 7.77 (d, J=2.4 Hz, 1H), 7.74-7.67 (m, 2H), 7.47 (d, J=8.0 Hz, 2H), 7.32 (d, J=8.4 Hz, 1H), 3.65 (s, 2H), 3.49-3.45 (m, 2H), 3.05-2.90 (m, 4H), 2.80 (s, 3H), 2.40-2.30 (m, 2H), 2.24 (s, 3H), 2.06-2.03 (m, 1H), 0.86-0.80 (m, 4H).

Example 73

3-Chloro-N-(3-(3-(cyclopropanecarboxamido)isoquinolin-7-yl)-4-methylphenyl)-4-(4-methylpiperazin-1-yl)methyl)benzamide

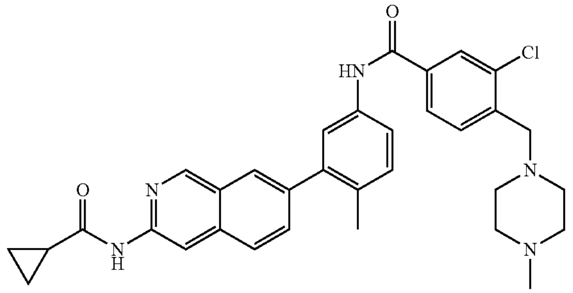 [SMILES: Cc1ccc(NC(=O)c2ccc(CN3CCN(C)CC3)c(Cl)c2)cc1-c1ccc2cc(NC(=O)C3CC3)ncc2c1]

Step 1: Methyl 4-(bromomethyl)-3-chlorobenzoate

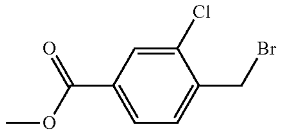

To a solution of methyl 3-chloro-4-methylbenzoate (920 mg, 5.0 mmol) in carbon tetrachloride (10 mL) were added N-bromosuccinimide (1.067 g, 6.0 mmol) and 2,2'-Azobis(2-methylpropionitrile) (81 mg, 0.50 mmol). The mixture was stirred at reflux overnight. The mixture was cooled to room temperature and concentrated. The residue was purified by column chromatography (Hexanes:ethyl acetate=10:1) to give the desired product (200 mg, 19%).

Step 2: Methyl 3-chloro-4-((4-methylpiperazin-1-yl)methyl)benzoate

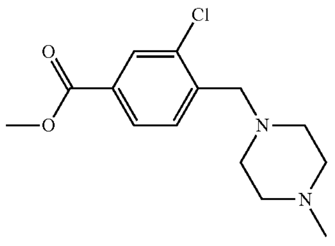

Methyl 4-(bromomethyl)-3-chlorobenzoate (400 mg, 1.5 mmol), 1-methylpiperazine (100 mg, 1.0 mmol), and potassium carbonate (276 mg, 2.0 mmol) in N,N-dimethylformamide (2.5 mL) were stirred at room temperature overnight. The mixture was concentrated and diluted with ethyl acetate and water. The aqueous layer was extracted with ethyl acetate.

The combined organic layers were dried and concentrated to give product (270 mg, 58%). LCMS (ESI): $R_T$ (min)=0.934, M+H$^+$=282.8, method=B.

Step 3: 3-Chloro-4-((4-methylpiperazin-1-yl)methyl)benzoic acid

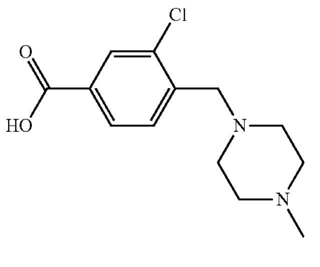 [SMILES: CN1CCN(Cc2ccc(C(=O)O)cc2Cl)CC1]

A solution of methyl 3-chloro-4-((4-methylpiperazin-1-yl)methyl)benzoate (270 mg, 0.96 mmol) in tetrahydrofuran was added to an aqueous sodium hydroxide solution (6 M, 1.5 mL) and the mixture was stirred at room temperature for 5 hours. The organic solvent was removed under reduced pressure and the residue was acidified with aqueous HCl until a white solid formed. The mixture was lyophilized to give a white solid (contained salt). LCMS (ESI): $R_T$ (min)=0.819, M+H$^+$=268.8, method=B.

Step 4: 3-Chloro-N-(3-(3-(cyclopropanecarboxamido)isoquinolin-7-yl)-4-methylphenyl)-4-(4-methylpiperazin-1-yl)methyl)benzamide

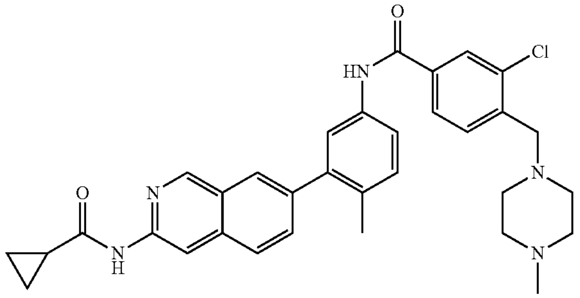 [SMILES: Cc1ccc(NC(=O)c2ccc(CN3CCN(C)CC3)c(Cl)c2)cc1-c1ccc2cc(NC(=O)C3CC3)ncc2c1]

To a solution of 3-chloro-4-((4-methylpiperazin-1-yl)methyl)benzoic acid (268 mg, 1.0 mmol) in anhydrous N,N-dimethylformamide (10 mL) were added O-(7-azabenzotriazol-1-yl)-N,N,N',N'-tetramethyluronium hexafluorophosphate (380 mg, 1.0 mmol) at 0° C. A solution of N-(7-(5-amino-2-methylphenyl)isoquinolin-3-yl)cyclopropanecarboxamide (317 mg, 1.0 mmol) in anhydrous N,N-dimethylformamide (5 mL) was mixed with pyridine (237 mg, 3.0 mmol) and added to the reaction mixture. It was stirred at 0° C. for 10 minutes and then at room temperature for 4-5 hours. The reaction was diluted with ethyl acetate (15 mL) and water (10 mL) and the aqueous layer was extracted with ethyl acetate (15 mL×3). The combined organic layers were dried, concentrated and purified prep-HPLC purification to give the product (14.8 mg, 2.6%). LCMS (ESI): $R_T$ (min)=0.922, M+H=568.1, method=A. $^1$H NMR (400 MHz, MeOH-$d_4$) 610.18 (s, 1H), 9.14 (s, 1H), 8.31 (s, 1H), 8.02-7.59 (m, 8H), 7.33 (d, J=8.4 Hz, 1H), 3.80 (s, 2H), 3.46 (s, 2H), 3.20-3.00 (m, 4H), 2.60-2.42 (m, 2H), 2.27 (s, 3H), 1.95-1.93 (m, 1H), 1.06-1.03 (m, 2H), 0.96-0.93 (m, 2H).

Example 74

N-(7-methoxyisoquinolin-3-yl)cyclopropanecarboxamide

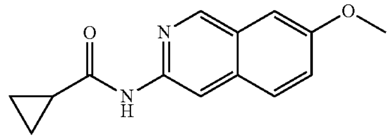 [SMILES: COc1ccc2cc(NC(=O)C3CC3)ncc2c1]

N-(7-bromoisoquinolin-3-yl)cyclopropanecarboxamide (150 mg, 0.52 mmol), copper(I) iodide (90 mg, 0.52 mmol), 1,10-phenanthroline (93 mg, 0.52 mmol) and cesium carbonate (219 mg, 0.67 mmol) were added to ethanol (5 mL) in a stainless container. The resulting mixture was stirred at 210° C. for 5 hours under nitrogen. The reaction mixture was concentrated and purified by prep-HPLC and TLC to give the product (7.2 mg, 5.7%). LCMS (ESI): $R_T$ (Min)=0.79, M+H$^+$=243.0, method=A. $^1$H NMR (400 MHz, DMSO-$d_6$): δ 10.76 (s, 1H), 8.99 (s, 1H), 8.35 (s, 1H), 7.77 (d, J=8.8 Hz, 1H), 7.42 (s, 1H), 7.32 (d, J=9.2 Hz, 1H), 3.96 (s, 3H), 2.01 (s, 1H), 0.81-0.79 (m, 4H).

Example 75

N-(7-cyclobutoxyisoquinolin-3-yl)cyclopropanecarboxamide

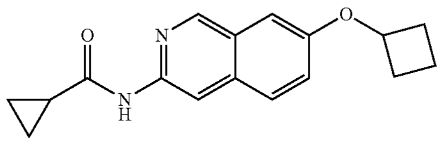 [SMILES: O=C(Nc1cc2ccc(OC3CCC3)cc2cn1)C1CC1]

N-(7-bromoisoquinolin-3-yl)cyclopropanecarboxamide (150 mg, 0.51 mmol), copper(I) iodide (96 mg, 0.51 mmol), 1,10-phenanthroline (100 mg, 0.51 mmol) and cesium carbonate (216 mg, 0.62 mmol) were combined in stainless container, and cyclobutanol (3.0 mL) was added. The reaction mixture was stirred at 120-140° C. for 12 h under nitrogen. It was concentrated and purified by HPLC and TLC to give the product (17.1 mg, 12.0%). LCMS (ESI): $R_T$ (Min)=1.15, M+H$^+$=282.9, method=A. $^1$H NMR (400 MHz, DMSO-$d_6$). 10.75 (s, 1H), 8.97 (s, 1H), 8.33 (s, 1H), 7.74 (d, J=9.0 Hz, 1H), 7.26 (d, J=6.8 Hz, 2H), 4.77 (t, J=6.8 Hz, 1H), 2.07-1.65 (m, 6H), 1.19 (s, 1H), 0.79-0.76 (m, 4H).

Example 76

N-(7-(2-hydroxyethoxy)isoquinolin-3-yl)cyclopropanecarboxamide

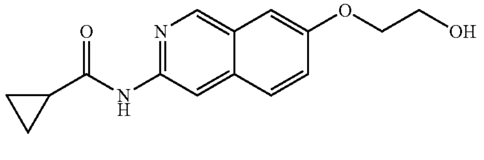 [SMILES: O=C(Nc1cc2ccc(OCCO)cc2cn1)C1CC1]

N-(7-bromoisoquinolin-3-yl)cyclopropanecarboxamide (150 mg, 0.52 mmol), copper(I) iodide (96 mg, 0.52 mmol), 1,10-phenanthroline (100 mg, 0.52 mmol) and cesium carbonate (219 mg, 0.67 mmol) were combined in ethylene glycol (5 mL). The resulting mixture was stirred at 120-140° C. overnight under nitrogen. The reaction mixture was concentrated and purified by prep-HPLC to give the product (20.1 mg, 14.3%). LCMS (ESI): $R_T$ (min)=0.86, M+H$^+$=273.0, method=A. $^1$H NMR (400 MHz, DMSO-$d_6$) δ 10.75 (s, 1H), 8.97 (s, 1H), 8.36 (s, 1H), 7.76 (d, J=9.2 Hz, 1H), 7.41 (s, 1H), 7.34 (d, J=9.2 Hz, 1H), 4.93-4.90 (m, 1H), 4.09 (t, J=4.8 Hz, 2H), 3.78-3.74 (m, 2H), 2.03-2.00 (m, 1H), 0.81-0.77 (m, 4H).

Example 77

N-(7-(3-hydroxypyrrolidin-1-yl)isoquinolin-3-yl) cyclopropanecarboxamide

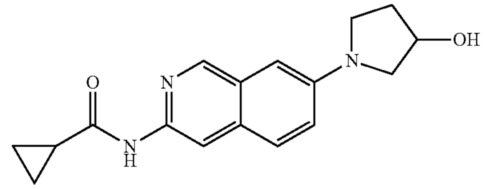 [SMILES: O=C(Nc1cc2ccc(N3CCC(O)C3)cc2cn1)C1CC1]

Dioxane (50 mL) was added to a mixture of N-(7-bromoisoquinolin-3-yl)cyclopropanecarbox-amide (200 mg, 0.69 mmol), pyrrolidin-3-ol (122 mg, 1.28 mmol), $Pd_2(dba)_3$ (120 mg, 0.14 mmol), biphenyl-2-yldi-tert-butylphosphine (78 mg, 0.25 mmol) and sodium tert-butoxide (80 mg, 0.82 mmol). After the reaction mixture was stirred at 100° C. under nitrogen overnight, the mixture was filtered, concentrated and purified by prep HPLC and prep TLC to give the product (33.1 mg, 16.2%). LCMS (ESI): $R_T$ (Min)=0.86, M+H$^+$=298.0, method=B. $^1$H NMR (400 MHz, DMSO-$d_6$) δ 10.58 (s, 1H), 8.82 (s, 1H), 8.22 (s, 1H), 7.65 (d, J=9.2 Hz, 1H), 7.19 (d, J=9.2 Hz, 1H), 6.80 (s, 1H), 4.99 (s, 1H), 4.45 (s, 1H), 3.50-3.48 (m, 1H), 3.45-3.36 (m, 2H), 3.20-3.12 (m, 1H), 2.25-2.05 (m, 1H), 1.85-2.05 (m, 2H), 0.80-0.75 (m, 4H).

Example 78

N-(7-(3-(hydroxymethyl)phenyl)isoquinolin-3-yl) cyclopropanecarboxamide

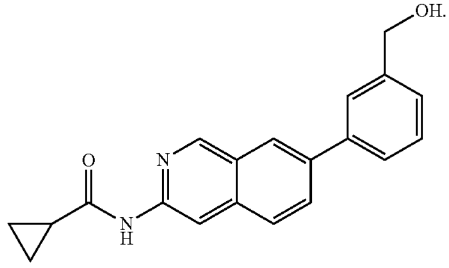 [SMILES: O=C(Nc1cc2ccc(-c3cccc(CO)c3)cc2cn1)C1CC1]

A mixture of N-(7-bromoisoquinolin-3-yl)cyclopropanecarboxamide (100 mg, 0.35 mmol), 3-(hydroxyl-methyl) phenylboronic acid (0.53 mmol), [1,1'-bis(diphenylphosphino)ferrocene]dichloropalladium(II) (26 mg, 0.035 mmol) and cesium carbonate (228 mg, 0.70 mmol) in 1,2-dimethoxyethane/water (10:1, 2.0 mL) was stirred under microwave irradiation at 130° C. for 20 minutes under nitrogen. Ethyl acetate (10 mL) was added to the reaction mixture and it was filtered. The residue was extracted with ethyl acetate (5.0 mL×3). The organic layer was combined, dried with sodium sulfate, filtered and concentrated. It was purified by column chromatography to give the product (10 mg, 13%). LCMS (ESI): $R_T$ (Min)=1.062, M+H$^+$=318.2, method=A. $^1$H NMR (400 MHz, $CDCl_3$) δ 10.91 (s, 1H), 9.18 (s, 1H), 8.44 (s, 1H), 8.30 (s, 1H), 8.01 (dd, J=1.6, 8.8 Hz, 1H), 7.92 (d, J=8.8 Hz, 1H), 7.73 (s, 1H), 7.66 (d, J=8.0 Hz, 1H), 7.46 (t, J=6.8 Hz, 1H), 7.34 (d, J=7.2 Hz, 1H), 5.29 (t, J=5.6 Hz, 1H), 4.58 (d, J=6.0 Hz, 2H), 2.07-2.04 (m, 1H), 0.83-0.79 (m, 4H).

Example 79

N-(5-(3-(cyclopropanecarboxamido)isoquinolin-7-yl)-6-methylpyridin-3-yl)-4-(4-methylpiperazin-1-yl) methyl)-3-(trifluoromethyl)benzamide

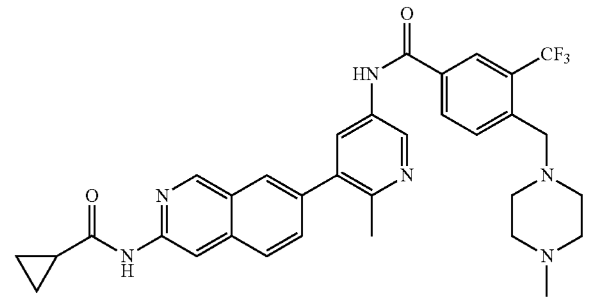

Step 1: Ethyl 4-(bromomethyl)-3-(trifluoromethyl)benzoate

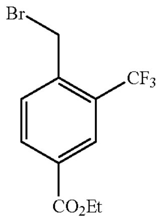

N-Bromosuccinimide (1.04 g, 5.83 mmol) and benzoyl peroxide (0.12 g, 0.49 mmol) were added to a solution of ethyl 4-methyl-3-(trifluoromethyl)benzoate (1.06 g, 4.56 mmol) in carbon tetrachloride (25 mL). The reaction mixture was heated at reflux overnight. After it was cooled to room temperature, it was diluted with dichloromethane (50 mL), and washed with water (20 mL). The aqueous layer was extracted with dichloromethane (20 mL). It was dried over $Na_2SO_4$ and concentrated. It was purified by prep-TLC (Hexanes:ethyl acetate=10:1) to give the product as an oil (0.60 g, 44%) $^1$H NMR (400 MHz, DMSO-$d_6$) δ 8.31 (d, J=1.6 Hz, 1H), 8.20 (dd, J=4.8, 1.6 Hz, 1H), 7.68 (d, J=8.0 Hz, 1H), 4.64 (s, 1H), 4.40 (q, J=7.2 Hz, 2 H), 1.40 (t, J=7.2 Hz, 3 H).

Step 2: Ethyl 4-((4-methylpiperazin-1-yl)methyl)-3-(trifluoromethyl)benzoate

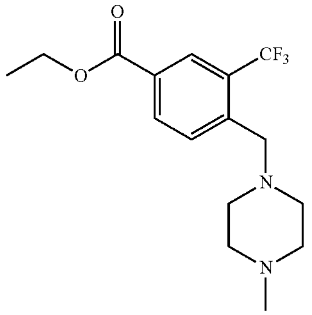 [SMILES: CCOC(=O)c1ccc(CN2CCN(C)CC2)c(C(F)(F)F)c1]

A mixture of 1-methylpiperazine (600 mg, 1.5 mmol), ethyl 4-(bromomethyl)-3-(trifluoromethyl)benzoate (310 mg, 1.0 mmol), and potassium carbonate (276 mg, 2.0 mmol) in N,N-dimethylformamide (8 mL) were stirred at room temperature overnight. The solvent was removed under reduced pressure and the residue was diluted with ethyl acetate and water. The aqueous layer was extracted with ethyl acetate. The combined organic layers were dried and concentrated to give the product without further purification (600 mg, 72%).

Step 3: 4-((4-methylpiperazin-1-yl)methyl)-3-(trifluoromethyl)benzoic acid

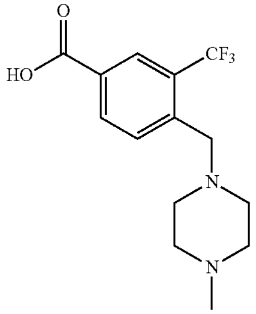 [SMILES: CN1CCN(Cc2ccc(C(=O)O)cc2C(F)(F)F)CC1]

A mixture of ethyl 4-((4-methylpiperazin-1-yl)methyl)-3-(trifluoromethyl)benzoate (330 mg, 0.96 mmol) and sodium hydroxide solution (1.5 M) in water/methanol (15/5 mL) were stirred at room temperature for 5 hours. The mixture was concentrated and acidified with aqueous hydrochloric acid until a white solid formed. The mixture was lyophilized to give a white solid (600 mg, contains salt).

Step 4: N-(5-(3-(cyclopropanecarboxamido)isoquinolin-7-yl)-6-methylpyridin-3-yl)-4-((4-methylpiperazin-1-yl)methyl)-3-(trifluoromethyl)benzamide

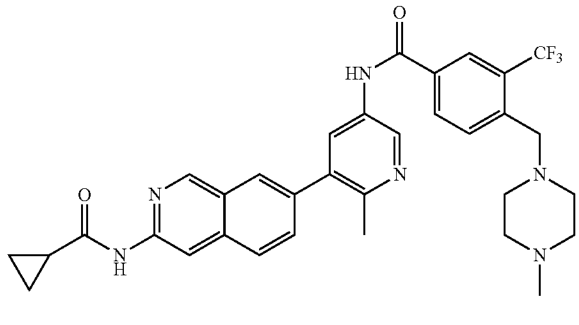

To a solution of 4-((4-methylpiperazin-1-yl)methyl)-3-(trifluoromethyl)benzoic acid (302 mg, 1.0 mmol) in anhydrous N,N-dimethylformamide (10 mL) was added O-(7-azabenzotriazol-1-yl)-N,N,N',N'-tetramethyluronium hexafluorophosphate (570 mg) at 0° C. A solution of N-(7-(5-amino-2-methylpyridin-3-yl)isoquinolin-3-yl)cyclopropanecarboxamide (318 mg, 1.0 mmol) in anhydrous N,N-dimethylformamide (5 mL) was mixed with N,N-diisopropylethylamine (387 mg, 3.0 mmol) and immediately added to the reaction at 0° C. It was stirred at 0° C. for 10 minutes and then at room temperature for 4-5 hours. The reaction was diluted with ethyl acetate (15 mL) and water (10 mL) and the aqueous layer was extracted with ethyl acetate (3×15 mL). The combined organic layers were dried, concentrated, and purified by prep-HPLC to give the product (6.4 mg, 1.1%). LCMS (ESI): $R_T$ (min)=0.760, $M+H^+$=603.4, method=A; $^1H$ NMR: (MeOH-$d_4$, 400 MHz): δ 9.40 (d, J=2.0 Hz, 1H), 9.18 (s, 1H), 8.59 (d, J=2.0 Hz, 1H), 8.51 (s, 1H), 8.37 (s, 1H), 8.29 (d, J=4.4 Hz, 1H), 8.19 (s, 1H), 8.07-01 (m, 2H), 7.83 (d, J=1.6 Hz, 1H), 3.88 (s, 2H), 3.51 (d, J=12.4 Hz, 2H), 3.31 (t, J=1.6 Hz, 2H), 3.22 (t, J=1.6 Hz, 2H), 3.06 (d, J=12.4 Hz, 2H), 2.92 (s, 3H), 2.72 (s, 3H), 2.51 (t, J=1.6 Hz, 2H), 2.02-1.97 (m, 1H), 1.05-1.04 (m, 2H), 0.95-093 (m, 2H).

Example 80

N-(7-(isopropylthio)isoquinolin-3-yl)cyclopropanecarboxamide

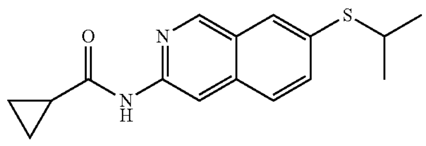

A mixture of N-(7-bromoisoquinolin-3-yl)cyclopropanecarboxamide (725 mg, 2.5 mmol), propane-2-thiol (281 mg, 3.75 mmol), palladium(II) acetate (11.2 mg, 0.05 mmol), 1,1'-bis(diphenylphosphino)ferrocene (33.4 mg, 0.06 mmol) and sodium tert-butoxide (480 mg, 5.0 mmol) in dioxane (5 mL) was stirred at 100° C. overnight under nitrogen. The reaction mixture was diluted with ethyl acetate (10 mL) and filtered. The solid was extracted with ethyl acetate (20 mL×3). The organic layer was combined, dried with sodium sulfate, filtered and concentrated in vacuo. It was purified by prep-HPLC to give the product (130 mg, 19%). LCMS (ESI): $R_T$ (Min)=1.285, M+H =286.9, method=A; $^1H$ NMR (MeOD-$d_4$, 400 MHz): δ 8.96 (s, 1H), 8.36 (s, 1H), 7.96 (t, J=0.8 Hz, 1H), 7.75 (d, J=8.8 Hz, 1H), 7.65 (dd, J=2.0, 8.8 Hz, 1H), 3.59-3.55 (m, 1H), 1.93-1.91 (m, 1H), 1.33 (d, J=6.4 Hz, 6H), 1.01-0.99 (m, 2H), 0.91-0.89 (m, 2H).

Example 81

N-(7-(isopropylsulfinyl)isoquinolin-3-yl)cyclopropanecarboxamide and N-(7-(isopropylsulfonyl)isoquinolin-3-yl)cyclopropanecarboxamide

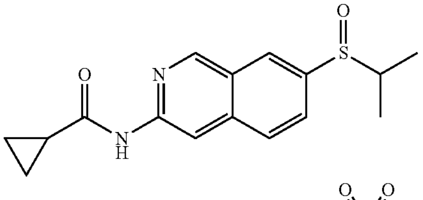

and

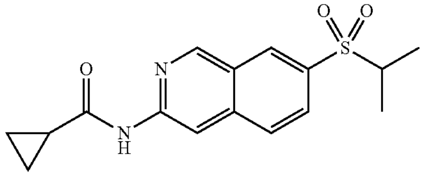

To a solution of N-(7-(isopropylthio)isoquinolin-3-yl)cyclopropanecarboxamide (see, Example 80) (85.8 mg, 0.35 mmol) in methanol (15 mL) was added a solution of Oxone (1 eq) in water (15 mL) at 0° C. It was warmed to room temperature and stirred for 5 hours. The reaction mixture was concentrated under reduced pressure and purified by prep-TLC to give the products N-(7-(isopropylsulfinyl)isoquinolin-3-yl)cyclopropanecarboxamide (26.1 mg, 24.7%) and N-(7-(isopropylsulfonyl)isoquinolin-3-yl)cyclopropanecarboxamide (28.1 mg, 25.2%).

N-(7-(isopropylsulfinyl)isoquinolin-3-yl)cyclopropanecarboxamide: LCMS (ESI): $R_T$ (Min) =1.011, $M+H^+$= 302.9, method=A; $^1H$ NMR (400 MHz, $CDCl_3$) δ 9.00 (s, 1H), 8.54 (s, 1H), 8.43 (s, 1H), 8.15 (t, J=0.8 Hz, 1H), 7.83 (d, J=8.8 Hz, 1H), 7.62 (dd, J=1.6, 8.8 Hz, 1H), 2.89-2.85 (m, 1H), 1.58-1.56 (m, 1H), 1.24-1.22 (m, 3H), 1.11-1.08 (m, 5H), 0.90-0.86 (m, 2H).

N-(7-(isopropylsulfonyl)isoquinolin-3-yl)cyclopropanecarboxamide: LCMS (ESI): $R_T$ (min)=1.090, $M+H^+$=318.9, method=A; $^1H$ NMR (400 MHz, $CDCl_3$) δ 9.12 (s, 1H), 8.65 (s, 1H), 8.50-8.47 (m, 2H), 7.99-7.91 (m, 2H), 3.31-3.24 (m, 1H), 1.66-1.64 (m, 1H), 1.35 (d, J=6.8 Hz, 6H), 1.19-1.15 (m, 2H), 0.99-0.96 (m, 2H).

Example 82

N-(7-(2-hydroxyethylamino)isoquinolin-3-yl)cyclopropanecarboxamide

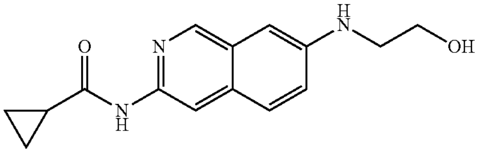 [SMILES: O=C(Nc1cc2ccc(NCCO)cc2cn1)C1CC1]

N-(7-bromoisoquinolin-3-yl)cyclopropanecarboxamide (150 mg, 0.51 mmol), copper(I) iodide (96 mg, 0.51 mmol), 1,10-phenanthroline (100 mg, 0.51 mmol) and cesium carbonate (216 mg, 0.66 mmol) were combined in a stainless steel container with 2-aminoethanol (3.0 mL). The resulting mixture was stirred at 120-140° C. for 12 hours under nitrogen. The reaction mixture was concentrated and purified via TLC to afford the desired product (23.4 mg, 17%). LCMS (ESI): $R_T$ (Min)=0.959, $M+H^+$=271.8, method=A; $^1H$ NMR (400 MHz, DMSO-$d_6$) δ 10.56 (s, 1H), 8.75 (s, 1H), 8.19 (s, 1H), 7.53 (d, J=8.8 Hz, 1H), 7.19 (d, J=8.0 Hz, 1H), 6.77 (s, 1H), 6.00 (s, 1H), 4.74 (s, 1H), 3.61 (d, J=5.6 Hz, 2H), 3.17 (d, J=4.8 Hz, 2H), 1.99-1.95 (m, 1H), 0.79-0.75 (m, 4H).

Example 83

2-(3-bromo-4-methylphenyl)propan-2-ol

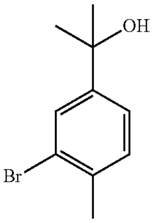

Methylmagnesium chloride (3.0M solution in tetrahydrofuran, 2.9 mL) was added dropwise to a solution of methyl 3-bromo-4-methylbenzoate (500 mg, 2.0 mmol) in tetrahydrofuran (9 mL) cooled at −78° C. The reaction mixture was stirred at this temperature for 15 minutes, warmed to −15° C. for 30 minutes, and then quenched with a few drops of saturated aqueous ammonium chloride solution. The reaction mixture was diluted with ethyl acetate (50 mL) and washed with water (50 mL). The organic layer was separated, dried over sodium sulfate, filtered, and evaporated in vacuo to afford a residue that was purified by flash chromatography (silica, 12 g, ISCO, 0-50% ethyl acetate in heptane) to afford the title compound as a colorless oil (400 mg, 80%). $^1H$ NMR (400 MHz, $CDCl_3$) δ 7.66 (s, 1H), 7.30 (d, J=7.8 Hz, 1H), 7.19 (d, J=7.9 Hz, 1H), 2.38 (s, 3H), 1.55 (d, J=6.5 Hz, 6H).

Example 84

(3-bromopyridin-2-yl)methanol

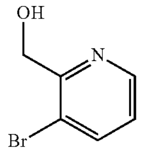

Step 1: 3-bromo-2-methylpyridine 1-oxide

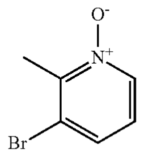

A mixture of 3-bromo-2-methylpyridine (0.14 mL, 1.2 mmol) and m-chloroperbenzoic acid (420 mg, 1.8 mmol) in methylene chloride (4 mL) was stirred at room temperature for 16 hours. The reaction mixture was diluted with ethyl acetate (50 mL) and washed with saturated aqueous sodium bicarbonate solution (20 mL). The organic layer was separated, dried over sodium sulfate, filtered, and evaporated in vacuo to afford a residue that was purified by flash chromatography (silica, 4 g, ISCO, 0-10% methanol in dichloromethane) to afford the title compound as a white solid (140 mg, 61%), which was used in the next step without further purification.

Step 2: (3-bromopyridin-2-yl)methanol

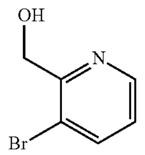

Trifluoroacetic anhydride (0.52 mL, 3.6 mmol) was added to a solution of 3-bromo-2-methylpyridine 1-oxide (140 mg, 0.72 mmol) in methylene chloride (2 mL) and the mixture was stirred for 16 hours at room temperature. The reaction mixture was diluted with ethyl acetate (50 mL) and washed with saturated aqueous sodium bicarbonate solution (20 mL). The organic layer was separated, dried over sodium sulfate, filtered, and evaporated in vacuo to afford a residue that was purified by flash chromatography (silica, 4 g, ISCO, 0-75% ethyl acetate in heptane) to afford the title compound as a yellow oil (110 mg, 75%). $^1$H NMR (400 MHz, DMSO) δ 8.56 (d, J =4.7 Hz, 1H), 8.10 (dd, J=8.0, 1.1 Hz, 1H), 7.32 (dd, J=8.0, 4.7 Hz, 1H), 4.64 (s, 2H); OH peak not observed.

Example 84B 2-bromo-3-methylpyridine 1-oxide

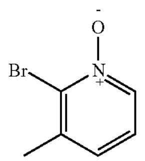

A mixture of 2-bromo-3-methyl-pyridine (1000 mg, 5.81 mmol) and 3-chloroperoxybenzoic acid (2150 mg, 8.72 mmol) in dichloromethane (8 mL) was stirred overnight at room temperature. The reaction mixture was diluted with DCM (50 mL) and washed with saturated aqueous sodium thiosulfite (10 mL) followed by saturated aqueous sodium bicarbonate (10 mL). The organic layer was separated, dried over sodium sulfate, filtered and concentrated in vacuo to provide a residue that was purified by flash chromatography (4 g, Silica, 0-10% methanol in DCM). Desired fractions were combined and evaporated in vacuo to afford the title compound as white solid (851 mg, 78%), which was used in the next step without further purification.

Example 84C 3-bromo-4-methylpyridine 1-oxide

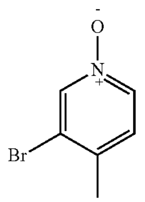

The title compound was prepared following a procedure similar to the one as described I Example 84B using 3-bromo-4-methylpyridine.

Example 85

(3-bromo-4-methylpyridin-2-yl)methanol

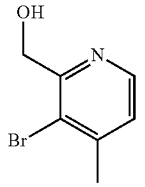

The title compound was prepared following a procedure similar to the procedure of example 84 using 3-bromo-2,4-dimethylpyridine in step 1.

Example 86

(3-bromopyridin-4-yl)methanol

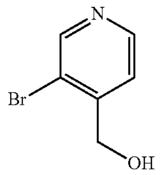

Diisobutylaluminum hydride (1.0M solution in tetrahydrofuran, 14 mL) was added to a solution of methyl 3-bromoisonicotinate (1.0 g, 4.6 mmol) in methylene chloride (15 mL) cooled at −15° C. After 1 hour at this temperature, the reaction was quenched by dropwise addition of saturated aqueous ammonium chloride solution (3 mL). The reaction mixture was diluted with ethyl acetate (50 mL) and washed with 1.0M citric acid solution in water (20 mL). The organic layer was separated, and the aqueous layer was neutralized via addition of solid sodium bicarbonate solution and then extracted with ethyl acetate (50 mL). The combined organic portions were dried over sodium sulfate, filtered, and evaporated in vacuo to afford a residue that was purified by flash chromatography (silica, 4 g, ISCO, 0-75% ethyl acetate in heptane) to afford the title compound as a white solid (110 mg, 75%), which was used in the next step without further purification.

Example 87

N-(7-(2-cyano-5-hydroxyphenyl)isoquinolin-3-yl)cyclopropanecarboxamide

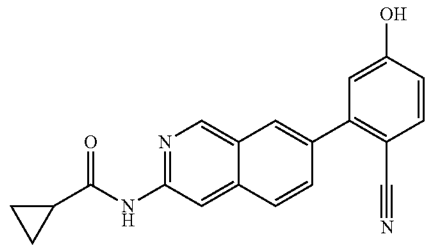 [SMILES: N#Cc1ccc(O)cc1-c1ccc2cc(NC(=O)C3CC3)ncc2c1]

A mixture of N-(7-(4,4,5,5-tetramethyl-1,3,2-dioxaborolan-2-yl)isoquinolin-3-yl)cyclopropanecarboxamide (48 mg, 0.1 mmol), 2-chloro-4-hydroxybenzonitrile (45 mg, 0.3 mmol), bis(di-tert-butyl(4-dimethylaminophenyl)phosphine)dichloropalladium(II) (10 mg, 0.015 mmol), and saturated aqueous sodium carbonate (0.1 mL) in acetonitrile (1 mL) was heated under microwave irradiation (Biotage, 200 watts) at 120° C. for 20 minutes. The cooled reaction mixture was diluted with ethyl acetate (50 mL) and washed with water (50 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as an off-white solid (30 mg, 60%). $^1$H NMR (400 MHz, DMSO) δ 10.98 (s, 1H), 10.95-10.68 (brs, 1H), 9.23 (s, 1H), 8.52 (s, 1H), 8.22 (s, 1H), 7.99 (d, J=8.6 Hz, 1H), 7.84 (d, J=8.6 Hz, 1H), 7.80 (d, J=8.5 Hz, 1H), 7.03 (d, J=2.1 Hz, 1H), 6.97 (dd, J=8.5, 2.2 Hz, 1H), 2.14-2.03 (m, 1H), 0.94-0.77 (m, 4H). LCMS (Method E): $R_T$=4.137 min, M+H$^+$=330.1.

Example 88

N-(7-(6-formyl-4-methylpyridin-3-yl)isoquinolin-3-yl)cyclopropanecarboxamide

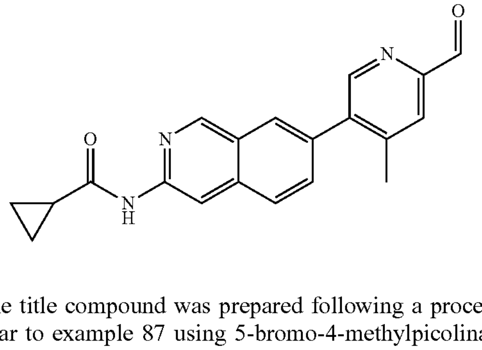

The title compound was prepared following a procedure similar to example 87 using 5-bromo-4-methylpicolinaldehyde, and was used in subsequent steps without further purification.

Example 89

N-(7-(6-(hydroxymethyl)-4-methylpyridin-3-yl)isoquinolin-3-yl)cyclopropanecarboxamide

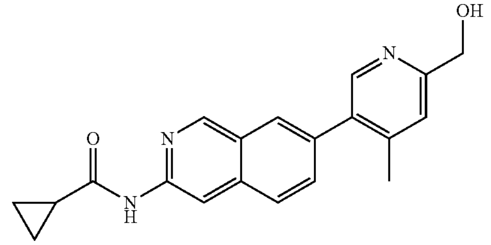 [SMILES: Cc1cc(CO)ncc1-c1ccc2cc(NC(=O)C3CC3)ncc2c1]

Sodium tertrahydroborate (10 mg, 0.27 mmol) was added to a solution of N-(7-(6-formyl-4-methylpyridin-3-yl)isoquinolin-3-yl)cyclopropanecarboxamide (45 mg, 0.14 mmol) in tetrahydrofuran (0.8 mL) cooled at 0° C. After 15 minutes, the reaction mixture was quenched with a few drops of water, diluted ethyl acetate (50 mL) and washed with water (50 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as an off-white solid (26 mg, 60%). $^1$H NMR (400 MHz, DMSO) δ 10.92 (s, 1H), 9.14 (s, 1H), 8.51 (s, 1H), 8.48 (d, J=5.0 Hz, 1H), 7.94 (m, 2H), 7.56 (d, J=8.5 Hz, 1H), 7.33 (d, J=5.0 Hz, 1H), 4.85 (t, J=5.3 Hz, 1H), 4.25 (d, J=5.2 Hz, 2H), 2.08 (m, 4H), 0.85 (m, 4H). LCMS (Method H): $R_T$=2.40 min, M+H$^+$=334.1.

Example 90

N-(7-(6-(2-hydroxypropan-2-yl)-4-methylpyridin-3-yl)isoquinolin-3-yl)cyclopropanecarboxamide

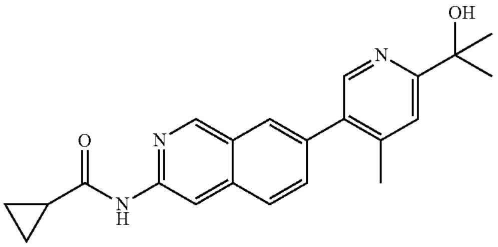 [SMILES: Cc1cc(C(C)(C)O)ncc1-c1ccc2cc(NC(=O)C3CC3)ncc2c1]

Step 1: N-(7-(6-chloro-4-methylpyridin-3-yl)isoquinolin-3-yl)cyclopropanecarboxamide

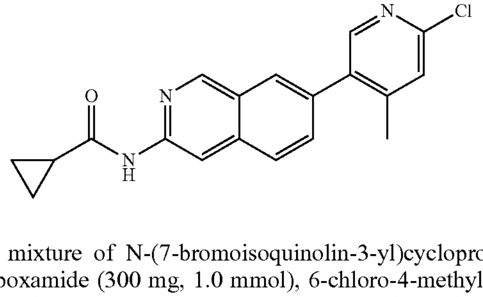

A mixture of N-(7-bromoisoquinolin-3-yl)cyclopropanecarboxamide (300 mg, 1.0 mmol), 6-chloro-4-methylpyridin-3-ylboronic acid (350 mg, 2.1 mmol), bis(di-tert-butyl(4-dimethylaminophenyl)phosphine)dichloropalladium(II) (56 mg, 0.08 mmol), and saturated aqueous sodium carbonate (0.5 mL) in acetonitrile (5 mL) was heated under microwave irradiation (Biotage, 200 watts) at 120° C. for 20 minutes. The cooled reaction mixture was diluted with ethyl acetate (50 mL) and washed with water (50 mL). The organic layer was separated, dried over sodium sulfate, filtered, and evaporated in vacuo to afford a residue that was purified by flash chromatography (silica, 12 g, ISCO, 0-75% ethyl acetate in heptane) to afford the title compound as an off-white solid (285 mg, 80%), which was used in the next step without further purification.

Step 2: methyl 5-(3-(cyclopropanecarboxamido)isoquinolin-7-yl)-4-methylpicolinate

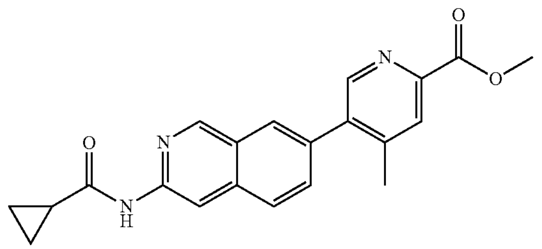 [SMILES: COC(=O)c1cc(C)c(-c2ccc3cc(NC(=O)C4CC4)ncc3c2)cn1]

A mixture of N-(7-(6-chloro-4-methylpyridin-3-yl)isoquinolin-3-yl)cyclopropanecarboxamide (50 mg, 0.1 mmol), palladium acetate (2 mg, 0.007 mmol), 1,3-bis(dicyclohexylphosphino)propane bis(tetrafluoroborate) (9 mg, 0.014 mmol), potassium carbonate (29 mg, 0.21 mmol), methanol (0.1 mL), and N,N-dimethylformamide (1 mL) was purged with nitrogen and evacuated (3×), flushed with carbon monoxide and evacuated (2×), and then left under a carbon monoxide balloon and heated at 100° C. for 2 hours. The cooled reaction mixture was diluted with ethyl acetate (50 mL) and washed with water (100 mL). The organic layer was separated, dried over sodium sulfate, filtered, and evaporated in vacuo to afford a residue that was purified by flash chromatography (silica, 4 g, ISCO, 0-60% ethyl acetate in heptane) to afford the title compound as a white solid (40 mg, 70%), which was used in the next step without further purification.

Step 3: N-(7-(6-(2-hydroxypropan-2-yl)-4-methylpyridin-3-yl)isoquinolin-3-yl)cyclopropanecarboxamide

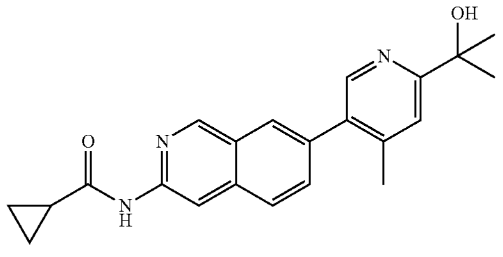 [SMILES: Cc1cc(C(C)(C)O)ncc1-c1ccc2cc(NC(=O)C3CC3)ncc2c1]

Methylmagnesium chloride (3.0M solution in tetrahydrofuran, 0.15 mL) was added dropwise to a solution of methyl 5-(3-(cyclopropanecarboxamido)isoquinolin-7-yl)-4-methylpicolinate (40 mg, 0.1 mmol) in tetrahydrofuran (1 mL) cooled at −15° C. The reaction mixture was stirred at this temperature for 15 minutes, warmed to −15° C. for 30 minutes, and then quenched with a few drops of saturated aqueous ammonium chloride solution. The reaction mixture was diluted with ethyl acetate (50 mL) and washed with water (50 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as an off-white solid (20 mg, 50%). $^1$H NMR (400 MHz, DMSO) δ 10.92 (s, 1H), 9.18 (s, 1H), 8.51 (s, 1H), 8.40 (s, 1H), 8.07 (s, 1H), 7.94 (d, J=8.6 Hz, 1H), 7.74 (d, J=8.5 Hz, 1H), 7.64 (s, 1H), 5.23 (s, 1H), 2.33 (s, 3H), 2.14-2.02 (m, 1H), 1.49 (s, 6H), 0.90-0.79 (m, 4H). LCMS (Method E): $R_T$=3.341 min, M+H$^+$=362.2.

Example 91

N-(7-(6-(hydroxy($^2H_2$)methyl)-4-methylpyridin-3-yl)isoquinolin-3-yl)cyclopropanecarboxamide

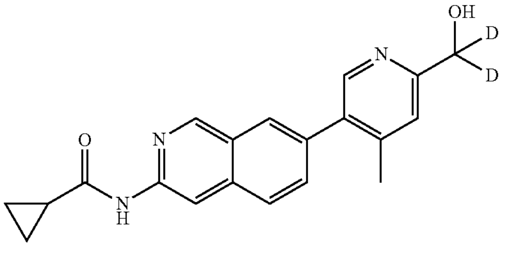 [SMILES: [2H]C([2H])(O)c1cc(C)c(-c2ccc3cc(NC(=O)C4CC4)ncc3c2)cn1]

The title compound was prepared following a procedure similar to step 3 in example 90 using lithium aluminum deuteride (1.0M solution in tetrahydrofuran).

$^1$H NMR (400 MHz, DMSO) δ 10.92 (s, 1H), 9.19 (s, 1H), 8.51 (s, 1H), 8.39 (s, 1H), 8.06 (s, 1H), 7.95 (d, J=8.6 Hz, 1H), 7.73 (dd, J=8.5, 1.6 Hz, 1H), 7.45 (s, 1H), 5.37 (s, 1H), 2.34 (s, 3H), 2.12-2.03 (m, 1H), 0.91-0.78 (m, 4H). LCMS (Method G): $R_T$=5.57 min, M+H$^+$=336.0.

Example 92

1-(5-bromo-4-methylpyridin-2-yl)-2,2,2-trifluoroethanol

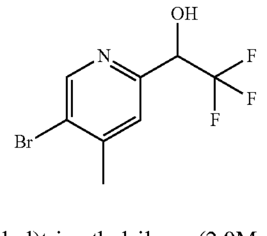

(Trifluoromethyl)trimethylsilane (2.0M solution in tetrahydrofuran, 0.75 mL) was added to a solution of 5-bromo-4-methylpicolinaldehyde (150 mg, 0.75 mmol). The mixture was cooled at 0° C. and tetra-N-butylammonium fluoride (1.0M solution in tetrahydrofuran, 2.2 mL) was added dropwise over 2 minutes. The reaction mixture was allowed to warm to room temperature and was stirred for 16 hours. The reaction mixture was diluted with ethyl acetate (50 mL) and washed with water (50 mL). The organic layer was separated, dried over sodium sulfate, filtered, and evaporated in vacuo to afford a residue that was purified by flash chromatography (silica, 4 g, ISCO, 0-50% ethyl acetate in heptane) to afford the title compound as a pale yellow solid (170 mg, 84%). $^1$H NMR (400 MHz, $CDCl_3$) δ 8.65 (s, 1H), 7.29 (s, 1H), 5.04 (d, J=7.2 Hz, 1H), 4.95 (p, J=6.7 Hz, 1H), 2.46 (s, 3H).

Example 93

(S)-N-(7-(4-methyl-6-(2,2,2-trifluoro-1-hydroxy-ethyl)pyridin-3-yl)isoquinolin-3-yl)cyclopropanecarboxamide and (R)-N-(7-(4-methyl-6-(2,2,2-trifluoro-1-hydroxyethyl)pyridin-3-yl)isoquinolin-3-yl)cyclopropanecarboxamide

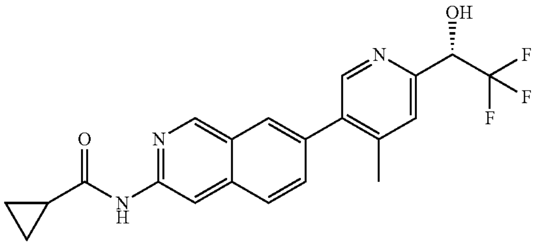

and

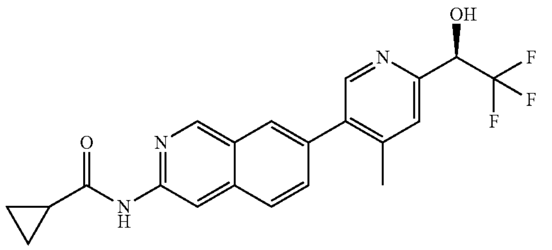

The title compounds were prepared as a racemic mixture following a procedure similar to example 87 using 1-(5-bromo-4-methylpyridin-2-yl)-2,2,2-trifluoroethanol, and then separated via chiral supercritical fluid chromotagraphy.

Enantiomer 1:

$^1$H NMR (400 MHz, DMSO) δ 10.93 (s, 1H), 9.19 (s, 1H), 8.51 (d, J=9.1 Hz, 2H), 8.11 (s, 1H), 7.96 (d, J=8.5 Hz, 1H), 7.77 (d, J=8.4 Hz, 1H), 7.61 (s, 1H), 7.03 (d, J=5.2 Hz, 1H), 5.15 (m, 1H), 2.37 (s, 3H), 2.08 (m, 1H), 0.93-0.77 (m, 4H). LCMS (Method E): $R_T$=4.146 min, M+H$^+$=402.1.

Enantiomer 2:

$^1$H NMR (400 MHz, DMSO) δ 10.94 (s, 1H), 9.19 (s, 1H), 8.52 (s, 1H), 8.50 (s, 1H), 8.12 (s, 1H), 7.96 (d, J=8.5 Hz, 1H), 7.77 (d, J=8.5 Hz, 1H), 7.61 (s, 1H), 7.03 (d, J=5.5 Hz, 1H), 5.23-5.05 (m, 1H), 2.37 (s, 3H), 2.08 (m, 1H), 0.92-0.77 (m, 4H). LCMS (Method E): $R_T$=4.146 min, M+H$^+$=402.1.

Example 94

5-(3-(cyclopropanecarboxamido)isoquinolin-7-yl)-N,4-dimethylpicolinamide

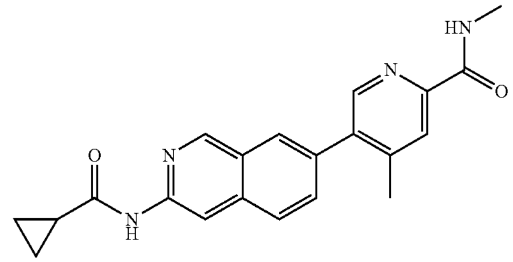 [SMILES: CNC(=O)c1cc(C)c(-c2ccc3cc(NC(=O)C4CC4)ncc3c2)cn1]

A mixture of N-(7-(6-chloro-4-methylpyridin-3-yl)isoquinolin-3-yl)cyclopropanecarboxamide (50 mg, 0.1 mmol), palladium acetate (2 mg, 0.007 mmol), 1,3-bis(dicyclohexylphosphino)propane bis(tetrafluoroborate) (9 mg, 0.014 mmol), potassium carbonate (29 mg, 0.21 mmol), methylamine (2.0M solution in tetrahydrofuran, 0.74 mL), and N,N-dimethylformamide (1 mL) was purged with nitrogen and evacuated (3×), flushed with carbon monoxide and evacuated (2×), and then left under a carbon monoxide balloon and heated at 100° C. for 2 hours. The cooled reaction mixture was diluted with ethyl acetate (50 mL) and washed with water (100 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as an off-white solid (25 mg, 50%). $^1$H NMR (400 MHz, DMSO) δ 10.94 (s, 1H), 9.21 (s, 1H), 8.79 (m, 1H), 8.54 (s, 1H), 8.52 (s, 1H), 8.14 (s, 1H), 8.03 (s, 1H), 7.98 (d, J=8.6 Hz, 1H), 7.78 (d, J=8.7 Hz, 1H), 2.85 (d, J=4.8 Hz, 3H), 2.41 (s, 3H), 2.14-2.03 (m, 1H), 0.92-0.78 (m, 4H). LCMS (Method E): $R_T$=4.054 min, M+H$^+$=361.1.

Example 95

N-(7-(5-fluoro-6-(hydroxymethyl)-4-methylpyridin-3-yl)isoquinolin-3-yl)cyclopropanecarboxamide

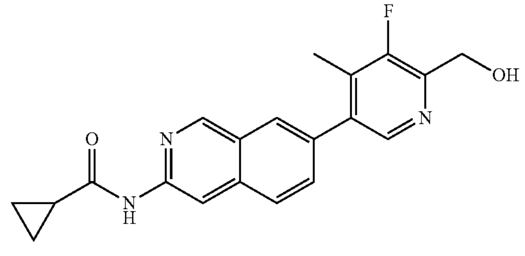 [SMILES: Cc1c(-c2ccc3cc(NC(=O)C4CC4)ncc3c2)cnc(CO)c1F]

Step 1: methyl 5-(3-(cyclopropanecarboxamido)isoquinolin-7-yl)-3-fluoro-4-methylpicolinate

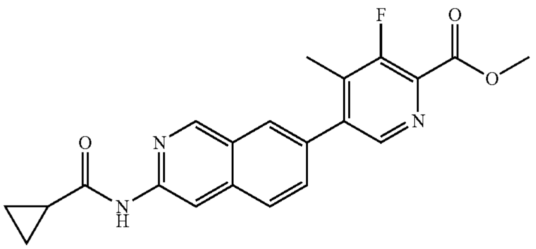 [SMILES: COC(=O)c1ncc(-c2ccc3cc(NC(=O)C4CC4)ncc3c2)c(C)c1F]

The title compound was prepared following a procedure similar to steps 1-2 in example 90 using 2-chloro-3-fluoro-5-iodo-4-methylpyridine in step 1, and was used in subsequent step without further purification.

Step 2: N-(7-(5-fluoro-6-(hydroxymethyl)-4-methylpyridin-3-yl)isoquinolin-3-yl)cyclopropanecarboxamide

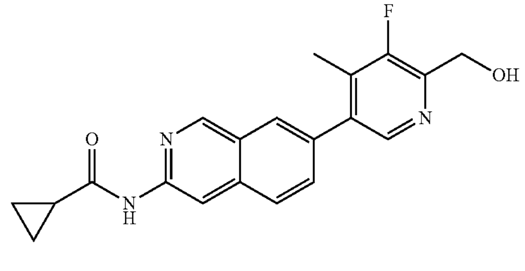 [SMILES: Cc1c(-c2ccc3cc(NC(=O)C4CC4)ncc3c2)cnc(CO)c1F]

Diisobutylaluminum hydride (1.0M solution in tetrahydrofuran, 0.73 mL) was added dropwise to a solution of methyl 5-(3-(cyclopropanecarboxamido)isoquinolin-7-yl)-3-fluoro-4-methylpicolinate (60 mg, 1.8 mmol) in methylene chloride (1.5 mL) cooled at −15° C. After 1 hour at this temperature, the reaction was quenched by dropwise addition of saturated aqueous ammonium chloride solution (3 mL). The reaction mixture was diluted with ethyl acetate (50 mL) and washed with 1.0M citric acid solution in water (20 mL). The organic layer was separated, and the aqueous layer was neutralized via addition of solid sodium bicarbonate solution and then extracted with ethyl acetate (50 mL). The combined organic portions were dried over sodium sulfate, filtered, and evaporated in vacuo to afford a residue that was purified by reverse phase HPLC (5-85% acetonitrile in water with 0.1% formic acid over 14 min) to afford the title compound as an off-white solid (15 mg, 23%). $^1$H NMR (400 MHz, DMSO) 10.94 (s, 1H), 9.21 (s, 1H), 8.52 (s, 1H), 8.35 (s, 1H), 8.11 (s, 1H), 7.98 (d, J=8.6 Hz, 1H), 7.75 (d, J=8.6 Hz, 1H), 5.31 (s, 1H), 4.65 (s, 2H), 2.26 (s, 3H), 2.12-2.04 (m, 1H), 0.91-0.80 (m, 4H). LCMS (Method G): $R_T$=7.53 min, M+H$^+$=352.1.

Example 96

(R)-N-(7-(6-(1-hydroxyethyl)-4-methylpyridin-3-yl)isoquinolin-3-yl)cyclopropanecarboxamide and (S)-N-(7-(6-(1-hydroxyethyl)-4-methylpyridin-3-yl)isoquinolin-3-yl)cyclopropanecarboxamide

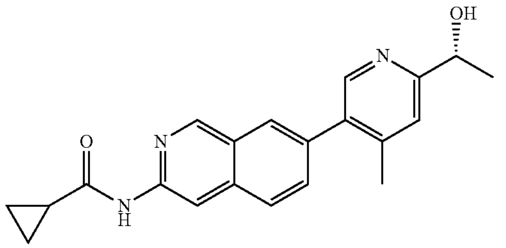

and

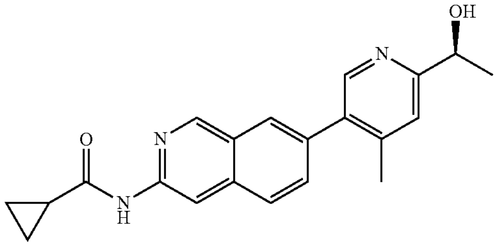

Methylmagnesium chloride (3.0M solution in tetrahydrofuran, 0.14 mL) was added dropwise to a solution of N-(7-(6-formyl-4-methylpyridin-3-yl)isoquinolin-3-yl)cyclopropanecarboxamide (65 mg, 0.2 mmol) in tetrahydrofuran (1 mL) cooled at −15° C. The reaction mixture was stirred at this temperature for 15 minutes, warmed to −15° C. for 30 minutes, and then quenched with a few drops of saturated aqueous ammonium chloride solution. The reaction mixture was diluted with ethyl acetate (50 mL) and washed with water (50 mL). The organic layer was separated, dried over sodium sulfate, filtered, and evaporated in vacuo to afford a residue that was purified by reverse phase HPLC (5-85% acetonitrile in water with 0.1% formic acid over 14 min) to provide a racemic mixture of the two title compounds. This mixture was then separated via chiral supercritical fluid chromotagraphy to yield 20 mg (30%) of one enantiomer and 20 mg (30%) of the other enantiomer.

Enantiomer 1:

$^1$H NMR (400 MHz, DMSO) δ 10.92 (s, 1H), 9.18 (s, 1H), 8.51 (s, 1H), 8.38 (s, 1H), 8.06 (s, 1H), 7.94 (d, J=8.6 Hz, 1H), 7.74 (dd, J=8.5, 1.5 Hz, 1H), 7.48 (s, 1H), 5.35 (d, J=4.7 Hz, 1H), 4.82-4.72 (m, 1H), 2.33 (s, 3H), 2.13-2.03 (m, 1H), 1.42 (d, J=6.5 Hz, 3H), 0.91-0.79 (m, 4H). LCMS (Method E): $R_T$=3.228 min, M+H$^+$=348.2.

Enantiomer 2:

$^1$H NMR (400 MHz, DMSO) δ 10.92 (s, 1H), 9.18 (s, 1H), 8.51 (s, 1H), 8.38 (s, 1H), 8.06 (s, 1H), 7.94 (d, J=8.6 Hz, 1H), 7.74 (dd, J=8.5, 1.5 Hz, 1H), 7.48 (s, 1H), 5.35 (d, J=4.7 Hz, 1H), 4.82-4.72 (m, 1H), 2.33 (s, 3H), 2.13-2.03 (m, 1H), 1.42 (d, J=6.5 Hz, 3H), 0.91-0.79 (m, 4H). LCMS (Method E): $R_T$=3.230 min, M+H$^+$=348.2.

Example 97

(R)-N-(7-(6-(1-hydroxypropyl)-4-methylpyridin-3-yl)isoquinolin-3-yl)cyclopropanecarboxamide and (S)-N-(7-(6-(1-hydroxypropyl)-4-methylpyridin-3-yl)isoquinolin-3-yl)cyclopropanecarboxamide

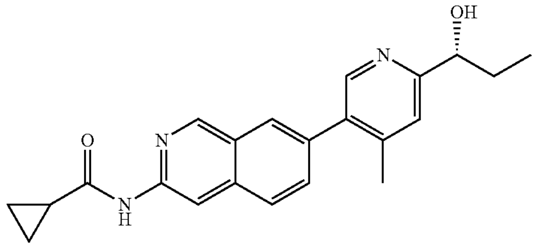

and

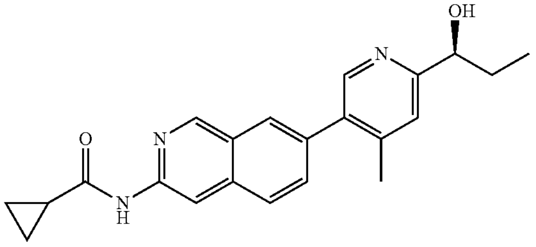

The title compounds were prepared following a procedure similar to example 96 using ethylmagnesium chloride.

Enantiomer 1:

$^1$H NMR (400 MHz, DMSO) δ 10.90 (s, 1H), 9.18 (s, 1H), 8.50 (s, 1H), 8.39 (s, 1H), 8.07 (s, 1H), 7.94 (d, J=8.5 Hz, 1H), 7.74 (d, J=8.6 Hz, 1H), 7.45 (s, 1H), 5.29 (d, J=4.9 Hz, 1H), 4.54 (dd, J=12.1, 4.9 Hz, 1H), 2.08 (m, 1H), 1.91-1.77 (m, 1H), 1.76-1.59 (m, 1H), 0.95-0.78 (m, 7H). LCMS (Method E): $R_T$=3.464 min, M+H$^+$=362.2.

Enantiomer 2:

$^1$H NMR (400 MHz, DMSO) δ 10.90 (s, 1H), 9.18 (s, 1H), 8.50 (s, 1H), 8.39 (s, 1H), 8.07 (s, 1H), 7.94 (d, J=8.5 Hz, 1H), 7.74 (d, J=8.6 Hz, 1H), 7.45 (s, 1H), 5.29 (d, J=4.9 Hz, 1H), 4.54 (dd, J=12.1, 4.9 Hz, 1H), 2.08 (m, 1H), 1.91-1.77 (m,

1H), 1.76-1.59 (m, 1H), 0.95-0.78 (m, 7H). LCMS (Method E): $R_T$=3.422 min, M+$H^+$=362.2.

Example 98

(1S,2S)-2-fluoro-N-(7-(4-methylpyridin-3-yl)isoquinolin-3-yl)cyclopropanecarboxamide

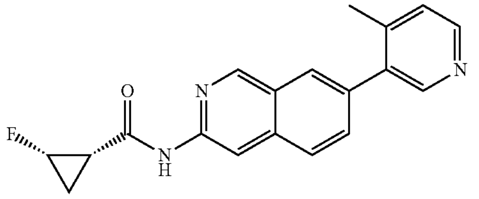 [SMILES: Cc1ccncc1-c1ccc2cc(NC(=O)[C@@H]3C[C@@H]3F)ncc2c1]

A mixture of 7-(4-methylpyridin-3-yl)-isoquinolin-3-amine (350 mg, 1.5 mmol), (1S,2S)-2-fluorocyclopropanecarboxylic acid (232 mg, 2.2 mmol), HATU (1.13 g, 3.0 mmol), and N,N-diisopropylethylamine (0.52 mL, 3.0 mmol) in N,N-dimethylformamide (3 mL) was heated at 70° C. for 3 hours. The cooled reaction mixture was diluted with ethyl acetate (100 mL) and washed with water (50 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as an off-white solid (15 mg, 23%). $^1$H NMR (400 MHz, DMSO) δ 10.97 (s, 1H), 9.20 (s, 1H), 8.53 (s, 1H), 8.50 (s, 1H), 8.49 (d, J=5.0 Hz, 1H), 8.09 (s, 1H), 7.98 (d, J=8.6 Hz, 1H), 7.76 (dd, J=8.5, 1.4 Hz, 1H), 7.40 (d, J=5.0 Hz, 1H), 4.95 (m, 1H), 2.33 (s, 3H), 2.28 (m, 1H), 1.70 (dtd, J=23.2, 6.8, 3.8 Hz, 1H), 1.25-1.14 (m, 1H). LCMS (Method E): $R_T$=3.063 min, M+$H^+$=322.1.

Example 99

(1R,2R)-2-fluoro-N-(7-(4-methylpyridin-3-yl)isoquinolin-3-yl)cyclopropanecarboxamide

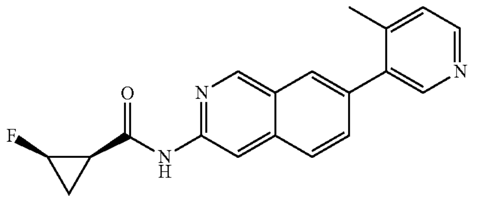

The title compound was prepared following a procedure similar to example 98 using (1R,2R)-2-fluorocyclopropanecarboxylic acid.

$^1$H NMR (400 MHz, DMSO) δ 10.97 (s, 1H), 9.20 (s, 1H), 8.53 (s, 1H), 8.50 (s, 1H), 8.49 (d, J=5.0 Hz, 1H), 8.09 (s, 1H), 7.98 (d, J=8.6 Hz, 1H), 7.76 (dd, J=8.5, 1.6 Hz, 1H), 7.40 (d, J=5.0 Hz, 1H), 4.95 (dtd, J=10.1, 6.2, 3.8 Hz, 1H), 2.33 (s, 3H), 2.28 (m, 1H), 1.70 (m, 1H), 1.20 (m, 1H). LCMS (Method E): $R_T$=3.062 min, M+$H^+$=322.1.

Example 100

N-(7-(4-methylpyridin-3-yl)isoquinolin-3-yl)-3-oxabicyclo[3.1.0]hexane-6-carboxamide

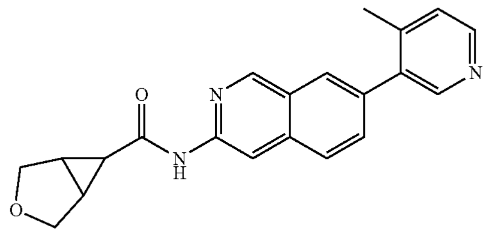 [SMILES: Cc1ccncc1-c1ccc2cc(NC(=O)C3C4COCC43)ncc2c1]

Step 1: 3-oxabicyclo[3.1.0]hexane-6-carboxylic acid

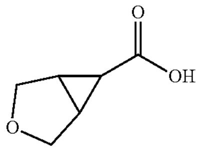

Ethyl diazoacetate (0.5 mL, 5.0 mmol) was added dropwise to a solution of 2,5-dihydrofuran (1.3 g, 19 mmol) and rhodium(II) acetate dimer (100 mg, 0.24 mmol) in methylene chloride (15 mL)—caution: gas evolution. The reaction mixture was stirred for 16 hours at room temperature, and then diluted with methylene chloride (50 mL) and washed with water (50 mL). The organic layer was separated, dried over sodium sulfate, filtered, and evaporated in vacuo to afford a residue that was redissolved in methanol (20 mL) and treated with lithium hydroxide (170 mg, 7.1 mmol). The mixture was stirred at room temperature for 3 hours, and then diluted with methylene chloride (100 mL), 1.0N sodium hydroxide solution in water (15 mL) and water (10 mL). The aqueous layer was separated, acidified to pH 3 via addition of solid citric acid, and then extracted with methylene chloride (100 mL). The organic layer was separated, dried over sodium sulfate, filtered, and evaporated in vacuo to afford a yellow solid that was used in the next step without further purification.

Step 2: N-(7-(4-methylpyridin-3-yl)isoquinolin-3-yl)-3-oxabicyclo[3.1.0]hexane-6-carboxamide (single stereoisomer)

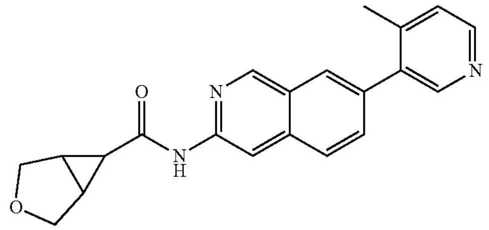 [SMILES: Cc1ccncc1-c1ccc2cc(NC(=O)C3C4COCC43)ncc2c1]

The title compound was prepared following a procedure similar to example 98 using 7-(4-methylpyridin-3-yl)isoquinolin-3-amine and 3-oxabicyclo[3.1.0]hexane-6-carboxylic acid.

$^1$H NMR (400 MHz, DMSO) δ 10.85 (s, 1H), 9.18 (s, 1H), 8.49 (t, J=5.6 Hz, 3H), 8.08 (s, 1H), 7.96 (d, J=8.5 Hz, 1H), 7.75 (dd, J=8.5, 1.5 Hz, 1H), 7.39 (d, J=5.0 Hz, 1H), 3.86 (d, J=8.6 Hz, 2H), 3.69 (d, J=8.4 Hz, 2H), 2.32 (s, 3H), 2.14 (m, 2H), 2.01 (t, J=3.0 Hz, 1H). LCMS (Method E): $R_T$=3.112 min, $M+H^+$=346.1.

Example 101

3-(3-(cyclopropanecarboxamido)isoquinolin-7-yl)-4-methyl-N-(tetrahydro-2H-pyran-4-yl)benzamide

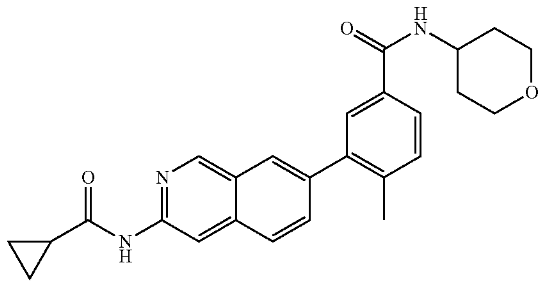 [SMILES: Cc1ccc(C(=O)NC2CCOCC2)cc1-c1ccc2cc(NC(=O)C3CC3)ncc2c1]

The title compound was prepared following a procedure similar to example 20 using tetrahydro-2H-pyran-4-amine.

$^1$H NMR (400 MHz, DMSO) δ 10.91 (s, 1H), 9.20 (s, 1H), 8.51 (s, 1H), 8.28 (d, J=7.7 Hz, 1H), 8.05 (s, 1H), 7.94 (d, J=8.6 Hz, 1H), 7.82 (m, 2H), 7.73 (dd, J=8.5, 1.5 Hz, 1H), 7.44 (d, J=7.8 Hz, 1H), 4.08-3.95 (m, 1H), 3.87 (m/z, 2H), 3.38 (m, 2H), 2.32 (s, 3H), 2.13-2.04 (m, 1H), 1.79-1.71 (m, 2H), 1.57 (m, 2H), 0.90-0.77 (m, 4H). LCMS (Method E): $R_T$=4.275 min, $M+H^+$=430.2.

Example 102

3-(3-(cyclopropanecarboxamido)isoquinolin-7-yl)-4-methyl-N-(oxetan-3-yl)benzamide

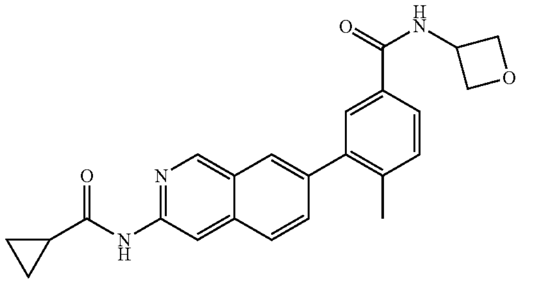 [SMILES: Cc1ccc(C(=O)NC2COC2)cc1-c1ccc2cc(NC(=O)C3CC3)ncc2c1]

The title compound was prepared following a procedure similar to example 20 using oxetan-3-amine hydrochloride.

$^1$H NMR (400 MHz, DMSO) δ 10.91 (s, 1H), 9.20 (s, 1H), 9.08 (d, J=6.4 Hz, 1H), 8.51 (s, 1H), 8.06 (s, 1H), 7.95 (d, J=8.5 Hz, 1H), 7.88 (s, 1H), 7.84 (d, J=7.9 Hz, 1H), 7.74 (d, J=8.5 Hz, 1H), 7.46 (d, J=8.0 Hz, 1H), 5.08-4.95 (m, 1H), 4.76 (t, J=6.9 Hz, 2H), 4.59 (t, J=6.4 Hz, 2H), 2.34 (s, 3H), 2.13-2.03 (m, 1H), 0.93-0.75 (m, 4H). LCMS (Method E): $R_T$=4.097 min, $M+H^+$=402.2.

Example 103

(4-bromo-5-methylpyridin-2-yl)methanol

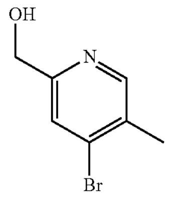

Step 1: 4-bromo-2,5-dimethylpyridine 1-oxide

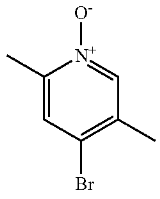

4-Bromo-2,5-dimethylpyridine (500 mg, 2.69 mmol) was added dropwise to a solution of m-chloroperbenzoic acid (816 mg, 3.55 mmol) in dichloromethane (10 mL) at ambient temperature. The mixture was stirred at room temperature for 17 hours, poured into saturated aqueous sodium bicarbonate and sodium sulfite (2 mL, 1.0M), and extracted twice into ethyl acetate. The combined organic phases were washed with brine, dried over sodium sulfate, filtered, and concentrated in vacuo to afford a yellow crystalline solid (413 mg) which was used without further purification. LCMS: $M+H^+$=202 & 204.

Step 2: (4-bromo-5-methylpyridin-2-yl)methanol

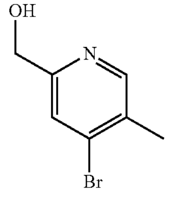

A solution of the crude N-oxide (413 mg) in dichloromethane (2.0 mL) was treated dropwise with trifluoroacetic anhydride (1.14 mL, 8.07 mmol), the mixture stirred at ambient temperature for 3 days and poured into saturated aqueous sodium bicarbonate. The reaction mixture was diluted with ethyl acetate (50 mL) and washed with saturated aqueous sodium bicarbonate. The mixture was extracted twice into dichloromethane and the combined organic phases washed with brine, dried over sodium sulfate, filtered, and concentrated in vacuo. The residue was purified by flash chromatography (silica, ISCO, 10-100% ethyl acetate in heptane) to afford the title compound as a yellow oil (253 mg, 47% over 2 steps). $^1$H NMR (400 MHz, $CDCl_3$) δ 8.35 (s, 1H), 7.47 (s, 1H), 4.71 (s, 2H), 3.26 (br s, 1H), 2.38 (s, 3H). LCMS: $M+H^+$=202 & 204.

Example 104

3-bromo-4-methoxypyridine

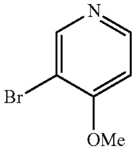

3-Bromo-4-fluoropyridine (253 mg, 1.44 mmol) was suspended in a solution of sodium methoxide in methanol (3.0 mL, 4.6 M, 14 mmol) at ambient temperature, the mixture stirred for 3 days, and then poured into aqueous citric acid (1M) and extracted twice into dichloromethane. The combined organic phases were washed with saturated aqueous sodium bicarbonate, dried over sodium sulfate, filtered and concentrated in vacuo to afford a yellow oil (108 mg, 40%) that was used without further purification. LCMS: M+$H^+$=188 & 190.

Example 105

4-bromo-5-methyl-1H-pyrazolo[3,4-c]pyridine

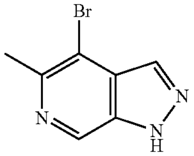

To a solution of 5-bromo-4,6-dimethylpyridin-3-amine (1.00 g, 4.98 mmol) in acetic acid (12 mL) at ambient temperature was added sodium nitrite (364 mg, 5.28 mmol) and the mixture heated to 60° C. for 1.5 hr. The cooled reaction mixture was concentrated in vacuo, the residue partitioned between ethyl acetate and saturated aqueous sodium bicarbonate and the biphasic mixture filtered through a celite pad. The separated aqueous phase was extracted with ethyl acetate, and the combined organic phases washed with brine, dried over sodium sulfate, filtered and concentrated in vacuo. The residue was purified by flash chromatography (silica, ISCO, 10-100% ethyl acetate in heptane) to afford the title compound as a pale brown solid (554 mg, 53%). $^1$H NMR (300 MHz, DMSO) δ 13.91 (s, 1H), 8.95 (s, 1H), 8.14 (s, 1H), 2.67 (s, 3H). LCMS: M+$H^+$=212 & 214.

Example 106

N-(4-methyl-3-(4,4,5,5-tetramethyl-1,3,2-dioxaborolan-2-yl)phenyl)-4-((4-methylpiperazin-1-yl)methyl) benzamide

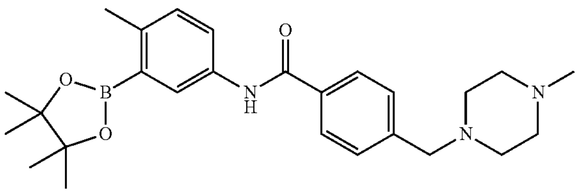

A solution of 5-amino-2-methylphenylboronic acid pinacol ester (1.001 g, 4.294 mmol), 4-((4-methylpiperazin-1-yl) methyl)benzoic acid (1.112 g, 4.746 mmol) and (7-azabenzotriazol-1-yloxy)tripyrrolidinophosphonium hexafluorophosphate (2.446 g, 4.691 mmol) in DMF (20 mL) at ambient temperature was added ethyldiisopropylamine (0.98 mL, 5.6 mmol), the mixture stirred at room temperature for 3d and poured into water (100 ml). The aqueous phase was washed with diethyl ether, treated with saturated aqueous sodium bicarbonate and extracted twice with ethyl acetate. The combined ethyl acetate extracts were washed with brine, dried over sodium sulfate, filtered and concentrated in vacuo. The residue was purified by flash chromatography (silica, ISCO, 10-100% ethyl acetate in heptane, and then 0-20% methanol in DCM modified with 1% ammonia) to afford the title compound as a white solid (456 mg, 24%). $^1$H NMR (400 MHz, $CDCl_3$) δ 7.97 (dd, J=8.2, 2.0 Hz, 1H), 7.80 (d, J=8.1 Hz, 2H), 7.74 (s, 1H), 7.64 (d, J=2.3 Hz, 1H), 7.44 (d, J=8.1 Hz, 2H), 7.19 (d, J=8.3 Hz, 1H), 3.57 (s, 2H), 2.52 (s, 3H), 2.5 (br s, 8H), 2.31 (s, 3H), 1.35 (s, 12H). LCMS: M+$H^+$=450.4.

Example 107

N-(7-(2,5-dimethylphenyl)isoquinolin-3-yl)cyclopropanecarboxamide

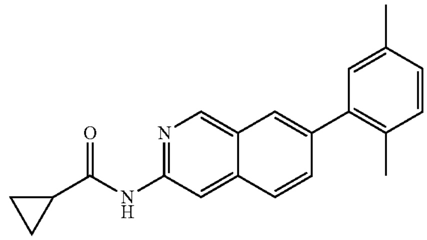 [SMILES: Cc1ccc(C)c(-c2ccc3cc(NC(=O)C4CC4)ncc3c2)c1]

A mixture of N-(7-bromoisoquinolin-3-yl)cyclopropanecarboxamide (49.0 mg, 168 mmol), 2,5-dimethylphenylboronic acid (52.0 mg, 347 woe, bis(di-tert-butyl(4-dimethylaminophenyl)-phosphine)dichloropalladium(II) (7.2 mg, 10 μmol) and aqueous sodium carbonate (1.0 M, 0.5 mL) and acetonitrile (1.5 mL) was heated under microwave irradiation (Biotage, 200 watts) at 120° C. for 10 minutes. The cooled reaction mixture was partitioned between ethyl acetate (20 mL) and water (20 mL), and the separated aqueous phase extracted with ethyl acetate (20 mL). The combined organic phases were washed with brine, dried over sodium sulfate, filtered and concentrated in vacuo to afford a clear oil. The crude residue was purified by reverse phase HPLC (gradient of acetonitrile in water with 0.1% formic acid) to yield the title compound as a white amorphous solid (42.3 mg, 79%). $^1$H NMR (400 MHz, DMSO) δ 10.88 (s, 1H), 9.16 (s, 1H), 8.48 (s, 1H), 7.98 (s, 1H), 7.89 (d, J=8.6 Hz, 1H), 7.68 (dd, J=8.5, 1.7 Hz, 1H), 7.22 (d, J=8.2 Hz, 1H), 7.15-7.11 (m, 2H), 2.33 (s, 3H), 2.23 (s, 3H), 2.12-2.03 (m, 1H), 0.91-0.78 (m, 4H). LCMS (Method E): $R_T$=5.442 min, M+$H^+$=317.1.

Example 108

N-(7-(3,5-dimethylpyridin-4-yl)isoquinolin-3-yl) cyclopropanecarboxamide

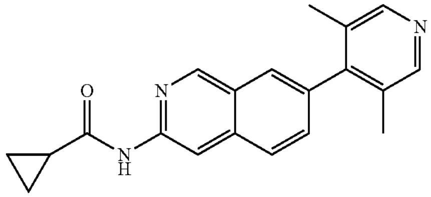 [SMILES: Cc1cncc(C)c1-c1ccc2cc(NC(=O)C3CC3)ncc2c1]

The title compound was prepared following a procedure similar to example 107 using 3,5-dimethyl-4-(4,4,5,5-tetramethyl-1,3,2-dioxaborolan-2-yl)pyridine and heating under microwave irradiation (Biotage, 200 watts) at 130° C. for 30 minutes. The crude residue was purified by reverse phase HPLC (gradient of acetonitrile in water with 0.1% formic acid) to yield the title compound as a white amorphous solid (65.5 mg, 61%). $^1$H NMR (400 MHz, DMSO) δ 10.92 (s, 1H), 9.16 (s, 1H), 8.51 (s, 1H), 8.39 (s, 2H), 7.97 (d, J=8.5 Hz, 1H), 7.90 (s, 1H), 7.52 (dd, J=8.4, 1.4 Hz, 1H), 2.12-2.04 (m, 1H), 2.03 (s, 6H), 0.91-0.79 (m, 4H). LCMS (Method E): $R_T$=3.256 min, M+H$^+$=318.2.

Example 109

N-(7-(2,5-dimethylpyridin-4-yl)isoquinolin-3-yl)cyclopropanecarboxamide

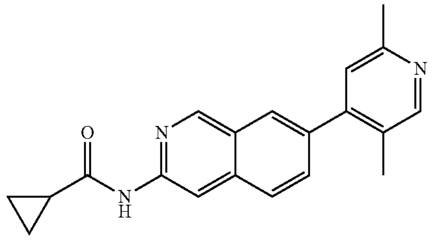 [SMILES: Cc1cc(-c2ccc3cc(NC(=O)C4CC4)ncc3c2)c(C)cn1]

The title compound was prepared following a procedure similar to example 87 using N-(7-(4,4,5,5-tetramethyl-1,3,2-dioxaborolan-2-yl)isoquinolin-3-yl)cyclopropanecarboxamide (201 mg, 594 μmol) and 4-bromo-2,5-dimethylpyridine (166 mg, 891 μmol) and heating under microwave irradiation (Biotage, 200 watts) at 130° C. for 20 minutes. The crude residue was purified by reverse phase HPLC (gradient of acetonitrile in water with 0.1% formic acid) to yield the title compound formate salt as a white amorphous solid (77.5 mg, 36%). $^1$H NMR (400 MHz, DMSO) δ 10.93 (s, 1H), 9.20 (s, 1H), 8.51 (s, 1H), 8.41 (s, 1H), 8.14 (s, 1H), 8.09 (s, 1H), 7.95 (d, J=8.5 Hz, 1H), 7.73 (d, J=8.5 Hz, 1H), 7.23 (s, 1H), 2.26 (s, 3H), 2.09 (s, 1H), 0.92-0.79 (m, 4H); obscured (s, 3H). $^1$H NMR (400 MHz, CD3CN) δ 9.10 (s, 1H), 9.04 (s, 1H), 8.58 (s, 1H), 8.43 (s, 1H), 8.08 (s, 1H), 7.98 (s, 1H), 7.96 (d, J=8.6 Hz, 1H), 7.70 (d, J=8.6 Hz, 1H), 7.20 (s, 1H), 2.54 (s, 3H), 2.29 (s, 3H), 1.95-1.85 (m, 1H), 1.05-0.96 (m, 2H), 0.96-0.86 (m, 2H). LCMS (Method E): $R_T$=3.278 min, M+H$^+$=318.1.

Example 110

N-(7-(1H-benzo[d]imidazol-4-yl)isoquinolin-3-yl)cyclopropanecarboxamide

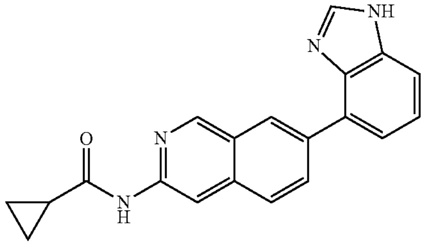 [SMILES: O=C(Nc1cc2ccc(-c3cccc4[nH]cnc34)cc2cn1)C1CC1]

The title compound was prepared following a procedure similar to example 87 using N-(7-(4,4,5,5-tetramethyl-1,3,2-dioxaborolan-2-yl)isoquinolin-3-yl)cyclopropanecarboxamide (106 mg, 314 μmol) and 4-bromo-1H-benzimidazole (91.3 mg, 463 μmol) and heating under microwave irradiation (Biotage, 200 watts) at 120° C. for 10 minutes. The crude residue was purified by reverse phase HPLC (gradient of acetonitrile in water with 0.1% formic acid) to yield the title compound formate salt as a white amorphous solid (63.3 mg, 54%). $^1$H NMR (400 MHz, MeOD) δ 9.14 (s, 1H), 8.47 (s, 1H), 8.42 (s, 1H), 8.30 (s, 1H, formate), 8.22 (s, 1H), 8.13 (d, J=8.4 Hz, 1H), 7.95 (d, J=8.6 Hz, 1H), 7.66 (d, J=8.0 Hz, 1H), 7.50 (d, J=7.3 Hz, 1H), 7.41 (t, J=7.7 Hz, 1H), 2.01-1.91 (m, 1H), 1.07-1.01 (m, 2H), 0.96-0.88 (m, 2H). LCMS (Method E): $R_T$=3.441 min, M+H$^+$=329.2.

Example 111

1-ethyl-3-(7-(5-fluoro-2-methylphenyl)isoquinolin-3-yl)urea

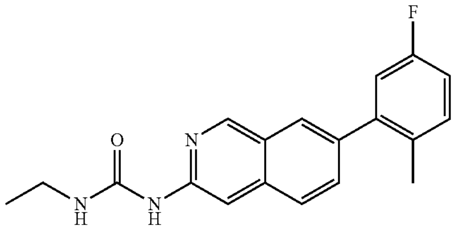 [SMILES: CCNC(=O)Nc1cc2ccc(-c3cc(F)ccc3C)cc2cn1]

A mixture of 7-(5-fluoro-2-methylphenyl)isoquinolin-3-amine (51.3 mg, 203 μmol) and ethyl isocyanate (20 uL, 0.26 mmol) in dichloromethane (2.0 mL) was heated at 40° C. for 4 days. The cooled mixture was treated with pyridine (20 uL, 0.25 mmol) and a further portion of ethyl isocyanate (20 uL, 0.26 mmol) at 40° C. for 24 h and concentrated in vacuo, and the residue purified by reverse phase HPLC (gradient of acetonitrile in water with 0.1% formic acid) to yield the title compound as a white amorphous solid (54.6 mg, 83%). $^1$H NMR (400 MHz, DMSO) δ 9.07 (s, 2H), 8.09 (s, 1H), 7.97 (s, 1H), 7.84 (d, J=8.5 Hz, 1H), 7.65 (d, J=8.4 Hz, 1H), 7.37 (t, J=7.2 Hz, 1H), 7.20-7.12 (m, 2H), 7.06-7.00 (s, 1H), 3.19 (dq, J=7, 7 Hz, 2H), 2.25 (s, 3H), 1.10 (t, J=7.2 Hz, 3H). LCMS (Method E): $R_T$=4.885 min, M+H$^+$=324.1.

Example 112

N-(4-bromo-7-(5-fluoro-2-methylphenyl)isoquinolin-3-yl)cyclopropanecarboxamide

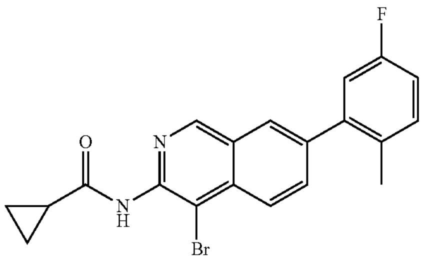 [SMILES: Cc1ccc(F)cc1-c1ccc2c(Br)c(NC(=O)C3CC3)ncc2c1]

4-bromo-7-(5-fluoro-2-methylphenyl)isoquinolin-3-amine

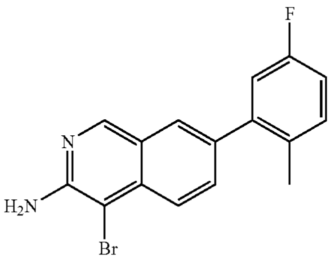 [SMILES: Cc1ccc(F)cc1-c1ccc2c(Br)c(N)ncc2c1]

7-(5-Fluoro-2-methylphenyl)isoquinolin-3-amine (51.3 mg, 203 mol) and N-bromosuccinimde (36.4 mg, 204 μmol) were dissolved together in methanol (2.0 mL) at ambient temperature. After 10 mins the mixture was poured into water and saturated aqueous sodium bicarbonate (1 mL), extracted twice into dichloromethane. The combined organic phases were washed with brine containing sodium thiosulfate (1 mL, 1M), dried over sodium sulfate, filtered and concentrated in vacuo to afford a residue that was purified by flash chromatography (silica, ISCO, 0-10% methanol in dichloromethane) to yield the title compound as a white solid (46.3 mg, 69%). 1H NMR (400 MHz, $CDCl_3$) δ 8.79 (s, 1H), 7.92 (t, J=9 Hz, 1H), 7.71 (s, 1H), 7.59 (d, J=9 Hz, 1H), 7.27-7.22 (m, 1H), 7.03-6.95 (m, 2H), 5.04 (s, 2H), 2.24 (s, 3H). LCMS: $M+H^+$= 331 & 333.

Step 2: N-(4-bromo-7-(5-fluoro-2-methylphenyl) isoquinolin-3-yl)cyclopropanecarboxamide

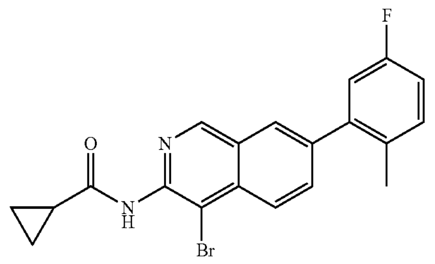 [SMILES: Cc1ccc(F)cc1-c1ccc2c(Br)c(NC(=O)C3CC3)ncc2c1]

To 4-bromo-7-(5-fluoro-2-methylphenyl)isoquinolin-3-amine (46 mg, 140 μmol) and pyridine (110 μl, 1.4 mmol) in dichloromethane (3.0 mL) at ambient temperature was added dropwise cyclopropanecarbonyl chloride (60 μl, 0.66 mmol). After 1 h the mixture was poured into saturated aqueous sodium bicarbonate, extracted twice into dichloromethane and the combined organic phases dried over sodium sulfate, filtered and concentrated in vacuo to afford a residue that was purified by reverse phase HPLC (gradient of acetonitrile in water with 0.1% formic acid) to yield the title compound as a white amorphous solid (57 mg, quant.). $^1H$ NMR (400 MHz, DMSO) δ 10.54 (s, 1H), 9.26 (s, 1H), 8.27-8.14 (m, 2H), 7.97 (d, J=8.6 Hz, 1H), 7.49-7.33 (m, 1H), 7.21 (t, J=9.2 Hz, 2H), 2.25 (s, 3H), 1.98-1.84 (m, 1H), 0.90-0.78 (m, 4H). LCMS (Method E): $R_T$=5.299 min, $M+H^+$=399.0 & 401.0.

Example 113

N-(4-chloro-7-(5-fluoro-2-methylphenyl)isoquinolin-3-yl)cyclopropanecarboxamide

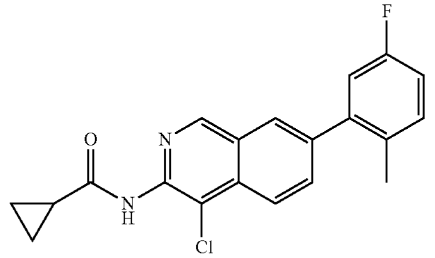

Step 1: 4-chloro-7-(5-fluoro-2-methylphenyl)isoquinolin-3-amine

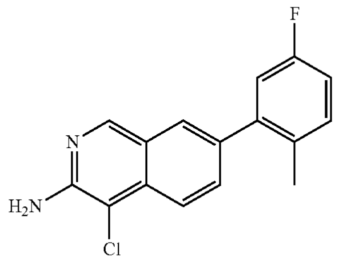 [SMILES: Cc1ccc(F)cc1-c1ccc2c(Cl)c(N)ncc2c1]

A solution of 7-(5-fluoro-2-methylphenyl)isoquinolin-3-amine (60.8 mg, 241 μmol) in dichloromethane (2.0 mL) was treated with N-chlorosuccinimde (35.2 mg, 264 μmol) at ambient temperature. After 24 h the mixture was absorbed directly onto silica gel in vacuo and purified by flash chromatography (silica, ISCO, 0-6% methanol in dichloromethane) to yield the title compound as a pale orange solid (59.0 mg, 85%). $^1H$ NMR (400 MHz, $CDCl_3$) δ 8.80 (s, 1H), 7.98 (d, J=8.7 Hz, 1H), 7.73 (s, 1H), 7.62 (d, J=8.7 Hz, 1H), 7.30-7.20 (m, 2H), 7.00 (t, J=8.3 Hz, 2H), 4.95 (s, 2H), 2.25 (s, 3H). $^1H$ NMR (400 MHz, DMSO) δ 8.90 (s, 1H), 7.93 (s, 1H), 7.84 (d, J=8.8 Hz, 1H), 7.70 (d, J=8.8 Hz, 1H), 7.40-7.34 (m, 1H), 7.18-7.12 (m, 2H), 6.40 (s, 2H), 2.24 (s, 3H). LCMS (Method E): $R_T$=5.508 min, $M+H^+$=287.0 & 289.0.

Step 2: N-(4-chloro-7-(5-fluoro-2-methylphenyl) isoquinolin-3-yl)cyclopropanecarboxamide

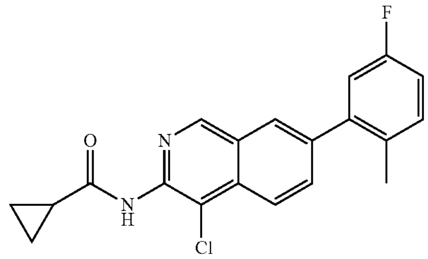

The title compound was prepared following a procedure similar to example 112 using 4-chloro-7-(5-fluoro-2-methylphenyl)isoquinolin-3-amine (24.6 mg, 86 μmol) to afford the title compound as a cream solid (24.1 mg, 79%). $^1H$ NMR (400 MHz, DMSO) δ 10.58 (s, 1H), 9.25 (s, 1H), 8.25 (s, 1H), 8.23 (d, J=8.5 Hz, 1H), 7.97 (d, J=8.7 Hz, 1H), 7.48-7.35 (m, 1H), 7.21 (m, 2H), 2.25 (s, 3H), 1.99-1.87 (m, 1H), 0.88-0.81 (m, 4H). LCMS (Method E): $R_T$=5.257 min, $M+H^+$=355.0 & 357.0.

Example 114

1-(4-chloro-7-(5-fluoro-2-methylphenyl)isoquinolin-3-yl)-3-ethylurea

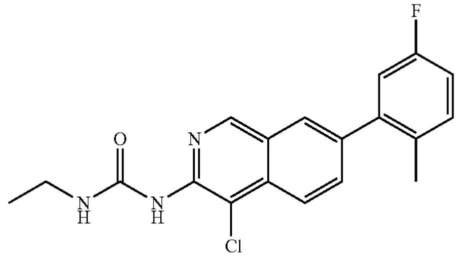 [SMILES: CCNC(=O)Nc1ncc2cc(-c3cc(F)ccc3C)ccc2c1Cl]

The title compound was prepared following a procedure similar to example 111 using 4-chloro-7-(5-fluoro-2-methylphenyl)isoquinolin-3-amine (21.3 mg, 74 μmol) to afford the title compound as a cream solid (5.1 mg, 19%). $^1$H NMR (400 MHz, DMSO) δ 9.19 (s, 1H), 8.34 (br s, 1H), 8.28 (s, 1H), 8.19 (s, 1H), 8.11 (d, J=8.7 Hz, 1H), 7.92 (d, J=8.7 Hz, 1H), 7.44-7.37 (m, 1H), 7.24-7.16 (m, 2H), 3.26 (q, J=7 Hz, 2H), 2.25 (s, 3H), 1.14 (t, J=7 Hz, 3H). LCMS (Method E): $R_T$=6.167 min, M+H$^+$=358.1 & 360.1.

Example 115

N-(4-fluoro-7-(5-fluoro-2-methylphenyl)isoquinolin-3-yl)cyclopropanecarboxamide

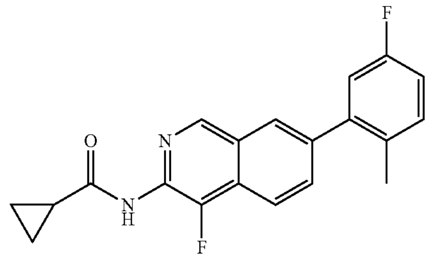 [SMILES: Cc1ccc(F)cc1-c1ccc2c(F)c(NC(=O)C3CC3)ncc2c1]

Step 1: 4-fluoro-7-(5-fluoro-2-methylphenyl)isoquinolin-3-amine

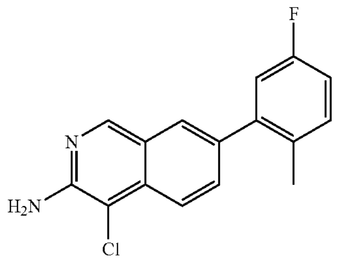 [SMILES: Cc1ccc(F)cc1-c1ccc2c(Cl)c(N)ncc2c1]

7-(5-Fluoro-2-methylphenyl)isoquinolin-3-amine (203 mg, 806 mop and 1-chloromethyl-4-fluoro-1,4-diazoniabicyclo[2.2.2]octane bis(tetrafluoroborate) (313 mg, 883 mop were dissolved together in acetonitrile (2.0 mL) at ambient temperature and the mixture stirred for 16 h, at which time LCMS indicated approx 40% conversion. The mixture was diluted with water, extracted three times into dichloromethane and the combined organic phases washed with brine, dried over sodium sulfate, filtered and concentrated in vacuo. The residue was purified by flash chromatography (silica, ISCO, 0-6% methanol in dichloromethane) to yield the impure title compound as a pale solid (107 mg), used without further purification.

Step 2: N-(4-fluoro-7-(5-fluoro-2-methylphenyl)isoquinolin-3-yl)cyclopropanecarboxamide

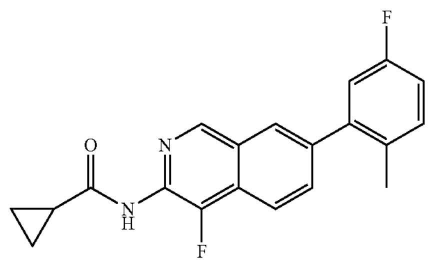 [SMILES: Cc1ccc(F)cc1-c1ccc2c(F)c(NC(=O)C3CC3)ncc2c1]

The title compound was prepared following a procedure similar to example 112 using 4-fluoro-7-(5-fluoro-2-methylphenyl)isoquinolin-3-amine (62.6 mg, 232 μmol) to afford the title compound as a white solid (13.6 mg, 8.5% for 2 steps). $^1$H NMR (400 MHz, DMSO) δ 10.56 (s, 1H), 9.12 (s, 1H), 8.22 (s, 1H), 8.14 (d, J=8.6 Hz, 1H), 7.90 (d, J=8.6 Hz, 1H), 7.41 (m, 1H), 7.20 (m, 2H), 2.25 (s, 3H), 1.98-1.90 (s, 1H), 0.91-0.79 (m, 4H). LCMS (Method E): $R_T$=5.065 min, M+H$^+$=339.1.

Example 116

1-ethyl-3-(4-fluoro-7-(5-fluoro-2-methylphenyl)isoquinolin-3-yl)urea

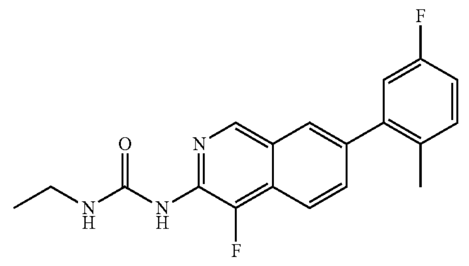

The title compound was prepared following a procedure similar to example 111 using 4-fluoro-7-(5-fluoro-2-methylphenyl)isoquinolin-3-amine (44.7 mg, 165 μmol) to afford the title compound as a beige solid (9.4 mg, 8.2% for 2 steps). $^1$H NMR (400 MHz, DMSO) δ 9.04 (s, 1H), 8.92 (s, 1H), 8.16 (s, 1H), 8.05 (d, J=8.8 Hz, 1H), 8.00 (br s, 1H), 7.84 (d, J=8.7 Hz, 1H), 7.43-7.37 (m, 1H), 7.23-7.15 (m, 2H), 3.23 (q, J=7 Hz, 2H), 2.25 (s, 3H), 1.13 (t, J=7 Hz, 3H). LCMS (Method E): $R_T$=5.690 min, M+H$^+$=342.1.

Example 117

N-(4-cyano-7-(4-methylpyridin-3-yl)isoquinolin-3-yl)cyclopropanecarboxamide

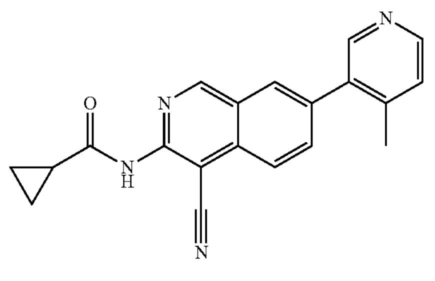 [SMILES: Cc1ccncc1-c1ccc2c(C#N)c(NC(=O)C3CC3)ncc2c1]

The title compound was prepared following a procedure similar to example 112 using 3-amino-7-(4-methylpyridin-3-yl)isoquinoline-4-carbonitrile (50.6 mg, 194 μmol) to afford the title compound as a cream amorphous solid (24.4 mg, 38%). $^1$H NMR (400 MHz, DMSO) δ 11.27 (s, 1H), 9.53 (s, 1H), 8.52 (d, J=5 Hz, 1H), 8.52 (s, 1H), 8.35 (s, 1H), 8.14 (d, J=8.6 Hz, 1H), 8.08 (dd, J=8.6, 1.5 Hz, 1H), 7.42 (d, J=5.0 Hz, 1H), 2.33 (s, 3H), 2.06-1.97 (m, 1H), 0.94-0.88 (m, 4H). LCMS (Method E): $R_T$=3.083 min, M+H$^+$=329.1.

Example 118

N-(7-(6-amino-4-methylpyridin-3-yl)isoquinolin-3-yl)cyclopropanecarboxamide

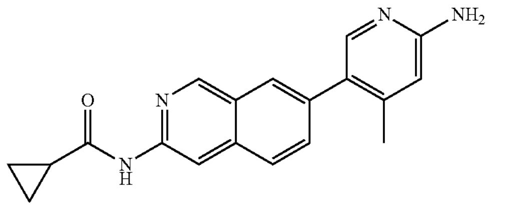 [SMILES: Cc1cc(N)ncc1-c1ccc2cc(NC(=O)C3CC3)ncc2c1]

Step 1: tert-butyl 5-(3-(cyclopropanecarboxamido)isoquinolin-7-yl)-4-methylpyridin-2-ylcarbamate

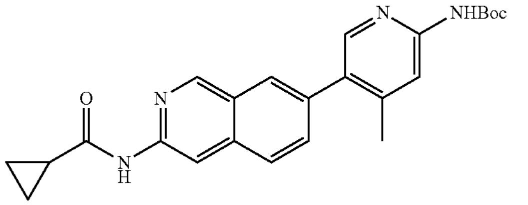 [SMILES: Cc1cc(NC(=O)OC(C)(C)C)ncc1-c1ccc2cc(NC(=O)C3CC3)ncc2c1]

A mixture of N-(7-(6-chloro-4-methylpyridin-3-yl)isoquinolin-3-yl)cyclopropanecarboxamide (63.5 mg, 188 μmol, tert-butyl carbamate (46.7 mg, 399 μmol), chloro[2-(dicyclohexylphosphino)-3,6-dimethoxy-2'-4'-6'-tri-1-propyl-1,1'-biphenyl][2-(2-aminoeth yl)phenyl]palladium(II) (16.9 mg, 21 μmol), 2-(dicyclohexylphosphino)-3,6-dimethoxy-2'-4'-6'-tri-1-propyl-1,1'-biphenyl (10.6 mg, 20 μmol), and cesium carbonate (127 mg, 390 μmol) in 1,4-dioxane (1.0 mL) was heated in a sealed vessel at 90° C. for 20 hours. The mixture was treated with further portions of tert-butyl carbamate (67.1 mg, 537 μmol), chloro[2-(dicyclohexylphosphino)-3,6-dimethoxy-2'-4'-6'-tri-1-propyl-1,1'-biphenyl][2-(2-aminoeth yl)phenyl]palladium(II) (20.1 mg, 25 μmol) and 2-(dicyclohexylphosphino)-3,6-dimethoxy-2'-4'-6'-tri-1-propyl-1,1'-biphenyl (12.9 mg, 24 μmol) and heated at 90° C. for a further 24 hours. The cooled mixture was diluted with brine, extracted twice into dichloromethane, and twice more with DCM to which methanol was added. The combined organic phases were dried over sodium sulfate, filtered, and concentrated in vacuo. The residue was dissolved in DCM, filtered through a celite pad and concentrated in vacuo to afford the impure title compound as a brown solid, used in the next step without purification. LCMS: $M+H^+$=419.

Step 2: N-(7-(6-amino-4-methylpyridin-3-yl)isoquinolin-3-yl)cyclopropanecarboxamide

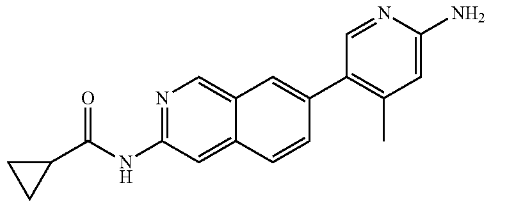

A solution of the crude tert-butyl 5-(3-(cyclopropanecarboxamido)isoquinolin-7-yl)-4-methylpyridin-2-ylcarbamate in dichloromethane (4 mL) and trifluoroacetic acid (4 mL) was stirred for 60 mins at ambient temperature and concentrated in vacuo. The residue was treated with saturated aqueous sodium bicarbonate and brine and extracted twice with dichloromethane, and the combined organic phases were washed with brine, dried over magnesium sulfate, filtered and concentrated in vacuo. The residue was purified by flash chromatography (silica, ISCO, 0.5-20% methanol in dichloromethane) and subsequently repurified by reverse phase HPLC (gradient of acetonitrile in water with 0.1% formic acid) to afford the title compound as a white amorphous solid (7.0 mg, 12% over 2 steps). $^1$H NMR (400 MHz, DMSO) δ 10.86 (s, 1H), 9.14 (s, 1H), 8.46 (s, 1H), 7.94 (s, 1H), 7.86 (d, J=8.8 Hz, 1H), 7.84, (s, 1H), 7.66 (dd, J=8.8, 1.4 Hz, 1H), 6.40 (s, 1H), 5.91 (s, 2H), 2.17 (s, 3H), 2.12-2.03 (m, 1H), 0.90-0.79 (m, 4H). LCMS (Method E): $R_T$=3.241 min, $M+H^+$=319.1.

Example 119 isopropyl 7-(5-fluoro-2-methylphenyl)isoquinolin-3-ylcarbamate

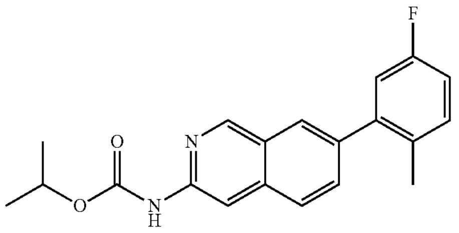 [SMILES: Cc1ccc(F)cc1-c1ccc2cc(NC(=O)OC(C)C)ncc2c1]

A solution 7-(5-fluoro-2-methylphenyl)isoquinolin-3-amine (52.0 mg, 206 mop in pyridine (1.0 mL) was treated dropwise with a solution isopropyl chloroformate (210μl, 1.0M, 210 μmol) at ambient temperature for 30 mins, and the mixture concentrated in vacuo. The residue was treated with saturated aqueous sodium bicarbonate and extracted twice with dichloromethane. The combined organic phases were washed with brine, dried over sodium sulfate, filtered, and concentrated in vacuo to afford a residue that was purified by reverse phase HPLC (gradient of acetonitrile in water with 0.1% formic acid) to yield the title compound as a white powder (51.6 mg, 74%). 1H NMR (400 MHz, DMSO) δ 10.16 (s, 1H), 9.13 (s, 1H), 8.23 (s, 1H), 8.02 (s, 1H), 7.94 (d, J=8.6 Hz, 1H), 7.71 (dd, J=8.5, 1.6 Hz, 1H), 7.37 (dd, J=7, 6 Hz, 1H), 7.22-7.13 (m, 2H), 4.96 (septet, J=6.2 Hz, 1H), 2.25 (s, 3H), 1.29 (d, J=6.3 Hz, 6H). LCMS (Method E): $R_T$=6.067 min, $M+H^+$=339.1.

Example 120

5-(tert-butoxycarbonylamino)-2-chloroisonicotinic acid

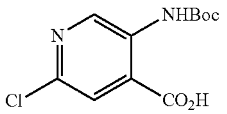

To a solution of tert-butyl 6-chloro-4-formylpyridin-3-yl carbamate (5.010 g, 19.52 mmol) and sulfamic Acid (2.57 g, 26.5 mmol) in 1,4-dioxane (120 mL) and water (50 mL) at ambient temperature was added dropwise over 5 mins a solution of sodium chlorite (2.07 g, 22.9 mmol) in water (10 mL) causing a precipitate to slowly appear. The mixture was stirred for 1 hour, filtered, and the solid washed three times with water and dried at the sinter, and then under high vacuum to yield the pure title compound (4.370 g, 82%). $^1$H NMR (400 MHz, DMSO) δ 9.94 (s, 1H), 9.88 (s, 1H), 8.90 (s, 1H), 7.81 (s, 1H), 1.49 (s, 9H). LCMS: M+H$^+$=273 & 275.

Example 121

N-(2-(2-chlorophenyl)-4-oxo-1,4-dihydro-1,7-naphthyridin-6-yl)cyclopropanecarboxamide

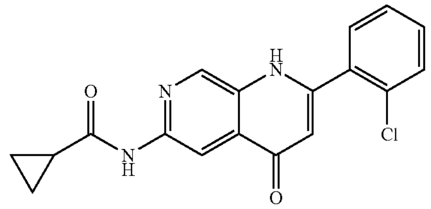 [SMILES: O=C(Nc1cc2c(=O)cc(-c3ccccc3Cl)[nH]c2cn1)C1CC1]

Step 1: 6-chloro-2-(2-chlorophenyl)-1,7-naphthyridin-4(1H)-one

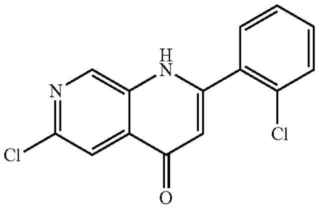 [SMILES: O=c1cc(-c2ccccc2Cl)[nH]c2cnc(Cl)cc12]

5-(tert-Butoxycarbonylamino)-2-chloroisonicotinic acid (502 mg, 1.84 mmol) was suspended in polyphosphoric acid (9.5 g, 102 mmol) at ambient temperature and stirred for 10 mins causing a bright yellow coloration and visible evolution of gas. 2'-Chloroacetophenone (570 mg, 3.69 mmol) was added and the mixture heated to 150° C. for 2.5 h. The mixture was diluted with cold water (50 mL), and then cooled in ice and treated with solid sodium hydroxide (6.0 g, 150 mmol) to pH~7. The mixture was filtered and the recovered oily solids washed with water, dissolved in methanol and reconcentrated in vacuo. The residue was purified by flash chromatography (silica, ISCO, 0.5-20% methanol in DCM) to afford the title compound as a cream solid (29.2 mg, 5.5%). 1H NMR (400 MHz, MeOD) δ 8.87 (s, 1H), 8.12 (s, 1H), 7.64-7.58 (m, 2H), 7.58-7.46 (m, 2H), 6.47 (s, 1H); NH absent. LCMS: M+H$^+$= 291 & 293.

Step 2: N-(2-(2-chlorophenyl)-4-oxo-1,4-dihydro-1,7-naphthyridin-6-yl)cyclopropanecarboxamide

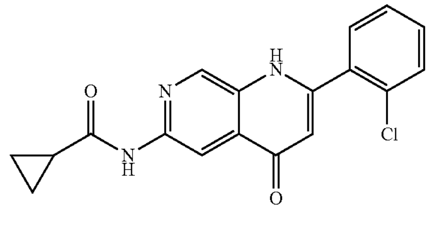 [SMILES: O=C(Nc1cc2c(=O)cc(-c3ccccc3Cl)[nH]c2cn1)C1CC1]

A mixture of 6-chloro-2-(2-chlorophenyl)-1,7-naphthyridin-4(1H)-one (29.2 mg, 100 μmol), cyclopropanecarboxamide (17.1 mg, 200 μmol), chloro[2-(dicyclohexylphosphino)-3,6-dimethoxy-2'-4'-6'-tri-1-propyl-1,1'-biphenyl][2-(2-aminoeth yl)phenyl]palladium(II) (8.0 mg, 10 μmol), 2-(dicyclohexylphosphino)-3,6-dimethoxy-2'-4'-6'-tri-1-propyl-1,1'-biphenyl (5.4 mg, 10 μmol), and cesium carbonate (98.0 mg, 301 μmol) in 1,4-dioxane (5.0 mL) was heated to reflux for 4 hours. Further portions of cyclopropanecarboxamide (17.1 mg, 200 μmol), chloro[2-(dicyclohexylphosphino)-3,6-dimethoxy-2'-4'-6'-tri-1-propyl-1,1'-biphenyl][2-(2-aminoeth yl)phenyl]palladium(II) (8.0 mg, 10 μmol) and 2-(dicyclohexylphosphino)-3,6-dimethoxy-2'-4'-6'-tri-1-propyl-1,1'-biphenyl (5.4 mg, 10 μmol) were added and the mixture heated to reflux for 16 hours. The cooled mixture was treated with water and brine and extracted with ethyl acetate, and the separated organic phase washed with brine, dried over sodium sulfate, filtered, and concentrated in vacuo. The residue was purified by reverse phase HPLC (gradient of acetonitrile in water with 0.1% formic acid) to afford the title compound as a white solid (2.1 mg, 6.2%). LCMS (Method E): $R_T$=3.715 min, M+H$^+$=340.0 & 342.0.

Example 122

N-(2-(5-fluoro-2-methylphenyl)-4-oxo-1,4-dihydro-1,7-naphthyridin-6-yl)cyclopropanecarboxamide

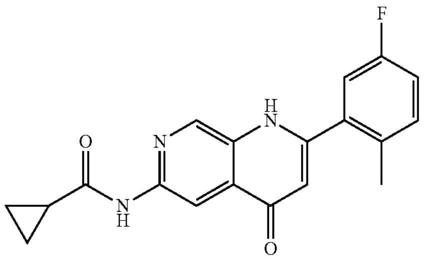 [SMILES: Cc1ccc(F)cc1-c1cc(=O)c2cc(NC(=O)C3CC3)ncc2[nH]1]

Step 1: 6-chloro-2-(5-fluoro-2-methylphenyl)-1,7-naphthyridin-4(1H)-one

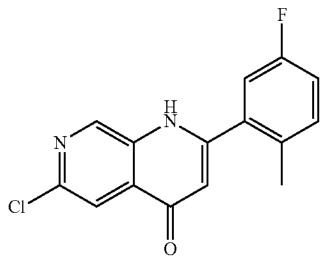 [SMILES: Cc1ccc(F)cc1-c1cc(=O)c2cc(Cl)ncc2[nH]1]

The title compound was prepared following a procedure similar to example 121 using 5-(tert-butoxycarbonylamino)-2-chloroisonicotinic acid (505 mg, 1.85 mmol) and 5'-fluoro-2'-methylacetophenone (566 mg, 3.72 mmol) to afford the impure title compound as a beige solid (128 mg), used without further purification. LCMS: M+H$^+$=289 & 291.

Step 2: N-(2-(5-fluoro-2-methylphenyl)-4-oxo-1,4-dihydro-1,7-naphthyridin-6-yl)cyclopropanecarboxamide

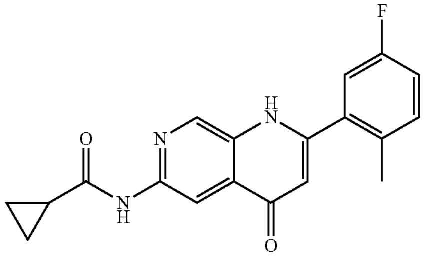 [SMILES: Cc1ccc(F)cc1-c1cc(=O)c2cc(NC(=O)C3CC3)ncc2[nH]1]

The title compound was prepared following a procedure similar to example 121 using 6-chloro-2-(5-fluoro-2-methylphenyl)-1,7-naphthyridin-4(1H)-one to afford after purification by reverse phase HPLC (gradient of acetonitrile in water with 0.1% formic acid) the title compound as a white solid (19.0 mg, 13%). 1H NMR (400 MHz, DMSO) δ 10.81 (s, 1H), 8.79 (s, 1H), 8.61 (s, 1H), 7.45-7.38 (m, 1H), 7.36-7.22 (m, 2H), 6.57 (s, 1H), 6.11 (s, 1H), 2.29 (s, 3H), 2.09-1.99 (m, 1H), 0.92-0.76 (m, 4H). LCMS (Method E): $R_T$=3.804 min, M+H$^+$=338.1.

Example 123

Each compound in Table 3 below was prepared following a similar experimental procedure (using appropriately substituted reagents) as described in another Example herein, such Example being referenced in the Synthesis Method column (e.g., a compound in Table 3 that is prepared following a similar experimental procedure as described in Example 12 will have "12" noted in the Syn. Method column.

TABLE 3

| Structure/Name | Syn. Method | LCMS $R_T$ (min), M + H$^+$, LCMS method | $^1$H NMR (ppm) |
|---|---|---|---|
| 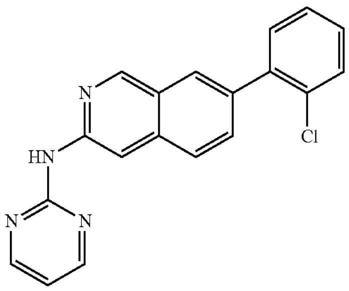 7-(2-chlorophenyl)-N-(pyrimidin-2-yl)isoquinolin-3-amine | 13 | 4.595, 333.0, E | $^1$H NMR (400 MHz, DMSO-$d_6$) δ 10.02 (s, 1H), 9.18 (s, 1H), 8.68 (s, 1H), 8.64 (d, J = 4.8 Hz, 2H), 8.09 (s, 1H), 7.94 (d, J = 8.6 Hz, 1H), 7.75 (dd, J = 8.5, 1.7 Hz, 1H), 7.66-7.60 (m, 1H), 7.56 (dd, J = 7.2, 2.1 Hz, 1H), 7.47 (qd, J = 7.3, 3.8 Hz, 2H), 7.00 (t, J = 4.8 Hz, 1H). |
| 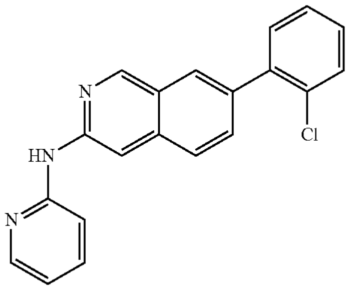 7-(2-chlorophenyl)-N-(pyridin-2-yl)isoquinolin-3-amine | 13 | 4.530, 332.1, E | $^1$H NMR (400 MHz, DMSO-$d_6$) δ 9.89 (s, 1H), 9.14 (s, 1H), 8.57 (s, 1H), 8.32 (d, J = 3.2 Hz, 1H), 8.04 (s, 1H), 7.87 (d, J = 8.6 Hz, 1H), 7.73-7.61 (m, 3H), 7.55 (d, J = 7.3 Hz, 1H), 7.51-7.42 (m, 2H), 7.32 (d, J = 8.2 Hz, 1H), 6.92-6.83 (m, 1H). |
| 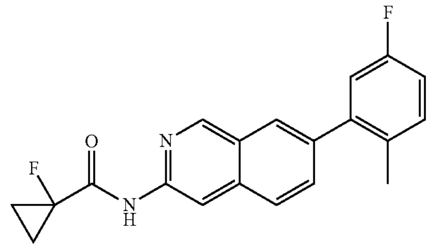 1-fluoro-N-(7-(5-fluoro-2-methylphenyl)isoquinolin-3-yl)cyclopropanecarboxamide | 8 | 5.970, 339.1, E | $^1$H NMR (400 MHz, DMSO-$d_6$ δ 10.30 (s, 1H), 9.24(s, 1H), 8.47 (s, 1H), 8.09 (s, 1H), 8.01 (d, J = 8.5 Hz, 1H), 7.76 (d, J = 8.5 Hz, 1H), 7.39 (t, J = 6.9 Hz, 1H), 7.18 (t, J = 8.8 Hz, 2H), 2.26 (s, 3H), 1.56-1.32 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 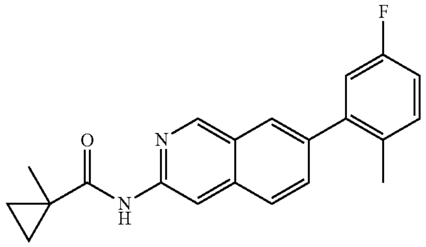 N-(7-(5-fluoro-2-methylphenyl) isoquinolin-3-yl)-1-methylcyclopropanecarboxamide | 8 | 5.772, 335.1, E | $^1$H NMR (400 MHz, DMSO-d$_6$) δ 9.58 (s, 1H), 9.19 (s, 1H), 8.47 (s, 1H), 8.06 (s, 1H), 7.95 (d, J = 8.5 Hz, 1H), 7.72 (d, J = 8.5 Hz, 1H), 7.39 (t, J = 6.9 Hz, 1H), 7.17 (t, J = 8.4 Hz, 2H), 2.25 (s, 3H), 1.48 (s, 3H), 1.19 (q, J = 3.6 Hz, 2H), 0.70 (q, J = 3.8 Hz, 2H). |
| 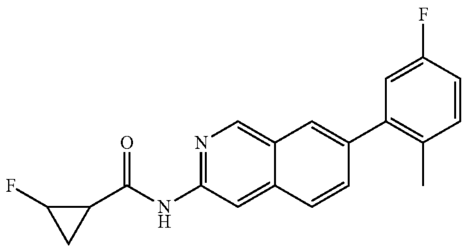 2-fluoro-N-(7-(5-fluoro-2-methylphenyl)isoquinolin-3-yl)cyclopropanecarboxamide (mixture of cis stereoisomers) | 8 | 5.254, 339.1, E | $^1$H NMR (400 MHz, DMSO-d$_6$) δ 10.96 (s, 1H), 9.19 (s, 1H), 8.51 (s, 1H), 8.05 (s, 1H), 7.95 (d, J = 8.4 Hz, 1H), 7.72 (d, J = 8.4 Hz, 1H), 7.39 (s, 1H), 7.18 (d, J = 8.8 Hz, 2H), 4.96 (d, J = 66.1 Hz, 1H), 2.25 (s, 4H), 1.70 (d, J = 23.0 Hz, 1H), 1.21 (s, 1H). |
| 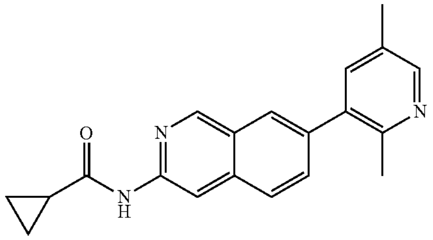 N-(7-(2,5-dimethylpyridin-3-yl) isoquinolin-3-yl) cyclopropanecarboxamide | 10 | 3.339, 318.1, E | $^1$H NMR (400 MHz, DMSO-d$_6$) δ 10.91 (s, 1H), 9.18 (s, 1H), 8.50 (s, 1H), 8.35 (s, 1H), 8.05 (s, 1H), 7.94 (d, J = 8.4 Hz, 1H), 7.73 (d, J = 8.2 Hz, 1H), 7.56 (s, 1H), 2.43 (s, 3H), 2.33 (s, 3H), 2.08 (s, 1H), 0.85 (d, J = 13.2 Hz, 4H). |
| 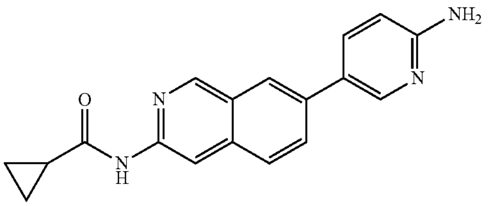 N-(7-(6-aminopyridin-3-yl) isoquinolin-3-yl) cyclopropanecarboxamide | 10 | 3.215, 305.0, E | $^1$H NMR (400 MHz, DMSO-d$_6$) δ 10.84 (s, 1H), 9.13 (s, 1H), 8.42 (d, J = 8.1 Hz, 2H), 8.21 (s, 1H), 7.96 (d, J = 8.5 Hz, 1H), 7.93-7.79 (m, 2H), 6.58 (d, J = 9.2 Hz, 1H), 6.12 (s, 2H), 2.07 (m, 1H), 0.94-0.74 (m, 4H). |

TABLE 3-continued

| Structure/Name | Syn. Meth-od | LCMS $R_T$ (min), M + $H^+$, LCMS method | $^1H$ NMR (ppm) |
|---|---|---|---|
| 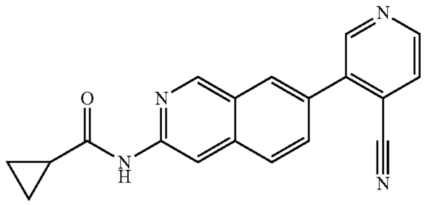 N-(7-(4-cyanopyridin-3-yl) isoquinolin-3-yl) cyclopropanecarboxamide | 12 | 4.153, 315.0, E | $^1H$ NMR (400 MHz, DMSO-$d_6$) δ 11.00 (s, 1H), 9.26 (s, 1H), 9.04 (s, 1H), 8.87 (d, J = 5.0 Hz, 1H), 8.55 (s, 1H), 8.37 (s, 1H), 8.05 (dd, J = 10.2, 6.9 Hz, 2H), 7.97 (dd, J = 8.6, 1.7 Hz, 1H), 2.10 (s, 1H), 0.93-0.79 (m, 4H). |
| 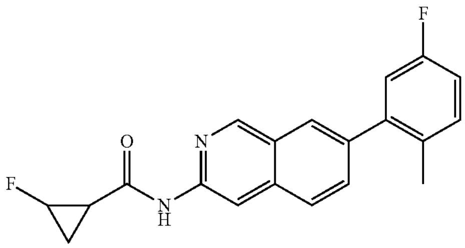 2-fluoro-N-(7-(5-fluoro-2-methylphenyl)isoquinolin-3-yl)cyclopropanecarboxamide (mixture of trans stereoisomers) | 8 | 5.574, 339.1, E | $^1H$ NMR (400 MHz, DMSO-$d_6$) δ 11.08 (s, 1H), 9.19 (s, 1H), 8.46 (s, 1H), 8.05 (s, 1H), 7.93 (d, J = 8.6 Hz, 1H), 7.72 (dd, J = 8.5, 1.4 Hz, 1H), 7.44-7.32 (m, 1H), 7.16 (dd, J = 12.5, 6.0 Hz, 2H), 4.93 (d, J = 64.7 Hz, 1H), 2.63 (ddd, J = 17.6, 10.3, 6.9 Hz, 1H), 2.25 (s, 3H), 1.65-1.46 (m, 1H), 1.29 (dq, J = 12.9, 6.4 Hz, 1H). |
| 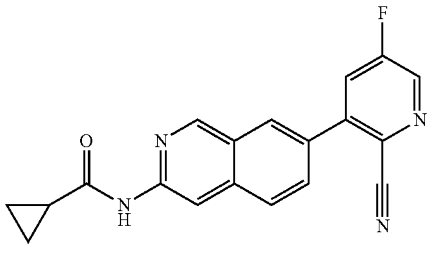 N-(7-(2-cyano-5-fluoropyridin-3-yl)isoquinolin-3-yl) cyclopropanecarboxamide | 12 | 4.524, 333.0, E | $^1H$ NMR (400 MHz, DMSO-$d_6$) δ 11.02 (s, 1H), 9.26 (s, 1H), 8.88 (d, J = 2.6 Hz, 1H), 8.56 (s, 1H), 8.40 (s, 1H), 8.31 (dd, J = 9.1, 2.6 Hz, 1H), 8.07 (d, J = 8.7 Hz, 1H), 7.97 (dd, J = 8.6, 1.6 Hz, 1H), 2.09 (td, J = 7.4, 3.6 Hz, 1H), 0.86 (dd, J = 9.6, 6.3 Hz, 4H). |
| 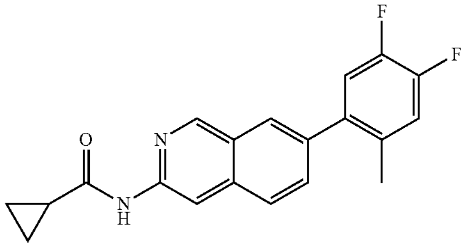 N-(7-(4,5-difluoro-2-methylphenyl)isoquinolin-3-yl)cyclopropanecarboxamide | 12 | 5.420, 339.1, E | $^1H$ NMR (400 MHz, DMSO-$d_6$) δ 10.91 (s, 1H), 9.17 (s, 1H), 8.50 (s, 1H), 8.02 (s, 1H), 7.92 (d, J = 8.5 Hz, 1H), 7.69 (d, J = 8.6 Hz, 1H), 7.52-7.36 (m, 2H), 2.25 (s, 3H), 2.08 (d, J = 4.6 Hz, 1H), 0.91-0.77 (m, 4H). |

TABLE 3-continued

| Structure/Name | Syn. Meth-od | LCMS $R_T$ (min), M + $H^+$, LCMS method | $^1$H NMR (ppm) |
|---|---|---|---|
| 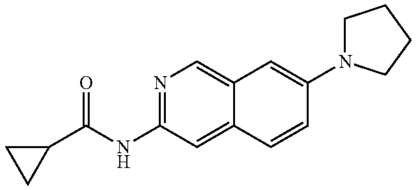 N-(7-(pyrrolidin-1-yl) isoquinolin-3-yl) cyclopropanecarboxamide | 22 | 3.933, 282.0, E | $^1$H NMR (400 MHz, DMSO-$d_6$) δ 10.55 (s, 1H), 8.84 (s, 1H), 8.24 (s, 1H), 7.68 (d, J = 9.0 Hz, 1H), 7.24 (dd, J = 9.0, 2.3 Hz, 1H), 6.84 (s, 1H), 3.35 (t, J = 6.4 Hz, 4H), 2.01 (dd, J = 8.2, 5.1 Hz, 5H), 0.85-0.71 (m, 4H). |
| 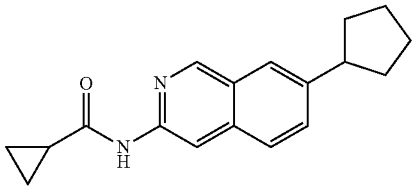 N-(7-cyclopentylisoquinolin-3-yl)cyclopropanecarboxamide | 23 | 4.917, 281.1, E | $^1$H NMR (400 MHz, DMSO-$d_6$) δ 10.84 (s, 1H), 9.05 (s, 1H), 8.40 (s, 1H), 7.85 (s, 1H), 7.78 (d, J = 8.6 Hz, 1H), 7.62 (d, J = 8.6 Hz, 1H), 3.16 (dd, J = 17.3, 9.3 Hz, 1H), 2.15-1.99 (m, 3H), 1.82 (s, 2H), 1.76-1.56 (m, 4H), 0.88-0.75 (m, 4H). |
| 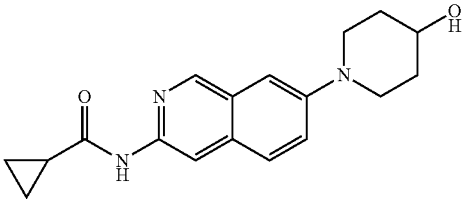 N-(7-(4-hydroxypiperidin-1-yl) isoquinolin-3-yl) cyclopropanecarboxamide | 22 | 3.052, 312.1, E | $^1$H NMR (400 MHz, DMSO-$d_6$) δ 10.67 (s, 1H), 8.89 (s, 1H), 8.28 (s, 1H), 7.68 (d, J = 9.1 Hz, 1H), 7.56 (d, J = 9.1 Hz, 1H), 7.27 (s, 1H), 4.70 (d, J = 3.9 Hz, 1H), 3.64 (m, 3H), 2.95 (t, J = 11.1 Hz, 2H), 2.02 (m, 1H), 1.86 (d, J = 10.3 Hz, 2H), 1.52 (dd, J = 18.6, 9.3 Hz, 2H), 0.81 (m, 4H). |
| 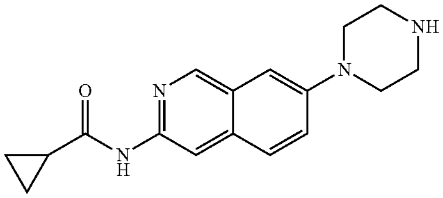 N-(7-(piperidin-1-yl) isoquinolin-3-yl) cyclopropanecarboxamide | 22 | 2.722, 297.1, E | $^1$H NMR (400 MHz, DMSO-$d_6$) δ 10.67 (s, 1H), 8.91 (s, 1H), 8.29 (s, 1H), 7.69 (d, J = 9.1 Hz, 1H), 7.56 (dd, J = 9.2, 2.3 Hz, 1H), 7.24 (s, 1H), 3.19-3.10 (m, 4H), 2.93-2.82 (m, 4H), 2.03 (m, 1H), 1.24 (s, 1H), 0.85-0.75 (m, 4H). |
| 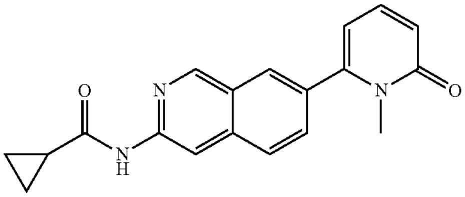 N-(7-(1-methyl-6-oxo-1,6-dihydropyridin-2-yl) isoquinolin-3-yl) cyclopropanecarboxamide | 12 | 3.839, 320.0, E | $^1$H NMR (400 MHz, DMSO-$d_6$) δ 10.99 (s, 1H), 9.20 (s, 1H), 8.53 (s, 1H), 8.17 (s, 1H), 7.97 (d, J = 8.6 Hz, 1H), 7.79 (d, J = 8.6 Hz, 1H), 7.49 (dd, J = 9.1, 6.9 Hz, 1H), 6.49 (d, J = 9.1 Hz, 1H), 6.26 (d, J = 6.8 Hz, 1H), 3.29 (s, 3H), 2.08 (m, 1H), 0.92-0.76 (m, 4H). |

TABLE 3-continued

| Structure/Name | Syn. Meth-od | LCMS $R_T$ (min), M + $H^+$, LCMS method | $^1H$ NMR (ppm) |
|---|---|---|---|
| 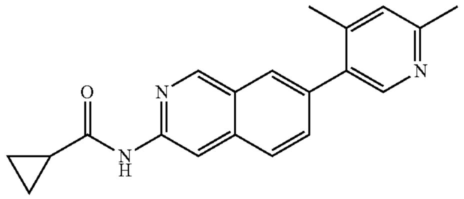 N-(7-(4,6-dimethylpyridin-3-yl) isoquinolin-3-yl) cyclopropanecarboxamide | 12 | 3.347, 318.1, E | $^1H$ NMR (400 MHz, DMSO-$d_6$) δ 10.93 (s, 1H), 9.18 (s, 1H), 8.50 (s, 1H), 8.35 (s, 1H), 8.05 (s, 1H), 7.94 (d, J = 8.6 Hz, 1H), 7.76-7.67 (m, 1H), 7.25 (s, 1H), 2.28 (s, 3H), 2.08 (s, 1H), 0.85 (dd, J = 9.9, 6.2 Hz, 4H). |
| 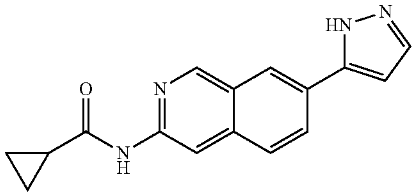 N-(7-(1H-pyrazol-5-yl) isoquinolin-3-yl) cyclopropanecarboxamide | 10 | 3.585, 279.0, E | $^1H$ NMR (400 MHz, DMSO-$d_6$) δ 12.99 (s, 1H), 10.87 (s, 1H), 9.15 (s, 1H), 8.43 (d, J = 5.1 Hz, 2H), 8.19 (d, J = 8.0 Hz, 1H), 7.97-7.75 (m, 2H), 6.86 (s, 1H), 2.15-2.01 (m, 1H), 0.84 (m, 4H). |
| 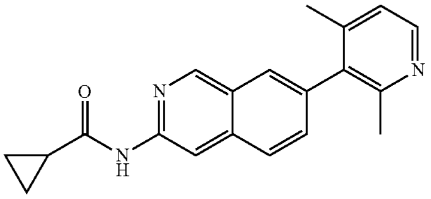 N-(7-(2,4-dimethylpyridin-3-yl) isoquinolin-3-yl) cyclopropanecarboxamide | 12 | 3.290, 318.1, E | $^1H$ NMR (400 MHz, DMSO-$d_6$) δ 10.93 (s, 1H), 9.15 (s, 1H), 8.51 (s, 1H), 8.35 (d, J = 5.1 Hz, 1H), 7.96 (d, J = 8.4 Hz, 1H), 7.91 (s, 1H), 7.55 (d, J = 8.4 Hz, 1H), 7.22 (d, J = 5.2 Hz, 1H), 2.21 (s, 3H), 2.08 (m, 1H), 2.03 (s, 3H), 0.85 (m, 4H). |
| 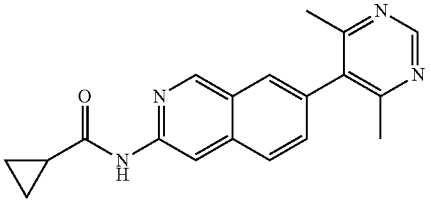 N-(7-(4,6-dimethylpyrimidin-5-yl)isoquinolin-3-yl) cyclopropanecarboxamide | 12 | 3.855, 319.1, E | $^1H$ NMR (400 MHz, DMSO-$d_6$) δ 10.96 (s, 1H), 9.16 (s, 1H), 8.93 (s, 1H), 8.53 (s, 1H), 7.99 (d, J = 8.9 Hz, 2H), 7.63 (d, J = 8.4 Hz, 1H), 2.23 (s, 6H), 2.07 (m, 1H), 0.86 (m, 4H). |
| 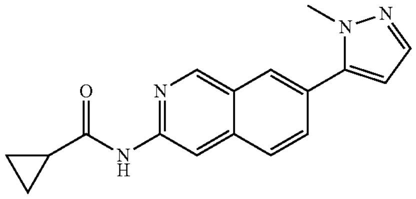 N-(7-(1-methyl-1H-pyrazol-5-yl) isoquinolin-3-yl) cyclopropanecarboxamide | 10 | 4.028, 293.0, E | $^1H$ NMR (400 MHz, DMSO-$d_6$) δ 10.96 (s, 1H), 9.21 (s, 1H), 8.50 (s, 1H), 8.23 (s, 1H), 7.97 (d, J = 8.6 Hz, 1H), 7.84 (d, J = 8.6 Hz, 1H), 7.52 (d, J = 1.6 Hz, 1H), 6.54 (d, J = 1.6 Hz, 1H), 3.95 (s, 3H), 2.16-2.00 (m, 1H), 0.85 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 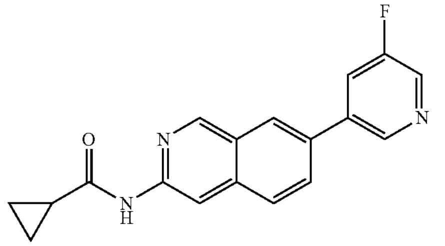 N-(7-(5-fluoropyridin-3-yl) isoquinolin-3-yl) cyclopropanecarboxamide | 10 | 4.267, 308.0, E | $^1$H NMR (400 MHz, DMSO-$d_6$) δ 10.97 (s, 1H), 9.21 (s, 1H), 8.97 (s, 1H), 8.63 (d, J = 2.5 Hz, 1H), 8.52 (d, J = 5.6 Hz, 2H), 8.23 (d, J = 10.3 Hz, 1H), 8.13 (d, J = 8.7 Hz, 1H), 8.00 (d, J = 8.7 Hz, 1H), 2.15-2.02 (m, 1H), 0.92-0.79 (m, 4H). |
| 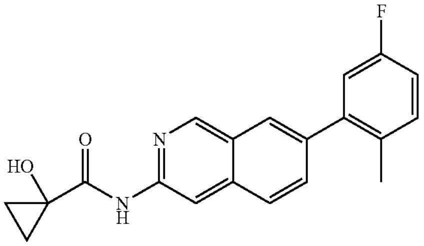 N-(7-(5-fluoro-2-methylphenyl) isoquinolin-3-yl)-1-hydroxycyclopropanecarboxamide | 8 | 5.066, 337.1, E | $^1$H NMR (400 MHz, DMSO-$d_6$) δ 9.56 (s, 1H), 9.21 (s, 1H), 8.51 (s, 1H), 8.08 (s, 1H), 7.99 (d, J = 8.5 Hz, 1H), 7.75 (d, J = 8.6 Hz, 1H), 7.46-7.34 (m, 1H), 7.17 (t, J = 8.4 Hz, 2H), 6.87 (s, 1H), 2.25 (s, 3H), 1.25 (dd, J = 7.6, 4.3 Hz, 2H), 1.08 (dd, J = 7.5, 4.3 Hz, 2H). (hydroxyl proton not observed) |
| 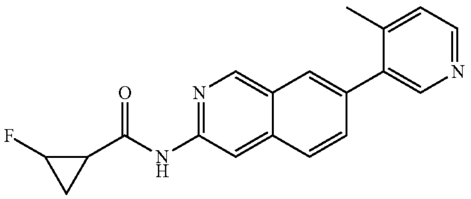 2-fluoro-N-(7-(4-methylpyridin-3-yl)isoquinolin-3-yl) cyclopropanecarboxamide (mixture of cis stereoisomers) | 8 | 5.36, 322.2, G | $^1$H NMR (400 MHz, DMSO-$d_6$) δ 10.99 (s, 1H), 9.21 (s, 1H), 8.50 (t, J = 10.8 Hz, 3H), 8.10 (s, 1H), 7.99 (d, J = 8.5 Hz, 1H), 7.77 (d, J = 8.4 Hz, 1H), 7.39 (d, J = 4.8 Hz, 1H), 4.96 (ddd, J = 66.2, 9.8, 5.9 Hz, 1H), 2.33 (s, 3H), 2.28 (dd, J = 13.7, 6.9 Hz, 1H), 1.70 (ddd, J = 23.1, 9.8, 6.7 Hz, 1H), 1.20 (dt, J = 14.9, 6.7 Hz, 1H). |
| 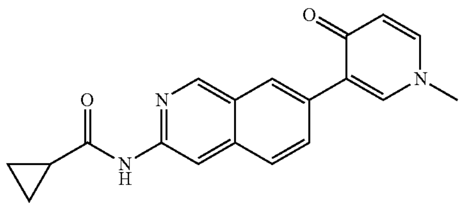 N-(7-(1-methyl-4-oxo-1,4-dihydropyridin-3-yl) isoquinolin-3-yl) cyclopropanecarboxamide | 12 | 3.176, 320.0, E | $^1$H NMR (400 MHz, DMSO-$d_6$) δ 10.85 (s, 1H), 9.10 (s, 1H), 8.42 (d, J = 10.9 Hz, 2H), 8.08 (d, J = 2.1 Hz, 1H), 7.99 (d, J = 8.9 Hz, 1H), 7.83 (d, J = 8.7 Hz, 1H), 7.66 (dd, J = 7.4, 2.1 Hz, 1H), 6.27 (d, J = 7.5 Hz, 1H), 3.73 (s, 3H), 2.07 (m, 1H), 0.84 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 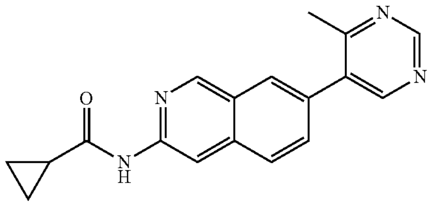 N-(7-(4-methylpyrimidin-5-yl)isoquinolin-3-yl)cyclopropanecarboxamide | 12 | 3.849, 305.0, E | $^1$H NMR (400 MHz, DMSO-$d_6$) δ 10.97 (s, 1H), 9.20 (s, 1H), 9.09 (s, 1H), 8.73 (s, 1H), 8.53 (s, 1H), 8.16 (s, 1H), 7.99 (d, J = 8.5 Hz, 1H), 7.81 (dd, J = 8.5, 1.6 Hz, 1H), 2.52 (s, 3H), 2.08 (m, 1H), 0.86 (m, 4H). |
| 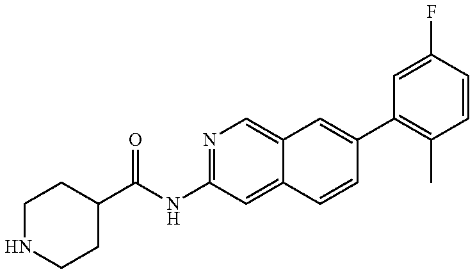 N-(7-(5-fluoro-2-methylphenyl)isoquinolin-3-yl)piperidine-4-carboxamide | 8 | 4.307, 364.1, E | $^1$H NMR (400 MHz, DMSO-$d_6$) δ 10.73 (s, 1H), 9.19 (s, 1H), 8.52 (s, 1H), 8.05 (s, 1H), 7.96 (d, J = 8.5 Hz, 1H), 7.73 (d, J = 8.5 Hz, 1H), 7.39 (dd, J = 9.3, 5.9 Hz, 1H), 7.24-7.11 (m, 2H), 3.37 (d, J = 12.7 Hz, 2H), 2.94 (dd, J = 12.5, 9.9 Hz, 2H), 2.86 (t, J = 11.1 Hz, 1H), 2.25 (s, 3H), 2.02 (d, J = 11.7 Hz, 2H), 1.85 (dd, J = 22.6, 10.9 Hz, 2H). |
| 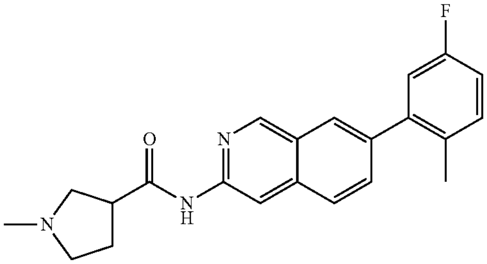 N-(7-(5-fluoro-2-methylphenyl)isoquinolin-3-yl)-1-methylpyrrolidine-3-carboxamide | 8 | 4.300, 364.1, E | $^1$H NMR (400 MHz, DMSO-$d_6$) δ 10.84 (s, 2H), 9.20 (s, 2H), 8.52 (s, 2H), 8.06 (s, 2H), 7.97 (d, J = 8.5 Hz, 2H), 7.74 (d, J = 8.4 Hz, 2H), 7.39 (s, 2H), 7.18 (d, J = 8.7 Hz, 4H), 3.49 (s, 3H), 3.14 (s, 5H), 2.72 (s, 6H), 2.30 (s, 2H), 2.25 (s, 6H), 2.16 (s, 2H). |
| 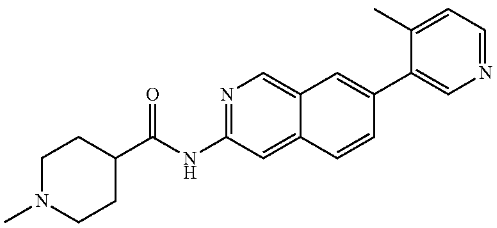 1-methyl-N-(7-(4-fluoro-2-methylpyridin-3-yl)isoquinolin-3-yl)piperidine-4-carboxamide | 10 | 2.662, 361.1, E | $^1$H NMR (400 MHz, DMSO-$d_6$) δ 10.56 (s, 1H), 9.18 (s, 1H), 8.52 (d, J = 21.6 Hz, 3H), 8.08 (s, 1H), 7.97 (d, J = 8.2 Hz, 1H), 7.75 (d, J = 9.1 Hz, 1H), 7.39 (s, 1H), 3.17 (unresolved, 1H), 2.82 (d, J = 10.4 Hz, 2H), 2.32 (s, 3H), 2.17 (s, 3H), 1.88 (t, J = 11.3 Hz, 2H), 1.79 (d, J = 11.3 Hz, 2H), 1.75-1.63 (m, 2H). |

TABLE 3-continued

| Structure/Name | Syn. Meth-od | LCMS $R_T$ (min), M + $H^+$, LCMS method | $^1H$ NMR (ppm) |
|---|---|---|---|
| 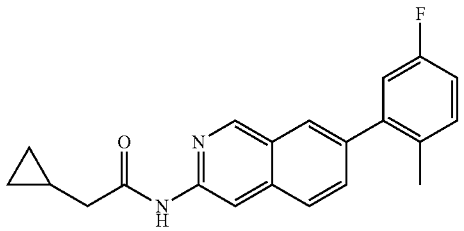 2-cyclopropyl-N-(7-(5-fluoro-2-methylphenyl)isoquinolin-3-yl) acetamide | 8 | 5.609, 335.1, E | $^1H$ NMR (400 MHz, DMSO-$d_6$) δ 10.48 (s, 1H), 9.17 (s, 1H), 8.54 (s, 1H), 8.04 (s, 1H), 7.95 (d, J = 8.4 Hz, 1H), 7.71 (d, J = 8.4 Hz, 1H), 7.37 (d, J = 6.7 Hz, 1H), 7.16 (t, J = 8.5 Hz, 2H), 2.35 (d, J = 6.9 Hz, 2H), 2.25 (s, 3H), 1.10 (s, 1H), 0.50 (d, J = 7.8 Hz, 2H), 0.23 (s, 2H). |
| 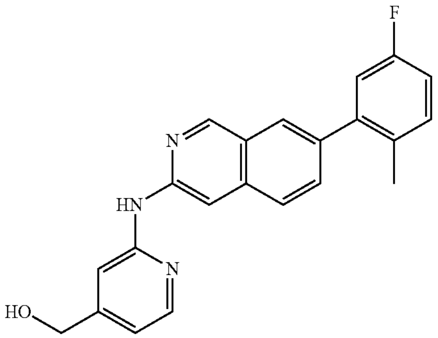 (2-(7-(5-fluoro-2-methylphenyl) isoquinolin-3-ylamino)pyridin-4-yl)methanol | 13 | 4.508, 360.1, E | $^1H$ NMR (400 MHz, DMSO-$d_6$) δ 9.78 (s, 1H), 9.11 (s, 1H), 8.56 (s, 1H), 8.23 (d, J = 4.7 Hz, 1H), 7.96 (s, 1H), 7.85 (d, J = 8.5 Hz, 1H), 7.63 (d, J = 8.5 Hz, 1H), 7.38 (t, J = 6.8 Hz, 1H), 7.29 (s, 1H), 7.16 (d, J = 9.7 Hz, 2H), 6.81 (d, J = 4.3 Hz, 1H), 5.35 (s, 1H), 4.50 (s, 2H), 2.27 (s, 3H). |
| 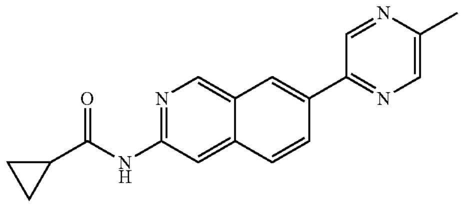 N-(7-(5-methylpyrazin-2-yl) isoquinolin-3-yl) cyclopropanecarboxamide | 12 | 4.300, 305.1 | $^1H$ NMR (400 MHz, DMSO-$d_6$) δ 10.94 (s, 1H), 9.26 (d, J = 5.6 Hz, 2H), 8.82 (s, 1H), 8.67 (s, 1H), 8.50 (s, 1H), 8.42 (d, J = 8.7 Hz, 1H), 7.99 (d, J = 8.8 Hz, 1H), 2.57 (s, 3H), 2.09 (s, 1H), 0.93-0.77 (m, 4H). |
| 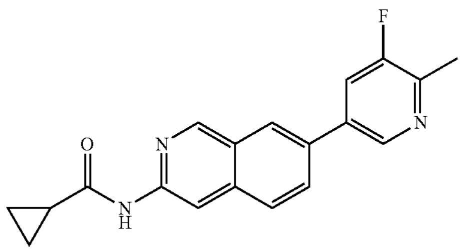 N-(7-(5-fluoro-6-methylpyridin-3-yl)isoquinolin-3-yl) cyclopropanecarboxamide | 30 | 4.477, 322.0, E | $^1H$ NMR (400 MHz, DMSO-$d_6$) δ 10.93 (s, 1H), 9.19 (s, 1H), 8.82 (s, 1H), 8.49 (d, J = 6.5 Hz, 2H), 8.11 (t, J = 9.3 Hz, 2H), 7.98 (d, J = 8.6 Hz, 1H), 2.50 (d, J = 2.5 Hz, 3H), 2.08 (d, J = 4.0 Hz, 1H), 0.93-0.73 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 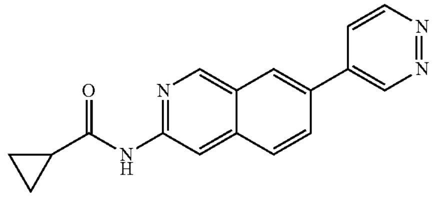 N-(7-(pyridazin-4-yl) isoquinolin-3-yl) cyclopropanecarboxamide | 30 | 3.628, 291.0, E | $^1$H NMR (500 MHz, DMSO-d$_6$) δ 11.04 (s, 1H), 9.84 (s, 1H), 9.39 (d, J = 5.1 Hz, 1H), 9.25 (s, 1H), 8.74 (s, 1H), 8.54 (s, 1H), 8.25 (s, 2H), 8.07 (d, J = 8.5 Hz, 1H), 2.10 (m, 1H), 0.86 (m, 4H). |
| 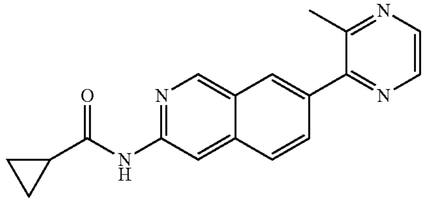 N-(7-(3-methylpyrazin-2-yl) isoquinolin-3-yl) cyclopropanecarboxamide | 12 | 3.902, 305.1, E | $^1$H NMR (400 MHz, DMSO-d$_6$) δ 11.01 (s, 1H), 9.25 (s, 1H), 8.63 (d, J = 2.3 Hz, 1H), 8.58 (d, J = 2.4 Hz, 1H), 8.53 (s, 1H), 8.36 (s, 1H), 7.98 (s, 2H), 2.67 (s, 3H), 2.15-2.03 (m, 1H), 0.86 (m, 4H). |
| 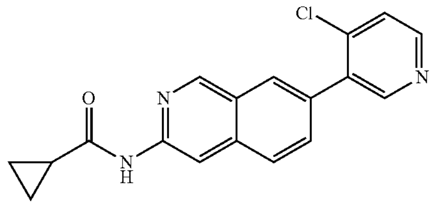 N-(7-(4-chloropyridin-3-yl) isoquinolin-3-yl) cyclopropanecarboxamide | 12 | 4.173, 324.0, E | $^1$H NMR (400 MHz, DMSO-d$_6$) δ 11.02 (s, 1H), 9.22 (s, 1H), 8.72 (s, 1H), 8.60 (d, J = 5.4 Hz, 1H), 8.53 (s, 1H), 8.20 (s, 1H), 7.99 (d, J = 8.6 Hz, 1H), 7.83 (dd, J = 8.6, 1.7 Hz, 1H), 7.74 (d, J = 5.3 Hz, 1H), 2.15-2.03 (m, 1H), 0.86 (m, 4H). |
| 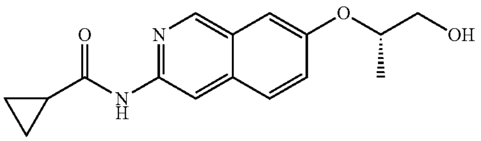 (S)-N-(7-(1-hydroxypropan-2-yloxy)isoquinolin-3-yl) cyclopropanecarboxamidc | 39 | 3.210, 287.1, E | $^1$H NMR (400 MHz, DMSO) δ 10.72 (s, 1H), 8.98 (s, 1H), 8.36 (s, 1H), 7.77 (d, J = 9.0 Hz, 1H), 7.47 (d, J = 2.0 Hz, 1H), 7.34 (dd, J = 9.0, 2.4 Hz, 1H), 4.88 (s, 1H), 4.58 (dd, J = 11.3, 5.6 Hz, 1H), 3.58 (dt, J = 11.3, 9.2 Hz, 2H), 2.04 (td, J = 7.7, 4.0 Hz, 1H), 1.28 (d, J = 6.1 Hz, 3H), 0.92-0.72 (m, 4H). |
| 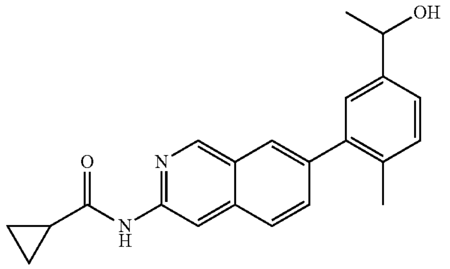 N-(7-(5-(1-hydroxyethyl)-2-methylphenyl)isoquinolin-3-yl) cyclopropanecarboxamide | 12 & 38 | 4.370, 347.1, E | $^1$H NMR (400 MHz, DMSO) δ 10.89 (s, 1H), 9.18 (s, 1H), 8.49 (s, 1H), 7.98 (s, 1H), 7.90 (d, J = 8.5 Hz, 1H), 7.68 (dd, J = 8.5, 1.5 Hz, 1H), 7.28 (s, 3H), 5.11 (d, J = 4.3 Hz, 1H), 4.83-4.65 (m, 1H), 2.26 (s, 3H), 2.14-2.02 (m, 1H), 1.35 (d, J = 6.4 Hz, 3H), 0.94-0.78 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 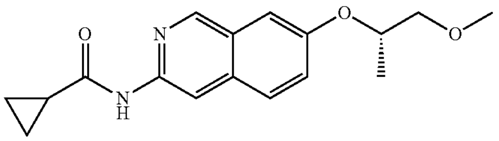 (S)-N-(7-(1-methoxypropan-2-yloxy)isoquinolin-3-yl) cyclopropanecarboxamide | 39 | 3.785, 301.1, E | $^1$H NMR (400 MHz, DMSO) δ 10.72 (s, 1H), 8.98 (s, 1H), 8.50 (s, 1H), 8.36 (s, 1H), 7.77 (d, J = 9.0 Hz, 1H), 7.49 (d, J = 2.1 Hz, 1H), 7.34 (dd, J = 9.0, 2.5 Hz, 1H), 6.73 (s, 1H), 4.76 (dd, J = 10.4, 6.0 Hz, 1H), 3.54 (qd, J = 10.5, 5.0 Hz, 2H), 2.10-1.96 (m, 1H), 1.29 (d, J = 6.2 Hz, 3H), 0.93-0.73 (m, 4H). |
| 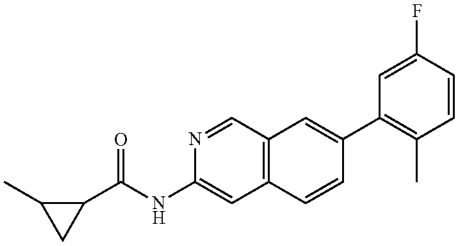 N-(7-(5-fluoro-2-methylphenyl) isoquinolin-3-yl)-2-methylcyclopropanecarboxamide (single trans isomer) | 8 | 5.511, 335.1, E | $^1$H NMR (400 MHz, DMSO) δ 10.82 (s, 1H), 9.17 (s, 1H), 8.48 (s, 1H), 8.03 (s, 1H), 7.91 (d, J = 8.6 Hz, 1H), 7.70 (dd, J = 8.5, 1.5 Hz, 1H), 7.45-7.32 (m, 1H), 7.16 (t, J = 8.0 Hz, 2H), 2.25 (s, 3H), 1.84 (dt, J = 8.2, 4.2 Hz, 1H), 1.37-1.24 (m, 1H), 1.11 (d, J = 6.0 Hz, 3H), 1.07 (dt, J = 8.3, 4.0 Hz, 1H), 0.75-0.64 (m, 1H). |
| 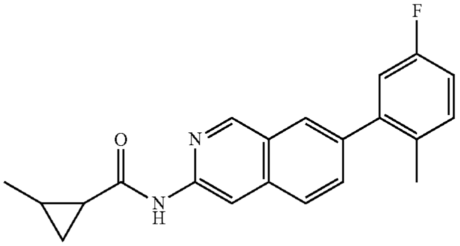 N-(7-(5-fluoro-2-methylphenyl) isoquinolin-3-yl)-2-methylcyclopropanecarboxamide (single trans isomer) | 8 | 4.90, 335.3, H | $^1$H NMR (400 MHz, DMSO) δ 10.82 (s, 1H), 9.17 (s, 1H), 8.48 (s, 1H), 8.03 (s, 1H), 7.91 (d, J = 8.6 Hz, 1H), 7.70 (dd, J = 8.5, 1.4 Hz, 1H), 7.47-7.30 (m, 1H), 7.16 (t, J = 8.0 Hz, 2H), 2.25 (s, 3H), 1.84 (dt, J = 8.2, 4.2 Hz, 1H), 1.36-1.22 (m, 1H), 1.11 (d, J = 6.0 Hz, 3H), 1.09-1.03 (m, 1H), 0.74-0.60 (m, 1H). |
| 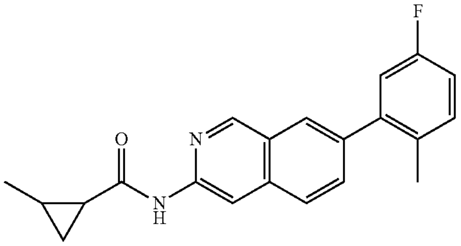 N-(7-(5-fluoro-2-methylphenyl) isoquinolin-3-yl)-2-methylcyclopropanecarboxamide (single cis isomer) | 8 | 5.513, 335.1, E | $^1$H NMR (400 MHz, DMSO) δ 10.80 (s, 1H), 9.17 (s, 1H), 8.52 (s, 1H), 8.03 (s, 1H), 7.94 (d, J = 8.6 Hz, 1H), 7.70 (dd, J = 8.5, 1.6 Hz, 1H), 7.38 (t, J = 7.0 Hz, 1H), 7.16 (t, J = 8.2 Hz, 2H), 2.25 (s, 3H), 2.10 (td, J = 8.1, 5.5 Hz, 1H), 1.37-1.23 (m, 1H), 1.17 (d, J = 6.1 Hz, 3H), 1.00 (td, J = 8.0, 3.8 Hz, 1H), 0.84 (dd, J = 10.7, 5.3 Hz, 1H). |

TABLE 3-continued

| Structure/Name | Syn. Meth-od | LCMS $R_T$ (min), M + $H^+$, LCMS method | $^1$H NMR (ppm) |
|---|---|---|---|
| 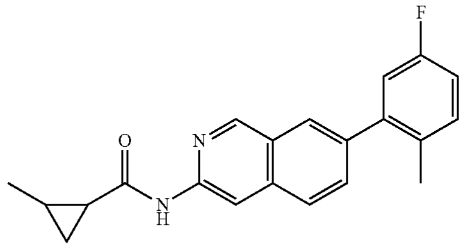 N-(7-(5-fluoro-2-methylphenyl) isoquinolin-3-yl)-2-methylcyclopropanecarboxamide (single cis isomer) | 8 | 5.508, 335.1, E | $^1$H NMR (400 MHz, DMSO) δ 10.80 (s, 1H), 9.17 (s, 1H), 8.52 (s, 1H), 8.03 (s, 1H), 7.94 (d, J = 8.6 Hz, 1H), 7.70 (dd, J = 8.5, 1.6 Hz, 1H), 7.38 (t, J = 7.1 Hz, 1H), 7.16 (t, J = 8.2 Hz, 2H), 2.25 (s, 3H), 2.10 (td, J = 8.1, 5.4 Hz, 1H), 1.37-1.24 (m, 1H), 1.17 (d, J = 6.1 Hz, 3H), 1.00 (td, J = 8.0, 3.8 Hz, 1H), 0.84 (dd, J = 10.7, 5.2 Hz, 1H). |
| 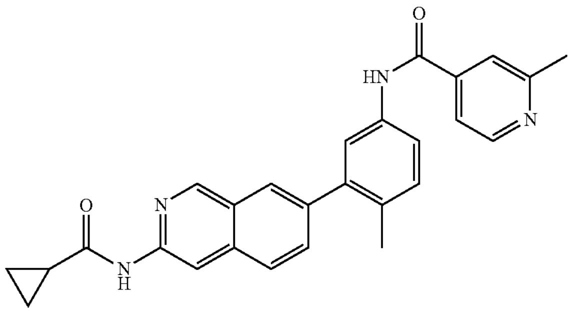 N-(3-(3-(cyclopropanecarboxamido) isoquinolin-7-yl)-4-methylphenyl)-2-methylisonicotinamide | 15 | 3.32, 437.2, H | $^1$H NMR (400 MHz, DMSO) δ 10.90 (s, 1H), 10.44 (s, 1H), 9.20 (s, 1H), 8.63 (d, J = 5.1 Hz, 1H), 8.50 (s, 1H), 8.02 (s, 1H), 7.94 (d, J = 8.5 Hz, 1H), 7.80-7.68 (m, 4H), 7.65 (d, J = 5.2 Hz, 1H), 7.35 (d, J = 8.3 Hz, 1H), 2.57 (s, 3H), 2.27 (s, 3H), 2.15-2.02 (m, 1H), 0.92-0.77 (m, 4H). |
| 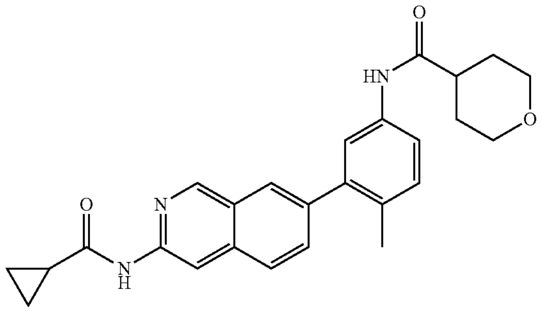 N-(3-(3-(cyclopropanecarboxamido) isoquinolin-7-yl)-4-methylphenyl) tetrahydro-2H-pyran-4-carboxamide | 15 | 3.68, 430.3, H | $^1$H NMR (400 MHz, DMSO) δ 10.89 (s, 1H), 9.87 (s, 1H), 9.18 (s, 1H), 8.49 (s, 1H), 7.98 (s, 1H), 7.91 (d, J = 8.6 Hz, 1H), 7.75-7.58 (m, 2H), 7.51 (dd, J = 8.3, 2.1 Hz, 1H), 7.25 (d, J = 8.3 Hz, 1H), 3.90 (dd, J = 8.1, 2.9 Hz, 2H), 3.35 (td, J = 11.3, 3.7 Hz, 2H), 2.57 (dd, J = 10.2, 4.9 Hz, 1H), 2.22 (s, 3H), 2.15-1.99 (m, 1H), 1.73-1.60 (m, 4H), 0.85 (m, 4H). |
| 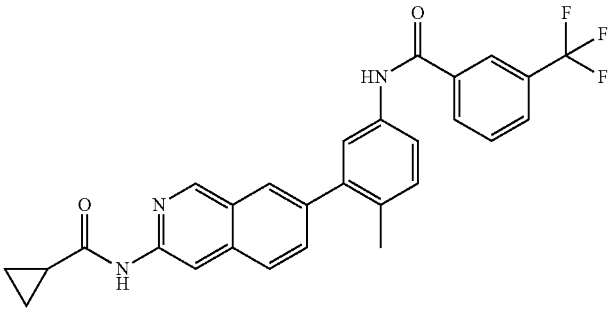 N-(3-(3-(cyclopropanecarboxamido) isoquinolin-7-yl)-4-methylphenyl)-3-(trifluoromethyl)benzamide | 16 | 4.94, 490.3, H | $^1$H NMR (400 MHz, DMSO) δ 10.90 (s, 1H), 10.47 (s, 1H), 9.20 (s, 1H), 8.50 (s, 1H), 8.31 (s, 1H), 8.27 (d, J = 8.0 Hz, 1H), 8.03 (s, 1H), 7.99-7.90 (m, 2H), 7.82-7.69 (m, 4H), 7.35 (d, J = 8.0 Hz, 1H), 2.27 (s, 3H), 2.15-2.01 (m, 1H), 0.98-0.74 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 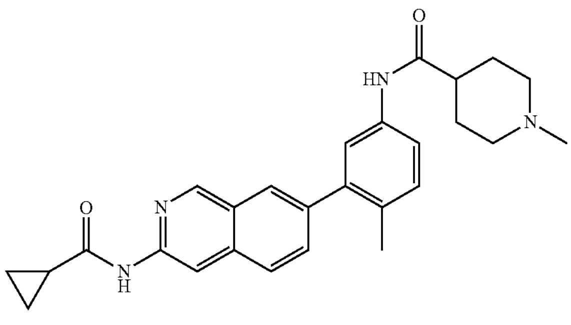 N-(3-(3-(cyclopropanecarboxamido) isoquinolin-7-yl)-4-methylphenyl)-1-methylpiperidine-4-carboxamide | 15 | 3.15, 443.2, H | $^1$H NMR (400 MHz, DMSO) δ 10.90 (s, 1H), 9.85 (s, 1H), 9.19 (s, 1H), 8.49 (s, 1H), 7.98 (s, 1H), 7.92 (d, J = 8.6 Hz, 1H), 7.75-7.62 (m, 2H), 7.51 (dd, J = 8.3, 2.1 Hz, 1H), 7.25 (d, J = 8.4 Hz, 1H), 2.81 (d, J = 11.4 Hz, 2H), 2.26 (d, J = 4.0 Hz, 1H), 2.22 (s, 3H), 2.16 (s, 3H), 2.13-2.04 (m, 1H), 1.86 (dd, J = 11.7, 9.3 Hz, 2H), 1.74 (d, J = 10.1 Hz, 2H), 1.66 (td, J = 12.1, 3.3 Hz, 2H), 0.86 (m, 4H). |
| 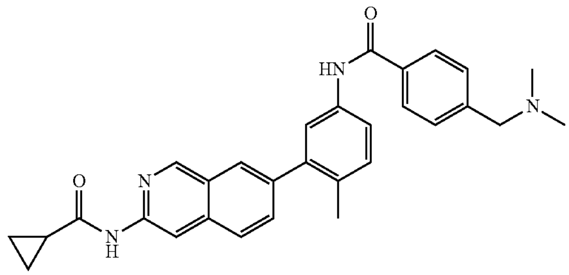 N-(3-(3-(cyclopropanecarboxamido) isoquinolin-7-y])-4-methylphenyl)-4-((dimethylamino)methyl)benzamide | 15 | 3.39, 479.3, H | $^1$H NMR (400 MHz, DMSO) δ 10.90 (s, 1H), 10.21 (s, 1H), 9.19 (s, 1H), 8.50 (s, 1H), 8.02 (s, 1H), 7.93 (dd, J = 8.4, 3.4 Hz, 3H), 7.79 (d, J = 1.9 Hz, 1H), 7.78-7.65 (m, 2H), 7.43 (d, J = 8.1 Hz, 2H), 7.32 (d, J = 8.3 Hz, 1H), 3.46 (s, 2H), 2.26 (s, 3H), 2.16 (s, 6H), 2.13-2.04 (m, 1H), 0.85 (dd, J = 12.1, 6.0 Hz, 4H). |
| 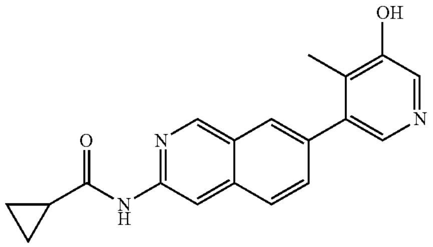 N-(7-(5-hydroxy-4-methylpyridin-3-yl)isoquinolin-3-yl) cyclopropanecarboxamide | 12 | 2.63, 320.2, H | $^1$H NMR (400 MHz, DMSO) δ 10.92 (s, 1H), 9.19 (s, 1H), 8.51 (s, 1H), 8.15 (s, 1H), 8.04 (s, 1H), 8.00 (s, 1H), 7.94 (d, J = 8.5 Hz, 1H), 7.70 (d, J = 8.1 Hz, 1H), 2.12 (s, 3H), 2.09 (m, 1H), 0.90-0.82 (m, 4H). |
| 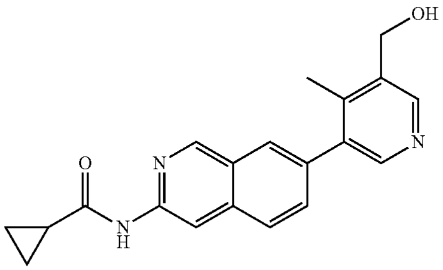 N-(7-(5-(hydroxymethyl)-4-methylpyridin-3-yl)isoquinolin-3-yl)cyclopropanecarboxamide | 12 & 38 | 3.093, 334.1, E | $^1$H NMR (400 MHz, DMSO) δ 10.92 (s, 1H), 9.19 (s, 1H), 8.52 (d, J = 3.6 Hz, 2H), 8.40 (s, 1H), 8.04 (s, 1H), 7.95 (d, J = 8.6 Hz, 1H), 7.69 (dd, J = 8.5, 1.6 Hz, 1H), 5.27 (d, J = 5.3 Hz, 1H), 4.64 (d, J = 5.3 Hz, 2H), 2.25 (s, 3H), 2.16-2.02 (m, 1H), 0.86 (dt, J = 10.4, 5.4 Hz, 4H). |

TABLE 3-continued

| Structure/Name | Syn. Meth-od | LCMS $R_T$ (min), M + H$^+$, LCMS method | $^1$H NMR (ppm) |
|---|---|---|---|
| 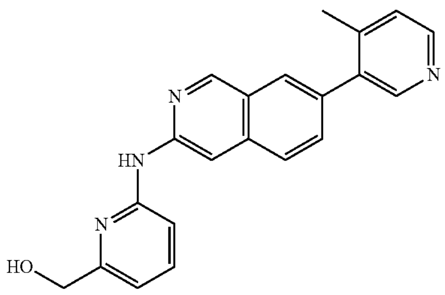 (6-(7-(4-methylpyridin-3-yl) isoquinolin-3-ylamino)pyridin-2-yl)methanol | 13 | 2.840, 343.1, E | $^1$H NMR (400 MHz, DMSO) δ 9.79 (s, 1H), 9.13 (s, 1H), 8.56 (s, 1H), 8.54-8.43 (m, 2H), 8.01 (s, 1H), 7.88 (d, J = 8.6 Hz, 1H), 7.73-7.61 (m, 2H), 7.39 (d, J = 5.0 Hz, 1H), 7.23 (d, J = 8.2 Hz, 1H), 6.97 (d, J = 7.3 Hz, 1H), 5.35 (s, 1H), 4.60 (s, 2H), 2.35 (s, 4H). |
| 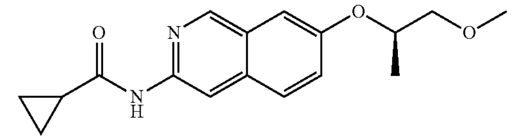 (R)-N-(7-(1-methoxypropan-2-yloxy)isoquinolin-3-yl) cyclopropanecarboxamide | 39 | 3.770, 301.1, E | $^1$H NMR (400 MHz, DMSO) δ 10.73 (s, 1H), 8.99 (s, 1H), 8.37 (s, 1H), 7.78 (d, J = 9.0 Hz, 1H), 7.49 (d, J = 2.0 Hz, 1H), 7.34 (dd, J = 9.0, 2.4 Hz, 1H), 4.77 (dd, J = 10.5, 6.0 Hz, 1H), 3.55 (qd, J = 10.5, 5.0 Hz, 2H), 3.32 (s, 3H), 2.10-2.00 (m, 1H), 1.30 (d, J = 6.2 Hz, 3H), 0.83 (m, 4H). |
| 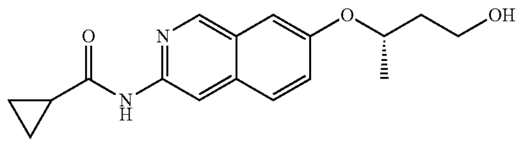 (S)-N-(7-(4-hydroxybutan-2-yloxy)isoquinolin-3-yl) cyclopropanecarboxamide | 43 | 3.460, 301.1, E | $^1$H NMR (400 MHz, DMSO) δ 10.72 (s, 1H), 8.98 (s, 1H), 8.36 (s, 1H), 7.76 (d, J = 9.0 Hz, 1H), 7.45 (d, J = 2.2 Hz, 1H), 7.32 (dd, J = 9.0, 2.4 Hz, 1H), 4.73 (h, J = 6.1 Hz, 1H), 4.52 (t, J = 4.5 Hz, 1H), 3.56 (dd, J = 10.5, 6.0 Hz, 2H), 2.04 (ddd, J = 12.5, 7.9, 4.9 Hz, 1H), 1.97-1.87 (m, 1H), 1.74 (td, J = 12.8, 6.5 Hz, 1H), 1.33 (d, J = 6.1 Hz, 3H), 0.93-0.69 (m, 4H). |
| 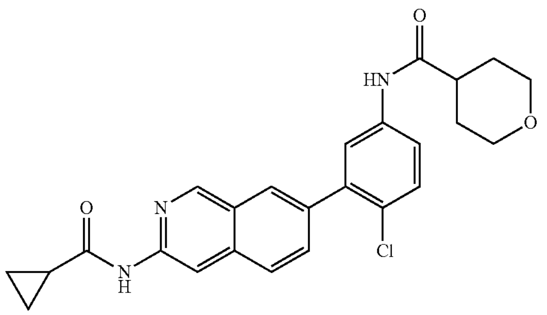 N-(4-chloro-3-(3-(cyclopropanecarboxamido) isoquinolin-7-yl)phenyl)tetrahydro-2H-pyran-4-carboxamide | 15 | 4.613, 450.1, E | $^1$H NMR (400 MHz, DMSO) δ 10.92 (s, 1H), 10.10 (s, 1H), 9.21 (s, 1H), 8.50 (s, 1H), 8.08 (s, 1H), 7.93 (d, J = 8.6 Hz, 1H), 7.86 (d, J = 2.4 Hz, 1H), 7.74 (d, J = 8.5 Hz, 1H), 7.64 (dd, J = 8.8, 2.5 Hz, 1H), 7.53 (d, J = 8.7 Hz, 1H), 3.90 (d, J = 10.9 Hz, 2H), 3.35 (td, J = 11.3, 2.8 Hz, 2H), 2.64-2.54 (m, 1H), 2.15-1.99 (m, 1H), 1.76-1.59 (m, 4H), 0.85 (m, 4H). |

TABLE 3-continued

| Structure/Name | Syn. Meth-od | LCMS $R_T$ (min), M + $H^+$, LCMS method | $^1H$ NMR (ppm) |
|---|---|---|---|
| 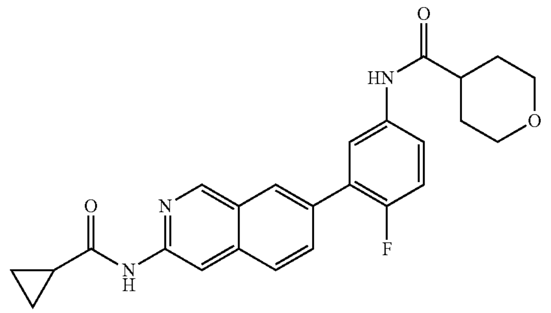 N-(3-(3-(cyclopropanecarboxamido) isoquinolin-7-yl)-4-fluorophenyl) tetrahydro-2H-pyran-4-carboxamide | 15 | 4.398, 434.2, E | $^1H$ NMR (400 MHz, DMSO) δ 10.92 1H), 10.04 (s, 1H), 9.23 (s, 1H), 8.49 (s, 1H), 8.19 (s, 1H), 8.00-7.90 (m, 2H), 7.82 (d, J = 8.6 Hz, 1H), 7.66-7.56 (m, 1H), 7.38-7.22 (m, 1H), 4.00-3.79 (m, 2H), 3.36 (td, J = 11.2, 3.2 Hz, 2H), 2.65-2.55 (m, 1H), 2.15-2.02 (m, 1H), 1.78-1.59 (m, 4H), 0.95-0.75 (m, 4H). |
| 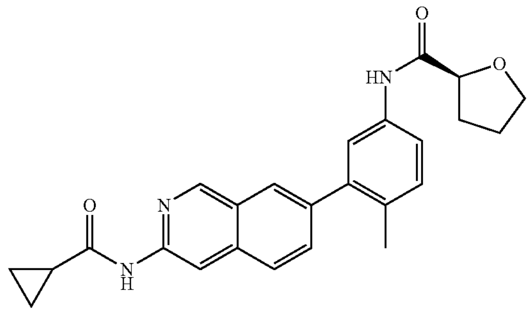 (S)-N-(3-(3-(cyclopropanecarboxamido) isoquinolin-7-yl)-4-methylphenyl) tetrahydrofuran-2-carboxamide | 15 | 4.596, 416.2, E | $^1H$ NMR (400 MHz, DMSO) δ 10.89 (s, 1H), 9.64 (s, 1H), 9.18 (s, 1H), 8.49 (s, 1H), 7.99 (s, 1H), 7.91 (d, J = 8.5 Hz, 1H), 7.68 (dd, J = 11.8, 1.7 Hz, 2H), 7.64 (dd, J = 8.3, 2.0 Hz, 1H), 7.27 (d, J = 8.3 Hz, 1H), 4.38 (dd, J = 8.1, 5.6 Hz, 1H), 3.98 (dd, J = 14.5, 6.8 Hz, 1H), 3.82 (dd, J = 14.5, 6.9 Hz, 1H), 2.23 (s, 3H), 2.14 (s, 1H), 2.13-2.04 (m, 1H), 1.98 (td, J = 12.6, 6.7 Hz, 1H), 1.86 (p, J = 6.9 Hz, 2H), 0.97-0.72 (m, 4H). |
| 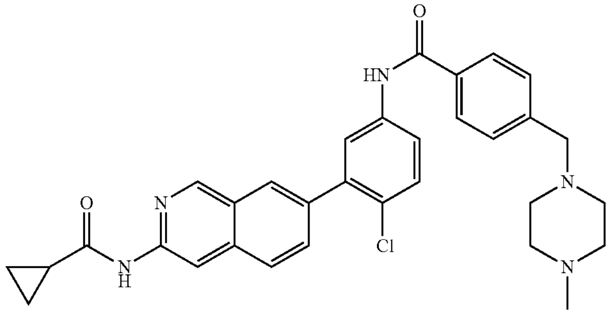 N-(4-chloro-3-(3-(cyclopropanecarboxamido) isoquinolin-7-yl)phenyl)-4-((4-methylpiperazin-1-yl)methyl)benzamide | 15 | 4.051, 554.2, E | $^1H$ NMR (400 MHz, DMSO) δ 10.93 (s, 1H), 10.40 (s, 1H), 9.22 (s, 1H), 8.51 (s, 1H), 8.13 (s, 1H), 8.02 (d, J = 2.5 Hz, 1H), 7.96 (d, J = 8.6 Hz, 1H), 7.92 (d, J = 8.2 Hz, 2H), 7.89 (dd, J = 8.8, 2.5 Hz, 1H), 7.78 (dd, J = 8.6, 1.5 Hz, 1H), 7.59 (d, J = 8.8 Hz, 1H), 7.45 (d, J = 8.1 Hz, 2H), 3.53 (s, 2H), 2.35 (d, J = 20.9 Hz, 8H), 2.15 (s, 3H), 2.09 (ddd, J = 12.5, 7.8, 4.8 Hz, 1H), 0.94-0.76 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 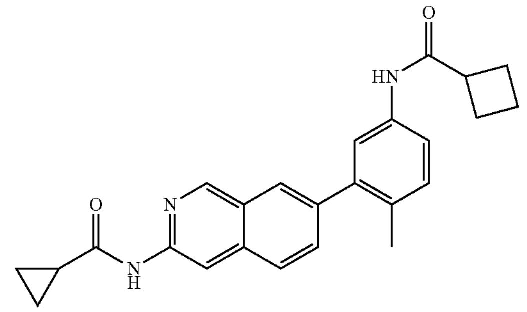<br>N-(3-(3-(cyclopropanecarboxamido) isoquinolin-7-yl)-4-methylphenyl) cyclobutanecarboxamide | 16 | 4.821, 400.2, E | $^1$H NMR (400 MHz, DMSO) δ 10.89 (s, 1H), 9.71 (s, 1H), 9.18 (s, 1H), 8.49 (s, 1H), 7.98 (s, 1H), 7.91 (d, J = 8.5 Hz, 1H), 7.72-7.65 (m, 1H), 7.63 (d, J = 1 .7 Hz, 1H), 7.57-7.49 (m, 1H), 7.25 (d, J = 8.3 Hz, 1H), 3.20 (dd, J = 16.7, 8.4 Hz, 1H), 2.29-2.14 (m, 5H), 2.14-2.01 (m, 3H), 1.99-1.87 (m, 1H), 1.80 (dd, J = 19.4, 9.4 Hz, 1H), 0.95-0.76 (m, 4H). |
| 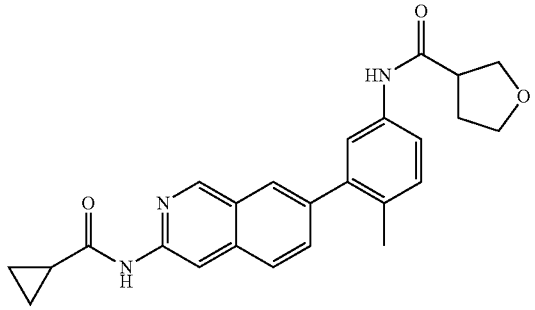<br>N-(3-(3-(cyclopropanecarboxamido) isoquinolin-7-yl)-4-methylphenyl) tetrahydrofuran-3-carboxamide (single enantiomer) | 15 | 4.338, 416.2, E | $^1$H NMR (400 MHz, DMSO) δ 10.89 (s, 1H), 10.02 (s, 1H), 9.18 (s, 1H), 8.49 (s, 1H), 7.98 (s, 1H), 7.91 (d, J = 8.6 Hz, 1H), 7.67 (d, J = 8.5 Hz, 1H), 7.62 (s, 1H), 7.56-7.47 (m, 1H), 7.27 (d, J = 8.3 Hz, 1H), 3.93 (t, J = 8.2 Hz, 1H), 3.83-3.63 (m, 3H), 3.14 (p, J = 7.7 Hz, 1H), 2.22 (s, 3H), 2.07 (q, J = 7.1 Hz, 3H), 0.93-0.77 (m, 4H). |
| 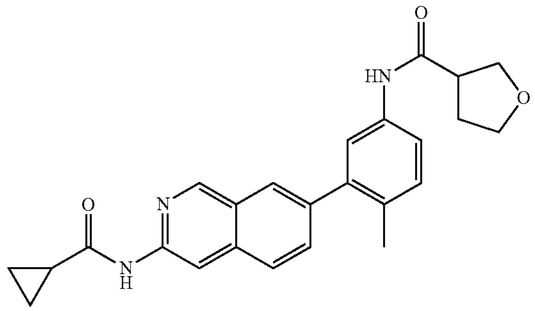<br>N-(3-(3-(cyclopropanecarboxamido) isoquinolin-7-yl)-4-methylphenyl) tetrahydrofuran-3-carboxamide (single enantiomer) | 15 | 4.330, 416.2, E | $^1$H NMR (400 MHz, DMSO) δ 10.89 (s, 1H), 10.01 (s, 1H), 9.18 (s, 1H), 8.49 (s, 1H), 7.98 (s, 1H), 7.91 (d, J = 8.5 Hz, 1H), 7.67 (dd, J = 8.5, 1.2 Hz, 1H), 7.62 (d, J = 1.7 Hz, 1H), 7.51 (dd, J = 8.2, 1.9 Hz, 1H), 7.27 (d, J = 8.3 Hz, 1H), 3.93 (t, J = 8.2 Hz, 1H), 3.83-3.64 (m, 3H), 3.14 (p, J = 7.6 Hz, 1H), 2.22 (s, 3H), 2.16-1.97 (m, 3H), 0.94-0.73 (m, 4H). |

TABLE 3-continued

| Structure/Name | Syn. Meth-od | LCMS $R_T$ (min), M + $H^+$, LCMS method | $^1H$ NMR (ppm) |
|---|---|---|---|
| 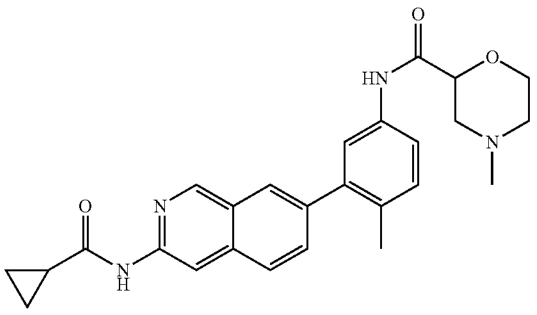 N-(3-(3-(cyclopropanecarboxamido) isoquinolin-7-yl)-4-methylphenyl)-4-methylmorpholine-2-carboxamidc | 15 | 3.805, 445.2, E | $^1H$ NMR (400 MHz, DMSO) δ 10.89 (s, 1H), 9.62 (s, 1H), 9.18 (s, 1H), 8.49 (s, 1H), 7.99 (s, 1H), 7.91 (d, J = 8.6 Hz, 1H), 7.69 (dd, J = 8.3, 5.2 Hz, 2H), 7.62 (dd, J = 8.3, 1.9 Hz, 1H), 7.27 (d, J = 8.3 Hz, 1H), 4.09 (dd, J = 9.9, 2.6 Hz, 1H), 3.93 (d, J = 11.3 Hz, 1H), 3.63 (dd, J = 11.0, 8.8 Hz, 1H), 2.92 (d, J = 11.7 Hz, 1H), 2.61 (d, J = 11.6 Hz, 1H), 2.23 (s, 3H), 2.22 (s, 3H), 2.06 (m, 3H), 0.95-0.69 (m, 4H). |
| 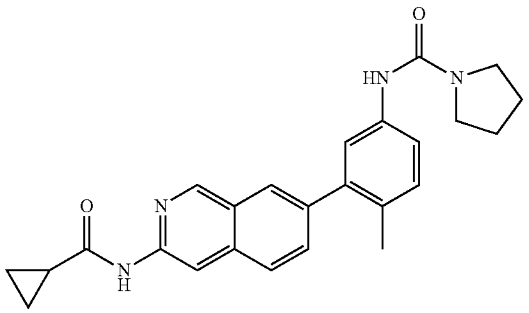 N-(3-(3-(cyclopropanecarboxamido) isoquinolin-7-yl)-4-methylphenyl) pyrrolidine-1-carboxamide | 17 | 4.489, 415.2, E | $^1H$ NMR (400 MHz, DMSO) δ 10.88 (s, 1H), 9.17 (s, 1H), 8.48 (s, 1H), 8.09 (s, 1H), 7.97 (s, 1H), 7.90 (d, J = 8.6 Hz, 1H), 7.67 (d, J = 8.5 Hz, 1H), 7.51 (s, 1H), 7.48 (d, J = 8.3 Hz, 1H), 7.18 (d, J = 8.3 Hz, 1H), 3.36 (t, J = 6.6 Hz, 4H), 2.21 (s, 3H), 2.15-2.01 (m, 1H), 1.84 (t, J = 6.5 Hz, 4H), 0.94-0.76 (m, 4H). |
| 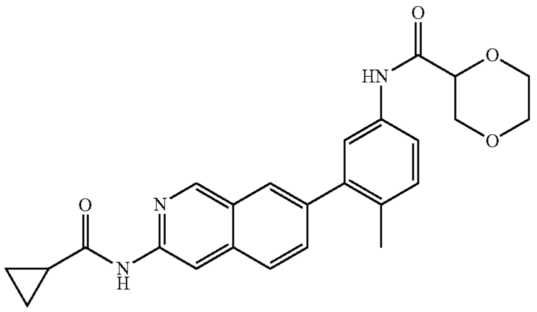 N-(3-(3-(cyclopropanecarboxamido) isoquinolin-7-yl)-4-methylphenyl)-1,4-dioxane-2-carboxamide (single enantiomer) | 15 | 4.504, 432.2, E | $^1H$ NMR (400 MHz, DMSO) δ 10.89 (s, 1H), 9.73 (s, 1H), 9.18 (s, 1H), 8.49 (s, 1H), 7.99 (s, 1H), 7.91 (d, J = 8.5 Hz, 1H), 7.68 (dd, J = 10.7, 1.8 Hz, 2H), 7.62 (dd, J = 8.3, 2.1 Hz, 1H), 7.27 (d, J = 8.3 Hz, 1H), 4.21 (dd, J = 9.3, 3.0 Hz, 1H), 3.97-3.85 (m, 2H), 3.72 (dd, J = 15.5, 6.6 Hz, 2H), 3.56 (dd, J = 17.6, 8.1 Hz, 2H), 2.23 (s, 3H), 2.08 m, 1H), 0.94-0.76 (m, 4H). |

TABLE 3-continued

| Structure/Name | Syn. Meth-od | LCMS $R_T$ (min), M + $H^+$, LCMS method | $^1$H NMR (ppm) |
|---|---|---|---|
| 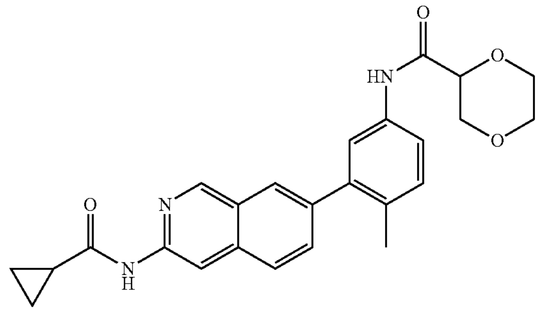 N-(3-(3-(cyclopropanecarboxamido) isoquinolin-7-yl)-4-methylphenyl)-1,4-dioxane-2-carboxamide (single enantiomer) | 15 | 4.503, 432.2, E | $^1$H NMR (400 MHz, DMSO) δ 10.89 (s, 1H), 9.73 (s, 1H), 9.18 (s, 1H), 8.49 (s, 1H), 7.99 (s, 1H), 7.91 (d, J = 8.6 Hz, 1H), 7.68 (d, J = 10.3 Hz, 2H), 7.62 (dd, J = 8.3, 2.0 Hz, 1H), 7.27 (d, J = 8.3 Hz, 1H), 4.21 (dd, J = 9.3, 3.0 Hz, 1H), 3.96-3.85 (m, 2H), 3.72 (dd, J = 15.5, 6.6 Hz, 2H), 3.56 (dd, J = 17.6, 8.1 Hz, 2H), 2.23 (s, 3H), 2.16-2.01 (m, 1H), 0.92-0.78 (m, 4H). |
| 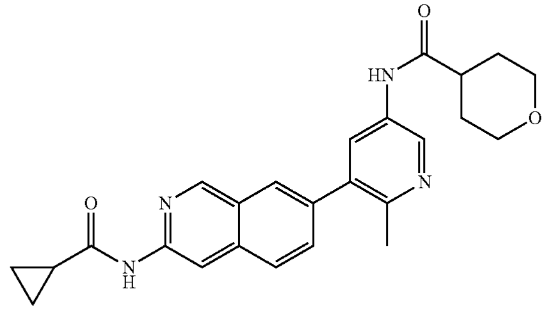 N-(5-(3-(cyclopropanecarboxamido) isoquinolin-7-yl)-6-methylpyridin-3-yl) tetrahydro-2H-pyran-4-carboxamide | 15 | 3.393, 431.2, E | $^1$H NMR (400 MHz, DMSO) δ 10.92 (s, 1H), 10.11 (s, 1H), 9.20 (s, 1H), 8.66 (d, J = 2.3 Hz, 1H), 8.51 (s, 1H), 8.06 (s, 2H), 7.95 (d, J = 8.6 Hz, 1H), 7.72 (d, J = 8.6 Hz, 1H), 3.91 (d, J = 11.1 Hz, 2H), 3.36 (dt, J = 11.3, 5.8 Hz, 2H), 2.70-2.55 (m, 1H), 2.42 (s, 3H), 2.14-2.03 (m, 1H), 1.78-1.59 (m, 4H), 0.85 (dd, J = 11.0, 6.0 Hz, 4H). |
| 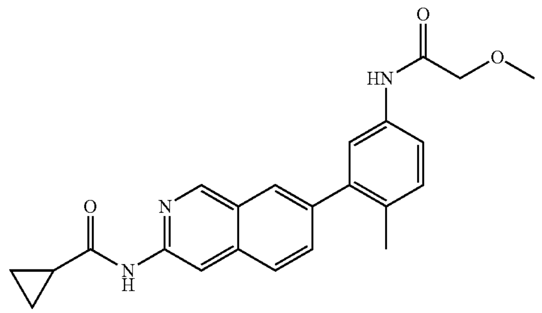 N-(7-(5-(2-methoxyacetamido)-2-methylphenyl)isoquinolin-3-yl)cyclopropanecarboxamide | 16 | 4.401, 390.2, E | $^1$H NMR (400 MHz, DMSO) δ 10.89 (s, 1H), 9.73 (s, 1H), 9.18 (s, 1H), 8.49 (s, 1H), 7.99 (s, 1H), 7.92 (d, J = 8.5 Hz, 1H), 7.71-7.65 (m, 2H), 7.61 (dd, J = 8.3, 1.9 Hz, 1H), 7.27 (d, J = 8.3 Hz, 1H), 3.99 (s, 2H), 3.38 (s, 3H), 2.23 (s, 3H), 2.14-2.03 (m, 1H), 0.92-0.78 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 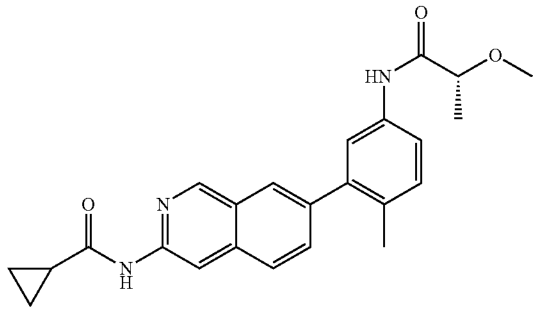 (R)-N-(7-(5-(2-methoxypropanamido)-2-methylphenyl)isoquinolin-3-yl) cyclopropanecarboxamide | 15 | 4.565, 404.2, E | $^1$H NMR (400 MHz, DMSO) δ 10.89 (s, 1H), 9.78 (s, 1H), 9.18 (s, 1H), 8.49 (s, 1H), 7.99 (s, 1H), 7.91 (d, J = 8.5 Hz, 1H), 7.71-7.65 (m, 2H), 7.63 (d, J = 8.3 Hz, 1H), 7.27 (d, J = 8.3 Hz, 1H), 3.86 (q, J = 6.7 Hz, 1H), 3.31 (s, 3H), 2.23 (s, 3H), 2.14-2.02 (m, 1H), 1.31 (d, J = 6.7 Hz, 3H), 0.93-0.77 (m, 4H). |
| 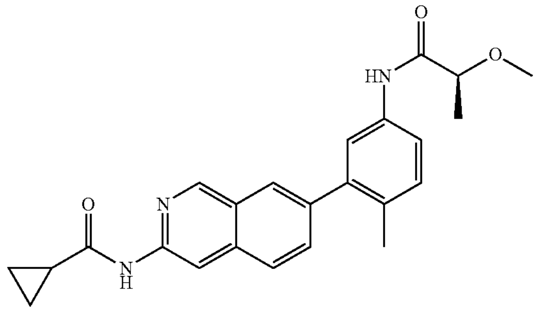 (S)-N-(7-(5-(2-methoxypropanamido)-2-methylphenyl)isoquinolin-3-yl) cyclopropanecarboxamide | 15 | 4.566, 404.2, E | $^1$H NMR (400 MHz, DMSO) δ 10.89 (s, 1H), 9.78 (s, 1H), 9.18 (s, 1H), 8.49 (s, 1H), 7.99 (s, 1H), 7.92 (d, J = 8.5 Hz, 1H), 7.70 (d, J = 1.6 Hz, 1H), 7.68 (dd, J = 8.6, 1.2 Hz, 1H), 7.63 (dd, J = 8.3, 1.9 Hz, 1H), 7.27 (d, J = 8.3 Hz, 1H), 3.86 (q, J = 6.7 Hz, 1H), 3.31 (s, 3H), 2.23 (s, 3H), 2.14-2.04 (m, 1H), 1.31 (d, J = 6.7 Hz, 3H), 0.90-0.78 (m, 4H). |
| 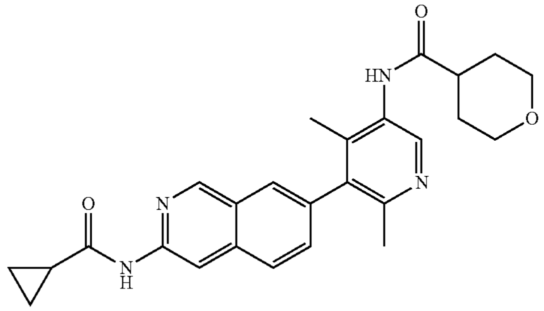 N-(5-(3-(cyclopropanecarboxamido) isoquinolin-7-yl)-4-methylpyridin-3-yl) tetrahydro-2H-pyran-4-carboxamide | 12 | 3.367, 431.2, E | $^1$H NMR (400 MHz, DMSO) δ 10.93 (s, 1H), 9.60 (s, 1H), 9.20 (s, 1H), 8.52 (s, 1H), 8.51 (s, 1H), 8.33 (s, 1H), 8.06 (s, 1H), 7.96 (d, J = 8.6 Hz, 1H), 7.70 (d, J = 8.6 Hz, 1H), 3.92 (d, J = 11.2 Hz, 2H), 3.39 (dd, J = 11.4, 9.4 Hz, 2H), 2.80-2.69 (m, 1H), 2.15 (s, 3H), 2.12-2.04 (m, 1H), 1.72 (tt, J = 12.9, 8.7 Hz, 4H), 0.91-0.76 (m, 4H). |
| 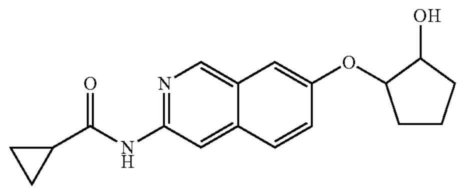 N-(7-(2-hydroxycyclopentyloxy) isoquinolin-3-yl) cyclopropanecarboxamide (single trans isomer) | 44 | 3.687, 313.1, E | $^1$H NMR (400 MHz, DMSO) δ 10.73 (s, 1H), 8.98 (s, 1H), 8.36 (s, 1H), 7.77 (d, J = 9.0 Hz, 1H), 7.46 (s, 1H), 7.32 (dd, J = 9.0, 2.4 Hz, 1H), 5.02 (d, J = 4.0 Hz, 1H), 4.65-4.52 (m, 1H), 4.14 (d, J = 3.5 Hz, 1H), 2.27-2.15 (m, 1H), 2.09-1.99 (m, 1H), 1.90 (m, 1H), 1.83-1.62 (m, 3H), 1.58 (m, 1H), 0.89-0.74 (m, 4H). |

TABLE 3-continued

| Structure/Name | Syn. Meth- od | LCMS $R_T$ (min), M + $H^+$, LCMS method | $^1H$ NMR (ppm) |
|---|---|---|---|
| 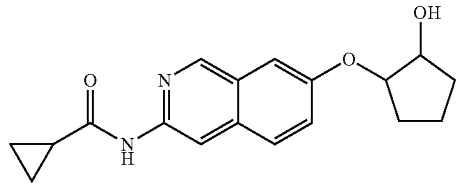 N-(7-(2-hydroxycyclopentyloxy) isoquinolin-3-yl) cyclopropanecarboxamide (single trans isomer) | 44 | 3.688, 313.1, E | $^1H$ NMR (400 MHz, DMSO) δ 10.73 (s, 1H), 8.98 (s, 1H), 8.37 (s, 1H), 7.77 (d, J = 9.0 Hz, 1H), 7.46 (d, J = 2.1 Hz, 1H), 7.32 (dd, J = 9.0, 2.4 Hz, 1H), 5.02 (d, J = 4.0 Hz, 1H), 4.65-4.54 (m, 1H), 4.14 (d, J = 3.5 Hz, 1H), 2.26-2.14 (m, 1H), 2.04 (m, 1H), 1.90 (m, 1H), 1.83-1.62 (m, 3H), 1.57 (m, 1H), 0.86-0.75 (m, 4H). |
| 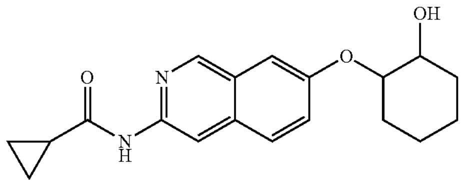 N-(7-(2-hydroxycyclohexyloxy) isoquinolin-3-yl) cyclopropanecarboxamide (single trans isomer) | 44 | 3.766, 327.1, E | $^1H$ NMR (400 MHz, DMSO) δ 10.70 (s, 1H), 8.98 (s, 1H), 8.35 (s, 1H), 7.76 (d, J = 9.0 Hz, 1H), 7.50 (d, J = 2.1 Hz, 1H), 7.36 (dd, J = 9.0, 2.4 Hz, 1H), 4.91 (d, J = 4.6 Hz, 1H), 4.20 (dd, J = 10.2, 6.4 Hz, 1H), 3.59 (tt, J = 9.2, 4.5 Hz, 1H), 2.10 (d, J = 5.0 Hz, 1H), 2.07-1.97 (m, 1H), 1.90 (d, J = 11.7 Hz, 1H), 1.66 (d, J = 9.7 Hz, 2H), 1.44-1.21 (m, 4H), 0.88-0.73 (m, 4H). |
| 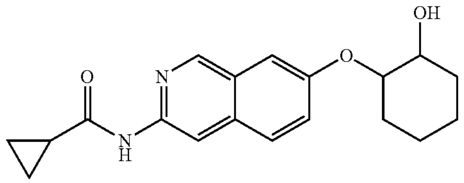 N-(7-(2-hydroxycyclohexyloxy) isoquinolin-3-yl) cyclopropanecarboxamide (single trans isomer) | 44 | 3.770, 327.2, E | $^1H$ NMR (400 MHz, DMSO) δ 10.71 (s, 1H), 8.98 (s, 1H), 8.35 (s, 1H), 7.76 (d, J = 9.0 Hz, 1H), 7.49 (s, 1H), 7.36 (dd, J = 9.0, 2.3 Hz, 1H), 4.91 (d, J = 4.6 Hz, 1H), 4.20 (t, J = 8.3 Hz, 1H), 3.67-3.52 (m, 1H), 2.10 (m, 1H), 2.04 (m, 1H), 1.90 (m, 1H), 1.66 (dm, 2H), 1.44-1.19 (m, 4H), 0.92-0.73 (m, 4H). |
| 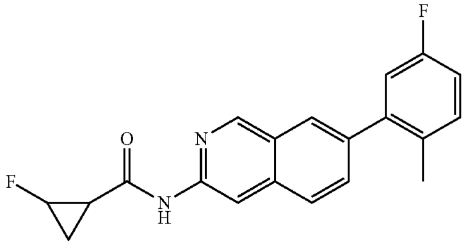 2-fluoro-N-(7-(5-fluoro-2-methylphenyl) isoquinolin-3-yl)cyclopropanecarboxamide (single cis isomer) | 8 | 5.253, 339.1, E | $^1H$ NMR (400 MHz, DMSO) δ 10.98 (s, 1H), 9.19 (s, 1H), 8.52 (s, 1H), 8.05 (s, 1H), 7.95 (d, J = 8.6 Hz, 1H), 7.72 (dd, J = 8.6, 1.5 Hz, 1H), 7.38 (d, J = 6.4 Hz, 1H), 7.18 (d, J = 9.1 Hz, 2H), 4.95 (ddd, J = 66.2, 10.1, 6.2 Hz, 1H), 2.41-2.14 (m, 4H), 1.78-1.61 (m, 1H), 1.20 (ddd, J = 15.5, 12.4, 6.2 Hz, 1H). |

TABLE 3-continued

| Structure/Name | Syn. Meth-od | LCMS $R_T$ (min), M + H$^+$, LCMS method | $^1$H NMR (ppm) |
|---|---|---|---|
| 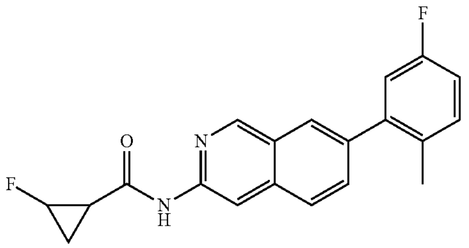 2-fluoro-N-(7-(5-fluoro-2-methylphenyl) isoquinolin-3-yl)cyclopropanecarboxamide (single cis isomer) | 8 | 5.254, 339.1, E | $^1$H NMR (400 MHz, DMSO) δ 10.98 (s, 1H), 9.19 (s, 1H), 8.52 (s, 1H), 8.05 (s, 1H), 7.95 (d, J = 8.5 Hz, 1H), 7.80-7.68 (m, 1H), 7.46-7.33 (m, 1H), 7.16 (dd, J = 13.9, 5.9 Hz, 2H), 4.95 (ddd, J = 66.3, 10.1, 6.4 Hz, 1H), 2.37-2.17 (m, 4H), 1.70 (ddd, J = 23.3, 10.5, 6.8 Hz, 1H), 1.20 (ddd, J = 15.3, 12.5, 6.3 Hz, 1H). |
| 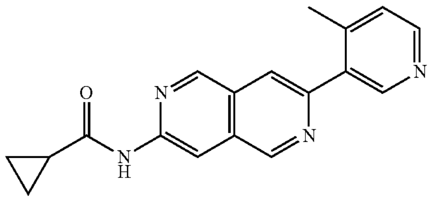 N-(7-(4-methylpyridin-3-yl)-2,6-naphthyridin-3-yl) cyclopropanecarboxamide | 48 | 3.105, 305.0, E | $^1$H NMR (400 MHz, DMSO) δ 11.17 (s, 1H), 9.47 (s, 1H), 9.33 (s, 1H), 8.67 (s, 2H), 8.50 (d, J = 5.0 Hz, 1H), 8.18 (s, 1H), 7.39 (d, J = 5.0 Hz, 1H), 2.44 (s, 3H), 2.10 (ddd, J = 12.1, 7.4, 4.7 Hz, 1H), 0.88 (dd, J = 8.0, 6.4 Hz, 4H). |
| 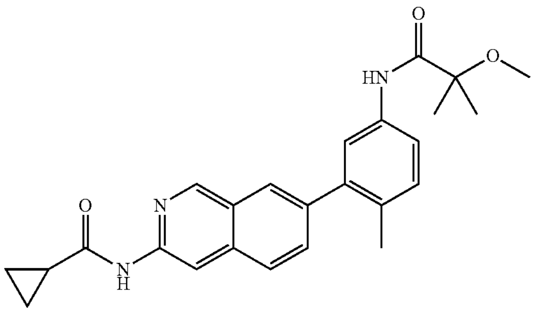 N-(7-(5-(2-methoxy-2-methylpropanamido)-2-methylphenyl)isoquinolin-3-yl) cyclopropanecarboxamide | 15 | 4.895, 418.2, E | $^1$H NMR (400 MHz, DMSO) δ 10.89 (s, 1H), 9.61 (s, 1H), 9.18 (s, 1H), 8.49 (s, 1H), 7.99 (s, 1H), 7.91 (d, J = 8.5 Hz, 1H), 7.74 (d, J = 1.9 Hz, 1H), 7.67 (dd, J = 11.9, 5.3 Hz, 2H), 7.26 (d, J = 8.3 Hz, 1H), 3.22 (s, 3H), 2.23 (s, 3H), 2.12-2.04 (m, 1H), 1.36 (s, 6H), 0.85 (m, 4H). |
| 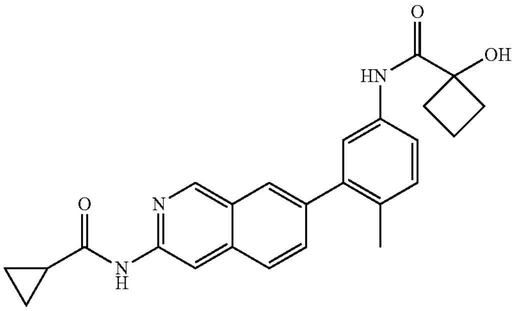 N-(3-(3-(cyclopropanecarboxamido) isoquinolin-7-yl)-4-methylphenyl)-1-hydroxycyclobutanecarboxamide | 15 | 4.481, 416.2, E | $^1$H NMR (400 MHz, DMSO) δ 10.89 (s, 1H), 9.44 (s, 1H), 9.18 (s, 1H), 8.49 (s, 1H), 7.99 (s, 1H), 7.91 (d, J = 8.6 Hz, 1H), 7.79 (d, J = 2.1 Hz, 1H), 7.71-7.63 (m, 2H), 7.26 (d, J = 8.4 Hz, 1H), 6.30 (s, 1H), 2.48-2.43 (m, 1H), 2.23 (s, 3H), 2.11 (m, 4H), 1.89-1.69 (m, 2H), 0.91-0.78 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 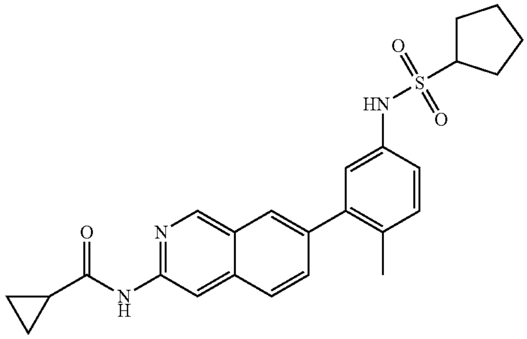 N-(7-(5-(cyclopentanesulfonamido)-2-methylphenyl)isoquinolin-3-yl)cyclopropanecarboxamide | 19 | 5.010, 450.2, E | $^1$H NMR (400 MHz, DMSO) δ 10.91 (s, 1H), 9.69 (s, 1H), 9.19 (s, 1H), 8.49 (s, 1H), 7.98 (s, 1H), 7.92 (d, J = 8.5 Hz, 1H), 7.66 (d, J = 8.4 Hz, 1H), 7.29 (d, J = 8.1 Hz, 1H), 7.18 (d, J = 16.1 Hz, 2H), 3.63-3.48 (m, 1H), 2.22 (s, 3H), 2.07 (unresolved, 1H), 1.89 (unresolved, 4H), 1.66 (unresolved, 2H), 1.54 (unresolved, 2H), 0.85 (m, 4H). |
| 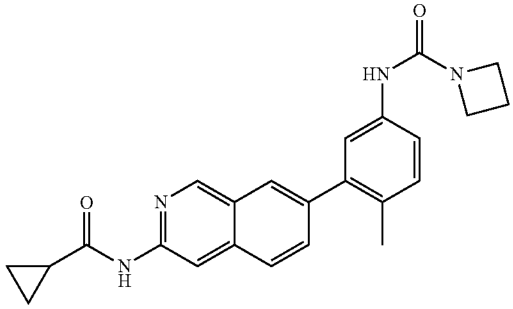 N-(3-(3-(cyclopropanecarboxamido) isoquinolin-7-yl)-4-methylphenyl) azetidine-1-carboxamide | 18 | 4.324, 401.2, E | $^1$H NMR (400 MHz, DMSO) δ 10.88 (s, 1H), 9.17 (s, 1H), 8.48 (s, 1H), 8.32 (s, 1H), 7.96 (s, 1H), 7.90 (d, J = 8.5 Hz, 1H), 7.66 (dd, J = 8.5, 1.6 Hz, 1H), 7.50-7.44 (m, 2H), 7.18 (d, J = 8.1 Hz, 1H), 3.93 (t, J = 7.5 Hz, 4H), 2.20 (s, 3H), 2.16 (m, 2H), 2.12-2.03 (m, 1H), 0.90-0.78 (m, 4H). |
| 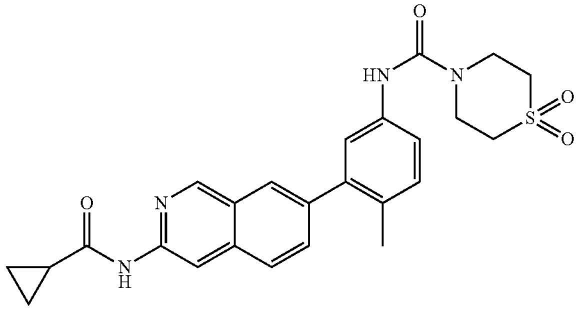 N-(3-(3-(cyclopropanecarboxamido) isoquinolin-7-yl)-4-methylphenyl)-1,1-dioxo-1-thiomorpholine-4-carboxamide | 18 | 4.175, 479.2, E | $^1$H NMR (400 MHz, DMSO) δ 10.88 (s, 1H), 9.18 (s, 1H), 8.80 (s, 1H), 8.49 (s, 1H), 7.97 (s, 1H), 7.91 (d, J = 8.6 Hz, 1H), 7.67 (dd, J = 8.5, 1.5 Hz, 1H), 7.46 (d, J = 1.9 Hz, 1H), 7.43 (dd, J = 8.3, 2.2 Hz, 1H), 7.22 (d, J = 8.3 Hz, 1H), 3.95-3.84 (m, 4H), 3.23-3.11 (m, 4H), 2.22 (s, 3H), 2.12-2.04 (m, 1H), 0.92-0.79 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 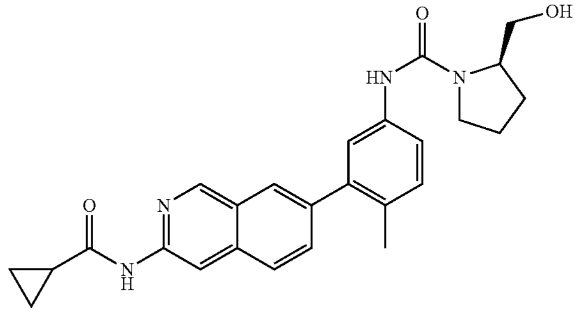 (R)-N-(3-(3-(cyclopropanecarboxamido) isoquinolin-7-yl)-4-methylphenyl)-2-(hydroxymethyl)pyrrolidine-1-carboxamide | 18 | 4.286, 445.2, E | $^1$H NMR (400 MHz, DMSO) δ 10.88 (s, 1H), 9.18 (s, 1H), 8.53 (s, 1H), 8.48 (s, 1H), 7.97 (s, 1H), 7.90 (d, J = 8.5 Hz, 1H), 7.67 (d, J = 8.5 Hz, 1H), 7.43 (s, 1H), 7.41 (d, J = 8.3 Hz, 1H), 7.19 (d, J = 8.2 Hz, 1H), 3.93 (d, J = 4.1 Hz, 1H), 3.52-3.35 (m, 4H), 2.20 (s, 3H), 2.14-2.03 (m, 1H), 1.94-1.82 (m, 2H), 1.82-1.72 (m, 2H), 0.92-0.79 (m, 4H). |
| 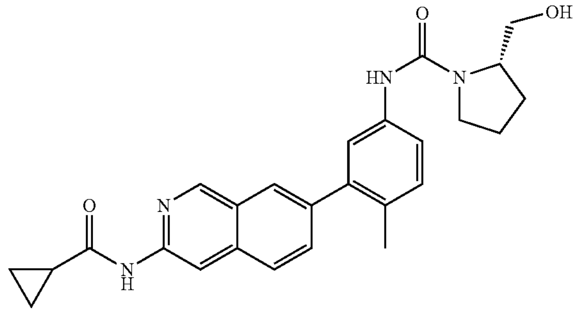 (S)-N-(3-(3-(cyclopropanecarboxamido) isoquinolin-7-yl)-4-methylphenyl)-2-(hydroxymethyl)pyrrolidine-1-carboxamide | 18 | 4.286, 445.2, E | $^1$H NMR (400 MHz, DMSO) δ 10.88 (s, 1H), 9.18 (s, 1H), 8.53 (s, 1H), 8.48 (s, 1H), 7.97 (s, 1H), 7.90 (d, J = 8.5 Hz, 1H), 7.67 (d, J = 8.5 Hz, 1H), 7.46-7.38 (m, 2H), 7.19 (d, J = 8.2 Hz, 1H), 3.93 (d, J = 4.3 Hz, 1H), 3.52-3.35 (m, 4H), 2.20 (s, 3H), 2.11-2.04 (m, 1H), 1.93-1.71 (m, 4H), 0.85 (m, 4H). |
| 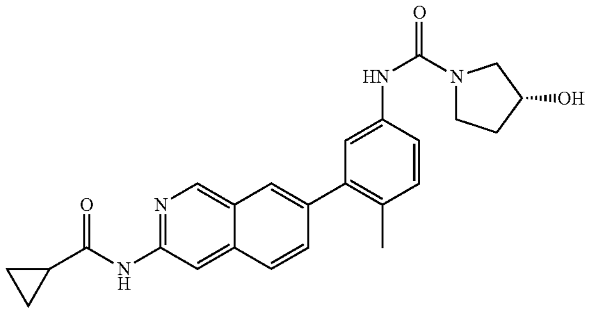 (R)-N-(3-(3-(cyclopropanecarboxamido) isoquinolin-7-yl)-4-methylphenyl)-3-hydroxypyrrolidine-1-carboxamide | 18 | 3.927, 431.2, E | $^1$H NMR (400 MHz, DMSO) δ 10.88 (s, 1H), 9.17 (s, 1H), 8.48 (s, 1H), 8.09 (s, 1H), 7.97 (s, 1H), 7.90 (d, J = 8.6 Hz, 1H), 7.67 (dd, J = 8.5, 1.4 Hz, 1H), 7.51 (d, J = 2.0 Hz, 1H), 7.50-7.46 (m, 1H), 7.18 (d, J = 8.3 Hz, 1H), 4.92 (d, J = 3.6 Hz, 1H), 4.29 (broad s, 1H), 3.44 (dd, J = 7.7, 5.0 Hz, 3H), 3.27 (unresolved, 1H), 2.21 (s, 3H), 2.13-2.03 (m, 1H), 1.92 (dtd, J = 13.1, 8.8, 4.5 Hz, 1H), 1.79 (m, 1H), 0.91-0.80 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 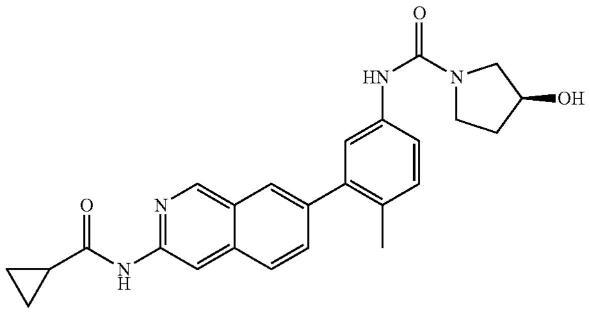 (S)-N-(3-(3-(cyclopropanecarboxamido) isoquinolin-7-yl)-4-methylphenyl)-3-hydroxypyrrolidine-1-carboxamide | 18 | 3.927, 431.2, E | $^1$H NMR (400 MHz, DMSO) δ 10.88 (s, 1H), 9.17 (s, 1H), 8.48 (s, 1H), 8.09 (s, 1H), 7.97 (s, 1H), 7.90 (d, J = 8.6 Hz, 1H), 7.67 (dd, J = 8.5, 1.4 Hz, 1H), 7.51 (d, J = 2.0 Hz, 1H), 7.48 (dd, J = 8.3, 2.2 Hz, 1H), 7.18 (d, J = 8.3 Hz, 1H), 4.92 (d, J = 3.6 Hz, 1H), 4.28 (s, 1H), 3.48-3.38 (m, 3H), 2.21 (s, 3H), 2.13-2.03 (m, 1H), 1.92 (dtd, J = 13.1, 8.8, 4.7 Hz, 1H), 1.84-1.74 (m, 1H), 0.92-0.77 (m, 4H). |
| 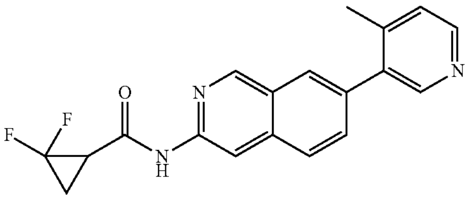 2,2-difluoro-N-(7-(4-methylpyridin-3-yl) isoquinolin-3-yl)cyclopropanecarboxamide (single enantiomer) | 8 | 3.399, 340.1, E | $^1$H NMR (400 MHz, DMSO) δ 11.15 (s, 1H), 9.22 (s, 1H), 8.50 (t, J = 7.1 Hz, 3H), 8.11 (s, 1H), 8.01 (d, J = 8.5 Hz, 1H), 7.78 (d, J = 8.6 Hz, 1H), 7.39 (d, J = 5.0 Hz, 1H), 3.07 (dd, J = 21.9, 10.6 Hz, 1H), 2.33 (s, 3H), 2.14-1.97 (m, 2H). |
| 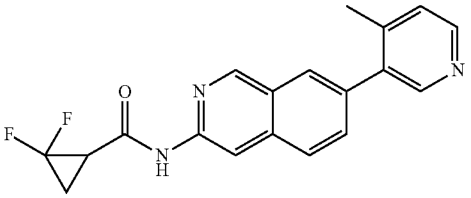 2,2-difluoro-N-(7-(4-methylpyridin-3-yl) isoquinolin-3-yl)cyclopropanecarboxamide (single enantiomer) | 8 | 3.406, 340.1, E | $^1$H NMR (400 MHz, DMSO) δ 11.15 (s, 1H), 9.22 (s, 1H), 8.50 (t, J = 7.1 Hz, 3H), 8.11 (s, 1H), 8.01 (d, J = 8.5 Hz, 1H), 7.78 (d, J = 8.5 Hz, 1H), 7.39 (d, J = 5.0 Hz, 1H), 3.07 (dd, J = 21.8, 10.7 Hz, 1H), 2.33 (s, 3H), 2.14-1.97 (m, 2H). |
| 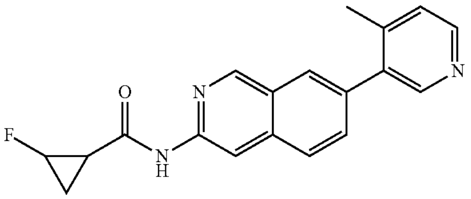 2-fluoro-N-(7-(4-methylpyridin-3-yl) isoquinolin-3-yl)cyclopropanecarboxamide (single trans isomer) | 8 | 3.316, 322.1, E | $^1$H NMR (400 MHz, DMSO) δ 11.09 (s, 1H), 9.21 (s, 1H), 8.48 (d, J = 7.4 Hz, 3H), 8.10 (s, 1H), 7.96 (d, J = 8.5 Hz, 1H), 7.76 (d, J = 8.6 Hz, 1H), 7.39 (d, J = 5.0 Hz, 1H), 4.93 (d, J = 65.4 Hz, 1H), 2.70-2.55 (m, 1H), 2.32 (s, 3H), 1.65-1.46 (m, 1H), 1.29 (dq, J = 13.0, 6.4 Hz, 1H). |
| 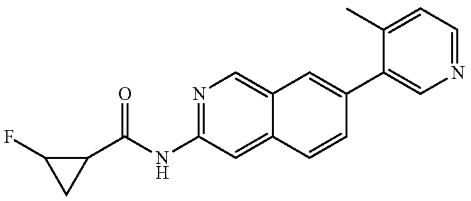 2-fluoro-N-(7-(4-methylpyridin-3-yl) isoquinolin-3-yl)cyclopropanecarboxamide (single trans isomer) | 8 | 3.322, 322.1, E | $^1$H NMR (400 MHz, DMSO) δ 11.09 (s, 1H), 9.21 (s, 1H), 8.48 (d, J = 5.9 Hz, 3H), 8.10 (s, 1H), 7.97 (d, J = 8.5 Hz, 1H), 7.76 (d, J = 8.4 Hz, 1H), 7.39 (d, J = 5.0 Hz, 1H), 4.93 (d, J = 65.7 Hz, 1H), 2.70-2.55 (m, 1H), 2.32 (s, 3H), 1.64-1.47 (m, 1H), 1.28 (tt, J = 12.9, 6.5 Hz, 1H). |

TABLE 3-continued

| Structure/Name | Syn. Meth-od | LCMS $R_T$ (min), M + H$^+$, LCMS method | $^1$H NMR (ppm) |
|---|---|---|---|
| 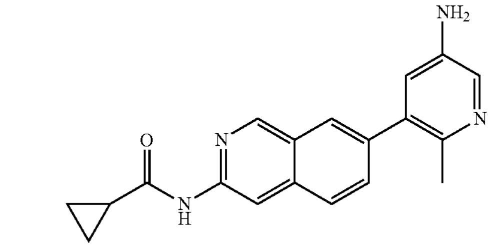 N-(7-(5-amino-2-methylpyridin-3-yl)isoquinolin-3-yl) cyclopropanecarboxamide | 12 | 3.147, 319.1, E | $^1$H NMR (400 MHz, DMSO) δ 10.90 (s, 1H), 9.17 (s, 1H), 8.48 (s, 1H), 7.99 (s, 1H), 7.90 (t, J = 5.2 Hz, 2H), 7.67 (dd, J = 8.5, 1.5 Hz, 1H), 6.88 (d, J = 2.6 Hz, 1H), 5.18 (s, 2H), 2.28 (s, 3H), 2.14-2.02 (m, 1H), 0.92-0.78 (m, 4H). |
| 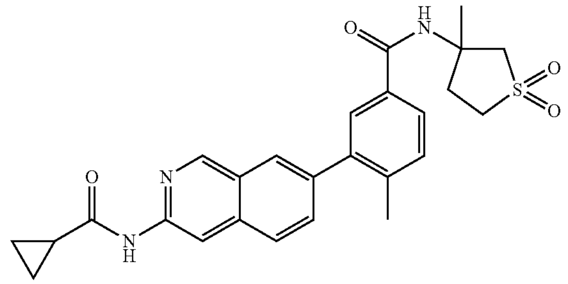 3-(3-(cyclopropanecarboxamido) isoquinolin-7-yl)-4-methyl-N-(1,1-dioxo-3-methyltetrahydrothiophen-3-yl)benzamide | 20 | 4.451, 478.2, E | $^1$H NMR (400 MHz, DMSO) δ 10.91 (s, 1H), 9.19 (s, 1H), 8.51 (s, 1H), 8.30 (s, 1H), 8.04 (s, 1H), 7.95 (d, J = 8.5 Hz, 1H), 7.82-7.77 (m, 2H), 7.72 (dd, J = 8.5, 1.6 Hz, 1H), 7.45 (d, J = 7.8 Hz, 1H), 3.96 (d, J = 13.3 Hz, 1H), 3.39-3.30 (m, 1H), 3.28-3.24 (m, 1H), 3.19 (d, J = 13.6 Hz, 1H), 2.82-2.69 (m, 1H), 2.32 (s, 3H), 2.19 (ddd, J = 13.7, 10.3, 8.1 Hz, 1H), 2.13-2.03 (m, 1H), 1.57 (s, 3H), 0.91-0.77 (m, 4H). |
| 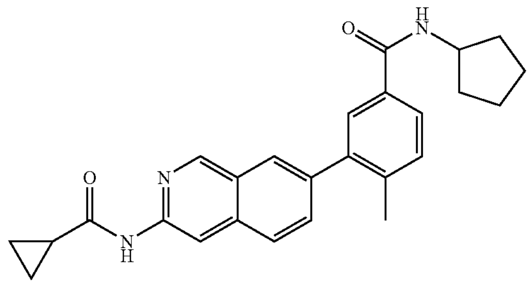 N-cyclopentyl-3-(3-(cyclopropanecarboxamido) isoquinolin-7-yl)-4-methylbenzamide | 20 | 5.081, 414.2, E | $^1$H NMR (400 MHz, DMSO) δ 10.90 (s, 1H), 9.19 (s, 1H), 8.51 (s, 1H), 8.25 (d, J = 7.3 Hz, 1H), 8.04 (s, 1H), 7.94 (d, J = 8.5 Hz, 1H), 7.81 (d, J = 9.0 Hz, 2H), 7.73 (d, J = 8.5 Hz, 1H), 7.42 (d, J = 7 .8 Hz, 1H), 4.24 (dd, J = 13.9, 7.1 Hz, 1H), 2.32 (s, 3H), 2.12-2.04 (m, 1H), 1.88 (unresolved, 2H), 1.68 (unresolved, 2H), 1.53 (m, 4H), 0.85 (m, 4H). |
| 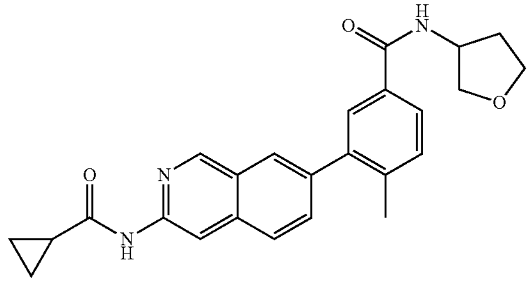 3-(3-(cyclopropanecarboxamido) isoquinolin-7-yl)-4-methyl-N-(tetrahydrofuran-3-yl)benzamide (single enantiomer) | 20 | 4.375, 416.2, E | $^1$H NMR (400 MHz, DMSO) δ 10.90 (s, 1H), 9.19 (s, 1H), 8.51 (s, 2H), 8.05 (s, 1H), 7.94 (d, J = 8.6 Hz, 1H), 7.86 (s, 1H), 7.83 (d, J = 8.0 Hz, 1H), 7.73 (d, J = 8.4 Hz, 1H), 7.44 (d, J = 7.9 Hz, 1H), 4.47 (d, J = 7.1 Hz, 1H), 3.93-3.76 (m, 2H), 3.70 (dd, J = 14.1, 8.0 Hz, 1H), 3.58 (dd, J = 8.9, 4.4 Hz, 1H), 2.32 (s, 3H), 2.20-2.03 (m, 2H), 1.91 (dt, J = 12.6, 5.4 Hz, 1H), 0.91-0.78 (m, 4H). |

TABLE 3-continued

| Structure/Name | Syn. Meth-od | LCMS $R_T$ (min), M + $H^+$, LCMS method | $^1H$ NMR (ppm) |
|---|---|---|---|
| 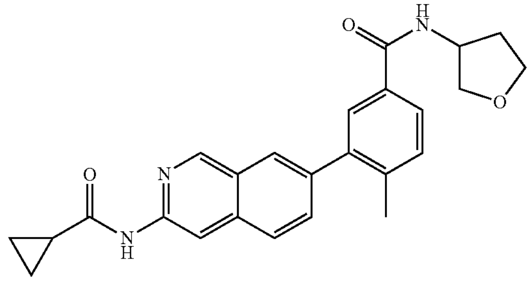 3-(3-(cyclopropanecarboxamido) isoquinolin-7-yl)-4-methyl-N-(tetrahydrofuran-3-yl)benzamide (single enantiomer) | 20 | 4.377, 416.2, E | $^1H$ NMR (400 MHz, DMSO) δ 10.91 (s, 1H), 9.19 (s, 1H), 8.51 (s, 2H), 8.05 (s, 1H), 7.94 (d, J = 8.5 Hz, 1H), 7.86 (s, 1H), 7.83 (d, J = 8.0 Hz, 1H), 7.73 (d, J = 8.5 Hz, 1H), 7.44 (d, J = 7.9 Hz, 1H), 4.47 (d, J = 7.2 Hz, 1H), 3.84 (dt, J = 9.8, 7.0 Hz, 2H), 3.70 (dd, J = 14.1, 8.0 Hz, 1H), 3.58 (dd, J = 8.8, 4.4 Hz, 1H), 2.32 (s, 3H), 2.21-2.02 (m, 2H), 1.91 (td, J = 12.6, 5.6 Hz, 1H), 0.91-0.79 (m, 4H). |
| 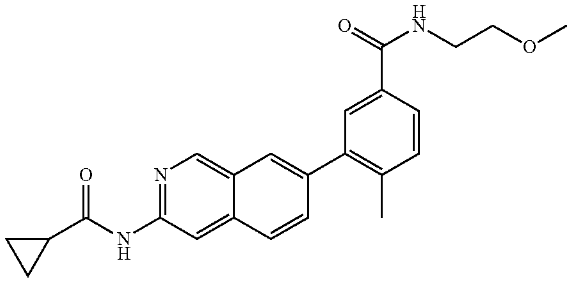 3-(3-(cyclopropanecarboxamido)isoquinolin-7-yl)-N-(2-methoxyethyl)-4-methylbenzamide | 20 | 4.383, 404.2, E | $^1H$ NMR (400 MHz, DMSO) δ 10.90 (s, 1H), 9.19 (s, 1H), 8.52 (d, J = 7.3 Hz, 2H, 8.05 (s, 1H, 7.94 (d, J = 8.6 Hz, 1H), 7.84-7.79 (m, 2H), 7.73 (dd, J = 8.5, 1.4 Hz, 1H), 7.44 (d, J = 7.9 Hz, 1H), 3.48-3.38 (m, 4H), 3.26 (s, 3H), 2.33 (s, 3H), 2.15-1.99 (m, 1H), 0.94-0.76 (m, 4H). |
| 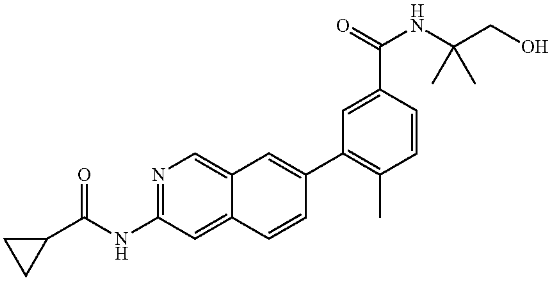 3-(3-(cyclopropanecarboxamido) isoquinolin-7-yl)-N-(1-hydroxy-2-methylpropan-2-yl)-4-methylbenzamide | 20 | 4.457, 418.2, E | $^1H$ NMR (400 MHz, DMSO) δ 10.90 (s, 1H), 9.19 (s, 1H), 8.51 (s, 1H), 8.04 (s, 1H) 7.94 (d, J = 8.6 Hz 1H), 7.77 (d, J = 7.1 Hz, 2H), 7.73 (dd, J = 8.5, 1.4 Hz, 1H), 7.54 (s, 1H), 7.41 (d, J = 8.2 Hz, 1H), 4.88 (s, 1H), 3.50 (s, 2H), 2.31 (s, 3H), 2.13-2.02 (m, 1H), 1.31 (s, 6H), 0.91-0.79 (m, 4H). |
| 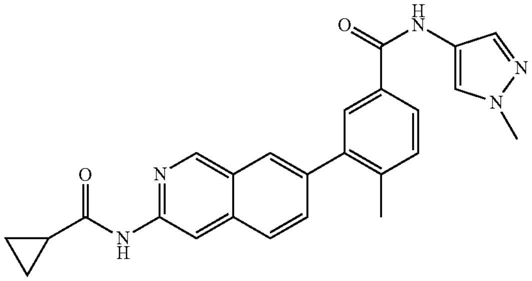 3-(3-(cyclopropanecarboxamido) isoquinolin-7-yl)-4-methyl-N-(1-methyl-1H-pyrazol-4-yl)benzamide | 20 | 4.536, 426.2, E | $^1H$ NMR (400 MHz, DMSO) δ 10.91 (s, 1H), 10.83 (s, 1H), 9.19 (s, 1H), 8.51 (s, 1H), 8.10 (s, 1H), 8.01 (s, 1H), 7.98-7.90 (m, 2H), 7.85-7.72 (m, 1H), 7.59 (d, J = 2.1 Hz, 1H), 7.47 (d, J = 8.0 Hz, 1H), 6.59 (d, J = 2.1 Hz, 1H), 3.77 (s, 3H), 2.36 (s, 3H), 2.15-2.03 (m, 1H), 0.92-0.78 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 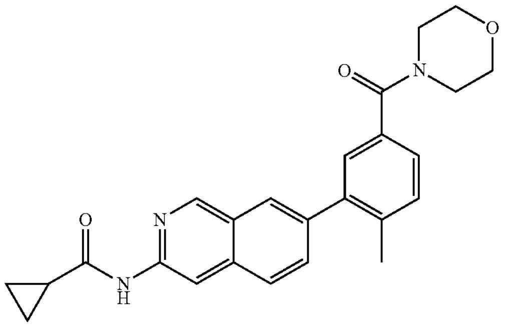 N-(7-(2-methyl-5-(morpholine-4-carbonyl)phenyl)isoquinolin-3-yl)cyclopropanecarboxamide | 20 | 4.415, 416.2, E | $^1$H NMR (400 MHz, DMSO) δ 10.90 (s, 1H), 9.18 (s, 1H), 8.50 (s, 1H), 8.04 (s, 1H), 7.92 (d, J = 8.6 Hz, 1H), 7.72 (dd, J = 8.5 1.5 Hz, 1H, 7.43 (d, J = 7.8 Hz, 1H), 7.37 (d, J = 7.8 Hz, 1H), 7.34 (s, 1H), 3.57 (m, 8H), 2.32 (s, 3H), 2.13-2.02 (m, 1H), 0.92-0.76 (m, 4H). |
| 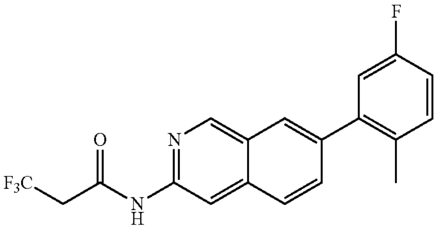 3,3,3-trifluoro-N-(7-(5-fluoro-2-methylphenyl)isoquinolin-3-yl) propanamide | 51 | 1.089, 362.9, I | $^1$H NMR (400 MHz, DMSO-$d_6$) δ 11.00 (s, 1H), 9.19 (s, 1H), 8.50 (s, 1H), 8.06 (s, 1H), 7.99 (d, J = 8.4 Hz, 1H), 7.73 (d, J = 8.4 Hz, 1H), 7.37 (s, 1H), 7.17 (d, J = 8.8 Hz, 2H), 3.70-3.62 (m, 2H), 2.23 (s, 3H). |
| 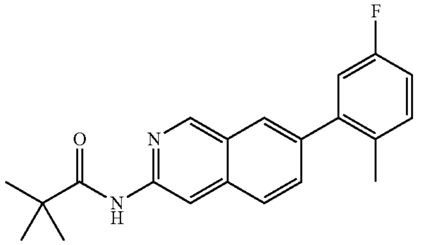 N-(7-(5-fluoro-2-methylphenyl) isoquinolin-3-yl)pivalamide | 51 | 1.254, 337.0, A | $^1$H NMR (400 MHz, DMSO-$d_6$) δ 9.87 (s, 1H), 9.18 (s, 1H), 8.50 (s, 1H), 8.04 (s, 1H), 7.93 (d, J = 8.4 Hz, 1H), 7.70 (d, J = 8.4 Hz, 1H), 7.16 (d, J = 9.2 Hz, 2H), 2.23 (s, 3H), 1.27 (s, 9H). |
| 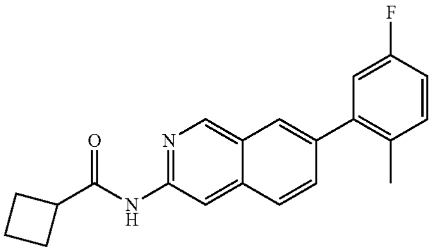 N-(7-(5-fluoro-2-methylphenyl)isoquinolin-3-yl)cyclobutanecarboxamide | 51 | 1.285, 334.9, I | $^1$H NMR (400 MHz, DMSO-$d_6$) δ 10.45 (s, 1H), 9.15 (s, 1H), 8.55 (s, 1H), 8.02 (s, 1H), 7.94 (d, J = 8.8 Hz, 1H), 7.71 (d, J = 8.4 Hz, 1H), 7.37 (s, 1H), 7.17 (d, J = 9.2 Hz, 2H), 3.43-3.41 (m, 1H), 2.28 (s, 1H), 2.24 (s, 3H), 2.14-2.09 (m, 3H), 1.93-1.90 (m, 1H), 1.87-1.84 (m, 1H). |

TABLE 3-continued

| Structure/Name | Syn. Meth-od | LCMS $R_T$ (min), M + H$^+$, LCMS method | $^1$H NMR (ppm) |
|---|---|---|---|
| 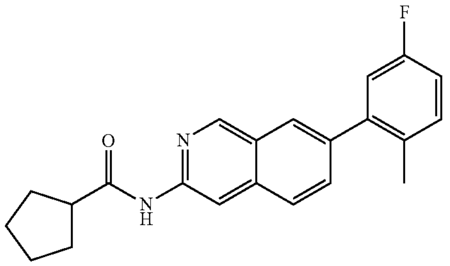 N-(7-(5-fluoro-2-methylphenyl)isoquinolin-3-yl)cyclopentanecarboxamide | 51 | 1.344, 348.9, I | $^1$H NMR (400 MHz, DMSO-$d_6$) δ 10.63 (s, 1H), 9.17 (s, 1H), 8.51 (s, 1H), 8.03 (s, 1H), 7.93 (d, J = 8.8 Hz, 1H), 7.70 (d, J = 8.4 Hz, 1H), 7.36 (s, 1H), 7.18-7.13 (m, 2H), 2.98 (s, 1H), 2.23 (s, 3H), 1.89-1.84 (m, 2H), 1.77-1.55 (m, 4H), 1.54 (m, 2H). |
| 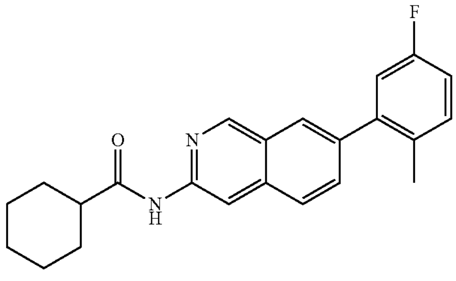 N-(7-(5-fluoro-2-methylphenyl)isoquinolin-3-yl)cyclohexanecarboxamide | 51 | 1.403, 362.9, I | $^1$H NMR (400 MHz, DMSO-$d_6$) δ 10.49 (s, 1H), 9.16 (s, 1H), 8.52 (s, 1H), 8.02 (s, 1H), 7.93 (d, J = 8.4 Hz, 1H), 7.70 (d, J = 8.4 Hz, 1H), 7.38-7.36 (m, 1H), 7.17 (d, J = 8.8 Hz, 2H), 2.50-2.48 (m, 1H), 2.24 (s, 3H), 1.84-1.74 (m, 5H), 1.45-1.23 (m, 5H). |
| 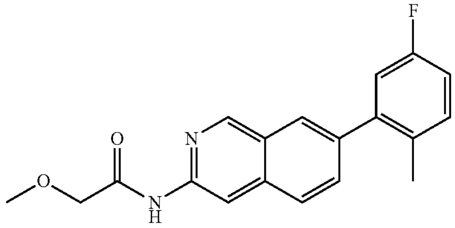 N-(7-(5-fluoro-2-methylphenyl)isoquinolin-3-yl)-2-methoxyacetamide | 51 | 1.157, 324.9, A | $^1$H NMR (400 MHz, DMSO-$d_6$) δ 10.10 (s, 1H), 9.16 (s, 1H), 8.49 (s, 1H), 8.03 (s, 1H), 7.96 (d, J = 8.8 Hz, 1H), 7.71 (d, J = 8.8 Hz, 1H), 7.35 (s, 1H), 7.15 (d, J = 9.2 Hz, 2H), 4.10 (s, 2H), 3.38 (s, 3H), 2.22 (s, 3H). |
| 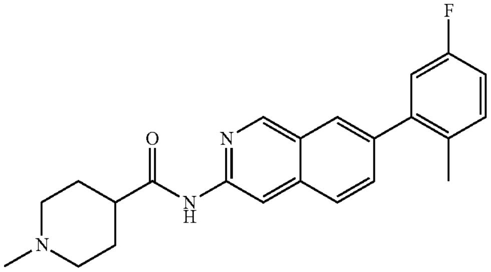 N-(7-(5-fluoro-2-methylphenyl)isoquinolin-3-yl)-1-methylpiperidine-4-carboxamide | 51 | 0.971, 378.0, A | $^1$H NMR (400 MHz, DMSO-$d_6$) δ 10.79 (s, 1H), 9.17 (s, 1H), 8.49 (s, 1H), 8.04 (s, 1H), 7.94 (d, J = 8.8 Hz, 1H), 7.71 (d, J = 8.8 Hz, 1H), 7.36 (s, 1H), 7.16 (d, J = 9.2 Hz, 2H), 3.50-3.47 (m, 2H), 3.01-2.85 (m, 2H), 2.80-2.79 (m, 4H), 2.23 (s, 3H), 2.03-2.06 (m, 2H), 1.90-1.79 (m, 2H). |

TABLE 3-continued

| Structure/Name | Syn. Method | LCMS $R_T$ (min), M + $H^+$, LCMS method | $^1H$ NMR (ppm) |
| --- | --- | --- | --- |
| 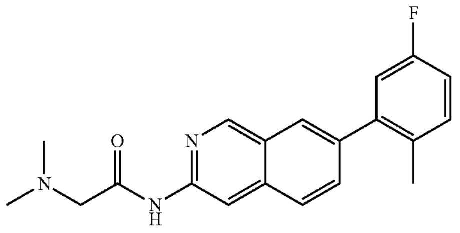 2-(dimethylamino)-N-(7-(5-fluoro-2-methylphenyl) isoquinolin-3-yl)acetamide | 51 | 0.849, 338.0, A | $^1H$ NMR (400 MHz, DMSO-$d_6$) δ 11.28 (s, 1H), 9.75 (s, 1H), 9.21 (s, 1H), 8.48 (s, 1H), 8.07 (s, 1H), 8.00 (d, J = 8.8 Hz, 1H), 7.43 (d, J = 8.8 Hz, 1H), 7.38-7.34 (d, J = 8.8 Hz, 1H), 7.15 (d, J = 9.2 Hz, 2H), 4.22 (s, 2H), 2.88 (s, 6H), 2.22 (s, 3H). |
| 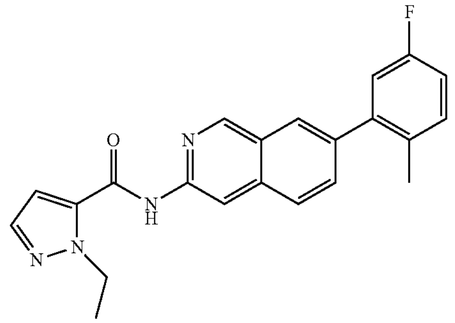 1-ethyl-N-(7-(5-fluoro-2-methylphenyl) isoquinolin-3-yl)-1H-pyrazole-5-carboxamide | 51 | 1.229, 375.1, A | $^1H$ NMR (400 MHz, DMSO-$d_6$) δ 10.93 (s, 1H), 9.23 (s, 1H), 8.62 (s, 1H), 8.06 (s, 1H), 8.02 (d, J = 8.8 Hz, 1H), 7.73 (d, J = 8.8 Hz, 1H), 7.53 (s, 1H), 7.36-7.32 (m, 2H), 7.15 (d, J = 8.8 Hz, 2H), 4.57 (q, J = 7.2 Hz, 2H), 2.23 (s, 3H), 1.37 (t, J = 7.2 Hz, 3H). |
| 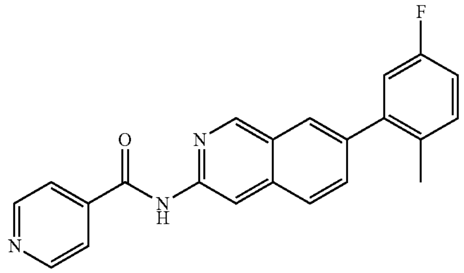 N-(7-(5-fluoro-2-methylphenyl) isoquinolin-3-yl)isonicotinamide | 51 | 1.120, 358.0, A | $^1H$ NMR (400 MHz, DMSO-$d_6$) δ 11.27 (s, 1H), 9.26 (s, 1H), 8.78 (dd, J = 1.6, 4.4 Hz, 2H), 8.68 (s, 1H), 8.09 (s, 1H), 8.04 (d, J = 8.8 Hz, 1H), 7.96 (s, 2H), 7.77 (dd, J = 2.0, 8.8 Hz, 1H), 7.40-7.35 (m, 1H), 7.19-7.16 (m, 2H), 2.25 (s, 3H). |
| 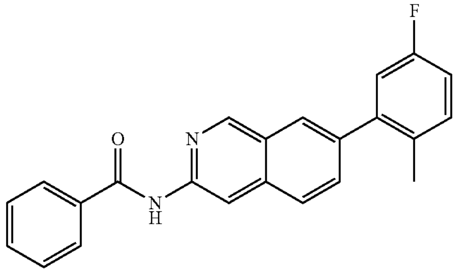 N-(7-(5-fluoro-2-methylphenyl) isoquinolin-3-yl)benzamide | 51 | 1.211, 357.0, I | $^1H$ NMR (400 MHz, DMSO-$d_6$) δ 10.93 (s, 1H), 9.24 (s, 1H), 8.68 (s, 1H), 8.09-8.01 (m, 4H), 7.76 (d, J = 8.0 Hz, 1H), 7.59 (d, J = 7.2 Hz, 1H), 7.54-7.50 (m, 3H), 7.37 (d, J = 6.0 Hz, 1H), 7.19-7.16 (m, 2H), 2.25 (s, 3H). |

TABLE 3-continued

| Structure/Name | Syn. Meth-od | LCMS $R_T$ (min), M + H$^+$, LCMS method | $^1$H NMR (ppm) |
|---|---|---|---|
| 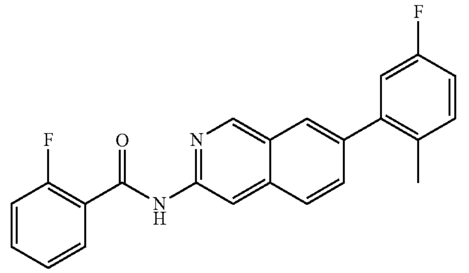 2-fluoro-N-(7-(5-fluoro-2-methylphenyl) isoquinolin-3-yl)benzamide | 51 | 1.448, 375.0, A | $^1$H NMR (400 MHz, DMSO-$d_6$) δ 10.91 (s, 1H), 9.21 (s, 1H), 8.65 (s, 1H), 8.07-8.02 (m, 2H), 7.76-7.73 (m, 2H), 7.60 (s, 1H), 7.33 (m, 3H), 7.19-7.16 (m, 2H), 2.24 (s, 3H). |
| 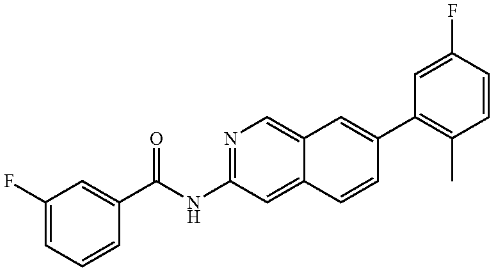 3-fluoro-N-(7-(5-fluoro-2-methylphenyl) isoquinolin-3-yl)benzamide | 51 | 1.408, 374.9, A | $^1$H NMR (400 MHz, DMSO-$d_6$) δ 11.05 (s, 1H), 9.24 (s, 1H), 8.66 (s, 1H), 8.07 (s, 1H), 8.01 (d, J = 8.4 Hz, 1H), 7.93-7.87 (m, 2H), 7.74 (d, J = 8.4 Hz, 1H), 7.57-7.56 (m, 1H), 7.44-7.13 (m, 4H), 2.23 (s, 3H). |
| 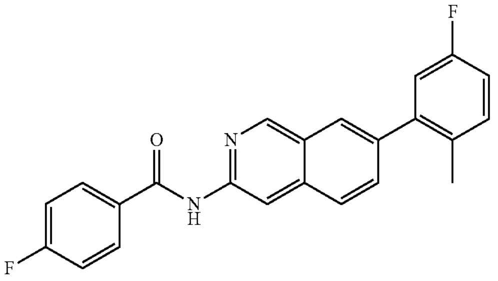 4-fluoro-N-(7-(5-fluoro-2-methylphenyl) isoquinolin-3-yl)benzamide | 51 | 1.383, 374.9, I | $^1$H NMR (400 MHz, DMSO-$d_6$) δ 10.99 (s, 1H), 9.24 (s, 1H), 8.67 (s, 1H), 8.18-8.14 (m, 2H), 8.08 (s, 1H), 8.02 (d, J = 8.8 Hz, 1H), 7.74 (d, J = 8.4 Hz, 1H), 7.39-7.33 (m, 3H), 7.20-7.14 (m, 2H), 2.25 (s, 3H). |
| 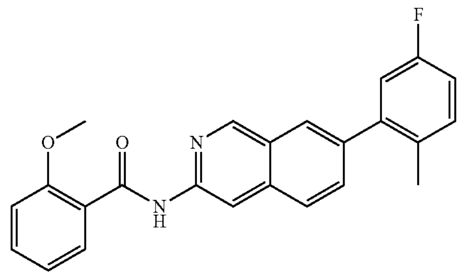 N-(7-(5-fluoro-2-methylphenyl)isoquinolin-3-yl)-2-methoxybenzamide | 51 | 1.259, 386.9, I | $^1$H NMR (400 MHz, DMSO-$d_6$) δ 10.62 (s, 1H), 9.19 (s, 1H), 8.70 (s, 1H), 8.06 (s, 1H), 8.00-7.96 (m, 2H), 7.74 (d, J = 8.4 Hz, 1H), 7.60-7.55 (m, 1H), 7.38-7.34 (m, 1H), 7.27 (d, J = 8.4 Hz, 1H),7.19-7.11 (m, 3H), 4.02 (s, 3H), 2.23 (s, 3H). |

TABLE 3-continued

| Structure/Name | Syn. Meth-od | LCMS $R_T$ (min), M + H$^+$, LCMS method | $^1$H NMR (ppm) |
| --- | --- | --- | --- |
| 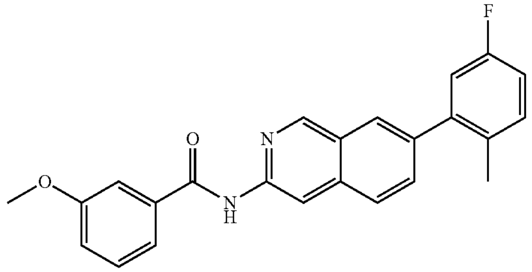 N-(7-(5-fluoro-2-methylphenyl)isoquinolin-3-yl)-3-methoxybenzamide | 52 | 1.285, 387, I | $^1$H NMR (400 MHz, DMSO-d$_6$) δ 10.94 (s, 1H), 9.24 (s, 1H), 8.68 (s, 1H), 8.07 (s, 1H), 8.01 (d, J = 8.4 Hz, 1H), 7.74 (d, J = 8.4 Hz, 1H), 7.66 (d, J = 7.6 Hz, 2H), 7.45-7.36 (m, 2H), 7.20-7.14 (m, 3H), 3.85 (s, 3H), 2.25 (s, 3H). |
| 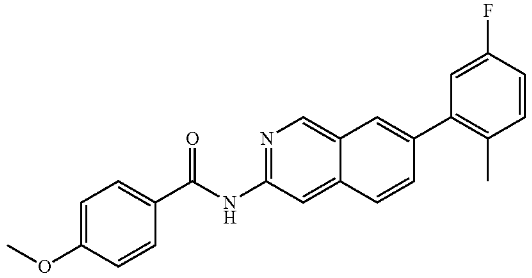 N-(7-(5-fluoro-2-methylphenyl)isoquinolin-3-yl)-4-methoxybenzamide | 51 | 1.351, 387.1, A | $^1$H NMR (400 MHz, DMSO-d$_6$) δ 10.75 (s, 1H), 9.23 (s, 1H), 8.66 (s, 1H), 8.11 (d, J = 8.8 Hz, 2H), 8.08-8.01 (m, 2H), 7.75-7.73 (m, 1H), 7.39-7.11 (m, 3H), 7.06 (d, J = 8.8 Hz, 2H), 3.83 (s, 3H), 2.25 (s, 3H). |
| 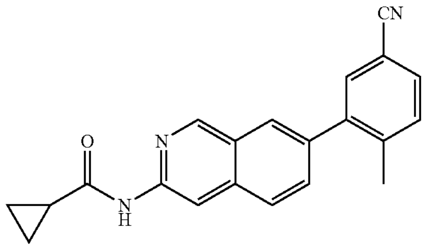 N-(7-(5-cyano-2-methylphenyl)isoquinolin-3-yl)cyclopropanecarboxamide | 62 | 1.072, 328.0, A | $^1$H NMR (400 MHz, DMSO-d$_6$) δ 10.95 (s, 1H), 9.18 (d, J = 5.6 Hz, 1H), 8.52 (d, J = 4.8 Hz, 1H), 8.08-7.58 (m, 6H), 2.36 (s, 3H), 2.09-2.05 (m, 1H), 0.86-0.81 (m, 4H) |
| 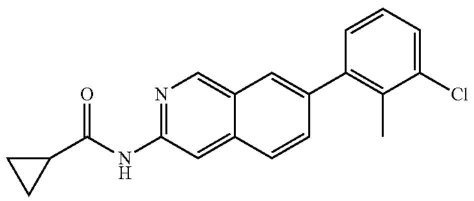 N-(7-(3-chloro-2-methylphenyl)isoquinolin-3-yl)cyclopropanecarboxamide | 63 | 1.354, 336.9, A | $^1$H NMR (400 MHz, DMSO-d$_6$) δ 10.95 (s, 1H), 9.16 (s, 1H), 8.49 (s, 1H), 7.99 (s, 1H), 7.93 (d, J = 8.8 Hz, 1H), 7.68 (dd, J = 1.6, 8.4 Hz, 1H), 7.51 (dd, J = 1.6, 7.2 Hz, 1H), 7.35-7.29 (m, 2H), 2.27 (s, 3H), 2.09-2.05 (m, 1H), 0.86-0.81 (m, 4H) |
| 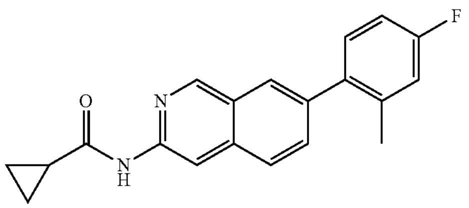 N-(7-(4-fluoro-2-methylphenyl)isoquinolin-3-yl)cyclopropanecarboxamide | 63 | 1.270, 320.9, A | $^1$H NMR (400 MHz, DMSO-d$_6$) δ 10.94 (s, 1H), 9.17 (s, 1H), 8.49 (s, 1H), 7.99 (s, 1H), 7.92 (d, J = 8.4 Hz, 1H), 7.69 (dd, J = 1.6, 8.4 Hz, 1H), 7.35-7.12 (m, 3H), 2.28 (s, 3H), 2.07-2.05 (m, 1H), 0.86-0.82 (m, 4H) |

TABLE 3-continued

| Structure/Name | Syn. Meth-od | LCMS $R_T$ (min), M + $H^+$, LCMS method | $^1H$ NMR (ppm) |
|---|---|---|---|
| 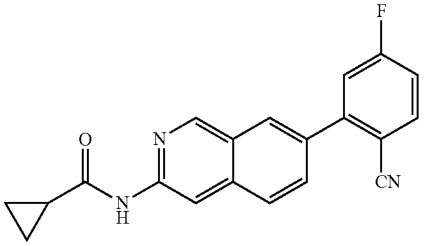 N-(7-(2-cyano-5-fluorophenyl)isoquinolin-3-yl)cyclopropanecarboxamide | 62 | 1.132, 331.9, A | $^1H$ NMR (400 MHz, DMSO-$d_6$) δ 11.01 (s, 1H), 9.24 (s, 1H), 8.54 (s, 1H), 8.31 (s, 1H), 8.14 (dd, J = 8.8, 5.6 Hz, 1H), 8.04 (d, J = 8.8 Hz, 1H), 7.92 (dd, J = 8.8, 2.0 Hz, 1H), 7.71-7.52 (m, 2H), 2.09-2.05 (m, 1H), 0.88-0.84 (m, 4H). |
| 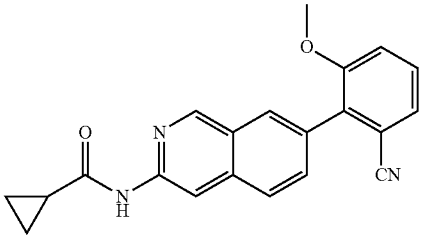 N-(7-(2-cyano-6-methoxyphenyl)isoquinolin-3-yl)cyclopropanecarboxamide | 62 | 1.000, 344.0, A | $^1H$ NMR (400 MHz, DMSO-$d_6$) δ 10.99 (s, 1H), 9.20 (s, 1H), 8.52 (s, 1H), 8.09 (s, 1H), 7.95 (d, J = 8.8 Hz, 1H), 7.69-7.52 (m, 4H), 3.79 (s, 3H), 2.09-2.05 (m, 1H), 0.88-0.83 (m, 4H). |
| 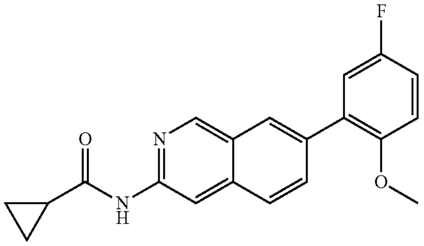 N-(7-(5-fluoro-6-methoxyphenyl)isoquinolin-3-yl)cyclopropanecarboxamide | 63 | 0.968, 336.9, A | $^1H$ NMR (400 MHz, DMSO-$d_6$) δ 11.00 (s, 1H), 9.22 (s, 1H), 8.54 (s, 1H), 8.22 (s, 1H), 7.93-7.88 (m, 2H), 7.39 (dd, J = 3.2, 9.2 Hz, 2H), 3.85 (s, 3H), 2.14-2.10 (m, 1H), 0.94-0.89 (m, 4H). |
| 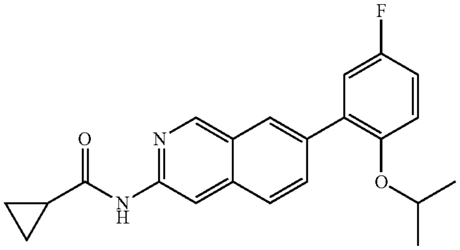 N-(7-(5-fluoro-2-isopropoxyphenyl)isoquinolin-3-yl)cyclopropanecarboxamide | 63 | 1.296, 364.9, A | $^1H$ NMR (400 MHz, DMSO-$d_6$) δ 10.94 (s, 1H), 9.15 (s, 1H), 8.46 (s, 1H), 8.19 (s, 1H), 7.87 (s, 1H), 8.34-8.18 (m, 3H), 4.55-4.47 (m, 1H), 2.09-2.05 (m, 1H), 1.19 (d, J = 6.0 Hz, 6H), 0.88-0.83 (m, 4H). |
| 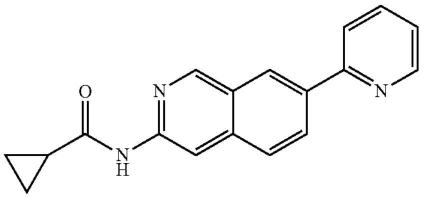 N-(7-(pyridin-2-yl)isoquinolin-3-yl)cyclopropanecarboxamide | 63 | 0.848, 289.9, A | $^1H$ NMR (400 MHz, DMSO-$d_6$) δ 11.10 (s, 1H), 9.28 (s, 1H), 8.87-8.84 (m, 2H), 8.52 (s, 1H), 8.41-8.35 (m, 3H), 8.07 (d, J = 8.8 Hz, 1H), 7.77-7.75 (m, 1H), 2.12-2.07 (m, 1H), 0.89-0.84 (m, 4H). |

TABLE 3-continued

| Structure/Name | Syn. Meth-od | LCMS $R_T$ (min), M + H$^+$, LCMS method | $^1$H NMR (ppm) |
| --- | --- | --- | --- |
| 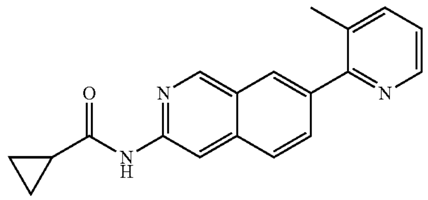 N-(7-(3-methylpyridin-2-yl)isoquinolin-3-yl)cyclopropanecarboxamide | 63 | 0.701, 304.0, A | $^1$H NMR (400 MHz, DMSO-$d_6$) δ 10.95 (s, 1H), 9.22 (s, 1H), 8.54 (d, J = 3.2 Hz, 1H), 8.50 (s, 1H), 8.24 (s, 1H), 7.92-7.91 (m, 1H), 7.79 (d, J = 6.8 Hz, 1H), 7.36 (dd, J = 4.8, 7.6 Hz, 1H), 2.42 (s, 3H), 2.09-2.05 (m, 1H), 0.88-0.82 (m, 4H). |
| 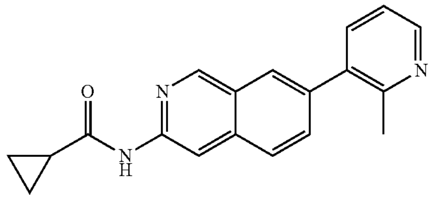 N-(7-(2-methylpyridin-3-yl)isoquinolin-3-yl)cyclopropanecarboxamide | 63 | 0.756, 303.9, A | $^1$H NMR (400 MHz, DMSO-$d_6$) δ 10.94 (s, 1H), 9.18 (s, 1H), 8.51 (dd, J = 1.6, 4.8 Hz, 1H), 8.13-7.93 (m, 2H), 7.75-7.71 (m, 2H), 7.38-7.35 (m, 1H), 2.48 (s, 3H), 2.09-2.05 (m, 1H), 0.86-0.82 (m, 4H). |
| 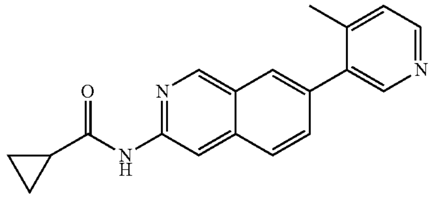 N-(7-(4-methylpyridin-3-yl)isoquinolin-3-yl)cyclopropanecarboxamide | 63 | 0.790, 303.9, A | $^1$H NMR (400 MHz, DMSO-$d_6$) δ 10.97 (s, 1H), 9.19 (s, 1H), 8.52-8.47 (m, 3H), 8.09 (s, 1H), 7.97 (d, J = 8.8 Hz, 1H), 7.76 (d, J = 2.0 Hz, 1H), 7.40 (d, J = 5.2 Hz, 1H), 2.32 (s, 3H), 2.09-2.05 (m, 1H), 0.88-0.83 (m, 4H). |
| 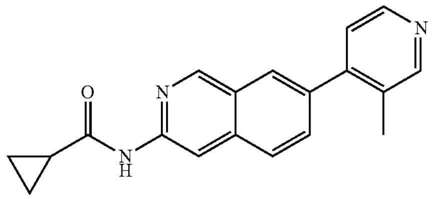 N-(7-(3-methylpyridin-4-yl)isoquinolin-3-yl)cyclopropanecarboxamide | 63 | 0.690, 303.9, A | $^1$H NMR (400 MHz, DMSO-$d_6$): δ 11.00 (s, 1H), 9.21 (s, 1H), 8.56-8.50 (m, 2H), 8.12-7.77 (m, 4H), 7.38 (d, J = 4.8 Hz, 1H), 2.32 (s, 3H), 2.09-2.05 (m, 1H), 0.87-0.84 (m, 4H). |
| 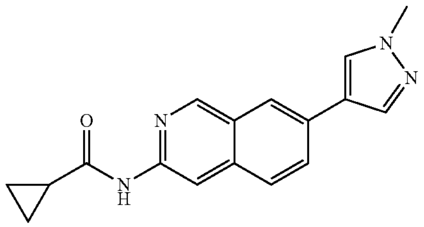 N-(7-(1-methyl-1H-pyrazol-4-yl)isoquinolin-3-yl)cyclopropanecarboxamide | 63 | 0.915, 292.9, A | $^1$H NMR (400 MHz, DMSO-$d_6$) δ 10.85 (s, 1H), 9.06 (s, 1H), 8.41 (s, 1H), 8.27 (s, 1H), 8.17 (s, 1H), 8.00 (d, J = 0.4 Hz, 1H), 7.91 (d, J = 1.6 Hz, 1H), 7.85 (d, J = 8.8 Hz, 1H), 3.90 (s, 3H), 2.09-2.05 (m, 1H), 0.88-0.83 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 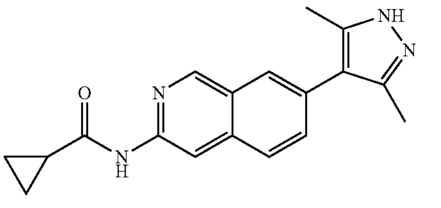 N-(7-(3,5-dimethyl-1H-pyrazol-4-yl)isoquinolin-3-yl)cyclopropanecarboxamide | 63 | 0.866, 306.9, A | $^1$H NMR (400 MHz, DMSO-d$_6$) δ 12.38 (s, 1H), 10.87 (s, 1H), 9.12 (s, 1H), 8.43 (s, 1H), 7.90-7.63 (m, 3H), 2.25 (s, 6H), 2.09-2.05 (m, 1H), 0.85-0.80 (m, 4H). |
| 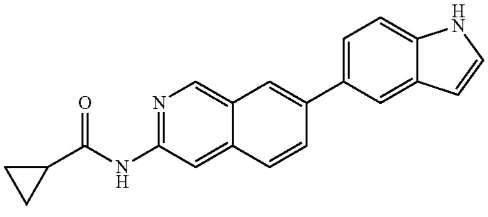 N-(7-(1H-indol-5-yl)isoquinolin-3-yl)cyclopropanecarboxamide | 63 | 0.993, 328.0, A | $^1$H NMR (400 MHz, DMSO-d$_6$) δ 11.21 (s, 1H), 10.88 (s, 1H), 9.18 (s, 1H), 8.46 (s, 1H), 8.31 (s, 1H), 8.07-7.41 (m, 6H), 6.52 (s, 1H), 2.09-2.05 (m, 1H), 0.87-0.82 (m, 4H). |
| 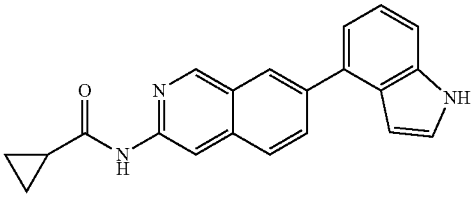 N-(7-(1H-indol-4-yl)isoquinolin-3-yl)cyclopropanecarboxamide | 63 | 3.191, 327.9, J | $^1$H NMR (400 MHz, DMSO-d$_6$) δ 11.23 (s, 1H), 10.84 (s, 1H), 9.14 (s, 1H), 8.40 (s, 1H), 8.22 (s, 1H), 7.92-7.86 (m, 2H), 7.37-7.13 (m, 2H), 6.57 (s, 1H), 2.09-2.05 (m, 1H), 0.87-0.82 (m, 4H). |
| 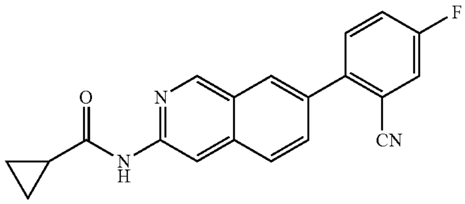 N-(7-(2-cyano-4-fluorophenyl)isoquinolin-3-yl)cyclopropanecarboxamide | 62 | 1.137, 331.9, A | $^1$H NMR (400 MHz, DMSO-d$_6$) δ 11.00 (s, 1H), 9.24 (s, 1H), 8.53 (s, 1H), 8.26 (d, J = 0.8 Hz, 1H), 8.03-7.75 (m, 5H), 2.09-2.05 (m, 1H), 0.87-0.82 (m, 4H). |
| 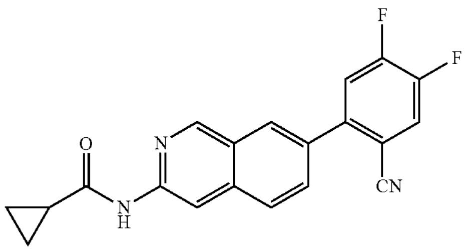 N-(7-(2-cyano-4,5-difluorophenyl)isoquinolin-3-yl)cyclopropanecarboxamide | 62 | 1.172, 249.9, A | $^1$H NMR (400 MHz, DMSO-d$_6$) δ 11.04 (s, 1H), 9.25 (s, 1H), 8.55 (s, 1H), 8.38-8.30 (m, 2H), 8.05-7.88 (m, 3H), 2.09-2.05 (m, 1H), 0.87-0.85 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 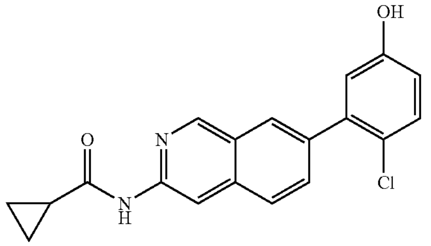 N-(7-(2-chloro-5-hydroxyphenyl)isoquinolin-3-yl)cyclopropanecarboxamide | 63 | 1.11, 338.9, A | $^1$H NMR (400 MHz, DMSO-$d_6$) δ 10.96 (s, 1H), 9.89 (s, 1H), 9.20 (s, 1H), 8.50 (s, 1H), 8.09 (s, 1H), 7.92-6.82 (m, 5H), 2.09-2.05 (m, 1H), 0.87-0.85 (m, 4H). |
| 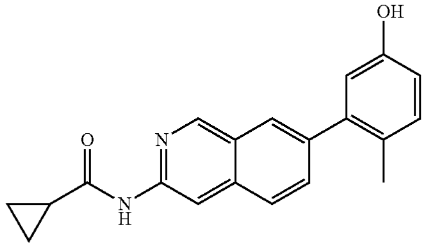 N-(7-(5-hydroxy-2-methylphenyl)isoquinolin-3-yl)cyclopropanecarboxamide | 63 | 0.959, 318.9, A | $^1$H NMR (400 MHz, DMSO-$d_6$) δ 10.92 (s, 1H), 9.33 (s, 1H), 9.16 (d, J = 2.4 Hz, 1H), 8.47 (s, 1H), 7.95 (s, 1H), 7.89 (dd, J = 2.4, 8.8 Hz, 1H), 7.66 (d, J = 8.8 Hz, 1H), 7.12 (d, J = 7.2 Hz, 1H), 6.73 (dd, J = 2.4, 8.4 Hz, 2H), 2.14 (s, 3H), 2.09-2.05 (m, 1H), 0.87-0.85 (m, 4H). |
| 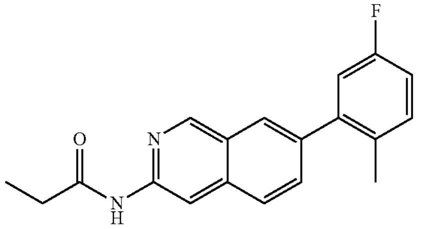 N-(7-(5-fluoro-2-methylphenyl)isoquinolin-3-yl)propionamide | 51 | 1.102, 309, A | $^1$H NMR (400 MHz, DMSO-$d_6$) δ 10.55 (s, 1H), 9.13 (s, 1H), 8.50 (s, 1H), 8.00 (s, 1H), 7.91(d, J = 8.8 Hz, 1H), 7.68 (d, J = 8.4 Hz, 1H), 7.36-7.33 (m, 1H), 7.14 (d, J = 9.2 Hz, 2H), 2.44-2.40 (m, 2H), 2.22 (s, 3H), 1.08 (t, J = 7.2 Hz, 3H). |
| 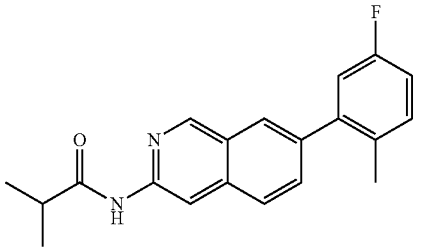 N-(7-(5-fluoro-2-methylphenyl)isoquinolin-3-yl)isobutyramide | 51 | 1.157, 322.9, A | $^1$H NMR (400 MHz, DMSO-$d_6$) δ 10.54 (s, 1H), 9.14 (s, 1H), 8.50 (s, 1H), 8.00 (s, 1H), 7.90 (d, J = 8.8 Hz, 1H), 7.68 (d, J = 8.8 Hz, 1H), 7.36-7.33 (m, 1H), 7.14 (d, J = 9.2 Hz, 2H), 2.81-2.78 (m, 1H), 2.21 (s, 3H), 1.10 (s, 6H). |
| 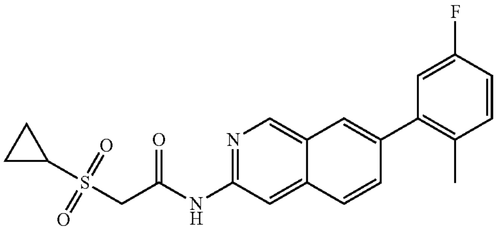 N-(7-(5-fluoro-2-methylphenyl)isoquinolin-3-yl)cyclopropanesulfonamide | 55 | 1.232, 356.9, A | $^1$H NMR (400 MHz, DMSO-$d_6$) δ 10.54 (s, 1H), 9.17 (s, 1H), 8.03 (s, 1H), 7.93 (d, J = 8.8 Hz, 1H), 7.72 (d, J = 8.4 Hz, 1H), 7.52 (s, 1H), 7.40-7.30 (m, 1H), 7.17 (d, J = 9.2 Hz, 2H), 3.10-2.99 (m, 1H), 2.22 (s, 3H), 1.05-1.00 (m, 2H), 1.05-0.90 (m, 2H). |

TABLE 3-continued

| Structure/Name | Syn. Meth-od | LCMS $R_T$ (min), M + $H^+$, LCMS method | $^1H$ NMR (ppm) |
|---|---|---|---|
| 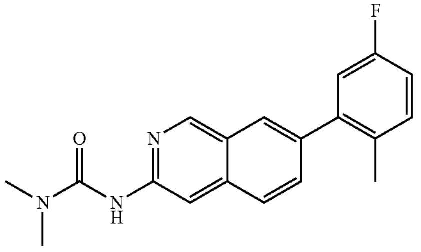 3-(7-(5-fluoro-2-methylphenyl)isoquinolin-3-yl)-1,1-dimethylurea | 56 | 1.086, 323.9, A | $^1H$ NMR (400 MHz, DMSO-$d_6$) δ 9.09 (s, 1H), 8.90 (s, 1H), 8.22 (s, 1H), 7.96 (s, 1H), 7.82 (d, J = 8.8 Hz, 1H), 7.63 (d, J = 8.4 Hz, 1H), 7.40-7.30 (m, 1H), 7.14 (d, J = 9.2 Hz, 2H), 2.96 (s, 6H), 2.22 (s, 3H). |
| 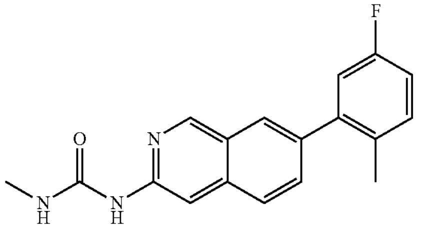 1-(7-(5-fluoro-2-methylphenyl)isoquinolin-3-yl)-3-methylurea | 56 | 1.008, 309.8, A | $^1H$ NMR (400 MHz, DMSO-$d_6$) δ 9.15 (s, 1H), 8.52 (s, 1H), 8.03 (s, 1H), 7.95 (s, 1H), 7.84 (d, J = 8.4 Hz, 1H), 7.63 (d, J = 8.4 Hz, 1H), 7.35-7.15 (m, 1H), 7.14 (d, J = 9.2 Hz, 2H), 6.97 (s, 1H), 2.71 (s, 3H), 2.05 (s, 3H). |
| 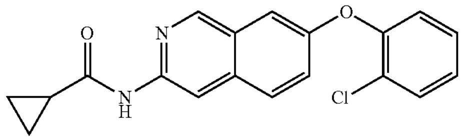 N-(7-(2-chlorophenoxy)isoquinolin-3-yl)cyclopropanecarboxamide | 65 | 1.148, 339.0, A | $^1H$ NMR (400 MHz, $CDCl_3$) δ 10.93 (s, 1H), 9.06 (s, 1H), 8.41 (s, 1H), 8.02 (t, J = 0.8 Hz, 1H), 7.84 (d, J = 8.8 Hz, 1H), 7.53 (dd, J = 1.6, 8.4 Hz, 1H), 7.38-7.31 (m, 5H), 2.09-1.99 (m, 1H), 0.83-0.79 (m, 4H). |
| 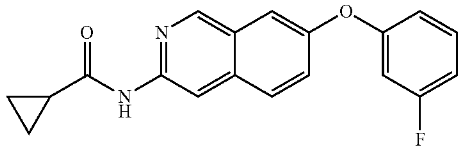 N-(7-(3-fluorophenoxy)isoquinolin-3-yl)cyclopropanecarboxamide | 19 and 65 | 1.135, 323.0, A | $^1H$ NMR (400 MHz, $CDCl_3$) δ 10.93 (s, 1H), 9.06 (s, 1H), 8.41 (s, 1H), 8.02 (t, J = 0.8 Hz, 1H), 7.84 (d, J = 8.8 Hz, 1H), 7.53 (dd, J = 1.6, 8.4 Hz, 1H), 7.38-7.31 (m, 5H), 2.09-1.99 (m, 1H), 0.83-0.79 (m, 4H). |
| 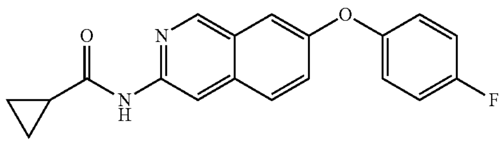 N-(7-(4-fluorophenoxy)isoquinolin-3-yl)cyclopropanecarboxamide | 65 | 1.163, 322.8, A | $^1H$ NMR (400 MHz, DMSO-$d_6$) δ 10.93 (s, 1H), 9.06 (s, 1H), 8.41 (s, 1H), 8.02 (t, J = 0.8 Hz, 1H), 7.84 (d, J = 8.8 Hz, 1H), 7.53 (dd, J = 1.6, 8.4 Hz, 1H), 7.38-7.31 (m, 5H), 2.09-1.99 (m, 1H), 0.83-0.79 (m, 4H). |
| 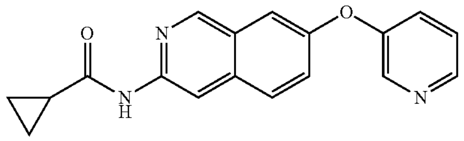 N-(7-(pyridin-3-yloxy)isoquinolin-3-yl)cyclopropanecarboxamide | 65 | 0.865, 305.8, A | $^1H$ NMR (400 MHz, DMSO-$d_6$) δ 10.93 (s, 1H), 9.06 (s, 1H), 8.41 (s, 1H), 8.02 (t, J = 0.8 Hz, 1H), 7.84 (d, J = 8.8 Hz, 1H), 7.53 (dd, J = 1.6, 8.4 Hz, 1H), 7.38-7.31 (m, 5H), 2.09-1.99 (m, 1H), 0.83-0.79 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 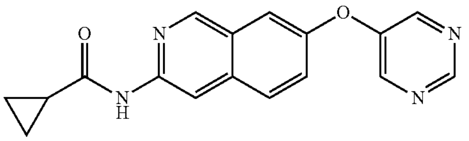 N-(7-(pyrimidin-5-yloxy)isoquinolin-3-yl)cyclopropanecarboxamide | 65 | 0.899, 307.0, A | $^1$H NMR (400 MHz, DMSO-$d_6$) δ 10.93 (s, 1H), 9.06 (s, 1H), 8.41 (s, 1H), 8.02 (t, J = 0.8 Hz, 1H), 7.84 (d, J = 8.8 Hz, 1H), 7.53 (dd, J = 1.6, 8.4 Hz, 1H), 7.38-7.31 (m, 5H), 2.09-1.99 (m, 1H), 0.83-0.79 (m, 4H). |
| 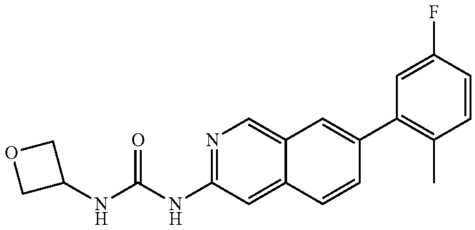 1-(7-(5-fluoro-2-methylphenyl)isoquinolin-3-yl)-3-(oxetan-3-yl)urea | 56 | 1.267, 351.8, A | $^1$H NMR (400 MHz, DMSO-$d_6$) δ 9.15 (s, 1H), 9.08 (s, 1H), 8.05 (s, 1H), 7.96 (s, 1H), 7.84 (d, J = 8.8 Hz, 114), 7.72 (d, J = 6.4 Hz, 1H), 7.65 (dd, J = 1.6, 8.4 Hz, 1H), 7.37-7.33 (m, 1H), 7.15-7.10 (m, 1H), 4.82-4.73 (m, 1H), 4.45 (t, J = 6.0 Hz, 1H), 2.22 (s, 3H). |
| 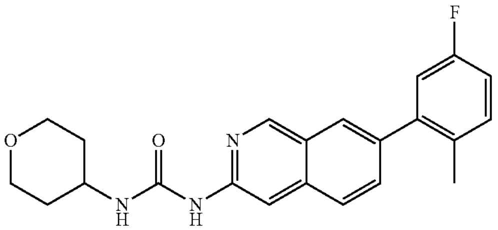 1-(7-(5-fluoro-2-methylphenyl)isoquinolin-3-yl)-3-(tetrahydro-2H-pyran-4-yl)urea | 56 | 1.143, 379.8, A | $^1$H NMR (400 MHz, DMSO-$d_6$) δ 9.14 (s, 1H), 9.07(s, 1H), 8.16 (s, 1H), 8.04 (t, J = 0.8 Hz, 1H), 7.92 (d, J = 8.8 Hz, 1H), 7.73 (dd, J = 1.6, 8.8 Hz, 1H), 7.45-7.42 (m, 1H), 7.24-7.18 (m, 3H), 3.92-3.81 (m, 3H), 3.51-3.45 (m, 2H), 2.31 (s, 3H), 1.94-1.90 (m, 2H), 1.52-1.46 (m, 2H). |
| 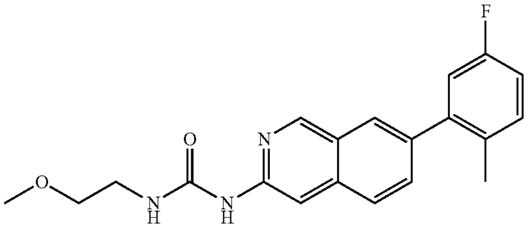 1-(7-(5-fluoro-2-methylphenyl)isoquinolin-3-yl)-3-(2-methoxyethyl)urea | 56 | 1.002, 354.1, A | $^1$H NMR (400 MHz, DMSO-$d_6$) δ 8.92 (s ,1H), 8.05-7.71 (m, 4H), 7.29-6.98 (m, 3H), 3.57 (s, 4H), 3.41 (s, 3H), 2.25 (s, 3H). |
| 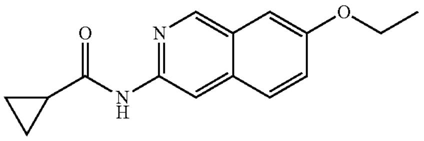 N-(7-ethoxyisoquinolin-3-yl) cyclopropanecarboxamide | 74 | 1.052, 256.9, A | $^1$H NMR (400 MHz, DMSO-$d_6$) δ 10.73 (s, 1H), 8.96 (s, 1H), 8.34 (s, 1H), 7.74 (d, J = 8.8 Hz, 1H), 7.39 (s, 1H), 7.32 (d, J = 9.2 Hz, 1H), 4.13-4.11 (q, J = 7.2 Hz, 2H), 2.03-2.01 (m, 1H), 1.39-1.35 (t, 3H), 0.80-0.77 (m, 4H). |

TABLE 3-continued

| Structure/Name | Syn. Meth-od | LCMS $R_T$ (min), M + $H^+$, LCMS method | $^1H$ NMR (ppm) |
| --- | --- | --- | --- |
| 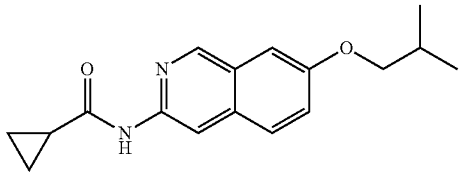 N-(7-isobutoxyisoquinolin-3-yl)cyclopropanecarboxamide | 65 | 1.04, 284.9, A | $^1H$ NMR (400 MHz, DMSO-$d_6$) δ 10.73 (s, 1H), 8.96 (s, 1H), 8.34 (s, 1H), 7.73 (d, J = 8.8 Hz, 1H), 7.39 (s, 1H), 7.32 (d, J = 8.8 Hz, 1H), 3.83 (d, J = 6.4 Hz, 2H), 2.07-1.99 (m, 2H), 0.99 (d, J = 6.8 Hz, 6H), 0.80-0.75 (m, 4H). |
| 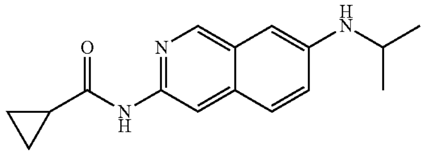 N-(7-(isopropylamino)isoquinolin-3-yl)cyclopropanecarboxamide | 77 | 1.02, 303.8, A | $^1H$ NMR (400 MHz, DMSO-$d_6$) δ 10.55 (s, 1H), 8.74 (s, 1H), 8.17 (s, 1H), 7.51 (d, J = 9.2 Hz, 1H), 7.13 (d, J = 9.2 Hz, 1H), 6.75 (s, 1H), 5.88 (d, J = 6.8 Hz, 1H), 3.65-3.57 (m, 1H), 2.05-1.95 (m, 1H), 1.17 (d, J = 6.0 Hz, 6H ), 0.79-0.74 (m, 4H). |
| 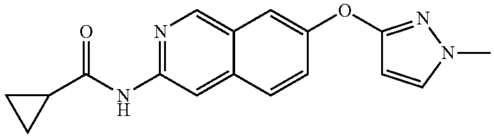 N-(7-(1-methyl-1H-pyrazol-3-yloxy)isoquinolin-3-yl)cyclopropanecarboxamide | 66 | 0.924, 309.0, A | $^1H$ NMR (400 MHz, DMSO-$d_6$) δ 8.88 (s, 1H), 8.35 (s, 1H), 7.79 (d, J = 8.8 Hz, 1H), 7.53-7.45 (m, 3H), 5.87 (d, J = 2.4 Hz, 1H), 3.80 (s, 3H), 1.92-1.85 (m, 1H), 1.00-0.99 (m, 2H), 0.89-0.87 (m, 2H). |
| 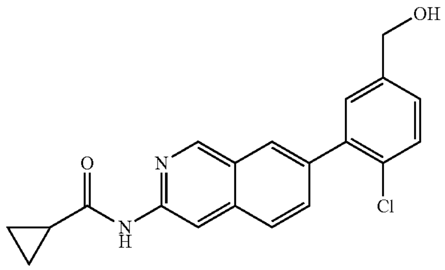 N-(7-(2-chloro-5-(hydroxymethyl)phenyl) isoquinolin-3-yl)cyclopropanecarboxamide | 78 | 1.141, 352.8, A | $^1H$ NMR (400 MHz, $CDCl_3$) 10.94 (s, 1H), 9.17 (s, 1H), 8.47 (s, 1H), 8.06 (s, 1H), 7.91 (d, J = 8.8 Hz, 1H), 7.73 (dd, J = 1.6, 8.4 Hz, 1H), 7.55 (d, J = 8.0 Hz, 1H), 7.43 (s, 1H), 7.37 (d, J = 2.0 Hz, 1H), 2.09-1.99 (m, 1H), 0.83-0.79 (m, 4H). |
| 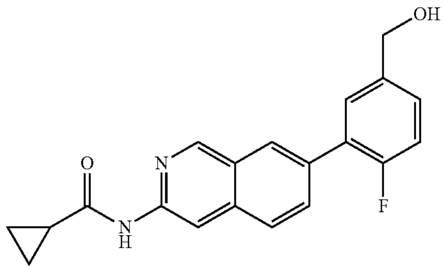 N-(7-(2-fluoro-5-(hydroxymethyl)phenyl) isoquinolin-3-yl)cyclopropanecarboxamide | 78 | 1.101, 336.9, A | $^1H$ NMR (400 MHz, $CDCl_3$) δ 10.94 (s, 1H), 9.19 (s, 1H), 8.46 (s, 1H), 8.19 (s, 1H), 7.93 (d, J = 8.8 Hz, 1H), 7.84 (d, J = 8.8 Hz, 1H), 7.56-7.41 (m, 1H), 7.38-7.27 (m, 2H), 5.32 (t, J = 5.6 Hz, 1H), 4.54 (d, J = 5.6 Hz, 2H), 2.06-2.03 (m, 4H) |

TABLE 3-continued

| Structure/Name | Syn. Meth-od | LCMS $R_T$ (min), M + $H^+$, LCMS method | $^1H$ NMR (ppm) |
|---|---|---|---|
| 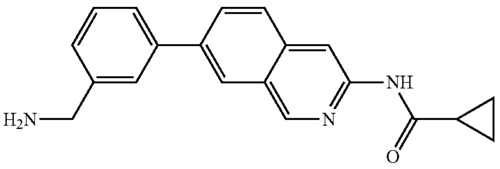 N-(7-(3-(aminomethyl)phenyl)isoquinolin-3-yl)cyclopropanecarboxamide | 63 | 0.896, 317.9, A | $^1$HNMR (MeOD-$d_4$, 400 MHz) δ 9.10 (s, 1H), 8.50 (s, 1H), 8.43 (s, 1H), 8.25 (s, 1H), 8.02 (dd, J = 1.6, 8.4 Hz, 1H), 7.92 (d, J = 8 .8 Hz, 1H), 7.86 (t, J = 8.0 Hz, 2H), 7.60 (t, J = 7.6 Hz, 1H), 7.48 (d, J = 8.0 Hz, 1H), 4.20 (s, 2H), 1.02-1.00 (m, 2H), 0.93-0.89 (m, 2H) |
| 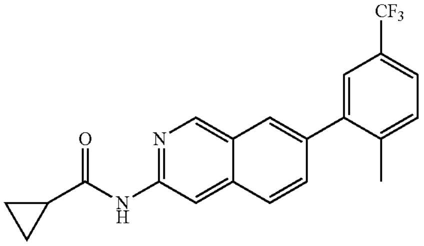 N-(7-(2-methyl-5-(trifluoromethyl)phenyl) isoquinolin-3-yl)cyclopropanecarboxamide | 61 | 1.242, 371.0, A | $^1$H NMR (400 MHz, DMSO-$d_6$) δ 10.98 (s, 1H), 9.20 (s, 1H), 8.52 (s, 1H), 8.09 (s, 1H), 7.96 (d, J = 8.8 Hz, 1H), 7.76 (dd, J = 8.4, 2.0 Hz, 1H), 7.71-7.60 (m, 3 H), 2.36 (s, 3H), 2.09-2.06 (m, 1H), 0.88-0.83 (m, 4H) |
| 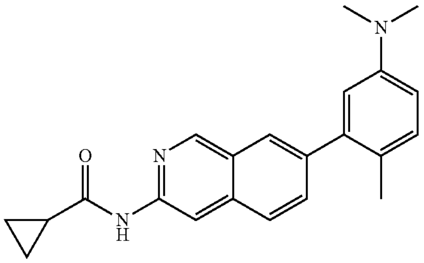 N-(7-(5-(dimethylamino)-2-methylphenyl) isoquinolin-3-yl)cyclopropanecarboxamide | 61 | 0.945, 345.9, A | $^1$H NMR (400 MHz, DMSO-$d_6$) δ 10.94 (s ,1H), 9.17 (s ,1H), 8.48 (s, 1H), 7.98 (s, 1H), 7.89 (d, J = 8.8 Hz, 1H), 7.69 (dd, J = 1.2, 8.4 Hz, 1H), 7.14 (d, J = 8.4 Hz, 1H), 6.73 (dd, J = 2.4, 8.4 Hz, 1H), 6.64 (d, J = 2.4 Hz, 1H), 2.88 (s, 6H), 2.14 (s, H), 2.09-2.06 (m, 1H), 0.86-0.82 (m, 4H). |
| 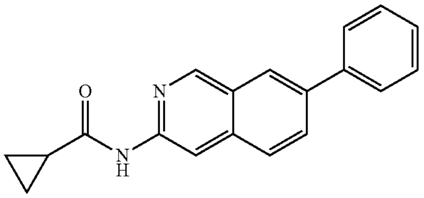 N-(7-phenylisoquinolin-3-yl) cyclopropanecarboxamide | 63 | 1.318, 288.9, A | $^1$H NMR (400 MHz, DMSO-$d_6$) δ 11.00 (s, 1H), 9.27 (s, 1H), 8.54 (s, 1H), 8.41 (s, 1H), 8.09 (d, J = 2.0 Hz, 1H), 8.01 (d, J = 8.8 Hz, 1H), 7.89 (m, 2H), 7.59 (m, 2H), 7.48 (m, 1H), 2.13 (m, 1H), 0.91 (m, 4H). |
| 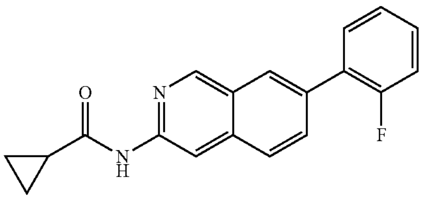 N-(7-(2-fluorophenyl)isoquinolin-3-yl)cyclopropanecarboxamide | 63 | 1.343, 306.9, A | $^1$H NMR (400 MHz, DMSO-$d_6$) δ 10.94 (s, 1H), 9.20 (s, 1H), 8.48 (s, 1H), 8.34 (s, 1H), 8.03 (dd, J = 8.6, 1.8 Hz, 1H), 7.94 (d, J = 8.4 Hz, 1H), 7.83 (m, 1H), 7.53 (t, J = 7.6 Hz, 2H), 7.43 (m, 1H), 2.05 (m, 1H), 0.84 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 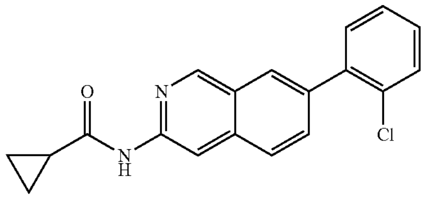 N-(7-(2-chlorophenyl)isoquinolin-3-yl)cyclopropanecarboxamide | 63 | 1.397, 322.9, A | $^1$H NMR (400 MHz, DMSO-$d_6$) δ 10.97 (s, 1H), 9.19 (s, 1H), 8.50 (s, 1H), 8.10 (s, 1H), 7.92 (d, J = 8.8 Hz, 1H), 7.76 (dd, J = 8.6, 1.6 Hz), 7.62 (m, 1H), 7.54 (m, 1H), 7.47 (m, 2H), 2.07 (m, 1H), 0.84 (m, 1H). |
| 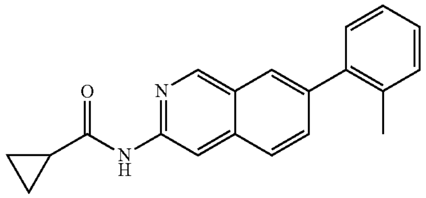 N-(7-o-tolylisoquinolin-3-yl) cyclopropanecarboxamide | 63 | 1.367, 302.9, A | $^1$H NMR (400 MHz, DMSO-$d_6$) δ 10.94 (s, 1H), 9.17 (s, 1H), 8.49 (s, 1H), 8.00 (s, 1H), 7.90 (d, J = 8.8 Hz, 1H), 7.69 (dd, J = 8.4, 1.6 Hz, 1H), 7.33 (m, 4H), 2.28 (s, 3H), 2.07 (m, 1H), 0.84 (m, 4H). |
| 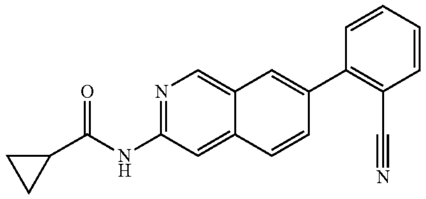 N-(7-(2-cyanophenyl)isoquinolin-3-yl)cyclopropanecarboxamide | 63 | 1.250, 314.1, A | $^1$H NMR (400 MHz, DMSO-$d_6$) δ 11.09 (s, 1H), 9.31 (s, 1H), 8.61 (s, 1H), 8.34 (d, J = 1.2 Hz, 1H), 8.08 (d, J = 8.0 Hz, 1H), 7.98-7.94 (m, 2H), 9.93-7.90 (m, 2H), 7.83 (d, J = 7.2 Hz, 1H), 7.73-7.69 (m, 1H), 2.16 (m, 1H), 0.94 (m, 4H). |
| 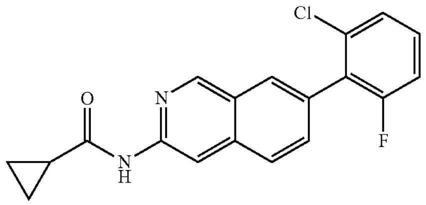 N-(7-(2-chloro-6-fluorophenyl)isoquinolin-3-yl)cyclopropanecarboxamide | 63 | 1.715, 341.0, A | $^1$H NMR (400 MHz, DMSO-$d_6$) δ 11.03 (s, 1H), 9.24 (s, 1H), 8.56 (s, 1H), 8.13 (s, 1H), 8.00 (d, J = 8.8 Hz, 1H), 7.70 (d, J = 8.8 Hz, 1H), 7.57 (m, 2H), 7.46 (m, 1H), 2.12 (m, 1H), 0.89 (m, 4 H). |
| 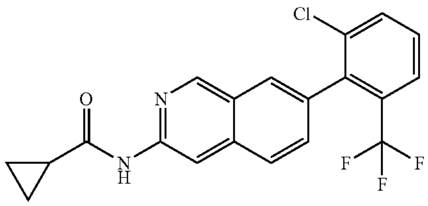 N-(7-(2-chloro-6-(trifluoromethyl)phenyl) isoquinolin-3-yl)cyclopropanecarboxamide | 63 | 1.438, 390.8, A | $^1$H NMR (400 MHz, DMSO-$d_6$) δ 11.04 (s, 1H), 9.26 (s, 1H), 8.57 (s, 1H), 8.21 (s, 1H), 8.10 (s, 1H), 8.02 (d, J = 8.8 Hz, 1H), 7.91 (d, J = 8.8 Hz, 1H), 7.83 (m, 2H), 2.12 (m, 1H), 0.90 (m, 4H). |

TABLE 3-continued

| Structure/Name | Syn. Meth-od | LCMS $R_T$ (min), M + $H^+$, LCMS method | $^1$H NMR (ppm) |
|---|---|---|---|
| 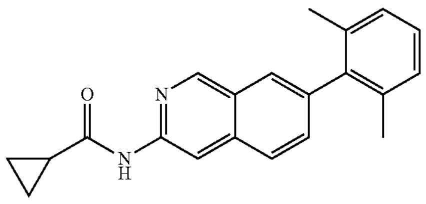 N-(7-(2,6-dimethylphenyl)isoquinolin-3-yl)cyclopropanecarboxamide | 63 | 1.408, 317.1, A | $^1$H NMR (400 MHz, DMSO-$d_6$) δ 10.97 (s, 1H), 9.18 (s, 1H), 8.54 (s, 1H), 7.97 (d, J = 8.4 Hz, 1H), 7.87 (s, 1H), 7.52 (dd, J = 8.6, 1.6 Hz, 1H), 7.25-7.20 (m, 3H). |
| 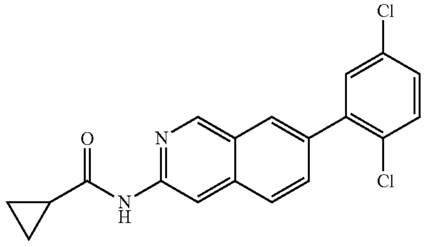 N-(7-(2,6-dichlorophenyl)isoquinolin-3-yl)cyclopropanecarboxamide | 63 | 1.401, 356.8, A | $^1$H NMR (400 MHz, DMSO-$d_6$) δ 11.02 (s, 1H), 9.24 (s, 1H), 8.55 (s, 1H), 8.19 (s, 1H), 7.98 (d, J = 8.8 Hz, 1H), 7.81 (dd, J = 8.6, 1.8 Hz, 1H), 7.72-7.69 (m, 2H), 7.60-7.57 (m, 1H), 2.12 (m, 1H), 0.89 (m, 1H). |
| 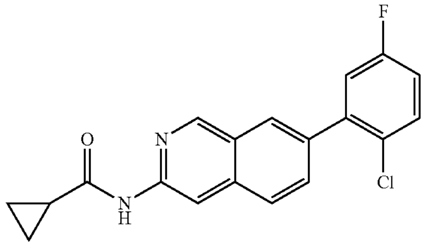 N-(7-(2-chloro-5-fluorophenyl)isoquinolin-3-yl)cyclopropanecarboxamide | 63 | 1.329, 340.8, A | $^1$H NMR (400 MHz, DMSO-$d_6$) δ 11.01 (s, 1H), 9.24 (s, 1H), 8.55 (s, 1H), 8.18 (s, 1H), 7.98 (d, J = 8.4 Hz, 1H), 7.82 (dd, J = 8.6, 1.8 Hz, 1H), 7.71 (dd, J = 8.8, 5.2 Hz, 1H), 7.51 (dd, J = 9.2, 2.8 Hz, 1H), 7.41-7.38 (m, 1H), 2.12 (m, 1H), 0.90 (m, 4H). |
| 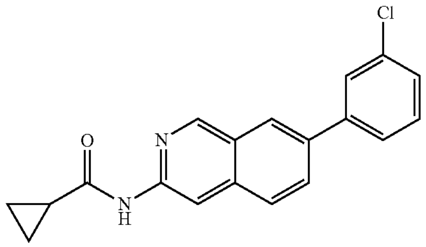 N-(7-(3-chlorophenyl)isoquinolin-3-yl)cyclopropanecarboxamide | 63 | 1.344, 322.7, A | $^1$H NMR (400 MHz, DMSO-$d_6$) δ 11.02 (s, 1H), 9.25 (s, 1H), 8.53 (s, 1H), 8.46 (s, 1H), 8.10 (dd, J = 8.8, 2.0 Hz), 7.99 (d, J = 8.8 Hz, 1H), 7.94 (s, 1H), 7.84 (d, J = 8.0 Hz, 1H), 7.62-7.53 (m, 2H), 2.11 (m, 1H), 0.89 (m, 4H). |
| 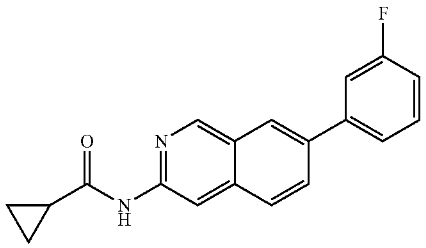 N-(7-(3-fluorophenyl)isoquinolin-3-yl)cyclopropanecarboxamide | 63 | 1.343, 307.1, A | $^1$H NMR (400 MHz, DMSO-$d_6$) δ 10.99 (s, 1H), 9.24 (s, 1H), 8.53 (s, 1H), 8.46 (s, 1H), 8.10 (dd, J = 8.8, 2.0 Hz, 1H), 7.99 (d, J = 8.8, 1H), 7.72 (d, J = 7.6 Hz, 2H), 7.65-7.55 (m, 1H), 7.32-7.25 (m, 1H), 2.12 (m, 1H), 0.89 (m, 1H). |

TABLE 3-continued

| Structure/Name | Syn. Meth-od | LCMS $R_T$ (min), M + $H^+$, LCMS method | $^1H$ NMR (ppm) |
|---|---|---|---|
| 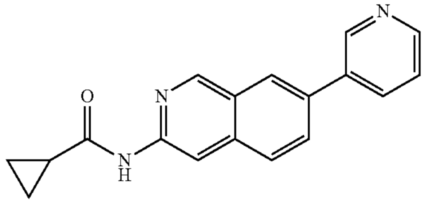 N-(7-(pyridin-3-yl)isoquinolin-3-yl)cyclopropanecarboxamide | 63 | 0.821, 289.8, A | $^1H$ NMR (400 MHz, DMSO-$d_6$) δ 11.01 (s, 1H), 9.26 (s, 1H), 9.09 (d, J = 2 Hz, 1H), 8.66 (dd, J = 4.6, 1.4 Hz, 1H), 8.54 (s, 1H), 8.49 (s, 1H), 8.28-8.26 (m, 1H), 8.13 (dd, J = 8.6, 1.8 Hz, 1H), 8.03 (d, J = 8.8 Hz, 1H), 7.59 (dd, J = 7.6, 4.8 Hz, 1H), 2.12 (s, 1H), 0.89 (s, 4H). |
| 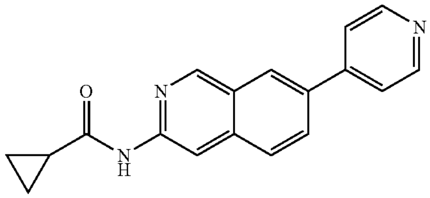 N-(7-(pyridin-4-yl)isoquinolin-3-yl)cyclopropanecarboxamide | 63 | 0.933, 290.1, A | $^1H$ NMR (400 MHz, DMSO-$d_6$) δ 11.03 (s, 1H), 9.28 (s, 1H), 8.73 (dd, J = 4.6, 1.4 Hz, 1H), 8.57 (d, J = 16 Hz, 1H), 8.17 (dd, J = 6.8, 2.0 Hz, 1H), 8.04 (d, J = 8.8 H, 1H), 7.90 (dd, J = 5.2, 2.4 Hz, 1H), 2.13 (m, 1H), 0.90 (m, 4H). |
| 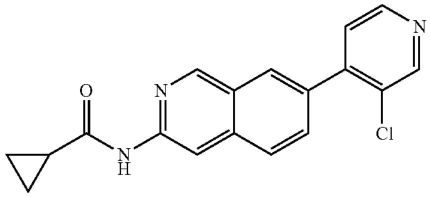 N-(7-(3-chloropyridin-4-yl)isoquinolin-3-yl)cyclopropanecarboxamide | 63 | 1.236, 323.9, A | $^1H$ NMR (400 MHz, DMSO-$d_6$) δ 11.05 (s, 1H), 9.28 (s, 1H), 8.83 (s, 1H), 8.68 (d, J = 4.8 Hz, 1H), 8.57 (s, 1H), 8.28 (s, 1H), 8.03 (d, J = 8.4 Hz, 1H), 7.89-7.86 (m, 1H), 7.67 (d, J = 4.8 Hz, 1H), 2.12 (m, 1H), 0.90 (m, 1H). |
| 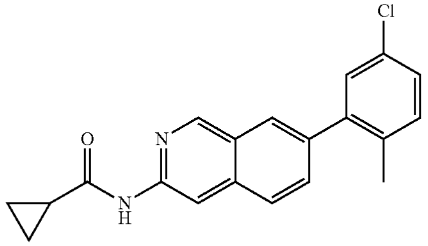 N-(7-(5-chloro-2-methylphenyl)isoquinolin-3-yl)cyclopropanecarboxamide | 63 | 1.410, 336.8, A | $^1H$ NMR (400 MHz, $CDCl_3$) δ 8.99 (s, 1H), 8.58 (1, 1H), 8.27 (s, 1H), 7.84-7.92 (m, 2H), 7.60-7.52 (s, 1H), 7.31-7.22 (m, 3H), 2.25 (s, 3H), 1.66-1.60 (m, 1H), 1.18-1.14 (m, 2H), 0.96-0.92 (m, 2H). |
| 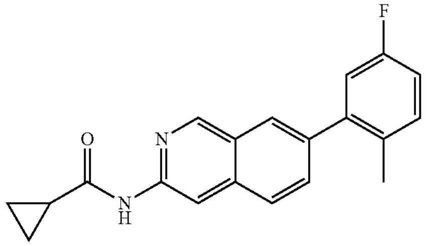 N-(7-(5-fluoro-2-methylphenyl)isoquinolin-3-yl)cyclopropanecarboxamide | 63 | 1.331, 320.8, A | $^1H$ NMR (400 MHz, $CDCl_3$) δ 8.99 (s, 1H), 8.58 (s, 1H), 8.27 (s, 1H), 7.84-7.80 (m, 3H), 7.59 (dd, J = 8.0, 1.2 Hz, 1H), 7.27-7.24 (m, 1H), 7.04-6.98 (m, 2H), 2.25 (s, 3H), 1.66-1.61 (m, 1H), 1.18-1.14 (m, 2H), 0.96-0.91 (m, 2H). |

TABLE 3-continued

| Structure/Name | Syn. Meth-od | LCMS $R_T$ (min), M + $H^+$, LCMS method | $^1$H NMR (ppm) |
|---|---|---|---|
| 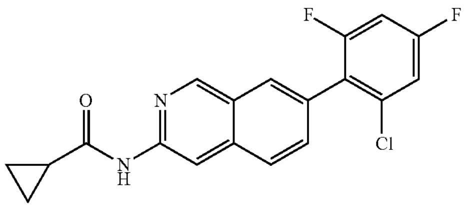 N-(7-(2-chloro-4,6-difluorophenyl)isoquinolin-3-yl)cyclopropanecarboxamide | 61 | 1.450, 358.8, A | $^1$H NMR (400 MHz, DMSO-$d_6$) δ 9.18 (s, 1H), 8.50 (s, 1H), 8.06 (s, 1H), 7.65-7.50 (m, 3H), 2.05 (m, 1H), 0.85-0.80 (m, 4H). |
| 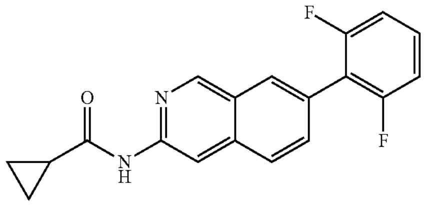 N-(7-(2,6-difluorophenyl)isoquinolin-3-yl)cyclopropanecarboxamide | 63 | 1.360, 324.9, A | $^1$H NMR (400 MHz, DMSO-$d_6$) δ 10.95 (s, 1H), 9.17 (s, 1H), 8.47 (s, 1H), 8.13 (s, 1H), 7.92 (d, J = 8.8 Hz, 1H), 7.69 (d, J = 8.8 Hz, 1H), 7.49 (s, 1H), 7.26-7.23 (m, 2H), 2.04 (m, 1H), 0.80 (m, 4H). |
| 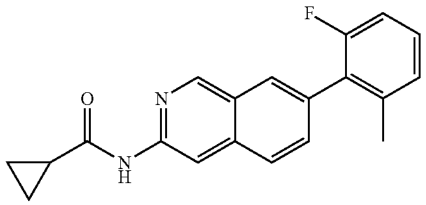 N-(7-(2-fluoro-6-methylphenyl)isoquinolin-3-yl)cyclopropanecarboxamide | 63 | 1.260, 321.1, A | $^1$H NMR (400 MHz, DMSO-$d_6$) δ 10.95 (s, 1H), 9.16 (s, 1H), 8.49 (s, 1H), 8.05-7.85 (m, 2H), 7.65-7.55 (m, 2H), 7.45-7.30 (m, 1H), 7.25-7.05 (m, 1H), 2.20-2.05 (m, 3H), 1.30-1.15 (m, 1H), 0.95-0.75 (m, 4H). |
| 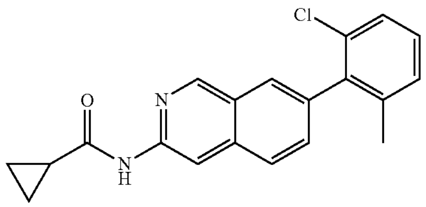 N-(7-(2-choro-6-methylphenyl)isoquinolin-3-yl)cyclopropanecarboxamide | 63 | 2.125, 337.0, A | $^1$H NMR (400 MHz, DMSO-$d_6$) δ 10.93 (s, 1H), 9.13 (s, 1H), 8.47 (s, 1H), 7.91-7.87 (m, 2H), 7.49 (dd, J = 1.6, 8.8 Hz, 1H), 7.41 (t, J = 4.8 Hz, 1H), 7.31 (d, J = 4.8 Hz, 1H), 2.06-2.03 (m, 4H), 0.84-0.79 (m, 4H) |
| 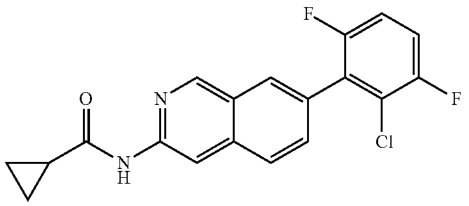 N-(7-(2-chloro-3,6-difluorophenyl)isoquinolin-3-yl)cyclopropanecarboxamide | 61 | 1.347, 358.9, A | $^1$H NMR (400 MHz, DMSO-$d_6$) δ 9.09 (s, 1H), 8.49 (s, 1H), 8.00 (s, 1H), 7.92 (d, J = 8.8 Hz, 1H), 7.64 (d, J = 8.4 Hz, 1H), 7.38-7.26 (m, 2H), 1.98-1.92 (m, 1H), 1.03-1.01 (m, 2H), 0.93-0.90 (m, 2H). |

TABLE 3-continued

| Structure/Name | Syn. Meth-od | LCMS $R_T$ (min), M + $H^+$, LCMS method | $^1H$ NMR (ppm) |
|---|---|---|---|
| 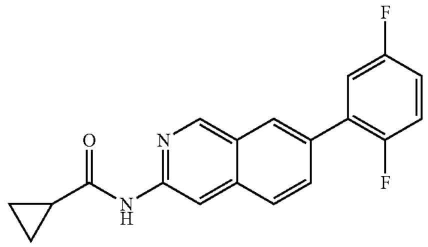 N-(7-(2,5-difluorophenyl)isoquinolin-3-yl)cyclopropanecarboxamide | 63 | 1.296, 324.8, A | $^1H$ NMR (400 MHz, DMSO-$d_6$) δ 10.94 (s, 1H), 9.17 (s, 1H), 8.46 (s, 1H), 8.23 (s, 1H), 7.93 (d, J = 8.8 Hz, 1H), 7.85 (d, J = 8.4 Hz, 1H), 7.55-7.50 (m, 1H), 7.43-7.36 (m, 1H), 7.30-7.22 (m, 1H), 2.08-2.02 (m, 1H), 0.84-0.79 (m, 4H). |
| 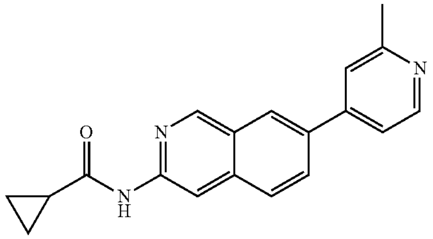 N-(7-(2-methylpyridin-4-yl)isoquinolin-3-yl)cyclopropanecarboxamide | 107 | 3.249, 304.1, E | 1H NMR (400 MHz, DMSO) δ 10.93 (s, 1H), 9.23 (s, 1H), 8.55 (d, J = 5.2 Hz, 1H), 8.51 (s, 1H), 8.50 (s, 1H), 8.11 (dd, J = 8.7, 1.8 Hz, 1H), 7.99 (d, J = 8.7 Hz, 1H), 7.73 (s, 1H), 7.64 (dd, J = 5.2, 1.4 Hz, 1H), 2.57 (s, 3H), 2.14-2.03 (m, 1H), 0.91-0.79 (m, 4H). |
| 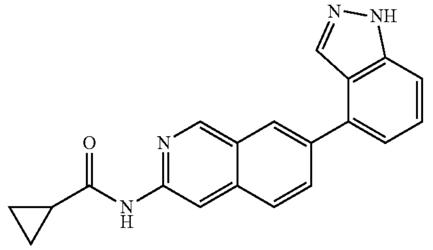 N-(7-(1H-indazol-4-yl)isoquinolin-3-yl)cyclopropanecarboxamide | 107 | 4.217, 329.1, E | 1H NMR (500 MHz, DMSO) δ 13.30 (s, 1H), 10.97 (s, 1H), 9.29 (s, 1H), 8.52 (s, 1H), 8.44 (s, 1H), 8.34 (s, 1H), 8.08 (d, J = 8.4 Hz, 1H), 8.01 (d, J = 8.5 Hz, 1H), 7.60 (d, J = 8.1 Hz, 1H), 7.50 (t, J = 7.6 Hz, 1H), 7.39 (d, J = 6.9 Hz, 1H), 2.15-2.05 (s, 1H), 0.92-0.80 (m, 3H). |
| 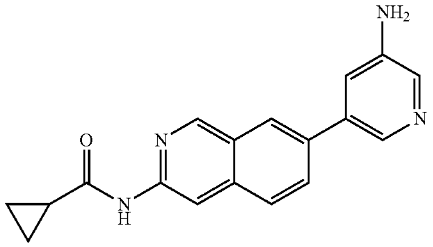 N-(7-(5-aminopyridin-3-yl)isoquinolin-3-yl)cyclopropanecarboxamide | 107 | 3.127, 305.1, E | 1H NMR (400 MHz, DMSO) δ 10.96 (s, 1H), 9.21 (s, 1H), 8.48 (s, 1H), 8.29 (s, 1H), 8.17 (d, J = 1.9 Hz, 1H), 7.97 (d, J = 2.5 Hz, 1H), 7.95 (s, 2H), 7.27 (t, J = 2.2 Hz, 1H), 5.49 (s, 2H), 2.15-2.02 (m, 1H), 0.91-0.78 (m, 4H). |
| 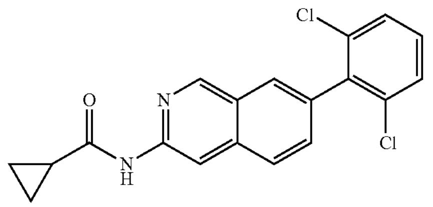 N-(7-(2,6-dichlorophenyl)isoquinolin-3-yl)cyclopropanecarboxamide | 107 | 5.368, 357.0 & 359.0, E | 1H NMR (400 MHz, DMSO) δ 10.94 (s, 1H), 9.19 (s, 1H), 8.51 (s, 1H), 7.99 (s, 1H), 7.96 (d, J = 8.5 Hz, 1H), 7.64 (d, J = 8.1 Hz, 2H), 7.57 (d, J = 8.5 Hz, 1H), 7.50 (t, J = 8.1 Hz, 1H), 2.14-2.04 (m, 1H), 0.91-0.79 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 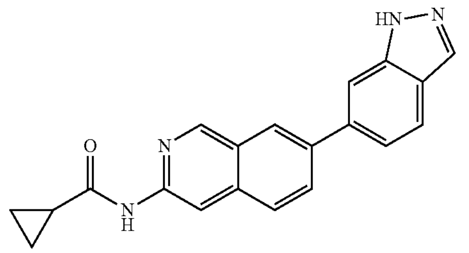 N-(7-(1H-indazol-6-yl)isoquinolin-3-yl)cyclopropanecarboxamide | 107 | 4.217, 329.1, E | 1H NMR (500 MHz, DMSO) δ 13.22 (s, 1H), 10.94 (s, 1H), 9.24 (s, 1H), 8.49 (s, 1H), 8.42 (s, 1H), 8.13 (s, 1H), 8.11 (d, J = 8 Hz, 1H), 7.97 (d, J = 8.2 Hz, 1H), 7.90 (d, J = 8 Hz, 1H), 7.89 (s, 1H), 7.58 (d, J = 8.1 Hz, 1H), 2.13-2.04 (s, 1H), 0.92-0.79 (m, 4H). |
| 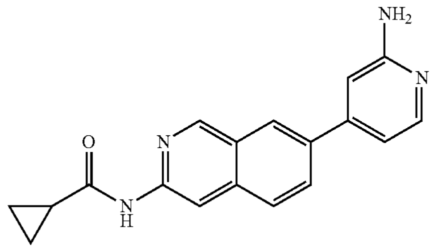 N-(7-(2-aminopyridin-3-yl)isoquinolin-3-yl)cyclopropanecarboxamide | 107 | 3.285, 305.1, E | 1H NMR (400 MHz, DMSO) δ 10.98 (s, 1H), 9.23 (s, 1H), 8.50 (s, 1H), 8.35 (s, 1H), 8.02 (d, J = 5.3 Hz, 1H), 7.99-7.89 (m, 2H), 6.92 (dd, J = 5.4, 1.5 Hz, 1H), 6.83 (s, 1H), 6.06 (s, 2H), 2.13-2.04 (m, 1H), 0.91-0.78 (m, 4H). |
| 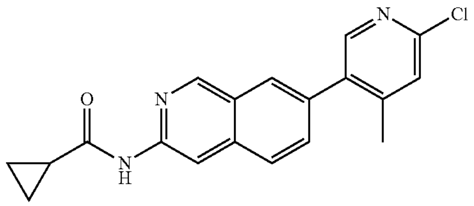 N-(7-(6-chloro-4-methylpyridin-3-yl) isoquinolin-3-yl)cyclopropanecarboxamide | 107 | 4.916, 338.0 & 340.0, E | 1H NMR (400 MHz, DMSO) δ 10.99 (s, 1H), 9.20 (s, 1H), 8.52 (s, 1H), 8.34 (s, 1H), 8.10 (s, 1H), 7.97 (d, J = 8.6 Hz, 1H), 7.75 (dd, J = 8.5, 1.6 Hz, 1H), 7.59 (s, 1H), 2.33 (s, 3H), 2.13-2.03 (m, 1H), 0.91-0.79 (m, 4H). |
| 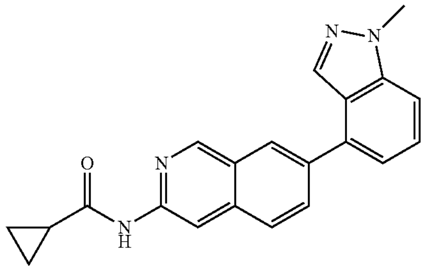 N-(7-(1-methyl-1H-indazol-4-yl) isoquinolin-3-yl)cyclopropanecarboxamide | 107 | 4.575, 343.0, E | 1H NMR (400 MHz, DMSO) δ 10.93 (s, 1H), 9.28 (s, 1H), 8.53 (s, 1H), 8.42 (s, 1H), 8.30 (s, 1H), 8.07 (dd, J = 8.6, 1.5 Hz, 1H), 8.00 (d, J = 8.6 Hz, 1H), 7.70 (d, J = 8.3 Hz, 1H), 7.54 (t, J = 7.8 Hz, 1H), 7.42 (d, J = 7.1 Hz, 1H), 4.12 (s, 3H), 2.14-2.04 (m, 1H), 0.93-0.78 (m, 4H) |

TABLE 3-continued

| Structure/Name | Syn. Meth-od | LCMS $R_T$ (min), M + H$^+$, LCMS method | $^1$H NMR (ppm) |
|---|---|---|---|
| 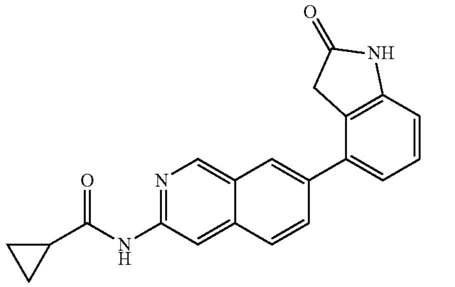 N-(7-(2-oxoindolin-4-yl)isoquinolin-3-yl)cyclopropanecarboxamide | 107 | 3.969, 344.0, E | 1H NMR (400 MHz, DMSO) δ 10.90 (s, 1H), 10.50 (s, 1H), 9.20 (s, 1H), 8.49 (s, 1H), 8.25 (s, 1H), 7.96-7.88 (m, 2H), 7.33 (t, J = 7.8 Hz, 1H), 7.16 (d, J = 7.8 Hz, 1H), 6.88 (d, J = 7.7 Hz, 1H), 3.72 (s, 2H), 2.13-2.03 (m, 1H), 0.91-0.79 (m, 4H). |
| 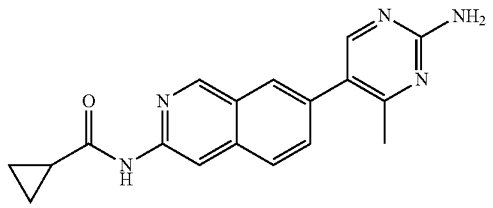 N-(7-(2-amino-4-methylpyrimidin-5-yl) isoquinolin-3-yl)cyclopropanecarboxamide | 107 | 3.166, 320.0, E | 1H NMR (400 MHz, DMSO) δ 10.89 (s, 1H), 9.15 (s, 1H), 8.47 (s, 1H), 8.17 (s, 1H), 8.00 (s, 1H), 7.90 (d, J = 8.5 Hz, 1H), 7.70 (d, J = 8.3 Hz, 1H), 6.64 (s, 2H), 2.30 (s, 3H), 2.14-2.01 (m, 1H), 0.93-0.77 (m, 4H). |
| 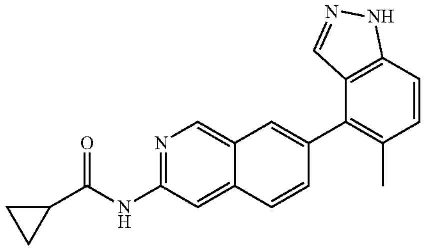 N-(7-(5-methyl-1H-indazol-4-yl)isoquinolin-3-yl)cyclopropanecarboxamide | 107 | 4.304, 343.1, E | 1H NMR (400 MHz, DMSO) δ 13.08 (s, 1H), 10.92 (s, 1H), 9.21 (s, 1H), 8.53 (s, 1H), 8.11 (s, 1H), 7.98 (d, J = 8.5 Hz, 1H), 7.75 (d, J = 8.6 Hz, 1H), 7.67 (s, 1H), 7.50 (d, J = 8.5 Hz, 1H), 7.35 (d J = 8.5 Hz, 1H), 2.33 (s, 3H), 2.14-2.06 (m, 1H), 0.92-0.80 (m, 4H). |
| 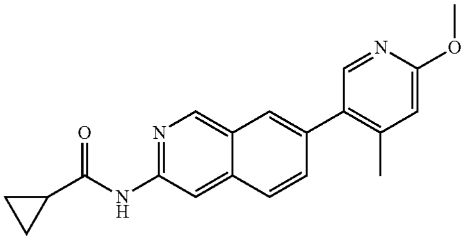 N-(7-(6-methoxy-4-methylpyridin-3-yl) isoquinolin-3-yl)cyclopropanecarboxamide | 107 | 4.196, 334.0, E | 1H NMR (400 MHz, DMSO) δ 10.91 (s, 1H), 9.17 (s, 1H), 8.49 (s, 1H), 8.09 (s, 1H), 8.02 (s, 1H), 7.92 (d, J = 8.6 Hz, 1H), 7.70 (d, J = 8.5 Hz, 1H), 6.83 (s, 1H), 3.89 (s, 3H), 2.27 (s, 3H), 2.13-2.02 (m, 1H), 0.91-0.78 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 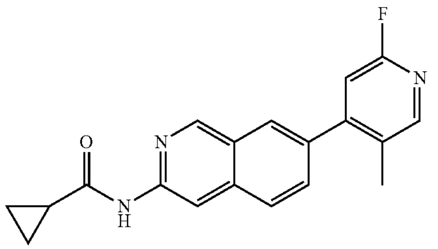 N-(7-(2-fluoro-5-methylpyridin-4-yl) isoquinolin-3-yl)cyclopropanecarboxamide | 107 | 4.566, 3222.0, E | 1H NMR (400 MHz, DMSO) δ 10.96 (s, 1H), 9.21 (s, 1H), 8.52 (s, 1H), 8.22 (s, 1H), 8.16 (s, 1H), 7.98 (d, J = 8.6 Hz, 1H), 7.78 (dd, J = 8.6, 1.6 Hz, 1H), 7.20 (d, J = 1.5 Hz, 1H), 2.29 (s, 3H), 2.13-2.04 (m, 1H), 0.91-0.80 (m, 4H). |
| 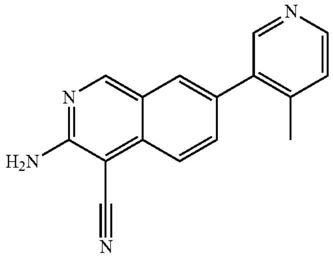 3-amino-7-(4-methylpyridin-3-yl)isoquinoline-4-carbonitrile | 107 | 2.974, 261.1, E | 1H NMR (400 MHz, DMSO) δ 9.13 (s, 1H), 8.47 (d, J = 5 Hz, 1H), 8.46 (s, 1H), 8.04 (d, J = 1.4 Hz, 1H), 7.81 (dd, J = 8.6, 1.7 Hz, 1H), 7.73 (d, J = 8.6 Hz, 1H), 7.37 (d, J = 5.0 Hz, 1H), 7.33 (s, 2H), 2.31 (s, 3H). |
| 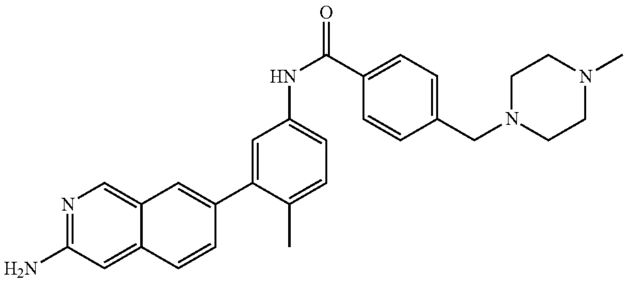 N-(3-(3-aminoisoquinolin-7-yl)-4-methylphenyl)-4-((4-methyl piperazin-1-yl)methyl)benzamide | 107 | 3.197, 466.3, E | 1H NMR (400 MHz, DMSO) δ 10.16 (s, 1H), 8.87 (s, 1H), 7.91 (d, J = 8.1 Hz, 2H), 7.76 (s, 1H), 7.73 (s, 1H), 7.71 (dd, J = 8, 2 Hz, 1H), 7.59 (d, J = 8.6 Hz, 1H), 7.47 (dd, J = 8.6, 1.5 Hz, 1H), 7.43 (d, J = 8.1 Hz, 2H), 7.28 (d, J = 8.2 Hz, 1H), 6.67 (s, 1H), 5.94 (s, 2H), 3.52 (s, 2H), 2.35 (d, J = 19.8 Hz, 7H), 2.25 (s, 3H), 2.15 (s, 3H). |
| 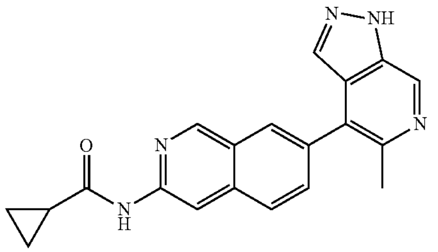 N-(7-(5-methyl-1H-pyrazolo[3,4-c]pyridin-4-yl)isoquinolin-3-yl)cyclopropanecarboxamide | 87 | 3.217, 344.2, E | 1H NMR (400 MHz, DMSO) δ 13.78 (s, 1H), 10.95 (s, 1H), 9.23 (s, 1H), 9.07 (s, 1H), 8.55 (s, 1H), 8.20 (s, 1H), 8.02 (d, J = 8.6 Hz, 1H), 7.96 (s, 1H), 7.82 (d, J = 8.5 Hz, 1H), 2.56 (s, 3H), 2.15-2.04 (m, 1H), 0.93-0.79 (m, 4H). |

TABLE 3-continued

| Structure/Name | Syn. Meth-od | LCMS $R_T$ (min), M + $H^+$, LCMS method | $^1H$ NMR (ppm) |
|---|---|---|---|
| 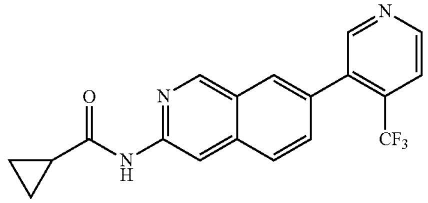 N-(7-(4-(trifluoromethyl)pyridin-3-yl) isoquinolin-3-yl)cyclopropanecarboxamide | 87 | 4.543, 358.1, E | 1H NMR (400 MHz, DMSO) δ 10.96 (s, 1H), 9.21 (s, 1H), 8.93 (d, J = 5.1 Hz, 1H), 8.81 (s, 1H), 8.53 (s, 1H), 8.09 (s, 1H), 7.97 (d, J = 8.6 Hz, 1H), 7.91 (d, J = 5.2 Hz, 1H), 7.69 (d, J = 8.5 Hz, 1H), 2.14-2.04 (m, 1H), 0.92-0.79 (m, 4H). |
| 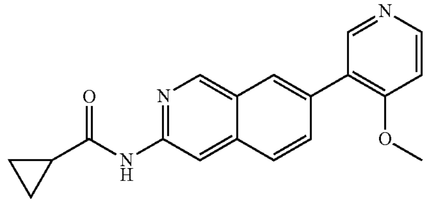 N-(7-(4-methoxypyridin-3-yl)isoquinolin-3-yl)cyclopropanecarboxamide | 87 | 3.119, 320.2, E | 1H NMR (400 MHz, DMSO) δ 10.91 (s, 1H), 9.17 (s, 1H), 8.50 (m, 3H), 8.17 (s, 1H), 7.90 (d, J = 8.6 Hz, 1H), 7.84 (dd, J = 8.6, 1.3 Hz, 1H), 7.22 (d, J = 5.8 Hz, 1H), 3.90 (s, 3H), 2.14-2.02 (m, 1H), 0.91-0.78 (m, 4H). |
| 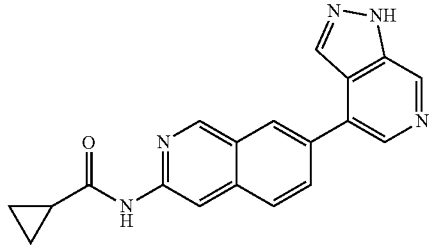 N-(7-(1H-pyrazolo[3,4-c]pyridin-4-yl)isoquinolin-3-yl)cyclopropanecarboxamide | 87 | 3.200, 330.1, E | 1H NMR (400 MHz, DMSO) δ 13.87 (br s, 1H), 10.95 (s, 1H), 9.30 (s, 1H), 9.09 (s, 1H), 8.58-8.50 (m, 4H), 8.15 (dd, J = 8.6, 1.4 Hz, 1H), 8.04 (d, J = 8.6 Hz, 1H), 2.14-2.05 (m, 1H), 0.93-0.79 (m, 4H). |
| 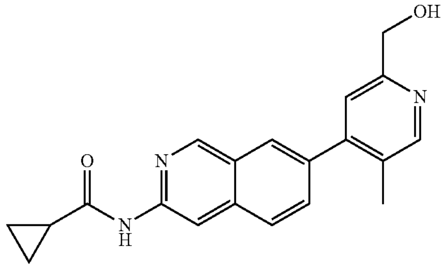 N-(7-(2-(hydroxymethyl)-5-methylpyridin-4-yl) isoquinolin-3-yl)cyclopropanecarboxamide | 87 | | 1H NMR (400 MHz, DMSO) δ 10.93 (s, 1H), 9.22 (s, 1H), 8.51 (s, 1H), 8.45 (s, 1H), 8.10 (s, 1H), 7.97 (d, J = 8.6 Hz, 1H), 7.74 (dd, J = 8.5, 1.6 Hz, 1H), 7.41 (s, 1H), 5.37 (s, 1H), 4.60 (s, 2H), 2.29 (s, 3H), 2.15-2.04 (m, 1H), 0.92-0.78 (m, 4H). |
| 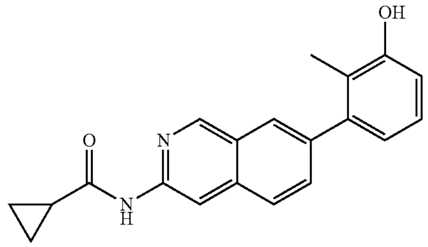 N-(7-(3-hydroxy-2-methylphenyl) isoquinolin-3-yl)cyclopropanecarboxamide | 87 | 4.274, 319.1, E | $^1H$ NMR (400 MHz, DMSO) δ 10.91 (s, 1H), 9.47 (s, 1H), 9.16 (s, 1H), 8.48 (s, 1H), 7.95 (s, 1H), 7.88 (d, J = 8.5 Hz, 1H), 7.65 (d, J = 8.4 Hz, 1H), 7.09 (t, J = 7.8 Hz, 1H), 6.86 (d, J = 8.0 Hz, 1H), 6.76 (d, J = 7.6 Hz, 1H), 2.08 (m, 1H), 2.06 (s, 3H), 0.85 (m, 4H). |

TABLE 3-continued

| Structure/Name | Syn. Meth-od | LCMS $R_T$ (min), M + $H^+$, LCMS method | $^1H$ NMR (ppm) |
|---|---|---|---|
| 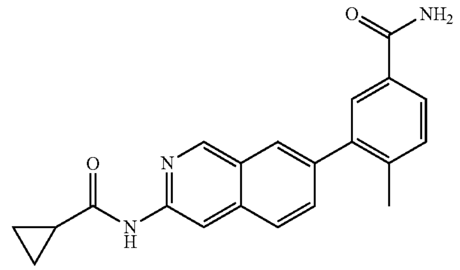 3-(3-(cyclopropanecarboxamidio) isoquinolin-7-yl)-4-methylbenzamide | 87 | 3.958, 346.1, E | $^1H$ NMR (400 MHz, DMSO) δ 10.93 (s, 1H), 9.19 (s, 1H), 8.51 (s, 1H), 8.05 (s, 1H), 7.98 (bs, 1H), 7.94 (d, J = 8.5 Hz, 1H), 7.86 (s, 1H), 7.83 (m, 1H), 7.78-7.70 (m, 1H), 7.43 (d, J = 7.9 Hz, 1H), 7.31 (bs, 1H), 2.33 (s, 3H), 2.14-2.03 (m, 1H), 0.85 (m, 4H). |
| 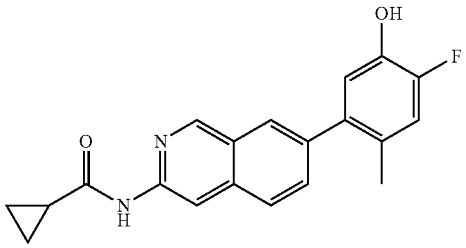 N-(7-(4-fluoro-5-hydroxy-2-methylphenyl) isoquinolin-3-yl)cyclopropanecarboxamide | 87 | 4.457, 337.1, E | $^1H$ NMR (400 MHz, DMSO) δ 10.91 (s, 1H), 9.77 (bs, 1H), 9.16 (s, 1H), 8.48 (s, 1H), 7.95 (s, 1H), 7.89 (d, J = 8.5 Hz, 1H), 7.64 (d, J = 8.4 Hz, 1H), 7.12 (d, J = 12.3 Hz, 1H), 6.88 (d, J = 9.0 Hz, 1H), 2.13 (s, 3H), 2.08 (m, 1H), 0.99-0.64 (m, 4H). |
| 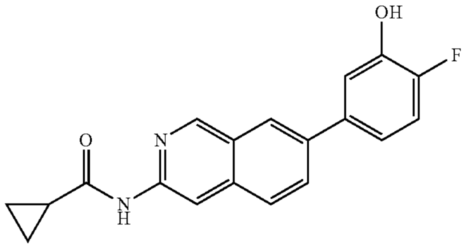 N-(7-(4-fluoro-3-hydroxyphenyl) isoquinolin-3-yl)cyclopropanecarboxamide | 87 | 4.268, 323.1, E | $^1H$ NMR (400 MHz, DMSO) δ 10.91 (s, 1H), 10.16 (bs, 1H), 9.19 (s, 1H), 8.49 (d, J = 19.0 Hz, 1H), 8.23 (s, 1H), 7.35 (d, J = 8.3 Hz, 1H), 7.26 (m, 2H), 2.08 (m, 1H), 1.06-0.57 (m, 4H). |
| 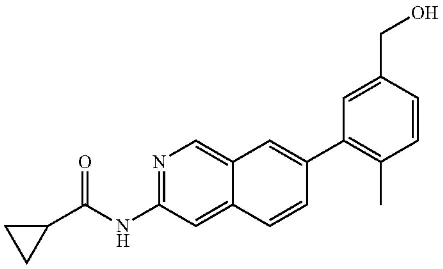 N-(7-(5-(hydroxymethyl)-2-methylphenyl) isoquinolin-3-yl)cyclopropanecarboxamide | 107 | 4.197, 333.1, E | $^1H$ NMR (400 MHz, DMSO) δ 10.91 (s, 1H), 9.18 (s, 1H), 8.49 (s, 1H), 7.99 (s, 1H), 7.91 (d, J = 8.6 Hz, 1H), 7.69 (d, J = 8.4 Hz, 1H), 7.41-7.13 (m, 3H), 5.16 (t, J = 5.5 Hz, 1H), 4.52 (d, J = 5.4 Hz, 2H), 2.26 (s, 3H), 2.08 (m, 1H), 0.98-0.63 (m, 4H). |

TABLE 3-continued

| Structure/Name | Syn. Meth-od | LCMS $R_T$ (min), M + $H^+$, LCMS method | $^1H$ NMR (ppm) |
|---|---|---|---|
| 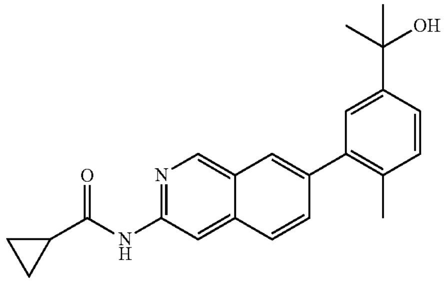 N-(7-(5-(2-hydroxypropan)-2-yl)-2-methylphenyl) isoquinolin-3-yl)cyclopropanecarboxamide | 87 | 4.595, 361.1, E | $^1H$ NMR (400 MHz, DMSO) δ 10.88 (s, 1H), 9.18 (s, 1H), 8.49 (s, 1H), 7.99 (s, 1H), 7.90 (d, J = 8.5 Hz, 1H), 7.69 (d, J = 8.4 Hz, 1H), 7.39 (m, 2H), 7.26 (m, 1H), 4.97 (s, 1H), 2.25 (s, 3H), 2.08 (m, 1H), 1.45 (s, 6H), 0.85 (m, 4H). |
| 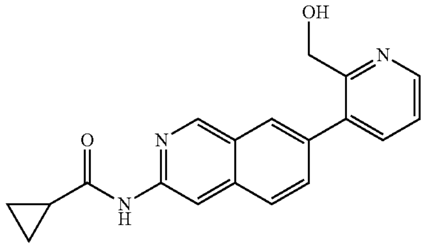 N-(7-(2-(hydroxymethyl)pyridin-3-yl) isoquinolin-3-yl)cyclopropanecarboxamide | 87 | 2.946, 320.1, E | $^1H$ NMR (400 MHz, DMSO) δ 10.92 (s, 1H), 9.17 (s, 1H), 8.63 (dd, J = 4.8, 1.5 Hz, 1H), 8.51 (s, 1H), 8.14 (s, 1H), 7.94 (d, J = 8.6 Hz, 1H), 7.87-7.79 (m, 2H), 7.47 (dd, J = 7.7, 4.8 Hz, 1H), 5.17 (t, J = 5.4 Hz, 1H), 4.53 (d, J = 5.4 Hz, 2H), 2.14-2.03 (m, 1H), 0.95-0.76 (m, 4H). |
| 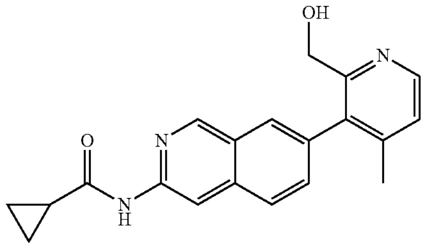 N-(7-(2-(hydroxymethyl)-4-methylpyridin-3-yl) isoquinolin-3-yl)cyclopropanecarboxamide | 87 | 2.37, 334.1, H | $^1H$ NMR (400 MHz, DMSO) δ 10.91 (s, 1H), 9.14 (s, 1H), 8.51 (s, 1H), 8.48 (d, J = 5.0 Hz, 1H), 7.94 (m, 2H), 7.60-7.51 (m, 1H), 7.33 (d, J = 5.0 Hz, 1H), 4.85 (t, J = 5.3 Hz, 1H), 4.25 (d, J = 5.2 Hz, 2H), 2.12-2.03 (m, 4H), 0.91-0.78 (m, 4H). |
| 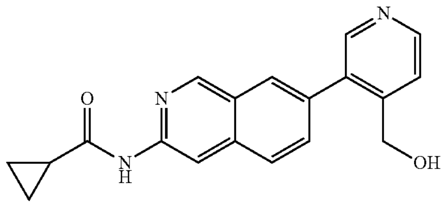 N-(7-(4-(hydroxymethyl)pyridin-3-yl) isoquinolin-3-yl)cyclopropanecarboxamide | 87 | 2.828, 320.1, E | $^1H$ NMR (400 MHz, DMSO) δ 10.93 (s, 1H), 9.19 (s, 1H), 8.62 (d, J = 5.1 Hz, 1H), 8.51 (s, 2H), 8.08 (s, 1H), 7.95 (d, J = 8.5 Hz, 1H), 7.74 (dd, J = 8.5, 1.5 Hz, 1H), 7.63 (d, J = 5.1 Hz, 1H), 5.44 (s, 1H), 4.53 (s, 2H), 2.15-2.04 (m, 1H), 0.95-0.76 (m, 4H). |
| 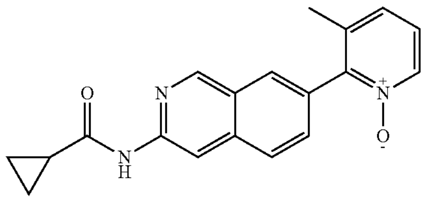 2-(3-(cyclopropanecarboxamido)isoquinolin-7-yl)-3-methylpyridine 1-oxide | 87 | 3.572, 320.2, E | $^1H$ NMR (400 MHz, DMSO-$d_6$) δ 10.94 (s, 1H), 9.15 (s, 1H), 8.50 (s, 1H), 8.24 (m, 1H), 8.05 (s, 1H), 7.92 (d, J = 8.6 Hz, 1H), 7.63 (d, J = 8.6 Hz, 1H), 7.37 (m, 2H), 2.12 (s, 3H), 2.08 (m, 1H), 0.90-0.80 (m, 4H). |

TABLE 3-continued

| Structure/Name | Syn. Meth-od | LCMS $R_T$ (min), M + $H^+$, LCMS method | $^1$H NMR (ppm) |
|---|---|---|---|
| 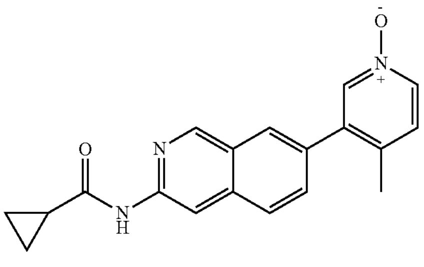 3-(3-(cyclopropanecarboxamido)isoquinolin-7-yl)-4-methylpyridine 1-oxide | 87 | 3.598, 320.1, E | $^1$H NMR (400 MHz, DMSO-$d_6$) δ 10.95 (s, 1H), 9.19 (s, 1H), 8.51 (s, 1H), 8.20 (s, 1H), 8.18 (d, J = 6.6 Hz, 1H), 8.12 (s, 1H), 7.96 (d, J = 8.6 Hz, 1H), 7.74 (dd, J = 8.5, 1.4 Hz, 1H), 7.40 (d, J = 6.5 Hz, 1H), 2.25 (s, 3H), 2.13-2.03 (m, 1H), 0.91-0.79 (m, 4H). |
| 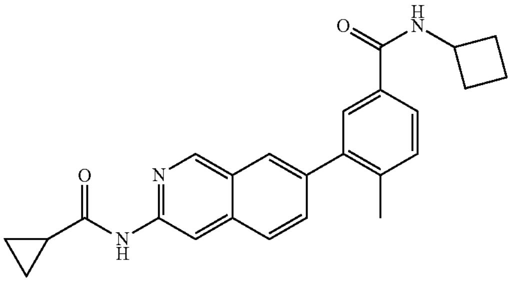 N-cyclobutyl-3-(3-(cyclopropanecarboxamido) isoquinolin-7-yl)-4-methylbenzamide | 20 | 3.94, 400.3, H | $^1$H NMR (400 MHz, DMSO) δ 10.91 (s, 1H), 9.19 (s, 1H), 8.58 (d, J = 7.5 Hz, 1H), 8.51 (s, 1H), 8.05 (s, 1H), 7.94 (d, J = 8.5 Hz, 1H), 7.83 (s, 1H), 7.81 (d, J = 7.9 Hz, 1H), 7.74 (d, J = 8.5 Hz, 1H), 7.43 (d, J = 7.9 Hz, 1H), 4.51-4.35 (m, 1H), 2.32 (s, 3H), 2.20 m, 2H), 2.15-1.98 (m, 3H), 1.73-1.58 (m, 2H), 0.94-0.79 (m, 4H). |
| 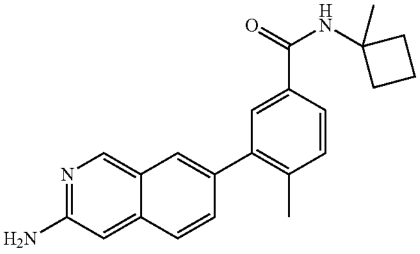 3-(3-aminoisoquinolin-7-yl)-4-methyl-N-(1-methylcyclobutyl)benzamide | 172 | 3.14, 346.3, H | $^1$H NMR (400 MHz, DMSO) δ 8.87 (s, 1H), 8.33 (s, 1H), 7.78 (s, 2H), 7.75 (d, J = 8.0 Hz, 1H), 7.59 (d, J = 8.6 Hz, 1H), 7.48 (d, J = 8.6 Hz, 1H), 7.37 (d, J = 7.9 Hz, 1H), 6.67 (s, 1H), 5.95 (s, 2H), 2.39-2.32 (m, 2H), 2.31 (s, 3H), 2.03-1.92 (m, 2H), 1.86-1.74 (m, 2H), 1.47 (s, 3H). |
| 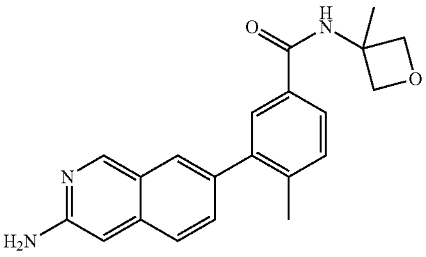 3-(3-aminoisoquinolin-7-yl)-4-methyl-N-(3-methyloxetan-3-yl)benzamide | 172 | 2.49, 348.3, H | $^1$H NMR (400 MHz, DMSO) δ 8.87 (s, 1H), 8.84 (s, 1H), 7.79 (s, 2H), 7.77 (d, J = 8.1 Hz, 1H), 7.60 (d, J = 8.6 Hz, 1H), 7.49 (dd, J = 8.6, 1.5 Hz, 1H), 7.42 (d, J = 7.9 Hz, 1H), 6.67 (s, 1H), 5.95 (s, 2H), 4.70 (d, J = 6.2 Hz, 2H), 4.36 (d, J = 6.3 Hz, 2H), 2.32 (s, 3H), 1.60 (s, 3H). |

TABLE 3-continued

| Structure/Name | Syn. Meth-od | LCMS $R_T$ (min), M + $H^+$, LCMS method | $^1H$ NMR (ppm) |
|---|---|---|---|
| 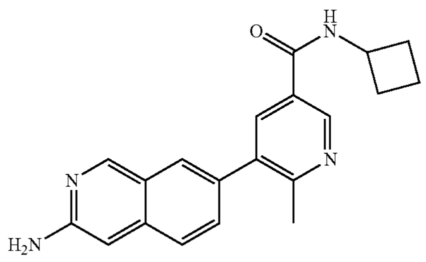 5-(3-aminoisoquinolin-7-yl)-N-cyclobutyl-6-methylnicotinamide | 175 | 2.930, 333.2, E | $^1H$ NMR (400 MHz, DMSO) δ 8.88 (m, 2H), 8.75 (d, J = 7.4 Hz, 1H), 8.11 (d, J = 1.6 Hz, 1H), 7.87 (s, 1H), 7.63 (d, J = 8.6 Hz, 1H), 7.54 (d, J = 8.6 Hz, 1H), 6.68 (s, 1H), 6.01 (s, 2H), 4.49-4.36 (m, 1H), 2.53 (s, 3H), 2.22 (m, 2H), 2.07 (p, J = 9.5 Hz, 2H), 1.75-1.61 (m, 2H). |
| 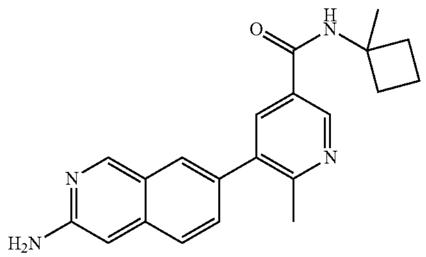 5-(3-aminoisoquinolin-7-yl)-6-methyl-N-(1-methylcyclobutyl)nicotinamide | 175 | 3.106, 347.2, E | $^1H$ NMR (400 MHz, DMSO) δ 8.88 (s, 2H), 8.53 (s, 1H), 8.10 (s, 1H), 7.86 (s, 1H), 7.63 (d, J = 8.6 Hz, 1H), 7.54 (d, J = 8.6 Hz, 1H), 6.68 (s, 1H), 6.01 (s, 2H), 2.52 (s, 3H), 2.36 (m, 2H), 2.05-1.93 (m, 2H), 1.88-1.75 (m, 2H), 1.48 (s, 3H). |
| 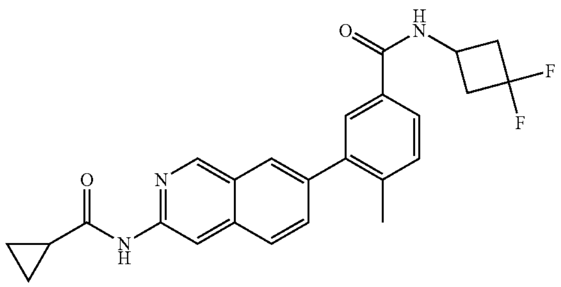 3-(3-(cyclopropanecarboxamido)isoquinolin-7-yl)-N-(3,3-difluorocyclobutyl)-4-methylbenzamide | 20 | 4.808, 436.2, E | $^1H$ NMR (400 MHz, DMSO) δ 10.91 (s, 1H), 9.20 (s, 1H), 8.79 (d, J = 6.5 Hz, 1H), 8.51 (s, 1H), 8.05 (s, 1H), 7.95 (d, J = 8.5 Hz, 1H), 7.83 (m, 2H), 7.73 (d, J = 8.5 Hz, 1H), 7.46 (d, J = 7.8 Hz, 1H), 4.29 (m, 1H), 3.03-2.85 (m, 2H), 2.75 (m, 2H), 2.33 (s, 3H), 2.15-2.02 (m, 1H), 0.85 (m, 4H). |
| 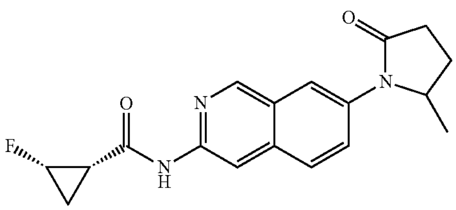 (1S,2S)-2-fluoro-N-(7-(2-methyl-5-oxopyrrolidin-1-yl)isoquinolin-3-yl)cyclopropanecarboxamide (single stereoisomer) | 21 | 3.656, 328.2, E | $^1H$ NMR (400 MHz, DMSO) δ 11.01 (s, 1H), 9.11 (s, 1H), 8.38 (s, 1H), 8.05 (s, 1H), 7.88 (s, 2H), 4.91 (m, 1H), 4.58-4.43 (m, 1H), 2.70-2.54 (m, 2H), 2.40 (m, 2H), 1.73 (m, 1H), 1.52 (m, 1H), 1.27 (m, 1H), 1.18 (d, J = 6.1 Hz, 3H). |

TABLE 3-continued

| Structure/Name | Syn. Meth-od | LCMS $R_T$ (min), M + H$^+$, LCMS method | $^1$H NMR (ppm) |
|---|---|---|---|
| 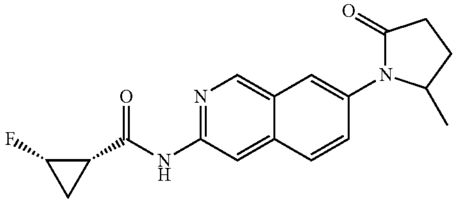 (1S,2S)-2-fluoro-N-(7-(2-methyl-5-oxopyrrolidin-1-yl)isoquinolin-3-yl)cyclopropanecarboxamide (single stereoisomer) | 21 | 3.908, 328.2, E | $^1$H NMR (400 MHz, DMSO) δ 10.88 (s, 1H), 9.11 (s, 1H), 8.44 (s, 1H), 8.05 (s, 1H), 7.93-7.85 (overlapping d and d, 2H), 4.94 m, 1H), 4.53 (m, 1H), 2.62 (m, 1H), 2.43 (m, 1H), 2.40-2.31 (m, 1H), 2.26 (m, 1H), 1.80-1.59 (m, 2H), 1.18 (d, J = 6.2 Hz, 4H). |
| 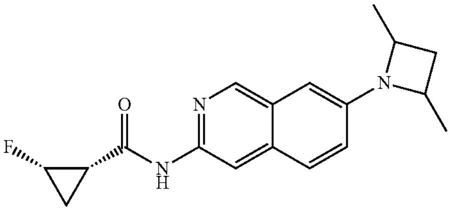 (1S,2S)-N-(7-(2,4-dimethylazetidin-1-yl)isoquinolin-3-yl)-2-fluorocyclopropanecarboxamide | 21 | 4.182, 314.2, E | $^1$H NMR (400 MHz, DMSO) δ 10.65 (s, 1H), 8.91 (s, 1H), 8.28 (s, 1H), 7.70 (d, J = 8.9 Hz, 1H), 7.13 (dd, J = 8.9, 2.3 Hz, 1H), 6.93 (s, 1H), 5.02-4.80 (m, 1H), 3.97-3.92 (m, 2H), 2.69-2.60 (m, 1H), 2.25-2.18 (m, 1H), 1.71-1.61 (m, 2H), 1.51 (s, 3H), 1.50 (s, 3H), 1.21-1.11 (m, 1H). |
| 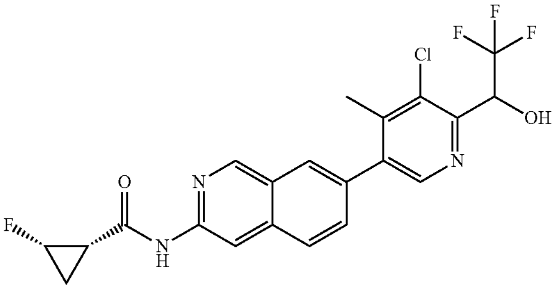 (1S,2S)-N-(7-(5-chloro-4-methyl-6-(2,2,2-trifluoro-1-hydroxyethyl)pyridin-3-yl)isoquinolin-3-yl)-2-fluorocyclopropanecarboxamide (single stereoisomer) | 171 | 5.376, 454.1, E | $^1$H NMR (400 MHz, DMSO) δ 11.00 (s, 1H), 9.21 (s, 1H), 8.57 (s, 1H), 8.55 (s, 1H), 8.15 (s, 1H), 8.02 (d, J = 8.6 Hz, 1H), 7.79 (dd, J = 8.5, 1.6 Hz, 1H), 6.86 (s, 1H), 5.68 (br s, 1H), 5.10-4.83 (m, 1H), 2.39 (s, 3H), 2.34-2.24 (m, 1H), 1.75-1.65 (m, 1H), 1.25-1.16 (m, 1H). |
| 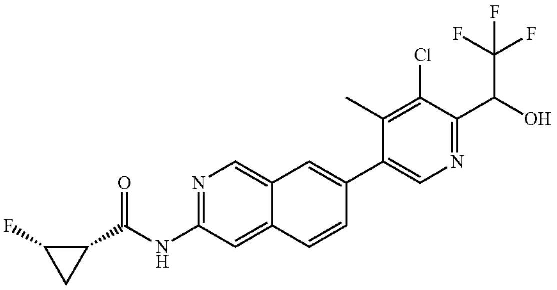 (1S,2S)-N-(7-(5-chloro-4-methyl-6-(2,2,2-trifluoro-1-hydroxyethyl)pyridin-3-yl)isoquinolin-3-yl)-2-fluorocyclopropanecarboxamide (single stereoisomer) | 171 | 5.381, 454.1, E | $^1$H NMR (400 MHz, DMSO) δ 11.01 (s, 1H), 9.21 (s, 1H), 8.57 (s, 1H), 8.55 (s, 1H), 8.15 (s, 1H), 8.02 (d, J = 8.6 Hz, 1H), 7.79 (dd, J = 8.5, 1.5 Hz, 1H), 6.86 (d, J = 7.6 Hz, 1H), 5.68 (p, J = 7.1 Hz, 1H), 5.06-4.85 (m, 1H), 2.39 (s, 3H), 2.35-2.23 (m, 1H), 1.75-1.65 (m, 1H), 1.25-1.16 (m, 1H). |

TABLE 3-continued

| Structure/Name | Syn. Meth-od | LCMS $R_T$ (min), M + $H^+$, LCMS method | $^1$H NMR (ppm) |
|---|---|---|---|
| 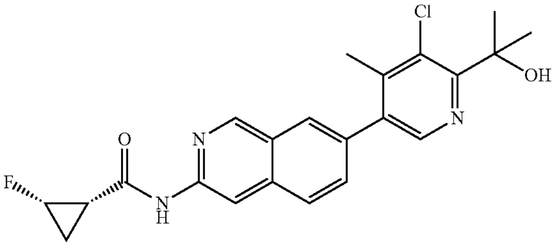 (1S,2S)-N-(7-(5-chloro-6-(2-hydroxypropan-2-yl)-4-methylpyridin-3-yl)isoquinolin-3-yl)-2-fluorocyclopropanecarboxamide | 171 | 4.336, 414.2, E | $^1$H NMR (400 MHz, DMSO) δ 11.00 (s, 1H), 9.20 (s, 1H), 8.54 (s, 1H), 8.43 (s, 1H), 8.10 (s, 1H), 8.00 (d, J = 8.6 Hz, 1H), 7.76 (dd, J = 8.5, 1.4 Hz, 1H), 5.61 (s, 1H), 5.06-4.85 (m, 1H), 2.37 (s, 3H), 2.39-2.25 (m, 1H), 1.76-1.67 (m, 1H), 1.66 (s, 6H), 1.24-1.16 (m, 1H). |
| 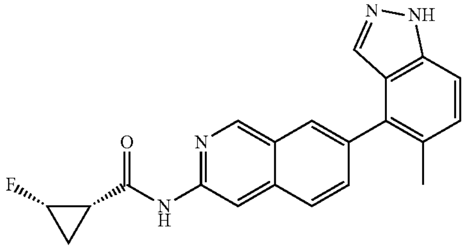 (1S,2S)-2-fluoro-N-(7-(5-methyl-1H-indazol-4-yl) isoquinolin-3-yl)cyclopropanecarboxamide | | 10.37, 361.0, G | $^1$H NMR (400 MHz, DMSO) δ 13.08 (s, 1H), 10.97 (s, 1H), 9.22 (s, 1H), 8.54 (s, 1H), 8.12 (s, 1H), 8.01 (d, J = 8.5 Hz, 1H), 7.77 (dd, J = 8.5, 1.6 Hz, 1H), 7.68 (s, 1H), 7.50 (d, J = 8.5 Hz, 1H), 7.35 (d, J = 8.5 Hz, 1H), 4.96 (dtd, J = 66, 6, 4 Hz, 1H), 2.33 (s, 3H), 2.35-2.25 (m, 1H), 1.71 (dtd, J = 23, 7, 4 Hz, 1H), 1.21 (ddt, J = 12, 9, 6 Hz, 1H). |
| 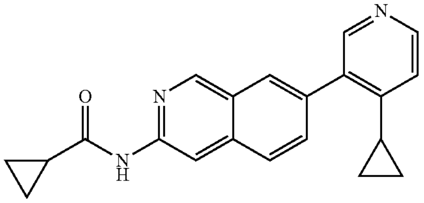 (N-(7-(4-cyclopropylpyridin-3-yl)isoquinolin-3-yl)cyclopropanecarboxamide | 87 | 3.645, 330.2, E | $^1$H NMR (400 MHz, DMSO) δ 10.93 (s, 1H), 9.21 (s, 1H), 8.51 (s, 1H), 8.46 (d, J = 5 Hz, 1H), 8.44 (s, 1H), 8.13 (s, 1H), 7.96 (d, J = 8.5 Hz, 1H), 7.79 (d, J = 8.5 Hz, 1H), 6.99 (d, J = 5.3 Hz, 1H), 2.13-2.05 (m, 1H), 1.91-1.82 (m, 1H), 1.05-0.96 (m, 2H), 0.85 (m, 6H). |
| 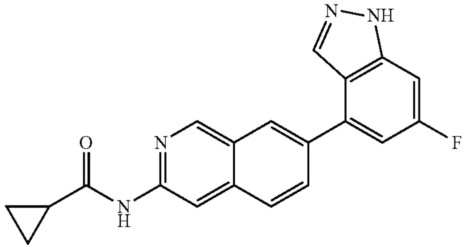 (N-(7-(6-fluoro-1H-indazol-4-yl)isoquinolin-3-yl)cyclopropanecarboxamide | 87 | 4.676, 347.2, E | $^1$H NMR (400 MHz, DMSO) δ 13.36 (s, 1H), 10.95 (s, 1H), 9.29 (s, 1H), 8.52 (s, 1H), 8.48 (s, 1H), 8.35 (s, 1H), 8.09 (d, J = 8.7 Hz, 1H), 8.01 (d, J = 8.6 Hz, 1H), 7.38 (d, J = 8.7 Hz, 1H), 7.30 (d, J = 10.4 Hz, 1H), 2.15-2.05 (m, 1H), 0.92-0.80 (m, 4H). |
| 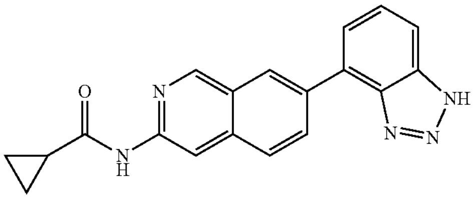 N-(7-(1H-benzo[d][1,2,3]triazol-4-yl)isoquinolin-3-yl)cyclopropanecarboxamide | 87 | 4.260, 330.2, E | $^1$H NMR (400 MHz, DMSO) δ 10.92 (s, 1H), 9.25 (s, 1H), 8.86 (s, 1H), 8.51 (s, 1H), 8.43 (d, J = 8.6 Hz, 1H), 8.01 (d, J = 8.7 Hz, 1H), 7.87 (d, J = 8.2 Hz, 1H), 7.74 (d, J = 7.1 Hz, 1H), 7.54 (t, J = 7.7 Hz, 1H), 6.51 (br s, 1H), 2.14-2.05 (m, 1H), 0.92-0.79 (m, 4H). |

TABLE 3-continued

| Structure/Name | Syn. Meth-od | LCMS $R_T$ (min), M + H$^+$, LCMS method | $^1$H NMR (ppm) |
|---|---|---|---|
| 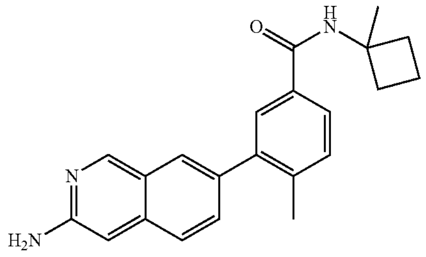 3-(3-aminoisoquinolin-7-yl)-4-methyl-N-(1-methylcyclobutyl) benzamide | 172 | 3.14, 346.3, H | $^1$H NMR (400 MHz, DMSO) δ 8.87 (s, 1H), 8.33 (s, 1H), 7.78 (s, 2H), 7.75 (d, J = 8.0 Hz, 1H), 7.59 (d, J = 8.6 Hz, 1H), 7.48 (d, J = 8.6 Hz, 1H), 7.37 (d, J = 7.9 Hz, 1H), 6.67 (s, 1H), 5.95 (s, 2H), 2.39-2.32 (m, 2H), 2.31 (s, 3H), 2.03-1.92 (m, 2H), 1.86-1.74 (m, 2H), 1.47 (s, 3H). |
| 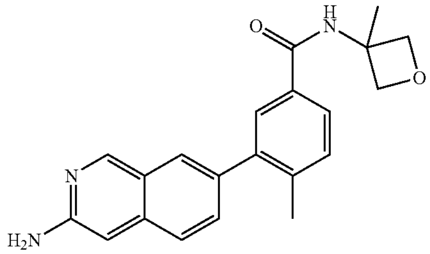 3-(3-aminoisoquinolin-7-yl)-4-methyl-N-(3-methyloxetan-3-yl)benzamide | 172 | 2.49, 348.3, H | $^1$H NMR (400 MHz, DMSO) δ 8.87 (s, 1H), 8.84 (s, 1H), 7.79 (s, 2H), 7.77 (d, J = 8.1 Hz, 1H), 7.60 (d, J = 8.6 Hz, 1H), 7.49 (dd, J = 8.6, 1.5 Hz, 1H), 7.42 (d, J = 7.9 Hz, 1H), 6.67 (s, 1H), 5.95 (s, 2H), 4.70 (d, J = 6.2 Hz, 2H), 4.36 (d, J = 6.3 Hz, 2H), 2.32 (s, 3H), 1.60 (s, 3H). |
| 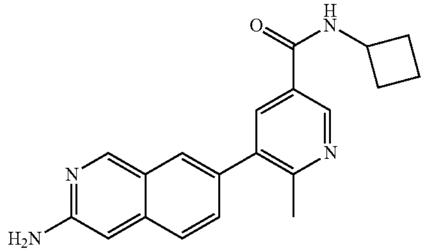 5-(3-aminoisoquinolin-7-yl)-N-cyclobutyl-6-methylnicotinamide | 175 | 2.930, 333.2, E | $^1$H NMR (400 MHz, DMSO) δ 8.88 (m, 2H), 8.75 (d, J = 7.4 Hz, 1H), 8.11 (d, J = 1.6 Hz, 1H), 7.87 (s, 1H), 7.63 (d, J = 8.6 Hz, 1H), 7.54 (d, J = 8.6 Hz, 1H), 6.68 (s, 1H), 6.01 (s, 2H), 4.49-4.36 (m, 1H), 2.53 (s, 3H), 2.22 (m, 2H), 2.07 (p, J = 9.5 Hz, 2H), 1.75-1.61 (m, 2H). |
| 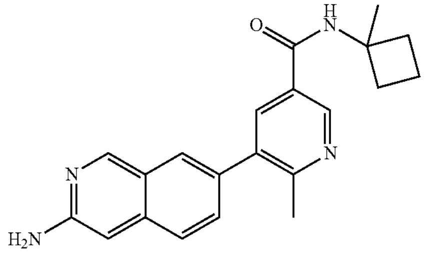 5-(3-aminoisoquinolin-7-yl)-6-methyl-N-(1-methylcyclobutyl)nicotinamide | 175 | 3.106, 347.2, E | $^1$H NMR (400 MHz, DMSO) δ 8.88 (s, 2H), 8.53 (s, 1H), 8.10 (s, 1H), 7.86 (s, 1H), 7.63 (d, J = 8.6 Hz, 1H), 7.54 (d, J = 8.6 Hz, 1H), 6.68 (s, 1H), 6.01 (s, 2H), 2.52 (s, 3H), 2.36 (m, 2H), 2.05-1.93 (m, 2H), 1.88-1.75 (m, 2H), 1.48 (s, 3H). |

Example 124

N-(7-(2-chlorophenyl)-2,6-naphthyridin-3-yl)cyclopropanecarboxamide

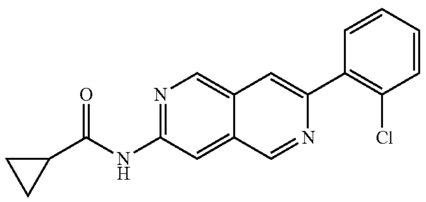

Step 1: 5-bromo-2-chloroisonicotinaldehyde

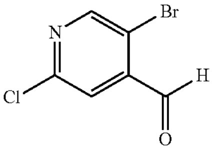

To a solution of 5-bromo-2-chloro-4-methylpyridine (5.0 g, 20 mmol) in N,N-dimethylformamide (38 mL) was added tert-butoxybis(dimethylamino)methane (7.0 mL, 33.9 mmol). The reaction mixture was heated at 120° C. for 2 hours. The cooled reaction mixture was concentrated in vacuo to afford a thick orange oil, which was redissolved in tetrahydrofuran (40 mL) and slowly poured into a separate flask containing slurry of sodium periodate in water (150 mL) at 0° C. The reaction flask was equipped with an overhead stirrer and allowed to warm to room temperature. The reaction mixture was mixed vigorously for three hours, and then diluted with dichloromethane (150 mL) and filtered. The collected solids were washed with dichloromethane (2 ×150 mL), and the organic layer was separated from the filtrate and washed with saturated sodium bicarbonate solution (50 mL). The aqueous layer was neutralized via addition of solid sodium bicarbonate, and then back-extracted with dichloromethane (100 mL). The organic portions were combined, dried over sodium sulfate, filtered, and evaporated in vacuo to afford a residue that was purified by flash chromatography (silica, 120 g, ISCO, 0-40% ethyl acetate in heptane) to afford the title compound as an off-white solid (4.03 g, 80%). $^1$H NMR (500 MHz, $d_6$-DMSO) δ 10.10 (s, 1H), 8.85 (s, 1H), 7.81 (s, 1H).

Step 2: 2-chloro-5-((2-chlorophenyl)ethynyl)isonicotinaldehyde

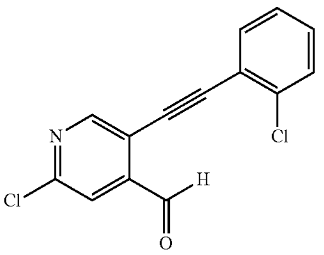 [SMILES: O=Cc1cc(Cl)ncc1C#Cc1ccccc1Cl]

A mixture of 5-bromo-2-chloroisonicotinaldehyde (1.0 g, 4.5 mmol), 1-chloro-2-ethynylbenzene (650 mg, 4.7 mmol), N,N-diisopropylethylamine (1.6 mL, 9.1 mmol), copper(I) iodide (43 mg, 0.23 mmol), and bis(triphenylphosphine)palladium(II) chloride (159 mg, 0.23 mmol) in 1,4-dioxane (21 mL) was heated at 50° C. for 1 hour. The cooled reaction mixture was diluted with ethyl acetate (100 mL) and washed with water (100 mL). The organic layer was separated, dried over sodium sulfate, filtered, and evaporated in vacuo to afford a residue that was purified by flash chromatography (silica, 40 g, ISCO, 0-30% ethyl acetate in heptane) to afford the title compound as an off-white solid (1.1 g, 88%). $^1$H NMR (400 MHz, $CDCl_3$) δ 10.64 (s, 1H), 8.77 (s, 1H), 7.77 (s, 1H), 7.62 (dd, J=7.5, 1.7 Hz, 1H), 7.49 (d, J=7.9 Hz, 1H), 7.38 (td, J=7.8, 1.8 Hz, 1H), 7.32 (td, J=7.5, 1.2 Hz, 1H).

Step 3: 2-chloro-5-((2-chlorophenyl)ethynyl)isonicotinaldehyde oxime

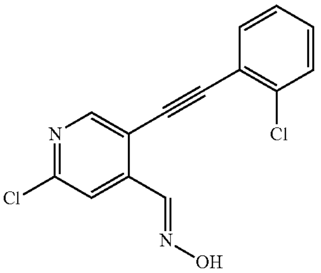 [SMILES: O/N=C/c1cc(Cl)ncc1C#Cc1ccccc1Cl]

A mixture of 2-chloro-5-((2-chlorophenyl)ethynyl)isonicotinaldehyde (1.1 g, 4.0 mmol), sodium acetate (490 mg, 6 mmol), and hyroxylamine hydrochloride (415 mg, 6 mmol) in ethanol (23 mL) and dichloroethane (13 mL) was heated at 50° C. for 15 minutes. The cooled reaction mixture was evaporated in vacuo to afford a residue that was redissolved in ethyl acetate (150 mL) and washed with water (100 mL). The organic layer was separated, dried over sodium sulfate, filtered, and evaporated in vacuo to afford a white solid that was used in the next step without further purification.

Step 4: 7-chloro-3-(2-chlorophenyl)-2,6-naphthyridine 2-oxide

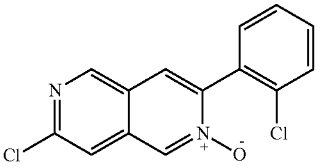

A mixture of 2-chloro-5-((2-chlorophenyl)ethynyl)isonicotinaldehyde oxime (235 mg, 0.81 mmol) and silver nitrate (~10 wt. % on silica gel, +230 mesh, 275 mg, 0.16 mmol) in chloroform (7 mL) was heated at 60° C. for 1 hour. The cooled reaction mixture was treated with silica gel (1 g), concentrated in vacuo, and purified by flash chromatography (silica, 12 g, ISCO, 0-90% ethyl acetate in heptane) to afford the title compound as pale yellow solid (200 mg, 80%).

Step 5: 3-(2-chlorophenyl)-7-(cyclopropanecarboxamido)-2,6-naphthyridine 2-oxide

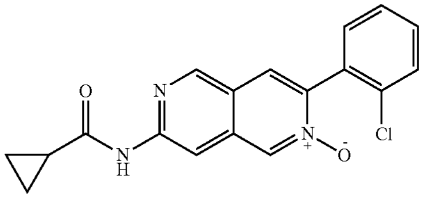

A mixture of 7-chloro-3-(2-chlorophenyl)-2,6-naphthyridine 2-oxide (2.0 g, 7.0 mmol), cyclopropanecarboxamide (653 mg, 7.7 mmol), Chloro[2-(dicyclohexylphosphino)-3-,6-dimethoxy-2,4'-6'-tri-i-pr-1,1'-biphenyl)][2-(2-aminoethyl)Ph]Pd(II) (167 mg, 0.21 mmol), (dicyclohexylphosphino)-3-,6-dimethoxy-2,4'-6'-tri-i-pr-1,1'-biphenyl (281 mg, 0.52 mmol), and cesium carbonate (4.5 g, 13.9 mmol) in 1,4-dioxane (19 mL) was heated at 90° C. for 4 hours. The cooled reaction mixture was diluted with dichloromethane (200 mL) and methanol (100 mL), mixed with Celite, filtered, the solids washed with 15% methanol/dichloromethane (2×100 mL), and the filtrate was dried over sodium sulfate, filtered, and evaporated in vacuo to afford a residue that was purified by flash chromatography (silica, 40 g, ISCO, 0-10% methanol in dichloromethane) to afford the title compound as an off-white solid (2.0 g, 84%). $^1$H NMR (400 MHz, DMSO) δ 11.15 (s, 1H), 9.13 (s, 1H), 9.09 (s, 1H), 8.42 (s, 1H), 8.17 (s, 1H), 7.62 (m, 1H), 7.58-7.45 (m, 3H), 2.14-2.03 (m, 1H), 0.91-0.82 (m, 4H). LCMS (Method G): $R_T$=8.18 min, M+H$^+$=340.0.

Step 6: N-(7-(2-chlorophenyl)-2,6-naphthyridin-3-yl) cyclopropanecarboxamide

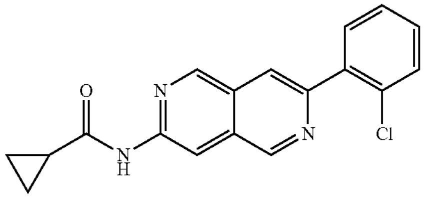

To a slurry of 3-(2-chlorophenyl)-7-(cyclopropanecarboxamido)-2,6-naphthyridine 2-oxide (170 mg, 0.5 mmol) in dichloromethane (2 mL) was added phosphorus trichloride (0.048 mL, 0.55 mmol) and the mixture was stirred at room temperature for 1 hour. The reaction mixture was then diluted with dichloromethane (50 mL) and washed with saturated sodium bicarbonate solution (30 mL). The organic layer was separated, dried over sodium sulfate, filtered, and evaporated in vacuo to afford a residue that was purified by flash chromatography (silica, 12 g, ISCO, 0-60% ethyl acetate in heptane) to afford the title compound as a white solid (75 mg, 46%). $^1$H NMR (400 MHz, DMSO) δ 11.17 (s, 1H), 9.46 (s, 1H), 9.35 (s, 1H), 8.66 (s, 1H), 8.23 (s, 1H), 7.76-7.67 (m, 1H), 7.63 (m, 1H), 7.55-7.43 (m, 2H), 2.14-2.06 (m, 1H), 0.88 (m, 4H). LCMS (Method D): $R_T$=13.170 min, M+H$^+$=324.0.

Example 125

1-chloro-2-ethynyl-4-fluorobenzene

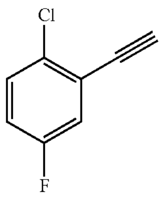

Step 1: ((2-chloro-5-fluorophenyl)ethynyl)trimethylsilane

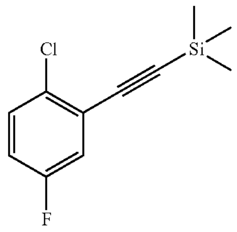

A mixture of 1-chloro-4-fluoro-2-iodobenzene (10 g, 40 mmol), (trimethylsilyl)acetylene (28 mL, 190 mmol), copper (I) iodide (740 mg, 3.9 mmol), (triphenylphosphine)palladium(0) (2.5 g, 2.2 mmol), and N,N-diisopropylethylamine (14 mL, 78 mmol) in 1,4-dioxane (100 mL) was heated at 90° C. for 2 hours. The cooled reaction mixture was then diluted with diethyl ether (200 mL) and washed with water (300 mL). The organic layer was separated, dried over sodium sulfate, filtered, and evaporated in vacuo to afford a residue that was purified by flash chromatography (silica, 220 g, ISCO, heptane) to afford the title compound as a pale yellow oil (5 g, 60%), which was used in the next step without further purification.

Step 2: 1-chloro-2-ethynyl-4-fluorobenzene

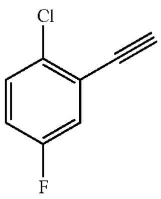

To a solution of ((2-chloro-5-fluorophenyl)ethynyl)trimethylsilane (4.2 g, 18 mmol) in methanol (40 mL) was added potassium carbonate (7.7 g, 56 mmol), and the reaction mixture was stirred for 2 hours at room temperature. The reaction mixture was then diluted with diethyl ether (100 mL) and washed with water (300 mL). The organic layer was separated, dried over sodium sulfate, filtered, and evaporated in vacuo to afford a residue that was purified by flash chromatography (silica, 220 g, ISCO, heptane) to afford the title compound as a pale yellow, waxy solid (2.0 g, 70%), which was used in the next step without further purification.

Example 126

2-ethynyl-4-fluoro-1-methylbenzene

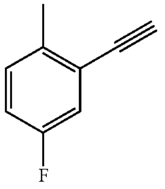

The title compound was prepared following a procedure similar to the previous described example 125 using 4-fluoro-2-iodo-1-methylbenzene in step 1, and was used in the next step without further purification.

Example 127

3-ethynyl-4-methylpyridine

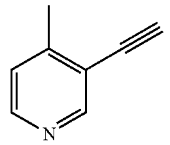

The title compound was prepared following a procedure similar to the previous described example 125 using 3-bromo-4-methylpyridine in step 1, and was used in the next step without further purification.

Example 128

N-(7-(2-chloro-5-fluorophenyl)-2,6-naphthyridin-3-yl)cyclopropanecarboxamide

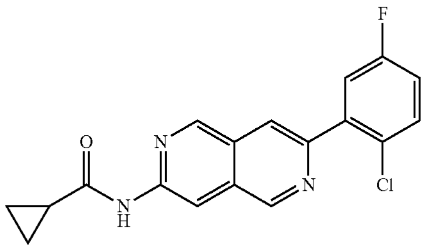 [SMILES: O=C(Nc1cc2cnc(-c3cc(F)ccc3Cl)cc2cn1)C1CC1]

The title compound was prepared following a procedure similar to example 124 using 1-chloro-2-ethynyl-4-fluorobenzene in step 2.

$^1$H NMR (400 MHz, $CDCl_3$) δ 9.37 (s, 1H), 9.11 (s, 1H), 8.72 (s, 1H), 8.32 (s, 1H), 8.13 (s, 1H), 7.54-7.43 (m, 2H), 7.14-7.04 (m, 1H), 1.70-1.60 (m, 1H), 1.22-1.16 (m, 2H), 1.02-0.93 (m, 2H). LCMS (Method E): $R_T$=4.973 min, M+H$^+$=342.0.

Example 129

7-(cyclopropanecarboxamido)-3-(5-fluoro-2-methylphenyl)-2,6-naphthyridine 2-oxide

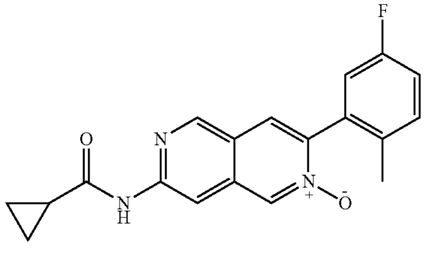

The title compound was prepared following a procedure similar to example 124 using 2-ethynyl-4-fluoro-1-methylbenzene in step 2.

$^1$H NMR (400 MHz, DMSO) δ 11.11 (s, 1H), 9.11 (s, 1H), 9.09 (s, 1H), 8.41 (s, 1H), 8.12 (s, 1H), 7.43-7.32 (m, 1H), 7.24 (m, 2H), 2.10 (s, 3H), 2.08 (m, 1H), 0.86 (m, 4H). LCMS (Method E): $R_T$=3.999 min, M+H$^+$=338.0.

Example 130

N-(7-(5-fluoro-2-methylphenyl)-2,6-naphthyridin-3-yl)cyclopropanecarboxamide

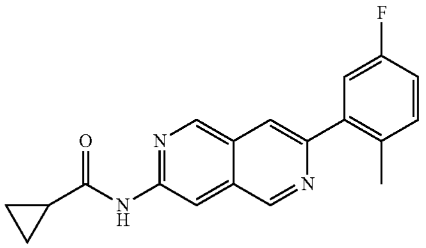

The title compound was prepared following a procedure similar to example 124 using 2-ethynyl-4-fluoro-1-methylbenzene in step 2.

$^1$H NMR (400 MHz, DMSO) δ 11.15 (s, 1H), 9.44 (s, 1H), 9.32 (s, 1H), 8.65 (s, 1H), 8.12 (s, 1H), 7.42-7.32 (m, 2H), 7.19 (td, J=8.5, 2.7 Hz, 1H), 2.37 (s, 3H), 2.15-2.05 (m, 1H), 0.94-0.80 (m, 4H). LCMS (Method D): $R_T$=13.570 min, M+H$^+$=322.1.

Example 131

N-(5-chloro-7-(2-chlorophenyl)-2,6-naphthyridin-3-yl)cyclopropanecarboxamide

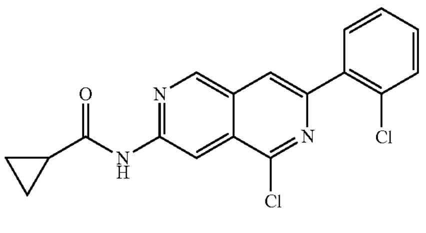 [SMILES: O=C(Nc1cc2c(Cl)nc(-c3ccccc3Cl)cc2cn1)C1CC1]

A mixture of 3-(2-chlorophenyl)-7-(cyclopropanecarboxamido)-2,6-naphthyridine 2-oxide (200 mg, 0.6 mmol) and methanesulfonyl chloride (0.47 mL, 5.9 mmol) in N,N-dimethylformamide (2.5 mL) was stirred at room temperature for 30 minutes. The reaction mixture was diluted with ethyl acetate (50 mL), washed with water (50 mL) and then saturated sodium bicarbonate solution (20 mL). The organic layer was separated, dried over sodium sulfate, filtered, and evaporated in vacuo to afford a residue that was purified by flash chromatography (silica, 12 g, ISCO, 0-60% ethyl acetate in heptane) to provide the title compound as an off-white solid (170 mg, 80%). $^1$H NMR (400 MHz, $CDCl_3$) δ 9.09 (s, 1H), 8.97 (s, 1H), 8.35 (s, 1H), 8.06 (s, 1H), 7.75 (dd, J=7.4, 2.0 Hz, 1H), 7.52 (m, 1H), 7.46-7.33 (m, 2H), 1.70-1.60 (m, 1H), 1.25-1.18 (m, 2H), 1.02-0.94 (m, 2H). LCMS (Method E): $R_T$=5.562 min, M+H$^+$=358.0.

Example 132

N-(5-chloro-7-(5-fluoro-2-methylphenyl)-2,6-naphthyridin-3-yl)cyclopropanecarboxamide

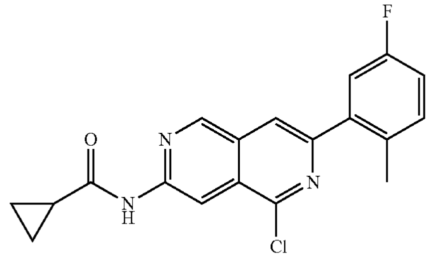 [SMILES: Cc1ccc(F)cc1-c1cc2cnc(NC(=O)C3CC3)cc2c(Cl)n1]

The title compound was prepared following a procedure similar to example 131 using 7-(cyclopropanecarboxamido)-3-(5-fluoro-2-methylphenyl)-2,6-naphthyridine 2-oxide.

$^1$H NMR (400 MHz, $CDCl_3$) δ 9.07 (s, 1H), 8.97 (s, 1H), 8.34 (s, 1H), 7.71 (s, 1H), 7.29-7.21 (m, 2H), 7.03 (td, J=8.3, 2.8 Hz, 1H), 2.40 (s, 3H), 1.65 (m, 1H), 1.21 (m, 2H), 1.02-0.94 (m, 2H).

Example 133

The compounds described in Table 4 below were prepared using one of the synthetic methods (Syn. Meth.) C-A to C-G described below.

Method C-A: A mixture of the appropriate N-(5-chloro-7-aryl-2,6-naphthyridin-3-yl)cyclopropanecarboxamide (1 eq.), the appropriate boronic acid or boronate ester (2 eq.), bis(di-tert-butyl(4-dimethylaminophenyl)phosphine)dichloropalladium(II) (0.1 eq.), and 2.0M sodium carbonate in water (4 eq.) in acetonitrile was heated between 100° C. and 150° C. under microwave irradiation (CEM microwave, 200 watts) until the reaction deemed complete. The reaction mixture was cooled then diluted with water and extracted with an appropriate solvent. The resultant residue was purified by one of the purification methods described below.

Method C-B: A mixture of the appropriate N-(5-chloro-7-aryl-2,6-naphthyridin-3-yl)cyclopropanecarboxamide (1 eq.), the appropriate amine (4 eq.), chloro[2-(dicyclohexylphosphino)-3-,6-dimethoxy-2,4'-6'-tri-i-pr-1,1'-biphenyl)] [2-(2-aminoethyl) Ph]Pd(II) (0.05 eq.), (dicyclohexylphosphino)-3-,6-dimethoxy-2,4'-6'-tri-i-pr-1,1'-biphenyl (0.1 eq.), and cesium carbonate (2 eq.) in 1,4-dioxane was heated between 90° C. to 110° C. until the reaction deemed complete. The reaction mixture was cooled then diluted with water and extracted with an appropriate solvent. The resultant residue was purified by one of the purification methods described below.

Method C-C: A mixture of the appropriate N-(5-chloro-7-aryl-2,6-naphthyridin-3-yl)cyclopropanecarboxamide (1 eq.), the appropriate alcohol (2-4 eq.), and sodium hydride as a 60% dispersion in mineral oil (2-8 eq.) in tetrahydrofuran was heated between 25° C. to 60° C. until the reaction deemed complete. The reaction mixture was cooled then diluted with water and extracted with an appropriate solvent. The resultant residue was purified by one of the purification methods described below.

Method C-D: A mixture of the appropriate N-(5-chloro-7-aryl-2,6-naphthyridin-3-yl)cyclopropanecarboxamide (1 eq.) and the appropriate amine (2-4 eq.) was heated in N,N-dimethylacetamide at between 80° C. to 120° C. until the reaction deemed complete. The reaction mixture was cooled then diluted with water and extracted with an appropriate solvent. The resultant residue was purified by one of the purification methods described below.

Method C-E: A mixture of the appropriate N-(5-chloro-7-aryl-2,6-naphthyridin-3-yl)cyclopropanecarboxamide (1 eq.) and the appropriate boc-protected amino alcohol (2-4 eq.), and sodium hydride as a 60% dispersion in mineral oil (2-8 eq.) in tetrahydrofuran was heated between 25° C. to 60° C. until the reaction deemed complete. The reaction mixture was cooled then diluted with water and extracted with an appropriate solvent. The resultant residue was redissolved in dichloromethane, treated with trifluoroacetic acid (20 eq.), and stirred at room temperature until the reaction deemed complete. The reaction mixture was then evaporated in vacuo to afford a residue that was purified by one of the purification methods described below.

Method C-F: A mixture of the appropriate N-(5-chloro-7-aryl-2,6-naphthyridin-3-yl)cyclopropanecarboxamide (1 eq.), the appropriate phenol (2-4 eq.), and potassium carbonate (3 eq.) was heated in N,N-dimethylacetamide at between 80° C. to 120° C. until the reaction deemed complete. The reaction mixture was cooled then diluted with water and extracted with an appropriate solvent. The resultant residue was purified by one of the purification methods described below.

Method C-G: A mixture of the appropriate N-(5-chloro-7-aryl-2,6-naphthyridin-3-yl)cyclopropanecarboxamide (1 eq.), trimethylboroxine (2-4 eq.), and potassium carbonate (2 eq.) was heated in 1,4-dioxane at 100° C. until the reaction deemed complete. The reaction mixture was cooled then diluted with water and extracted with an appropriate solvent. The resultant residue was purified by one of the purification methods described below.

General Purification Methods for compounds in Table 4: Compounds were typically purified by reverse phase HPLC using a Gemini-NX column (10 μm, 3 cm×10 cm) from Phenomenex. Samples were run on a gradient of 5-50%, 5-85%, or 20-60% acetonitrile or methanol in water with 0.1% ammonium hydroxide or 0.1% formic acid over 14 minutes at a flow rate of 60 mL/min. In some cases, pure racemic compounds were resolved using a Berger MG2 semi-prep system using Chiral Technologies AD, OD, OJ, AS, IA, IB, or IB columns (5 μm, 21.2 mm×250 mm) at a flow rate of 50-70 mL/min. Solvents typically used include methanol, ethanol, or TPA with 0.1% triethylamine.

TABLE 4

| Structure/Name | Syn. Meth. | LCMS $R_T$ (min), M + $H^+$, LCMS Method | $^1H$ NMR (ppm) |
|---|---|---|---|
| 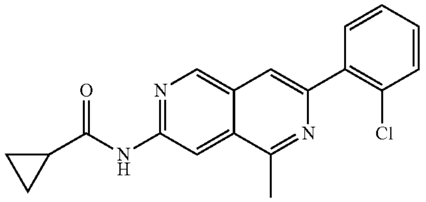 [SMILES: Cc1nc(-c2ccccc2Cl)cc2cnc(NC(=O)C3CC3)cc12] N-(7-(2-chlorophenyl)-5-methyl-2,6-naphthyridin-3-yl)cyclopropanecarboxamide | C-G | 12.205, 338.0, D | $^1H$ NMR (400 MHz, DMSO) δ 11.19 (s, 1H), 9.31 (s, 1H), 8.73 (s, 1H), 8.07 (s, 1H), 7.73-7.66 (m, 1H), 7.61 (m, 1H), 7.54-7.42 (m, 2H), 2.87 (s, 3H), 2.11 (m, 1H), 0.94-0.81 (m, 4H). |
| 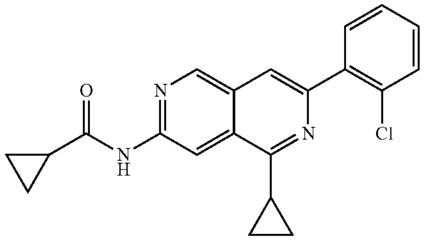 [SMILES: O=C(Nc1cc2c(C3CC3)nc(-c3ccccc3Cl)cc2cn1)C1CC1] N-(7-(2-chlorophenyl)-5-cyclopropyl-2,6-naphthyridin-3-yl)cyclopropanecarboxamide | C-A | 5.877, 364.1, E | $^1H$ NMR (400 MHz, DMSO) δ 11.17 (s, 1H), 9.29 (s, 1H), 9.01 (s, 1H), 7.99 (s, 1H), 7.68 (m, 1H), 7.59 (m, 1H), 7.46 (m, 2H), 2.77-2.67 (m, 1H), 2.11 (m, 1H), 1.23-1.11 (m, 4H), 0.95-0.82 (m, 4H). |
| 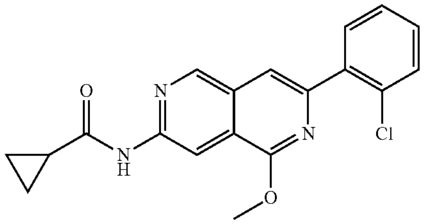 N-(7-(2-chlorophenyl)-5-methoxy-2,6-naphthyridin-3-yl)cyclopropanecarboxamide | C-C | 5.735, 354.0, E | $^1H$ NMR (400 MHz, DMSO) δ 11.14 (s, 1H), 9.22 (s, 1H), 8.72 (s, 1H), 7.80 (m, 1H), 7.76 (m, 1H), 7.60 (m, 1H), 7.48 (s, 2H), 4.11 (s, 3H), 2.08 (m, 1H), 0.87 (m, 4H). |
| 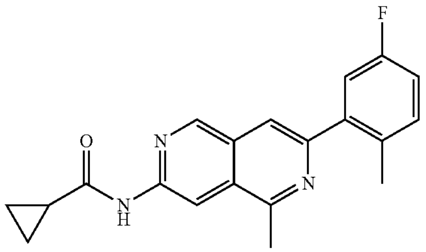 [SMILES: Cc1ccc(F)cc1-c1cc2cnc(NC(=O)C3CC3)cc2c(C)n1] N-(7-(5-fluoro-2-methylphenyl)-5-methyl-2,6-naphthyridin-3-yl)cyclopropanecarboxamide | C-G | 12.441, 336.1, D | $^1H$ NMR (400 MHz, DMSO) δ 11.17 (s, 1H), 9.28 (s, 1H), 8.72 (s, 1H), 7.96 (s, 1H), 7.43-7.27 (m, 2H), 7.18 (td, J = 8.5, 2.8 Hz, 1H), 2.86 (s, 3H), 2.36 (s, 3H), 2.10 (m, 1H), 0.94-0.80 (m, 4H). |

TABLE 4-continued

| Structure/Name | Syn. Meth. | LCMS $R_T$(min), M + H$^+$, LCMS Method | $^1$H NMR (ppm) |
|---|---|---|---|
| 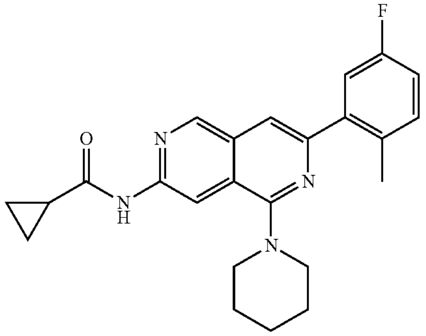 [SMILES: Cc1ccc(F)cc1-c1cc2cnc(NC(=O)C3CC3)cc2c(N2CCCCC2)n1] N-(7-(5-fluoro-2-methylphenyl)-5-(piperidin-1-yl)-2,6-naphthyridin-3-yl) cyclopropanecarboxamide | C-D | 5.689, 405.1, E | $^1$H NMR (400 MHz, DMSO) δ 11.06 (s, 1H), 9.15 (s, 1H), 8.67 (s, 1H), 7.60 (s, 1H), 7.35 (m, 2H), 7.19-7.08 (m, 1H), 3.36 (m, 4H), 2.39 (s, 3H), 2.08 (m, 1H), 1.77 (m, 4H), 1.65 (m, 2H), 0.94-0.78 (m, 4H). |
| 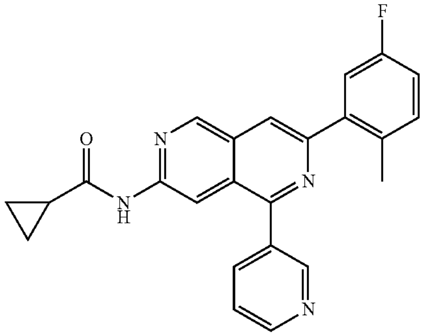 [SMILES: Cc1ccc(F)cc1-c1cc2cnc(NC(=O)C3CC3)cc2c(-c2cccnc2)n1] N-(7-(5-fluoro-2-methylphenyl)-5-(pyridin-3-yl)-2,6-naphthyridin-3-yl) cyclopropanecarboxamide | C-A | 4.277, 399.1, E | $^1$H NMR (400 MHz, DMSO) δ 11.20 (s, 1H), 9.41 (s, 1H), 8.97 (s, 1H), 8.76 (m, 1H), 8.73 (s, 1H), 8.24 (s, 1H), 8.20 (m, 1H), 7.65 (dd, J = 7.9, 4.9 Hz, 1H), 7.46 (dd, J = 9.8, 2.7 Hz, 1H), 7.43-7.35 (m, 1H), 7.25-7.17 (m, 1H), 2.43 (s, 3H), 2.10-2.03 (m, 1H), 0.83 (m, 4H). |
| 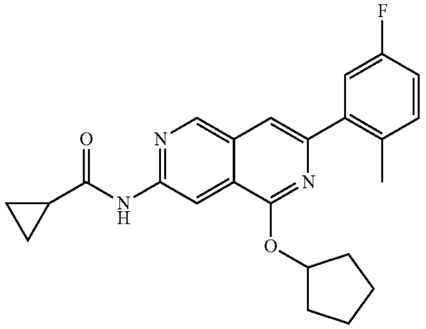 [SMILES: Cc1ccc(F)cc1-c1cc2cnc(NC(=O)C3CC3)cc2c(OC2CCCC2)n1] N-(5-(cyclopentyloxy)-7-(5-fluoro-2-methylphenyl)-2,6-naphthyridin-3-yl) cyclopropanecarboxamide | C-C | 6.877, 406.1, E | $^1$H NMR (400 MHz, DMSO) δ 11.10 (s, 1H), 9.17 (s, 1H), 8.67 (s, 1H), 7.64 (s, 1H), 7.43-7.29 (m, 2H), 7.23-7.11 (m, 1H), 5.62 (m, 1H), 2.42 (s, 3H), 2.12-1.95 (m, 3H), 1.92-1.72 (m, 4H), 1.65 (m, 2H), 0.96-0.75 (m, 4H). |

TABLE 4-continued

| Structure/Name | Syn. Meth. | LCMS $R_T$ (min), M + H⁺, LCMS Method | ¹H NMR (ppm) |
|---|---|---|---|
| 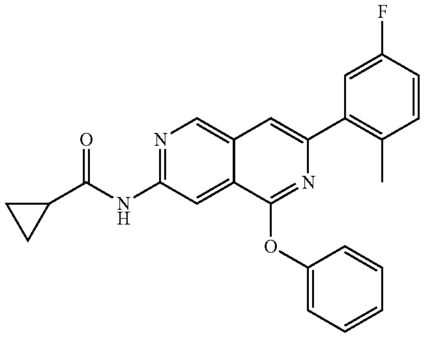 [SMILES: Cc1ccc(F)cc1-c1cc2cnc(NC(=O)C3CC3)cc2c(Oc2ccccc2)n1] N-(7-(5-fluoro-2-methylphenyl)-5-phenoxy-2,6-naphthyridin-3-yl)cyclopropanecarboxamide | C-F | 6.284, 414.1, E | $^1H$ NMR (400 MHz, DMSO) δ 11.23 (s, 1H), 9.28 (s, 1H), 8.89 (s, 1H), 7.84 (s, 1H), 7.47 (m, 2H), 7.37-7.18 (m, 5H), 7.13-7.06 (m, 1H), 2.15 (s, 3H), 2.10 (m, 1H), 0.87 (m, 4H). |
| 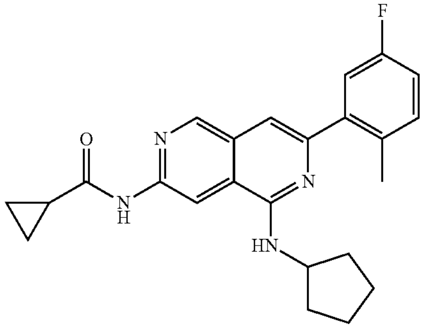 [SMILES: Cc1ccc(F)cc1-c1cc2cnc(NC(=O)C3CC3)cc2c(NC2CCCC2)n1] N-(5-(cyclopentylamino)-7-(5-fluoro-2-methylphenyl)-2,6-naphthyridin-3-yl) cyclopropanecarboxamide | C-D | 4.600, 405.2, E | $^1H$ NMR (400 MHz, DMSO) δ 10.91 (s, 1H), 8.97 (s, 1H), 8.62 (s, 1H), 7.40 (d, J = 6.7 Hz, 1H), 7.31 (m, 2H), 7.13 (s, 1H), 7.11 (mz, 1H), 4.48 (m, 1H), 2.40 (s, 3H), 2.05 (m, 1H), 1.99 (m, 2H), 1.73 (m, 2H), 1.65 (m, 2H), 1.55 (m, 2H). 0.86 (m, 4H). |
| 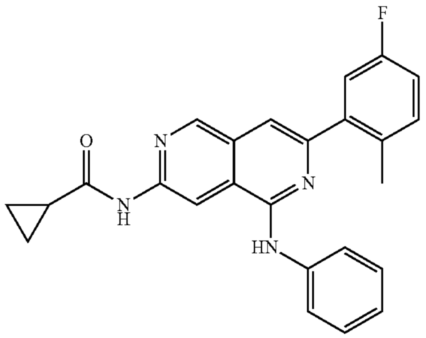 N-(7-(5-fluoro-2-methylphenyl)-5-(phenylamino)-2,6-naphthyridin-3-yl) cyclopropanecarboxamide | C-B | 5.431, 413.1, E | $^1H$ NMR (400 MHz, DMSO) δ 11.04 (s, 1H), 9.45 (s, 1H), 9.11 (s, 1H), 8.88 (s, 1H), 7.78 (d, J = 8.2 Hz, 2H), 7.45 (s, 1H), 7.31 (m, 4H), 7.13 (m, 1H), 6.99 (t, J = 7.3 Hz, 1H), 2.36 (s, 3H), 2.09 (m, 1H), 0.88 (m, 4H). |

TABLE 4-continued

| Structure/Name | Syn. Meth. | LCMS $R_T$ (min), M + H⁺, LCMS Method | ¹H NMR (ppm) |
|---|---|---|---|
| 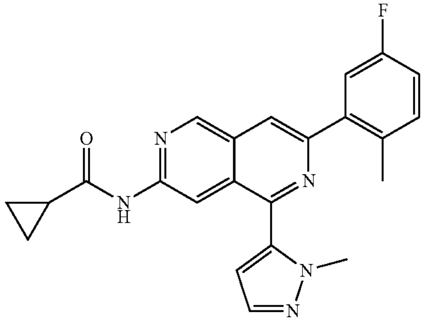 [SMILES: Cc1ccc(F)cc1-c1cc2cnc(NC(=O)C3CC3)cc2c(-c2ccnn2C)n1] N-(7-(5-fluoro-2-methylphenyl)-5-(1-methyl-1H-pyrazol-5-yl)-2,6-naphthyridin-3-yl) cyclopropanecarboxamide | C-A | 5.203, 402.1, E | ¹H NMR (400 MHz, DMSO) δ 11.20 (s, 1H), 9.40 (s, 1H), 8.79 (s, 1H), 8.22 (s, 1H), 7.67 (s, 1H), 7.41 (m, 2H), 7.22 (m, 1H), 6.75 (s, 1H), 3.94 (s, 3H), 2.40 (s, 3H), 2.07 (m, 1H), 0.84 (m, 4H). |
| 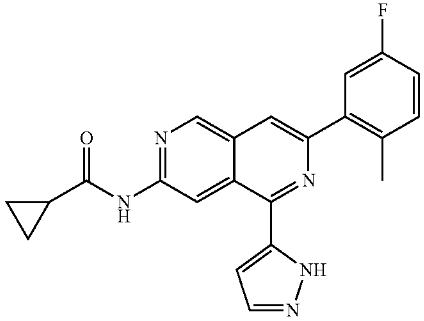 [SMILES: Cc1ccc(F)cc1-c1cc2cnc(NC(=O)C3CC3)cc2c(-c2ccn[nH]2)n1] N-(7-(5-fluoro-2-methylphenyl)-5-(1H-pyrazol-5-yl)-2,6-naphthyridin-3-yl) cyclopropanecarboxamide | C-A | 4.964, 388.1, E | ¹H NMR (400 MHz, DMSO) δ 13.37 (s, 1H), 11.02 (s, 1H), 9.96 (s, 1H), 9.30 (s, 1H), 8.08 (s, 1H), 7.90 (s, 1H), 7.50-7.33 (m, 2H), 7.20 (t, J = 8.3 Hz, 1H), 6.98 (s, 1H), 2.44 (s, 3H), 2.10 (m, 1H), 0.87 (s, 4H). |
| 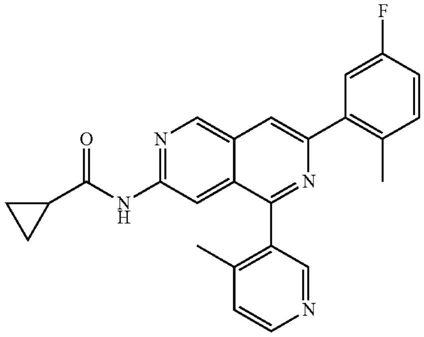 [SMILES: Cc1ccc(F)cc1-c1cc2cnc(NC(=O)C3CC3)cc2c(-c2cnccc2C)n1] N-(7-(5-fluoro-2-methylphenyl)-5-(4-methylpyridin-3-yl)-2,6-naphthyridin-3-yl) cyclopropanecarboxamide | C-A | 4.083, 413.1, E | ¹H NMR (400 MHz, DMSO) δ 11.15 (s, 1H), 9.42 (s, 1H), 8.61 (d, J = 4.3 Hz, 1H), 8.53 (s, 1H), 8.24 (s, 1H), 8.20 (s, 1H), 7.49 (s, 1H), 7.41 (m, 2H), 7.20 (t, J = 8.3 Hz, 1H), 2.39 (s, 3H), 2.13 (s, 3H), 2.03 (m, 1H), 0.80 (m, 4H). |

TABLE 4-continued

| Structure/Name | Syn. Meth. | LCMS $R_T$ (min), M + H$^+$, LCMS Method | $^1$H NMR (ppm) |
|---|---|---|---|
| 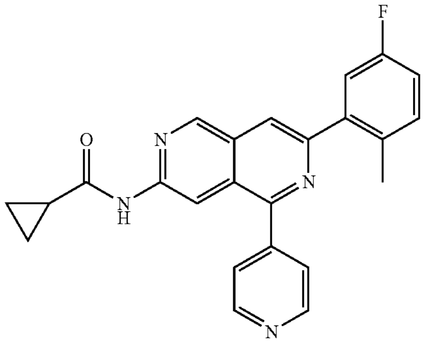 [SMILES: Cc1ccc(F)cc1-c1cc2cnc(NC(=O)C3CC3)cc2c(-c2ccncc2)n1] N-(7-(5-fluoro-2-methylphenyl)-5-(pyridin-4-yl)-2,6-naphthyridin-3-yl)cyclopropanecarboxamide | C-A | 4.160, 399.1, E | $^1$H NMR (400 MHz, DMSO) δ 11.19 (s, 1H), 9.42 (s, 1H), 8.82 (s, 2H), 8.72 (s, 1H), 8.26 (s, 1H), 7.77 (s, 2H), 7.48-7.36 (m, 2H), 7.21 (t, J = 8.1 Hz, 1H), 2.42 (s, 3H), 2.07 (m, 1H), 0.84 (m, 4H). |
| 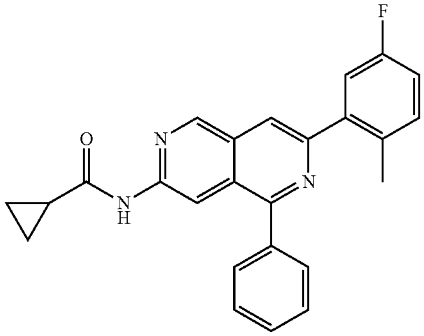 N-(7-(5-fluoro-2-methylphenyl)-5-phenyl-2,6-naphthyridin-3-yl)cyclopropanecarboxamide | C-A | 6.002, 398.1, E | $^1$H NMR (400 MHz, DMSO) δ 11.12 (s, 1H), 9.38 (s, 1H), 8.76 (s, 1H), 8.16 (s, 1H), 7.77 (m, 2H), 7.59 (m, 3H), 7.41 (m, 2H), 7.20 (t, J = 8.4 Hz, 1H), 2.43 (s, 3H), 2.06 (m, 1H), 0.83 (m, 4H). |
| 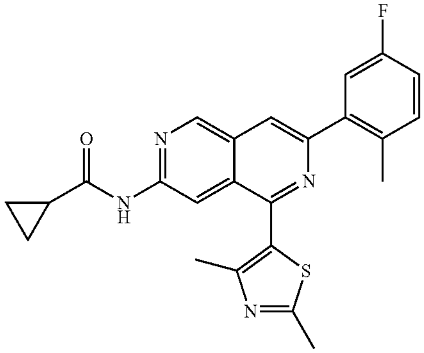 [SMILES: Cc1nc(C)c(-c2nc(-c3cc(F)ccc3C)cc3cnc(NC(=O)C4CC4)cc23)s1] N-(5-(2,4-dimethylthiazol-5-yl)-7-(5-fluoro-2-methylphenyl)-2,6-naphthyridin-3-yl) cyclopropanecarboxamide | C-A | 5.268, 433.1, E | $^1$H NMR (400 MHz, DMSO) δ 11.20 (s, 1H), 9.40 (s, 1H), 8.54 (s, 1H), 8.20 (s, 1H), 7.40 (m, 2H), 7.20 (t, J = 8.3 Hz, 1H), 2.72 (s, 3H), 2.39 (s, 3H), 2.26 (s, 3H), 2.08 (m, 1H), 0.85 (m, 4H). |

TABLE 4-continued

| Structure/Name | Syn. Meth. | LCMS $R_T$ (min), M + H$^+$, LCMS Method | $^1$H NMR (ppm) |
|---|---|---|---|
| 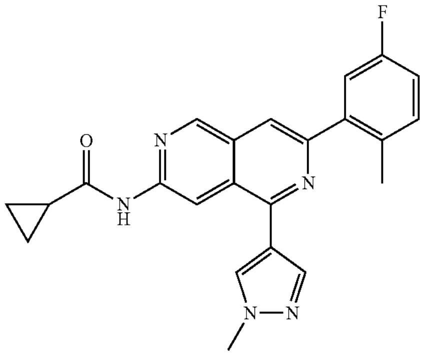 [SMILES: Cc1ccc(F)cc1-c1cc2cnc(NC(=O)C3CC3)cc2c(-c2cnn(C)c2)n1] N-(7-(5-fluoro-2-methylphenyl)-5-(1-methyl-1H-pyrazol-4-yl)-2,6-naphthyridin-3-yl) cyclopropanecarboxamide | C-A | 5.039, 402.1, E | $^1$H NMR (400 MHz, DMSO) δ 11.17 (s, 1H), 9.31 (s, 1H), 9.05 (s, 1H), 8.36 (s, 1H), 8.07 (s, 1H), 8.00 (s, 1H), 7.41 (m, 2H), 7.19 (t, J = 8.2 Hz, 1H), 3.98 (s, 3H), 2.41 (s, 3H), 2.11 (m, 1H), 0.94-0.81 (m, 4H). |
| 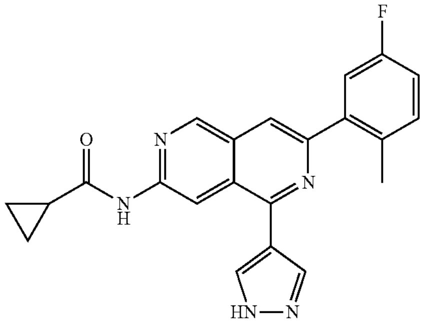 [SMILES: Cc1ccc(F)cc1-c1cc2cnc(NC(=O)C3CC3)cc2c(-c2cn[nH]c2)n1] N-(7-(5-fluoro-2-methylphenyl)-5-(1H-pyrazol-4-yl)-2,6-naphthyridin-3-yl) cyclopropanecarboxamide | C-A | 4.676, 388.1, E | $^1$H NMR (400 MHz, DMSO) δ 13.32 (s, 1H), 11.18 (s, 1H), 9.31 (s, 1H), 9.07 (s, 1H), 8.38 (s, 1H), 8.13 (s, 1H), 8.00 (s, 1H), 7.40 (m, 2H), 7.19 (t, J = 8.4 Hz, 1H), 2.42 (s, 3H), 2.10 (m, 1H), 0.96-0.79 (m, 4H). |
| 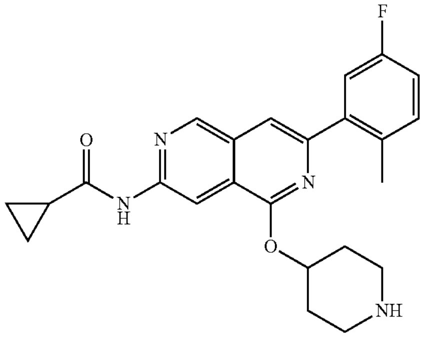 [SMILES: Cc1ccc(F)cc1-c1cc2cnc(NC(=O)C3CC3)cc2c(OC2CCNCC2)n1] N-(7-(5-fluoro-2-methylphenyl)-5-(piperidin-4-yloxy)-2,6-naphthyridin-3-yl) cyclopropanecarboxamide | C-E | 4.258, 421.2, E | $^1$H NMR (400 MHz, DMSO) δ 11.11 (s, 1H), 9.18 (s, 1H), 8.73 (s, 1H), 7.67 (s, 1H), 7.40-7.29 (m, 2H), 7.17 (td, J = 8.5, 2.7 Hz, 1H), 5.48-5.35 (m, 1H), 3.13-3.04 (m, 2H), 2.83 (m, 2H), 2.40 (s, 3H), 2.08 (m, 3H), 1.79 (m, 2H), 0.91-0.81 (m, 4H). |

TABLE 4-continued

| Structure/Name | Syn. Meth. | LCMS $R_T$ (min), M + H$^+$, LCMS Method | $^1$H NMR (ppm) |
|---|---|---|---|
| 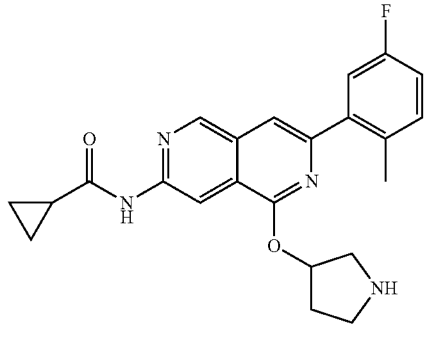 [SMILES: Cc1ccc(F)cc1-c1cc2cnc(NC(=O)C3CC3)cc2c(OC2CCNC2)n1] N-(7-(5-fluoro-2-methylphenyl)-5-(pyrrolidin-3-yloxy)-2,6-naphthyridin-3-yl) cyclopropanecarboxamide | C-E | 3.60, 407.1, Waters, Short | $^1$H NMR (400 MHz, DMSO) δ 11.09 (s, 1H), 9.18 (s, 1H), 8.68 (s, 1H), 7.65 (s, 1H), 7.37 (m, 2H), 7.17 (td, J = 8.5, 2.8 Hz, 1H), 5.60 (m, 1H), 3.20 (m, 1H), 3.01-2.90 (m, 2H), 2.89-2.79 (m, 1H), 2.42 (s, 3H), 2.15-2.03 (m, 2H), 1.97-1.86 (m, 1H), 1.50 (m, 1H), 0.95-0.79 (m, 4H). |
| 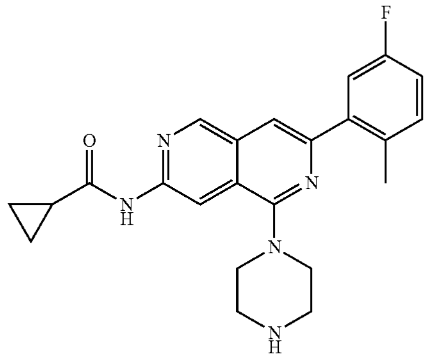 [SMILES: Cc1ccc(F)cc1-c1cc2cnc(NC(=O)C3CC3)cc2c(N2CCNCC2)n1] N-(7-(5-fluoro-2-methylphenyl)-5-(piperazin-1-yl)-2,6-naphthyridin-3-yl) cyclopropanecarboxamide | C-E | 4.063, 406.1, E | $^1$H NMR (400 MHz, DMSO) δ 11.05 (s, 1H), 9.15 (s, 1H), 8.67 (s, 1H), 7.62 (s, 1H), 7.39-7.28 (m, 2H), 7.14 (td, J = 8.5, 2.8 Hz, 1H), 3.30-3.30 (m, 4H), 2.94 (s, 4H), 2.39 (s, 3H), 2.07 (m, 1H), 0.91-0.81 (m, 4H). |

Example 134

N-(7-(2-chlorophenyl)-5-oxo-5,6-dihydro-2,6-naphthyridin-3-yl)cyclopropanecarboxamide

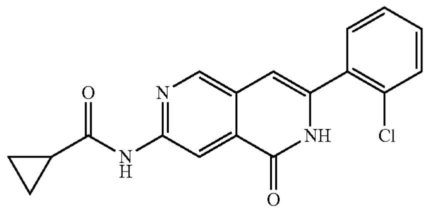 [SMILES: O=C(Nc1cc2c(=O)[nH]c(-c3ccccc3Cl)cc2cn1)C1CC1]

To a slurry of 3-(2-chlorophenyl)-7-(cyclopropanecarboxamido)-2,6-naphthyridine 2-oxide (50 mg, 0.1 mmol) in tetrahydrofuran (0.5 mL) at 0° C. was added trifluoroacetic anhydride (0.04 mL, 0.29 mmol) dropwise over 2 minutes. The mixture was allowed to warm to room temperature and stir for 2 hours. The reaction mixture was diluted with ethyl acetate (50 mL) and washed with saturated sodium bicarbonate solution (10 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as a yellow solid (10 mg, 20%). $^1$H NMR (400 MHz, DMSO) δ 11.10 (s, 1H), 10.33 (s, 1H), 9.51 (s, 1H), 8.86 (s, 1H), 8.54 (s, 1H), 7.62-7.52 (m, 1H), 7.53-7.38 (m, 3H), 2.08 (m, 1H), 0.88 (m, 4H). LCMS (Method E): $R_T$=3.759 min, M+H$^+$=340.0.

Example 135

N-(7-(2-chlorophenyl)-5-ethyl-2,6-naphthyridin-3-yl)cyclopropanecarboxamide

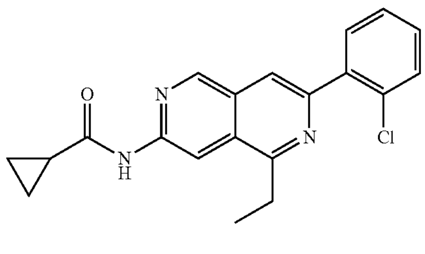 [SMILES: CCc1nc(-c2ccccc2Cl)cc2cnc(NC(=O)C3CC3)cc12]

Step 1: N-(7-(2-chlorophenyl)-5-ethynyl-2,6-naphthyridin-3-yl)cyclopropanecarboxamide

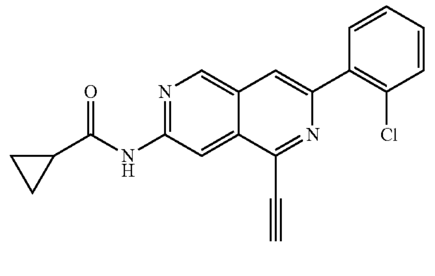 [SMILES: C#Cc1nc(-c2ccccc2Cl)cc2cnc(NC(=O)C3CC3)cc12]

A mixture of N-(5-chloro-7-(2-chlorophenyl)-2,6-naphthyridin-3-yl)cyclopropanecarboxamide (110 mg, 0.31 mmol), (trimethylsilyl)acetylene (45 mg, 0.46 mmol), N,N-diisopropylethylamine (0.1 mL, 0.61 mmol), copper(I) iodide (6 mg, 0.03 mmol), and bis(triphenylphosphine)palladium (II) chloride (15 mg, 0.02 mmol) in 1,4-dioxane (2 mL) was heated at 50° C. for 1 hour. The cooled reaction mixture was diluted with ethyl acetate (100 mL) and washed with water (100 mL). The organic layer was separated, dried over sodium sulfate, filtered, and evaporated in vacuo to afford a residue that was redissolved in methanol (4 mL) and treated with potassium carbonate (210 mg, 1.5 mmol). The reaction mixture was stirred at room temperature for 1 h, and then diluted with dichloromethane (100 mL) and washed with water (100 mL). The organic layer was separated, dried over sodium sulfate, filtered, and evaporated in vacuo to afford a residue that was purified by flash chromatography (silica, 12 g, ISCO, 0-50% ethyl acetate in heptane) to afford the title compound as a pale yellow solid (50 mg, 50%), which was used in the next step without further purification.

Step 2: N-(7-(2-chlorophenyl)-5-ethyl-2,6-naphthyridin-3-yl)cyclopropanecarboxamide

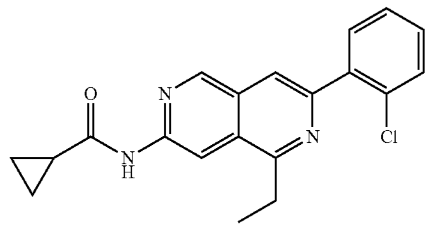 [SMILES: CCc1nc(-c2ccccc2Cl)cc2cnc(NC(=O)C3CC3)cc12]

N-(7-(2-chlorophenyl)-5-ethynyl-2,6-naphthyridin-3-yl) cyclopropanecarboxamide (40 mg, 0.1 mmol) was dissolved in ethanol (15 mL) and treated with platinum dioxide (3 mg, 0.01 mmol). The reaction flask was flushed with nitrogen and evacuated three times and then flushed with hydrogen gas, evacuated once, and then left under a balloon of hydrogen. The reaction mixture was stirred for 16 hours at room temperature and then filtered over a pad of Celite. The filtrate was evaporated in vacuo to afford a residue that was purified by reverse phase HPLC (5-85% acetonitrile in water with 0.1% ammonium hydroxide over 14 min) to afford the title compound as an off-white solid (20 mg, 50%). $^1$H NMR (400 MHz, DMSO) δ 11.16 (s, 1H), 9.31 (s, 1H), 8.78 (s, 1H), 8.08 (s, 1H), 7.77-7.69 (m, 1H), 7.61 (m, 1H), 7.54-7.42 (m, 2H), 3.24 (dd, J=15.2, 7.7 Hz, 2H), 2.15-2.07 (m, 1H), 1.38 (t, J=7.4 Hz, 3H), 0.95-0.80 (m, 4H). LCMS (Method E): $R_T$=5.052 min, M+H$^+$=352.1.

Example 136

N-(5-cyano-7-(5-fluoro-2-methylphenyl)-2,6-naphthyridin-3-yl)cyclopropanecarboxamide

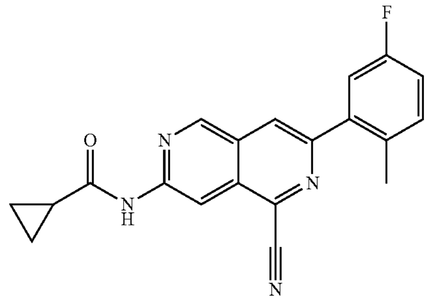 [SMILES: Cc1ccc(F)cc1-c1cc2cnc(NC(=O)C3CC3)cc2c(C#N)n1]

To a slurry of 3-(5-fluoro-2-methylphenyl)-7-(cyclopropanecarboxamido)-2,6-naphthyridine 2-oxide (50 mg, 0.1 mmol) in acetonitrile (0.4 mL) was added N,N-diisopropylethylamine (0.05 mL, 0.3 mmol), followed by trimethylsilyl cyanide (0.06 mL, 0.44 mmol). The mixture was heated at 100° C. for 2 hours. The cooled reaction mixture was diluted with ethyl acetate (50 mL) and washed with water (20 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as a white solid (10 mg, 20%). $^1$H NMR (400 MHz, DMSO) δ 11.47 (s, 1H), 9.52 (s, 1H), 8.84 (s, 1H), 8.56 (s, 1H), 7.48-7.35 (m, 2H), 7.26 (td, J=8.5, 2.8 Hz, 1H), 2.37 (s, 3H), 2.13 (m, 1H), 0.99-0.83 (m, 4H). LCMS (Method E): $R_T$=5.495 min, M+H$^+$=347.1.

Example 137

N-(7-(2-chlorophenyl)-8-hydroxy-2,6-naphthyridin-3-yl)cyclopropanecarboxamide

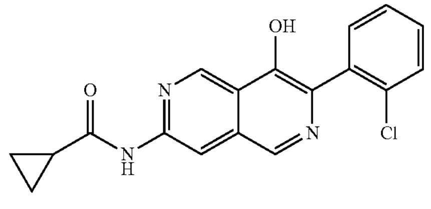 [SMILES: O=C(Nc1cc2cnc(-c3ccccc3Cl)c(O)c2cn1)C1CC1]

Step 1: 7-chloro-3-(2-chlorophenyl)-4-iodo-2,6-naphthyridine 2-oxide

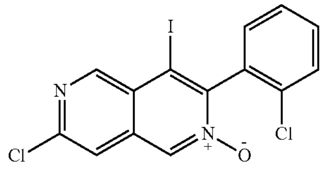

To a slurry of 2-chloro-5-((2-chlorophenyl)ethynyl)isonicotinaldehyde oxime (850 mg, 2.9 mmol) in acetonitrile (8 mL) was added iodine monochloride (1.4 g, 8.8 mmol). The reaction mixture instantly became homogeneous and was stirred at room temperature. After 15 minutes the reaction mixture was diluted with ethyl acetate (100 mL) and washed with water (100 mL). The organic layer was separated, dried over sodium sulfate, filtered, and evaporated in vacuo to afford an orange residue that was used in the next step without further purification (1.2 g, 98%).

Step 2: 7-chloro-3-(2-chlorophenyl)-4-iodo-2,6-naphthyridine

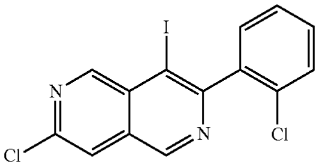 [SMILES: Clc1cc2cnc(-c3ccccc3Cl)c(I)c2cn1]

To a solution of 7-chloro-3-(2-chlorophenyl)-4-iodo-2,6-naphthyridine 2-oxide (870 mg, 2.1 mmol) in dichloromethane (13 mL) was added phosphorus trichloride (0.2 mL, 2.3 mmol). The reaction mixture was stirred at room temperature for 1 hour, and then diluted with dichloromethane (50 mL) and washed with saturated aqueous sodium bicarbonate solution (20 mL). The organic layer was separated, dried over sodium sulfate, filtered, and evaporated in vacuo to afford an orange residue that was purified by flash chromatography (silica, 40 g, ISCO, 0-30% ethyl acetate in heptane) to afford the title compound as an orange solid (400 mg, 50%). $^1H$ NMR (400 MHz, $CDCl_3$) δ 9.40 (s, 1H), 9.21 (s, 1H), 7.83 (s, 1H), 7.57-7.53 (m, 1H), 7.49-7.40 (m, 2H), 7.40-7.35 (m, 1H).

Step 3: 7-chloro-3-(2-chlorophenyl)-4-(4,4,5,5-tetramethyl-1,3,2-dioxaborolan-2-yl)-2,6-naphthyridine

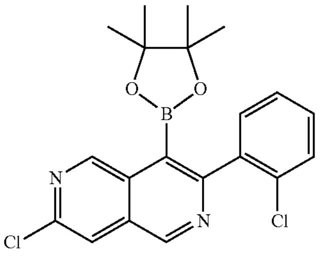 [SMILES: CC1(C)OB(c2c(-c3ccccc3Cl)ncc3cc(Cl)ncc23)OC1(C)C]

A mixture of 7-chloro-3-(2-chlorophenyl)-4-iodo-2,6-naphthyridine (130 mg, 0.32 mmol), bispinacol ester boronate (110 mg, 0.42 mmol), bis(di-tert-butyl(4-dimethylaminophenyl)phosphine)dichloropalladium(II) (23 mg, 0.032 mmol), and potassium acetate (64 mg, 0.65 mmol) in 1,4-dioxane was heated at 100° C. for 9 hours. The cooled reaction mixture was diluted with ethyl acetate (50 mL) and washed with water (50 mL). The organic layer was separated, dried over sodium sulfate, filtered, and evaporated in vacuo to afford an orange residue that was purified by flash chromatography (silica, 4 g, ISCO, 0-50% ethyl acetate in heptane) to afford the title compound as an orange solid (60 mg, 50%), which was used in the next step without further purification.

Step 4:
7-chloro-3-(2-chlorophenyl)-2,6-naphthyridin-4-ol

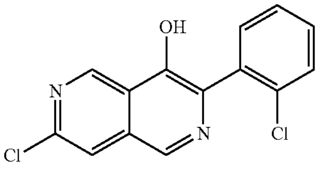 [SMILES: Oc1c(-c2ccccc2Cl)ncc2cc(Cl)ncc12]

A mixture of 7-chloro-3-(2-chlorophenyl)-4-(4,4,5,5-tetramethyl-1,3,2-dioxaborolan-2-yl)-2,6-naphthyridine (60 mg, 0.1 mmol) and Oxone® (370 mg, 0.6 mmol) in wet methanol (0.6 mL) and dichloromethane (0.2 mL) was stirred at 35° C. for 3 hours. The cooled reaction mixture was diluted with dichloromethane (50 mL) and washed with 1.0M citric acid in water (20 mL). The organic layer was separated, dried over sodium sulfate, filtered, and evaporated in vacuo to afford an orange/red residue that was used in the next step without further purification (50 mg, 100%).

Step 5: N-(7-(2-chlorophenyl)-8-hydroxy-2,6-naphthyridin-3-yl)cyclopropanecarboxamide

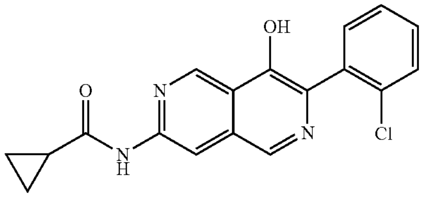 [SMILES: O=C(Nc1cc2cnc(-c3ccccc3Cl)c(O)c2cn1)C1CC1]

A mixture of 7-chloro-3-(2-chlorophenyl)-2,6-naphthyridin-4-ol (75 mg, 0.26 mmol), cyclopropanecarboxamide (66 mg, 0.77 mmol), chloro[2-(dicyclohexylphosphino)-3-,6-dimethoxy-2,4'-6'-tri-i-pr-1,1'-biphenyl)][2-(2-aminoethyl)Ph]Pd(II) (40 mg, 0.05 mmol), (dicyclohexylphosphino)-3-,6-dimethoxy-2,4'-6'-tri-i-pr-1,1'-biphenyl (28 mg, 0.05 mmol), and cesium carbonate (250 mg, 0.77 mmol) in tetrahydrofuran (2 mL) was heated at 90° C. for 1 hour. The cooled reaction mixture was diluted with ethyl acetate (50 mL) and washed with 1.0M citric acid in water (20 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as an off-white solid (35 mg, 40%). $^1H$ NMR (400 MHz, DMSO) δ 11.09 (s, 1H), 9.51 (d, J=6.6 Hz, 1H), 8.82 (s, 1H), 8.53 (s, 1H), 7.55 (m, 1H), 7.46 (m, 4H), 2.15-2.04 (m, 1H), 0.88 (m, 4H). LCMS (Method E): $R_T$=3.746 min, $M+H^+$=340.0.

Example 138

7-(cyclopropanecarboxamido)-3-(5-fluoro-2-methylphenyl)-1-methyl-2,6-naphthyridine 2-oxide

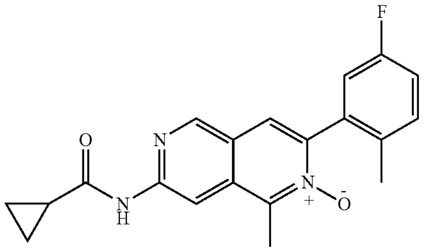

Step 1: 1-(2-chloro-5-((5-fluoro-2-methylphenyl)ethynyl)pyridin-4-yl)ethanone

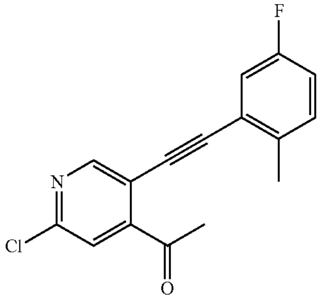 [SMILES: CC(=O)c1cc(Cl)ncc1C#Cc1cc(F)ccc1C]

To a solution of 2-chloro-5-((5-fluoro-2-methylphenyl)ethynyl)isonicotinaldehyde (705 mg, 2.6 mmol) in tetrahydrofuran (11 mL) cooled at −15° C. was added a solution of 3.0M methylmagnesium chloride in tetrahydrofuran (1 mL, 3.1 mmol) dropwise over 1 minute. The reaction mixture was stirred at this temperature for 15 minutes and then quenched with a few drops of saturated aqueous ammonium chloride solution, tetrahydrofuran was evaporated in vacuo, and the resulting residue was redissolved in dichloromethane (50 mL) and washed with water (50 mL). The organic layer was separated, dried over sodium sulfate, filtered, and evaporated in vacuo to afford a colorless oil that was redissolved in dichloromethane (10 mL) and treated with Dess-Martin periodinane (1.4 g, 3.4 mmol). The reaction mixture was stirred at room temperature for 1 hour, and then diluted with dichloromethane (100 mL) and washed with saturated aqueous sodium bicarbonate solution (50 mL). The organic layer was separated, dried over sodium sulfate, filtered, and evaporated in vacuo to afford a residue that was purified by flash chromatography (silica, 40 g, ISCO, 0-50% ethyl acetate in heptane) to afford the title compound as a pale yellow solid (700 mg, 90%), which was used in the next step without further purification.

Step 2: 1-(2-chloro-5-((5-fluoro-2-methylphenyl)ethynyl)pyridin-4-yl)ethanone oxime

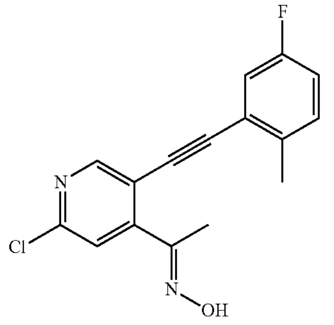 [SMILES: C/C(=N\O)c1cc(Cl)ncc1C#Cc1cc(F)ccc1C]

A mixture of 1-(2-chloro-5-((5-fluoro-2-methylphenyl)ethynyl)pyridin-4-yl)ethanone (700 mg, 2.0 mmol), sodium acetate (320 mg, 3.9 mmol), and hyroxylamine hydrochloride (254 mg, 3.65 mmol) in ethanol (11 mL) and dichloroethane (1.6 mL) was heated at 70° C. for 15 minutes. The cooled reaction mixture was evaporated in vacuo to afford a residue that was redissolved in ethyl acetate (150 mL) and washed with water (100 mL). The organic layer was separated, dried over sodium sulfate, filtered, and evaporated in vacuo to afford a white solid that was used in the next step without further purification.

Step 3: 7-chloro-3-(5-fluoro-2-methylphenyl)-1-methyl-2,6-naphthyridine 2-oxide

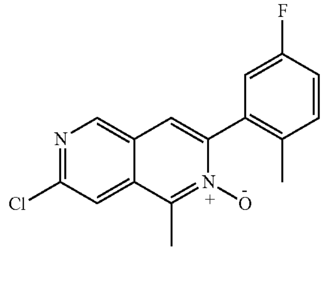

A mixture of 1-(2-chloro-5-((5-fluoro-2-methylphenyl)ethynyl)pyridin-4-yl)ethanone oxime (700 mg, 2.0 mmol) and silver nitrate (~10 wt. % on silica gel, +230 mesh, 825 mg, 0.5 mmol) in chloroform (12 mL) was heated at 60° C. for 1 hour. The cooled reaction mixture was treated with silica gel (2 g), concentrated in vacuo, and purified by flash chromatography (silica, 12 g, ISCO, 0-90% ethyl acetate in heptane) to afford the title compound as pale yellow solid (350 mg, 50% over two steps), which was used in the next step without further purification.

Step 4: 7-(cyclopropanecarboxamido)-3-(5-fluoro-2-methylphenyl)-1-methyl-2,6-naphthyridine 2-oxide

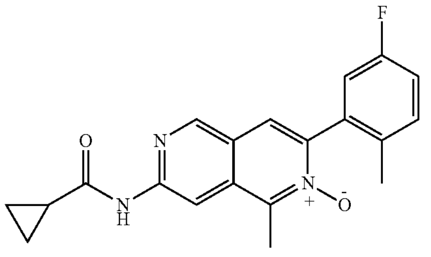

A mixture of 7-chloro-3-(5-fluoro-2-methylphenyl)-1-methyl-2,6-naphthyridine 2-oxide (350 mg, 1.2 mmol), cyclopropanecarboxamide (295 mg, 3.5 mmol), Chloro[2-(dicyclohexylphosphino)-3-,6-dimethoxy-2,4'-6'-tri-i-pr-1,1'-biphenyl)][2-(2-aminoethyl) Ph]Pd(II) (46 mg, 0.06 mmol), (dicyclohexylphosphino)-3-,6-dimethoxy-2,4'-6'-tri-i-pr-1,1'-biphenyl (120 mg, 0.2 mmol), and cesium carbonate (750 mg, 2.3 mmol) in 1,4-dioxane (5 mL) was heated at 90° C. for 4 hours. The cooled reaction mixture was diluted with dichloromethane (200 mL) and methanol (100 mL), mixed with Celite, filtered, the solids washed with 15% methanol/dichloromethane (2×100 mL), and the filtrate was dried over sodium sulfate, filtered, and evaporated in vacuo to afford a residue that was purified by flash chromatography (silica, 40 g, ISCO, 0-10% methanol in dichloromethane) to afford the title compound as an off-white solid (400 mg, 100%). $^1$H NMR (400 MHz, DMSO) δ 11.16 (s, 1H), 9.11 (s, 1H), 8.56 (s, 1H), 8.02 (s, 1H), 7.41-7.31 (m, 1H), 7.22 (m, 2H), 2.66 (s, 3H), 2.10 (m, 1H), 2.08 (s, 3H), 0.94-0.81 (m, 4H). LCMS (Method D): $R_T$=11.358 min, M+H$^+$=352.1.

Example 139

3-(2-chlorophenyl)-7-(cyclopropanecarboxamido)-1-methyl-2,6-naphthyridine 2-oxide

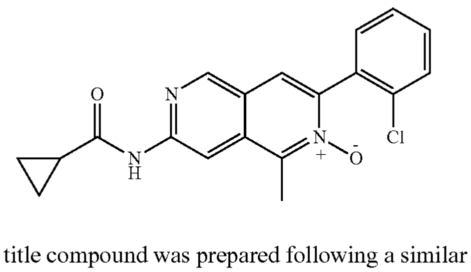

The title compound was prepared following a similar procedure to the previous example 138 using 2-chloro-5-((2-chlorophenyl)ethynyl)isonicotinaldehyde in step 1.

$^1$H NMR (400 MHz, DMSO) δ 11.16 (s, 1H), 9.12 (s, 1H), 8.55 (s, 1H), 8.06 (s, 1H), 7.61 (m, 1H), 7.56-7.42 (m, 3H), 2.65 (s, 3H), 2.10 (m, 1H), 0.94-0.80 (m, 4H).

LCMS (Method E): $R_T$=4.039 min, M+H$^+$=354.1.

Example 140

N-(7-(5-fluoro-2-methylphenyl)-5-(hydroxymethyl)-2,6-naphthyridin-3-yl)cyclopropanecarboxamide

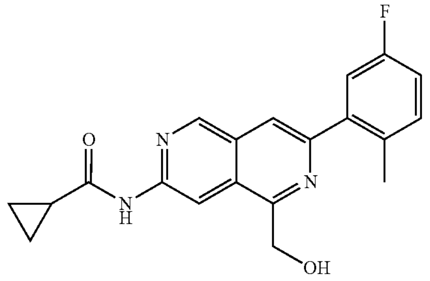

To a slurry of 7-(cyclopropanecarboxamido)-3-(5-fluoro-2-methylphenyl)-1-methyl-2,6-naphthyridine 2-oxide (100 mg, 0.3 mmol) in dichloromethane (3 mL) was added trifluoroacetic anhydride (0.08 mL, 0.57 mmol) and the reaction mixture was stirred at room temperature for 30 minutes. The mixture was diluted with dichloromethane (50 mL) and washed with saturated aqueous sodium bicarbonate solution (20 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as an off-white solid (50 mg, 50%). $^{1}$H NMR (400 MHz, DMSO) δ 11.13 (s, 1H), 9.31 (s, 1H), 8.89 (s, 1H), 8.06 (s, 1H), 7.43-7.33 (m, 2H), 7.19 (td, J=8.4, 2.6 Hz, 1H), 5.43 (t, J=5.4 Hz, 1H), 5.00 (d, J=5.4 Hz, 2H), 2.38 (s, 3H), 2.09 (m, 1H), 0.88 (m, 4H). LCMS (Method E): $R_T$=4.553 min, M+H$^+$=352.1.

Example 141

N-(5-((dimethylamino)methyl)-7-(5-fluoro-2-methylphenyl)-2,6-naphthyridin-3-yl)cyclopropanecarboxamide

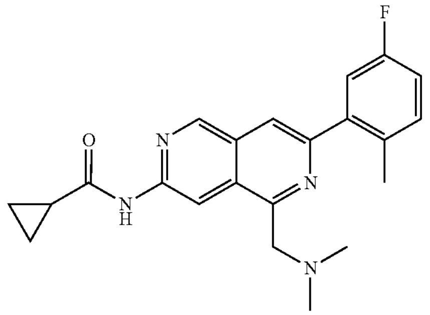 [SMILES: Cc1ccc(F)cc1-c1cc2cnc(NC(=O)C3CC3)cc2c(CN(C)C)n1]

Step 1: N-(7-(5-fluoro-2-methylphenyl)-5-formyl-2,6-naphthyridin-3-yl)cyclopropanecarboxamide

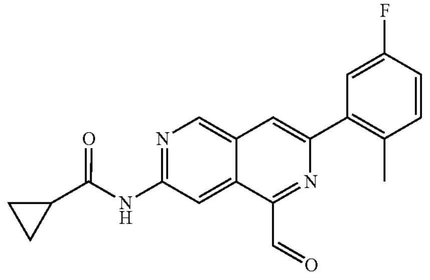 [SMILES: Cc1ccc(F)cc1-c1cc2cnc(NC(=O)C3CC3)cc2c(C=O)n1]

A mixture of N-(7-(5-fluoro-2-methylphenyl)-5-(hydroxymethyl)-2,6-naphthyridin-3-yl)cyclopropanecarboxamide (80 mg, 0.2 mmol) and Dess-Martin periodinane (120 mg, 0.27 mmol) and methylene chloride (1 mL) was stirred at room temperature for 1 hour. The reaction mixture was diluted with ethyl acetate (50 mL) and washed with saturated aqueous sodium bicarbonate solution (20 mL). The organic layer was separated, dried over sodium sulfate, filtered, and evaporated in vacuo to afford a residue that was purified by flash chromatography (silica, 4 g, ISCO, 0-50% ethyl acetate in heptane) to afford the title compound as a pale yellow solid (65 mg, 80%), which was used in the next step without further purification.

Step 2: N-(5-((dimethylamino)methyl)-7-(5-fluoro-2-methyl-phenyl)-2,6-naphthyridin-3-yl)cyclopropanecarboxamide

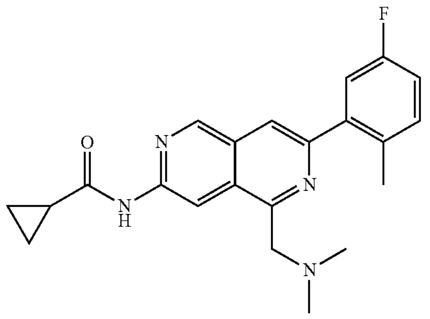 [SMILES: Cc1ccc(F)cc1-c1cc2cnc(NC(=O)C3CC3)cc2c(CN(C)C)n1]

To a slurry of N-(7-(5-fluoro-2-methylphenyl)-5-formyl-2,6-naphthyridin-3-yl)cyclopropanecarboxamide (30 mg, 0.08 mmol) in methylene chloride (0.5 mL) was added a 2.0M solution of dimethylamine in tetrahyrdofuran (0.052 mL, 0.1 mmol) and the reaction mixture was stirred at room temperature. After 1 hour, sodium triacetoxyborohydride (27 mg, 0.13 mmol) was added, and the reaction mixture was stirred for another 1 hour at room temperature. The reaction mixture was diluted with ethyl acetate (50 mL) and washed with water (50 mL). The organic layer was separated, dried over sodium sulfate, filtered, and evaporated in vacuo to afford a residue that was purified by reverse phase HPLC (5-85% acetonitrile in water with 0.1% ammonium hydroxide over 14 min) to afford the title compound as a pale yellow solid (22 mg, 70%). $^{1}$H NMR (400 MHz, DMSO) δ 11.07 (s, 1H), 9.28 (s, 1H), 8.96 (s, 1H), 8.03 (s, 1H), 7.41-7.28 (m, 2H), 7.18 (td, J=8.5, 2.8 Hz, 1H), 3.92 (s, 2H), 2.36 (s, 3H), 2.25 (s, 6H), 2.14-2.07 (m, 1H), 0.87 (m, 4H). LCMS (Method E): $R_T$=3.929 min, M+H$^+$=379.1.

Example 142

N-(7-(5-fluoro-2-methylphenyl)-5-((methylamino)methyl)-2,6-naphthyridin-3-yl)cyclopropanecarboxamide

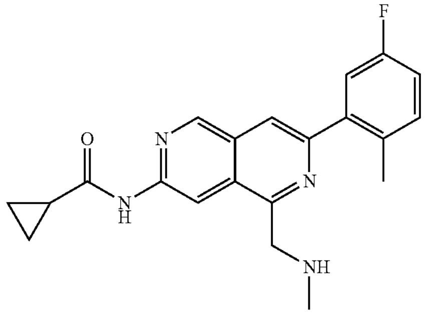 [SMILES: CNCc1nc(-c2cc(F)ccc2C)cc2cnc(NC(=O)C3CC3)cc12]

The title compound was prepared following a procedure similar to the previous example 141 using methylamine in step 2.

$^1$H NMR (400 MHz, DMSO) δ 11.15 (s, 1H), 9.30 (s, 1H), 8.80 (s, 1H), 8.04 (s, 1H), 7.42-7.34 (m, 2H), 7.19 (td, J=8.5, 2.8 Hz, 1H), 4.30 (s, 2H), 2.45 (s, 3H), 2.39 (s, 3H), 2.10 (m, 1H), 0.93-0.83 (m, 4H); amine NH peak not observed. LCMS (Method E): $R_T$=3.812 min, M+H$^+$=365.1.

Example 143

N-(7-(5-fluoro-2-methylphenyl)-5-(fluoromethyl)-2,6-naphthyridin-3-yl)cyclopropanecarboxamide

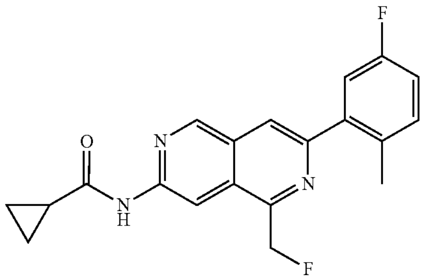

To a slurry of N-(7-(5-fluoro-2-methylphenyl)-5-(hydroxymethyl)-2,6-naphthyridin-3-yl)cyclopropanecarboxamide (60 mg, 0.1 mmol), in dichloromethane (0.7 mL) cooled at −15° C. was added bis(2-methoxyethyl)aminosulfur trifluoride (0.045 mL, 0.2 mmol). After 15 minutes at this temperature, the reaction mixture was diluted with dichlormethane (50 mL) and washed with water (20 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as an off-white solid (50 mg, 50%). $^1$H NMR (400 MHz, DMSO) δ 11.23 (s, 1H), 9.38 (s, 1H), 8.85 (s, 1H), 8.21 (s, 1H), 7.47-7.33 (m, 2H), 7.21 (m, 1H), 5.99 (s, 1H), 5.88 (s, 1H), 2.37 (s, 3H), 2.11 (m, 1H), 0.89 (m, 4H). LCMS (Method G): $R_T$=14.65 min, M+H$^+$=354.4.

Example 144

N-(7-(5-fluoro-2-methylphenyl)-5-(methylsulfonyl)-2,6-naphthyridin-3-yl)cyclopropanecarboxamide

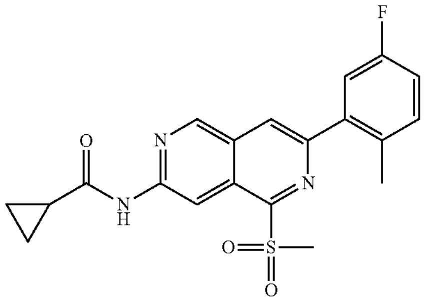 [SMILES: Cc1ccc(F)cc1-c1cc2cnc(NC(=O)C3CC3)cc2c(S(C)(=O)=O)n1]

A mixture of N-(5-chloro-7-(5-fluoro-2-methylphenyl)-2,6-naphthyridin-3-yl)cyclopropanecarboxamide (40 mg, 0.1 mmol), sodium methyl sulfide (12 mg, 0.17 mmol) and tetrahydrofuran (1 mL) was heated at 75° C. for 30 minutes. The mixture was diluted with dichloromethane (50 mL) and washed with water (20 mL). The organic layer was separated, dried over sodium sulfate, filtered, and evaporated in vacuo to afford a residue that was redissolved in methanol (1 mL) and treated with Oxone® (270 mg, 0.45 mmol). The reaction was mixed at room temperature for 2 hours and then diluted with dichloromethane (50 mL) and washed with water (20 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as an off-white solid (10 mg, 50%). $^1$H NMR (400 MHz, DMSO) δ 11.30 (s, 1H), 9.50 (s, 1H), 9.36 (s, 1H), 8.52 (s, 1H), 7.54-7.37 (m, 2H), 7.26 (m, 1H), 3.55 (s, 3H), 2.43 (s, 3H), 2.11 (m, 1H), 0.97-0.79 (m, 4H). LCMS (Method E): $R_T$=4.997 min, M+H$^+$=400.1.

Example 145

N-(7-(5-fluoro-2-methylphenyl)-5-(2-hydroxypropan-2-yl)-2,6-naphthyridin-3-yl)cyclopropanecarboxamide

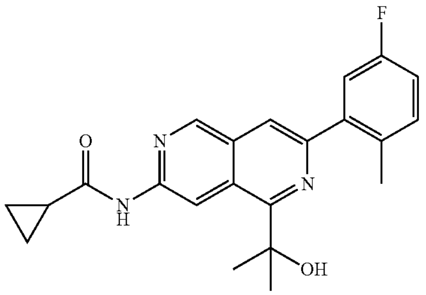 [SMILES: Cc1ccc(F)cc1-c1cc2cnc(NC(=O)C3CC3)cc2c(C(C)(C)O)n1]

Step 1: Methyl 7-(cyclopropanecarboxamido)-3-(5-fluoro-2-methylphenyl)-2,6-naphthyridine-1-carboxylate

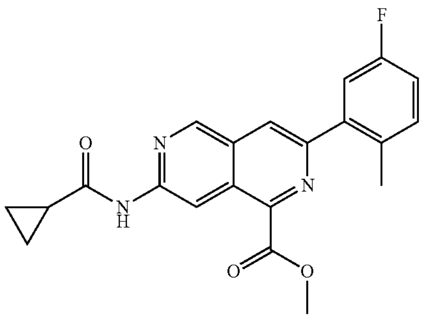 [SMILES: COC(=O)c1nc(-c2cc(F)ccc2C)cc2cnc(NC(=O)C3CC3)cc12]

A mixture of N-(5-chloro-7-(5-fluoro-2-methylphenyl)-2,6-naphthyridin-3-yl)cyclopropanecarboxamide (50 mg, 0.14 mmol), palladium acetate (2 mg, 0.007 mmol), 1,3-bis(dicyclohexylphosphino)propane bis(tetrafluoroborate) (9 mg, 0.014 mmol), potassium carbonate (29 mg, 0.21 mmol), methanol (0.1 mL), and N,N-dimethylformamide (1 mL) was purged with nitrogen and evacuated (3×), flushed with carbon monoxide and evacuated (2×), and then left under a carbon monoxide balloon and heated at 100° C. for 2 hours. The cooled reaction mixture was diluted with ethyl acetate (50 mL) and washed with water (100 mL). The organic layer was separated, dried over sodium sulfate, filtered, and evaporated in vacuo to afford a residue that was purified by flash chromatography (silica, 4 g, ISCO, 0-50% ethyl acetate in hep- 'tane) to afford the title compound as a pale yellow solid (50 mg, 90%), which was used in the next step without further purification.

Step 2: N-(7-(5-fluoro-2-methylphenyl)-5-(2-hydroxypropan-2-yl)-2,6-naphthyridin-3-yl)cyclopropanecarboxamide

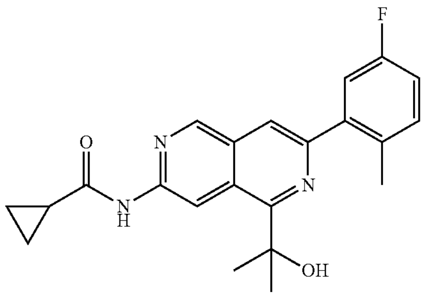 [SMILES: Cc1ccc(F)cc1-c1cc2cnc(NC(=O)C3CC3)cc2c(C(C)(C)O)n1]

A solution of methyl 7-(cyclopropanecarboxamido)-3-(5-fluoro-2-methylphenyl)-2,6-naphthyridine-1-carboxylate (50 mg, 0.1 mmol) in tetrahydrofuran (1 mL) cooled at −78° C. was treated with a 3.0M solution of methylmagnesium chloride in tetrahydrofuran (0.18 mL) dropwise over 5 minutes. The reaction mixture was stirred at this temperature for 15 minutes and then warmed to −15° C. for 30 minutes. The reaction mixture was quenched with a few drops of saturated aqueous ammonium chloride solution, diluted with ethyl acetate (50 mL) and washed with water (100 mL). The organic layer was separated, dried over sodium sulfate, filtered, and evaporated in vacuo to afford a residue that was purified by flash chromatography (silica, 4 g, ISCO, 0-50% ethyl acetate in heptane) and then repurified by reverse phase HPLC (5-85% acetonitrile in water with 0.1% formic acid over 14 min) to afford the title compound as an off-white solid (30 mg, 60%). $^1$H NMR (400 MHz, DMSO)δ 10.98 (s, 1H), 9.53 (s, 1H), 9.27 (s, 1H), 8.03 (s, 1H), 7.38 (m, 2H), 7.18 (t, J=8.3 Hz, 1H), 5.59 (s, 1H), 2.41 (s, 3H), 2.07 (m, 1H), 1.69 (s, 6H), 0.93-0.79 (m, 4H). LCMS (Method E): $R_T$=5.266 min, M+H$^+$=380.1.

Example 146

N-(7-(5-fluoro-2-methylphenyl)-5-(tetrahydrofuran-3-yl)-2,6-naphthyridin-3-yl)cyclopropanecarboxamide

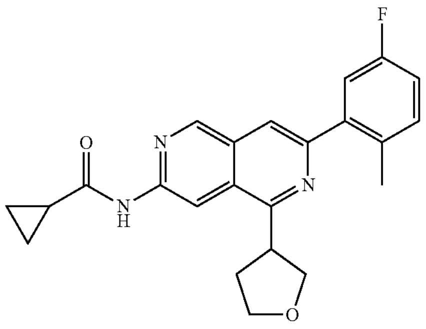 [SMILES: Cc1ccc(F)cc1-c1cc2cnc(NC(=O)C3CC3)cc2c(C2CCOC2)n1]

Step 1: N-(7-(5-fluoro-2-methylphenyl)-5-(5-hydroxytetrahydrofuran-3-yl)-2,6-naphthyridin-3-yl) cyclopropanecarboxamide

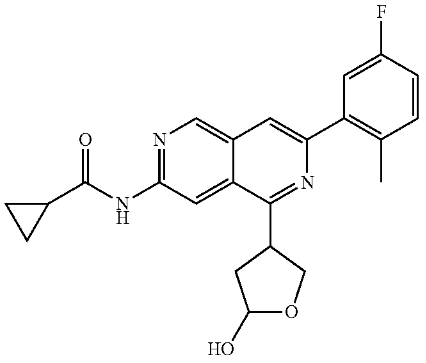 [SMILES: Cc1ccc(F)cc1-c1cc2cnc(NC(=O)C3CC3)cc2c(C2COC(O)C2)n1]

A mixture of N-(5-chloro-7-(2-chlorophenyl)-2,6-naphthyridin-3-yl)cyclopropanecarboxamide (50 mg, 0.13 mmol), (Z)-2-butene-1,4-diol (0.023 mL, 0.28 mmol), palladium acetate (3.2 mg, 0.014 mmol), tetra-N-butylammonium chloride (78 mg, 0.28 mmol), and sodium bicarbonate (24 mg, 0.28 mmol) in N,N-dimethylformamide (0.6 mL) was heated in a sealed vial at 110° C. for 4 hours. The cooled reaction mixture was diluted with ethyl acetate (50 mL) and washed with water (50 mL). The organic layer was separated, dried over sodium sulfate, filtered, and evaporated in vacuo to afford a residue that was purified by flash chromatography (silica, 4 g, ISCO, 0-60% ethyl acetate in heptane) to afford the title compound as a pale yellow oil, which was used in the next step without further purification (50 mg, 80%).

Step 2: N-(5-(1,4-dihydroxybutan-2-yl)-7-(5-fluoro-2-methylphenyl)-2,6-naphthyridin-3-yl)cyclopropanecarboxamide

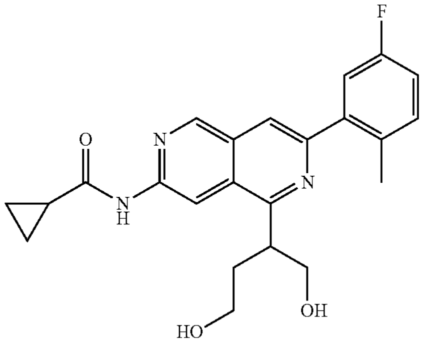 [SMILES: Cc1ccc(F)cc1-c1cc2cnc(NC(=O)C3CC3)cc2c(C(CO)CCO)n1]

To a solution of N-(7-(5-fluoro-2-methylphenyl)-5-(5-hydroxytetrahydrofuran-3-yl)-2,6-naphthyridin-3-yl)cyclopropanecarboxamide (45 mg, 0.11 mmol) in tetrahydrofuran (1 mL) cooled at 0° C. was added sodium tetrahydroborate (8.4 mg, 0.22 mmol), and the reaction mixture was stirred at this temperature for 1 hour. The reaction mixture was diluted with ethyl acetate (50 mL) and washed with water (100 mL). The organic layer was separated, dried over sodium sulfate, filtered, and evaporated in vacuo to afford a residue that was used in the next step without further purification.

Step 3: N-(7-(5-fluoro-2-methylphenyl)-5-(tetrahydrofuran-3-yl)-2,6-naphthyridin-3-yl)cyclopropanecarboxamide

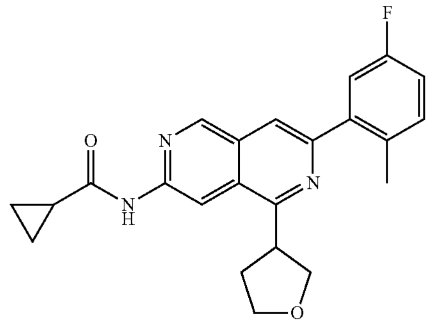 [SMILES: Cc1ccc(F)cc1-c1cc2cnc(NC(=O)C3CC3)cc2c(C2CCOC2)n1]

To a solution of N-(5-(1,4-dihydroxybutan-2-yl)-7-(5-fluoro-2-methylphenyl)-2,6-naphthyridin-3-yl)cyclopropanecarboxamide (45 mg, 0.1 mmol) in tetrahydrofuran (1 mL) was added triphenylphosphine (61 mg, 0.23 mmol) followed by diisopropyl azodicarboxylate (0.028 mL, 0.14 mmol), and the reaction mixture was stirred at room temperature for 1 hour. The reaction mixture was diluted with ethyl acetate (50 mL) and washed with water (50 mL). The organic layer was separated, dried over sodium sulfate, filtered, and evaporated in vacuo to afford a residue that was purified by flash chromatography (silica, 4 g, ISCO, 0-60% ethyl acetate in heptane) and then repurified by reverse phase HPLC (5-85% acetonitrile in water with 0.1% formic acid over 14 min) to afford the title compound as an off-white solid (10 mg, 20% over two steps). $^1$H NMR (400 MHz, DMSO) δ 11.18 (s, 1H), 9.30 (s, 1H), 8.83 (s, 1H), 8.03 (s, 1H), 7.41-7.31 (m, 2H), 7.19 (td, J=8.5, 2.8 Hz, 1H), 4.31-4.23 (m, 1H), 4.20 (t, J=7.7 Hz, 1H), 4.00-3.95 (m, 1H), 3.94-3.86 (m, 2H), 2.42-2.35 (m, 5H), 2.10 (m, 1H), 0.95-0.82 (m, 4H). LCMS (Method E): $R_T$=5.416 min, M+H$^+$=392.2.

Example 147

N-(2-(2-chlorophenyl)-1,7-naphthyridin-6-yl)cyclopropanecarboxamide

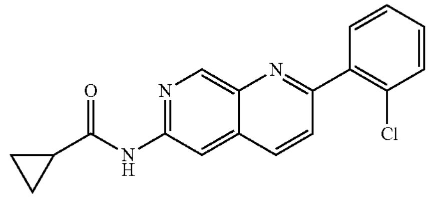 [SMILES: O=C(Nc1cc2ccc(-c3ccccc3Cl)nc2cn1)C1CC1]

Step 1: 6-chloro-2-(2-chlorophenyl)-1,7-naphthyridine

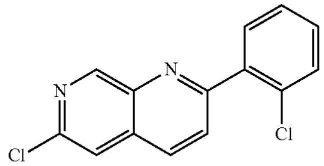 [SMILES: Clc1cc2ccc(-c3ccccc3Cl)nc2cn1]

To a slurry of potassium tert-butoxide (1.2 g, 9.7 mmol) in 1,4-dioxane (23 mL) was added chloroacetophenone (720 mg, 4.7 mmol). The reaction mixture was stirred for 10 minutes at room temperature, and then tert-butyl 6-chloro-4-formylpyridin-3-ylcarbamate (1 g, 3.9 mmol), which was prepared as described in WO 2010088177, was added in one portion as a solid. The reaction mixture was stirred for 30 minutes at room temperature and then a 5.0M solution of hydrogen chloride in water (7.8 mL) was added. The reaction mixture was heated at 100° C. for 1 hour. The cooled reaction mixture was diluted with ethyl acetate (50 mL) and washed with water (100 mL). The organic layer was separated, dried over sodium sulfate, filtered, and evaporated in vacuo to afford a residue that was purified by flash chromatography (silica, 40 g, ISCO, 0-50% ethyl acetate in heptane) to afford the title compound as a white solid (300 mg, 30%). $^1$H NMR (400 MHz, $CDCl_3$) δ 9.39 (s, 1H), 8.15 (d, J=8.7 Hz, 1H), 8.00 (d, J=8.7 Hz, 1H), 7.78 (s, 1H), 7.75-7.69 (m, 1H), 7.57-7.50 (m, 1H), 7.49-7.40 (m, 2H).

Step 2: N-(2-(2-chlorophenyl)-1,7-naphthyridin-6-yl)cyclopropanecarboxamide

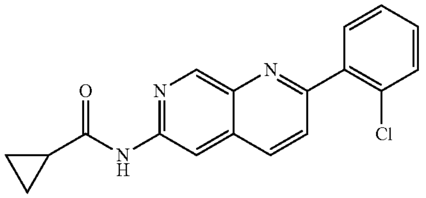 [SMILES: O=C(Nc1cc2ccc(-c3ccccc3Cl)nc2cn1)C1CC1]

A mixture of 6-chloro-2-(2-chlorophenyl)-1,7-naphthyridine (50 mg, 0.2 mmol), cyclopropanecarboxamide (27 mg, 0.32 mmol), 4,5-bis(diphenylphosphino)-9,9-dimethylxanthene (16 mg, 0.03 mmol), palladium acetate (4 mg, 0.02 mmol), and cesium carbonate (118 mg, 0.36 mmol) in 1,4-dioxane (1 mL) was heated at 90° C. for 3 hours. The cooled reaction mixture was diluted with ethyl acetate (50 mL) and washed with water (100 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as an off-white solid (15 mg, 20%). $^1$H NMR (400 MHz, $CDCl_3$) δ 9.28 (s, 1H), 8.58 (s, 1H), 8.28 (s, 1H), 8.16 (d, J=8.6 Hz, 1H), 7.90 (d, J=8.6 Hz, 1H), 7.71 (m, 1H), 7.53 (m, 1H), 7.42 (m, 2H), 1.64 (m, 1H), 1.21-1.14 (m, 2H), 1.01-0.91 (m, 2H). LCMS (Method E): $R_T$=4.970 min, M+H$^+$=324.1.

Example 148

(3-(2-(2-chlorophenyl)-1,7-naphthyridin-6-ylamino) phenyl)methanol

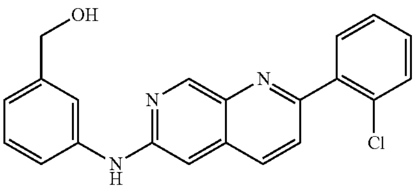 [SMILES: OCc1cccc(Nc2cc3ccc(-c4ccccc4Cl)nc3cn2)c1]

The title compound was prepared following a procedure similar to example 147 using (3-aminophenyl)methanol in step 2.

$^1$H NMR (400 MHz, DMSO) δ 9.24 (s, 1H), 9.13 (s, 1H), 8.24 (d, J=8.7 Hz, 1H), 7.79 (d, J=8.7 Hz, 1H), 7.74-7.65 (m, 1H), 7.62 (m, 1H), 7.51 (m, 4H), 7.27 (t, J=8.1 Hz, 1H), 7.22 (s, 1H), 6.91 (d, J=7.4 Hz, 1H), 5.17 (t, J=5.7 Hz, 1H), 4.50 (d, J=5.4 Hz, 2H). LCMS (Method E): $R_T$=4.702 min, $M+H^+$=362.0.

Example 149

N-(2-(2,6-dichlorophenyl)-1,7-naphthyridin-6-yl) cyclopropanecarboxamide

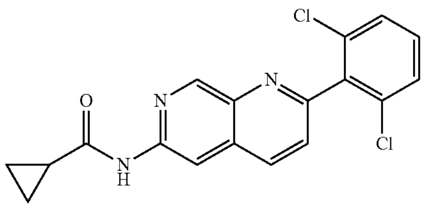

The title compound was prepared following a procedure similar to example 147 using 1-(2,6-dichlorophenyl)ethanone in step 1.

$^1$H NMR (400 MHz, DMSO) δ 11.12 (s, 1H), 9.25 (s, 1H), 8.59 (s, 1H), 8.50 (d, J=8.6 Hz, 1H), 7.74 (d, J=8.6 Hz, 1H), 7.67 (s, 1H), 7.65 (s, 1H), 7.56 (dd, J=8.9, 7.3 Hz, 1H), 2.11 (m, 1H), 0.87 (m, 4H). LCMS (Method E): $R_T$=5.087 min, $M+H^+$=358.0.

Example 150

2-(2-chlorophenyl)acetaldehyde

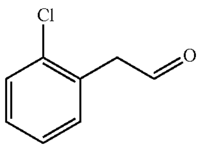

Step 1: 1-chloro-2-(2-methoxyvinyl)benzene

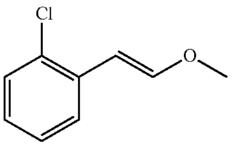

To a stirred solution of (methoxymethyl)triphenylphosphonium chloride (10 g, 28 mmol) in tetrahydrofuran (46 mL) cooled at −15° C. was added potassium tert-butoxide (3.7 g, 31 mmol) as a solid in one portion. After 5 minutes, 2-chlorobenzaldehyde (2.0 g, 14 mmol) was added, and the reaction mixture was warmed to room temperature and stirred for two hours. The reaction was quenched with saturated aqueous ammonium chloride solution (5 mL), tetrahydrofuran evaporated in vacuo, and the resulting residue was diluted with diethyl ether (100 mL) and water (100 mL). The organic layer was separated, dried over sodium sulfate, filtered, and evaporated in vacuo to afford a residue that was purified by flash chromatography (silica, 80 g, ISCO, 0-10% ethyl acetate in heptane) to afford the title compound as a colorless oil (2.4 g, 100%), which was used in the next step without further purification.

Step 2: 2-(2-chlorophenyl)acetaldehyde

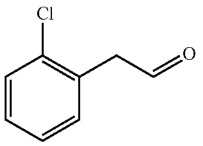

A mixture of 1-chloro-2-(2-methoxyvinyl)benzene (2.4 g, 14 mmol) in a solution of 4.0M hydrogen chloride in 1,4-dioxane (36 mL) was stirred for 30 minutes at room temperature. The reaction mixture was then diluted with diethyl ether (100 mL) and treated with saturated aqueous sodium bicarbonate solution (60 mL)—caution: gas evolution. The organic layer was separated, washed with a sodium phosphate buffer (1.0M solution in water, pH=8, 2×40 mL), dried over sodium sulfate, filtered, and evaporated in vacuo to afford the title compound as a colorless oil (2.0 g, 90%), which was used in the next step without further purification.

Example 151

2-(2-chloro-5-fluorophenyl)acetaldehyde

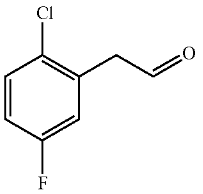 [SMILES: O=CCc1cc(F)ccc1Cl]

The title compound was prepared following a procedure similar to the previous example using 2-chloro-5-fluorobenzaldehyde in step 1.

Example 152

1-(5-chloro-2-fluorophenyl)propan-1-one

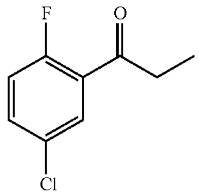

Step 1: 1-(5-chloro-2-fluorophenyl)propan-1-ol

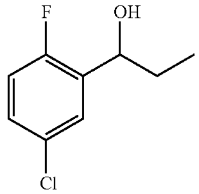

To a solution of 5-chloro-2-fluorobenzaldehyde (1 g, 6.3 mmol) in diethyl ether (20 mL) cooled at −78° C. was added a solution of 3.0M ethylmagnesium bromide in ether (4.2 mL, 13 mmol) dropwise over 5 minutes. The reaction mixture was warmed to 0° C. and after 30 minutes was quenched with a few drops of saturated aqueous ammonium chloride solution. The reaction mixture was diluted with ethyl acetate (50 mL) and washed with water (50 mL). The organic layer was separated, dried over sodium sulfate, filtered, and evaporated in vacuo to afford a residue that was purified by flash chromatography (silica, 4 g, ISCO, 0-30% ethyl acetate in heptane) to afford the title compound as a pale yellow oil (850 mg, 71%), which was used in the next step without further purification.

Step 2: 1-(5-chloro-2-fluorophenyl)propan-1-one

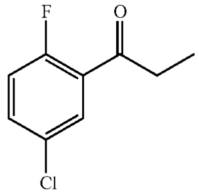

A mixture of 1-(5-chloro-2-fluorophenyl)propan-1-ol (850 mg, 4.5 mmol) and pyridinium chlorochromate (1.7 g, 7.9 mmol) in methylene chloride (30 mL) was stirred at room temperature for 3 hours. The reaction mixture was diluted with methylene chloride (20 mL), filtered over Celite, and evaporated in vacuo to afford a residue that was purified by flash chromatography (silica, 12 g, ISCO, 0-30% ethyl acetate in heptane) to afford the title compound as a pale yellow oil (550 mg, 65%). $^1$H NMR (400 MHz, $CDCl_3$) δ 7.38 (dd, J=8.8, 4.8 Hz, 1H), 7.16 (dd, J=8.3, 3.0 Hz, 1H), 7.09 (ddd, J=8.8, 7.7, 3.0 Hz, 1H), 2.95 (q, J=7.2 Hz, 2H), 1.21 (t, J=7.2 Hz, 3H).

Example 153

1-(2-chlorophenyl)butan-2-one

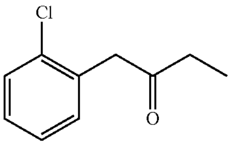

The title compound was prepared following a procedure similar to the previous example using 2-(2-chlorophenyl)acetaldehyde in step 1.

Example 154

6-chloro-2-(2-chloro-5-fluorophenyl)-3-methyl-1,7-naphthyridine

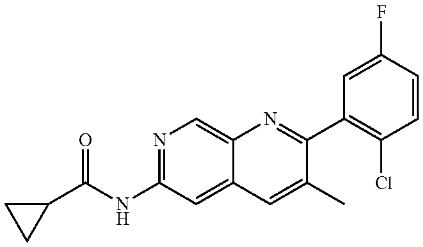 [SMILES: Cc1cc2cc(NC(=O)C3CC3)ncc2nc1-c1cc(F)ccc1Cl]

The title compound was prepared following a procedure similar to example 147 using 1-(5-chloro-2-fluorophenyl)propan-1-one in step 1.

$^1$H NMR (400 MHz, DMSO) δ 11.05 (s, 1H), 9.17 (s, 1H), 8.49 (s, 1H), 8.29 (s, 1H), 7.69 m, 1H), 7.43 (m, 2H), 2.25 (s, 3H), 2.10 (m, 1H), 0.87 (m, 4H). LCMS (Method E): $R_T$=5.110 min, M+H$^+$=356.0.

Example 155

N-(3-(2-chloro-5-fluorophenyl)-1,6-naphthyridin-7-yl)cyclopropanecarboxamide

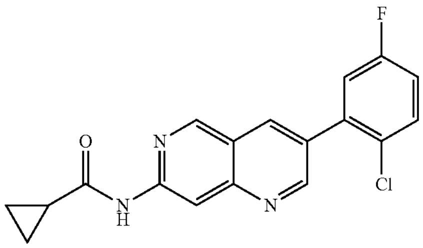

Step 1: 6-bromo-4-iodonicotinic acid

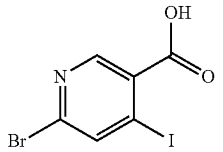 [SMILES: O=C(O)c1cnc(Br)cc1I]

n-Butyllithium (2.5M in hexanes, 297 mL, 0.743 mol) was added over 1 h to a cooled (−25° C.) solution of 2,2,6,6,-tetramethylpiperidine (131 mL, 0.77 mol) in tetrahydrofuran (1 L). The mixture was left to stir for 16 h at −25° C. then cooled to −55° C. before addition of solid 6-bromonicotinic acid (50.0 g, 0.25 mmol). The mixture was allowed to warm to −20° C. and stirred for 2 h. The reaction mixture was cooled to −70° C. then poured onto a pre-cooled (−70° C.) solution of iodine (188.5 g, 0.74 mol) in tetrahydrofuran (500 mL). The mixture was then poured into the original reaction vessel and the contents allowed to warm to ambient temperature and stirred for 1 hour. The solvent was evaporated and the resultant residue dissolved in water (500 mL) and washed with dichloromethane (3×300 mL). The aqueous phase was separated and the pH adjusted to 2 by the addition of concentrated hydrochloric acid. Aqueous sodium metabisulfite solution (20% w/w, 30 mL) was added and the solid which deposited was collected by filtration. The resultant solid was washed with water (75 mL) and pentane (75 mL) and dried at 75° C. under vacuum to furnish the title compound as a tan solid (53.1 g, 65%). $^1$H NMR (DMSO-$D_6$, 300 MHz) 8.62 (s, 1H); 8.35 (s, 1H). LCMS (Method B): $R_T$=2.16 min, M+H$^+$=328/330.

Step 2: methyl 6-bromo-4-iodonicotinate

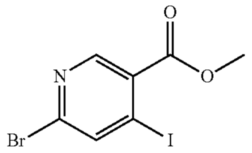

A mixture of 6-bromo-4-iodonicotinic acid (75 mg, 0.23 mmol), potassium carbonate (63 mg, 0.46 mmol), and methyl iodide (0.017 mL, 0.27 mmol) in N,N-dimethylformamide (0.5 mL) was heated at 60° C. for 30 minutes. The cooled reaction mixture was diluted with ethyl acetate (20 mL) and washed with water (15 mL). The organic layer was separated, dried over sodium sulfate, filtered, and evaporated in vacuo to afford a residue that was purified by flash chromatography (silica, 4 g, ISCO, 0-50% ethyl acetate in heptane) to afford the title compound as a white solid (65 mg, 83%), which was used in the next step without further purification.

Step 3: (6-bromo-4-iodopyridin-3-yl)methanol

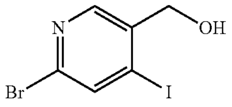

To a solution of methyl 6-bromo-4-iodonicotinate (500 mg, 1.0 mmol) in methylene chloride (6 mL) cooled at 0° C. was added a 1.0M solution of diisobutylaluminum hydride in tetrahydrofuran (5.85 mL) dropwise over 5 minutes. The reaction mixture was stirred at this temperature for 30 minutes and then quenched by dropwise addition of a 1.0M solution of citric acid in water (1 mL). The reaction mixture was diluted with dichloromethane (20 mL) and washed with water (15 mL). The organic layer was separated, dried over sodium sulfate, filtered, and evaporated in vacuo to afford a residue that was purified by flash chromatography (silica, 12 g, ISCO, 0-50% ethyl acetate in heptane) to afford the title compound as a white solid (430 mg, 90%), which was used in the next step without further purification.

Step 4: 6-bromo-4-iodonicotinaldehyde

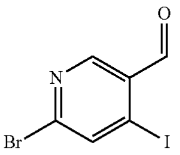

A mixture of (6-bromo-4-iodopyridin-3-yl)methanol (300 mg, 1.0 mmol) and pyridinium dichromate (720 mg, 1.9 mmol) in methylene chloride (4 mL) was stirred at room temperature for 4 hours. The reaction mixture was diluted with methylene chloride (20 mL), filtered over Celite, and evaporated in vacuo to afford a residue that was purified by flash chromatography (silica, 4 g, ISCO, 0-40% ethyl acetate in heptane) to afford the title compound as a white solid (180 mg, 60%), which was used in the next step without further purification.

Step 5: tert-butyl 2-bromo-5-formylpyridin-4-ylcarbamate

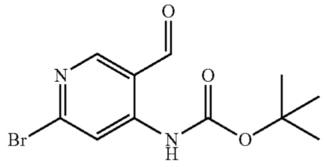 [SMILES: CC(C)(C)OC(=O)Nc1cc(Br)ncc1C=O]

A mixture of 6-bromo-4-iodonicotinaldehyde (50 mg, 0.2 mmol), tert-butyl carbamate (28 mg, 0.24 mmol), 4,5-bis (diphenylphosphino)-9,9-dimethylxanthene (18 mg, 0.03 mmol), palladium acetate (5 mg, 0.02 mmol), and cesium carbonate (100 mg, 0.32 mmol) in 1,4-dioxane (1 mL) was heated at 90° C. for 1 hour. The cooled reaction mixture was diluted with ethyl acetate (50 mL) and washed with water (100 mL). The organic layer was separated, dried over sodium sulfate, filtered, and evaporated in vacuo to afford a residue that was purified by flash chromatography (silica, 4 g, ISCO, 0-50% ethyl acetate in heptane) to afford the title compound as a white solid (18 mg, 40%). $^1$H NMR (400 MHz, $CDCl_3$) δ 10.42 (s, 1H), 9.93 (s, 1H), 8.61 (s, 1H), 8.50 (s, 1H), 1.55 (s, 9H).

Step 6: 7-bromo-3-(2-chloro-5-fluorophenyl)-1,6-naphthyridine

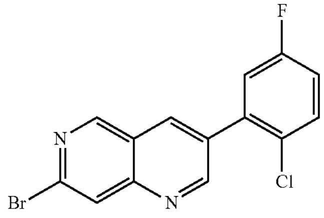

To a slurry of potassium tert-butoxide (94 mg, 0.8 mmol) in 1,4-dioxane (1 mL) cooled at 0° C. was added 2-(2-chloro-5-fluorophenyl)acetaldehyde (98 mg, 0.4 mmol) as a solution in 1,4-dioxane (0.6 mL). The reaction mixture was stirred for 10 minutes at this temperature, and then tert-butyl 2-bromo-5-formylpyridin-4-ylcarbamate (60 mg, 0.2 mmol) was added as a solution in dioxane (0.6 mL). The reaction mixture was allowed to warm to room temperature, and after 30 minutes a 5.0M solution of hydrogen chloride in water (0.5 mL) was added and the mixture was heated at 100° C. for 1 hour. The cooled reaction mixture was diluted with ethyl acetate (50 mL) and washed with water (50 mL). The organic layer was separated, dried over sodium sulfate, filtered, and evaporated in vacuo to afford a residue that was purified by flash chromatography (silica, 4 g, ISCO, 0-50% ethyl acetate in heptane) to afford the title compound as an off-white solid (20 mg, 30%), which was used in the next step without further purification.

Step 7: N-(3-(2-chloro-5-fluorophenyl)-1,6-naphthyridin-7-yl)cyclopropanecarboxamide

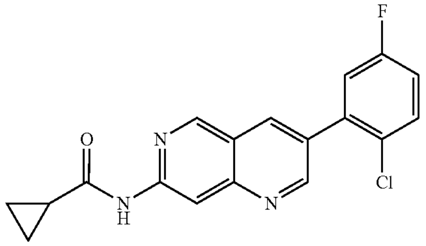 [SMILES: O=C(Nc1cc2ncc(-c3cc(F)ccc3Cl)cc2cn1)C1CC1]

A mixture of 7-bromo-3-(2-chloro-5-fluorophenyl)-1,6-naphthyridine (40 mg, 0.1 mmol), cyclopropanecarboxamide (30 mg, 0.35 mmol), 4,5-bis(diphenylphosphino)-9,9-dimethylxanthene (14 mg, 0.024 mmol), palladium acetate (5 mg, 0.024 mmol), and cesium carbonate (77 mg, 0.24 mmol) in 1,4-dioxane (1 mL) was heated at 90° C. for 1 hour. The cooled reaction mixture was diluted with ethyl acetate (50 mL) and washed with water (100 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as an off-white solid (15 mg, 40%). $^1$H NMR (400 MHz, DMSO) δ 11.17 (s, 1H), 9.29 (s, 1H), 9.11 (d, J=2.2 Hz, 1H), 8.66-8.55 (m, 2H), 7.73 (dd, J=8.9, 5.2 Hz, 1H), 7.60 (dd, J=9.1, 3.1 Hz, 1H), 7.40 (td, J=8.5, 3.1 Hz, 1H), 2.18-2.06 (m, 1H), 0.96-0.81 (m, 4H). LCMS (Method E): $R_T$=4.646 min, M+H$^+$=342.0.

Example 156

N-(3-(2-chlorophenyl)-2-ethyl-1,6-naphthyridin-7-yl)cyclopropanecarboxamide

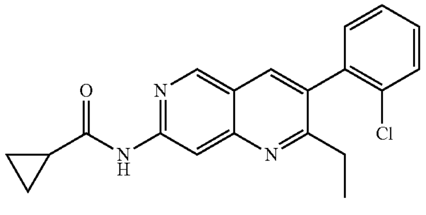 [SMILES: CCc1nc2cc(NC(=O)C3CC3)ncc2cc1-c1ccccc1Cl]

The title compound was prepared following a procedure similar to example 155 using 1-(2-chlorophenyl)butan-2-one in step 6.

$^1$H NMR (400 MHz, DMSO) δ 10.92 (s, 1H), 9.07 (s, 1H), 8.30 (s, 1H), 8.19 (s, 1H), 7.47 (m, 1H), 7.36-7.20 (m, 2H), 7.15 (m, 1H), 4.40 (s, 2H), 2.44 (s, 3H), 2.05 (m, 1H), 0.81 (m, 4H). LCMS (Method E): $R_T$=4.452 min, M+H$^+$=352.1.

Example 157

N-(2-(1-hydroxycyclopentyl)-1,7-naphthyridin-6-yl)cyclopropanecarboxamide

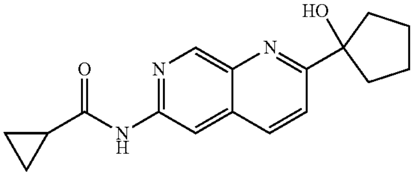 [SMILES: O=C(Nc1cc2ccc(C3(O)CCCC3)nc2cn1)C1CC1]

Step 1: 6-chloro-1,7-naphthyridin-2(1H)-one

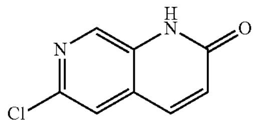 [SMILES: O=c1ccc2cc(Cl)ncc2[nH]1]

To a solution of N,N-diisopropylamine (4.6 mL, 33 mmol) in anhydrous ethyl ether cooled at −78° C. was added n-butyllithium (1.0M solution in hexanes, 22 mL, 36 mmol). After 30 minutes at this temperature, tert-butyl acetate (3.8 g, 33 mmol) was added slowly to the reaction mixture as a solution in anhydrous diethyl ether (10 mL). After another 20 minutes of stirring at −78° C., tert-butyl 6-chloro-4-formylpyridin-3-ylcarbamate (4.0 g, 16 mmol) was slowly added to the mixture as a solution in tetrahydrofuran (10 mL). The reaction mixture was warmed to room temperature and then poured onto ice. The organic layer was separated, dried over sodium sulfate, and evaporated in vacuo to afford a residue that was redissolved in 1,4-dioxane (30 mL), treated with a 5.0M solution of hydrogen chloride in water (30 mL), and heated at 90° C. for 2 hours. The cooled reaction mixture was neutralized by addition of solid sodium bicarbonate, producing a fine white precipitate. Solids were collected via vacuum filtration, washing with water (25 mL) and then tetrahydrofuran (25 mL) to afford the title compound as a white solid (2.3 g, 82%), which was used in the next step without further purification.

Step 2: 2-bromo-6-chloro-1,7-naphthyridine

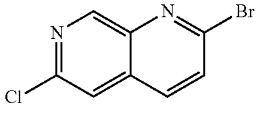 [SMILES: Clc1cc2ccc(Br)nc2cn1]

A mixture of 6-chloro-1,7-naphthyridin-2(1H)-one (1.0 g, 5.5 mmol) and phosphorus tribromide (10 mL) was heated in a sealed tube at 130° C. for 20 hours. The cooled reaction mixture was poured onto ice, diluted with saturated aqueous sodium carbonate solution (100 mL), and extracted with ethyl acetate (2×200 mL). The combined organic layers were dried over sodium sulfate, filtered, and evaporated in vacuo to afford a residue that was purified by flash chromatography (silica, 40 g, ISCO, 0-80% ethyl acetate in heptane) to afford the title compound as a white solid (700 mg, 50%). $^1$H NMR (400 MHz, DMSO) δ 9.24 (s, 1H), 8.38 (d, J=8.7 Hz, 1H), 8.20 (s, 1H), 8.02 (d, J=8.7 Hz, 1H).

Step 3: 1-(6-chloro-1,7-naphthyridin-2-yl)cyclopentanol

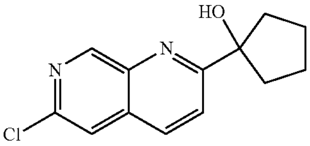 [SMILES: OC1(c2ccc3cc(Cl)ncc3n2)CCCC1]

A suspension of 2-bromo-6-chloro-1,7-naphthyridine (300 mg, 1 mmol) in toluene (8 mL) cooled at −78° C. under an atmosphere of nitrogen was treated with n-butyllithium (1.6M solution in hexanes, 2.3 mL, 3.7 mmol) dropwise over 5 minutes. The reaction mixture was stirred at this temperature for 6 hours and then cyclopentanone (0.33 mL, 3.7 mmol) was added slowly as a solution in toluene (1.3 mL). After 15 minutes, the mixture was allowed to warm to room temperature and then quenched with a few drops of saturated aqueous ammonium chloride solution. The reaction mixture was diluted with ethyl acetate (50 mL) and washed with water (50 mL). The organic layer was separated, dried over sodium sulfate, filtered, and evaporated in vacuo to afford a residue that was purified by flash chromatography (silica, 12 g, ISCO, 0-50% ethyl acetate in heptane) to afford the title compound as an orange, waxy solid (65 mg, 20%), which was used in the next step without further purification.

Step 4: N-(2-(1-hydroxycyclopentyl)-1,7-naphthyridin-6-yl)cyclopropanecarboxamide

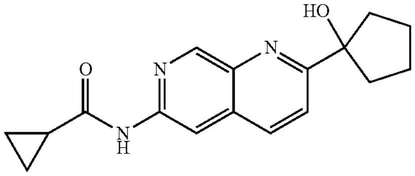 [SMILES: O=C(Nc1cc2ccc(C3(O)CCCC3)nc2cn1)C1CC1]

A mixture of 1-(6-chloro-1,7-naphthyridin-2-yl)cyclopentanol (65 mg, 0.26 mmol), cyclopropanecarboxamide (67 mg, 0.8 mmol), Chloro[2-(dicyclohexylphosphino)-3-,6-dimethoxy-2,4'-6'-tri-1-pr-1,1'-biphenyl)][2-(2-aminoethyl) Ph]Pd(II) (31 mg, 0.04 mmol), (dicyclohexylphosphino)-3-, 6-dimethoxy-2,4'-6'-tri-i-pr-1,1'-biphenyl (21 mg, 0.04 mmol), and cesium carbonate (170 mg, 0.52 mmol) in 1,4-dioxane (1.5 mL) was heated at 90° C. for 1 hour. The cooled reaction mixture was diluted with ethyl acetate (50 mL) and washed with water (50 mL). The organic layer was separated, dried over sodium sulfate, filtered, and evaporated in vacuo to afford a residue that was purified by by reverse phase HPLC (5-85% acetonitrile in water with 0.1% formic acid over 14 min) to afford the title compound as an off-white solid (35 mg, 45%). $^1$H NMR (400 MHz, DMSO) δ 10.97 (s, 1H), 9.12 (s, 1H), 8.47 (s, 1H), 8.30 (d, J=8.8 Hz, 1H), 8.00 (d, J=8.8 Hz, 1H), 5.32 (s, 1H), 2.29-2.17 (m, 2H), 2.11-2.03 (m, 1H), 1.95-1.75 (m, 6H), 0.91-0.78 (m, 4H). LCMS (Method E): $R_T$=3.811 min, M+H$^+$=298.1.

Example 158

N-(2-(1-hydroxycyclohexyl)-1,7-naphthyridin-6-yl) cyclopropanecarboxamide

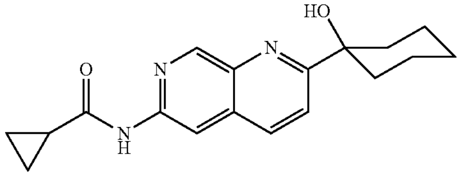 [SMILES: O=C(Nc1cc2ccc(C3(O)CCCCC3)nc2cn1)C1CC1]

The title compound was prepared following a procedure similar to example 157 using cyclopentanone in step 3.

$^1$H NMR (400 MHz, DMSO) δ 11.00 (s, 1H), 9.14 (s, 1H), 8.47 (s, 1H), 8.31 (d, J=8.7 Hz, 1H), 8.00 (d, J=8.8 Hz, 1H), 5.23 (s, 1H), 2.12-1.93 (m, 3H), 1.83-1.63 (m, 5H), 1.57 (m, 2H), 1.30 (m, 1H), 0.85 (m, 4H). LCMS (Method E): $R_T$=4.255 min, M+H$^+$=312.1.

Example 159

(1R,2R)-2-fluorocyclopropanecarboxylic acid and (1S,2S)-2-fluorocyclopropanecarboxylic acid

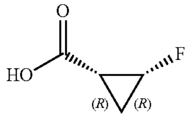

and

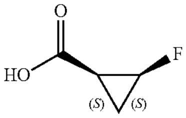

Step 1: Ethyl 2-chloro-2-fluorocyclopropanecarboxylate

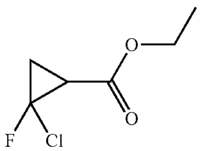

To a suspension of tetrakis(triphenylacetate)dirhodium (3.66 g) and powdered molecule sieves (45 g) in dichloromethane (2.0 L) was added 1-chloro-1-fluoroethene (82 g, 1.02 mol) at −60° C. The reaction mixture was warmed to −35~−40° C., ethyl 2-diazoacetate (90 g, 790 mmol) in DCM (200 mL) was added and the reaction mixture was stirred at room temperature overnight. The reaction mixture was filtered and evaporated in vacuo to yield 100 g Ethyl 2-chloro-2-fluorocyclopropanecarboxylate as yellow oil which was used directly in the next step without purification.

Step 2: 2-chloro-2-fluorocyclopropanecarboxylic acid

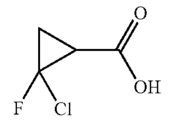

To a solution of Ethyl 2-chloro-2-fluorocyclopropanecarboxylate (100 g, 600 mmol) in THF (1000 mL) at 0° C. was added aqueous LiOH (1N, 800 mL). The reaction mixture was stirred at room temperature overnight. The solvent was then evaporated in vacuo and the resulting residue acidified by 2N aqueous HCl and extracted with ethyl acetate. The organic extract was washed with brine, dried over $Na_2SO_4$, filtered and concentrated to yield 2-chloro-2-fluorocyclopropanecarboxylic acid as yellow oil (77.2 g, 70% yield over two steps), which was used directly in the next step without purification.

Step 3: 2-chloro-2-fluoro-N-((R)-1-phenylethyl)cyclopropanecarboxamide

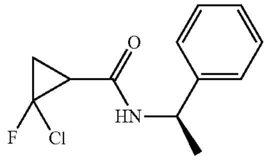 [SMILES: C[C@@H](NC(=O)C1CC1(F)Cl)c1ccccc1]

To a solution of 2-chloro-2-fluorocyclopropanecarboxylic acid (112 g, 809 mmol) in THF (2.0 L) was added 1,1'-carbonyldiimidazole (170 g, 1.05 mmol). The reaction mixture was stirred at room temperature for 1 hour and then (R)-(+)-1-phenylethylamine (117.5 g, 971 mmol) was added. The reaction mixture was stirred at room temperature overnight. The solvent was evaporated in vacuo and the residue was extracted with ethyl acetate. The organic extract was washed with 2N aqueous HCl, brine, dried over $Na_2SO_4$, filtered and concentrated. The crude product was purified via flash chromatography on silica gel (solvent gradient: 15-33% ethyl acetate in petroleum ether) to yield 2-chloro-2-fluoro-N—((R)-1-phenylethyl)cyclopropanecarboxamide as a white solid (149 g, 50% yield over three steps).

Step 4: cis-2-fluoro-N-((R)-1-phenylethyl)cyclopropanecarboxamide

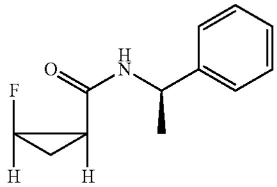

A mixture of 2-chloro-2-fluoro-N-((R)-1-phenylethyl)cyclopropanecarboxamide (151.7 g, 629 mmol), Raney Ni (35 g, wet) and ethylenediamine (113 g) in NMP (1200 mL) was stirred at 80° C. under $H_2$ atmosphere for 8 hours. The reaction mixture was then cooled to room temperature, diluted with ethyl acetate (1500 mL), and filtered. The filtrate was washed with 2N aqueous HCl, brine, dried over $Na_2SO_4$, filtered and evaporated in vacuo to yield a crude mixture of cis-2-fluoro-N-((R)-1-phenylethyl)cyclopropanecarboxamide and trans-2-fluoro-N-((R)-1-phenylethyl)cyclopropanecarboxamide. The crude product was purified via flash chromatography on silica gel (solvent gradient: 15-33% ethyl acetate in petroleum ether) to separate the diastereomers and yield cis-2-fluoro-N-((R)-1-phenylethyl)cyclopropanecarboxamide (mixture of enantiomers) as white solid (40 g, yield 15% over four steps).

Step 5: (1R,2R)-2-fluoro-N-((R)-1-phenylethyl)cyclopropanecarboxamide and (1S,2S)-2-fluoro-N-((R)-1-phenylethyl)cyclopropanecarboxamide

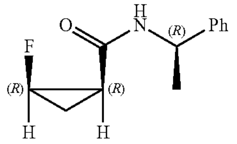
and
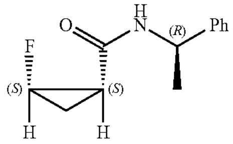

71 g of cis-2-fluoro-N-((R)-1-phenylethyl)cyclopropanecarboxamide was subjected to chiral separation to give (1R,2R)-2-fluoro-N-((R)-1-phenylethyl)cyclopropanecarboxamide as an off-white solid (36.3 g, ee>99%, $[a]^{20°}$=+55.6, c=1.0, in $CHCl_3$; $[a]^{ref}$=+62.0, in $CHCl_3$) and (1S,2S)-2-fluoro-N-((R)-1-phenylethyl)cyclopropanecarboxamide as a white solid (30 g, ee>99%, $[a]^{20°}$=+142.2, c=1.0, in $CHCl_3$; $[a]^{ref}$=+143.6, in $CHCl_3$).

Step 6: (1R,2R)-2-fluorocyclopropanecarboxylic acid

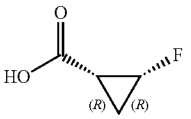

A mixture of (1R,2R)-2-fluoro-N-((R)-1-phenylethyl)cyclopropanecarboxamide (34 g, 164 mmol) in concentrated HCl (360 mL) was stirred at reflux for 5 hours. The reaction mixture was cooled to room temperature, the pH adjusted to pH 8-9 with $NaHCO_3$, and washed with dichloromethane. The aqueous layer was then acidified to pH 4 with 2N aqueous HCl and extracted with ethyl acetate. The organic extract was washed with brine, dried over $Na_2SO_4$, filtered and evaporated in vacuo to yield the crude product as yellow oil. Purification by flash chromatography on silica gel gave (1R,2R)-2-fluorocyclopropanecarboxylic acid as white solid (10.4 g, 60% yield).

LCMS (ESI): M−H=102.9; $[a]^{20°}$=−6.4, c=1.0, in $CHCl_3$; $[a]^{ref}$=−23.1, in $CHCl_3$. Reference: J. Med. Chem., 1994, 37, 3345.

Step 7: (1S,2S)-2-fluorocyclopropanecarboxylic acid

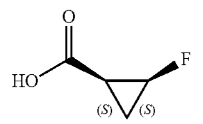

A mixture of (1S,2S)-2-fluoro-N-((R)-1-phenylethyl)cyclopropanecarboxamide (30 g, 145 mmol) in concentrated HCl (300 mL) was stirred at reflux for 5 hours. The reaction mixture was cooled to room temperature, the pH adjusted to pH 8-9 with $NaHCO_3$, and washed with dichloromethane. The aqueous layer was then acidified to pH 4 with 2N aqueous HCl and extracted with ethyl acetate. The organic extract was washed with brine, dried over $Na_2SO_4$, filtered and evaporated in vacuo to yield the crude product as yellow oil. Purification by flash chromatography on silica gel gave (1S,2S)-2-fluorocyclopropanecarboxylic acid as a white solid (9.2 g, 61% yield). LCMS (ESI): M−H=103.1; $[a]^{20°}$=+7.8, c=1.0, in $CHCl_3$; $[a]^{ref}$=+21.6, in $CHCl_3$. Reference: J. Med. Chem., 1994, 37, 3345.

Example 160

(1S,2S)-N-(7-chloro-2,6-naphthyridin-3-yl)-2-fluorocyclopropanecarboxamide

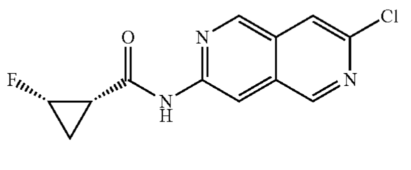

Step 1: 3-((tert-butyldimethylsilyloxy)methyl)-7-chloro-2,6-naphthyridine

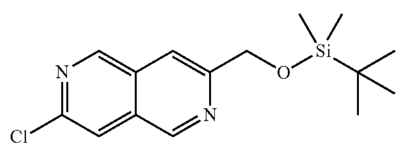 [SMILES: CC(C)(C)[Si](C)(C)OCc1cc2cnc(Cl)cc2cn1]

A mixture of N-((5-bromo-2-chloropyridin-4-yl)methylene)-2-methylpropan-2-amine (530 mg, 1.9 mmol), tert-butyldimethyl(2-propynyloxy)silane (0.59 mL, 2.9 mmol), $NiCl_2$(DPPP) (52 mg, 0.1 mmol), and zinc (252 mg, 3.9 mmol) in acetonitrile (5 mL) was heated at 70° C. under an atmosphere of nitrogen. The cooled reaction mixture was diluted with methylene chloride (50 mL), filtered over Celite, and evaporated in vacuo to afford a residue that was purified by flash chromatography (silica, 12 g, ISCO, 0-40% ethyl acetate in heptane) to afford the title compound as an orange waxy solid (340 mg, 57%), which was used in the next step without further purification.

Step 2: (7-chloro-2,6-naphthyridin-3-yl)methanol

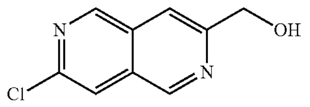 [SMILES: OCc1cc2cnc(Cl)cc2cn1]

A solution of 5.0M hydrogen chloride in water (0.73 mL) was added to a solution of 3-((tert-butyldimethylsilyloxy)methyl)-7-chloro-2,6-naphthyridine (1.13 g, 3.7 mmol) in methanol (15 mL), and the mixture was stirred at room temperature for 2 hours. The reaction mixture was diluted with methylene chloride (150 mL), and washed with saturated aqueous sodium bicarbonate solution. The organic layer was separated, dried over sodium sulfate, filtered, and evaporated in vacuo to afford a residue that was suspended in heptane (10 mL) and filtered to provide the title compound as a white powder (645 mg, 90%). $^1$H NMR (400 MHz, DMSO) δ 9.37 (s, 2H), 8.23 (s, 1H), 8.06 (s, 1H), 5.65 (t, J=5.6 Hz, 1H), 4.78 (d, J=5.6 Hz, 2H).

Step 3: 7-chloro-2,6-naphthyridine-3-carboxylic acid

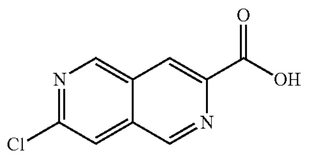 [SMILES: O=C(O)c1cc2cnc(Cl)cc2cn1]

Potassium permanganate (280 mg, 1.8 mmol) was added in small portions to a slurry of (7-chloro-2,6-naphthyridin-3-yl)methanol (105 mg, 0.54 mmol) in water (2 mL). The mixture was stirred for 30 minutes at room temperature, and was then diluted with sodium hydroxide (1.0 M solution in water, 5 mL) and filtered over Celite. The filtrate was acidified to a pH of ~3 via addition of citric acid, and the resulting precipitate was collected by vacuum filtration and washed with water (2×5 mL) to afford the title compound as a white solid (55 mg, 50%). $^1$H NMR (400 MHz, DMSO) δ 13.40 (s, 1H), 9.54 (s, 1H), 9.51 (s, 1H), 8.82 (s, 1H), 8.36 (s, 1H).

Step 4: tert-butyl 7-chloro-2,6-naphthyridin-3-ylcarbamate

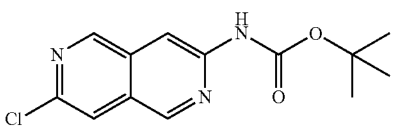 [SMILES: CC(C)(C)OC(=O)Nc1cc2cnc(Cl)cc2cn1]

A mixture of 7-chloro-2,6-naphthyridine-3-carboxylic acid (360 mg, 1.8 mmol), tert-butyl alcohol (3.4 mL), N,N-diisopropylethylamine (1 mL, 5.6 mmol), and diphenylphosphonic azide (1.0 mL, 4.5 mmol) in toluene (6 mL) was heated at 110° C. for 1 hour. The cooled reaction mixture was diluted with ethyl acetate (50 mL) and washed with water (50 mL). The organic layer was separated, dried over sodium sulfate, filtered, and evaporated in vacuo to afford a residue that was purified by flash chromatography (silica, 12 g, ISCO, 0-60% ethyl acetate in heptane) to afford the title compound as a pale yellow solid (410 mg, 83%), which was used in the next step without further purification.

Step 5: 7-chloro-2,6-naphthyridin-3-amine

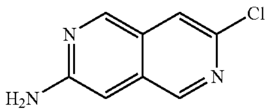 [SMILES: Nc1cc2cnc(Cl)cc2cn1]

Trifluoroacetic acid (0.43 mL, 5.5 mmol) was added to a solution of tert-butyl 7-chloro-2,6-naphthyridin-3-ylcarbamate (410 mg, 1.4 mmol) in dichloroethane (7 mL). After 4 hours, the reaction mixture was concentrated in vacuo, diluted with methylene chloride (50 mL), and washed with saturated aqueous sodium bicarbonate solution (20 mL). The organic layer was separated, dried over sodium sulfate, filtered, and evaporated in vacuo to afford a residue that was purified by flash chromatography (silica, 4 g, ISCO, 0-100% ethyl acetate in heptane) to afford the title compound as a yellow solid (230 mg, 86%), which was used in the next step without further purification.

Step 6: (1S,2S)-N-(7-chloro-2,6-naphthyridin-3-yl)-2-fluorocyclopropanecarboxamide

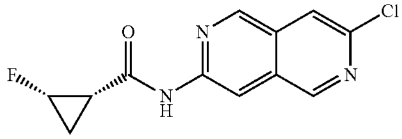 [SMILES: O=C(Nc1cc2cnc(Cl)cc2cn1)[C@@H]1C[C@@H]1F]

A mixture of 7-chloro-2,6-naphthyridin-3-amine (230 mg, 1.3 mmol), (1S,2S)-2-fluorocyclopropanecarboxylic acid (266 mg, 2.6 mmol), HATU (1.1 g, 2.8 mmol), and N,N-diisopropylethylamine (0.45 mL, 2.6 mmol) in N,N-dimethylformamide (3 mL) was heated at 70° C. for 16 hours. The cooled reaction mixture was diluted with ethyl acetate (50 mL) and washed with water (50 mL). The organic layer was separated, dried over sodium sulfate, filtered, and evaporated in vacuo to afford a residue that was purified by flash chromatography (silica, 12 g, ISCO, 0-60% ethyl acetate in heptane) to afford the title compound as a white solid (150 mg, 44%). $^1$H NMR (400 MHz, DMSO) δ 11.22 (s, 1H), 9.29 (s, 1H), 9.28 (s, 1H), 8.66 (s, 1H), 8.16 (s, 1H), 5.08-4.85 (m, 1H), 2.29 (m, 1H), 1.71 (m, 1H), 1.22 (m, 1H).

Example 161

N-(7-chloro-2,6-naphthyridin-3-yl)cyclopropanecarboxamide

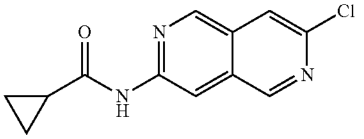 [SMILES: O=C(Nc1cc2cnc(Cl)cc2cn1)C1CC1]

The title compound was prepared following a procedure similar to the previous example 160 using cyclopropanecarboxylic acid in step 6. $^1$H NMR (400 MHz, DMSO) δ 11.16 (s, 1H), 9.26 (s, 2H), 8.64 (s, 1H), 8.14 (s, 1H), 2.08 (m, 1H), 0.87 (m, 4H).

Example 162

(1S,2S)-2-fluoro-N-(7-(4-methylpyridin-3-yl)-2,6-naphthyridin-3-yl)cyclopropanecarboxamide

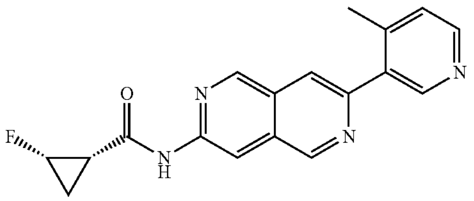 [SMILES: Cc1ccncc1-c1cc2cnc(NC(=O)[C@@H]3C[C@@H]3F)cc2cn1]

A mixture of (1S,2S)-N-(7-chloro-2,6-naphthyridin-3-yl)-2-fluorocyclopropanecarboxamide (40 mg, 0.2 mmol), 4-methylpyridine-3-boronic acid (62 mg, 0.45 mmol), bis(di-tert-butyl(4-dimethylaminophenyl)phosphine) dichloropalladium(II) (11 mg, 0.015 mmol), and saturated aqueous sodium carbonate (0.1 mL) in acetonitrile (1 mL) was heated under microwave irradiation (Biotage, 200 watts) at 130° C. for 30 minutes. The cooled reaction mixture was diluted with ethyl acetate (50 mL) and washed with water (50 mL). The organic layer was separated, dried over sodium sulfate, filtered, and evaporated in vacuo to afford a residue that was purified by reverse phase HPLC (5-85% acetonitrile in water with 0.1% formic acid over 14 min) to afford the title compound as an off-white solid (23 mg, 50%). $^1$H NMR (400 MHz, DMSO) δ 11.19 (s, 1H), 9.50 (s, 1H), 9.34 (s, 1H), 8.68 (s, 1H), 8.68 (s, 1H), 8.50 (d, J=5.0 Hz, 1H), 8.19 (s, 1H), 7.39 (d, J=5.0 Hz, 1H), 4.97 (m, 1H), 2.44 (s, 3H), 2.31 (m, 1H), 1.72 (m, 1H), 1.28-1.16 (m, 1H). LCMS (Method E): $R_T$=2.980 min, M+H$^+$=323.1.

Example 163

(3-(4,4,5,5-tetramethyl-1,3,2-dioxaborolan-2-yl)phenyl)methanol

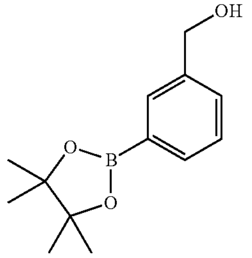 [SMILES: CC1(C)OB(c2cccc(CO)c2)OC1(C)C]

Lithium tetrahydroaluminate (1.0M solution in tetrahydrofuran, 6.1 mL, 6.0 mmol) was added dropwise to a solution of 4-methyl-3-(4,4,5,5-tetramethyl-1,3,2-dioxaborolan-2-yl) benzoic acid (0.4 g, 1.5 mmol) in tetrahydrofuran (6 mL) cooled at 0° C. The reaction mixture was warmed to room temperature, stirred for 2 hours, and then quenched via dropwise addition of saturated aqueous ammonium chloride solution (1 mL). The reaction mixture was diluted with ethyl acetate (50 mL) and washed with water (50 mL). The organic layer was separated, dried over sodium sulfate, filtered, and evaporated in vacuo to afford a residue that was purified by flash chromatography (silica, 12 g, ISCO, 0-100% ethyl acetate in heptane) to afford the title compound as a white solid (276 mg, 61%). $^{1}$H NMR (400 MHz, $CDCl_3$) δ 7.73 (d, J=1.3 Hz, 1H), 7.32 (dd, J=7.8, 1.8 Hz, 1H), 7.16 (d, J=7.8 Hz, 1H), 4.63 (s, 2H), 3.01 (s, 1H), 2.52 (s, 3H), 1.34 (s, 12H).

Example 164

N-(7-(3-(hydroxymethyl)phenyl)-2,6-naphthyridin-3-yl)cyclopropanecarboxamide

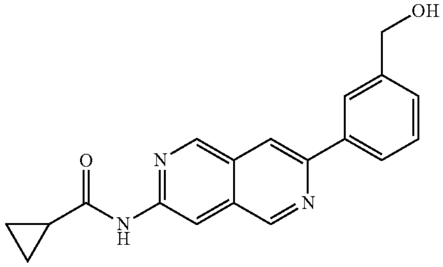

The title compound was prepared following a procedure similar to example 162 using N-(7-chloro-2,6-naphthyridin-3-yl)cyclopropanecarboxamide and (3-(4,4,5,5-tetramethyl-1,3,2-dioxaborolan-2-yl)phenyl)methanol.

$^{1}$H NMR (400 MHz, DMSO) δ 11.11 (s, 1H), 9.43 (s, 1H), 9.32 (s, 1H), 8.64 (s, 1H), 8.04 (s, 1H), 7.47 (s, 1H), 7.30 (m, 2H), 5.16 (t, J=5.5 Hz, 1H), 4.54 (d, J=5.2 Hz, 2H), 2.35 (s, 3H), 2.10 (m, 1H), 0.96-0.78 (m, 4H). LCMS (Method E): $R_T$=3.969 min, M+H$^+$=334.1.

Example 165

(1S,2S)-2-fluoro-N-(7-(5-methyl-1H-indazol-4-yl)-2,6-naphthyridin-3-yl)cyclopropanecarboxamide

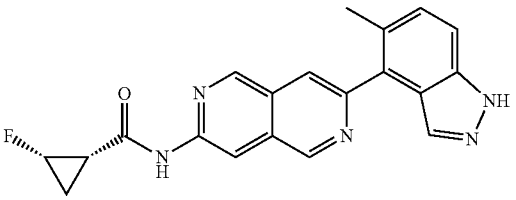 [SMILES: Cc1ccc2[nH]ncc2c1-c1cc2cnc(NC(=O)[C@@H]3C[C@@H]3F)cc2cn1]

The title compound was prepared following a procedure similar to example 162 using 5-methyl-1H-indazol-4-ylboronic acid.

$^{1}$H NMR (400 MHz, DMSO) δ 13.05 (s, 1H), 11.18 (s, 1H), 9.53 (s, 1H), 9.36 (s, 1H), 8.69 (s, 1H), 8.15 (s, 1H), 7.84 (s, 1H), 7.52 (d, J=8.5 Hz, 1H), 7.35 (d, J=8.5 Hz, 1H), 4.98 (ddd, J=66.1, 10.0, 6.2 Hz, 1H), 2.41 (s, 3H), 2.31 (m, 1H), 1.73 (dtd, J=23.2, 6.8, 3.7 Hz, 1H), 1.30-1.16 (m, 1H). LCMS (Method E): $R_T$=3.885 min, M+H$^+$=362.1.

Example 166

(S)-N-(7-(4-methylpyridin-3-yl)isoquinolin-3-yl)oxetane-2-carboxamide and (R)-N-(7-(4-methylpyridin-3-yl)isoquinolin-3-yl)oxetane-2-carboxamide

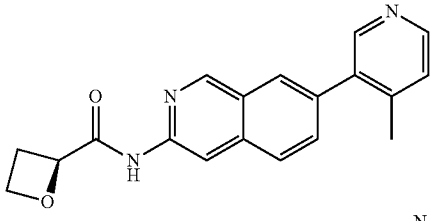

and

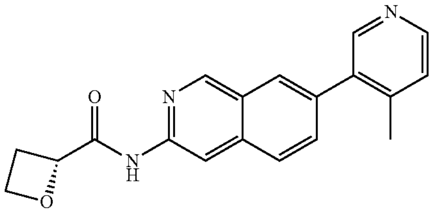

The title compounds were prepared as a racemate following a procedure similar to example 8 using 7-(4-methylpyridin-3-yl)isoquinolin-3-amine and oxetane-2-carboxylic acid, and then separated via chiral supercritical fluid chromotagraphy: Enantiomer 1: $^{1}$H NMR (400 MHz, DMSO) δ 10.02 (s, 1H), 9.23 (s, 1H), 8.58 (s, 1H), 8.50 (s, 1H), 8.49 (d, J=5.0 Hz, 1H), 8.13 (s, 1H), 8.06 (d, J=8.5 Hz, 1H), 7.80 (dd, J=8.5, 1.4 Hz, 1H), 7.39 (d, J=5.0 Hz, 1H), 5.26 (dd, J=8.8, 6.7 Hz, 1H), 4.69 (t, J=7.7 Hz, 2H), 3.00 (dq, J=11, 8 Hz, 1H), 2.71 (dq, J=11, 8 Hz, 1H), 2.33 (s, 3H). LCMS (Method E): $R_T$=3.038 min, M+H$^+$=320.1; Enantiomer 2: $^{1}$H NMR (400 MHz, DMSO) δ 10.02 (s, 1H), 9.23 (s, 1H), 8.58 (s, 1H), 8.50 (s, 1H), 8.49 (d, J=5.0 Hz, 1H), 8.13 (s, 1H), 8.06 (d, J=8.6 Hz, 1H), 7.80 (d, J=8.5 Hz, 1H), 7.40 (d, J=5.0 Hz, 1H), 5.26 (dd, J=8.8, 6.7 Hz, 1H), 4.69 (t, J=7.7 Hz, 2H), 3.00 (dq, J=11.0, 7.7 Hz, 1H), 2.71 (dq, J=11.0, 7.7 Hz, 1H), 2.33 (s, 3H). LCMS (Method E): $R_T$=3.046 min, M+H$^+$=320.1.

Example 167

(1R,2R)-2-ethoxy-N-(7-(4-methylpyridin-3-yl)isoquinolin-3-yl)cyclopropanecarboxamide and (1S,2S)-2-ethoxy-N-(7-(4-methylpyridin-3-yl)isoquinolin-3-yl)cyclopropanecarboxamide

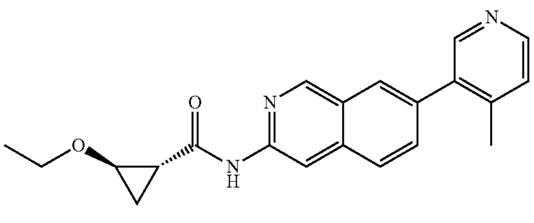

and

-continued

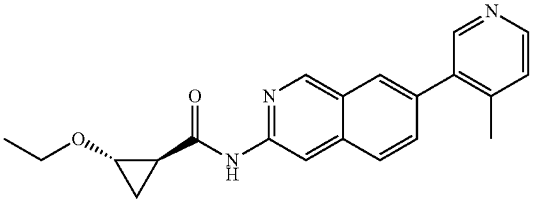

Step 1: ethyl 2-ethoxycyclopropanecarboxylate

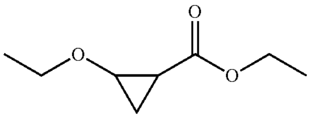

A solution of ethyl vinyl ether (4.5 mL, 47 mmol, 4.9 equiv.) and rhodium(II) acetate dimer (20.0 mg, 45.2 μmol, 4.8 mol %) in DCM (20 mL) at ambient temperature was treated with ethyl 2-diazoacetate (1.00 mL, 9.51 mmol) in 0.1 mL portions over 10 mins, allowing effervescence to subside between additions. The resulting green solution was stirred at ambient temperature for 2 h and concentrated in vacuo. The residue was dissolved in diethyl ether and washed with water, and with brine, dried over magnesium sulfate, filtered and concentrated in vacuo to afford crude ethyl 2-ethoxycyclopropanecarboxylate as a golden yellow oil (1.36 g, 90%) which was used without further purification.

Step 2: 2-ethoxycyclopropanecarboxylate lithium salt

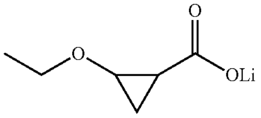

A solution of the crude ethyl 2-ethoxycyclopropanecarboxylate in methanol (10 mL) was treated with aqueous lithium hydroxide (8.6 mL, 1.0 M, 8.6 mmol, 1.0 equiv.), the mixture stirred at ambient temperature for 16 h, and concentrated in vacuo. The resulting orange syrup was twice redissolved in methanol and concentrated in vacuo to afford crude 2-ethoxycyclopropane-carboxylic acid lithium salt as an orange foam (1.21 g, 104%).

Step 3: 3H-[1,2,3]triazolo[4,5-b]pyridin-3-yl 2-ethoxycyclopropanecarboxylate

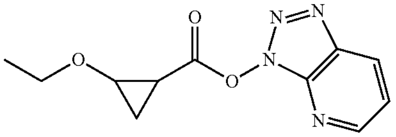 [SMILES: CCOC1CC1C(=O)On1nnc2cccnc21]

An orange solution of the crude 2-ethoxycyclopropanecarboxylic acid lithium salt (8.60 mmol) in DMF (20 mL) and treated with solid N,N,N',N'-tetramethyl-O-(7-azabenzotriazol-1-yl)uronium hexafluorophospate (3.26 g, 8.57 mmol, 1.00 equiv.) in one portion, causing the orange color to become a dark brown, and stirred at ambient temperature for 3 h. The resulting solution of 3H-[1,2,3]triazolo[4,5-b]pyridin-3-yl 2-ethoxycyclopropanecarboxylate in DMF (0.43 M) was used directly in the subsequent couplings.

Step 4: trans-2-ethoxy-N-(7-(4-methylpyridin-3-yl) isoquinolin-3-yl)cyclopropanecarboxamide

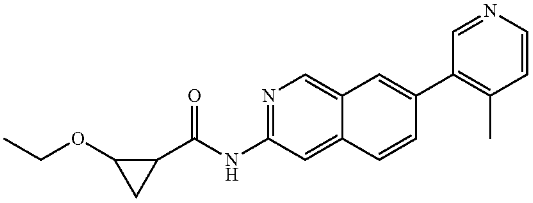 [SMILES: CCOC1CC1C(=O)Nc1cc2ccc(-c3cnccc3C)cc2cn1]

7-(4-Methyl-3-pyridyl)isoquinolin-3-amine (304 mg, 1.29 mmol) was treated with a DMF solution of triazolo[4,5-b] pyridin-3-yl 2-ethoxycyclopropanecarboxylate (6.0 ml, 0.43 M, 2.6 mmol, 2.0 equiv.) at ambient temperature. The resulting deep yellow-brown solution was stirred at ambient temperature for 40 h and concentrated in vacuo to a dark brown oil. The residue was treated with ethyl acetate and saturated aqueous sodium bicarbonate, filtered, and the separated aqueous phase again extracted with ethyl acetate. The combined organic phases were washed with brine, dried over sodium sulfate, filtered and concentrated in vacuo to a dark brown oil. The crude residue was absorbed onto silica and purified by automated flash chromatography (silica, gradient of 10-100% ethyl acetate in heptane) to afford a racemic trans-product (117 mg), which was separated via chiral supercritical fluid chromotagraphy to afford enantiomer 1 (37.0 mg, 8.3%) and enantiomer 2 (37.9 mg, 8.5%): Enantiomer 1: $^1$H NMR (400 MHz, DMSO) δ 10.94 (s, 1H), 9.19 (s, 1H), 8.49 (s, 3H), 8.08 (s, 1H), 7.95 (d, J=8.6 Hz, 1H), 7.75 (d, J=8.5 Hz, 1H), 7.39 (d, J=5.0 Hz, 1H), 3.58 (q, J=7.0 Hz, 2H), 3.57-3.50 (m, 1H), 2.32 (s, 3H), 2.26 (t, J=7.5 Hz, 1H), 1.22-1.15 (m, 2H), 1.14 (t, J=7.0 Hz, 3H). LCMS (Method E): $R_T$=3.482 min, M+H$^+$=348.2; Enantiomer 2: $^1$H NMR (400 MHz, DMSO) δ 10.94 (s, 1H), 9.19 (s, 1H), 8.49 (s, 3H), 8.08 (s, 1H), 7.95 (d, J=8.5 Hz, 1H), 7.75 (d, J=8.5 Hz, 1H), 7.39 (d, J=5.0 Hz, 1H), 3.58 (q, J=7.0 Hz, 2H), 3.56-3.50 (m, 1H), 2.32 (s, 3H), 2.26 (t, J=7.3 Hz, 1H), 1.22-1.15 (m, 2H), 1.14 (t, J=7.0 Hz, 3H). LCMS (Method E): $R_T$=3.478 min, M+H$^+$=348.2.

Example 168

-(7-(2-chloro-4-methylpyrimidin-5-yl)isoquinolin-3-yl)cyclopropanecarboxamide

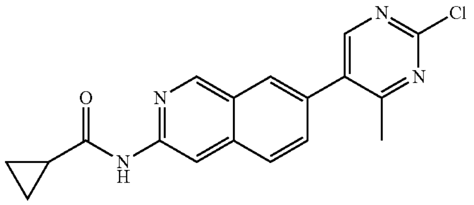 [SMILES: Cc1nc(Cl)ncc1-c1ccc2cc(NC(=O)C3CC3)ncc2c1]

A suspension of N-(7-(2-amino-4-methylpyrimidin-5-yl)isoquinolin-3-yl)cyclopropane-carboxamide (100 mg, 0.314 mmol) in DCM (4 mL) was treated at 0° C. with amyl nitrite (63 μl, 55 mg, 0.47 mmol) and allowed to come to ambient temperature for 2 h. The mixture was treated with a second portion of amyl nitrite (210 μl, 184 mg, 1.57 mmol) and stirred at ambient temperature for 18 h. 1,2-Dichloroethane (5 mL) was added and the mixture heated to reflux for 2 h and allowed to cool, diluted with 10:1-DCM:methanol and washed twice with brine, dried over sodium sulfate, filtered through a celite pad and concentrated in vacuo to afford an orange solid (148 mg). The residue was absorbed onto silica and purified by automated flash chromatography (gradient of 0.5-10% methanol in DCM) to recover starting material (21.7 mg) and yield a yellow solid (14.8 mg) that was repurified by reverse-phase HPLC to afford the desired product as a pale yellow powder (7.6 mg, 7.1%). $^1$H NMR (400 MHz, DMSO) δ 10.96 (s, 1H), 9.20 (s, 1H), 8.71 (s, 1H), 8.53 (s, 1H), 8.17 (s, 1H), 8.00 (d, J=8.6 Hz, 1H), 7.80 (dd, J=8.6, 1.4 Hz, 1H), 2.52 (s, 3H), 2.13-2.04 (m, 1H), 0.91-0.79 (m, 4H). LCMS (Method H): $R_T$=3.53 min, M+H$^+$=339.2/341.2

Example 169

1-(5-bromo-3-chloro-4-methylpyridin-2-yl)-2,2,2-trifluoroethanol

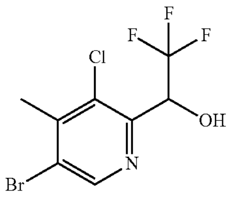

Step 1: 5-bromo-3-chloro-2,4-dimethylpyridine

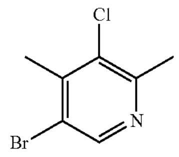

To a solution of 5-chloro-4,6-dimethylpyridin-3-amine (504 mg; 3.2182 mmol) in acetonitrile (15 mL; 287 mmol) was added copper(II) bromide (1.4436 g; 6.4632 mmol) and tert-butyl nitrite (0.70 mL; 5.3 mmol). The reaction mixture was heated at 50° C. for 3 days. The reaction mixture was poured into ethyl acetate (200 mL) and washed with 10% aqueous solution of sodium thiosulfate (100 mL) and brine. The ethyl acetate layer was dried over magnesium sulfate, filtered, and evaporated in vacuo. The crude product was purified via flash chromatography on silica gel (24 g silica, solvent gradient: 0-100% ethyl acetate in heptanes) to yield 443.0 mg (62%) of the title compound. LCMS (ESI): M+H=220.2; $^1$H NMR (400 MHz, DMSO) δ 8.52 (s, 1H), 2.52 (s, 3H), 2.49 (s, 3H).

Step 2: 5-bromo-3-chloro-2,4-dimethylpyridine 1-oxide

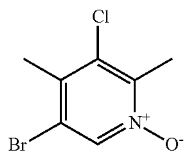

To a solution of 5-bromo-3-chloro-2,4-dimethylpyridine (441 mg; 2.0001 mmol) in dichloromethane (10 mL; 156.0 mmol) was added 3-chloroperoxybenzoic acid (70%, 0.5547 g; 2.250 mmol). The reaction mixture was stirred at room temperature for 3 hours. The reaction mixture was diluted with additional dichloromethane (100 mL), washed with saturated sodium bicarbonate, dried over magnesium sulfate, filtered, and evaporated in vacuo. The crude product was purified via flash chromatography on silica gel (40 g silica, solvent gradient: 0-100% ethyl acetate in dichloromethane) to yield 374.1 mg (79%) of the title compound. LCMS (ESI): M+H=236.2; $^1$H NMR (400 MHz, DMSO) δ 8.65 (s, 1H), 2.47 (s, 3H), 2.43 (s, 3H).

Step 3: (5-bromo-3-chloro-4-methylpyridin-2-yl)methanol

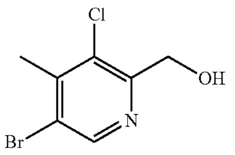

To a solution of 5-bromo-3-chloro-2,4-dimethylpyridine 1-oxide (373 mg; 1.5772 mmol) in dichloromethane (10 mL; 156.0 mmol) was added trifluoroacetic anhydride (0.70 mL; 5.0 mmol). The reaction mixture was stirred at room temperature for 20 hours. Trifluoroacetic anhydride (0.5 mL; 4 mmol) was then added and the reaction mixture stirred for an additional 4 hours at room temperature. The reaction mixture was poured into 2M aqueous potassium carbonate and extracted twice with dichloromethane. The combined dichloromethane extracts were dried over magnesium sulfate, filtered, and evaporated in vacuo. The resulting residue was dissolved in tetrahydrofuran (6 mL), and treated with sodium hydroxide (10 mol/L) in water (0.60 mL; 6.0 mmol). The mixture was stirred at room temperature for 2 hours, and then neutralized with 5M aqueous HCl (1.3 mL). The reaction mixture was poured into saturated aqueous sodium bicarbonate and extracted with dichloromethane (3×100 mL). The combined organic extracts were dried over magnesium sulfate, filtered, and concentrated. The crude product was purified via flash chromatography on silica gel (24 g silica, solvent gradient: 20-100% ethyl acetate in dichloromethane) to yield 255.6 mg (69%) of the title compound. LCMS (ESI): M+H=236.2; $^1$H NMR (400 MHz, $CDCl_3$) δ 8.55 (s, 1H), 4.73 (d, J=4.8 Hz, 2H), 4.05 (s, 1H), 2.55 (s, 3H).

Step 4: 5-bromo-3-chloro-4-methyl-pyridine-2-carbaldehyde

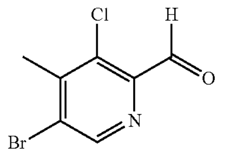

To a solution of (5-bromo-3-chloro-4-methylpyridin-2-yl) methanol (255.6 mg; 1.081 mmol) in methylene chloride (8 mL; 124.8 mmol) was added Dess-Martin periodinane (0.5655 g; 1.293 mmol). The reaction mixture was stirred at room temperature for 17 hours. The reaction mixture was diluted with additional dichloromethane, washed with saturated aqueous sodium bicarbonate, dried over magnesium sulfate, filtered, and evaporated in vacuo. The crude product was purified via flash chromatography on silica gel (24 g silica, solvent gradient: 0-80% ethyl acetate in dichloromethane) to yield 226.5 mg (89%) of the title compound. LCMS (ESI): M+H=234.2; $^1$H NMR (400 MHz, $CDCl_3$) δ 10.30 (s, 1H), 8.75 (s, 1H), 2.63 (s, 3H).

Step 5: 1-(5-bromo-3-chloro-4-methylpyridin-2-yl)-2,2,2-trifluoroethanol

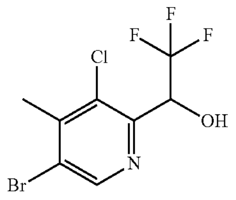

To a solution of 5-bromo-3-chloro-4-methyl-pyridine-2-carbaldehyde (123.9 mg; 0.5284 mmol) in tetrahydrofuran (5.0 mL; 62 mmol) at 0° C. was added (trifluoromethyl) trimethylsilane (0.170 mL; 1.1 mmol) followed by tetrabutylammonium fluoride (1 mol/L) in THF (1.6 mL; 1.6 mmol). The resulting mixture was stirred at room temperature for 17 hours. The reaction mixture was then diluted with ethyl acetate, washed with water, dried over magnesium sulfate, filtered, and evaporated in vacuo. The crude product was purified via flash chromatography on silica gel (12 g silica, solvent gradient: 0-50% ethyl acetate in heptanes) to yield 119.7 mg (74%) of the title compound. LCMS (ESI): M+H=304.0; $^1$H NMR (400 MHz, DMSO) 8.76 (s, 1H), 6.92 (d, J=6.9 Hz, 1H), 5.58 (p, J=6.9 Hz, 1H), 2.55 (s, 3H).

Example 170

2-(5-bromo-3-chloro-4-methylpyridin-2-yl)propan-2-ol

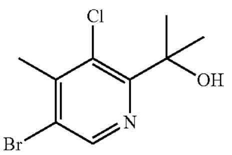

Step 1: methyl 5-bromo-3-chloro-4-methyl-pyridine-2-carboxylate

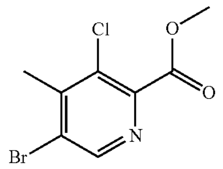

To a 0° C. solution of 5-bromo-3-chloro-4-methyl-pyridine-2-carbaldehyde (102 mg; 0.43501 mmol) in methanol (4 mL) was sequentially added a solution of potassium hydroxide (105 mg; 1.87149 mmol) in methanol (2 mL) and (dropwise) a solution of iodine (229 mg; 0.898 mmol) in methanol (4 mL). The reaction mixture was stirred at 0° C. for 2 hours, and then a 10% aqueous solution of sodium thiosulfate was added dropwise until the disappearance of the brown color. The reaction mixture was partitioned between ethyl acetate and water, and the organic layer dried with brine and magnesium sulfate, filtered, and evaporated in vacuo to yield 101.8 mg (88%) of the title compound which was carried forward without further purification. LCMS (ESI): M+H=264.0; $^1$H NMR (400 MHz, DMSO) δ 8.72 (s, 1H), 3.91 (s, 3H), 2.54 (s, 3H).

Step 2: 2-(5-bromo-3-chloro-4-methylpyridin-2-yl) propan-2-ol

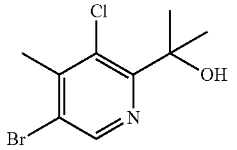

To a −10° C. solution of methyl 5-bromo-3-chloro-4-methyl-pyridine-2-carboxylate (101.8 mg; 0.3849 mmol) in tetrahydrofuran (2.0 mL; 25 mmol) was added methylmagnesium chloride (3.0 mol/L) in tetrahydrofuran (0.30 mL; 0.90 mmol). After one hour, the reaction was quenched with saturated aqueous ammonium chloride. The reaction mixture was diluted with ethyl acetate, washed with water and brine, dried over magnesium sulfate, filtered, and evaporated in vacuo. The crude product was purified via flash chromatography on silica gel (12 g silica, solvent gradient: 0-100% ethyl acetate in dichloromethane) to yield 74.0 mg (73%) of the title compound. LCMS (ESI): M+H=264.2; $^1$H NMR (400 MHz, DMSO) δ 8.59 (s, 1H), 5.32 (s, 1H), 2.53 (s, 3H), 1.57 (s, 6H).

Example 171

(1S,2S)-2-fluoro-N-(7-(2-(hydroxymethyl)-4-methylpyridin-3-yl)isoquinolin-3-yl)cyclopropanecarboxamide

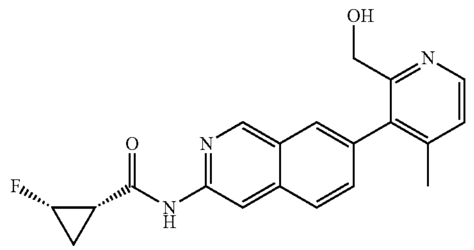 [SMILES: Cc1ccnc(CO)c1-c1ccc2cc(NC(=O)[C@@H]3C[C@@H]3F)ncc2c1]

Step 1: (1S,2S)-N-(7-bromoisoquinolin-3-yl)-2-fluorocyclopropanecarboxamide

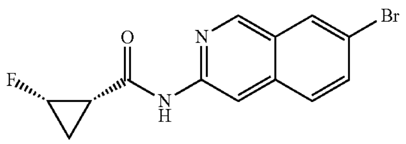 [SMILES: O=C(Nc1cc2ccc(Br)cc2cn1)[C@@H]1C[C@@H]1F]

A mixture of 7-bromoisoquinolin-3-amine (4.531 g, 20.31 mmol), (1S,2S)-2-fluorocyclopropanecarboxylic acid (2.002 g, 19.24 mmol), (7-azabenzotriazol-1-yloxy)tripyrrolidinophosphonium hexafluorophosphate (12.148 g, 23.433 mmol), N,N-diisopropylethylamine (8.50 mL, 48.8 mmol), 4-dimethylaminopyridine (0.245 g, 2.00 mmol), and N,N-dimethylformamide (100 mL, 1000 mmol) was stirred at 50° C. for 18 hours. The reaction mixture was cooled to room temperature, diluted with ethyl acetate, washed with water and brine, dried over $MgSO_4$, filtered, and concentrated. The crude residue was purified via flash chromatography on silica gel (120 g silica, solvent gradient: 0-30% ethyl acetate in dichloromethane) to yield 6.5208 g of the title compound. LCMS (ESI): M+H=309.2.

Step 2: (1S,2S)-2-fluoro-N-(7-(4,4,5,5-tetramethyl-1,3,2-dioxaborolan-2-yl)isoquinolin-3-yl)cyclopropanecarboxamide

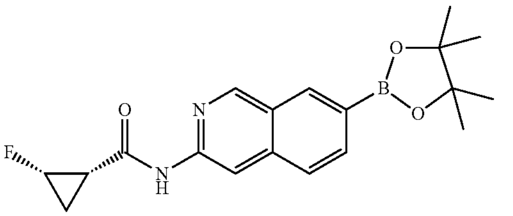 [SMILES: CC1(C)OB(c2ccc3cc(NC(=O)[C@@H]4C[C@@H]4F)ncc3c2)OC1(C)C]

The title compound was prepared following a procedure similar to Example 12 (Step 1) using (1S,2S)-N-(7-bromoisoquinolin-3-yl)-2-fluorocyclopropanecarboxamide; 1.5477 g (46% yield). LCMS (ESI): M+H=357.2; $^1$H NMR (400 MHz, DMSO) δ 10.95 (s, 1H), 9.22 (s, 1H), 8.44 (s, 1H), 8.43 (s, 1H), 7.87 (d, J=8.4 Hz, 1H), 7.83 (d, J=8.4 Hz, 1H), 5.07-4.81 (m, 1H), 2.28 (m, 1H), 1.69 (m, 1H), 1.34 (s, 12H), 1.23-1.18 (m, 1H).

Step 3: (1S,2S)-2-fluoro-N-(7-(2-(hydroxymethyl)-4-methylpyridin-3-yl)isoquinolin-3-yl)cyclopropanecarboxamide

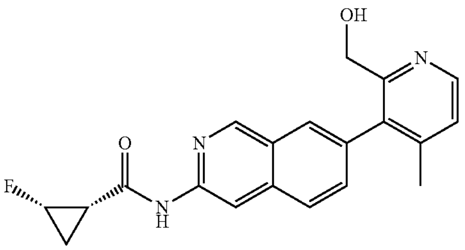 [SMILES: Cc1ccnc(CO)c1-c1ccc2cc(NC(=O)[C@@H]3C[C@@H]3F)ncc2c1]

A mixture of (1S,2S)-2-fluoro-N-(7-(4,4,5,5-tetramethyl-1,3,2-dioxaborolan-2-yl)isoquinolin-3-yl)cyclopropanecarboxamide (56.5 mg; 0.159 mmol), (3-bromo-4-methylpyridin-2-yl)methanol (75 mg; 0.37120 mmol), bis(di-tert-butyl(4-dimethylaminophenyl)phosphine)dichloropalladium(II) (9.1 mg; 0.013 mmol), potassium carbonate (65.2 mg; 0.472 mmol), dioxane (2.0 mL; 23 mmol), and water (0.2 mL; 10 mmol) was subjected to microwave irradiation at 100° C. for 60 minutes. The reaction mixture was diluted with ethyl acetate, washed with water and brine, dried over magnesium sulfate, filtered, and evaporated in vacuo. The crude reaction mixture was purified via reverse-phase preparatory HPLC and lyophilized to yield 3.9 mg (7%) of the title compound. LCMS (ESI): $R_T$ (min)=2.16, M+H=352.2, method=H; $^1$H NMR (400 MHz, DMSO) δ 10.96 (s, 1H), 9.15 (s, 1H), 8.53 (s, 1H), 8.48 (d, J=5.0 Hz, 1H), 7.97 (d, J=8.5 Hz, 1H), 7.94 (s, 1H), 7.57 (d, J=8.4 Hz, 1H), 7.34 (d, J=5.0 Hz, 1H), 4.95 (m, 2H), 4.25 (s, 2H), 2.28 (m, 1H), 2.07 (s, 3H), 1.77-1.61 (m, 1H), 1.28-1.12 (m, 1H).

Example 172

3-(3-aminoisoquinolin-7-yl)-N-cyclobutyl-4-methylbenzamid

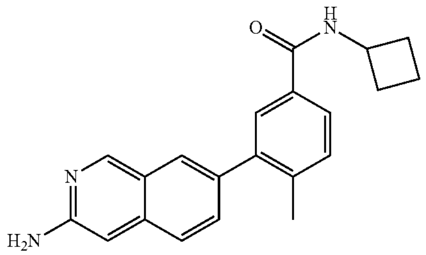

Step 1: 3-(3-aminoisoquinolin-7-yl)-4-methylbenzoic acid

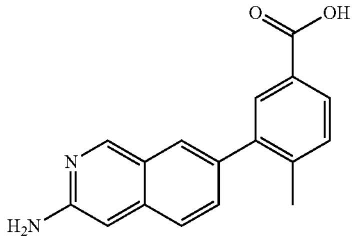 [SMILES: Cc1ccc(C(=O)O)cc1-c1ccc2cc(N)ncc2c1]

A mixture of 7-bromoisoquinolin-3-amine (299.9 mg; 1.344 mmol), 4-methyl-3-(4,4,5-trimethyl-1,3,2-dioxaborolan-2-yl)benzoic acid (387.1 mg; 1.560 mmol), bis(di-tert-butyl(4-dimethylaminophenyl)phosphine)dichloropalladium(II) (51.5 mg; 0.0727 mmol), potassium carbonate (569.3 mg; 4.119 mmol), dioxane (10 mL) and water (1 mL) was stirred at 90° C. for 24 hours and then cooled to room temperature. The reaction mixture was acidified with 10% aqueous citric acid (10 mL). The product was recovered as a red-brown precipitate via filtration, rinsed with water and ethyl acetate, and dried under vacuum to yield 253.4 mg (68%) of the title compound which was carried forward without additional purification. LCMS (ESI): M+H=279.2; $^1$H NMR (400 MHz, DMSO) δ 8.87 (s, 1H), 7.84 (d, J=7.9 Hz, 1H), 7.81 (d, J=13.1 Hz, 2H), 7.59 (d, J=8.6 Hz, 1H), 7.46 (t, J=9.5 Hz, 2H), 6.67 (s, 1H), 5.96 (s, 2H), 2.34 (s, 3H).

Step 2: 3-(3-aminoisoquinolin-7-yl)-N-cyclobutyl-4-methylbenzamide

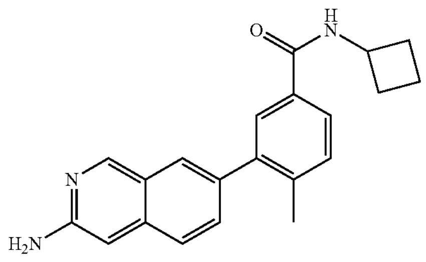

A mixture of 3-(3-aminoisoquinolin-7-yl)-4-methylbenzoic acid (43.0 mg; 0.155 mmol), cyclobutylamine (27 μL; 0.310 mmol), (7-azabenzotriazol-1-yloxy)tripyrrolidinophosphonium hexafluorophosphate (129.5 mg; 0.2384 mmol), N,N-diisopropylethylamine (0.1 mL; 0.6 mmol), 4-(dimethylamino)pyridine (0.1 equiv.; 0.0155 mmol) and N,N-dimethylformamide (2.0 mL; 26 mmol) was stirred at room temperature for 2 hours. The reaction mixture was diluted with ethyl acetate, washed with water (2×) and brine, dried over magnesium sulfate, and filtered through a plug of silica gel, rinsing with additional ethyl acetate. The filtrate was evaporated in vacuo to yield 53.6 mg crude product. 20.2 mg of crude product was purified via preparatory reverse-phase HPLC and lyophilized to yield 4.2 mg of the title compound. LCMS (ESI): $R_T$ (Min)=2.88, M+H=327.3, method=H; $^1$H NMR (400 MHz, DMSO) δ 8.87 (s, 1H), 8.56 (d, J=8.0 Hz, 1H), 7.82-7.74 (m, 3H), 7.60 (d, J=8.6 Hz, 1H), 7.49 (d, J=8.6 Hz, 1H), 7.39 (d, J=7.9 Hz, 1H), 6.67 (s, 1H), 5.95 (s, 2H), 4.50-4.34 (m, 1H), 2.31 (s, 3H), 2.26-2.13 (m, 2H), 2.06 (m, 2H), 1.73-1.57 (m, 2H).

Example 173

3-(3-(cyclopropanecarboxamido)isoquinolin-7-yl)-N-(1-(hydroxymethyl)cyclobutyl)-4-methylbenzamide

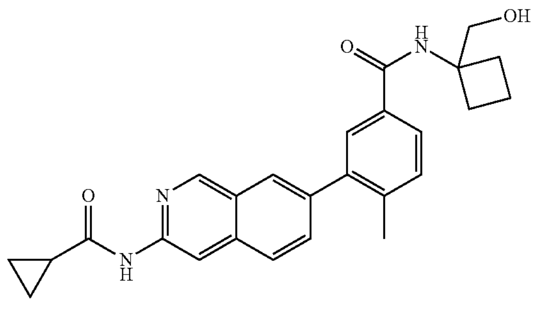 [SMILES: Cc1ccc(C(=O)NC2(CO)CCC2)cc1-c1ccc2cc(NC(=O)C3CC3)ncc2c1]

Step 1: ethyl 1-(3-(3-(cyclopropanecarboxamido)isoquinolin-7-yl)-4-methylbenzamido)cyclobutanecarboxylate

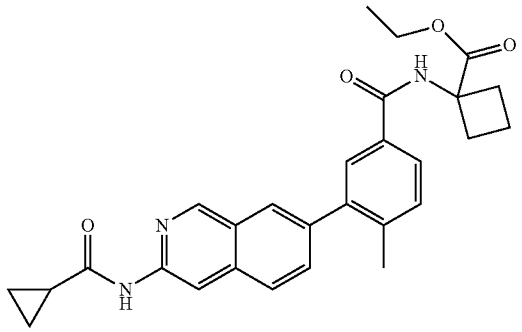 [SMILES: CCOC(=O)C1(NC(=O)c2ccc(C)c(-c3ccc4cc(NC(=O)C5CC5)ncc4c3)c2)CCC1]

The title compound was prepared following a procedure similar to Example 20 using 1-amino-cyclobutane-carboxylic acid ethyl ester hydrochloride, and was carried forward without purification. LCMS (ESI): M+H=472.2.

Step 2: 3-(3-(cyclopropanecarboxamido)isoquinolin-7-yl)-N-(1-(hydroxymethyl)cyclobutyl)-4-methylbenzamide

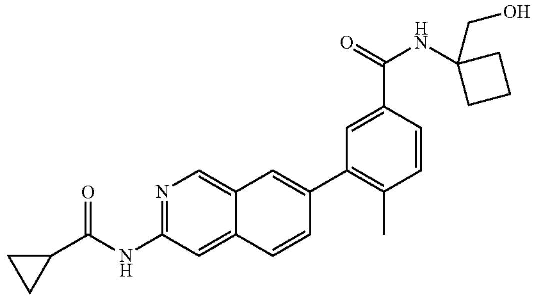 [SMILES: Cc1ccc(C(=O)NC2(CO)CCC2)cc1-c1ccc2cc(NC(=O)C3CC3)ncc2c1]

To a solution of ethyl 1-(3-(3-(cyclopropanecarboxamido)isoquinolin-7-yl)-4-methylbenzamido)cyclobutanecarboxylate (153.8 mg; 0.3261 mmol) in tetrahydrofuran (5.0 mL; 62 mmol) at 0° C. was dropwise added lithium aluminum hydride (1.0 M in THF) (0.50 mL; 0.50 mmol). The reaction mixture was stirred at 0° C. for 1.5 hours, followed by the addition of lithium aluminum hydride (1.0 M in THF) (0.20 mL; 0.2 mmol). After an additional 3 hours, the reaction was quenched by the sequential addition of 27 μL water, 27 μL 15% aqueous NaOH, and 80 μL water. The reaction mixture was diluted with dichloromethane, dried over $MgSO_4$, filtered through celite, and evaporated in vacuo to yield 109.2 mg crude product. 36.8 mg of the crude product was purified via preparatory reverse-phase HPLC and lyophilized to yield 14.7 mg of the title compound. LCMS (ESI): $R_T$ (min)=3.55, M+H=430.3, method=H; $^1$H NMR (400 MHz, DMSO) δ 10.90 (s, 1H), 9.19 (s, 1H), 8.51 (s, 1H), 8.24 (s, 1H), 8.04 (s, 1H), 7.94 (d, J=8.5 Hz, 1H), 7.86 (s, 1H), 7.81 (d, J=8.0 Hz, 1H), 7.73 (d, J=8.5 Hz, 1H), 7.42 (d, J=8.0 Hz, 1H), 4.78 (t, J=5.8 Hz, 1H), 3.64 (d, J=5.8 Hz, 2H), 2.32 (s, 3H), 2.24 (m, 2H), 2.17-2.01 (m, 3H), 1.91-1.63 (m, 2H), 0.85 (m, 4H).

Example 174

3-(3-aminoisoquinolin-7-yl)-2-fluoro-4-methyl-N-(3-methyloxetan-3-yl)benzamide

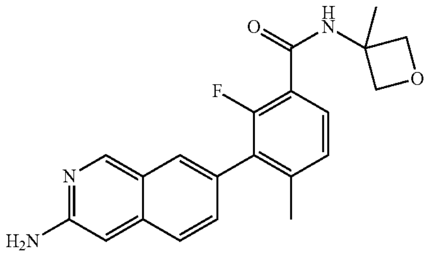

Step 1: 2-fluoro-3-iodo-4-methylbenzonitrile

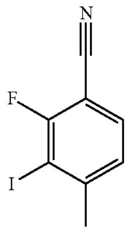

To a mixture of 2,2,6,6-tetramethyl-piperidine (4.50 mL, 26.6 mmol) and tetrahydrofuran (40 mL, 500 mmol) at −78° C. was slowly added n-butyllithium (2.5 mol/L in hexane, 11.5 mL, 28.8 mmol). The reaction vessel was transferred to a 0° C. ice bath for 60 minutes and then recooled at −78° C. 2-fluoro-4-methylbenzonitrile (3.1095 g, 23.010 mmol) as a solution in tetrahydrofuran (20 mL, 200 mmol) was then slowly added. The reaction mixture was stirred at −78° C. for 2 hours, and then a solution of iodine (7.33 g, 28.9 mmol) in tetrahydrofuran (10 mL, 100 mmol) was slowly added and then the reaction mixture was allowed to warm to room temperature. After 1.5 hours the reaction mixture was poured into a solution of sodium thiosulfate (20 g) in water (40 mL) and stirred at room temperature for 15 minutes. The layers were separated, and the aqueous layer extracted with ethyl acetate. The organic layers were combined, dried over $MgSO_4$, filtered, and evaporated in vacuo. The crude product was purified via flash chromatography on silica gel (80 g silica, solvent gradient 0-10% ethyl acetate in heptanes) to yield a mixture of regioisomeric products, with the desired product as the major component (3.9385 g, 76% pure). LCMS (ESI): M+H=262.1; $^1$H NMR (400 MHz, $CDCl_3$) δ 7.51-7.44 (m, 1H), 7.14 (d, J=7.9 Hz, 1H), 2.56 (s, 3H).

Step 2: 2-fluoro-3-iodo-4-methylbenzoic acid

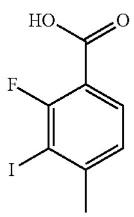

To a solution of 2-fluoro-3-iodo-4-methylbenzonitrile (3.9385 g, 11.316 mmol; 76% mass % pure) in 1,4-dioxane (10.0 mL, 128 mmol) was added water (4.0 mL, 220 mmol) and sulfuric acid (6.0 mL, 110 mmol). The reaction mixture was heated at 110° C. for 20 hours. The reaction mixture was cooled to room temperature and then poured into ~200 mL ice water. The resulting tan precipitate was collected by filtration, washed with water and ethyl acetate, and dried under vacuum to provide the title product. The filtrate was transferred to a separatory funnel, and the ethyl acetate layer was separated, washed with brine, dried over $MgSO_4$, and evaporated in vacuo to yield additional desired product for a combined yield of 3.8743 g which was carried forward without purification.

Step 3: 3-(3-aminoisoquinolin-7-yl)-2-fluoro-4-methylbenzoic acid

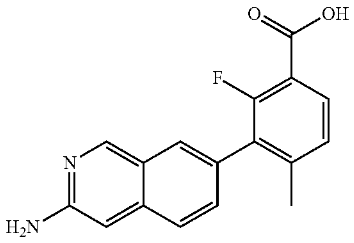

The title compound was prepared following a procedure similar to Example 172 and using 2-fluoro-3-iodo-4-methylbenzoic acid. LCMS (ESI): M+H=297.2.

Step 4: 3-(3-aminoisoquinolin-7-yl)-2-fluoro-4-methyl-N-(3-methyloxetan-3-yl)benzamide

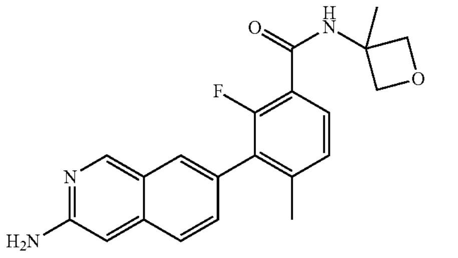

The title compound was prepared following a procedure similar to Example 172 and using 3-(3-aminoisoquinolin-7-yl)-2-fluoro-4-methylbenzoic acid. LCMS (ESI): $R_T$ (Min)=3.3880, M+H=366.1, method=E; $^1$H NMR (400 MHz, DMSO) δ 8.85 (s, 1H), 8.68 (s, 1H), 7.74 (s, 1H), 7.61 (d, J=8.6 Hz, 1H), 7.55 (t, J=7.6 Hz, 1H), 7.37 (d, J=8.5 Hz, 1H), 7.25 (d, J=8.0 Hz, 1H), 6.67 (s, 1H), 5.99 (s, 2H), 4.67 (d, J=6.3 Hz, 2H), 4.34 (d, J=6.3 Hz, 2H), 2.19 (s, 3H), 1.59 (s, 3H).

Example 175

5-(3-aminoisoquinolin-7-yl)-6-methyl-N-(3-methyloxetan-3-yl)nicotinamide

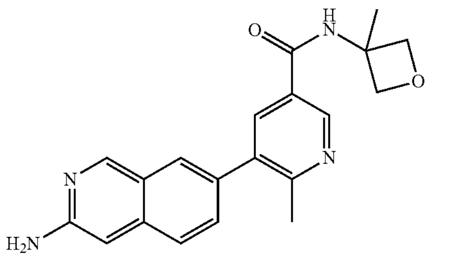 [SMILES: Cc1ncc(C(=O)NC2(C)COC2)cc1-c1ccc2cc(N)ncc2c1]

Step 1: methyl 5-bromo-6-methyl-pyridine-3-carboxylate

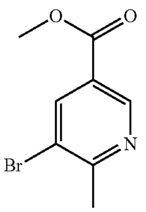

To a solution of methyl 5,6-dibromopyridine-3-carboxylate (0.5122 g; 1.737 mmol) in tetrahydrofuran (10.0 mL; 123 mmol) at 0° C. (using an oven-dried flask) was added 1,3-bis (diphenylphosphino)propane nickel(II) chloride (98.0 mg; 0.179 mmol). After 5 minutes, methylmagnesium bromide (1.4 mol/L) in THF:toluene (1:3) (1.6 mL; 2.2 mmol) was added dropwise. After addition was complete, the reaction mixture was stirred at room temperature. After 8 hours, methylmagnesium bromide (1.4 mol/L) in THF:toluene (1:3) (1.0 mL) was added and the reaction stirred at room temperature overnight. The reaction mixture was quenched with saturated aqueous $NH_4Cl$ and extracted with ethyl acetate. The organic portion was dried over $MgSO_4$, filtered, and evaporated in vacuo. The crude product was purified via flash chromatography on silica gel (25 g silica, solvent gradient: 0-30% ethyl acetate in dichloromethane) to yield 174.1 mg (44%) of the title compound. LCMS (ESI): M+H=230.2; $^1$H NMR (400 MHz, DMSO) δ 8.93 (d, J=1.4 Hz, 1H), 8.39 (d, J=1.4 Hz, 1H), 3.89 (s, 4H), 2.67 (s, 4H).

Step 2: methyl 5-(3-aminoisoquinolin-7-yl)-6-methylnicotinate

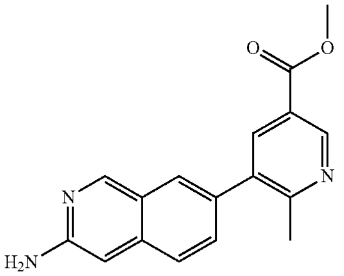 [SMILES: COC(=O)c1cnc(C)c(-c2ccc3cc(N)ncc3c2)c1]

A mixture of 7-(4,4,5,5-tetramethyl-1,3,2-dioxaborolan-2-yl)isoquinolin-3-amine (337.3 mg; 0.8742 mmol), methyl 5-bromo-6-methyl-pyridine-3-carboxylate (214.2 mg; 0.9311 mmol), bis(di-tert-butyl(4-dimethylaminophenyl) phosphine)dichloropalladium(II) (63.3 mg; 0.0894 mmol), potassium carbonate (307.2 mg; 2.223 mmol), 1,2-dimethoxyethane (3.0 mL; 28 mmol), and water (0.3 mL; 20 mmol) was subjected to microwave irradiation at 110° C. for 90 minutes. The reaction mixture was diluted with ethyl acetate, washed with water and brine, dried over magnesium sulfate, filtered, and evaporated in vacuo. The crude product was purified via flash chromatography on silica gel (40 g silica, solvent gradient: 0-10% methanol in dichloromethane) to yield 189.8 mg (74%) of the title compound. LCMS (ESI): M+H=294.2; $^1$H NMR (400 MHz, DMSO) δ 8.98 (d, J=1.9 Hz, 1H), 8.88 (s, 1H), 8.10 (d, J=1.9 Hz, 1H), 7.88 (s, 1H), 7.62 (d, J=8.6 Hz, 1H), 7.54 (d, J=8.6 Hz, 1H), 6.67 (s, 1H), 6.03 (s, 2H), 3.90 (s, 3H), 2.57 (s, 3H).

Step 3: 5-(3-aminoisoquinolin-7-yl)-6-methylnicotinic acid

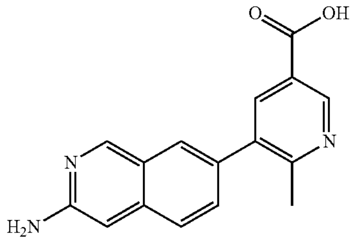

To a mixture of methyl 5-(3-aminoisoquinolin-7-yl)-6-methylnicotinate (189 mg; 0.6444 mmol) and tetrahydrofuran (4.0 mL; 49 mmol) was added lithium hydroxide (2.0 mL; 2.0 mmol). The reaction mixture was stirred at room temperature for 16 hours. The reaction mixture was acidified with 10% aqueous citric acid (2 mL), and the resulting yellow precipitate recovered via filtration, washed with water and tetrahydrofuran, and dried under vacuum to yield 114.6 mg of the title compound, which was carried forward without purification. LCMS (ESI): M+H=280.1.

Step 4: 5-(3-aminoisoquinolin-7-yl)-6-methyl-N-(3-methyloxetan-3-yl)nicotinamide

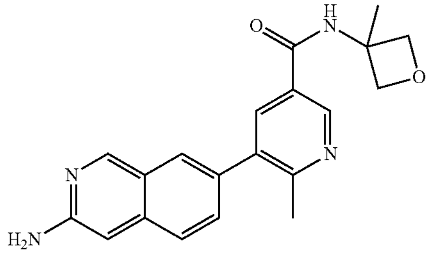 [SMILES: Cc1ncc(C(=O)NC2(C)COC2)cc1-c1ccc2cc(N)ncc2c1]

The title compound was prepared following a procedure similar to Example 172 using 5-(3-aminoisoquinolin-7-yl)-6-methylnicotinic acid; 7.1 mg (8.7% yield). LCMS (ESI): $R_T$ (min)=2.670, M+H=349.2, method=E; $^1$H NMR (400 MHz, DMSO) δ 9.02 (s, 1H), 8.90 (d, J=1.9 Hz, 1H), 8.88 (s, 1H), 8.11 (d, J=1.9 Hz, 1H), 7.87 (s, 1H), 7.63 (d, J=8.6 Hz, 1H), 7.54 (d, J=8.5 Hz, 1H), 6.68 (s, 1H), 6.02 (s, 2H), 4.72 (d, J=6.2 Hz, 2H), 4.38 (d, J=6.2 Hz, 2H), 2.53 (s, 3H), 1.62 (s, 3H).

Example 176

(1S,2S)-N-(7-(6-(2,2-difluoro-1-hydroxyethyl)-4-methylpyridin-3-yl)isoquinolin-3-yl)-2-fluorocyclopropanecarboxamide

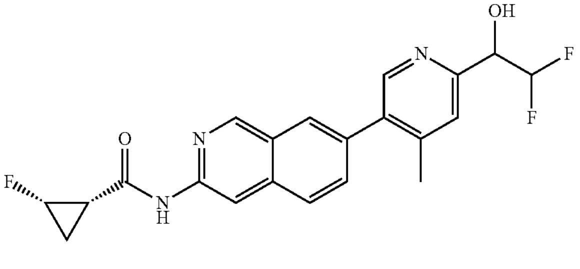 [SMILES: Cc1cc(C(O)C(F)F)ncc1-c1ccc2cc(NC(=O)[C@@H]3C[C@@H]3F)ncc2c1]

Step 1: 1-(5-bromo-4-methylpyridin-2-yl)-2,2,2-trifluoroethane-1,1-diol

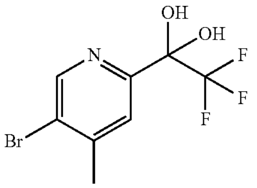

To a solution of 1-(5-bromo-4-methylpyridin-2-yl)-2,2,2-trifluoro-ethanol (345 mg; 1.2775 mmol) in dichloromethane (10 mL; 156.0 mmol) was added Dess-Martin periodinane (0.7313 g; 1.672 mmol). The reaction mixture was stirred at room temperature for 5 hours. 20 mL of a 10% aqueous solution of sodium thiosulfate was added and the reaction stirred for an additional 10 minutes. The reaction mixture was washed with 2 M aqueous sodium carbonate, dried over $MgSO_4$, filtered, and concentrated. The crude product was carried forward without purification. LCMS (ESI): M+H=286.0; $^1$H NMR (400 MHz, DMSO) δ 8.70 (s, 1H), 7.72 (s, 1H), 7.59 (s, 2H), 2.43 (s, 3H).

Step 2: 1-(5-bromo-4-methylpyridin-2-yl)-2,2,2-trifluoro-N-(4-methoxybenzylidene)ethanamine

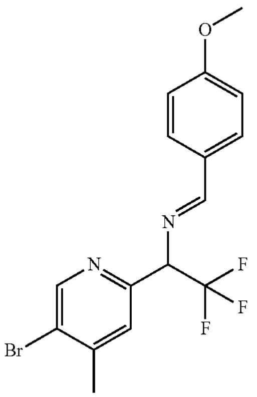 [SMILES: COc1ccc(/C=N/C(c2cc(C)c(Br)cn2)C(F)(F)F)cc1]

A solution of 1-(5-bromo-4-methylpyridin-2-yl)-2,2,2-trifluoroethane-1,1-diol (163.1 mg; 0.5702 mmol) in 2.0 mL toluene was added at room temperature to a solution of 4-methoxybenzylamine (118 μL; 0.858 mmol) and acetic acid (49 μL; 0.854 mmol) in 2.0 mL toluene. A scoop of oven-dried 3 A molecular sieves was added, and the reaction mixture heated at 110° C. for 3 days. The mixture was poured into saturated aqueous sodium bicarbonate and extracted twice with dichloromethane. The combined organic extracts were dried over magnesium sulfate, filtered, and concentrated. The crude product was purified via flash chromatography on silica gel (24 g silica, solvent gradient: 0-100% ethyl acetate in dichloromethane) to yield 164.2 mg of the title compound. LCMS (ESI): M-(4-methoxybenzaldehyde)+H=269.2; $^1$H NMR (400 MHz, DMSO)S 8.69 (s, 1H), 8.57 (s, 1H), 7.80 (d, J=8.7 Hz, 2H), 7.66 (s, 1H), 7.05 (d, J=8.7 Hz, 2H), 5.28 (q, J=8.0 Hz, 1H), 3.82 (s, 3H), 2.41 (s, 3H).

Step 3: 1-(5-bromo-4-methylpyridin-2-yl)-2,2,2-trifluoroethanamine

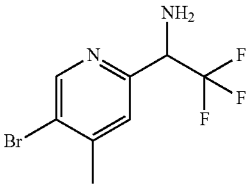

To a solution of 1-(5-bromo-4-methylpyridin-2-yl)-2,2,2-trifluoro-N-(4-methoxybenzylidene)ethanamine (77 mg; 0.1989 mmol) in dioxane (1.0 mL; 12 mmol) was added a 1 mol/L solution of hydrochloric acid in water (1.0 mL; 1.0 mmol). The reaction mixture was stirred at room temperature for 2 hours and then heated at 60° C. for 4 hours. The reaction mixture was partitioned between ethyl acetate and water. The layers were separated, and the aqueous layer adjusted to pH 7 with saturated aqueous sodium bicarbonate. The aqueous layer was extracted twice with dichloromethane. The combined dichloromethane extracts were dried over magnesium sulfate, filtered, and concentrated to yield 33.3 mg (62%) of the title compound, which was carried forward without purification. LCMS (ESI): M+H=269.2; $^1$H NMR (400 MHz, DMSO) δ 8.67 (s, 1H), 7.59 (s, 1H), 4.54 (dd, J=15.9, 7.9 Hz, 1H), 2.55 (d, J=7.8 Hz, 2H), 2.39 (s, 3H).

Step 4: (1S,2S)-N-(7-(6-(2,2-difluoro-1-hydroxyethyl)-4-methylpyridin-3-yl)isoquinolin-3-yl)-2-fluorocyclopropanecarboxamide

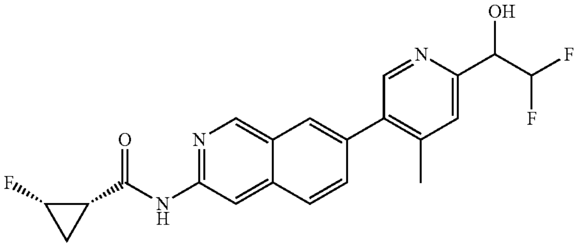 [SMILES: Cc1cc(C(O)C(F)F)ncc1-c1ccc2cc(NC(=O)[C@@H]3C[C@@H]3F)ncc2c1]

A mixture of (1S,2S)-2-fluoro-N-(7-(4,4,5,5-tetramethyl-1,3,2-dioxaborolan-2-yl)isoquinolin-3-yl)cyclopropanecarboxamide (53 mg; 0.1488 mmol), 1-(5-bromo-4-methylpyridin-2-yl)-2,2,2-trifluoroethanamine (32 mg; 0.11893 mmol), bis(di-tert-butyl(4-dimethylaminophenyl)phosphine)dichloropalladium(II) (8.2 mg; 0.012 mmol), potassium carbonate (51.3 mg; 0.371 mmol), dioxane (1.5 mL; 18 mmol), and water (0.2 mL; 10 mmol) was subjected to microwave irradiation at 110° C. for 30 minutes. LCMS analysis indicated complete conversion to the corresponding 2,2,2-trifluoro-1-imino-ethyl product instead of the expected 2,2,2-trifluoro-2-aminoethyl product. The reaction mixture was diluted with ethyl acetate, washed with water and brine, dried over magnesium sulfate, filtered, and concentrated. The resulting residue was taken up in 5 mL methanol and treated with sodium borohydride (17 mg; 0.444854 mmol) and stirred at room temperature for 2 hours. The reaction mixture was partitioned between water and ethyl acetate, and the organic layer washed with brine, dried over magnesium sulfate, and concentrated. The crude product was purified and the preparatory SFC to yield 13.4 mg (28%) of the title compound, presumably due to aqueous hydrolysis of the imine to the ketone, followed by reduction to produce the 2,2-difluoro-1-hydroxy-ethyl product. LCMS (ESI): $R_T$ (Min)=3.589, M+H=402.2, method=E; $^1$H NMR (400 MHz, DMSO) δ 10.98 (s, 1H), 9.20 (s, 1H), 8.53 (s, 1H), 8.48 (s, 1H), 8.11 (s, 1H), 7.99 (d, J=8.6 Hz, 1H), 7.77 (d, J=8.5 Hz, 1H), 7.55 (s, 1H), 6.36 (d, J=5.4 Hz, 1H), 6.29 (t of d, d J=3.2 Hz, 1H), 5.06-4.83 (m, 2H), 2.36 (s, 3H), 2.29 (m, 1H), 1.70 (ddd, J=23.3, 10.5, 6.8 Hz, 1H), 1.29-1.12 (m, 1H).

Example 177

3-(3-amino-4-chloroisoquinolin-7-yl)-4-methyl-N-(1-methylcyclobutyl)benzamide

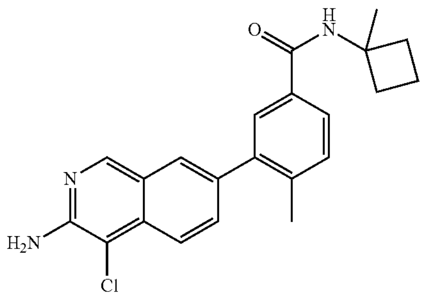 [SMILES: Cc1ccc(C(=O)NC2(C)CCC2)cc1-c1ccc2c(Cl)c(N)ncc2c1]

A solution of 3-(3-aminoisoquinolin-7-yl)-4-methyl-N-(1-methylcyclobutyl)benzamide (50.0 mg; 0.145 mmol) in dichloromethane (3 mL; 46.80 mmol) was treated with N-chlorosuccinimide (27.9 mg; 0.209 mmol). The reaction mixture was stirred at room temperature for 7 hours. The crude reaction mixture was filtered through a plug of silica gel, which was rinsed with ethyl acetate. The filtrate was evaporated in vacuo and the resulting residue was purified via preparatory reverse-phase HPLC and lyophilized to yield 17.3 mg (32%) of the title compound. LCMS (ESI): $R_T$ (min)=5.078, M+H=380.2, method=E; $^1$H NMR (400 MHz, DMSO) δ 8.92 (s, 1H), 8.35 (s, 1H), 7.94 (s, 1H), 7.86 (d, J=8.8 Hz, 1H), 7.80 (s, 1H), 7.78 (d, J=8.0 Hz, 1H), 7.72 (d, J=8.9 Hz, 1H), 7.40 (d, J=7.9 Hz, 1H), 6.36 (s, 2H), 2.39-2.32 (m, 2H), 2.31 (s, 3H), 2.02-1.93 (m, 2H), 1.86-1.75 (m, 2H), 1.47 (s, 3H).

Example 178

(1S,2S)-2-fluoro-N-(7-(4-methyl-6-(methylsulfinyl)pyridin-3-yl)isoquinolin-3-yl)cyclopropanecarboxamide

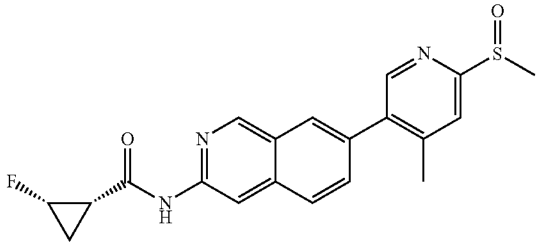 [SMILES: Cc1cc(S(C)=O)ncc1-c1ccc2cc(NC(=O)[C@@H]3C[C@@H]3F)ncc2c1]

Step 1: 7-(6-fluoro-4-methylpyridin-3-yl)isoquinolin-3-amine

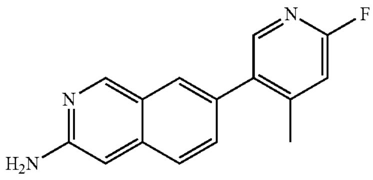 [SMILES: Cc1cc(F)ncc1-c1ccc2cc(N)ncc2c1]

A mixture of 7-bromoisoquinolin-3-amine (410.5 mg; 1.840 mmol), (6-fluoro-4-methyl-3-pyridyl)boronic acid (374.1 mg; 2.414 mmol), bis(di-tert-butyl(4-dimethylaminophenyl)phosphine)dichloropalladium(II) (70.4 mg; 0.0994 mmol), potassium carbonate (624.3 mg; 4.517 mmol), dioxane (6.0 mL; 70 mmol) and water (0.6 mL; 30 mmol) was subjected to microwave irradiation at 120° C. for 40 minutes. The reaction mixture was diluted with ethyl acetate, washed with water and brine, dried over magnesium sulfate, filtered, and evaporated in vacuo. The crude product was purified via flash chromatography on silica gel (40 g silica, solvent gradient: 20-100% ethyl acetate in dichloromethane) to yield 389.0 mg (83%) of the title compound. LCMS (ESI): M+H=254.2.

Step 2: 7-(4-methyl-6-(methylthio)pyridin-3-yl)isoquinolin-3-amine

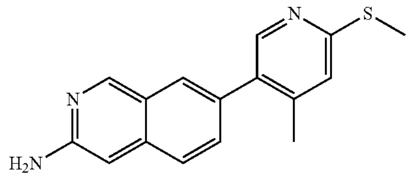 [SMILES: CSc1cc(C)c(-c2ccc3cc(N)ncc3c2)cn1]

A mixture of 7-(6-fluoro-4-methylpyridin-3-yl)isoquinolin-3-amine (389 mg; 1.536 mmol) and sodium thiomethoxide (344 mg; 4.66253 mmol) in N,N-dimethylacetamide (3.0 mL; 32 mmol) was subjected to microwave irradiation at 150° C. for 30 minutes to produce a mixture of the desired product and the demethylated thiol product. To the reaction mixture was added a 10 mol/L solution sodium hydroxide in water (1.5 mL; 15 mmol) followed by iodomethane (0.10 mL; 1.6 mmol). The reaction mixture was stirred at room temperature for 4 hours, and then additional iodomethane (0.05 mL; 0.8 mmol) was added. After an additional 4 hours, the reaction mixture was diluted with ethyl acetate, washed with water and brine, dried over magnesium sulfate, filtered, and evaporated in vacuo to yield 419.9 mg of the title compound, which was carried forward without purification. LCMS (ESI): M+H=282.2; $^1$H NMR (400 MHz, DMSO) δ 8.85 (s, 1H), 8.30 (s, 1H), 7.79 (s, 1H), 7.59 (d, J=8.6 Hz, 1H), 7.47 (d, J=8.6 Hz, 1H), 7.27 (s, 1H), 6.66 (s, 1H), 5.98 (s, 2H), 2.54 (s, 3H), 2.27 (s, 3H).

Step 3: (1S,2S)-2-fluoro-N-(7-(4-methyl-6-(methylthio)pyridin-3-yl)isoquinolin-3-yl)cyclopropanecarboxamide

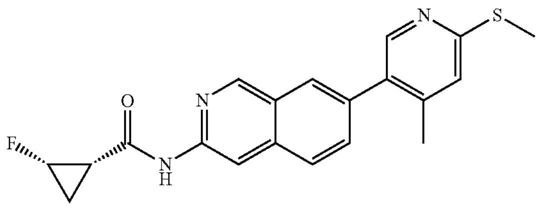 [SMILES: CSc1cc(C)c(-c2ccc3cc(NC(=O)[C@@H]4C[C@@H]4F)ncc3c2)cn1]

The title compound was prepared following a procedure similar to Example 171 using 7-(4-methyl-6-(methylthio)pyridin-3-yl)isoquinolin-3-amine. LCMS (ESI): M+H=368.2.

Step 4: (1S,2S)-2-fluoro-N-(7-(4-methyl-6-(methylsulfinyl)pyridin-3-yl)isoquinolin-3-yl)cyclopropanecarboxamide

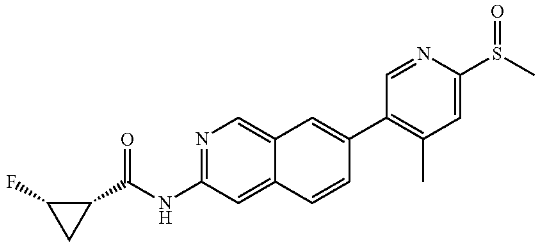 [SMILES: Cc1cc(S(C)=O)ncc1-c1ccc2cc(NC(=O)[C@@H]3C[C@@H]3F)ncc2c1]

A mixture of (1S,2S)-2-fluoro-N-(7-(4-methyl-6-(methylthio)pyridin-3-yl)isoquinolin-3-yl)cyclopropanecarboxamide (150 mg, 0.3674 mmol) and acetic acid (4.0 mL) was treated with hydrogen peroxide (35 mass % in water, 0.16 mL, 1.8 mmol) at room temperature. After 3 hours, additional hydrogen peroxide was added (35 mass % in water, 0.03 mL; 0.3 mmol). After an additional 30 minutes, the reaction mixture was poured into water (50 mL) and extracted with dichloromethane (2×50 mL). The combined organic extracts were dried over $MgSO_4$, filtered, and concentrated. The crude product was purified via preparatory reverse-phase HPLC and lyophilized to yield 63.1 mg (45%) of the title compound. LCMS (ESI): $R_T$ (Min)=4.013, M+H=384.2, method=E; $^1$H NMR (400 MHz, DMSO) δ 1H NMR (400 MHz, DMSO) δ 11.00 (s, 1H), 9.22 (s, 1H), 8.61 (s, 1H), 8.54 (s, 1H), 8.15 (s, 1H), 8.01 (d, J=8.6 Hz, 1H), 7.91 (s, 1H), 7.80 (d, J=8.5 Hz, 1H), 4.96 (m, 1H), 2.86 (s, 3H), 2.46 (s, 3H), 2.35-2.24 (m, 1H), 1.78-1.63 (m, 1H), 1.29-1.12 (m, 1H).

Example 179

(1S,2S)-N-(7-(6-((R)-1-amino-2,2,2-trifluoroethyl)-4-methylpyridin-3-yl)isoquinolin-3-yl)-2-fluoro cyclopropanecarboxamide and (1S,2S)-N-(7-(6-((S)-1-amino-2,2,2-trifluoroethyl)-4-methylpyridin-3-yl) isoquinolin-3-yl)-2-fluoro cyclopropanecarboxamide

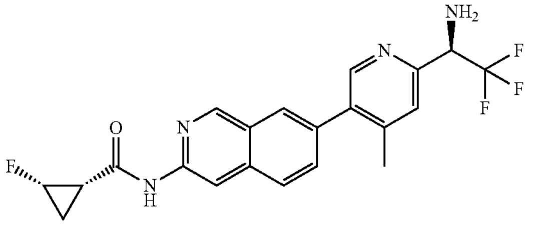

And

-continued

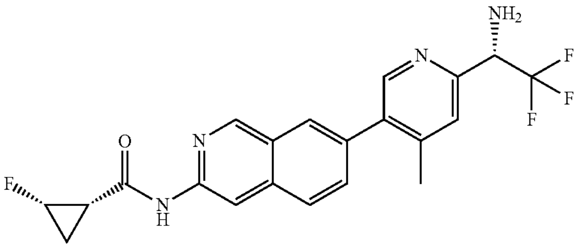

Step 1: (1S,2S)-2-fluoro-N-(7-(4-methyl-6-(2,2,2-trifluoro-1-hydroxyethyl)pyridin-3-yl)isoquinolin-3-yl)cyclopropanecarboxamide

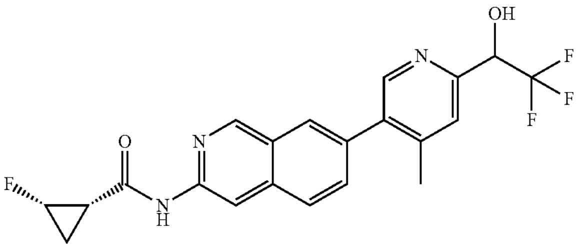 [SMILES: Cc1cc(C(O)C(F)(F)F)ncc1-c1ccc2cc(NC(=O)[C@@H]3C[C@@H]3F)ncc2c1]

The title compound was prepared following a procedure similar to Example 171 using 1-(4-bromo-5-methylpyridin-2-yl)-2,2,2-trifluoroethanol. LCMS (ESI): M+H=420.2.

Step 2: (1S,2S)-2-fluoro-N-(7-(4-methyl-6-(2,2,2-trifluoro-1,1-dihydroxyethyl)pyridin-3-yl)isoquinolin-3-yl)cyclopropanecarboxamide

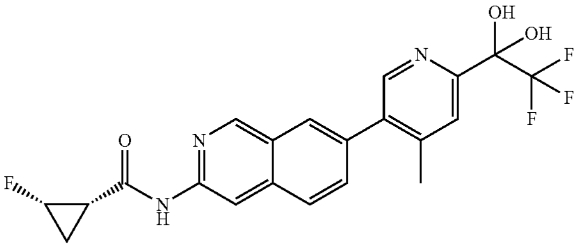 [SMILES: Cc1cc(C(O)(O)C(F)(F)F)ncc1-c1ccc2cc(NC(=O)[C@@H]3C[C@@H]3F)ncc2c1]

A solution of (1S,2S)-2-fluoro-N-(7-(4-methyl-6-(2,2,2-trifluoro-1-hydroxyethyl)pyridin-3-yl)isoquinolin-3-yl)cyclopropanecarboxamide (139.1 mg; 0.3317 mmol) in dichloromethane (5 mL; 78.00 mmol) was treated with Dess-Martin periodinane (172.7 mg; 0.3950 mmol) and stirred at room temperature. After 3 hours, additional Dess-Martin periodinane was added (142 mg). After an additional 5 hours, 30 mL of 10% aqueous sodium thiosulfate was added and the reaction mixture stirred for 10 minutes. The reaction mixture was washed with 2 M aqueous sodium carbonate, dried over $MgSO_4$, filtered, and concentrated to yield 113.8 mg (79%) of the title compound. LCMS (ESI): M+H=436.2.

Step 3: (1S,2S)-2-fluoro-N-(7-(4-methyl-6-((Z)-2,2,2-trifluoro-1-(4-methoxybenzylimino)ethyl)pyridin-3-yl)isoquinolin-3-yl)cyclopropanecarboxamide

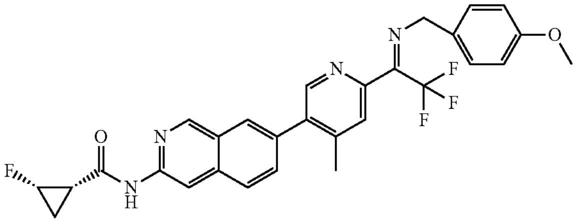 [SMILES: COc1ccc(C/N=C(/c2cc(C)c(-c3ccc4cc(NC(=O)[C@@H]5C[C@@H]5F)ncc4c3)cn2)C(F)(F)F)cc1]

To a mixture of (1S,2S)-2-fluoro-N-(7-(4-methyl-6-(2,2,2-trifluoro-1,1-dihydroxyethyl)pyridin-3-yl)isoquinolin-3-yl) cyclopropanecarboxamide (113.8 mg; 0.2614 mmol) and toluene (2 mL) was added a scoop of oven-dried 4 angstrom molecular sieves and a premixed solution of 4-methoxybenzylamine (54 μL; 0.393 mmol) and acetic acid (23 μL; 0.401 mmol) in toluene (1 mL). The reaction mixture was then heated at 100° C. for 3 days. The reaction mixture was cooled to room temperature and partitioned between dichloromethane and saturated aqueous sodium bicarbonate. The organic layer was dried over magnesium sulfate, filtered, and evaporated in vacuo. The crude product was purified via flash chromatography on silica gel (12 g silica, solvent gradient: 0-10% methanol in dichloromethane) to yield 99.7 mg of a 1:1 mixture of the title compound and unreacted starting material. LCMS (ESI): M +H=419.2.

Step 4: (1S,2S)-N-(7-(6-((R)-1-amino-2,2,2-trifluoroethyl)-4-methylpyridin-3-yl)isoquinolin-3-yl)-2-fluoro cyclopropanecarboxamide and (1S,2S)-N-(7-(6-((S)-1-amino-2,2,2-trifluoroethyl)-4-methylpyridin-3-yl)isoquinolin-3-yl)-2-fluoro cyclopropanecarboxamide

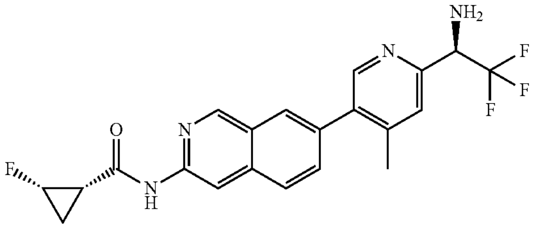

and

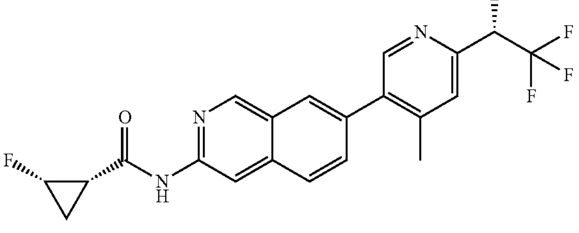

A solution of (1S,2S)-2-fluoro-N-(7-(4-methyl-6-((Z)-2,2,2-trifluoro-1-(4-methoxybenzylimino)ethyl)pyridin-3-yl) isoquinolin-3-yl)cyclopropanecarboxamide (50% pure, 99.7 mg; 0.0929 mmol) in dioxane (1.0 mL; 12 mmol) was treated with hydrochloric acid in water (1 mol/L, 1.0 mL; 1.0 mmol). The resulting mixture was stirred at 50° C. for 1.5 hours and then poured into saturated aqueous sodium bicarbonate and extracted with dichloromethane (2×50 mL). The crude product was purified via flash chromatography on silica gel (12 g silica, solvent gradient: 0-10% methanol in dichloromethane) to yield 29.7 mg as a mixture of stereoisomers. The stereoisomers were separated via chiral supercritical fluid chromotagraphy to yield 9.8 mg (25%) of one stereoisomer and 10.8 mg (28%) of the other stereoisomer.

Stereoisomer 1:

LCMS (ESI): $R_T$ (Min)=3.769, M+H=419.2, method=E; $^1$H NMR (400 MHz, DMSO) δ 10.98 (s, 1H), 9.20 (s, 1H), 8.53 (s, 1H), 8.51 (s, 1H), 8.12 (s, 1H), 7.99 (d, J=8.5 Hz, 1H), 7.78 (d, J=8.6 Hz, 1H), 7.57 (s, 1H), 4.95 (m, 1H), 4.68-4.54 (m, 1H), 2.60 (d, J=7.9 Hz, 2H), 2.35 (s, 3H), 2.28 (m, 1H), 1.78-1.63 (m, 1H), 1.27-1.17 (m, 1H).

Stereoisomer 2:

LCMS (ESI): $R_T$ (Min)=3.757, M+H=419.2, method=E; $^1$H NMR (400 MHz, DMSO) δ 10.98 (s, 1H), 9.20 (s, 1H), 8.53 (s, 1H), 8.51 (s, 1H), 8.12 (s, 1H), 7.99 (d, J=8.5 Hz, 1H), 7.78 (d, J=8.5 Hz, 1H), 7.57 (s, 1H), 5.08-4.83 (m, 1H), 4.61 (m, 1H), 2.60 (d, J=7.6 Hz, 2H), 2.35 (s, 3H), 2.33-2.24 (m, 1H), 1.70 (m, 1H), 1.28-1.14 (m, 1H).

Example 180

1S,2S)-2-fluoro-N-(7-(5-hydroxy-4-methylpyridin-3-yl)isoquinolin-3-yl)cyclopropanecarboxamide

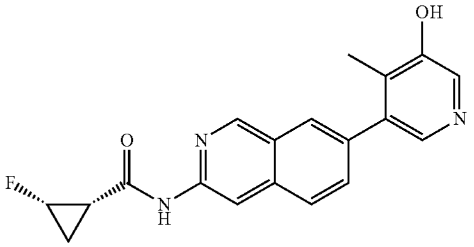

Step 1: (1S,2S)-N-(7-(5-amino-4-methylpyridin-3-yl)isoquinolin-3-yl)-2-fluorocyclopropanecarboxamide

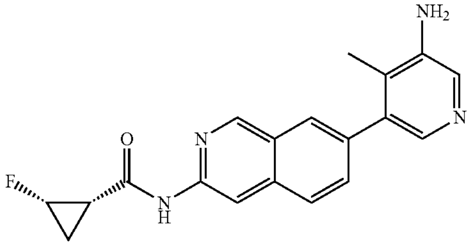

The title compound was prepared following a procedure similar to that described for Example 171 and using 5-bromo-4-methyl-pyridin-3-amine, 46.2 mg (61%). LCMS (ESI): M+H=337.2.

Step 2: (1S,2S)-2-fluoro-N-(7-(5-hydroxy-4-methylpyridin-3-yl)isoquinolin-3-yl)cyclopropanecarboxamide

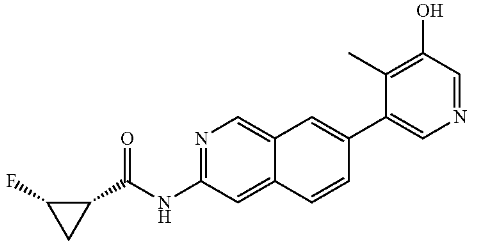 [SMILES: Cc1c(O)cncc1-c1ccc2cc(NC(=O)[C@@H]3C[C@@H]3F)ncc2c1]

To a solution of (1S,2S)-N-(7-(5-amino-4-methylpyridin-3-yl)isoquinolin-3-yl)-2-fluorocyclopropanecarboxamide (46.2 mg; 0.137 mmol) in trifluoroacetic acid (1.0 mL; 13 mmol) at 0° C. was added N-amyl nitrite (29 μL; 0.21 mmol). The reaction mixture was stirred at room temperature for 4 hours. The reaction mixture was concentrated, and then partitioned between dichloromethane and 2 M aqueous sodium carbonate. The aqueous layer was neutralized to pH 7 with citric acid, and then extracted twice more with dichloromethane. The combined dichloromethane layers were dried over magnesium sulfate and evaporated in vacuo. The crude product was purified via flash chromatography on silica gel (12 g silica, solvent gradient: 0-10% methanol in dichloromethane) followed by preparatory reverse-phase HPLC to yield 8.4 mg (18%) of the title compound. LCMS (ESI): $R_T$ (min)=3.583, M+H=338.1, method=E; $^1$H NMR (400 MHz, DMSO) δ 10.96 (s, 1H), 9.94 (broad s, 1H), 9.19 (s, 1H), 8.52 (s, 1H), 8.15 (s, 1H), 8.04 (s, 1H), 8.00 (s, 1H), 7.96 (d, J=8.6 Hz, 1H), 7.71 (d, J=8.5 Hz, 1H), 4.95 m, 1H), 2.27 (m, 1H), 2.12 (s, 3H), 1.70 (m, 1H), 1.20 (m, 1H).

Example 181

(1S,2S)-2-fluoro-N-(7-(5-fluoro-4-methylpyridin-3-yl)isoquinolin-3-yl)cyclopropanecarboxamide

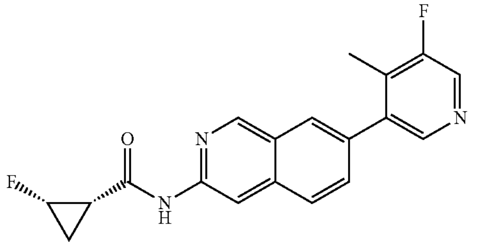

Step 1: 2-chloro-3-fluoro-4-methyl-5-(4,4,5,5-tetramethyl-1,3,2-dioxaborolan-2-yl)pyridine

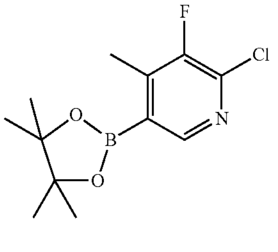 [SMILES: Cc1c(B2OC(C)(C)C(C)(C)O2)cnc(Cl)c1F]

To a −78° C. solution of 2-chloro-3-fluoro-5-iodo-4-methyl-pyridine (498.6 mg; 1.837 mmol) in tetrahydrofuran (6.0 mL; 74 mmol) was added isopropylmagnesium chloride lithium chloride complex (1.3 mol/L) in THF (5.8 mL; 7.5 mmol). The reaction mixture was warmed to room temperature and stirred for 2 hours. The mixture was then re-cooled to −78° C. and triisopropyl borate (2.20 mL; 9.34 mmol) was added. The reaction mixture was stirred at room temperature for 18 hours. The reaction mixture was quenched with a few drops of saturated aqueous ammonium chloride solution, and then a few drops of saturated aqueous sodium carbonate solution were added to cleave the boronate ester. The reaction mixture was dried over magnesium sulfate to afford the boronic acid as a THF solution. To this mixture was added pinacol (3.8865 g; 32.230 mmol), and the mixture was then heated at 40° C. for 24 hours. The reaction mixture was concentrated, absorbed onto silica gel and purified by flash chromatography (40 g silica, solvent gradient: 0-50% ethyl acetate in heptane) to yield 0.2622 g (53%) of the title compound. LCMS (ESI): M+H=272.2; $^1$H NMR (400 MHz, DMSO) δ 8.30 (s, 1H), 2.47 (d, J=2.3 Hz, 3H), 1.32 (s, 12H).

Step 2: 3-fluoro-4-methyl-5-(4,4,5,5-tetramethyl-1,3,2-dioxaborolan-2-yl)pyridine

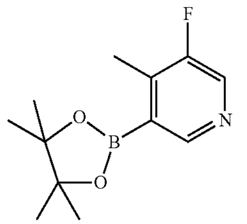 [SMILES: Cc1c(F)cncc1B1OC(C)(C)C(C)(C)O1]

A mixture of 2-chloro-3-fluoro-4-methyl-5-(4,4,5,5-tetramethyl-1,3,2-dioxaborolan-2-yl)pyridine (212 mg; 0.7808 mmol), zinc powder (155.3 mg; 2.37 mmol), and acetic acid (3.0 mL; 47 mmol) was heated at 60° C. for 3 hours. The reaction mixture was then cooled to room temperature, diluted with ethyl acetate (30 mL) filtered through celite, and evaporated under vacuum to yield the title compound in quantitative yield. LCMS (ESI): [M-pinacol]+H=156.4; $^1$H NMR (400 MHz, DMSO) δ 8.55-8.47 (m, 2H), 2.42 (d, J=2.0 Hz, 3H), 1.33 (s, 12H).

Step 3: 7-(5-fluoro-4-methylpyridin-3-yl)isoquinolin-3-amine

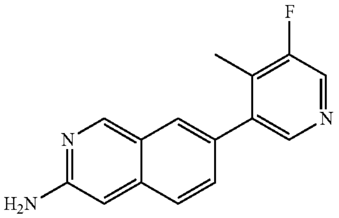

A mixture of 3-fluoro-4-methyl-5-(4,4,5,5-tetramethyl-1,3,2-dioxaborolan-2-yl)pyridine (261 mg; 0.7706 mmol), 7-bromoisoquinolin-3-amine (233.1 mg; 1.045 mmol), bis(di-tert-butyl(4-dimethylaminophenyl)phosphine)dichloropalladium(II) (52.8 mg; 0.0746 mmol), potassium carbonate (338 mg; 2.44566 mmol), acetonitrile (3.0 mL; 57 mmol) and water (0.30 mL; 17 mmol) was heated at 120° C. for 40 minutes. The reaction mixture was diluted with ethyl acetate, washed with water and brine, dried over magnesium sulfate, filtered, and evaporated in vacuo. The crude product was purified via flash chromatography on silica gel (25 g silica, solvent gradient: 0-5% methanol in dichloromethane) to yield 162.4 mg (83%) of the title compound. LCMS (ESI): M+H=254.2; $^1$H NMR (400 MHz, DMSO) δ 8.88 (s, 1H), 8.50 (s, 1H), 8.37 (s, 1H), 7.86 (s, 1H), 7.63 (d, J=8.6 Hz, 1H), 7.51 (dd, J=8.6, 1.6 Hz, 1H), 6.67 (s, 1H), 6.04 (s, 2H), 2.25 (d, J=2.0 Hz, 3H).

Step 4: (1S,2S)-2-fluoro-N-(7-(5-fluoro-4-methylpyridin-3-yl)isoquinolin-3-yl)cyclopropanecarboxamide

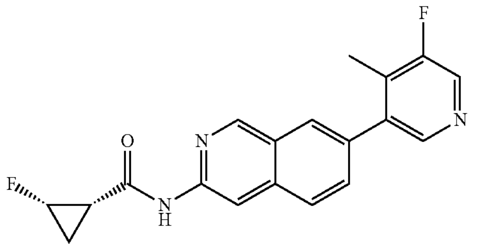 [SMILES: Cc1c(F)cncc1-c1ccc2cc(NC(=O)[C@@H]3C[C@@H]3F)ncc2c1]

A mixture of 7-(5-fluoro-4-methylpyridin-3-yl)isoquinolin-3-amine (161.4 mg; 0.6372 mmol), (1S,2S)-2-fluorocyclopropanecarboxylic acid (80.3 mg; 0.772 mmol), (7-azabenzotriazol-1-yloxy)tripyrrolidinophosphonium hexafluorophosphate (496.9 mg; 0.9149 mmol), N,N-diisopropylethylamine (0.30 mL; 1.7 mmol), 4-(dimethylamino) pyridine (0.06372 mmol) and N,N-dimethylformamide (5 mL; 64.4 mmol) was heated at 40° C. for 16 hours. The reaction mixture was diluted with ethyl acetate, washed with water and brine, dried over magnesium sulfate, filtered, and evaporated in vacuo. The crude product was purified via flash chromatography on silica gel (25 g silica, solvent gradient: 30-90% ethyl acetate in dichloromethane) followed by preparatory reverse-phase HPLC to yield 124 mg (57%) of the title compound. LCMS (ESI): $R_T$ (Min)=8.33, M+H=340.2, method=G; $^1$H NMR (400 MHz, DMSO) δ 10.99 (s, 1H), 9.21 (s, 1H), 8.55 (d, J=4.5 Hz, 2H), 8.42 (s, 1H), 8.13 (s, 1H), 8.01 (d, J=8.6 Hz, 1H), 7.78 (dd, J=8.5, 1.6 Hz, 1H), 5.06-4.85 (m, 1H), 2.34-2.27 (m, 1H), 2.26 (d, J=1.9 Hz, 3H), 1.75-1.65 (m, 1H), 1.25-1.16 (m, 1H).

Example 182

(1S,2S)-2-fluoro-N-(7-(5-fluoro-6-(2-hydroxypropan-2-yl)-4-methylpyridin-3-yl)isoquinolin-3-yl) cyclopropanecarboxamide

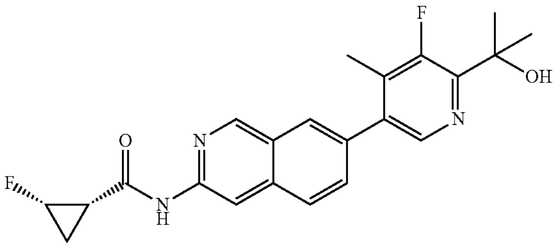 [SMILES: Cc1c(-c2ccc3cc(NC(=O)[C@@H]4C[C@@H]4F)ncc3c2)cnc(C(C)(C)O)c1F]

Step 1: (1S,2S)-N-(7-(6-chloro-5-fluoro-4-methylpyridin-3-yl)isoquinolin-3-yl)-2-fluorocyclopropanecarboxamide

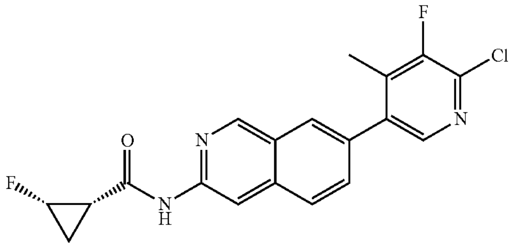 [SMILES: Cc1c(-c2ccc3cc(NC(=O)[C@@H]4C[C@@H]4F)ncc3c2)cnc(Cl)c1F]

The title compound was prepared following a procedure similar to that described for Example 12, using 2-chloro-3-fluoro-5-iodo-4-methyl-pyridine and (1S,2S)-2-fluoro-N-(7-(4,4,5,5-tetramethyl-1,3,2-dioxaborolan-2-yl)isoquinolin-3-yl)cyclopropanecarboxamide, and was carried forward without purification; 0.407 g (98%).

Step 2: methyl 3-fluoro-5-(3-((1S,2S)-2-fluorocyclopropanecarboxamido)isoquinolin-7-yl)-4-methylpicolinate

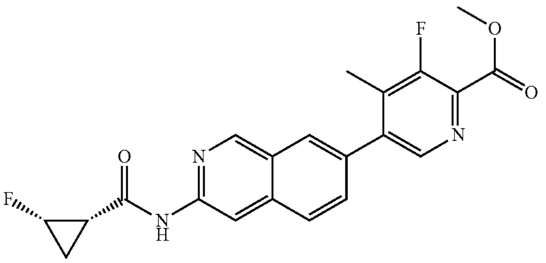 [SMILES: COC(=O)c1ncc(-c2ccc3cc(NC(=O)[C@@H]4C[C@@H]4F)ncc3c2)c(C)c1F]

A flask charged with (1S,2S)-N-(7-(6-chloro-5-fluoro-4-methylpyridin-3-yl)-isoquinolin-3-yl)-2-fluoro-cyclopropanecarboxamide (261 mg; 0.5237 mmol), palladium(II) acetate (13.7 mg; 0.0610 mmol), 1,3-bis(dicyclohexylphosphino)propane bis(tetrafluoroborate) (66.8 mg; 0.106 mmol), potassium carbonate (136.1 mg; 0.9749 mmol), N,N-dimethylformamide (3.0 mL; 38 mmol) and methanol (0.75 mL; 18 mmol) was evacuated and backfilled with CO gas 3 times, and then stirred under a balloon of CO gas at 100° C. for 20 hours. To the reaction mixture was then added triethylamine (0.20 mL; 1.4 mmol) and 1,1'-bis(diphenylphosphino)ferrocene-palladium(II)dichloride dichloromethane complex (64.9 mg; 0.0795 mmol). The reaction vessel was re-purged with CO gas and stirred at 100° C. for an additional 3 hours. The reaction mixture was diluted with ethyl acetate, washed with water and brine, dried over magnesium sulfate, filtered, and evaporated in vacuo. The crude product was purified via flash chromatography on silica gel (24 g silica, solvent gradient: 0-10% methanol in dichloromethane) to yield 134.9 mg (70% pure, 45% yield) of the title compound. LCMS (ESI): M+H=398.2.

Step 3: (1S,2S)-2-fluoro-N-(7-(5-fluoro-6-(2-hydroxypropan-2-yl)-4-methylpyridin-3-yl)isoquinolin-3-yl)cyclopropanecarboxamide

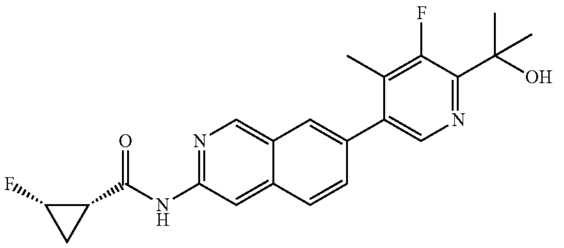 [SMILES: Cc1c(-c2ccc3cc(NC(=O)[C@@H]4C[C@@H]4F)ncc3c2)cnc(C(C)(C)O)c1F]

To a solution of methyl 3-fluoro-5-(3-((1S,2S)-2-fluorocyclopropanecarboxamido)isoquinolin-7-yl)-4-methylpicolinate (134.9 mg; 0.2376 mmol) in tetrahydrofuran (2.0 mL; 25 mmol) at −10° C. was dropwise added methylmagnesium chloride (3.0 mol/L) in tetrahydrofuran (0.35 mL; 1.1 mmol). After 30 minutes, the reaction mixture was quenched with the addition of saturated aqueous ammonium chloride. The reaction mixture was diluted with ethyl acetate, washed with water and brine, dried over magnesium sulfate, filtered, and evaporated in vacuo. The crude product was purified via flash chromatography on silica gel (12 g silica, solvent gradient: 0-100% ethyl acetate in dichloromethane) followed by preparatory reverse phase HPLC to yield 8.1 mg (9%) of the title compound. LCMS (ESI): $R_T$ (min)=4.207, M+H=398.2, method=E; $^1$H NMR (400 MHz, DMSO) δ 10.99 (s, 1H), 9.21 (s, 1H), 8.54 (s, 1H), 8.33 (s, 1H), 8.12 (s, 1H), 8.01 (d, J=8.6 Hz, 1H), 7.78 (d, J=8.5 Hz, 1H), 5.32 (s, 1H), 5.10-4.81 (m, 1H), 2.38-2.22 (m, 4H), 1.70 (m, 1H), 1.56 (s, 6H), 1.21 (m, 1H).

Example 183

(1S,2S)-2-fluoro-N-(7-(2-methoxy-4-methylpyridin-3-yl)isoquinolin-3-yl)cyclopropanecarboxamide

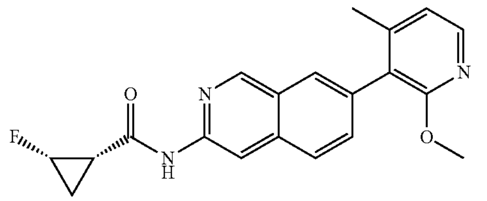 [SMILES: COc1nccc(C)c1-c1ccc2cc(NC(=O)[C@@H]3C[C@@H]3F)ncc2c1]

Step 1: 7-(2-fluoro-4-methylpyridin-3-yl)isoquinolin-3-amine

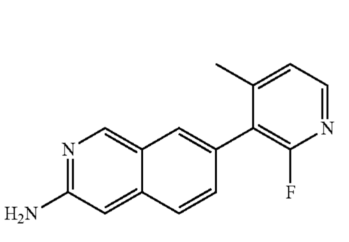 [SMILES: Cc1ccnc(F)c1-c1ccc2cc(N)ncc2c1]

The title compound was prepared following a procedure similar to that described for Example 8 using (2-fluoro-4-methyl-3-pyridyl)boronic acid. LCMS (ESI): M+H=254.2; $^1$H NMR (400 MHz, DMSO) δ 8.85 (s, 1H), 8.11 (d, J=5.1 Hz, 1H), 7.79 (s, 1H), 7.61 (d, J=8.6 Hz, 1H), 7.39 (d, J=8.5 Hz, 1H), 7.35 (d, J=5.1 Hz, 1H), 6.67 (s, 1H), 6.02 (s, 2H), 2.25 (s, 3H).

Step 2: 7-(2-methoxy-4-methylpyridin-3-yl)isoquinolin-3-amine

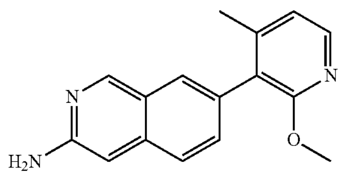 [SMILES: COc1nccc(C)c1-c1ccc2cc(N)ncc2c1]

To a solution of 7-(2-fluoro-4-methylpyridin-3-yl)isoquinolin-3-amine (94.8 mg; 0.374 mmol) in methanol (2.0 mL; 50 mmol) was added a solution of sodium methoxide (25 mass %) in methanol (1.0 mL; 4.5 mmol). The reaction mixture was heated at 50° C. for 5 days. The reaction mixture was poured into saturated aqueous sodium bicarbonate and extracted with dichloromethane (2×50 mL). The combined dichloromethane extracts were dried over magnesium sulfate, filtered, and evaporated in vacuo to yield the title compound in quantitative yield, which was carried forward without purification. LCMS (ESI): M+H=266.2; $^1$H NMR (400 MHz, DMSO) δ 8.80 (s, 1H), 8.04 (d, J=5.1 Hz, 1H), 7.64 (s, 1H), 7.55 (d, J=8.5 Hz, 1H), 7.29 (d, J=8.6 Hz, 1H), 6.98 (d, J=5.1 Hz, 1H), 6.65 (s, 1H), 5.92 (s, 2H), 3.76 (s, 3H), 2.10 (s, 3H).

Step 3: (1S,2S)-2-fluoro-N-(7-(2-methoxy-4-methylpyridin-3-yl)isoquinolin-3-yl)cyclopropanecarboxamide

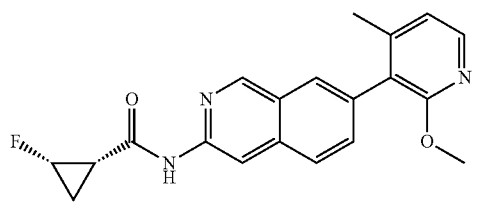 [SMILES: COc1nccc(C)c1-c1ccc2cc(NC(=O)[C@@H]3C[C@@H]3F)ncc2c1]

The title compound was prepared following a procedure similar to that described for Example 181 using 7-(2-methoxy-4-methylpyridin-3-yl)isoquinolin-3-amine; 68.5 mg (52% yield). LCMS (ESI): $R_T$ (Min)=4.728, M+H=352.2, method=E; $^1$H NMR (400 MHz, DMSO) δ 10.94 (s, 1H), 9.14 (s, 1H), 8.50 (s, 1H), 8.09 (overlapping s and d, J=5.2 Hz, 1H), 7.92 (d, J=5.4 Hz, 2H), 7.62-7.50 (m, 1H), 7.02 (d, J=5.2 Hz, 1H), 5.10-4.80 (m, 1H), 3.77 (s, 3H), 2.32-2.25 (m, 1H), 2.11 (s, 3H), 1.75-1.65 (m, 1H), 1.24-1.17 m, 1H).

Example 184

(1S,2S)-2-fluoro-N-(7-(2-(trifluoromethoxy)phenyl)-2,6-naphthyridin-3-yl)cyclopropanecarboxamide

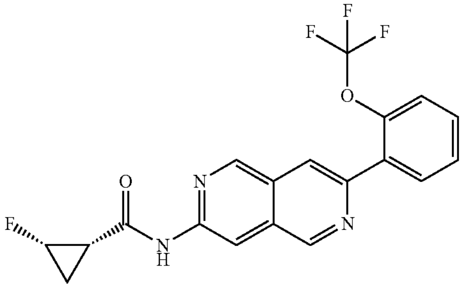 [SMILES: O=C(Nc1cc2cnc(-c3ccccc3OC(F)(F)F)cc2cn1)[C@@H]1C[C@@H]1F]

The title compound was prepared following a procedure similar to example 162 using 2-(trifluoromethoxy)phenylboronic acid: $^{1}$H NMR (400 MHz, DMSO) δ 11.21 (s, 1H), 9.50 (s, 1H), 9.37 (s, 1H), 8.68 (s, 1H), 8.25 (s, 1H), 7.94 (dd, J=7.2, 2.1 Hz, 1H), 7.65-7.50 (m, 3H), 4.97 (m, 1H), 2.31 (m, 1H), 1.72 (dtd, J=23.2, 6.8, 3.8 Hz, 1H), 1.28-1.16 (m, 1H). LCMS (Method H): $R_T$=4.26 min, M+H$^+$=392.1.

Example 185

6-(1-(tert-butyldimethylsilyloxy)-2,2,2-trifluoroethyl)-4-methylpyridin-3-ylboronic acid

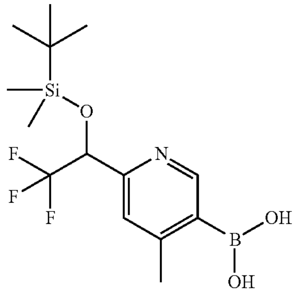 [SMILES: Cc1cc(C(O[Si](C)(C)C(C)(C)C)C(F)(F)F)ncc1B(O)O]

Step 1: 5-bromo-2-(1-(tert-butyldimethylsilyloxy)-2,2,2-trifluoroethyl)-4-methylpyridine

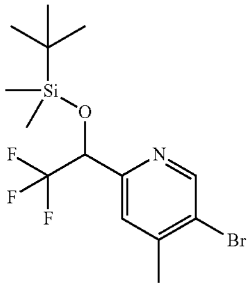 [SMILES: Cc1cc(C(O[Si](C)(C)C(C)(C)C)C(F)(F)F)ncc1Br]

A mixture of 1-(5-bromo-4-methyl-2-pyridyl)-2,2,2-trifluoro-ethanol (100 mg, 0.370 mmol), imidazole (56.02 mg, 0.815 mmol), tert-butyldimethylsilyl (115 mg, 0.741 mmol), and 4-(dimethylamino)pyridine (9.14 mg, 0.074 mmol) in dichloromethane (1 mL) was stirred overnight at room temperature. After 16 hours, the reaction mixture was diluted with ethyl acetate (20 mL) and washed with water (15 mL). The organic layer was separated, dried over sodium sulfate, filtered and concentrated in vacuo to provide a residue that was purified by flash chromatography (4 g, Silica, 0-20% ethyl acetate in heptane). Desired fractions were combined and evaporated in vacuo to afford the title compound as a colorless oil (138 mg, 96%), which was used in the next step without further purification.

Step 2: 6-(1-(tert-butyldimethylsilyloxy)-2,2,2-trifluoroethyl)-4-methylpyridin-3-ylboronic acid

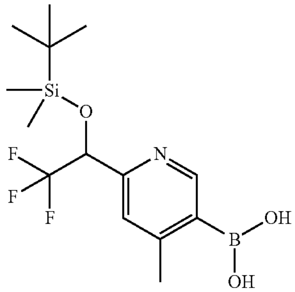 [SMILES: Cc1cc(C(O[Si](C)(C)C(C)(C)C)C(F)(F)F)ncc1B(O)O]

Isopropylmagnesium chloride lithium chloride complex (1.3 mol/L) in THF (0.72 mL, 0.94 mmol) was added to a solution of 5-bromo-2-(1-(tert-butyldimethylsilyloxy)-2,2,2-trifluoroethyl)-4-methylpyridine (120 mg, 0.312 mmol) in THF (1 mL) cooled at −78° C. The reaction mixture was warmed to room temperature and stirred for 1 hour. The mixture was then cooled at −78° C. and triisopropyl borate (0.26 ml, 1.09 mmol) was added. After 5 minutes, the reaction mixture was warmed to room temperature. After 1 hour at room temperature, the reaction was quenched with a few drops of saturated aqueous ammonium chloride solution. The reaction mixture was diluted with ethyl acetate (15 mL) and washed with water (5 ml). The organic layer was separated, dried over sodium sulfate, filtered and concentrated in vacuo to provide a residue that was purified by flash chromatography (4 g, silica, 0-10% methanol in dichloromethane). Desired fractions were combined and evaporated in vacuo to afford the title compound as a white solid (40 mg, 37%), which was used in the next step without further purification.

Example 186

(1S,2S)-2-fluoro-N-(7-(4-methyl-6-((R)-2,2,2-trifluoro-1-hydroxyethyl)pyridin-3-yl)-2,6-naphthyridin-3-yl)cyclopropanecarboxamide and (1S,2S)-2-fluoro-N-(7-(4-methyl-6-((S)-2,2,2-trifluoro-1-hydroxyethyl)pyridin-3-yl)-2,6-naphthyridin-3-yl)cyclopropanecarboxamide

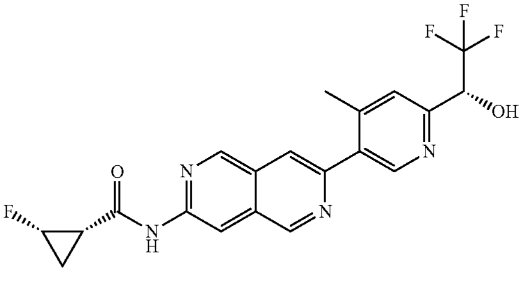

and

-continued

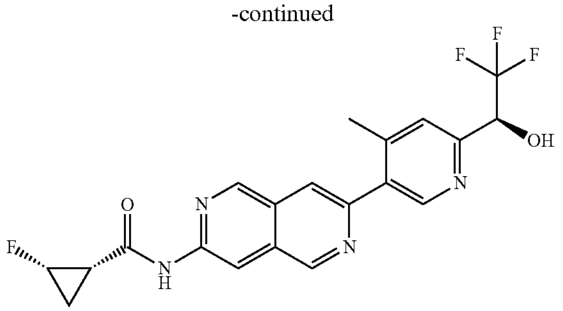

The title compounds were prepared as a racemic mixture following a procedure similar to example 162 using 6-(1-(tert-butyldimethylsilyloxy)-2,2,2-trifluoroethyl)-4-methylpyridin-3-ylboronic acid, followed by a TBAF promoted tert-butyldimethylsilyloxy deprotection in THF, and then separated via chiral supercritical fluid chromotagraphy.

Enantiomer 1:

$^1$H NMR (400 MHz, DMSO) δ 11.20 (s, 1H), 9.51 (s, 1H), 9.34 (s, 1H), 8.69 (s, 1H), 8.68 (s, 1H), 8.23 (s, 1H), 7.62 (s, 1H), 7.04 (d, J=5.9 Hz, 1H), 5.16 (m, 1H), 4.97 (m, 1H), 2.49 (s, 3H), 2.30 (m, 1H), 1.79-1.63 (m, 1H), 1.23 (m, 1H). LCMS (Method E): $R_T$=3.846 min, M+H$^+$=421.1.

Enantiomer 2:

$^1$H NMR (400 MHz, DMSO) δ 11.20 (s, 1H), 9.51 (s, 1H), 9.34 (s, 1H), 8.69 (s, 1H), 8.68 (s, 1H), 8.23 (s, 1H), 7.62 (s, 1H), 7.04 (d, J=6.1 Hz, 1H), 5.17 (m, 1H), 4.97 (m, 1H), 2.49 (s, 3H), 2.30 (m, 1H), 1.78-1.64 (m, 1H), 1.23 (m, 1H). LCMS (Method E): $R_T$=3.846 min, M+H$^+$=421.1.

Example 187

Methyl 4-methyl-5-(4,4,5,5-tetramethyl-1,3,2-dioxaborolan-2-yl)picolinate

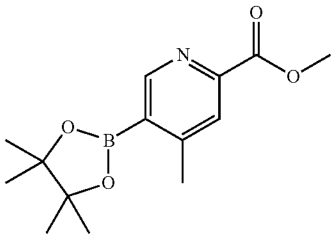

A mixture of 2-chloro-4-methyl-5-(4,4,5,5-tetramethyl-1,3,2-dioxaborolan-2-yl)pyridine (500 mg, 1.97 mmol), 1,3-bis(dicyclohexylphosphino)propane bis(tetrafluoroborate) (125 mg, 0.20 mmol), palladium(II) acetate (22 mg, 0.10 mmol), potassium carbonate (413 mg, 2.96 mmol), and methanol (1.20 mL, 29.59 mmol) in DMF (6 mL) was evacuated and then filled with nitrogen (3×), and then evacuated and filled with carbon monoxide (2×). The reaction mixture was then heated at 100° C. for 2 hours under a balloon of carbon monoxide. The cooled reaction was diluted with ethyl acetate (10 mL), filtered over Celite, and concentrated in vacuo to provide a dark red residue that was filtered through a silica plug, eluting with ethyl acetate (60 mL). The pale yellow eluent was concentrated in vacuo to afford the title compound as a yellow oil (350 mg, 64%). $^1$H NMR (400 MHz, $CDCl_3$) δ 8.92 (s, 1H), 7.91 (s, 1H), 4.00 (s, 3H), 2.59 (s, 3H), 1.36 (s, 12H).

Example 188

(1S,2S)-2-fluoro-N-(7-(6-(2-hydroxypropan-2-yl)-4-methylpyridin-3-yl)-2,6-naphthyridin-3-yl)cyclopropanecarboxamide

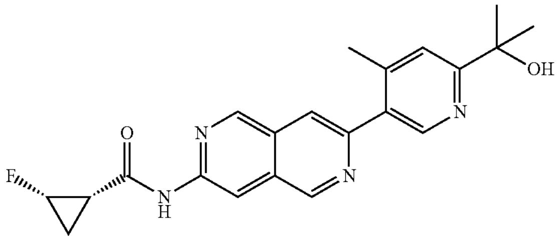 [SMILES: Cc1cc(C(C)(C)O)ncc1-c1cc2cnc(NC(=O)[C@@H]3C[C@@H]3F)cc2cn1]

Step 1: methyl 5-(7-((1S,2S)-2-fluorocyclopropanecarboxamido)-2,6-naphthyridin-3-yl)-4-methylpicolinate

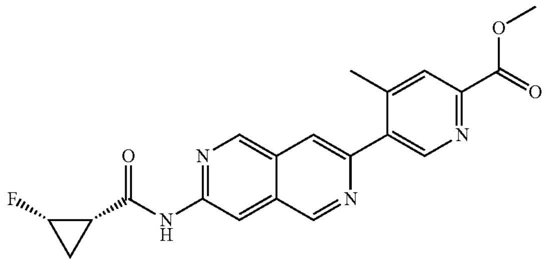 [SMILES: COC(=O)c1cc(C)c(-c2cc3cnc(NC(=O)[C@@H]4C[C@@H]4F)cc3cn2)cn1]

A mixture of (1S,2S)-N-(7-chloro-2,6-naphthyridin-3-yl)-2-fluorocyclopropanecarboxamide (100 mg, 0.376 mmol), methyl 4-methyl-5-(4,4,5,5-tetramethyl-1,3,2-dioxaborolan-2-yl)picolinate (156 mg, 0.565 mmol), bis(di-tert-butyl(4-dimethylaminophenyl)phosphine)dichloropalladium(II) (26.6 mg, 0.038 mmol) and saturated aqueous sodium carbonate solution (0.1 mL) in acetonitrile (1 mL) was heated under microwave irradiation (Biotage) at 130° C. for 30 minutes. The reaction mixture was diluted with ethyl acetate (50 mL) and washed with water (20 mL). The organic layer was separated, dried over sodium sulfate, filtered and concentrated in vacuo to provide a residue that was purified by flash chromatography (4 g, Silica, 0-100% ethyl acetate in heptane). Desired fractions were combined and evaporated in vacuo to afford the title compound as a pale yellow solid (75 mg, 52%), which was used in the next step without further purification.

Step 2: (1S,2S)-2-fluoro-N-(7-(6-(2-hydroxypropan-2-yl)-4-methylpyridin-3-yl)-2,6-naphthyridin-3-yl)cyclopropanecarboxamide

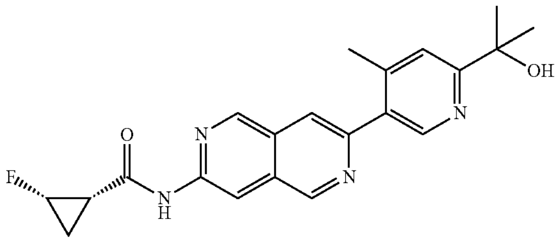 [SMILES: Cc1cc(C(C)(C)O)ncc1-c1cc2cnc(NC(=O)[C@@H]3C[C@@H]3F)cc2cn1]

To a solution of methyl 5-(7-((1S,2S)-2-fluorocyclopropanecarboxamido)-2,6-naphthyridin-3-yl)-4-methylpicolinate (75 mg, 0.197 mmol) in THF (1.5 mL) cooled at −15° C. was added methylmagnesium chloride (3.0 mol/L) in THF (0.26 mL, 0.789 mmol) dropwise over 3 minutes. After 5 minutes, the reaction was quenched with a few drops of saturated aqueous ammonium chloride solution. The reaction mixture was diluted with ethyl acetate (50 mL) and washed with water (25 mL). The organic layer was separated, dried over sodium sulfate, filtered and concentrated in vacuo to provide a residue that was purified by reverse phase HPLC (5-85% acetonitrile in water w/0.1% $NH_4OH$, 14 min). Desired fractions were combined and evaporated in vacuo to afford the title compound as an off-white solid (33 mg, 44%). $^1H$ NMR (400 MHz, DMSO) δ 11.19 (s, 1H), 9.49 (s, 1H), 9.32 (s, 1H), 8.67 (s, 1H), 8.58 (s, 1H), 8.16 (s, 1H), 7.64 (s, 1H), 5.24 (s, 1H), 4.97 (m, 1H), 2.44 (s, 3H), 2.29 (m, 1H), 1.78-1.65 (m, 1H), 1.49 (s, 6H), 1.22 (m, 1H). LCMS (Method G): $R_T$=5.65 min, M+H$^+$=381.1.

Example 189

(1S,2S)-2-fluoro-N-(7-(6-(2-hydroxypropan-2-yl)-4-methylpyridin-3-yl)isoquinolin-3-yl)cyclopropanecarboxamide

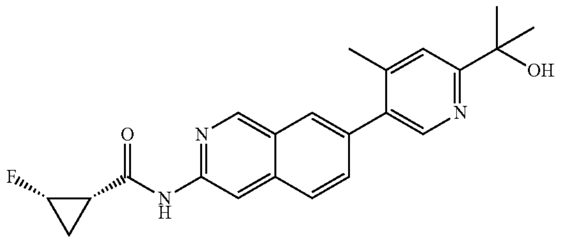 [SMILES: Cc1cc(C(C)(C)O)ncc1-c1ccc2cc(NC(=O)[C@@H]3C[C@@H]3F)ncc2c1]

The title compound was prepared following a procedure similar to Example 188 using (1S,2S)-N-(7-bromoisoquinolin-3-yl)-2-fluorocyclopropanecarboxamide: $^1H$ NMR (400 MHz, DMSO) δ 10.97 (s, 1H), 9.19 (s, 1H), 8.52 (s, 1H), 8.40 (s, 1H), 8.08 (s, 1H), 7.97 (d, J=8.6 Hz, 1H), 7.76 (dd, J=8.5, 1.5 Hz, 1H), 7.64 (s, 1H), 5.23 (s, 1H), 4.95 (m, 1H), 2.32 (s, 3H), 2.27 (m, 1H), 1.70 (m, 1H), 1.49 (s, 6H), 1.20 (m, 1H). LCMS (Method G): $R_T$=6.28 min, M+H$^+$=380.1.

Example 190

1-(5-(3-aminoisoquinolin-7-yl)-4-methylpyridin-2-yl)-2,2,2-trifluoroethanol

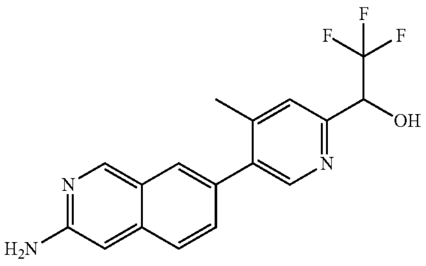 [SMILES: Cc1cc(C(O)C(F)(F)F)ncc1-c1ccc2cc(N)ncc2c1]

A mixture of 7-(4,4,5,5-tetramethyl-1,3,2-dioxaborolan-2-yl)isoquinolin-3-amine (225 mg, 0.583 mmol), 1-(5-bromo-4-methyl-2-pyridyl)-2,2,2-trifluoro-ethanol (200 mg, 0.741 mmol), bis(di-tert-butyl(4-dimethylaminophenyl) phosphine)dichloropalladium(II) (41 mg, 0.06 mmol) and saturated aqueous sodium carbonate solution (0.3 mL) in acetonitrile (3 mL) was heated under microwave irradiation (Biotage) at 130° C. for 30 minutes. The reaction mixture was diluted with ethyl acetate (30 mL) and washed with water (15 mL). The organic layer was separated, dried over sodium sulfate, filtered and concentrated in vacuo to provide a residue that was purified by flash chromatography (4 g, Silica, 0-100% ethyl acetate in heptane). Desired fractions were combined and evaporated in vacuo to afford the title compound as yellow oil (150 mg, 77%), which was used in the next step without further purification.

Example 191

(S)-N-(7-(4-methyl-6-(2,2,2-trifluoro-1-hydroxyethyl)pyridin-3-yl)-2,6-naphthyridin-3-yl)isobutyramide and (R)-N-(7-(4-methyl-6-(2,2,2-trifluoro-1-hydroxyethyl)pyridin-3-yl)-2,6-naphthyridin-3-yl) isobutyramide

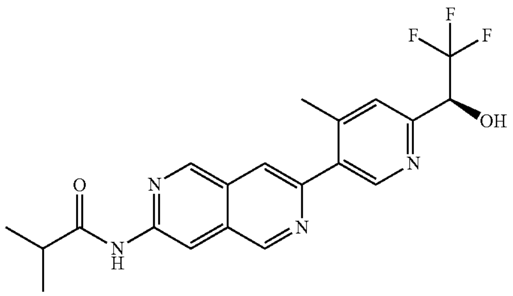

and

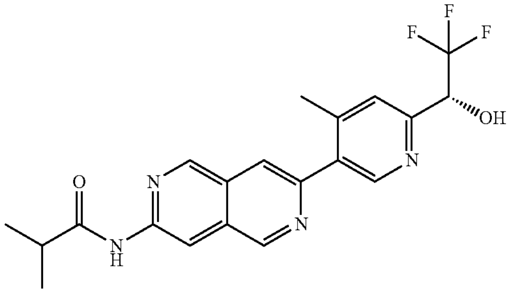

Isobutyryl chloride (24.5 mg, 0.225 mmol) was added a solution of 1-[5-(3-amino-7-isoquinolyl)-4-methyl-2-pyridyl]-2,2,2-trifluoro-ethanol (50 mg, 0.150 mmol) in DCM (0.75 mL) and pyridine (0.12 mL, 1.50 mmol) cooled at 0° C. The reaction mixture was warmed to room temperature and stirred for 30 minutes. The reaction mixture was diluted with DCM (20 mL) and washed with water (10 mL). The organic layer was separated, dried over sodium sulfate, filtered and concentrated in vacuo to provide a residue that was purified by reverse phase HPLC (5-85% acetonitrile in water w/0.1% $NH_4OH$). The purified racemic mixture was then separated via chiral supercritical fluid chromotagraphy.

Enantiomer 1: $^1H$ NMR (400 MHz, DMSO) δ 10.56 (s, 1H), 9.18 (s, 1H), 8.55 (s, 1H), 8.50 (s, 1H), 8.11 (s, 1H), 7.98 (d, J=8.6 Hz, 1H), 7.78 (d, J=8.5 Hz, 1H), 7.61 (s, 1H), 7.02

(d, J=6.1 Hz, 1H), 5.22-5.10 (m, 1H), 2.83 (m, 1H), 2.37 (s, 3H), 1.14 (d, J=6.8 Hz, 6H). LCMS (Method E): $R_T$=4.365 min, M+H$^+$=404.2.

Enantiomer 2:

1H NMR (400 MHz, DMSO) δ 10.56 (s, 1H), 9.18 (s, 1H), 8.55 (s, 1H), 8.50 (s, 1H), 8.11 (s, 1H), 7.98 (d, J=8.6 Hz, 1H), 7.78 (d, J=8.5 Hz, 1H), 7.61 (s, 1H), 7.02 (d, J=6.1 Hz, 1H), 5.16 (p, J=7.1 Hz, 1H), 2.83 (dt, J=13.5, 6.8 Hz, 1H), 2.37 (s, 3H), 1.14 (d, J=6.8 Hz, 6H). LCMS (Method E): $R_T$=4.365 min, M+H$^+$=404.2.

Examples 192

1-(3-bromo-4-methylpyridin-2-yl)ethanol

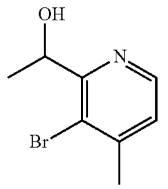

Step 1: 3-bromo-4-methylpicolinaldehyde

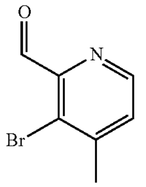

A mixture of (3-bromo-4-methyl-2-pyridyl)methanol (600 mg, 2.97 mmol) and Dess-Martin Periodinane (1688 mg, 3.86 mmol) in DCM (20 mL) was stirred at room temperature for 3 hours. The reaction mixture was diluted with dichloromethane (50 mL) and washed with saturated aqueous sodium bicarbonate (2×25 mL). The organic layer was separated, dried over sodium sulfate, filtered and concentrated in vacuo to provide a residue that was purified by flash chromatography (12 g, Silica, 0-80% ethyl acetate in heptane). Desired fractions were combined and evaporated in vacuo to afford the title compound as pale yellow solid (470 mg, 79%), which was used in the next step without further purification.

Step 2: 1-(3-bromo-4-methylpyridin-2-yl)ethanol

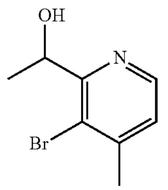

Methylmagnesium chloride (3.0 mol/L) in THF (0.17 mL, 0.525 mmol) was added dropwise to a solution of 3-bromo-4-methyl-pyridine-2-carbaldehyde (100 mg, 0.50 mmol) in THF (2 mL) cooled at −15° C. After 5 min, the reaction was quenched with a few drops of saturated aqueous ammonium chloride solution. The reaction mixture was diluted with ethyl acetate (25 mL) and washed with water (5 mL). The organic layer was separated, dried over sodium sulfate, filtered and concentrated in vacuo to provide the title compound as a yellow oil (100 mg, 92%), which was used in subsequent steps without further purification.

Example 193

(1S,2S)-2-fluoro-N-(7-(2-((S)-1-hydroxyethyl)-4-methylpyridin-3-yl)isoquinolin-3-yl)cyclopropanecarboxamide and (1S,2S)-2-fluoro-N-(7-(2-((R)-1-hydroxyethyl)-4-methylpyridin-3-yl)isoquinolin-3-yl)cyclopropanecarboxamide

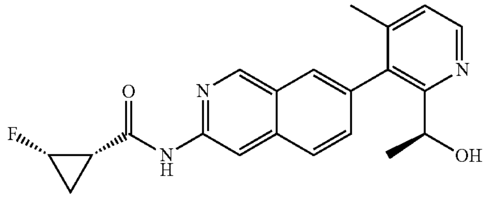

and

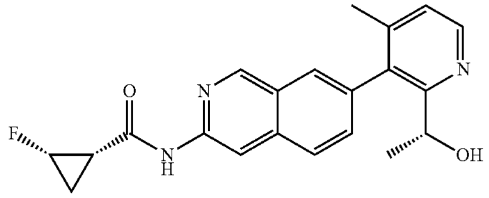

The title compounds were prepared following a procedure similar to Example 171 using 1-(3-bromo-4-methylpyridin-2-yl)ethanol, and then separated via chiral supercritical fluid chromotagraphy.

Enantiomer 1:

$^1$H NMR (400 MHz, DMSO) δ 10.97 (s, 1H), 9.16 (s, 1H), 8.53 (s, 1H), 8.51 (d, J=4.9 Hz, 1H), 7.98 (dd, J=8.5, 4.0 Hz, 1H), 7.92 (d, J=25.6 Hz, 1H), 7.56 (dd, J=21.4, 8.4 Hz, 1H), 7.31 (d, J=4.8 Hz, 1H), 5.07-4.83 (m, 1H), 4.76 (dd, J=16.6, 6.5 Hz, 1H), 4.49 (m, 1H), 2.28 (m, 1H), 2.03 (s, 3H), 1.70 (m, 1H), 1.20 (m, 4H). LCMS (Method E): $R_T$=3.219 min, M+H$^+$=366.2.

Enantiomer 2:

$^1$H NMR (400 MHz, DMSO) δ 10.97 (s, 1H), 9.16 (s, 1H), 8.53 (s, 1H), 8.51 (d, J=4.9 Hz, 1H), 7.98 (dd, J=8.6, 3.9 Hz, 1H), 7.96-7.87 (d, J=25.6 Hz, 1H), 7.56 (dd, J=21.7, 8.4 Hz, 1H), 7.31 (d, J=4.9 Hz, 1H), 5.07-4.84 (m, 1H), 4.76 (dd, J=18.1, 6.7 Hz, 1H), 4.49 (dt, J=19.5, 6.5 Hz, 1H), 2.29 (m, 1H), 2.03 (s, 3H), 1.70 (m, 1H), 1.20 (m, 4H). LCMS (Method E): $R_T$=3.327 min, M+H$^+$=366.2.

Example 194

1-(3-bromo-4-methylpyridin-2-yl)-2,2,2-trifluoroethanol

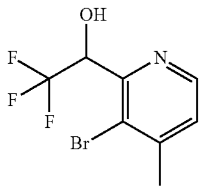

Tetrabutylammonium fluoride (1.0 mol/L) in THF (1.2 mL, 1.20 mmol) was added dropwise to a solution of 3-bromo-4-methyl-pyridine-2-carbaldehyde (150 mg, 0.75 mmol), and (trifluoromethyl)trimethylsilane (2.0 mol/L) in THF (0.49 mL, 0.975 mmol) in THF (10 mL) cooled at −15° C. The reaction mixture was warmed to room temperature and stirred overnight. The reaction mixture was diluted with ethyl acetate (50 mL) and washed with water (25 mL). The organic layer was separated, dried over sodium sulfate, filtered and concentrated in vacuo to provide a residue that was purified by flash chromatography (12 g, Silica, 0-30% ethyl acetate in heptane). Desired fractions were combined and evaporated in vacuo to afford the title compound as a white solid (90 mg, 44%), which was used in the next step without further purification.

Example 195

(1S,2S)-2-fluoro-N-(7-(4-methyl-2-((R)-2,2,2-trifluoro-1-hydroxyethyl)pyridin-3-yl)isoquinolin-3-yl)cyclopropanecarboxamide and (1S,2S)-2-fluoro-N-(7-(4-methyl-2-((S)-2,2,2-trifluoro-1-hydroxyethyl)pyridin-3-yl)isoquinolin-3-yl)cyclopropanecarboxamide

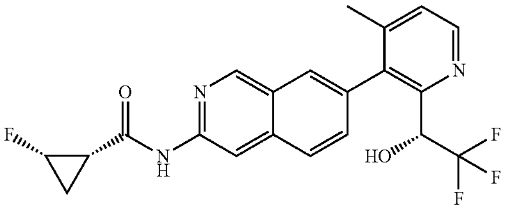

and

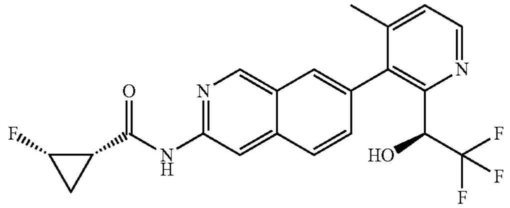

The title compound was prepared following a procedure similar to Example 171 using 1-(3-bromo-4-methylpyridin-2-yl)-2,2,2-trifluoroethanol, and then separated via chiral supercritical fluid chromotagraphy.

Enantiomer 1:

$^1$H NMR (400 MHz, DMSO) δ 10.99 (s, 1H), 9.19 (s, 1H), 8.59 (d, J=4.9 Hz, 1H), 8.55 (s, 1H), 8.06-7.98 (m, 1H), 7.92 (d, J=18.0 Hz, 1H), 7.53 (dd, J=16.2, 8.5 Hz, 1H), 7.47 (d, J=4.7 Hz, 1H), 6.51-6.44 (m, 1H), 5.07-4.84 (m, 1H), 4.78 (dt, J=24.7, 7.3 Hz, 1H), 2.35-2.24 (m, 1H), 2.06 (s, 3H), 1.70 (m, 1H), 1.19 (m, 1H). LCMS (Method E): $R_T$=3.963 min, M+H$^+$=420.2.

Enantiomer 2:

$^1$H NMR (400 MHz, DMSO) δ 10.99 (s, 1H), 9.19 (s, 1H), 8.59 (d, J=4.9 Hz, 1H), 8.54 (s, 1H), 8.05-7.99 (m, 1H), 7.92 (d, J=17.6 Hz, 1H), 7.53 (dd, J=16.6, 8.5 Hz, 1H), 7.47 (d, J=4.9 Hz, 1H), 6.48 (d, J=7.9 Hz, 1H), 4.95 (m, 1H), 4.84-4.72 (m, 1H), 2.35-2.23 (m, 1H), 2.06 (s, 3H), 1.76-1.63 (m, 1H), 1.19 (m, 1H). LCMS (Method E): $R_T$=3.990 min, M+H$^+$=420.2.

Example 196

(1S,2S)-2-fluoro-N-(7-(5-fluoro-2-(hydroxymethyl)-4-methylpyridin-3-yl)isoquinolin-3-yl)cyclopropanecarboxamide

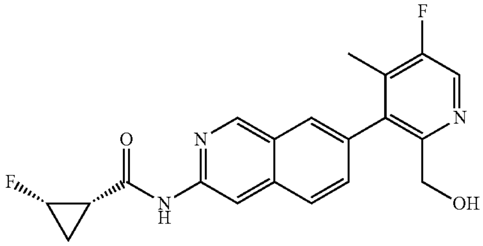 [SMILES: Cc1c(F)cnc(CO)c1-c1ccc2cc(NC(=O)[C@@H]3C[C@@H]3F)ncc2c1]

Step 1: 3-bromo-5-fluoro-2,4-dimethylpyridine

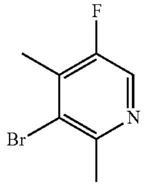

A mixture of 5-bromo-4,6-dimethyl-pyridin-3-amine (500 mg, 2.49 mmol) and nitrosyl tetrafluoroborate (445 mg, 3.73 mmol) in 1-butyl-3-methylimidazolium tetrafluoroborate (9.48 mL, 49.74 mmol) was heated at 60° C. for 2 hours (caution: exothermic). The reaction mixture was diluted with ethyl acetate (50 mL) and washed with water (2×20 mL), and then saturated aqueous sodium bicarbonate (20 mL). The organic layer was separated, dried over sodium sulfate, filtered and concentrated in vacuo to provide a residue that was purified by flash chromatography (4 g, Silica, 0-50% ethyl acetate in heptane). Desired fractions were combined and evaporated in vacuo to afford the title compound as pale yellow oil (220 mg, 43%), which was used in the next step without further purification.

Step 2: 3-bromo-5-fluoro-2,4-dimethylpyridine 1-oxide

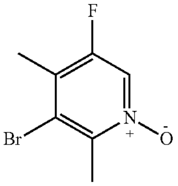

A mixture of 3-bromo-5-fluoro-2,4-dimethyl-pyridine (220 mg, 1.08 mmol) and 3-chloroperoxybenzoic acid (399 mg, 1.62 mmol) in dichloromethane (3 mL) was stirred overnight at room temperature. The reaction mixture was diluted with DCM (50 mL) and washed with saturated aqueous sodium thiosulfite (10 mL) followed by saturated aqueous sodium bicarbonate (10 mL). The organic layer was separated, dried over sodium sulfate, filtered and concentrated in vacuo to provide a residue that was purified by flash chromatography (4 g, Silica, 0-10% methanol in DCM). Desired fractions were combined and evaporated in vacuo to afford the title compound as a white solid (220 mg, 93%), which was used in the next step without further purification.

Step 3: (3-bromo-5-fluoro-4-methylpyridin-2-yl)methanol

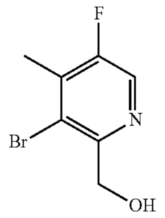

Trifluoroacetic anhydride (0.35 mL, 2.5 mmol) was added dropwise to a solution of 3-bromo-5-fluoro-2,4-dimethylpyridine 1-oxide (220 mg; 1.0 mmol) in DCM (3 mL). The reaction mixture was stirred at room temperature overnight and then diluted with ethyl acetate (50 mL) and washed with saturated aqueous sodium bicarbonate solution (20 mL). The organic layer was separated, dried over sodium sulfate, filtered and concentrated in vacuo to provide a residue that was purified by flash chromatography (4 g, Silica, 0-100% ethyl acetate in heptane). Desired fractions were combined and evaporated in vacuo to afford the title compound as a pale yellow oil (150 mg, 68%), which was used in the next step without further purification.

Step 4: (1S,2S)-2-fluoro-N-(7-(5-fluoro-2-(hydroxymethyl)-4-methylpyridin-3-yl)isoquinolin-3-yl)cyclopropanecarboxamide

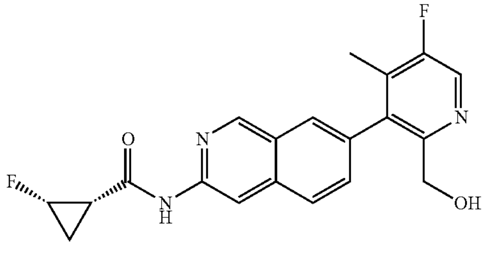 [SMILES: Cc1c(F)cnc(CO)c1-c1ccc2cc(NC(=O)[C@@H]3C[C@@H]3F)ncc2c1]

A mixture of (1S,2S)-2-fluoro-N-(7-(4,4,5,5-tetramethyl-1,3,2-dioxaborolan-2-yl)isoquinolin-3-yl)cyclopropanecarboxamide (230 mg, 0.648 mmol), (3-bromo-5-fluoro-4-methyl-2-pyridyl)methanol (143 mg, 0.648 mmol), bis(di-tert-butyl(4-dimethylaminophenyl)phosphine) dichloropalladium(II) (46 mg, 0.065 mmol) and saturated aqueous sodium carbonate solution (0.3 mL) in acetonitrile (3 mL) was heated under microwave irradiation (Biotage) at 130° C. for 30 minutes. The reaction mixture was diluted with ethyl acetate (30 mL) and washed with water (15 mL). The organic layer was separated, dried over sodium sulfate, filtered and concentrated in vacuo to provide a residue that was purified by reverse phase HPLC (5-85% acetonitrile in water w/0.1% $NH_4OH$, 14 min). Desired fractions were combined and evaporated in vacuo to afford the title compound as an off-white solid (26 mg, 11%). $^1H$ NMR (400 MHz, DMSO) δ 10.98 (s, 1H), 9.16 (s, 1H), 8.54 (s, 2H), 7.99 (m, 2H), 7.59 (d, J=8.4 Hz, 1H), 5.08-4.81 (m, 2H), 4.24 (s, 2H), 2.34-2.22 (m, 1H), 2.00 (s, 3H), 1.70 (m, 1H), 1.20 (m, 1H). LCMS (Method E): $R_T$=6.66 min, M+H$^+$=370.0.

Example 197

(1S,2S)-2-fluoro-N-(7-(5-fluoro-4-methylpyridin-3-yl)-2,6-naphthyridin-3-yl)cyclopropanecarboxamide

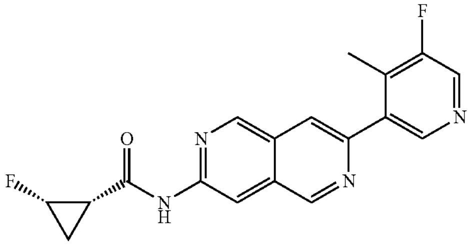 [SMILES: Cc1c(F)cncc1-c1cc2cnc(NC(=O)[C@@H]3C[C@@H]3F)cc2cn1]

Step 1: 2-chloro-3-fluoro-4-methyl-5-((trimethylsilyl)ethynyl)pyridine

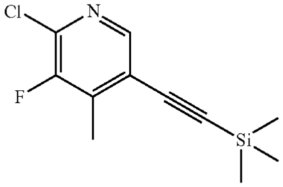

A mixture of 2-chloro-3-fluoro-5-iodo-4-methyl-pyridine (2960 mg, 10.9 mmol), ethynyltrimethylsilane (1.89 mL, 13.1 mmol), N,N-diisopropylethylamine (3.80 mL, 21.8 mmol), dichlorobis(triphenylphosphine)palladium(II) (390 mg, 0.545 mmol), and cuprous iodide (104 mg, 0.55 mmol) in dioxane (40 mL) was heated at 60° C. for 2 hours. The reaction mixture was filtered through a short plug of silica, rinsed with 50 mL of ethyl acetate/heptane (1:1), and the filtrate was evaporated in vacuo to provide an orange oil that was purified by flash chromatography (12 g, Silica, 0-20% ethyl acetate in heptane). Desired fractions were combined and evaporated in vacuo to afford the title compound as a pale yellow oil, (2.35 mg, 89%). $^1H$ NMR (400 MHz, $CDCl_3$) δ 8.21 (s, 1H), 2.40 (d, J=1.9 Hz, 3H), 0.28 (s, 11H).

Step 2: 3-ethynyl-5-fluoro-4-methylpyridine

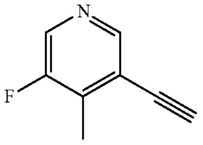

To a solution of 2-(6-chloro-5-fluoro-4-methyl-3-pyridyl)ethynyl-trimethyl-silane (2300 mg, 9.5 mmol) in AcOH (12 mL) was added zinc (1200 mg, 19 mmol). The mixture was heated at 70° C. for 1 hour. The reaction mixture was diluted with ethyl acetate (50 mL), filtered over Celite, evaporated in vacuo and then re-dissolved in ethyl acetate (50 mL) and washed with saturated aqueous sodium bicarbonate solution (20 mL). The organic layer was separated, dried over sodium sulfate, filtered and concentrated in vacuo to provide a residue that was dissolved in MeOH (15 mL) and treated with potassium carbonate (270 mg, 1.9 mmol). The reaction mixture was stirred for 15 minutes at room temperature and then diluted with dichloromethane (50 mL), filtered over Celite, and concentrated in vacuo to provide a residue that was purified by flash chromatography (40 g, Silica, 0-50% diethyl ether in pentane). Desired fractions were combined and evaporated in vacuo to afford the title compound as colorless, crystalline solid (1005 mg, 82%). $^1$H NMR (400 MHz, $CDCl_3$) δ 8.46 (s, 1H), 8.33 (s, 1H), 3.42 (s, 1H), 2.40 (s, 3H).

Step 3: 2-chloro-5-((5-fluoro-4-methylpyridin-3-yl)ethynyl)isonicotinaldehyde

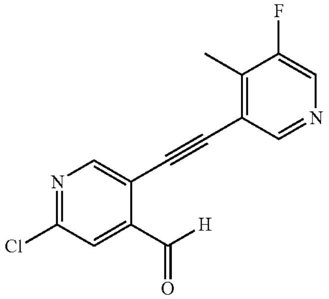 [SMILES: Cc1c(F)cncc1C#Cc1cnc(Cl)cc1C=O]

A mixture of 3-ethynyl-5-fluoro-4-methyl-pyridine (240 mg, 1.78 mmol), 5-bromo-2-chloro-pyridine-4-carbaldehyde (392 mg, 1.78 mmol), N,N-diisopropylethylamine (0.62 mL, 3.55 mmol), dichlorobis(triphenylphosphine)palladium(II) (64 mg, 0.089 mmol), and cuprous iodide (17 mg, 0.089 mmol) in dioxane (5 mL) was heated at 60° C. for 1 hour. The reaction mixture was diluted with ethyl acetate (50 mL) and washed with water (50 mL). The organic layer was separated, dried over sodium sulfate, filtered and concentrated in vacuo to provide a residue that was purified by flash chromatography (12 g, Silica, 0-70% ethyl acetate in heptane). Desired fractions were combined and evaporated in vacuo to afford the title compound as a pale yellow solid (380 mg, 78%), which was used in the next step without further purification.

Step 4: 2-chloro-5-((5-fluoro-4-methylpyridin-3-yl)ethynyl)isonicotinaldehyde oxime

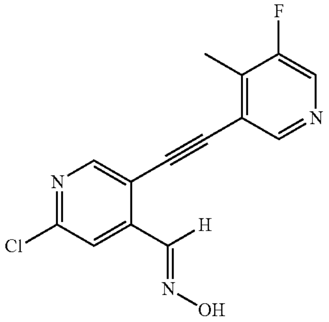 [SMILES: Cc1c(F)cncc1C#Cc1cnc(Cl)cc1/C=N/O]

A mixture of 2-chloro-5-((5-fluoro-4-methylpyridin-3-yl)ethynyl)isonicotinaldehyde (385 mg, 1.4 mmol), hydroxylamine hydrochloride (107 mg, 1.54 mmol), and sodium acetate (138 mg, 1.68 mmol) in ethanol (5 mL) was stirred at 40° C. for 30 minutes. The reaction mixture was then evaporated in vacuo, re-dissolved in DCM and methanol and washed with water (15 mL). The organic layer was separated, dried over sodium sulfate, filtered, and concentrated in vacuo to afford the title compound as a pale yellow solid that was used in the next step without further purification.

Step 5: 7-chloro-3-(5-fluoro-4-methylpyridin-3-yl)-2,6-naphthyridine 2-oxide

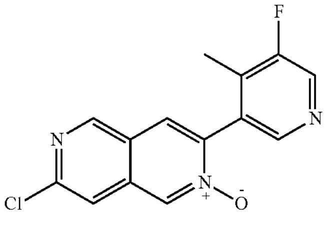

A slurry of 2-chloro-5-((5-fluoro-4-methylpyridin-3-yl)ethynyl)isonicotinaldehyde oxime (400 mg, 1.38 mmol) in chloroform (10 mL) was treated with silver nitrate on silica gel (10% w/w, 357 mg, 0.210 mmol). The reaction mixture was heated at 60° C. for 2 hours and then diluted with DCM (20 mL) and methanol (5 mL), loaded on silica gel, and purified by flash chromatography (12 g, Silica, 0-10% methanol in dichloromethane). Desired fractions were combined and evaporated in vacuo to afford the title compound as an off-white solid (270 mg, 66% over two steps). $^1$H NMR (400 MHz, DMSO) δ 9.20 (s, 1H), 9.14 (s, 1H), 8.65 (s, 1H), 8.40 (s, 2H), 8.01 (s, 1H), 2.12 (s, 3H).

Step 6: 7-(tert-butoxycarbonylamino)-3-(5-fluoro-4-methylpyridin-3-yl)-2,6-naphthyridine 2-oxide

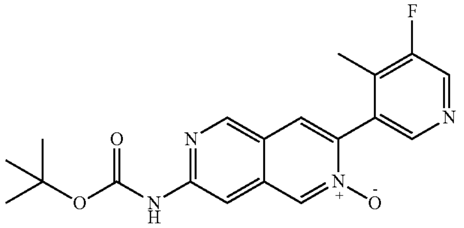

A mixture of 7-chloro-3-(5-fluoro-4-methylpyridin-3-yl)-2,6-naphthyridine 2-oxide (150 mg, 0.52 mmol), tert-butyl carbamate (121 mg, 1.04 mmol), 2-(dicyclohexylphosphino)3,6-dimethoxy-2',4',6'-triisopropyl-1,1'-biphenyl (58 mg, 0.10 mmol), chloro[2-(dicyclohexylphosphino)-3,6-dimethoxy-2'-4'-6'-tri-1-propyl-1,1'-biphenyl][2-(2-aminoethyl)phenyl]palladium(II) (42 mg, 0.052 mmol), and cesium carbonate (341 mg, 1.04 mmol) in dioxane (2.5 mL) was heated at 100° C. for 8 hours in a vial sealed with a Teflon cap. The reaction mixture was diluted with dichloromethane (50 mL) and methanol (5 mL), filtered over Celite, and concentrated in vacuo to provide a residue that was purified by flash chromatography (12 g, Silica, 0-10% methanol in dichloromethane). Desired fractions were combined and evaporated in vacuo to afford the title compound as a yellow solid (73 mg, 38%). $^1$H NMR (400 MHz, DMSO) δ 10.16 (s, 1H), 9.14 (s, 1H), 9.08 (s, 1H), 8.62 (s, 1H), 8.39 (s, 1H), 8.21 (s, 1H), 8.16 (s, 1H), 1.52 (s, 9H).

Step 7: tert-butyl 7-(5-fluoro-4-methylpyridin-3-yl)-2,6-naphthyridin-3-ylcarbamate

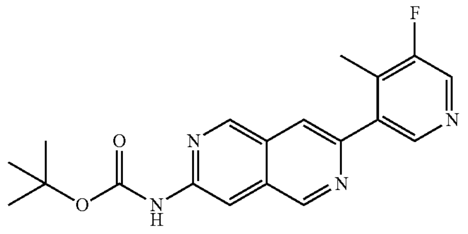 [SMILES: Cc1c(F)cncc1-c1cc2cnc(NC(=O)OC(C)(C)C)cc2cn1]

To a solution of 7-chloro-3-(5-fluoro-4-methylpyridin-3-yl)-2,6-naphthyridine 2-oxide (100 mg, 0.27 mmol) in DCM (2 mL) was added phosphorus(III) chloride (0.031 mL, 0.351 mmol) and the reaction mixture was stirred at room temperature for 1 hour. The reaction mixture was diluted with ethyl acetate (50 mL) and washed with saturated aqueous sodium bicarbonate (25 mL). The organic layer was separated, dried over sodium sulfate, filtered and concentrated in vacuo to provide a residue that was purified by flash chromatography (4 g, Silica, 0-90% ethyl acetate in heptane). Desired fractions were combined and evaporated in vacuo to afford the title compound as a pale yellow solid (50 mg, 52%), which was used in the next step without further purification.

Step 8: 7-(5-fluoro-4-methylpyridin-3-yl)-2,6-naphthyridin-3-amine

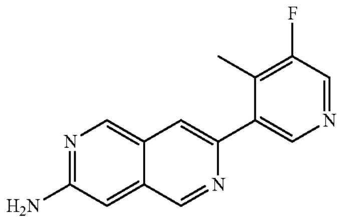 [SMILES: Cc1c(F)cncc1-c1cc2cnc(N)cc2cn1]

A suspension of tert-butyl 7-(5-fluoro-4-methylpyridin-3-yl)-2,6-naphthyridin-3-ylcarbamate (50 mg, 0.14 mmol) in 1,2-dichloroethane (1 mL) was treated with trifluoroacetic acid (0.11 mL, 1.41 mmol), and the mixture was stirred at 40° C. for 3 hours. The mixture was concentrated in vacuo and then diluted with ethyl acetate (50 mL) and washed with saturated aqueous sodium bicarbonate solution (10 mL). The organic layer was separated, dried over sodium sulfate, filtered, and evaporated in vacuo to afford the title compound as a bright yellow solid (36 mg, 98%), which was used in the next step without further purification.

Step 9: (1S,2S)-2-fluoro-N-(7-(5-fluoro-4-methylpyridin-3-yl)-2,6-naphthyridin-3-yl)cyclopropanecarboxamile

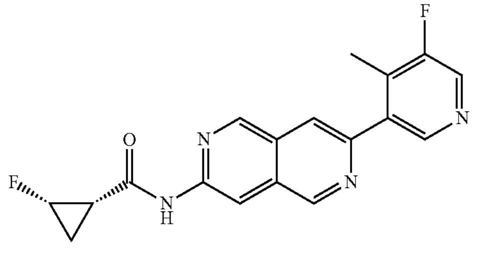 [SMILES: Cc1c(F)cncc1-c1cc2cnc(NC(=O)[C@@H]3C[C@@H]3F)cc2cn1]

A mixture of 7-(5-fluoro-4-methyl-3-pyridyl)-2,6-naphthyridin-3-amine (35 mg, 0.14 mmol), HATU (113 mg, 0.29 mmol), (1S,2S)-2-fluorocyclopropanecarboxylic acid (29 mg, 0.28 mmol), and N,N-diisopropylethylamine (0.10 mL, 0.55 mmol) in DMF (1 mL) was heated at 70° C. for 8 hours. The reaction mixture was diluted with ethyl acetate (50 mL) and washed with water (25 mL). The organic layer was separated, dried over sodium sulfate, filtered and concentrated in vacuo to provide a residue that was purified by reverse phase HPLC purification (5-85% ACN in water w/0.1% $NH_4OH$, 14 min). Desired fractions were combined and evaporated in vacuo to afford the title compound as an off-white solid (20 mg, 43%). $^1$H NMR (400 MHz, DMSO) δ 11.22 (s, 1H), 9.35 (s, 1H), 8.70 (s, 1H), 8.59 (sz, 1H), 8.58 (s, 1H), 8.24 (s, 1H), 4.98 (m, 1H), 2.37 (d, J=1.9 Hz, 3H), 2.31 (m, 1H), 1.72 (m, 1H), 1.23 (m, 1H). LCMS (Method E): $R_T$=3.978 min, M+H$^+$=341.2.

Example 198

(1S,2S)-2-fluoro-N-(7-(5-fluoro-4-methylpyridin-3-yl)-5-methyl-2,6-naphthyridin-3-yl)cyclopropanecarboxamide

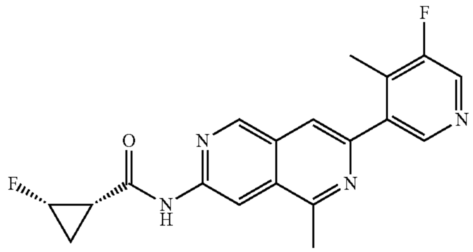 [SMILES: Cc1c(F)cncc1-c1cc2cnc(NC(=O)[C@@H]3C[C@@H]3F)cc2c(C)n1]

Step 1: tert-butyl 5-chloro-7-(5-fluoro-4-methylpyridin-3-yl)-2,6-naphthyridin-3-ylcarbamate

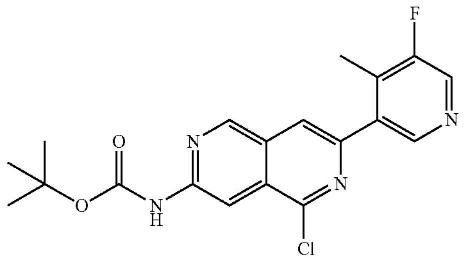 [SMILES: Cc1c(F)cncc1-c1cc2cnc(NC(=O)OC(C)(C)C)cc2c(Cl)n1]

7-chloro-3-(5-fluoro-4-methylpyridin-3-yl)-2,6-naphthyridine 2-oxide (760 mg, 2.05 mmol) was suspended in DMF (7 mL) and treated with mesyl chloride (0.81 mL, 10.3 mmol). The reaction mixture was stirred at room temperature for 1 hour and then diluted with ethyl acetate (150 mL) and washed with water (100 mL). The biphasic mixture was then filtered through Celite, and the organic layer was separated, dried over sodium sulfate, filtered and concentrated in vacuo to provide a residue that was purified by flash chromatography (12 g, Silica, 0-10% methanol in dichloromethane). Desired fractions were combined and evaporated in vacuo to afford the title compound as a yellow solid (230 mg, 29%), which was used in the next step without further purification.

Step 2: tert-butyl 7-(5-fluoro-4-methylpyridin-3-yl)-5-methyl-2,6-naphthyridin-3-ylcarbamate

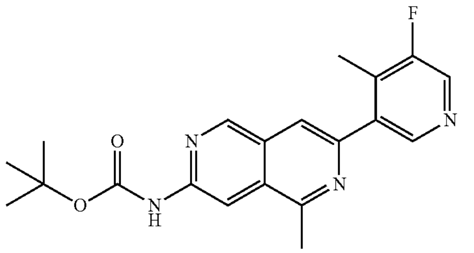 [SMILES: Cc1c(F)cncc1-c1cc2cnc(NC(=O)OC(C)(C)C)cc2c(C)n1]

A mixture of tert-butyl 5-chloro-7-(5-fluoro-4-methylpyridin-3-yl)-2,6-naphthyridin-3-ylcarbamate (230 mg, 0.592 mmol), trimethylboroxine (225 mg, 1.78 mmol), bis(di-tert-butyl(4-dimethylaminophenyl)phosphine)dichloropalladium(II) (42 mg, 0.059 mmol), and potassium carbonate (165 mg, 1.18 mmol) in dioxane (3 mL) was heated at 100° C. for 2 hours. The reaction mixture was diluted with ethyl acetate (75 mL) and washed with water (50 mL). The organic layer was separated, dried over sodium sulfate, filtered and concentrated in vacuo to provide a residue that was purified by flash chromatography (4 g, Silica, 0-100% ethyl acetate in heptane). Desired fractions were combined and evaporated in vacuo to afford the title compound as pale yellow solid (110 mg, 50%), which was used in the next step without further purification.

Step 3: 7-(5-fluoro-4-methylpyridin-3-yl)-5-methyl-2,6-naphthyridin-3-amine

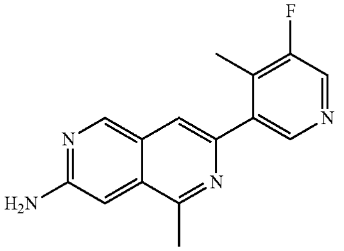 [SMILES: Cc1c(F)cncc1-c1cc2cnc(N)cc2c(C)n1]

A suspension of tert-butyl 7-(5-fluoro-4-methylpyridin-3-yl)-5-methyl-2,6-naphthyridin-3-ylcarbamate (110 mg, 0.30 mmol) in 1,2-dichloroethane (2 mL) was treated with trifluoroacetic acid (0.23 mL, 3.0 mmol), and the mixture was stirred at 40° C. for 2 hours. The mixture was concentrated in vacuo and then diluted with dichloromethane (50 mL) and washed with saturated aqueous sodium bicarbonate solution (10 mL). The organic layer was separated, dried over sodium sulfate, filtered, and evaporated in vacuo to afford the title compound as a bright yellow solid (80 mg, 99%), which was used in the next step without further purification.

Step 4: (1S,2S)-2-fluoro-N-(7-(5-fluoro-4-methylpyridin-3-yl)-2,6-naphthyridin-3-yl)cyclopropanecarboxamide

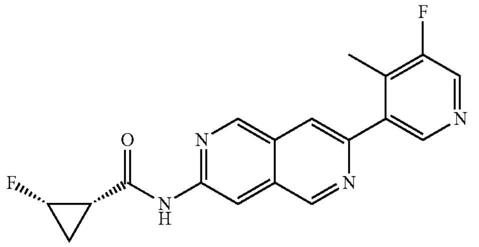 [SMILES: Cc1c(F)cncc1-c1cc2cnc(NC(=O)[C@@H]3C[C@@H]3F)cc2cn1]

A mixture of 7-(5-fluoro-4-methylpyridin-3-yl)-5-methyl-2,6-naphthyridin-3-amine (80 mg, 0.30 mmol), HATU (246 mg, 0.63 mmol), (1S,2S)-2-fluorocyclopropanecarboxylic acid (62 mg, 0.60 mmol), and N,N-diisopropylethylamine (0.21 mL, 1.19 mmol) in DMF (2 mL) was heated at 70° C. for 8 hours. The reaction mixture was diluted with ethyl acetate (50 mL) and washed with water (25 mL). The organic layer was separated, dried over sodium sulfate, filtered and concentrated in vacuo to provide a residue that was purified by reverse phase HPLC purification (5-85% acetonitrile in water w/0.1% $NH_4OH$, 14 minutes). Desired fractions were combined and evaporated in vacuo to afford the title compound as an off-white solid (45 mg, 43%). $^1H$ NMR (400 MHz, DMSO) δ 11.24 (s, 1H), 9.31 (s, 1H), 8.74 (s, 1H), 8.57 (s, 1H), 8.56 (s, 1H), 8.07 (s, 1H), 4.98 (m, 1H), 2.90 (s, 3H), 2.36 (s, 3H), 2.30 (m, 1H), 1.78-1.66 (m, 1H), 1.28-1.17 (m, 1H). LCMS (Method G): $R_T$=7.78 min, M+H$^+$=355.0.

Example 199

7-(cyclopropanecarboxamido)-3-(5-fluoro-4-methylpyridin-3-yl)-2,6-naphthyridine 2-oxide

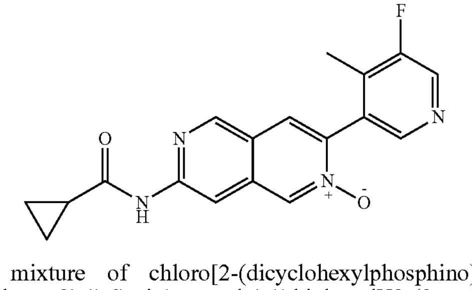

A mixture of chloro[2-(dicyclohexylphosphino)-3,6-dimethoxy-2'-4'-6'-tri-1-propyl-1,1'-biphenyl][2-(2-aminoethyl)phenyl]palladium(II) (28 mg, 0.035 mmol), cesium carbonate (227 mg, 0.69 mmol), 2-(dicyclohexylphosphino)3,6-dimethoxy-2',4',6'-triisopropyl-1,1'-biphenyl (19 mg, 0.035 mmol), 7-chloro-3-(5-fluoro-4-methylpyridin-3-yl)-2,6-naphthyridine 2-oxide (100 mg, 0.35 mmol), and cyclopropanecarboxamide (59 mg, 0.69 mmol) in dioxane (2 mL) was heated at 100° C. for 8 hours in a vial sealed with a Teflon cap. The reaction mixture was diluted with dichloromethane (50 mL) and methanol (5 mL), filtered over Celite, and concentrated in vacuo to provide a residue that was purified by reverse phase HPLC purification (5-85% ACN in water w/0.1% $NH_4OH$, 14 min) Desired fractions were combined and evaporated in vacuo to afford the title compound as a white solid. $^1H$ NMR (400 MHz, DMSO) δ 11.12 (s, 1H), 9.14 (s, 2H), 8.63 (s, 1H), 8.44 (s, 1H), 8.39 (s, 1H), 8.24 (s, 1H), 2.12 (d, J=1.5 Hz, 3H), 2.08 (m, 1H), 0.86 (m, 4H). LCMS (Method E): $R_T$=3.626 min, M+H$^+$=339.2.

Example 200

(1R,2R)-2-fluoro-N-(7-(4-methylpyridin-3-yl)-2,6-naphthyridin-3-yl)cyclopropanecarboxamide

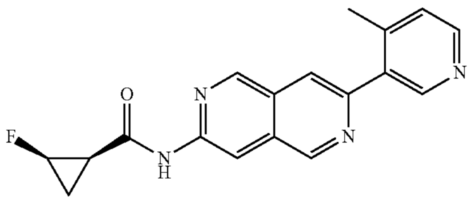 [SMILES: Cc1ccncc1-c1cc2cnc(NC(=O)[C@H]3C[C@H]3F)cc2cn1]

Step 1: tert-butyl 7-(4-methylpyridin-3-yl)-2,6-naphthyridin-3-ylcarbamate

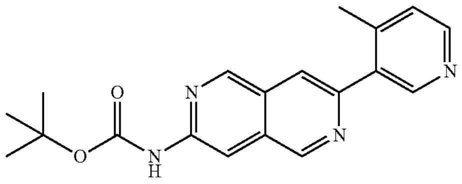 [SMILES: Cc1ccncc1-c1cc2cnc(NC(=O)OC(C)(C)C)cc2cn1]

A mixture of tert-butyl N-(7-chloro-2,6-naphthyridin-3-yl)carbamate (460 mg, 1.65 mmol), (4-methyl-3-pyridyl)boronic acid (450 mg, 3.3 mmol), bis(di-tert-butyl(4-dimethylaminophenyl)phosphine)dichloropalladium(II) (117 mg, 0.165 mmol) and saturated aqueous sodium carbonate solution (0.5 mL) in acetonitrile (5 mL) was heated under microwave irradiation (Biotage) at 130° C. for 30 minutes. The reaction mixture was diluted with ethyl acetate (150 mL) and washed with water (50 mL). The organic layer was separated, dried over sodium sulfate, filtered and concentrated in vacuo to provide a residue that was purified by flash chromatography (12 g, Silica, 0-10% methanol in dichloromethane). Desired fractions were combined and evaporated in vacuo to afford the title compound as a white solid (190 mg, 34%), which was used in the next step without further purification.

Step 2: 7-(4-methylpyridin-3-yl)-2,6-naphthyridin-3-amine

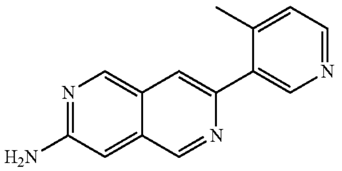 [SMILES: Cc1ccncc1-c1cc2cnc(N)cc2cn1]

A suspension of tert-butyl 7-(4-methylpyridin-3-yl)-2,6-naphthyridin-3-ylcarbamate (190 mg, 0.565 mmol) in DCE (3 mL) was treated with trifluoroacetic acid (0.437 mL, 5.65 mmol) and the mixture was stirred at 40° C. for 3 hours. The reaction mixture was concentrated in vacuo and then diluted with ethyl acetate (50 mL) and washed with saturated aqueous sodium bicarbonate solution (10 mL). The organic layer was separated, dried over sodium sulfate, filtered, and evaporated in vacuo to afford the title compound as a bright yellow solid (133 mg, 99%), which was used without further purification.

Step 3: (1R,2R)-2-fluoro-N-(7-(4-methylpyridin-3-yl)-2,6-naphthyridin-3-yl)cyclopropanecarboxamide

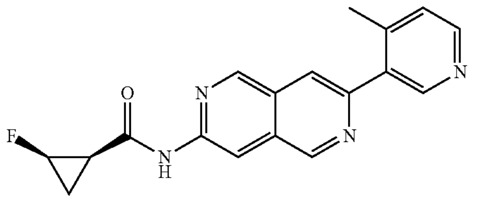 [SMILES: Cc1ccncc1-c1cc2cnc(NC(=O)[C@H]3C[C@H]3F)cc2cn1]

A mixture of (1R,2R)-2-fluorocyclopropanecarboxylic acid (35 mg, 0.34 mmol), HATU (139 mg, 0.36 mmol), and N,N-diisopropylethylamine (89 mg, 0.68 mmol) in DMF (1 mL) was heated at 70° C. for 8 hours. The reaction mixture was diluted with ethyl acetate (50 mL) and washed with water (25 mL). The organic layer was separated, dried over sodium sulfate, filtered and concentrated in vacuo to provide a residue that was purified by reverse phase HPLC purification (5-85% ACN in water w/0.1% $NH_4OH$, 14 min). Desired fractions were combined and evaporated in vacuo to afford the title compound as an off-white solid (25 mg, 46%). $^1H$ NMR (400 MHz, DMSO) δ 11.20 (s, 1H), 9.50 (s, 1H), 9.34 (s, 1H), 8.68 (s, 1H), 8.68 (s, 1H), 8.50 (d, J=5.0 Hz, 1H), 8.19 (s, 1H), 7.39 (d, J=5.0 Hz, 1H), 5.08-4.85 (m, 1H), 2.44 (s, 3H), 2.30 (m, 1H), 1.72 (m, 1H), 1.23 (m, 1H). LCMS (Method E): $R_T$=3.166 min, M+H$^+$=323.2.

Example 201

(1S,2R)-2-fluoro-N-(7-(4-methylpyridin-3-yl)-2,6-naphthyridin-3-yl)cyclopropanecarboxamide and (1R,2S)-2-fluoro-N-(7-(4-methylpyridin-3-yl)-2,6-naphthyridin-3-yl)cyclopropanecarboxamide

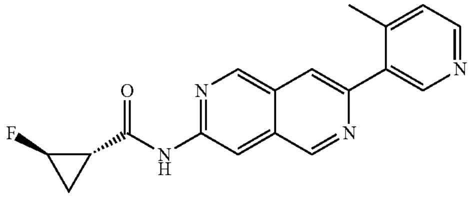

and

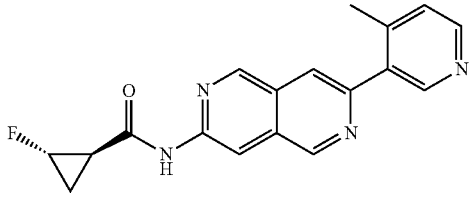

The title compounds were prepared as a racemic mixture following a procedure similar to Example 200 using a racemic mixture of (1S,2R)-2-fluorocyclopropanecarboxylic acid and (1R,2S)-2-fluorocyclopropanecarboxylic acid, and then separated via chiral supercritical fluid chromotagraphy.

Enantiomer 1:

$^1H$ NMR (400 MHz, DMSO) δ 11.31 (s, 1H), 9.48 (s, 1H), 9.34 (s, 1H), 8.67 (s, 1H), 8.62 (s, 1H), 8.50 (d, J=5.0 Hz, 1H), 8.19 (s, 1H), 7.39 (d, J=5.0 Hz, 1H), 4.95 (m, 1H), 2.69-2.58 (m, 1H), 2.43 (s, 3H), 1.64-1.51 (m, 1H), 1.31 (m, 1H). LCMS (Method E): $R_T$=3.397 min, M+H$^+$=323.2.

Enantiomer 2:

$^1H$ NMR (400 MHz, DMSO) δ 11.31 (s, 1H), 9.49 (s, 1H), 9.34 (s, 1H), 8.67 (s, 1H), 8.62 (s, 1H), 8.50 (d, J=5.0 Hz, 1H), 8.19 (s, 1H), 7.39 (d, J=5.0 Hz, 1H), 4.95 (m, 1H), 2.69-2.59 (m, 1H), 2.43 (s, 3H), 1.65-1.51 (m, 1H), 1.31 (m, 1H). LCMS (Method E): $R_T$=3.375 min, M+H$^+$=323.2.

Example 202

N-(7-(5-fluoro-4-(hydroxymethyl)-2-methylphenyl)isoquinolin-3-yl)cyclopropanecarboxamide

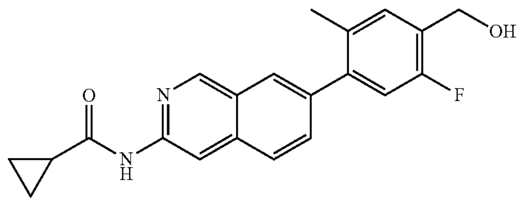 [SMILES: Cc1cc(CO)c(F)cc1-c1ccc2cc(NC(=O)C3CC3)ncc2c1]

Step 1: N-(7-(4-bromo-5-fluoro-2-methylphenyl)isoquinolin-3-yl)cyclopropanecarboxamide

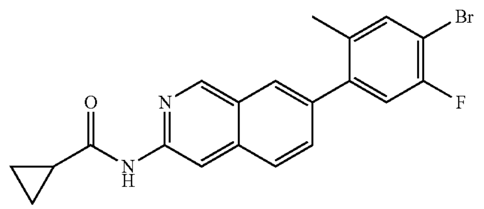 [SMILES: Cc1cc(Br)c(F)cc1-c1ccc2cc(NC(=O)C3CC3)ncc2c1]

A mixture of N-[7-(4,4,5,5-tetramethyl-1,3,2-dioxaborolan-2-yl)-3-isoquinolyl]cyclopropanecarboxamide (500 mg, 1.48 mmol), 1-bromo-2-fluoro-4-iodo-5-methyl-benzene (559 mg, 1.77 mmol), and bis(di-tert-butyl(4-dimethylaminophenyl)phosphine)dichloropalladium(II) (105 mg, 0.15 mmol) in ACN (6 mL) and saturated aqueous sodium carbonate (1 mL) was heated under microwave irradiation (Biotage) 120° C. for 20 minutes. The reaction mixture was diluted with ethyl acetate (50 mL) and washed with water (50 mL). The organic layer was separated, dried over sodium sulfate, filtered and concentrated in vacuo to provide a residue that was purified by flash chromatography (12 g, Silica, 0-60% ethyl acetate in heptane). Desired fractions were combined and evaporated in vacuo to afford the title compound as a white solid (385, 65%), which was used in the next step without further purification.

Step 2: methyl 4-(3-(cyclopropanecarboxamido)isoquinolin-7-yl)-2-fluoro-5-methylbenzoate

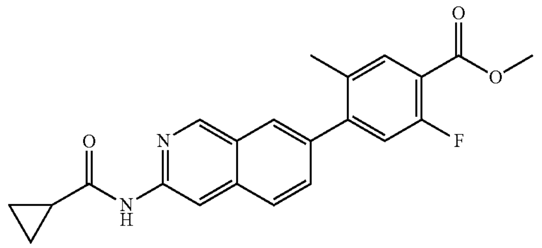 [SMILES: COC(=O)c1cc(C)c(-c2ccc3cc(NC(=O)C4CC4)ncc3c2)cc1F]

A mixture of N-[7-(4-bromo-5-fluoro-2-methyl-phenyl)-3-isoquinolyl]cyclopropanecarboxamide (385 mg, 0.964 mmol), 1,3-bis(dicyclohexylphosphino)propane bis(tetrafluoroborate) (61 mg, 0.096 mmol), palladium(II) acetate (11 mg, 0.048 mmol), potassium carbonate (202 mg, 1.45 mmol), and methanol (0.78 mL, 19.3 mmol) in DMF (1 mL) was evacuated and then filled with nitrogen (3×), and then evacuated and filled with carbon monoxide (2×). The reaction mixture was then heated at 100° C. for 2 hours under a balloon of carbon monoxide. The cooled reaction mixture was diluted with ethyl acetate (50 mL) and washed with water (50 mL). The organic layer was separated, dried over sodium sulfate, filtered and concentrated in vacuo to provide a residue that was purified by flash chromatography (4 g, Silica, 0-100% ethyl acetate in heptane). Desired fractions were combined and evaporated in vacuo to afford the title compound as a white solid (285, 78%), which was used in the next step without further purification.

Step 3: N-(7-(5-fluoro-4-(hydroxymethyl)-2-methylphenyl)isoquinolin-3-yl)cyclopropanecarboxamide

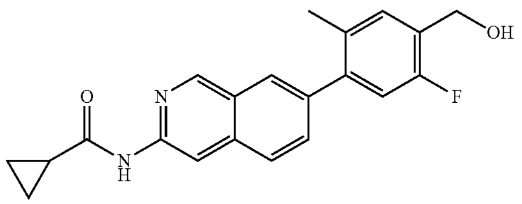 [SMILES: Cc1cc(CO)c(F)cc1-c1ccc2cc(NC(=O)C3CC3)ncc2c1]

Diisobutylaluminum hydride (1.0 mol/L) in THF (1.1 mL, 1.06 mmol) was added dropwise to a solution of methyl 4-[3-(cyclopropanecarbonylamino)-7-isoquinolyl]-2-fluoro-5-methyl-benzoate (100 mg, 0.26 mmol) in THF (1 mL) cooled at −15° C. The reaction mixture warmed to room temperature. After 1 hour, the reaction mixture was quenched with saturated aqueous ammonium chloride, diluted with ethyl acetate (50 mL) and washed with 1.0M citric acid solution in water (20 mL). The organic layer was separated, dried over sodium sulfate, filtered and concentrated in vacuo to provide a residue that was purified by reverse phase HPLC (5-85% acetonitrile in water w/0.1% $NH_4OH$, 14 minutes). Desired fractions were combined and evaporated in vacuo to afford the title compound as a white solid (52 mg, 56%). $^1H$ NMR (400 MHz, DMSO) δ 10.90 (s, 1H), 9.17 (s, 1H), 8.49 (s, 1H), 8.02 (s, 1H), 7.92 (d, J=8.6 Hz, 1H), 7.69 (dd, J=8.5, 1.6 Hz, 1H), 7.42 (d, J=7.7 Hz, 1H), 7.11 (d, J=10.7 Hz, 1H), 5.26 (s, 1H), 4.58 (s, 2H), 2.26 (s, 3H), 2.13-2.03 (m, 1H), 0.92-0.77 (m, 4H). LCMS (Method E): $R_T$=4.595 min, $M+H^+$=351.2.

Example 203

N-(7-(5-fluoro-4-(2-hydroxypropan-2-yl)-2-methylphenyl)isoquinolin-3-yl)cyclopropanecarboxamide

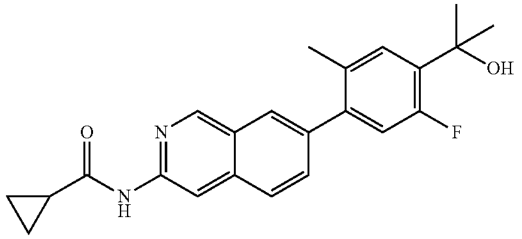 [SMILES: Cc1cc(C(C)(C)O)c(F)cc1-c1ccc2cc(NC(=O)C3CC3)ncc2c1]

To a solution of methyl 4-[3-(cyclopropanecarbonylamino)-7-isoquinolyl]-2-fluoro-5-methyl-benzoate (100 mg, 0.26 mmol) in THF (2 mL) cooled at −15° C. was added methylmagnesium chloride (3.0 mol/L) in tetrahydrofuran (0.35 mL, 1.06 mmol) dropwise over 5 minutes. After 15 minutes, the reaction mixture was quenched with a few drops of saturated aqueous ammonium chloride solution. The reaction mixture was diluted with ethyl acetate (50 mL) and washed with water (25 mL). The organic layer was separated, dried over sodium sulfate, filtered and concentrated in vacuo to provide a residue that was purified by reverse phase HPLC (5-85% acetonitrile in water w/0.1% $NH_4OH$, 14 min). Desired fractions were combined and evaporated in vacuo to afford the title compound as an off-white solid (66 mg, 66%). $^1H$ NMR (400 MHz, DMSO) δ 10.91 (s, 1H), 9.16 (s, 1H), 8.49 (s, 1H), 8.02 (s, 1H), 7.91 (d, J=8.6 Hz, 1H), 7.71 (dd, J=8.5, 1.5 Hz, 1H), 7.57 (d, J=8.6 Hz, 1H), 7.07 (d, J=12.4 Hz, 1H), 5.27 (s, 1H), 2.26 (s, 3H), 2.12-2.02 (m, 1H), 1.53 (s, 6H), 0.90-0.77 (m, 4H). LCMS (Method E): $R_T$=5.055 min, $M+H^+$=379.2.

Example 204

N-(7-(3-fluoro-2-(hydroxymethyl)-6-methylphenyl)isoquinolin-3-yl)cyclopropanecarboxamide

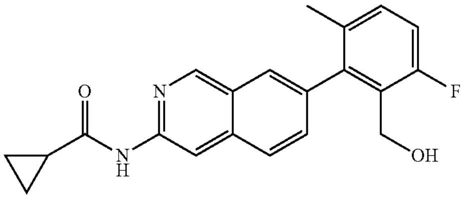 [SMILES: Cc1ccc(F)c(CO)c1-c1ccc2cc(NC(=O)C3CC3)ncc2c1]

Step 1: N-(7-(3-fluoro-2-formyl-6-methylphenyl)isoquinolin-3-yl)cyclopropanecarboxamide

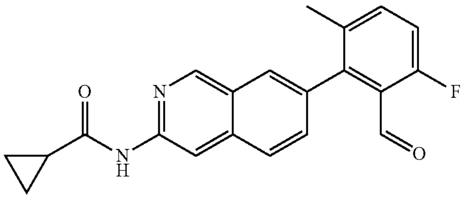 [SMILES: Cc1ccc(F)c(C=O)c1-c1ccc2cc(NC(=O)C3CC3)ncc2c1]

A mixture of N-[7-(4,4,5,5-tetramethyl-1,3,2-dioxaborolan-2-yl)-3-isoquinolyl]cyclopropanecarboxamide (100 mg, 0.30 mmol), 2-bromo-6-fluoro-3-methyl-benzaldehyde (77 mg; 0.35 mmol), bis(di-tert-butyl(4-dimethylaminophenyl)phosphine)dichloropalladium(II) (21 mg, 0.03 mmol) and saturated aqueous sodium carbonate solution (0.1 mL) in acetonitrile (1 mL) was heated under microwave irradiation (Biotage) at 120° C. for 30 minutes. The reaction mixture was diluted with ethyl acetate (30 mL) and washed with water (15 mL). The organic layer was separated, dried over sodium sulfate, filtered and concentrated in vacuo to provide a residue that was purified by flash chromatography (4 g, Silica, 0-60% ethyl acetate in heptane). Desired fractions were combined and evaporated in vacuo to afford the title compound as light brown solid (100 mg, 97%), which was used in the next step without further purification.

Step 2: N-(7-(3-fluoro-2-(hydroxymethyl)-6-methylphenyl)isoquinolin-3-yl)cyclopropanecarboxamide

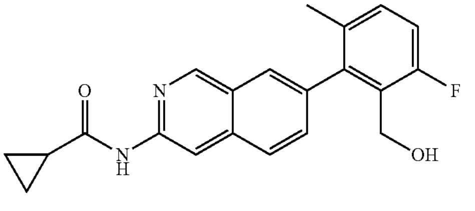 [SMILES: Cc1ccc(F)c(CO)c1-c1ccc2cc(NC(=O)C3CC3)ncc2c1]

Sodium borohydride (11 mg, 0.29 mmol) was added to a solution of N-[7-(3-fluoro-2-formyl-6-methyl-phenyl)-3-isoquinolyl]cyclopropanecarboxamide (50 mg, 0.14 mmol) in THF (1 mL). The reaction mixture was heated at 40° C. for 1 hour and then diluted with ethyl acetate (40 mL) and washed with water (40 mL). The organic layer was separated, dried over sodium sulfate, filtered and concentrated in vacuo to provide a residue that was purified by reverse phase HPLC (5-85% acetonitrile in water w/0.1% $NH_4OH$, 14 minutes). Desired fractions were combined and evaporated in vacuo to afford the title compound as an off-white solid (20 mg, 40%). $^1H$ NMR (400 MHz, DMSO) δ 10.90 (s, 1H), 9.14 (s, 1H), 8.50 (s, 1H), 7.92 (d, J=8.5 Hz, 1H), 7.89 (s, 1H), 7.54 (dd, J=8.5, 1.4 Hz, 1H), 7.31 (dd, J=8.3, 5.8 Hz, 1H), 7.20-7.12 (m, 1H), 4.79 (t, J=4.9 Hz, 1H), 4.25-4.10 (m, 2H), 2.13-2.03 (m, 1H), 1.99 (s, 3H), 0.91-0.79 (m, 4H). LCMS (Method E): $R_T$=4.648 min, $M+H^+$=351.2.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:

1. A compound of formula (I)

(I)

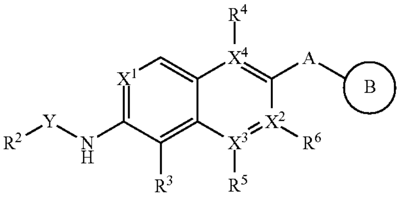

or a pharmaceutically acceptable salt thereof, having the subformula Ia, Ib, Ic, or Id, selected from the group consisting of Ia

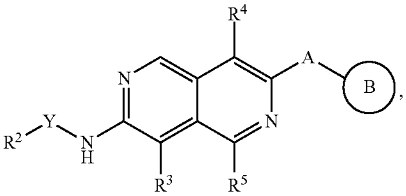

,

Ib

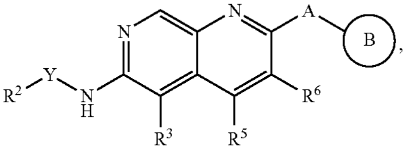

,

Ic

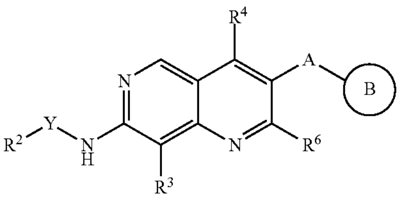

and

-continued

Id

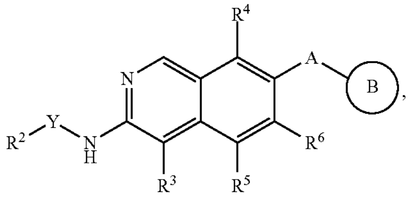

or an N-oxide thereof; wherein

Y is absent or is selected from the group consisting of —C(═O)—, —N(H)C(═O)—, —N($R^a$)C(═O)—, —O—C(═O)—, —N(H)S(O)$_{1-2}$—, —N($R^a$)S(O)$_{1-2}$— and —S(O)$_2$—, wherein $R^a$ is selected from the group consisting of $C_{1-6}$ alkyl, $C_{1-6}$ haloalkyl, $C_{1-6}$ alkoxy, $C_{1-6}$ heteroalkyl, $C_{2-6}$ alkenyl and $C_{2-6}$ alkynyl;

$R^2$ is —($X^b$)$_{0-1}$—$R^b$, wherein $X^b$ is selected from the group consisting of $C_{1-6}$ alkylene, $C_{2-6}$ alkenylene, $C_{2-6}$ alkynylene, $C_{1-6}$ heteroalkylene, 3-6 membered cycloalkylene and 3-6 membered heterocycloalkylene, $R^b$ is selected from the group consisting of hydrogen, $C_{1-6}$ alkyl, $C_{1-6}$ haloalkyl, $C_{1-6}$ heteroalkyl, $C_{2-6}$ alkenyl, $C_{2-6}$ alkynyl,3-6 membered cycloalkyl, 3-6 membered heterocycloalkyl, 6-10 membered aryl and 5-10 membered heteroaryl, wherein the aliphatic and aromatic portions of $X^b$ and $R^b$ are each independently optionally substituted with 1 to 5 $R^{b1}$ substituents selected from the group consisting of $C_{1-6}$ alkyl, $C_{1-6}$ haloalkyl, $C_{1-6}$ heteroalkyl, F, Cl, Br, I, —OH, —$NH_2$, —SH, —CN, —$NO_2$, —$N_3$, —C(═O)OH, $C_{1-6}$ alkoxy, $C_{1-6}$ alkylamino, $C_{1-6}$ dialkylamino, —($C_{1-4}$ alkenylene)$_{0-1}$-C(═O)—($C_{1-4}$ alkyl), —($C_{1-4}$ alkenylene)$_{0-1}$-C(═O)O—($C_{1-4}$ alkyl), —($C_{1-4}$ alkenylene)$_{0-1}$ -C(═O)N(H)—($C_{1-4}$ alkyl), —($C_{1-4}$ alkenylene)$_{0-1}$-C(═O)N($C_{1-4}$ alkyl)$_2$, —($C_{1-4}$ alkenylene)$_{0-1}$-S(O)$_2$—($C_{1-4}$ alkyl), —($C_{1-4}$ alkenylene)$_{0-1}$-C(═O)—($C_{1-4}$ heteroalkyl) and —($C_{1-4}$ alkenylene)$_{0-1}$-C(═O)—($C_{3-6}$ heterocycloalkyl), and wherein if $R^b$ is a 6 membered aryl or a 5-6 membered heteroaryl then any two substituents attached to adjacent atoms said aryl or heteroaryl are optionally combined to from a 3-6 membered carbocyclic or a 3-6 membered heterocyclic ring comprising 1-3 heteroatoms selected from N, O and S, and optionally substituted with 1 to 3 $R^{b1}$ substituents;

$X^1$ is N or $N^+$—$O^-$;

$X^2$, $X^3$ and $X^4$ are each C, or one of $X^2$, $X^3$ and $X^4$ is N or $N^+$—$O^-$ and the remainder of $X^2$, $X^3$ and $X^4$ are each C;

$R^3$ is selected from the group consisting of hydrogen, $C_{1-6}$ alkyl, $C_{1-6}$ haloalkyl, $C_{1-6}$ alkoxy, $C_{1-6}$ alkylamino, $C_{1-6}$ dialkyamino, F, Cl, Br, I, —CN, —$CF_3$, —$OCF_3$, —$SF_5$ and —$N_3$;

$R^4$ is selected from the group consisting of hydrogen, $C_{1-6}$ alkyl, $C_{1-6}$ haloalkyl, F, Cl, Br, I, —CN, —$NO_2$, —$N_3$, —SH, —OH, $C_{1-6}$ alkoxy, —$CF_3$, —$OCF_3$, —$SF_5$, $C_{1-6}$ alkylamino and $C_{1-6}$ dialkylamino, or is absent if $X^4$ is N or $N^+$—O;

$R^5$ is ($X^c$)$_{0-1}$—$R^c$, wherein $X^c$ is selected from the group consisting of $C_{1-6}$ alkylene, $C_{2-6}$ alkenylene, $C_{2-6}$ heteroalkylene, $C_{2-6}$alkynylene, —N(H)—, —N($R^{xc}$)—, —O—, —S(O)$_2$—, —C(═O)—, —C(═O)O—, —C(═O)N(H)—, —N(H)C(═O)— and —OC(═O)—, wherein $R^{xc}$ is selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, and wherein $R^c$ is selected from the group consisting of hydrogen, F, Cl, Br, I, —CN,—$NO_2$, —$NH_2$, —OH, —$CF_3$, —$OCF_3$, —$SF_5$, $C_{1-6}$ alkoxy, $C_{1-6}$ alkylamino, $C_{1-6}$ dialkylamino, $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 3-6 membered heterocycloalkyl, 6 membered aryl and 5-6 membered heteroaryl, wherein the aliphatic and aromatic portions of $X^c$ and $R^c$ are optionally substituted with 1 to 5 $R^{c1}$ substituents selected from the group consisting of $C_{1-6}$ alkyl, $C_{1-6}$ heteroalkyl, F, Cl, Br, I, —OH, —$NH_2$, —SH, —CN, —$NO_2$, —$N_3$, —C(═O)OH, —N($C_{1-6}$ alkyl)$_2$, —NH($C_{1-6}$ alkyl), —O($C_{1-6}$ alkyl), —($C_{1-4}$ alkenylene)$_{0-1}$-C(═O)—($C_{1-4}$ alkyl), —($C_{1-4}$ alkenylene)$_{0-1}$-C(═O)O—($C_{1-4}$ alkyl), —($C_{1-4}$ alkenylene)$_{0-1}$-C(═O)N(H)—($C_{1-4}$ alkyl), —($C_{1-4}$ alkenylene)$_{0-1}$-C(═O)N($C_{1-4}$ alkyl)$_2$, —($C_{1-4}$ alkenylene)$_{0-1}$-S(O)$_2$—($C_{1-4}$ alkyl), —($C_{1-4}$ alkenylene)$_{0-1}$-C(═O)—($C_{1-4}$heteroalkyl) and —($C_{1-4}$alkenylene)$_{0-1}$-C(═O)—($C_{3-6}$ heterocycloalkyl), or $R^5$ is absent if $X^3$ is N or $N^+$—$O^-$;

$R^6$ is selected from the group consisting of hydrogen, $C_{1-6}$ alkyl, $C_{1-6}$ haloalkyl, $C_{1-6}$ heteroalkyl, $C_{1-6}$ alkoxy, $C_{1-6}$ alkylamino, $C_{1-6}$ dialkylamino, $C_{2-6}$ alkenyl, $C_{2-6}$ alkynyl, F, Cl, Br, I, —OH, —$NH_2$, —SH, —CN, —$NO_2$, —$CF_3$, —$OCF_3$, —$SF_5$ and —$N_3$, or $R^6$ is absent if $X^2$ is N or $N^+$—$O^-$;

A is selected from the group consisting of —($X^d$)$_{0-1}$—N(H)C(═O)—, —($X^d$)$_{0-1}$—N($R^d$)C(═O)—, —$X^d$—, —($X^d$)$_{0-1}$—C(═O)N(H)—, —($X^d$)$_{0-1}$—C(═O)N($R^d$)—, —($X^d$)$_{0-1}$—C(═O)—, —C(═O)—($X^d$)$_{0-1}$—, —($X^d$)$_{0-1}$—OC(═O)—, —($X^d$)$_{0-1}$C(═O)O— and wherein the $X^d$ group in A is selected from the group consisting of $C_{1-6}$ alkylene, $C_{2-6}$ alkenylene $C_{1-6}$ heteroalkylene, 6-10 membered arylene and a 5-10 membered heteroarylene comprising 1 to 3 heteroatoms selected from N, O and S, wherein said $X^d$ is optionally substituted with 1 to 5 $R^{d1}$ substituents selected from the group consisting of $C_{1-6}$ alkyl, $C_{1-6}$ haloalkyl, $C_{2-6}$ alkenyl, $C_{2-6}$ alkynyl, $C_{1-6}$ alkylamino, $C_{1-6}$ dialkylamino, F, Cl, Br, I, —OH, —$NH_2$, —SH, —CN, —$NO_2$ —$CF_3$ —$OCF_3$, —$SF_5$, and —$N_3$;

B is selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 4-9 membered heterocycloalkyl, 6-10 membered aryl and 5-6 membered heteroaryl, wherein the aliphatic or aromatic portions of B are independently optionally substituted with 1 to 5 $R^{B1}$ substituents selected from the group consisting of $C_{1-6}$ alkyl, $C_{1-6}$ haloalkyl, $C_{1-6}$ heteroalkyl, $C_{1-6}$ alkoxy, $C_{1-6}$ alkylamino, $C_{1-6}$ dialkylamino, $C_{3-6}$ heterocycloalkyl, F, Cl, Br, I, —OH, —$NH_2$, —SH, —$CF_3$, —$OCF_3$, —$SF_5$, —($X^e$)$_{0-1}$—CN, —($X^e$)$_{0-1}$—$NO_2$, —($X^e$)$_{0-1}$—$N_3$, —($X^e$)$_{0-1}$—OH, —($X^e$)$_{0-1}$—H, —($X^e$)$_{0-1}$—N(H)$R^e$, —($X^e$)$_{0-1}$—N($R^e$)$_2$, —($X^e$)$_{0-1}$—S$R^e$, —($X^e$)$_{0-1}$—C(O)$R^e$, —($X^e$)$_{0-1}$—S(O)$_2R^e$, —($X^e$)$_{0-1}$—S(O)$R^e$, —N(H)S(O)$_2R^e$, —N($R^e$)S(O)$_2R^e$, —($X^e$)$_{0-1}$C(═O)O$R^e$, —($X^e$)$_{0-1}$—C(═O)OH, —($X^e$)$_{0-1}$—C(═O)N(H)$R^e$, —($X^e$)$_{0-1}$—C(═O)N($R^e$)$R^e$, —($X^e$)$_{0-1}$—N(H)C(═O)$R^e$, —($X^e$)$_{0-1}$—N($R^e$)C(═O)$R^e$, wherein if B is a 6 membered aryl or a 5-6 membered heteroaryl then any two substituents attached to adjacent atoms of said aryl or heteroaryl are optionally combined to from a 3-6 membered carbocyclic or a 3-6 membered heterocyclic ring optionally comprising 1-3 heteroatoms selected from N, O and S, and optionally substituted with 1 to 3 $R^{B1}$ substituents; wherein $X^e$ is selected from the group consisting of $C_{1-6}$ alkylene, $C_{2-6}$ alkenylene, $C_{2-6}$ alkynylene, $C_{1-6}$ heteroalkylene, $C_{3-6}$ cycloalkylene and $C_{3-6}$ heterocycloalkylene, and $R^e$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl, 3-7 membered heterocycloalkyl, phenyl and 5-6 membered heteroaryl, wherein the aliphatic or aromatic portions of $X^e$ and $R^e$ are each independently optionally substituted with 1 to 5 $R^{e1}$ substituents selected from the group consisting of $C_{1-6}$ alkyl, $C_{1-6}$ haloalkyl, $C_{2-6}$ alkenyl, $C_{2-6}$ alkynyl, $C_{1-6}$ alkylamino, $C_{1-6}$ dialkylamino, F, Cl, Br, I, —OH, —$NH_2$, —SH, —CN, —$NO_2$, —$CF_3$, —$OCF_3$, —$SF_5$ and —$N_3$, and wherein any two $R^e$ groups attached to the same nitrogen atom are optionally combined to form a 3-7 membered heterocyclic or 5-10 membered heteroaryl ring comprising 1-3 heteroatoms selected from N, O and S; and wherein if $X^3$ is N, $R^3$ is H, $R^4$ is H or $NH_2$, $R^6$ is —OH and —Y—$R^2$ is other than H, then -A-B is not thiazol-4-yl substituted with 2-thiophenyl-$S(O)_2CH_2$—, phenyl-$S(O)_2$—$CH_2$—, 4-pyridyl, or pyridyl-$S(O)_2CH_2$—, if $X^3$ is N, $R^3$ is H or Cl, $R^4$ is H, $R^6$ is —OH, —$NH_2$, or —$NHCH_3$ and —Y—$R^2$ is hydrogen, 4-tetrahydropyranyl, 4-($(CH_3CH_2)_2N(CH_2)_{3-4}O$)-phenyl, $(CH_3CH_2)_2N(CH_2)_4$—, 3-(4-methylpiperazinyl)-propyl or trifluoroacetyl, then -A-B is not 2-chlorophenyl, 2-methylphenyl, 2,6-dichlorophenyl, 3,5-dimethoxyphenyl, 3,4-dimethoxypheny, phenyl, 2-chloro-6-(2-ethoxyethoxy)phenyl, if $X^3$ is N, $R^3$, $R^4$ and $R^6$ are each H, and —Y—$R^2$ is hydrogen, cyclohexyl, $(CH_3CH_2)_2NCH_2CH_2$—, $CH_3N(H)CH_2CH_2$—, $(CH_3)_2NCH_2CH_2$—, $(CH_3)_3CC$(═O)— or 2-(4-morpholinyl) ethyl, then -A-B is not 3,4-dimethoxyphenyl or optionally substituted pyridine-2-on-3-yl, if $X^4$ is N, $R^3$ is H, $R^5$ is isopropyl, $R^6$ is methoxy, -A-B is propyl or isopropyl, then —Y—$R^2$ is other than optionally substituted pyridyl, if $X^4$ is N, $R^3$, $R^5$, $R^6$ are each H, -A-B is methyl, then —Y—$R^2$ is other than hydrogen, if $R^3$, $R^4$, $R^5$ and $R^6$ are each H, and —Y—$R^2$ is hydrogen, cyclohexyl, $(CH_3CH_2)_2NCH_2CH_2$—, $CH_3N(H)CH_2CH_2$—, $(CH_3)_2NCH_2CH_2$—, $(CH_3)_3CC$(═O)— or 2-(4-morpholinyl) ethyl, then -A-B is not 3,4-dimethoxyphenyl or optionally substituted pyridine-2-on-3-yl, if $R^3$, $R^4$ and $R^5$ are each hydrogen, —Y—$R^2$ is other than hydrogen, then one of $R^6$ and -A-B is other than ethoxy.

2. The compound of claim 1, wherein $R^3$, $R^4$ and $R^6$, if present, are each independently selected from the group consisting of hydrogen, $C_{1-6}$ alkyl, $C_{1-6}$ haloalkyl, —$CF_3$, —$OCF_3$, —$SF_5$, F, Cl, Br and I.

3. The compound of claim 1, wherein in $R^2$, $X^b$ is absent or is selected from $C_{1-6}$ alkylene and 3-6 membered cycloalkylene; and $R^b$ is selected from the group consisting of hydrogen, $C_{1-6}$ alkyl, $C_{1-6}$ haloalkyl, $C_{1-6}$ heteroalkyl, $C_{2-6}$ alkenyl, $C_{2-6}$ alkynyl, 3-6 membered cycloalkyl, 3-6 membered heterocycloalkyl, 6-10 membered aryl, and 5-10 membered heteroaryl, wherein $X^b$ and $R^b$ are each independently optionally substituted.

4. The compound of claim 3, wherein in $R^2$, $X^b$ is absent.

5. The compound of claim 3, wherein in $R^2$, $R^b$ is selected from the group consisting of hydrogen, $C_{1-6}$ alkyl, $C_{1-6}$ haloalkyl, $C_{1-6}$ heteroalkyl, $C_{2-6}$ alkenyl and $C_{2-6}$ alkynyl.

6. The compound of claim 3, wherein in $R^2$, $R^b$ is optionally substituted with from 1 to 5 $R^{b1}$ groups selected from the group consisting of F, Cl, Br, I, OH, $NH_2$, SH, CN, $NO_2$, $C_{1-6}$ alkoxy, $C_{1-6}$ alkylamino and $C_{1-6}$ dialkylamino.

7. The compound of claim 1, wherein in $R^2$, $R^b$ is selected from the group consisting of cycloprop-1-yl, cyclobut-1-yl, cyclopent-1-yl, pyrimidin-2-yl, pyrimidin-4-yl, pyrimidin-5-yl, pyridin-2-yl, pyridin-4-yl, pyridin-3-yl, pyridin-2-on-6-yl, pyridine-2-on-5-yl, pyridine-2-on-4-yl, pyridine-2-on-3-yl, cyclohex-1-yl, phenyl, 4,5-dihydrooxazol-2-yl, oxazol-2-yl, piperidin-4-yl, piperidin-3-yl, piperidin-2-yl, piperidin-1-yl, piperazin-1-yl, piperazin-2-yl, piperazin-3-yl, morpholin-2-yl, morpholin-3-yl, morpholin-4-yl, tetrahydropyran-4-yl, tetrahydropyran-2-yl, tetrahydropyran-3-yl, oxetan-3-yl, oxetan-2-yl, pyrazol-5-yl, pyrazol-1-yl, pyrazol-3-yl, pyrazol-4-yl, methyl, ethyl, propyl, isopropyl, butyl, iso-butyl, tert-butyl, pyrrolidin-3-yl, pyrrolidin-2-yl, 2-tetrahydrofuranyl, 3-tetrahydrofuranyl and 3-oxabicyclo[3.1.0]hexan-6-yl, wherein said $R^b$ is further optionally substituted.

8. The compound of claim 1, wherein Y is absent or is selected from the group consisting of —C(═O)—, —N(H)C(═O)—, —N($R^a$)C(═O)— and —$S(O)_2$—.

9. The compound of claim 8, wherein in $R^2$ $R^b$ is selected from the group consisting of cycloprop-1-yl, cyclobut-1-yl, cyclopent-1-yl, pyrimidin-2-yl, pyrimidin-4-yl, pyrimidin-5-yl, pyridin-2-yl, pyridin-4-yl, pyridin-3-yl, pyridin-2-on-6-yl, pyridine-2-on-5-yl, pyridine-2-on-4-yl, pyridine-2-on-3-yl, cyclohex-1-yl, phenyl, 4,5-dihydrooxazol-2-yl, oxazol-2-yl, piperidin-4-yl, piperidin-3-yl, piperidin-2-yl, piperidin-1-yl, piperazin-1-yl, piperazin-2-yl, piperazin-3-yl, morpholin-2-yl, morpholin-3-yl, morpholin-4-yl, tetrahydropyran-4-yl, tetrahydropyran-2-yl, tetrahydropyran-3-yl, oxetan-3-yl, oxetan-2-yl, pyrazol-5-yl, pyrazol-1-yl, pyrazol-3-yl, pyrazol-4-yl, methyl, ethyl, propyl, isopropyl, butyl, iso-butyl, tert-butyl, pyrrolidin-3-yl, pyrrolidin-2-yl, 2-tetrahydrofuranyl, 3-tetrahydrofuranyl and 3-oxabicyclo[3.1.0]hexan-6-yl, and wherein $R^2$ is optionally substituted.

10. The compound of claim 9, wherein Y is —C(═O)—.

11. The compound of claim 7, wherein in $R^2$, $R^b$ is selected from the group as set forth on FIG. 1-A and FIG. 1-B.

12. The compound of claim 1, wherein the $X^d$ group in A is selected from the group consisting of phenylene, pyridylene, pyrimidinylene, pyridazinylene, pyrazinylene, and wherein said $X^d$ is optionally substituted.

13. The compound of claim 12, wherein A is selected from the group consisting of

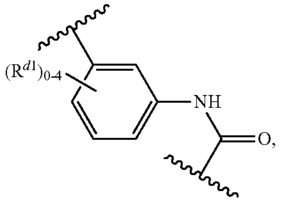
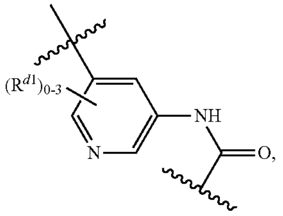
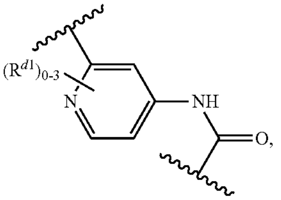
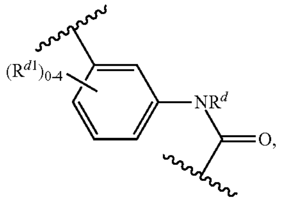
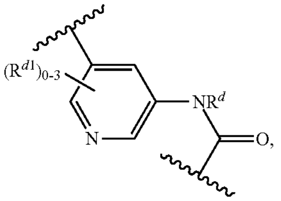
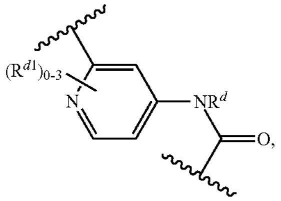

-continued

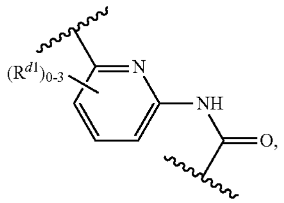

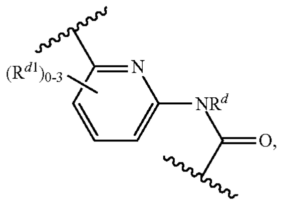

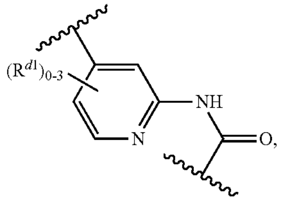

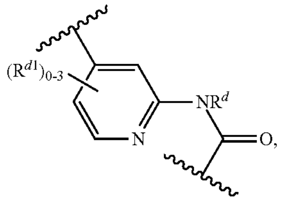

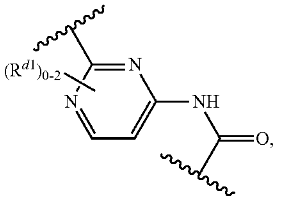

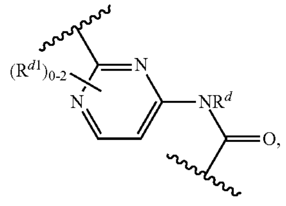

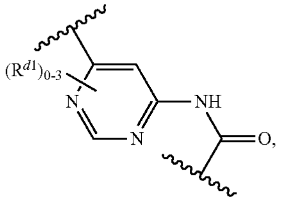

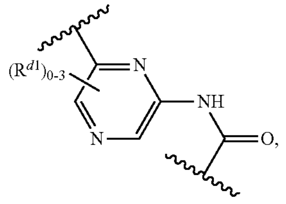

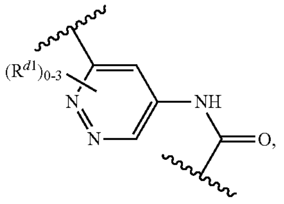

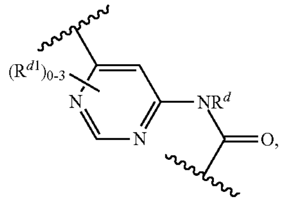

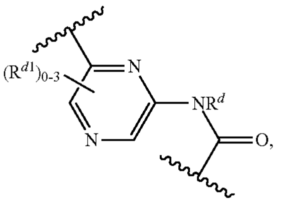

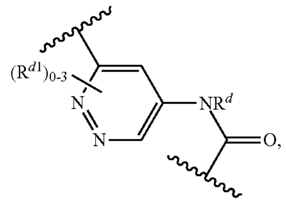

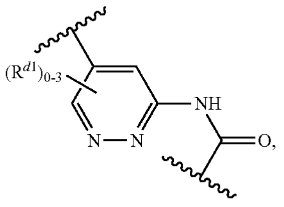

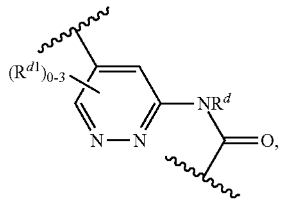

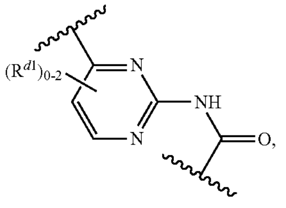

and

-continued

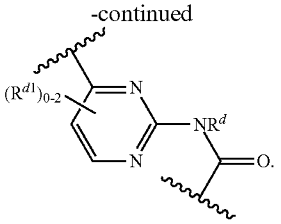

14. The compound of claim 1, wherein A is selected from the group consisting of:

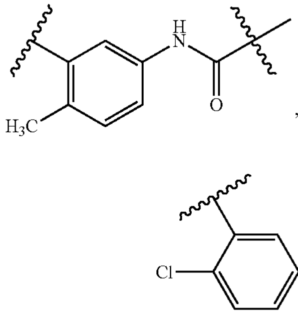

,

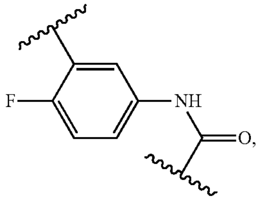

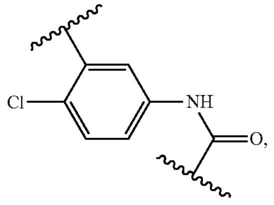

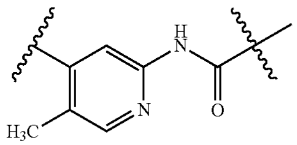

and

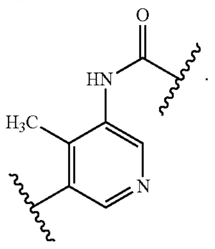

15. The compound of claim 1, wherein B is selected from the group consisting of phenyl, pyridin-2-yl, pyridin-3-yl, pyridin-4-yl, pyrrolidin-1-yl, pyrrolidin-2-yl, pyrrolidin-3-yl, pyrazol-1-yl, pyrazol-3-yl, pyrazol-4-yl, pyrazol-5-yl, thiazol-2-yl, thiazol-4-yl, thiazol-5-yl, pyridin-4-on-3-yl, pyridin-4-on-2-yl, pyridin-4-on-1-yl, pyridin-2-on-1-yl, pyridin-2-on-3-yl, pyridin-2-on-4-yl, pyrrol-1-yl, pyrrol-3-yl, pyrrol-4-yl, pyridazin-3-yl, pyridazin-4-yl, pyridazin-5-yl, pyrazin-2-yl, cyclohexyl, cyclobutyl, cyclopropyl, cyclopentyl, morpholin-4-yl, morpholin-2-yl, morpholin-3-yl, piperazin-1-yl, piperazin-2-yl, cyclopentyl, piperidin-1-yl, piperidin-4-yl, piperidin-2-yl, piperidin-3-yl, indol-5-yl, indol-4-yl, indol-3-yl, indol-2-yl, pyridimdin-5-yl, pyridimdin-4-yl, pyrimidin-2-yl, indazol-3-yl, indazol-4-yl, indazol-5-yl, indazol-6-yl, indazol-7-yl, indolin-2-on-4-yl, indolin-2-on-5-yl, indolin-2-on-6-yl, indolin-2-on-7-yl, tetrahydropyran-4-yl, tetrahydropyran-3-yl, tetrahydropyran-2-yl, tetrahydrofuran-2-yl, tetrahydrofuran-3-yl, tetrahydrofuran-4-yl, wherein B is optionally substituted and wherein any two substituent located on adjacent atoms of B are optionally combined to form an optionally substuted 5 to 7 membered heterocyclic ring comprising 1 to 3 heteroatoms selected from N, O and S.

16. The compound of claim 1, wherein B is selected from the group consisting of methyl, ethyl, propyl, isopropyl, butyl, isobutyl, tert-butyl, wherein B is optionally substituted.

17. The compound of claim 12, wherein B is selected from the group consisting of phenyl, pyridin-2-yl, pyridin-3-yl and pyridin-4-yl, wherein the B is optionally substituted with 1 to 3 $R^{B1}$ substitutents selected from the group consisting of $C_{1-6}$ alkyl, $C_{1-6}$ haloalkyl, $C_{1-6}$ heteroalkyl, $C_{1-6}$ alkoxy, $C_{1-6}$ alkylamino, $C_{1-6}$ dialkylamino, F, Cl, Br, I, —OH, —$NH_2$, —SH, —$(X^e)_{0-1}$—CN, —$(X^e)_{0-1}$—$NO_2$, —$(X^e)_{0-1}$—$N_3$, —$(X^e)_{0-1}$—N(H)$R^e$, —$(X^e)_{0-1}$—N$(R^2)_2$, —$(X^e)_{0-1}$—S$R^e$, —$(X^e)_{0-1}$—C(O)$R^e$, —$(X^e)_{0-1}$—S$(O)_2R^e$, —$(X^e)_{0-1}$—S(O)$R^e$, —$(X^e)_{0-1}$—C(═O)O$R^e$, —$(X^e)_{0-1}$—C(═O)N(H)$R^e$, —$(X^e)_{0-1}$—C(═O)N$(R^e)R^e$, —$(X^e)_{0-1}$—N(H)C(═O)$R^e$ and —$(X^e)_{0-1}$—N$(R^e)$C(═O)$R^e$, and wherein any two substituent located on adjacent atoms of B are optionally combined to form an optionally substuted 5 to 7 membered heterocyclic ring comprising 1 to 3 heteroatoms selected from N, O and S.

18. The compound of claim 14, wherein B is selected from the group consisting of

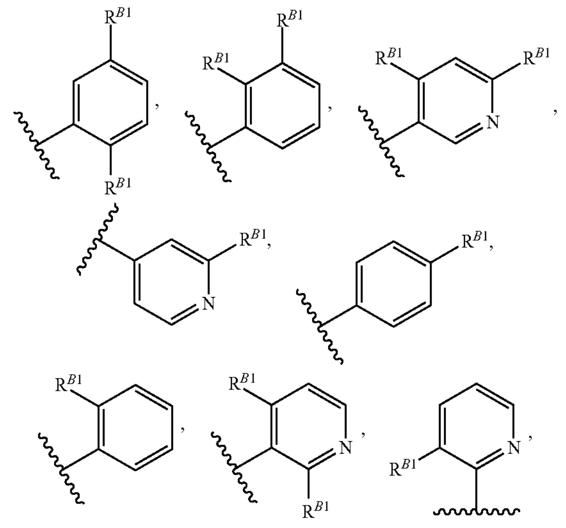

-continued

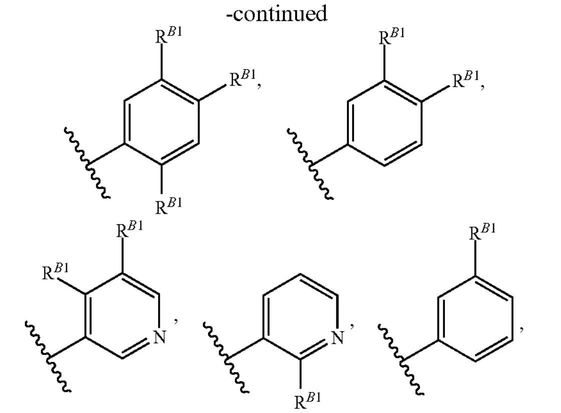

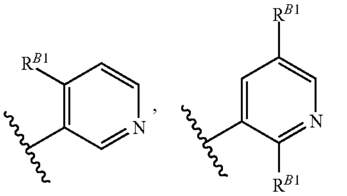

and

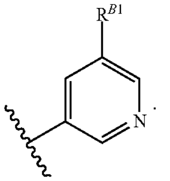

19. The compound of claim 1, wherein B is selected from the group as set forth on FIG. 2-A, FIG. 2-B, FIG. 2-C, FIG. 2-D and FIG. 2-E.

20. The compound of claim 1, wherein $R^5$ is $(X^c)$—$R^c$, wherein $X^c$ is absent or is selected from the group consisting of $C_{1-6}$ alkylene, —N(H)—, —N$(R^{xc})$—, —O—, —S$(O)_2$—, and $R^c$ is selected from the group consisting of hydrogen, F, Cl, Br, I, —CN, —$NO_2$, —$CF_3$, —$OCF_3$, —$SF_5$, $C_{1-6}$ alkyl, $C_{1-6}$ heteroalkyl, piperidin-1-yl, piperidin-2-yl, piperidin-3-yl, piperidin-4-yl, cyclopropyl, cyclopentyl, phenyl, pyrdin-2-yl, pyridin-3-yl, pyridine-4-yl- pyrazol-3-yl, pyrazol-4-yl, pyrazol-5-yl, thiazol-2-yl, thiazol-3-yl, thiazol-5-yl, piperazin-1yl, piperazin-2-yl, pyrrolidin-1-yl, pyrrolidin-2-yl, pyrroldin-3-yl, tetrahydrofuran-2-yl, tetrahydrofuran-3-yl, wherein $R^c$ is optionally substituted.

21. A compound of formula I of claim 1 selected from the group consisting of the compounds in Table 1 and Table 1b.

22. A pharmaceutical composition comprising a compound in accordance with claim 1 and a pharmaceutically acceptable carrier, diluent or excipient.

* * * * *